US011691962B2

(12) United States Patent
Chenard et al.

(10) Patent No.: US 11,691,962 B2
(45) Date of Patent: Jul. 4, 2023

(54) THERAPEUTIC COMPOUNDS AND COMPOSITIONS

(71) Applicant: eXIthera Pharmaceuticals, Inc., Westborough, MA (US)

(72) Inventors: Bertrand L. Chenard, Waterford, CT (US); Yuelian Xu, East Haven, CT (US); Frans L. Stassen, Cambridge, MA (US); Neil J. Hayward, Westborough, MA (US); Zhiyao Teng, Newington, CT (US)

(73) Assignee: EXITHERA PHARMACEUTICALS, INC., Westborough, MA (US)

( * ) Notice: Subject to any disclaimer, the term of this patent is extended or adjusted under 35 U.S.C. 154(b) by 221 days.

(21) Appl. No.: 16/986,658

(22) Filed: Aug. 6, 2020

(65) Prior Publication Data
US 2021/0188812 A1    Jun. 24, 2021

Related U.S. Application Data

(63) Continuation of application No. PCT/US2019/016503, filed on Feb. 4, 2019.

(60) Provisional application No. 62/627,435, filed on Feb. 7, 2018.

(51) Int. Cl.
| C07D 401/14 | (2006.01) |
| C07D 405/14 | (2006.01) |
| C07D 409/14 | (2006.01) |
| C07D 417/14 | (2006.01) |

(52) U.S. Cl.
CPC ......... *C07D 401/14* (2013.01); *C07D 405/14* (2013.01); *C07D 409/14* (2013.01); *C07D 417/14* (2013.01)

(58) Field of Classification Search
CPC .. C07D 401/14; C07D 405/14; C07D 409/14; C07D 417/14
See application file for complete search history.

(56) References Cited

U.S. PATENT DOCUMENTS

| 4,595,532 | A | 6/1986 | Miller |
| 6,335,324 | B1 | 1/2002 | Bisacchi et al. |
| 6,740,647 | B1 | 5/2004 | Baucke et al. |
| 7,501,404 | B2 * | 3/2009 | Bannister ............ C07D 401/06 540/200 |
| 9,499,532 | B2 | 11/2016 | Chrusciel et al. |
| 9,994,521 | B2 | 6/2018 | Chrusciel et al. |
| 10,259,785 | B2 | 4/2019 | Chrusciel et al. |
| 2007/0105832 | A1 | 5/2007 | Bannister et al. |
| 2010/0144698 | A1 | 6/2010 | Bannister et al. |
| 2015/0157624 | A1 | 6/2015 | Orwat et al. |
| 2015/0225389 | A1 | 8/2015 | Chrusciel et al. |
| 2017/0037003 | A1 | 2/2017 | Chrusciel et al. |
| 2018/0244614 | A1 | 8/2018 | Chrusciel et al. |
| 2019/0315711 | A1 | 10/2019 | Chenard et al. |
| 2019/0359567 | A1 | 11/2019 | Chrusciel et al. |
| 2021/0188812 | A1 | 6/2021 | Chenard et al. |
| 2021/0253550 | A1 | 8/2021 | Hayward et al. |
| 2021/0261524 | A1 | 8/2021 | Hayward et al. |

FOREIGN PATENT DOCUMENTS

| CA | 2536435 | A1 | 3/2005 |
| CN | 1289341 | A | 3/2001 |
| EP | 1099690 | A4 | 10/2001 |
| WO | 1999067215 | A1 | 12/1999 |
| WO | 2006108039 | A2 | 10/2006 |
| WO | 2007102771 | A1 | 9/2007 |
| WO | 2011100401 | A1 | 8/2011 |
| WO | 2011100402 | A1 | 8/2011 |
| WO | 2013148366 | A1 | 10/2013 |
| WO | 2015120062 | A2 | 8/2015 |
| WO | 2018118705 | A1 | 6/2018 |
| WO | 2020092592 | A1 | 5/2020 |
| WO | 2020092594 | A1 | 5/2020 |
| WO | 2020159824 | A1 | 8/2020 |

OTHER PUBLICATIONS

Silverman, R. "The Organic Chemistry of Drug Design and Drug Action," 2004, Elsevier, pp. 20-32.*
Arooj et al., "3D QSAR Pharmacophore Modeling, in Silico Screening, and Density Functional Theory (DFT) Approaches for Identification of Human Chymase Inhibitors", International Journal of Molecular Science, 2011, 12, pp. 9236-9264.
Brodie et al., "Extracorporeal life support for adults with respiratory failure and related indications". Journal of American Medical Association, 2019, vol. 322, No. 6, pp. 557-568.
CAS Registry No. 1025878-09-4 entered STN Jun. 5, 2008.
CAS Registry No. 1348355-33-8 entered STN Dec. 4, 2011.
CAS Registry No. 931425-82-0 entered STN Apr. 20, 2007.
EXIthera Pharmaceuticals, "eXIthera Presents Clinical Data on Novel Small Molecule FXIa Inhibitor EP-7041 at American Heart Association", Press Release, Nov. 13, 2017.
Gailani et al. "Factor XI as a Therapeutic Target" Vanderbilt University, Arterioscler Thromb Vasc Biol, 2016, pp. 1316-1322.
International Search Report and Written Opinion for International Application No. PCT/US2015/014478, dated Jul. 23, 2015.
International Search Report and Written Opinion for International Application No. PCT/US2017/066787 dated Feb. 13, 2018.
International Search Report and Written Opinion for International Application No. PCT/US2019/016503 dated Jun. 11, 2019.
International Search Report and Written Opinion for International Application No. PCT/US2019/058896, dated Feb. 25, 2020.
International Search Report and Written Opinion for International Application No. PCT/US2019/058898, dated Feb. 27, 2020.
Kossman et al. "Platelet-localized FXI promotes a vascular coagulation-inflammatory circuit in arterial hypertension" Science Translational Medicine, 2017, pp. 1-16.

(Continued)

*Primary Examiner* — Sikarl A Witherspoon
(74) *Attorney, Agent, or Firm* — Goodwin Procter LLP

(57) ABSTRACT

The present invention provides compounds that inhibit Factor XIa or kallikrein and pharmaceutically acceptable salts thereof and compositions thereof. The present invention also provides methods of using these compounds and compositions.

14 Claims, No Drawings

(56) References Cited

OTHER PUBLICATIONS

MedicineNet. MedicineNet.com Deep Vein Thrombosis. (2015). <http://www.medicinenet.com/deep_vein_thrombosis/article.htm>.

Meijers et al., "High Levels of Coagulation Factor XI as a Risk Factor for Venous Thrombosis," The N.E. Journal of Medicine, 342(10):696-701 (2000).

Phillips et al., "Studies on monobactams I. Synthesis and b-lactamase inhibitory activity of 4-substituted 3-[N-methyl-1,2,3-triazol-4-yl)-2-azetidinone-1-sulfonates", Chemistry of Heterocyclic Compounds, 1998, 34(11), pp. 1308-1318.

Sato et al., "Stereoselective synthesis of (E)-Xaa-Pro dipeptide isosteres by palladium-catalyzed allylic reactions", Peptide Science (2006), Volume Date 2005, 42nd, pp. 145-148.

Sikora et al., "Citropin 1.1 trifluoroacetate to chloride counter-ion exchange in hcl-saturated organic solutions: an alternative approach", International Journal of Peptide Research and Therapeutics, (2017), vol. 24, pp. 265-270.

The NIH. How Can Deep Vein Thrombosis be Prevented? (2011). <http://www.nhlbi.nih.gov/health/health-topics/topics/dvt/prevention#>.

WebMd. Deep Vein Thrombosis Health Center: How to Prevent Deep Vein Thrombosis (DVT). (2015). <http:www.webmd.com/dvt/deep-vein-thrombosis-prevent-dvt>.

Weitz et al. "Factors XI and XII as Targets for New Anticoagulants" Department of Biochemistry and Biomedical Sciences, McCaster University, 2017, pp. 1-6.

Wermuth, Camille, "Molecular Variations Based on Isoteric Replacements", The Practice of Medicinal Chemistry. Academic Press, 1996, pp. 203-237.

International Search Report and Written Opinion for International Application No. PCT/US2020/015002, dated Apr. 16, 2020.

\* cited by examiner

THERAPEUTIC COMPOUNDS AND COMPOSITIONS

CROSS-REFERENCE TO RELATED APPLICATIONS

This application is a continuation of International Application Number PCT/US2019/016503 filed Feb.4, 2019, which claims priority to U.S. Ser. No. 62/627,435 filed Feb. 7, 2018, the contents of each of which are incorporated herein by reference in their entirety.

BACKGROUND OF THE INVENTION

Blood coagulation is the first line of defense against blood loss following injury. The blood coagulation "cascade" involves a number of circulating serine protease zymogens, regulatory cofactors and inhibitors. Each enzyme, once generated from its zymogen, specifically cleaves the next zymogen in the cascade to produce an active protease. This process is repeated until finally thrombin cleaves the fibrinopeptides from fibrinogen to produce fibrin that polymerizes to form a blood clot. Although efficient clotting limits the loss of blood at a site of trauma, it also poses the risk of systemic coagulation resulting in massive thrombosis. Under normal circumstances, hemostasis maintains a balance between clot formation (coagulation) and clot dissolution (fibrinolysis). However, in certain disease states such as acute myocardial infarction and unstable angina, the rupture of an established atherosclerotic plaque results in abnormal thrombus formation in the coronary arterial vasculature.

Diseases that stem from blood coagulation, such as myocardial infarction, unstable angina, atrial fibrillation, stroke, pulmonary embolism, and deep vein thrombosis, are among the leading causes of death in developed countries. Current anticoagulant therapies, such as injectable unfractionated and low molecular weight (LMW) heparin and orally administered warfarin (coumadin), carry the risk of bleeding episodes and display patient-to-patient variability that results in the need for close monitoring and titration of therapeutic doses. Consequently, there is a large medical need for novel anticoagulation drugs that lack some or all of the side effects of currently available drugs.

Factor XIa is an attractive therapeutic target involved in the pathway associated with these diseases. Increased levels of Factor XIa or Factor XIa activity have been observed in several thromboembolic disorders, including venous thrombosis (Meijers et al., N. Engl. J. Med. 342:696, 2000), acute myocardial infarction (Minnema et al., Arterioscler Thromb Vasc Biol 20:2489, 2000), acute coronary syndrome (Butenas et al., Thromb Haemost 99:142, 2008), coronary artery disease (Butenas et al., Thromb Haemost 99:142, 2008), chronic obstructive pulmonary disease (Jankowski et al., Thromb Res 127:242, 2011), aortic stenosis (Blood Coagul Fibrinolysis, 22:473, 2011), acute cerebrovascular ischemia (Undas et al., Eur J Clin Invest, 42:123, 2012), and systolic heart failure due to ischemic cardiomyopathy (Zabcyk et al., Pol Arch Med Wewn. 120:334, 2010). Patients that lack Factor XI because of a genetic Factor XI deficiency exhibit few, if any, ischemic strokes (Salomon et al., Blood, 111: 4113, 2008). At the same time, loss of Factor XIa activity, which leaves one of the pathways that initiate coagulation intact, does not disrupt hemostasis. In humans, Factor XI deficiency can result in a mild-to-moderate bleeding disorder, especially in tissues with high levels of local fibrinolytic activity, such as the urinary tract, nose, oral cavity, and tonsils. Moreover, hemostasis is nearly normal in Factor XI-deficient mice (Gailani, Blood Coagul Fibrinolysis, 8:134, 1997). Furthermore, inhibition of Factor XI has also been found to attenuate arterial hypertension and other diseases and dysfunctions, including vascular inflammation (Kossmann et al. Sci. Transl. Med. 9, eaah4923 (2017)).

Consequently, compounds that inhibit Factor XIa have the potential to prevent or treat a wide range of disorders while avoiding the side effects and therapeutic challenges that plague drugs that inhibit other components of the coagulation pathway. Moreover, due to the limited efficacy and adverse side effects of some current therapeutics for the inhibition of undesirable thrombosis (e.g., deep vein thrombosis, hepatic vein thrombosis, and stroke), improved compounds and methods (e.g., those associated with Factor XIa) are needed for preventing or treating undesirable thrombosis.

Another therapeutic target is the enzyme kallikrein. Human plasma kallikrein is a serine protease that may be responsible for activating several downstream factors (e.g., bradykinin and plasmin) that are critical for coagulation and control of e.g., blood pressure, inflammation, and pain. Kallikreins are expressed e.g., in the prostate, epidermis, and the central nervous system (CNS) and may participate in e.g., the regulation of semen liquefaction, cleavage of cellular adhesion proteins, and neuronal plasticity in the CNS. Moreover, kallikreins may be involved in tumorigenesis and the development of cancer and angioedema, e.g., hereditary angioedema. Overactivation of the kallikrein-kinin pathway can result in a number of disorders, including angioedema, e.g., hereditary angioedema (Schneider et al., J. Allergy Clin. Immunol. 120:2, 416, 2007). To date, there are limited treatment options for HAE (e.g., WO2003/076458). As such, therapeutics are needed for preventing or treating these diseases.

SUMMARY OF THE INVENTION

The present invention features compounds that inhibit Factor XIa or kallikrein and methods for preventing or treating undesired thrombosis or angiodema (e.g., hereditary angiodema) by administering one or more of these compounds alone or in combination with other molecules to a mammal. The invention also provides methods for designing or selecting additional Factor XIa or kallikrein inhibitors using these structures. Desirably, these compounds have certain structural, physical, and spatial characteristics that enable the compounds to interact with specific residues of the active site of Factor XIa or kallikrein.

In one aspect, the present invention is directed to a compound of formula (II):

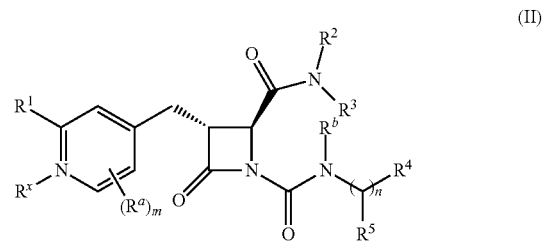

(II)

or a pharmaceutically acceptable salt thereof, wherein $R^1$ is hydrogen or $-NR^8R^9$; $R^a$ is $C_{1-6}$ alkyl, $C_{1-6}$ haloalkyl, halo, cyano, or $-OR^6$; $R^b$ is hydrogen or $C_{1-6}$ alkyl; $R^2$ is optionally substituted 5-membered heteroaryl or optionally substituted 5-membered heterocylyl; $R^3$ is hydrogen, $C_{1-6}$ alkyl, or $C_{1-6}$ haloalkyl; $R^4$ is $C_{1-6}$ alkyl, $C_{1-6}$ haloalkyl, cycloalkyl, heterocyclyl, aryl, or heteroaryl, wherein the cycloalkyl, heterocyclyl, aryl, or heteroaryl is optionally substituted with one, two, or three independent occurrences of halo, $C_{1-6}$ alkyl, $C_{1-6}$ haloalkyl, cyano, or —$OR^6$; $R^5$ is hydrogen, $C_{1-6}$ alkyl, $C_{1-6}$ haloalkyl, cycloalkyl, or aryl, wherein the cycloalkyl or aryl is optionally substituted with one, two, or three independent occurrences of halo, $C_{1-6}$ alkyl, $C_{1-6}$ haloalkyl, cyano, or —$OR^6$ or $R^4$ and $R^5$, taken together with the carbon atom to which they are attached form a ring; $R^6$ is hydrogen, $C_{1-6}$ alkyl, or $C_{1-6}$ haloalkyl; each $R^8$ and $R^9$ is independently hydrogen, $C_{1-6}$ alkyl, —$C(O)R^{10}$, or —$C(O)OR^{10}$; $R^{10}$ is $C_{1-6}$ alkyl or $C_{1-6}$ haloalkyl; $R^x$ is —O or absent, wherein when $R^x$ is —O, the nitrogen atom of the pyridyl ring is positively charged and $R^x$ is negatively charged, thereby forming a pyridyl N-oxide; m is 0, 1, 2, or, 3; and n is 0 or 1, wherein if n is 0, then $R^5$ is hydrogen and $R^4$ is absent.

In one aspect, described herein is a compound of formula (II):

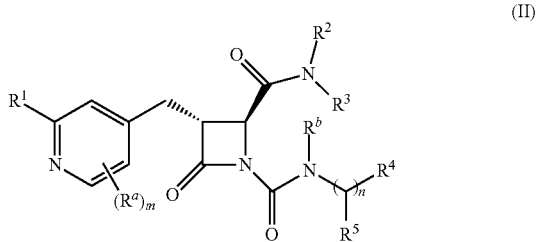

(II)

or a pharmaceutically acceptable salt thereof, wherein $R^1$ is hydrogen or —$NR^8R^9$; $R^a$ is $C_{1-6}$ alkyl, $C_{1-6}$ haloalkyl, halo, cyano, or —$OR^6$; $R^b$ is hydrogen or $C_{1-6}$ alkyl; $R^2$ is optionally substituted 5-membered heteroaryl; $R^3$ is hydrogen, $C_{1-6}$ alkyl, or $C_{1-6}$ haloalkyl; $R^4$ is $C_{1-6}$ alkyl, $C_{1-6}$ haloalkyl, cycloalkyl, heterocyclyl, aryl, or heteroaryl, wherein the cycloalkyl, heterocyclyl, aryl, or heteroaryl is optionally substituted with one, two, or three independent occurrences of halo, $C_{1-6}$ alkyl, $C_{1-6}$ haloalkyl, cyano, or —$OR^6$; $R^5$ is hydrogen, $C_{1-6}$ alkyl, $C_{1-6}$ haloalkyl, cycloalkyl, or aryl, wherein the cycloalkyl or aryl is optionally substituted with one, two, or three independent occurrences of halo, $C_{1-6}$ alkyl, $C_{1-6}$ haloalkyl, cyano, or —$OR^6$, or $R^4$ and $R^5$, taken together with the carbon atom to which they are attached form a ring; $R^6$ is hydrogen, $C_{1-6}$ alkyl, or $C_{1-6}$ haloalkyl; each $R^8$ and $R^9$ is independently hydrogen, $C_{1-6}$ alkyl, —$C(O)R^{10}$, or —$C(O)OR^{10}$; $R^{10}$ is $C_{1-6}$ alkyl or $C_{1-6}$ haloalkyl; m is 0, 1, 2, or 3; and n is 0 or 1, wherein if n is 0, then $R^5$ is hydrogen and $R^4$ is absent.

In some embodiments, the compound is a compound of Formula (I):

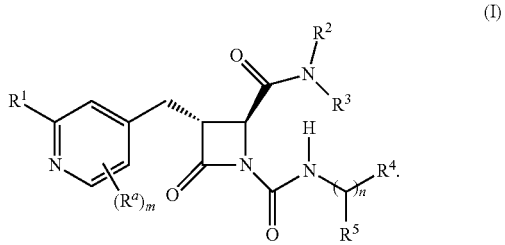

(I)

In some embodiments, $R^6$ is $C_{1-6}$ alkyl or $C_{1-6}$ haloalkyl. In some embodiments, $R^6$ is —$CH_3$ or —$CF_3$.

In some embodiments, $R^1$ is hydrogen, —$NH_2$, or —$NHCH_3$.

In some embodiments, $R^2$ is 5-membered heteroaryl optionally substituted with one or two independent occurrences of $C_{1-6}$ alkyl. In some embodiments, $R^2$ is pyrazolyl, imidazolyl, thienyl, isothiazolyl, or thiazolyl, wherein the imidazolyl, thienyl, isothiazolyl, or thiazolyl is optionally substituted with one or two independent occurrences of $C_{1-6}$ alkyl. In some embodiments, $R^2$ is pyrazolyl, imidazolyl, thienyl, isothiazolyl, or thiazolyl, wherein the imidazolyl, thienyl, isothiazolyl, or thiazolyl is optionally substituted with one or two occurrences of —$CH_3$.

In some embodiments, $R^2$ is

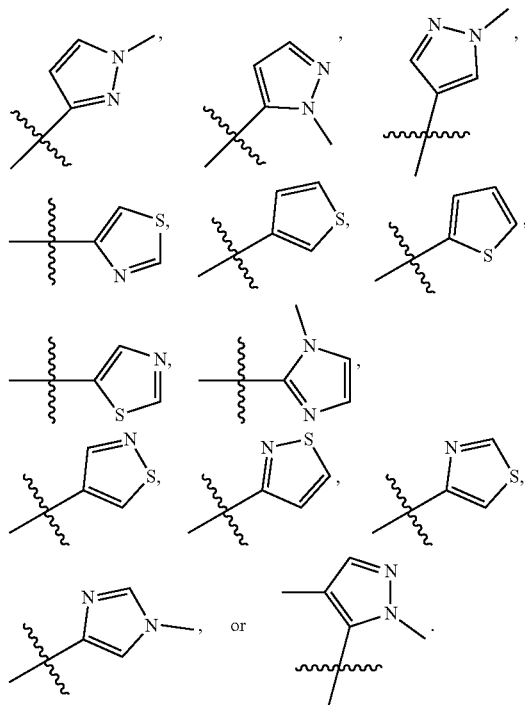

In some embodiments, $R^3$ is —$CH_3$.

In some embodiments, $R^4$ is $C_{1-6}$ alkyl, cycloalkyl, aryl, or heteroaryl, wherein the cycloalkyl, aryl, or heteroaryl is optionally substituted with one, two, or three independent occurrences of halo or $C_{1-6}$ alkyl. In some embodiments, $R^4$ is cyclohexyl, cylcopropyl, phenyl, pyridyl, pyrazolyl, thienyl, or $C_{1-6}$ alkyl, wherein the cyclohexyl, cylcopropyl, phenyl, pyridyl, pyrazolyl, or thienyl is optionally substituted with one, two, or three independent occurrences of halo or $C_{1-6}$ alkyl. In some embodiments, $R^4$ is cyclohexyl, phenyl, pyridyl, pyrazolyl, or thienyl, wherein the cyclohexyl, phenyl, pyridyl, pyrazolyl, or thienyl is optionally substituted with one, two, or three independent occurrences of halo or $C_{1-6}$ alkyl. In some embodiments, $R^4$ is phenyl optionally substituted with one, two, or three occurrences of —F, —Cl, or $C_{1-6}$ alkyl.

In some embodiments, $R^5$ is hydrogen, —$CH_3$, —$CH_2CH_3$, —$CH_2C_2CH_3$, —$CH(CH_3)_2$, —$CH_2CH_2CH_2CH_3$, —$CF_3$, or unsubstituted cyclopropyl. In some embodiments, $R^5$ is —$CH_2CH_3$, —$CF_3$, or unsubstituted cyclopropyl.

In some embodiments, $R^4$ is $C_{1-6}$ alkyl, $C_{1-6}$ haloalkyl, cycloalkyl, heterocyclyl, aryl, or heteroaryl, wherein the cycloalkyl, heterocyclyl, aryl, or heteroaryl is optionally substituted with one, two, or three independent occurrences of halo, $C_{1-6}$ alkyl, $C_{1-6}$ haloalkyl, cyano, or $-OR^6$ and $R^5$ is hydrogen, $C_{1-6}$ alkyl, $C_{1-6}$ haloalkyl, cycloalkyl, or aryl, wherein the cycloalkyl or aryl is optionally substituted with one, two, or three independent occurrences of halo, $C_{1-6}$ alkyl, $C_{1-6}$ haloalkyl, or $-OR^6$ or $R^4$ and $R^5$, taken together with the carbon atom to which they are attached form a ring.

In some embodiments, the compound is a compound of formula (I-a):

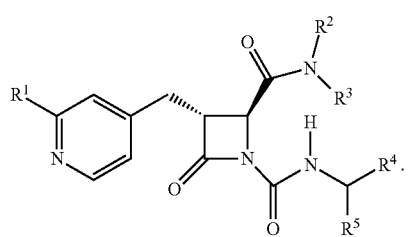

(I-a)

In some embodiments, the compound is a compound of formula (I-b):

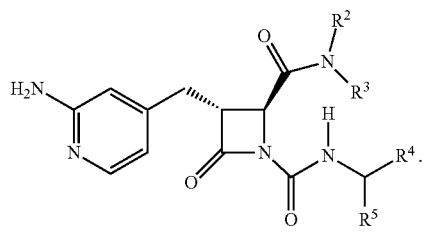

(I-b)

In some embodiments, the compound is a compound of formula (I-c), formula (I-d), formula (I-e), formula (I-f), formula (I-g), formula (I-i), or formula (I-j):

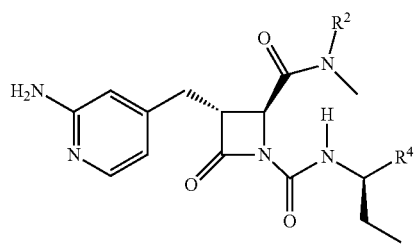

(I-c)

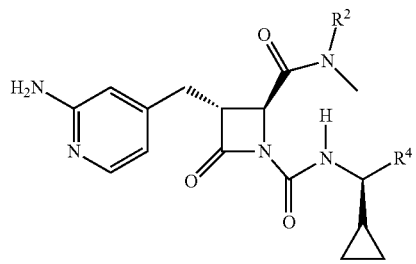

(I-d)

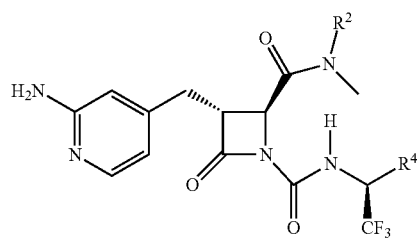

(I-e)

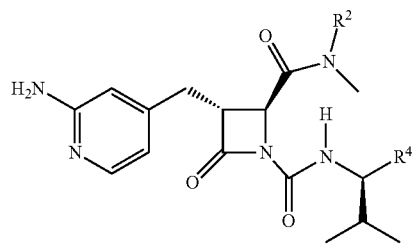

(I-f)

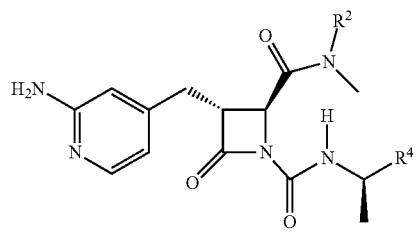

(I-g)

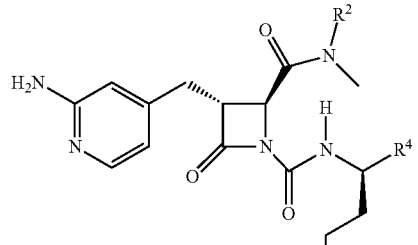

(I-h)

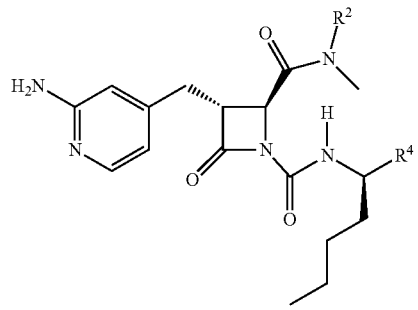

(I-i)

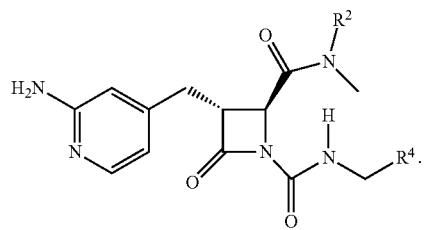

(I-j)

In some embodiments, the compound is a compound of formula (I-c):

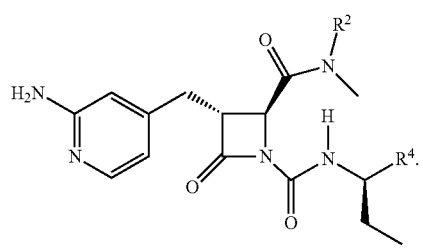
(I-c)

In some embodiments, the compound is a compound of formula (I-e), formula (I-k), formula (I-l), formula (I-m), formula (I-o), or formula (I-p):

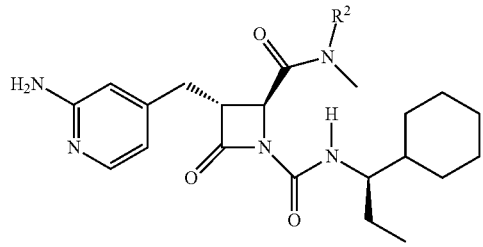
(I-k)

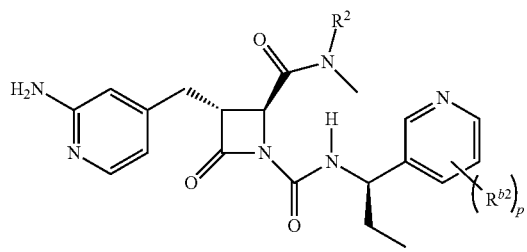
(I-l)

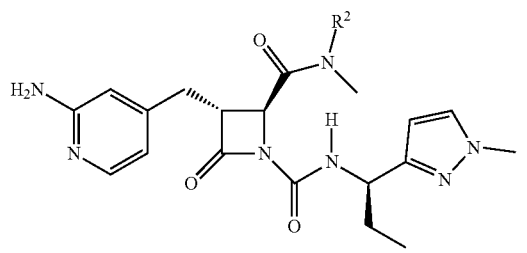
(I-m)

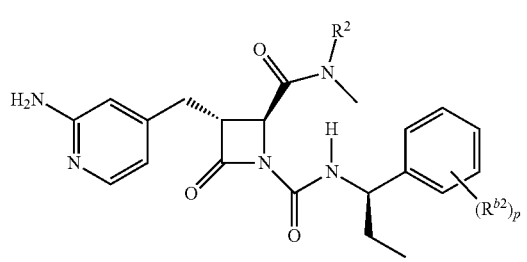
(I-n)

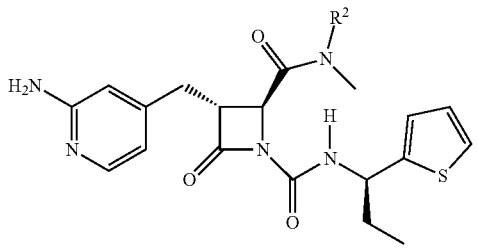
(I-o)

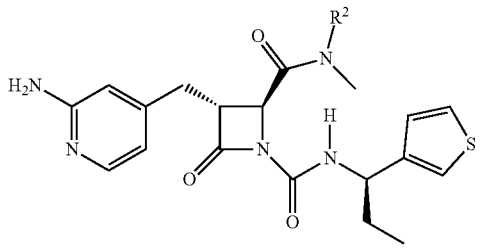
(I-p)

wherein each of $R^{b2}$ is independently halo, $C_{1-6}$ alkyl, $C_{1-6}$ haloalkyl, cyano, or —$OR^6$; and p is 0, 1, 2, or 3. In some embodiments, $R^a$ is —$C_{1-6}$ alkyl.

In some embodiments, $R^a$ is —$CH_3$. In some embodiments, $R^a$ is —$CH_3$ and m is 1. In some embodiments, m is 1. In some embodiments, $R^b$ is $C_{1-6}$ alkyl. In some embodiments, $R^b$ is —$CH_3$.

In some embodiments, the compound is a compound selected from a compound listed in Table 1.

In some embodiments, the compound is a pharmaceutically acceptable salt (e.g., a hydrochloride (HCl), hydrobromide (HBr), tartrate, oleate, or citrate salt). In a preferred embodiment, the pharmaceutically acceptable salt is a hydrochloride (HCl) salt.

In one aspect, the present invention is directed to a pharmaceutical composition comprising a compound of formula (II) or a pharmaceutically acceptable salt thereof and one or more pharmaceutically acceptable excipients. In some embodiments, the composition is provided as a liquid formulation (e.g., a solution). In some embodiments, the composition is provided as a solid formulation (e.g., a capsule, pill, tablet, or powder).

In one aspect, the present invention is directed to a method of reducing the risk of stroke (e.g., ischemia, e.g., a transient ischemic event) in a subject that has suffered an ischemic event (e.g., a transient ischemic event), comprising administering to the subject an effective amount of a compound of formula (II) or a pharmaceutically acceptable salt thereof, or of a composition described herein (e.g., a composition comprising a compound of formula (II)). In some embodiments, the administering reduces the risk of stroke in a subject as compared to a subject who is not administered with the compound. In some embodiments, the administering reduces the risk of atrial fibrillation in a subject as compared to a subject who is not administered with the compound.

In one aspect, the present invention is directed to a method of reducing non-central nervous system systemic embolism (e.g., ischemia, e.g., a transient ischemic event) in a subject that has suffered an ischemic event (e.g., a transient ischemic event), comprising administering to the subject an effective amount of a compound of formula (II) or a pharmaceutically acceptable salt thereof, or of a composition described herein (e.g., a composition comprising a compound of formula (II)). In some embodiments, the administering reduces non-central nervous system systemic embolism in a subject as compared to a subject who is not administered with the compound.

In one aspect, the present invention is directed to a method of treating deep vein thrombosis comprising administering to the subject that has suffered an ischemic event (e.g., a transient ischemic event), an effective amount of a compound of formula (II) or a pharmaceutically acceptable salt thereof, or of a composition described herein (e.g., a composition comprising a compound of formula (II)).

In an aspect, provided herein is a method of treating acute coronary syndrome in a subject, comprising administering to a subject in need thereof a compound described herein, e.g., a compound of formula (II) or a pharmaceutically acceptable salt thereof, or a composition described herein, e.g., a composition comprising a compound of formula (II).

In one aspect, the present invention is directed to a method of prophylaxis of deep vein thrombosis comprising administering to the subject that has suffered a deep vein thrombosis (e.g., a subject that has been previously treated for a deep vein thrombosis), an effective amount of a compound of formula (II) or a pharmaceutically acceptable salt thereof, or of a composition described herein (e.g., a composition comprising a compound of formula (II)). In one aspect, the present invention is directed to a method of reducing the risk of recurrence of deep vein thrombosis comprising administering to the subject that has suffered a deep vein thrombosis (e.g., a subject that has been previously treated for a deep vein thrombosis), an effective amount of a compound of formula (II) or a pharmaceutically acceptable salt thereof, or of a composition described herein (e.g., a composition comprising a compound of formula (II)). In some embodiments, the administering reduces the risk of recurrence of deep vein thrombosis in a subject as compared to a subject who is not administered with the compound.

In one aspect, the present invention is directed to a method of prophylaxis of venous thromboembolism, e.g., deep vein thrombosis or pulmonary embolism in a subject, comprising administering to the subject an effective amount of a compound of formula (II) or a pharmaceutically acceptable salt thereof, or of a composition described herein (e.g., a composition comprising a compound of formula (II)). In some embodiments, the subject is undergoing surgery. In some embodiments, the subject is administered the compound, pharmaceutically acceptable salt thereof, or composition thereof before, during, or after surgery. In some embodiments, the subject is undergoing knee or hip replacement surgery. In some embodiments, the subject is undergoing orthopedic surgery. In some embodiments, the subject is undergoing lung surgery. In some embodiments, the subject is being treated for cancer, e.g., by surgery. In some embodiments, the subject is suffering from a chronic medical condition. In some embodiments, the venous thromboembolism is associated with cancer. In some embodiments, the compound, pharmaceutically acceptable salt thereof, or composition described herein is a primary agent in prophylaxis of the deep vein thrombosis or venous thromboembolism. In some embodiments, the compound, pharmaceutically acceptable salt thereof, or composition described herein is used as an extended therapy. In one aspect, the present invention is directed to a method of reducing the risk of venous thromboembolism, e.g., deep vein thrombosis or pulmonary embolism, in a subject, comprising administering to the subject an effective amount of a compound of formula (II) or a pharmaceutically acceptable salt thereof, or of a composition described herein (e.g., a composition comprising a compound of formula (II)). In some embodiments, the subject is undergoing surgery. In some embodiments, the subject is administered the compound, pharmaceutically acceptable salt thereof, or composition thereof after surgery. In some embodiments, the subject is undergoing knee or hip replacement surgery. In some embodiments, the subject is undergoing orthopedic surgery. In some embodiments, the subject is undergoing lung surgery. In some embodiments, the subject is being treated for cancer, e.g., by surgery. In some embodiments, the subject is suffering from a chronic medical condition. In some embodiments, the thromboembolic disorder is associated with cancer. In some embodiments, the compound, pharmaceutically acceptable salt thereof, or composition described herein is a primary agent in reducing the risk of the thromboembolic disorder. In some embodiments, the compound, pharmaceutically acceptable salt thereof, or composition described herein is used as an extended therapy.

In one aspect, the present invention is directed to a method of reducing the risk of stroke or systemic embolism in a subject in need thereof, comprising administering to the subject an effective amount of a compound described herein, e.g, a compound of formula (II), or a pharmaceutically acceptable salt thereof, or a composition described herein, e.g., a composition comprising a compound of formula (II). In some embodiments, the subject is suffering from atrial fibrillation (e.g., non-valvular atrial fibrillation). In some embodiments, the subject is suffering from a renal disorder (e.g., end-stage renal disease).

In one aspect, the present invention is directed to a method of prophylaxis of stroke or systemic embolism in a subject in need thereof, comprising administering to the subject an effective amount of a compound described herein, e.g, a compound of formula (II), or a pharmaceutically acceptable salt thereof, or a composition described herein, e.g., a composition comprising a compound of formula (II). In some embodiments, the subject is suffering from atrial fibrillation (e.g., non-valvular atrial fibrillation). In some embodiments, the subject is suffering from a renal disorder (e.g., end-stage renal disease).

In one aspect, the present invention is directed to a method of reducing the risk of recurrence of pulmonary embolism (e.g., symptomatic pulmonary embolism) comprising administering to the subject that has suffered a pulmonary embolism (e.g., a subject that has been previously treated for a pulmonary embolism), an effective amount of a compound of formula (II) or a pharmaceutically acceptable salt thereof, or of a composition described herein (e.g., a composition comprising a compound of formula (II)). In some embodiments, the administering reduces the risk of recurrence of pulmonary embolism in a subject as compared to a subject who is not administered with the compound.

In one aspect, the present invention is directed to a method of prophylaxis of pulmonary embolism in a subject that has suffered a pulmonary embolism (e.g., a subject that has been previously treated for a pulmonary embolism), comprising administering to the subject an effective amount of a compound of formula (II) or a pharmaceutically acceptable salt thereof, or of a composition described herein (e.g., a composition comprising a compound of formula (II)).

In one aspect, the present invention is directed to a method of reducing the risk of recurrence of pulmonary embolism (e.g., symptomatic pulmonary embolism) comprising administering to the subject that has suffered a deep vein thrombosis (e.g., a subject that has been previously treated for a deep vein thrombosis), an effective amount of a compound of formula (II) or a pharmaceutically acceptable salt thereof, or of a composition described herein (e.g., a composition comprising a compound of formula (II)). In some embodiments, the administering reduces the risk of recurrence of pulmonary embolism in a subject as compared to a subject who is not administered with the compound.

In one aspect, the present invention is directed to a method of prophylaxis of pulmonary embolism in a subject that has suffered a deep vein thrombosis (e.g., a subject that has been previously treated for a deep vein thrombosis), comprising administering to the subject an effective amount of a compound of formula (II) or a pharmaceutically acceptable salt thereof, or of a composition described herein (e.g., a composition comprising a compound of formula (II)).

In an aspect, provided herein is a method of treating pulmonary embolism in a subject that has suffered deep vein thrombosis, comprising administering to a subject an effective amount of a compound described herein, e.g., a compound of formula (II) or a pharmaceutically acceptable salt thereof, or a composition described herein, e.g., a composition comprising a compound of formula (II).

In one aspect, the present invention features a method of treating deep vein thrombosis in a subject that has been previously administered an anticoagulant, comprising administering to the subject an effective amount of a compound of formula (II) or a pharmaceutically acceptable salt thereof, or of a composition described herein (e.g., a composition comprising a compound of formula (II)). In some embodiments, the anticoagulant was administered parenterally for 5-10 days.

In one aspect, the present invention features a method of treating a pulmonary embolism in a subject that has been previously administered an anticoagulant, comprising administering to the subject an effective amount of a compound of formula (II) or a pharmaceutically acceptable salt thereof, or of a composition described herein (e.g., a composition comprising a compound of formula (II)). In some embodiments, the anticoagulant was administered parenterally for 5-10 days.

In one aspect, the present invention is directed to a method of treating a subject that has had an ischemic event (e.g., transient ischemia), comprising: administering a compound of formula (II) or a pharmaceutically acceptable salt thereof, or of a composition described herein (e.g., a composition comprising a compound of formula (II)) to the subject. In some embodiments, the compound is administered to the subject within 24 hours or less, e.g., 12, 10, 9, 8, 7, 6 hours or less, after the onset of the ischemic event in the subject.

In one aspect, the present invention is directed to a method of treating a subject that has had an ischemic event (e.g., transient ischemia), comprising: administering a compound of formula (II) or a pharmaceutically acceptable salt thereof, or of a composition described herein (e.g., a composition comprising a compound of formula (II)) to the subject. In some embodiments, the compound is administered to the subject within more than 2 hours to 12 hours, e.g., more than 2 hours to 10 hours or less, more than 2 hours to 8 hours or less, after the onset of the ischemic event in the subject.

In one aspect, the present invention is directed to a method of treating hypertension, e.g., arterial hypertension, in a subject, comprising administering to the subject an effective amount of a compound of formula (II) or a pharmaceutically acceptable salt thereof, or of a composition described herein (e.g., a composition comprising a compound of formula (II)). In some embodiments, the hypertension, e.g., arterial hypertension, results in atherosclerosis. In some embodiments, the hypertension is pulmonary arterial hypertension.

In one aspect, the present invention is directed to a method of reducing the risk of hypertension, e.g., arterial hypertension, in a subject, comprising administering to the subject an effective amount of a compound of formula (II) or a pharmaceutically acceptable salt thereof, or of a composition described herein (e.g., a composition comprising a compound of formula (II)). In some embodiments, the hypertension, e.g., arterial hypertension, results in atherosclerosis. In some embodiments, the hypertension is pulmonary arterial hypertension.

In one aspect, the present invention is directed to a method of prophylaxis of hypertension, e.g., arterial hypertension, in a subject, comprising administering to the subject an effective amount of a compound of formula (II) or a pharmaceutically acceptable salt thereof, or of a composition described herein (e.g., a composition comprising a compound of formula (II)). In some embodiments, the hypertension, e.g., arterial hypertension, results in atherosclerosis. In some embodiments, the hypertension is pulmonary arterial hypertension.

In one aspect, the present invention is directed to a method of reducing inflammation in a subject, comprising administering to the subject an effective amount of a compound of formula (II) or a pharmaceutically acceptable salt thereof, or of a composition described herein (e.g., a composition comprising a compound of formula (II)). In some embodiments, the inflammation is vascular inflammation. In some embodiments, the vascular inflammation is accompanied by atherosclerosis. In some embodiments, the vascular inflammation is accompanied by a thromboembolic disease in the subject. In some embodiments, the vascular inflammation is angiotensin II-induced vascular inflammation.

In one aspect, the present invention is directed to a method of preventing vascular leukocyte infiltration in a subject, comprising administering to the subject an effective amount of a compound of formula (II) or a pharmaceutically acceptable salt thereof, or of a composition described herein (e.g., a composition comprising a compound of formula (II)).

In one aspect, the present invention is directed to a method of preventing angiotensin II-induced endothelial dysfunction in a subject, comprising administering to the subject an effective amount of a compound of formula (II) or a pharmaceutically acceptable salt thereof, or of a composition described herein (e.g., a composition comprising a compound of formula (II)).

In one aspect, the present invention is directed to a method of preventing thrombin propagation in a subject, comprising administering to the subject an effective amount of a compound of formula (II) or a pharmaceutically acceptable salt thereof, or of a composition described herein (e.g., a composition comprising a compound of formula (II)). In some embodiments, the thrombin propagation occurs on platelets.

In one aspect, the present invention is directed to a method of treating hypertension-associated renal dysfunction in a subject, comprising administering to the subject an effective amount of a compound of formula (II) or a pharmaceutically acceptable salt thereof, or of a composition described herein (e.g., a composition comprising a compound of formula (II)).

In one aspect, the present invention is directed to a method of prophylaxis of hypertension-associated renal dysfunction in a subject, comprising administering to the subject an effective amount of a compound of formula (II) or a pharmaceutically acceptable salt thereof, or of a composition described herein (e.g., a composition comprising a compound of formula (II)).

In one aspect, the present invention is directed to a method of reducing the risk of hypertension-associated renal dysfunction in a subject, comprising administering to the subject an effective amount of a compound of formula (II) or a pharmaceutically acceptable salt thereof, or of a composition described herein (e.g., a composition comprising a compound of formula (II)).

In one aspect, the present invention is directed to a method of treating kidney fibrosis in a subject, comprising administering to the subject an effective amount of a compound of formula (II) or a pharmaceutically acceptable salt thereof, or of a composition described herein (e.g., a composition comprising a compound of formula (II)).

In one aspect, the present invention is directed to a method of prophylaxis of kidney fibrosis in a subject, comprising administering to the subject an effective amount of a compound of formula (II) or a pharmaceutically acceptable salt thereof, or of a composition described herein (e.g., a composition comprising a compound of formula (II)).

In one aspect, the present invention is directed to a method of reducing the risk of kidney fibrosis in a subject, comprising administering to the subject an effective amount of a compound of formula (II) or a pharmaceutically acceptable salt thereof, or of a composition described herein (e.g., a composition comprising a compound of formula (II)).

In one aspect, the present invention is directed to a method of treating kidney injury in a subject, comprising administering to the subject an effective amount of a compound of formula (II) or a pharmaceutically acceptable salt thereof, or of a composition described herein (e.g., a composition comprising a compound of formula (II)).

In one aspect, the present invention is directed to a method of prophylaxis of kidney injury in a subject, comprising administering to the subject an effective amount of a compound of formula (II) or a pharmaceutically acceptable salt thereof, or of a composition described herein (e.g., a composition comprising a compound of formula (II)).

In one aspect, the present invention is directed to a method of reducing the risk of kidney injury in a subject, comprising administering to the subject an effective amount of a compound of formula (II) or a pharmaceutically acceptable salt thereof, or of a composition described herein (e.g., a composition comprising a compound of formula (II)). In one aspect, the present invention is directed to a method of inhibiting Factor XIa in a subject, comprising administering to the subject that has suffered ischemia an effective amount of a compound of formula (II) or a pharmaceutically acceptable salt thereof, or of a composition described herein (e.g., a composition comprising a compound of formula (II)). In some embodiments, the ischemia is coronary ischemia. In some embodiments, the subject is a mammal (e.g., a human). In some embodiments, the subject is undergoing surgery (e.g., knee replacement surgery or hip replacement surgery). In some embodiments, the ischemia is coronary ischemia. In some embodiments, the subject is a subject with non-valvular atrial fibrillation. In some embodiments, the subject has one or more of the following risk factors for stroke: a prior stroke (e.g., ischemic, unknown, hemorrhagic), transient ischemic attack, or non-CNS systemic embolism. In some embodiments, the subject has one or more of the following risk factors for stroke: 75 years or older of age, hypertension, heart failure or left ventricular ejection fraction (e.g., less than or equal to 35%), or diabetes mellitus.

In some embodiments, the compound is administered by oral or parenteral (e.g., intravenous) administration. In some embodiments, the compound is administered by oral administration.

In some embodiments, the compound is administered prior to an ischemic event (e.g., to a subject is at risk of an ischemic event).

In some embodiments, the compound is administered after an ischemic event (e.g., a transient ischemic event). In some embodiments, the compound is administered about 1, 2, 3, 4, 5, 6, 7, 8, 9, 10, 11, 12, 13, or 14 days or more after an ischemic event (e.g., a transient ischemic event). In some embodiments, the compound is administered about 1, 2, 3, 4, 5, 6, 7, or 8 weeks or more after an ischemic event (e.g., a transient ischemic event).

In some embodiments, the compound is administered in combination with an additional therapeutic agent. In some embodiments, the additional therapeutic agent is administered after administration of the compound. In some embodiments, the additional therapeutic agent is administered orally. In some embodiments, the additional therapeutic agent is administered at least 1, 2, 3, 4, 5, 6, 7, 8, 10, 12, 14, 16, 18, 20, or 24 hours or more after administration of the compound. In some embodiments, the additional therapeutic agent is administered at least 1, 2, 3, 4, 5, 6, 7, 14, 21, or 28 days or more after administration of the compound. In some embodiments, the additional therapeutic agent is administered about 1 day, about 2 days, about 3 days, about 4 days, about 5 days, about 6 days, about 7 days or more after administration of the compound.

In some embodiments, the additional therapeutic agent is administered chronically (e.g., for about 1 day, about 2 days, about 3 days, about 4 days, about 5 days, about 6 days, about 7 days, about 8 days, about 9 days, about 10 days, about 11 days, about 12 days, about 13 days, or about 14 days or more) after administration of the compound.

In some embodiments, the additional therapeutic agent treats a side effect (e.g., active pathological bleeding or severe hypersensitivity reactions (e.g., anaphylactic reactions), spinal and or epidural hematoma, gastrointestinal disorder (e.g., abdominal pain upper, dyspepsia, toothache), general disorders and administration site conditions (e.g., fatigue), infections and infestations (e.g., sinusitis, urinary tract infection), musculoskeletal and connective tissues disorders (e.g., back pain, osteoarthritis), respiratory, thoracic and mediastinal disorders (e.g., oropharyngeal pain), injury, poisoning, and procedural complications (e.g., wound secretion), musculoskeletal and connective tissues disorders (e.g., pain in extremity, muscle spasm), nervous system disorders (e.g., syncope), skin and subcutaneous tissue disorders (e.g., pruritus, blister), blood and lymphatic system disorders (e.g., agranulocytosis), gastrointestinal disorders (e.g., retroperitoneal hemorrhage), hepatobiliary disorders (e.g., jaundice, cholestasis, cytolytic hepatitis), immune system disorders (e.g., hypersensitivity, anaphylactic reaction, anaphylactic shock, angioedema), nervous system disorders (e.g., cerebral hemorrhage, subdural hematoma, epidural hematoma, hemiparesis), skin and subcutaneous tissue disorders (e.g., Stevens-Johnson syndrome).

In some embodiments, the additional therapeutic agent is a NSAID (e.g., aspirin or naproxen), platelet aggregation inhibitor (e.g., clopidogrel), or anticoagulant (e.g., warfarin or enoxaparin).

In some embodiments, the additional therapeutic agent results in an additive therapeutic effect. In some embodiments, the additional therapeutic agent results in a synergistic therapeutic effect.

In another aspect, the present invention features a pharmaceutical composition comprising a compound described herein (e.g., a compound of formula (II)) and a pharmaceutically acceptable excipient.

In another aspect, the present invention features a method of modulating (e.g., inhibiting) Factor XIa in a patient. The method comprises the step of administering an effective amount of a compound described herein (e.g., a compound of formula (II)) or a pharmaceutically acceptable salt thereof, or of a composition described herein (e.g., a composition comprising a compound of formula (II)) to a patient in need thereof, thereby modulating (e.g., inhibiting) Factor XIa.

In another aspect, the present invention features a method of treating a subj ect in need thereof for a thromboembolic disorder. The method comprises administering to the subject an effective amount of a compound described herein (e.g., a compound of formula (II)) or a pharmaceutically acceptable salt thereof, or of a composition described herein (e.g., a composition comprising a compound of formula (II)). The thromboembolic disorder can be arterial cardiovascular thromboembolic disorders, arterial thrombosis, venous cardiovascular thromboembolic disorders, and thromboembolic disorders in the chambers of the heart; including unstable angina, an acute coronary syndrome, first myocardial infarction, recurrent myocardial infarction, ischemia (e.g., coronary ischemia, ischemic sudden death, or transient ischemic attack), stroke, atherosclerosis, peripheral occlusive arterial disease, venous thromboembolism, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from (a) prosthetic valves or other implants, (b) indwelling catheters, (c) stents, (d) cardiopulmonary bypass, (e) hemodialysis, or (f) other procedures in which blood is exposed to an artificial surface that promotes thrombosis.

In another aspect, the present invention features a method of prophylaxis of a thromboembolic disorder in a subject. The method comprises administering to the subject an effective amount of a compound described herein (e.g., a compound of formula (II)) or a pharmaceutically acceptable salt thereof, or of a composition described herein (e.g., a composition comprising a compound of formula (II)). The thromboembolic disorder can be arterial cardiovascular thromboembolic disorders, arterial thrombosis, venous cardiovascular thromboembolic disorders, and thromboembolic disorders in the chambers of the heart; including unstable angina, an acute coronary syndrome, first myocardial infarction, recurrent myocardial infarction, ischemia (e.g., coronary ischemia, ischemic sudden death, or transient ischemic attack), stroke, atherosclerosis, peripheral occlusive arterial disease, venous thromboembolism, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from (a) prosthetic valves or other implants, (b) indwelling catheters, (c) stents, (d) cardiopulmonary bypass, (e) hemodialysis, or (f) other procedures in which blood is exposed to an artificial surface that promotes thrombosis.

In another aspect, the present invention features a method of reducing the risk of a thromboembolic disorder in a subject. The method comprises administering to the subject an effective amount of a compound described herein (e.g., a compound of formula (II)) or a pharmaceutically acceptable salt thereof, or of a composition described herein (e.g., a composition comprising a compound of formula (II)). The thromboembolic disorder can be arterial cardiovascular thromboembolic disorders, arterial thrombosis, venous cardiovascular thromboembolic disorders, and thromboembolic disorders in the chambers of the heart; including unstable angina, an acute coronary syndrome, first myocardial infarction, recurrent myocardial infarction, ischemia (e.g., coronary ischemia, ischemic sudden death, or transient ischemic attack), stroke, atherosclerosis, peripheral occlusive arterial disease, venous thromboembolism, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from (a) prosthetic valves or other implants, (b) indwelling catheters, (c) stents, (d) cardiopulmonary bypass, (e) hemodialysis, or (f) other procedures in which blood is exposed to an artificial surface that promotes thrombosis.

In one aspect, the present invention is directed to a method of treating end-stage renal disease in a subject, comprising administering to the subject an effective amount of a compound of formula (II) or a pharmaceutically acceptable salt thereof, or of a composition described herein (e.g., a composition comprising a compound of formula (II)).

In one aspect, the present invention is directed to a method of prophylaxis of end-stage renal disease in a subject, comprising administering to the subject an effective amount of a compound of formula (II) or a pharmaceutically acceptable salt thereof, or of a composition described herein (e.g., a composition comprising a compound of formula (II)).

In one aspect, the present invention is directed to a method of reducing the risk of end-stage renal disease in a subject, comprising administering to the subject an effective amount of a compound of formula (II) or a pharmaceutically acceptable salt thereof, or of a composition described herein (e.g., a composition comprising a compound of formula (II)).

In another aspect, the present invention features a method of treating a thromboembolic disorder in a subject need thereof, the method comprising administering to the subject an effective amount of a compound described herein (e.g., a compound of formula (II)) or a pharmaceutically acceptable salt thereof, or of a composition described herein (e.g., a composition comprising a compound of formula (II)), wherein the subject is exposed to an artificial surface. In some embodiments, the artificial surface contacts the subject's blood. In some embodiments, the artificial surface is an extracorporeal surface. In some embodiments, the artificial surface is that of an implantable device, e.g., a mechanical valve. In some embodiments, the artificial surface is that of a dialysis catheter. In some embodiments, the artificial surface is that of a cardiopulmonary bypass circuit. In some embodiments, the artificial surface is that of an artificial heart valve. In some embodiments, the artificial surface is that of a ventricular assist device. In some embodiments, the artificial surface is that of a small caliber graft. In some embodiments, the artificial surface is that of a central venous catheter. In some embodiments, In some embodiments, the artificial surface is that of a extracorporeal membrane oxygenation (ECMO) apparatus. In some embodiments, the artificial surface causes or is associated with the thromboembolic disorder. In some embodiments, the thromboembolic disorder is a venous thromboembolism. In some embodiments, the thromboembolic disorder is deep vein thrombosis. In some embodiments, the thromboembolic disorder is pulmonary embolism.

In another aspect, the present invention features a method of reducing the risk of a thromboembolic disorder in a subject need thereof, the method comprising administering to the subject an effective amount of a compound described herein (e.g., a compound of formula (II)) or a pharmaceutically acceptable salt thereof, or of a composition described herein (e.g., a composition comprising a compound of formula (II)), wherein the subject is exposed to an artificial surface. In some embodiments, the artificial surface contacts the subject's blood. In some embodiments, the artificial surface is an extracorporeal surface. In some embodiments, the artificial surface is that of an implantable device, e.g., a mechanical valve. In some embodiments, the artificial surface is that of a dialysis catheter. In some embodiments, the artificial surface is that of a cardiopulmonary bypass circuit. In some embodiments, the artificial surface is that of an artificial heart valve. In some embodiments, the artificial surface is that of a ventricular assist device. In some embodiments, the artificial surface is that of a small caliber graft. In some embodiments, the artificial surface is that of a central venous catheter. In some embodiments, the artificial surface is that of a extracorporeal membrane oxygenation (ECMO) apparatus. In some embodiments, the artificial surface causes or is associated with the thromboembolic disorder. In some embodiments, the thromboembolic disorder is a venous thromboembolism. In some embodiments, the thromboembolic disorder is deep vein thrombosis. In some embodiments, the thromboembolic disorder is pulmonary embolism.

In another aspect, the present invention features a method of prophylaxis of a thromboembolic disorder in a subject need thereof, the method comprising administering to the subject an effective amount of a compound described herein (e.g., a compound of formula (II)) or a pharmaceutically acceptable salt thereof, or of a composition described herein (e.g., a composition comprising a compound of formula (II)), wherein the subject is exposed to an artificial surface. In some embodiments, the artificial surface contacts the subject's blood. In some embodiments, the artificial surface is an extracorporeal surface. In some embodiments, the artificial surface is that of an implantable device, e.g., a mechanical valve. In some embodiments, the artificial surface is that of a dialysis catheter. In some embodiments, the artificial surface is that of a cardiopulmonary bypass circuit. In some embodiments, the artificial surface is that of an artificial heart valve. In some embodiments, the artificial surface is that of a ventricular assist device. In some embodiments, the artificial surface is that of a small caliber graft. In some embodiments, the artificial surface is that of a central venous catheter. In some embodiments, the artificial surface is that of a extracorporeal membrane oxygenation (ECMO) apparatus. In some embodiments, the artificial surface causes or is associated with the thromboembolic disorder. In some embodiments, the thromboembolic disorder is a venous thromboembolism. In some embodiments, the thromboembolic disorder is deep vein thrombosis. In some embodiments, the thromboembolic disorder is pulmonary embolism.

In another aspect, the present invention features a method of treating atrial fibrillation, in a subject in need thereof, the method comprising administering to the subject an effective amount of a compound described herein (e.g., a compound of formula (II)) or a pharmaceutically acceptable salt thereof, or of a composition described herein (e.g., a composition comprising a compound of formula (II)). In some embodiments, the subject is also in need of dialysis, e.g., renal dialysis. In some embodiments, the compound described herein is administered to the subject while the subject is undergoing dialysis. In some embodiments, the compound or pharmaceutically acceptable salt or composition is administered to the subject before or after receiving dialysis. In some embodiments, the patient has end-stage renal disease. In some embodiments, the subject is not in need of dialysis, e.g., renal dialysis. In some embodiments, the patient is at a high risk for bleeding. In some embodiments, the atrial fibrillation is associated with another thromboembolic disorder, e.g., a blood clot.

In another aspect, the present invention features a method of reducing the risk of atrial fibrillation, in a subject in need thereof, the method comprising administering to the subject an effective amount of a compound described herein (e.g., a compound of formula (II)) or a pharmaceutically acceptable salt thereof, or of a composition described herein (e.g., a composition comprising a compound of formula (II)). In some embodiments, the subject is at a high risk of developing atrial fibrillation. In some embodiments, the subject is also in need of dialysis, e.g., renal dialysis. In some embodiments, the compound described herein is administered to the subject while the subject is undergoing dialysis. In some embodiments, the compound or pharmaceutically acceptable salt or composition is administered to the subject before or after receiving dialysis. In some embodiments, the patient has end-stage renal disease. In some embodiments, the subject is not in need of dialysis, e.g., renal dialysis. In some embodiments, the patient is at a high risk for bleeding. In some embodiments, the atrial fibrillation is associated with another thromboembolic disorder, e.g., a blood clot.

In another aspect, the present invention features a method of prophylaxis of atrial fibrillation, in a subject in need thereof, the method comprising administering to the subject an effective amount of a compound described herein (e.g., a compound of formula (II)) or a pharmaceutically acceptable salt thereof, or of a composition described herein (e.g., a composition comprising a compound of formula (II)). In some embodiments, the subject is at a high risk of developing atrial fibrillation. In some embodiments, the subject is also in need of dialysis, e.g., renal dialysis. In some embodiments, the compound described herein is administered to the subject while the subject is undergoing dialysis. In some embodiments, the compound or pharmaceutically acceptable salt or composition is administered to the subject before or after receiving dialysis. In some embodiments, the patient has end-stage renal disease. In some embodiments, the subject is not in need of dialysis, e.g., renal dialysis. In some embodiments, the patient is at a high risk for bleeding. In some embodiments, the atrial fibrillation is associated with another thromboembolic disorder, e.g., a blood clot.

In another aspect, the present invention features a method of treating heparin-induced thrombocytopenia in a subject in need thereof, the method comprising administering to the subject an effective amount of a compound described herein (e.g., a compound of formula (II)) or a pharmaceutically acceptable salt thereof, or of a composition described herein (e.g., a composition comprising a compound of formula (II)).

In another aspect, the present invention features a method of reducing the risk of heparin-induced thrombocytopenia in a subject in need thereof, the method comprising administering to the subject an effective amount of a compound described herein (e.g., a compound of formula (II)) or a pharmaceutically acceptable salt thereof, or of a composition described herein (e.g., a composition comprising a compound of formula (II)).

In another aspect, the present invention features a method of prophylaxis of heparin-induced thrombocytopenia in a subject in need thereof, the method comprising administering to the subject an effective amount of a compound described herein (e.g., a compound of formula (II)) or a pharmaceutically acceptable salt thereof, or of a composition described herein (e.g., a composition comprising a compound of formula (II)).

In another aspect, the present invention features a method of treating heparin-induced thrombocytopenia thrombosis in a subject in need thereof, the method comprising administering to the subject an effective amount of a compound described herein (e.g., a compound of formula (II)) or a pharmaceutically acceptable salt thereof, or of a composition described herein (e.g., a composition comprising a compound of formula (II)).

In another aspect, the present invention features a method of reducing the risk of heparin-induced thrombocytopenia thrombosis in a subject in need thereof, the method comprising administering to the subject an effective amount of a compound described herein (e.g., a compound of formula (II)) or a pharmaceutically acceptable salt thereof, or of a composition described herein (e.g., a composition comprising a compound of formula (II)).

In another aspect, the present invention features a method of prophylaxis of heparin-induced thrombocytopenia thrombosis in a subject in need thereof, the method comprising administering to the subject an effective amount of a compound described herein (e.g., a compound of formula (II)) or a pharmaceutically acceptable salt thereof, or of a composition described herein (e.g., a composition comprising a compound of formula (II)).

In another aspect, the present invention features a method of prophylaxis of a thromboembolic disorder in a subject in need thereof, the method comprising administering to the subject an effective amount of a compound described herein (e.g., a compound of formula (II)) or a pharmaceutically acceptable salt thereof, or of a composition described herein (e.g., a composition comprising a compound of formula (II)), wherein the subject has cancer or is being with a chemotherapeutic. In some embodiments, the subject is concurrently receiving chemotherapy. In some embodiments, the subject has elevated lactase dehydrogenase levels. In some embodiments, the thromboembolic disorder is venous thromboembolism. In some embodiments, the thromboembolic disorder is deep vein thrombosis. In some embodiments, the thromboembolic disorder is pulmonary embolism.

In another aspect, the present invention features a method of treating thrombotic microangiopathy in a subject in need thereof, the method comprising administering to the subject an effective amount of a compound described herein (e.g., a compound of formula (II)) or a pharmaceutically acceptable salt thereof, or of a composition described herein (e.g., a composition comprising a compound of formula (II)). In some embodiments, the thrombotic microangiopathy is hemolytic uremic syndrome (HUS). In some embodiments, the thrombotic microangiopathy is thrombotic thrombocytopenic purpura (TTP).

In another aspect, the present invention features a method of reducing the risk of thrombotic microangiopathy in a subject in need thereof, the method comprising administering to the subject an effective amount of a compound described herein (e.g., a compound of formula (II)) or a pharmaceutically acceptable salt thereof, or of a composition described herein (e.g., a composition comprising a compound of formula (II)). In some embodiments, the thrombotic microangiopathy is hemolytic uremic syndrome (HUS). In some embodiments, the thrombotic microangiopathy is thrombotic thrombocytopenic purpura (TTP).

In another aspect, the present invention features a method of prophylaxis of thrombotic microangiopathy in a subject in need thereof, the method comprising administering to the subject an effective amount of a compound described herein (e.g., a compound of formula (II)) or a pharmaceutically acceptable salt thereof, or of a composition described herein (e.g., a composition comprising a compound of formula (II)). In some embodiments, the thrombotic microangiopathy is hemolytic uremic syndrome (HUS). In some embodiments, the thrombotic microangiopathy is thrombotic thrombocytopenic purpura (TTP).

In another aspect, the present invention features a method of prophylaxis of recurrent ischemia in a subject in need thereof, the method comprising administering to the subject an effective amount of a compound described herein (e.g., a compound of formula (II)) or a pharmaceutically acceptable salt thereof, or of a composition described herein (e.g., a composition comprising a compound of formula (II)), wherein the subject has acute coronary syndrome. In some embodiments, the subject has atrial fibrillation. In some embodiments, the subject does not have atrial fibrillation. In another aspect, the present invention features a method of treating a subject identified as being at risk, e.g., high risk, for stroke or thrombosis thereby reducing the likelihood of stroke or thrombosis in the subject. In some embodiments, the subject is further identified as being at risk for bleeding (e.g., excessive bleeding) or sepsis. In some embodiments, the treatment is effective without bleeding liabilities. In some embodiments, the treatment is effective to maintain the patency of infusion ports and lines. In addition, the compounds described herein (e.g., compounds of formula (II)) are useful in the treatment and prevention of other diseases in which the generation of thrombin has been implicated as playing a physiologic role. For example, thrombin has been implicated in contributing to the morbidity and mortality of chronic and degenerative diseases, such as cancer, arthritis, atherosclerosis, vascular dementia, and Alzheimer's disease, by its ability to regulate many different cell types through specific cleavage and activation of a cell surface thrombin receptor, mitogenic effects, diverse cellular functions such as cell proliferation, for example, abnormal proliferation of vascular cells resulting in restenosis or angiogenesis, release of PDGF, and DNA synthesis. Inhibition of Factor XIa effectively blocks thrombin generation and therefore neutralizes any physiologic effects of thrombin on various cell types. The representative indications discussed above include some, but not all, of the potential clinical situations amenable to treatment with a Factor XIa inhibitor.

In another aspect, the present invention features a method of treating a subject that has edema (e.g., angioedema, e.g., hereditary angioedema), comprising administering a compound of formula (II) or a pharmaceutically acceptable salt thereof, or a composition described herein (e.g., a composition comprising a compound of formula (II)) to the subject.

In another aspect, the present invention features a method of prophyaxis of edema (e.g., angioedema, e.g., hereditary angioedema) in a subject, comprising administering a compound of formula (II) or a pharmaceutically acceptable salt thereof, or a composition described herein (e.g., a composition comprising a compound of formula (II)) to the subject.

In another aspect, the present invention features a method of reducing the risk of edema (e.g., angioedema, e.g., hereditary angioedema) in a subject, comprising administering a compound of formula (II) or a pharmaceutically acceptable salt thereof, or a composition described herein (e.g., a composition comprising a compound of formula (II)) to the subject.

In another aspect, the present invention features a method of inhibiting kallikrein in a subject, comprising administering to the subject with edema (e.g., angioedema, e.g., hereditary angioedema), an effective amount of a compound of formula (II) or a pharmaceutically acceptable salt thereof, or of a composition described herein (e.g., a composition comprising a compound of formula (II)) to the subject.

In another aspect, the present invention features a method of treating a thromboembolic consequence or complication in a subject, comprising administering to a subject an effective amount of a compound of formula (II) or a pharmaceutically acceptable salt thereof, or of a composition described herein (e.g., a composition comprising a compound of formula (II)). In some embodiments, the thromboembolic consequence or complication is associated with a peripheral vascular intervention (e.g., of the limbs), hemodialysis, catheter ablation, a cerebrovascular intervention, transplantation of an organ (e.g., liver), surgery (e.g., orthopedic surgery, lung surgery, abdominal surgery, or cardiac surgery, (e.g., open-heart surgery)), a trans-catheter aeortic valve implantation, a large bore intervention used to treat an aneurysm, a percutaneous coronary intervention, or hemophilia therapy. In some embodiments, the surgery is orthopedic surgery, lung surgery, abdominal surgery, or cardiac surgery.

In another aspect, the present invention features a method of prophylaxis of a thromboembolic consequence or complication in a subject, comprising administering to a subject an effective amount of a compound of formula (II) or a pharmaceutically acceptable salt thereof, or of a composition described herein (e.g., a composition comprising a compound of formula (II)). In some embodiments, the thromboembolic consequence or complication is associated with a peripheral vascular intervention (e.g., of the limbs), hemodialysis, catheter ablation, e.g., catheter ablation for atrial fibriliaton, a cerebrovascular intervention, transplantation of an organ (e.g., liver), surgery (e.g., orthopedic surgery, lung surgery, abdominal surgery, or cardiac surgery, (e.g., open-heart surgery)), a trans-catheter aeortic valve implantation, a large bore intervention used to treat an aneurysm, a percutaneous coronary intervention, or hemophilia therapy. In some embodiments, the surgery is orthopedic surgery, lung surgery, abdominal surgery, or cardiac surgery.

In another aspect, the present invention features a method of reducing the risk of a thromboembolic consequence or complication in a subject, comprising administering to a subject an effective amount of a compound of formula (II) or a pharmaceutically acceptable salt thereof, or of a composition described herein (e.g., a composition comprising a compound of formula (II)). In some embodiments, the thromboembolic consequence or complication is associated with a peripheral vascular intervention (e.g., of the limbs), hemodialysis, catheter ablation, e.g., catheter ablation for atrial fibriliaton, a cerebrovascular intervention, transplantation of an organ (e.g., liver), surgery (e.g., orthopedic surgery, lung surgery, abdominal surgery, or cardiac surgery, (e.g., open-heart surgery)), a trans-catheter aeortic valve implantation, a large bore intervention used to treat an aneurysm, a percutaneous coronary intervention, or hemophilia therapy. In some embodiments, the surgery is orthopedic surgery, lung surgery, abdominal surgery, or cardiac surgery.

In another aspect, the invention features a method of treating restenosis following arterial injury in a subject, comprising administering to a subject an effective amount of a compound of formula (II) or a pharmaceutically acceptable salt thereof, or of a composition described herein (e.g., a composition comprising a compound of formula (II)). In some embodiments, the arterial injury occurs after a cranial artery stenting.

In another aspect, the present invention features a method of prophylaxis of restenosis following arterial injury in a subject, comprising administering to a subject an effective amount of a compound of formula (II) or a pharmaceutically acceptable salt thereof, or of a composition described herein (e.g., a composition comprising a compound of formula (II)). In some embodiments, the arterial injury occurs after a cranial artery stenting.

In another aspect, the present invention features a method of reducing the risk of restenosis following arterial injury in a subject, comprising administering to a subject an effective amount of a compound of formula (II) or a pharmaceutically acceptable salt thereof, or of a composition described herein (e.g., a composition comprising a compound of formula (II)). In some embodiments, the arterial injury occurs after a cranial artery stenting.

In another aspect, the present invention features a method of treating hepatic vessel thrombosis in a subject, comprising administering to a subject an effective amount of a compound of formula (II) or a pharmaceutically acceptable salt thereof, or of a composition described herein (e.g., a composition comprising a compound of formula (II)).

In another aspect, the present invention features a method of prophylaxis of hepatic vessel thrombosis in a subject, comprising administering to a subject an effective amount of a compound of formula (II) or a pharmaceutically acceptable salt thereof, or of a composition described herein (e.g., a composition comprising a compound of formula (II)).

In another aspect, the present invention features a method of reducing the risk of hepatic vessel thrombosis in a subject, comprising administering to a subject an effective amount of a compound of formula (II) or a pharmaceutically acceptable salt thereof, or of a composition described herein (e.g., a composition comprising a compound of formula (II)).

In another aspect, the present invention features a method of treating a non-ST-elevation myocardial infarction or ST-elevetion myocardial infarction), comprising administering to a subject an effective amount of a compound of formula (II) or a pharmaceutically acceptable salt thereof, or of a composition described herein (e.g., a composition comprising a compound of formula (II)).

In another aspect, the present invention features a method of prophylaxis of a non-ST-elevation myocardial infarction or ST-elevetion myocardial infarction in a subject, comprising administering to the subject an effective amount of a compound of formula (II) or a pharmaceutically acceptable salt thereof, or of a composition described herein (e.g., a composition comprising a compound of formula (II)).

In another aspect, the present invention features a method of reducing the risk of a non-ST-elevation myocardial infarction or ST-elevetion myocardial infarction in a subject, comprising administering to the subject an effective amount of a compound of formula (II) or a pharmaceutically acceptable salt thereof, or of a composition described herein (e.g., a composition comprising a compound of formula (II)).

In another aspect, the present invention features a method of maintaining blood vessel patency, comprising administering to a subject an effective amount of a compound of formula (II) or a pharmaceutically acceptable salt thereof, or of a composition described herein (e.g., a composition comprising a compound of formula (II)). In some embodiments, the subject is has acute kidney injury. In some embodiments, the subject additionally undergoes continuous renal replacement therapy.

In some embodiments of any of the foregoing, the compound described herein or composition thereof is administered orally or parenterally. In certain embodiments, the compound or composition thereof is administered orally. In certain embodiments, the compound or composition thereof is administered after the subject has discontinued use of a direct oral anticoagulant. In certain embodiments, the subject used the direct oral anticoagulant for up to about 2.5 years. In certain embodiments, the subject is a mammal, e.g., a human.

DETAILED DESCRIPTION

Definitions

The term "alkyl," by itself or as part of another substituent, means, unless otherwise stated, a straight or branched chain, or cyclic hydrocarbon radical, or combination thereof, which may be fully saturated, mono- or polyunsaturated and can include di- and multivalent radicals, having the number of carbon atoms designated (i.e., $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, is also meant to include those derivatives of alkyl defined in more detail below, such as "heteroalkyl." Alkyl groups that are limited to hydrocarbon groups are termed "homoalkyl". Unless otherwise specified, each instance of an alkyl group is independently optionally substituted, i.e., unsubstituted (an "unsubstituted alkyl") or substituted (a "substituted alkyl") with one or more substituents; e.g., for instance from 1 to 5 substituents, 1 to 3 substituents, or 1 substituent. In certain embodiments, the alkyl group is unsubstituted $C_{1-10}$ alkyl (e.g., —$CH_3$). In certain embodiments, the alkyl group is substituted $C_{1-10}$ alkyl. Common alkyl abbreviations include Me (—$CH_3$), Et (—$CH_2CH_3$), iPr (—$CH(CH_3)_2$), nPr (—$CH_2CH_2CH_3$), n-Bu (—$CH_2CH_2CH_2CH_3$), or i-Bu (—$CH_2CH(CH_3)_2$).

The term "alkylene" by itself or as part of another substituent means a divalent radical derived from an alkane, as exemplified, but not limited, by —$CH_2CH_2CH_2CH_2$—, and further includes those groups described below as "heteroalkylene." Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The term "alkenyl" refers to a straight or branched hydrocarbon chain containing 2-12 carbon atoms (unless otherwise noted) and having one or more double bonds. Examples of alkenyl groups include, but are not limited to, allyl, propenyl, 2-butenyl, 3-hexenyl and 3-octenyl groups. One of the double bond carbons may optionally be the point of attachment of the alkenyl substituent.

The term "alkenylene" refers to a divalent alkenyl, e.g. —CH=CH—, —$CH_2$—CH=CH—, and —CH=CH—$CH_2$—.

The term "alkynyl" refers to a straight or branched hydrocarbon chain containing 2-12 carbon atoms (unless otherwise noted) and characterized in having one or more triple bonds. Examples of alkynyl groups include, but are not limited to, ethynyl, propargyl, and 3-hexynyl. One of the triple bond carbons may optionally be the point of attachment of the alkynyl substituent.

The term "alkynylene" refers to a divalent alkynyl, e.g. —C≡C—, —$CH_2$—C≡C—, and —C≡C—$CH_2$—.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The terms "cyano" and "nitrile" refer to the radical —CN.

The terms "cycloalkyl", "heterocycloalkyl" or "heterocyclyl", by themselves or in combination with other terms, represent, unless otherwise stated, cyclic versions of "alkyl" and "heteroalkyl", respectively. Additionally, for heterocycloalkyl or heterocyclyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, cyclooctanyl, and the like. Examples of heterocycloalkyl and heterocyclyl include, but are not limited to, 1-1,2,5,6-tetrahydropyridyl, 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, 2-tetrahydropyranyl, 3-tetrahydropyranyl, 4-tetrahydropyranyl, 1-methyl-1,5-dihydro-2-imidazol-4-one-yl, and the like.

The term "heteroalkyl," as used herein, refers to an alkyl group, as defined herein, which further comprises 1 or more (e.g., 1, 2, 3, or 4) heteroatoms (e.g., oxygen, sulfur, nitrogen, boron, silicon, phosphorus) within the parent chain, wherein the one or more heteroatoms is inserted between adjacent carbon atoms within the parent carbon chain and/or one or more heteroatoms is inserted between a carbon atom and the parent molecule, i.e., between the point of attachment. In certain embodiments, a heteroalkyl group refers to a saturated group having from 1 to 10 carbon atoms and 1, 2, 3, or 4 heteroatoms ("hetero$C_{1-10}$ alkyl"). In some embodiments, a heteroalkyl group is a saturated group having 1 to 9 carbon atoms and 1, 2, 3, or 4 heteroatoms ("hetero$C_{1-9}$ alkyl"). In some embodiments, a heteroalkyl group is a saturated group having 1 to 8 carbon atoms and 1, 2, 3, or 4 heteroatoms ("hetero$C_{1-8}$ alkyl"). In some embodiments, a heteroalkyl group is a saturated group having 1 to 7 carbon atoms and 1, 2, 3, or 4 heteroatoms ("hetero$C_{1-7}$ alkyl"). In some embodiments, a heteroalkyl group is a group having 1 to 6 carbon atoms and 1, 2, or 3 heteroatoms ("hetero$C_{1-6}$ alkyl"). In some embodiments, a heteroalkyl group is a saturated group having 1 to 5 carbon atoms and 1 or 2 heteroatoms ("hetero$C_{1-5}$ alkyl"). In some embodiments, a heteroalkyl group is a saturated group having 1 to 4 carbon atoms and 1 or 2 heteroatoms ("hetero$C_{1-4}$ alkyl"). In some embodiments, a heteroalkyl group is a saturated group having 1 to 3 carbon atoms and 1 heteroatom ("heteroC$_{1-3}$ alkyl"). In some embodiments, a heteroalkyl group is a saturated group having 1 to 2 carbon atoms and 1 heteroatom ("heteroC$_{1-2}$ alkyl"). In some embodiments, a heteroalkyl group is a saturated group having 1 carbon atom and 1 heteroatom ("heteroC$_1$ alkyl"). In some embodiments, a heteroalkyl group is a saturated group having 2 to 6 carbon atoms and 1 or 2 heteroatoms ("heteroC$_{2-6}$ alkyl"). Unless otherwise specified, each instance of a heteroalkyl group is independently unsubstituted (an "unsubstituted heteroalkyl") or substituted (a "substituted heteroalkyl") with one or more substituents. In certain embodiments, the heteroalkyl group is an unsubstituted heteroC$_{1-10}$ alkyl. In certain embodiments, the heteroalkyl group is a substituted heteroC$_{1-10}$ alkyl.

The terms "heterocyclyl" when used in combination with other terms (e.g., heterocyclylalkyl) includes heterocyclyl rings as defined above. Thus, the term "heterocyclylalkyl" is meant to include those radicals in which a heterocyclyl group is attached to an alkyl group including those alkyl groups in which a carbon atom (e.g., a methylene group) has been replaced by, for example, an oxygen atom.

The terms "halo" or "halogen," by themselves or as part of another substituent, mean, unless otherwise stated, a fluorine, chlorine, bromine, or iodine atom.

The term "haloalkyl," as used herein, refers to an alkyl group, as defined herein, which further comprises 1 or more (e.g., 1, 2, 3, or 4) halogen atoms (e.g., fluorine, chlorine, bromine, or iodine), wherein the alkyl group is substituted with one or more halogen atoms. In certain embodiments, a haloalkyl group refers to a saturated group having from 1 to 10 carbon atoms and 1, 2, 3, or 4 halogen atoms ("haloC$_{1-10}$ alkyl"). Additionally, the term "haloalkyl," is meant to include monohaloalkyl and polyhaloalkyl. For example, the term "haloalkyl" is mean to include, but not be limited to, trifluoromethyl, 2,2,2-trifluoroethyl, 4-chlorobutyl, 3-bromopropyl, and the like.

The terms "haloalkoxy" or "haloalkoxyl" as used herein, refer to an alkoxy group, as defined herein, which further comprises 1 or more (e.g., 1, 2, 3, or 4) halogen atoms (e.g., fluorine, chlorine, bromine, or iodine), wherein the alkoxy group is substituted with one or more halogen atoms.

The term "hydroxyl" refers to the radical —OH.

The term "aryl" means, unless otherwise stated, a polyunsaturated, aromatic, hydrocarbon substituent that can be a single ring or multiple rings (preferably from 1 to 3 rings), which are fused together or linked covalently. The term "heteroaryl" refers to aryl groups (or rings) that contain from one to four heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 2-imidazolyl, 4-imidazolyl, 5-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 1,3,4-oxadiazolyl, 1,2,3-triazolyl, 1,2,4-triazolyl, 3-isothiazolyl, 4-isothiazolyl, 5-isothiazolyl, 2-thiazolyl, 4-thiazolyl, 5-thiazolyl, 1,3,4-thiadiazolyl, 3-pyrazolyl, 4-pyrazolyl, 5-pyrazolyl, 2-thienyl, 3-thienyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, 6-quinolyl, and tetrazolyl. Each of the above noted aryl and heteroaryl ring systems may be substituted, and substituents are selected from the group of acceptable substituents described below. For example, non-limiting examples of substituted pyrazolyl include 1-methyl-3-pyrazolyl, 1-methyl-4-pyrazolyl , 1-methyl-5-pyrazolyl and non-limiting examples of substituted imidazolyl include 1-methyl-2-imidazolyl, 1-methyl-4-imidazolyl and 1-methyl-5-imidazolyl. For brevity, the term "aryl" when used in combination with other terms (e.g., aryloxy, arylthio, arylalkyl, aralkyl, heteroaralkyl) includes both aryl and heteroaryl rings as defined above. Thus, the terms "arylalkyl", "aralkyl" and "heteroaralkyl" are meant to include those radicals in which an aryl or heteroaryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

The term "nitro" refers to the radical —NO$_2$.

"Protecting group," as used herein refers to a portion of a substrate that is substantially stable under a particular reaction condition, but which is cleaved from the substrate under a different reaction condition. A protecting group can also be selected such that it participates in the direct oxidation of the aromatic ring component of the compounds of the invention. For examples of useful protecting groups, see, for example, Greene et al., *Protective Groups in Organic Synthesis*, John Wiley & Sons, New York, 1991.

Alkyl, alkenyl, alkynyl, cycloalkyl, heterocyclyl, aryl, and heteroaryl groups, as defined herein, are optionally substituted (e.g., "substituted" or "unsubstituted" alkyl, "substituted" or "unsubstituted" alkenyl, "substituted" or "unsubstituted" alkynyl, "substituted" or "unsubstituted" cycloalkyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds described herein that results in the formation of a stable compound. For purposes of this invention, heteroatoms such as nitrogen may have hydrogen substituents and/or any suitable substituent as described herein which satisfy the valencies of the heteroatoms and results in the formation of a stable moiety.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(O)R$^{aa}$—S(=O)R$^{aa}$, —OS(=O)R$^{aa}$, —Si(R$^{aa}$)$_3$, —Osi $(R^{aa})_3$—C(=S)N($R^{bb}$)$_2$, —C(=O)S$R^{aa}$, —C(=S)S$R^{aa}$, —SC(=S)S$R^{aa}$, —SC(=O)S$R^{aa}$, —OC(=O)S$R^{aa}$, —SC(=O)O$R^{aa}$, —SC(=O)$R^{aa}$, —P(=O)$_2$$R^{aa}$, —OP(=O)$_2$$R^{aa}$, —P(=O)($R^{aa}$)$_2$, —OP(=O)($R^{aa}$)$_2$, —OP(=O)(O$R^{cc}$)$_2$, —P(=O)$_2$N($R^{bb}$)$_2$, —OP(=O)$_2$N($R^{bb}$)$_2$, —P(=O)(N$R^{bb}$)$_2$, —OP(=O)(N$R^{bb}$)$_2$, —N$R^{bb}$P(=O)(O$R^{cc}$)$_2$, —N$R^{bb}$P(=O)(N$R^{bb}$)$_2$, —P($R^{cc}$)$_2$, —P($R^{cc}$)$_3$, —OP($R^{cc}$)$_2$, —OP($R^{cc}$)$_3$, —B($R^{aa}$)$_2$, —B(O$R^{cc}$)$_2$, —B$R^{aa}$(O$C^{cc}$), $C_{1-10}$ alkyl, $C_{1-10}$ perhaloalkyl, $C_{2-10}$ alkenyl, $C_{2-10}$ alkynyl, $C_{3-10}$ cycloalkyl, 3-14 membered heterocyclyl, $C_{6-14}$ aryl, and 5-14 membered heteroaryl, wherein each alkyl, alkenyl, alkynyl, cycloalkyl, heterocyclyl, aryl, and heteroaryl is independently substituted with 0, 1, 2, 3, 4, or 5 $R^{dd}$ groups;

each instance of $R^{aa}$ is, independently, selected from $C_{1-10}$ alkyl, $C_{1-10}$ perhaloalkyl, $C_{2-10}$ alkenyl, $C_{2-10}$ alkynyl, $C_{3-10}$ cycloalkyl, 3-14 membered heterocyclyl, $C_{6-14}$ aryl, and 5-14 membered heteroaryl, or two $R^{aa}$ groups are joined to form a 3-14 membered heterocyclyl or 5-14 membered heteroaryl ring, wherein each alkyl, alkenyl, alkynyl, cycloalkyl, heterocyclyl, aryl, and heteroaryl is independently substituted with 0, 1, 2, 3, 4, or 5 $R^{dd}$ groups;

each instance of $R^{bb}$ is, independently, selected from hydrogen, —OH, —O$R^{aa}$, —N($R^{cc}$)$_2$, —CN, —C(=O)$R^{aa}$, —C(=O)N($R^{cc}$)$_2$, —CO$_2$$R^{aa}$, —SO$_2$$R^{aa}$, —C(=N$R^{cc}$)O$R^{aa}$, —C(=N$R^{cc}$)N($R^{cc}$)$_2$, —SO$_2$N($R^{cc}$)$_2$, —SO$_2$$R^{cc}$, —SO$_2$O$R^{cc}$, —SO$R^{aa}$, —C(=S)N($R^{cc}$)$_2$, —C(=O)S$R^{cc}$, —C(=S)S$R^{cc}$, —P(=O)$_2$$R^{aa}$, —P(=O)($R^{aa}$)$_2$, —P(=O)$_2$N($R^{cc}$)$_2$, —P(=O)(N$R^{cc}$)$_2$, $C_{1-10}$ alkyl, $C_{1-10}$ perhaloalkyl, $C_{2-10}$ alkenyl, $C_{2-10}$ alkynyl, $C_{3-10}$ cycloalkyl, 3-14 membered heterocyclyl, $C_{6-14}$ aryl, and 5-14 membered heteroaryl, or two $R^{bb}$ groups are joined to form a 3-14 membered heterocyclyl or 5-14 membered heteroaryl ring, wherein each alkyl, alkenyl, alkynyl, cycloalkyl, heterocyclyl, aryl, and heteroaryl is independently substituted with 0, 1, 2, 3, 4, or 5 $R^{dd}$ groups;

each instance of $R^{cc}$ is, independently, selected from hydrogen, $C_{1-10}$ alkyl, $C_{1-10}$ perhaloalkyl, $C_{2-10}$ alkenyl, $C_{2-10}$ alkynyl, $C_{3-10}$ cycloalkyl, 3-14 membered heterocyclyl, $C_{6-14}$ aryl, and 5-14 membered heteroaryl, or two $R^{cc}$ groups are joined to form a 3-14 membered heterocyclyl or 5-14 membered heteroaryl ring, wherein each alkyl, alkenyl, alkynyl, cycloalkyl, heterocyclyl, aryl, and heteroaryl is independently substituted with 0, 1, 2, 3, 4, or 5 $R^{dd}$ groups;

each instance of $R^{dd}$ is, independently, selected from halogen, —CN, —NO$_2$, —N$_3$, —SO$_2$H, —SO$_3$H, —OH, —O$R^{ee}$, —ON($R^{ff}$)$_2$, —N($R^{ff}$)$_2$, —N($R^{ff}$)$_3$$^+$X$^-$, —N(O$R^{ee}$)$R^{ff}$, —SH, —S$R^{ee}$, —SS$R^{ee}$, —C(=O)$R^{ee}$, —CO$_2$H, —CO$_2$$R^{ee}$, —OC(=O)$R^{ee}$, —OCO$_2$$R^{ee}$, —C(=O)N($R^{ff}$)$_2$, —OC(=O)N($R^{ff}$)$_2$, —N$R^{ff}$C(=O)$R^{ee}$, —N$R^{ff}$CO$_2$$R^{ee}$, —N$R^{ff}$C(=O)N($R^{ff}$)$_2$, —C(=N$R^{ff}$)O$R^{ee}$, —OC(=N$R^{ff}$)$R^{ee}$, —OC(=N$R^{ff}$)O$R^{ee}$, —C(=N$R^{ff}$)N($R^{ff}$)$_2$, —OC(=N$R^{ff}$)N($R^{ff}$)$_2$, —N$R^{ff}$C(=N$R^{ff}$)N($R^{ff}$)$_2$, —N$R^{ff}$SO$_2$$R^{ee}$, —SO$_2$N($R^{ff}$)$_2$, —SO$_2$$R^{ee}$, —SO$_2$O$R^{ee}$, —OSO$_2$$R^{ee}$, —S(=O)$R^{ee}$, —Si($R^{ee}$)$_3$, —Osi($R^{ee}$)$_3$, —C(=S)N($R^{ff}$)$_2$, —C(=O)S$R^{ee}$, —C(=S)S$R^{ee}$, —SC(=S)S$R^{ee}$, —P(=O)$_2$$R^{ee}$, —P(=O)($R^{ee}$)$_2$, —OP(=O)($R^{ee}$)$_2$, —OP(=O)(O$R^{ee}$)$_2$, $C_{1-6}$ alkyl, $C_{1-6}$ perhaloalkyl, $C_{2-6}$ alkenyl, $C_{2-6}$ alkynyl, $C_{3-10}$ cycloalkyl, 3-10 membered heterocyclyl, $C_{6-10}$ aryl, 5-10 membered heteroaryl, wherein each alkyl, alkenyl, alkynyl, cycloalkyl, heterocyclyl, aryl, and heteroaryl is independently substituted with 0, 1, 2, 3, 4, or 5 $R^{gg}$ groups, or two terminal $R^{dd}$ substituents can be joined to form =O or =S;

each instance of $R^{ee}$ is, independently, selected from $C_{1-6}$ alkyl, $C_{1-6}$ perhaloalkyl, $C_{2-6}$ alkenyl, $C_{2-6}$ alkynyl, $C_{3-10}$ cycloalkyl, $C_{6-10}$ aryl, 3-10 membered heterocyclyl, and 3-10 membered heteroaryl, wherein each alkyl, alkenyl, alkynyl, cycloalkyl, heterocyclyl, aryl, and heteroaryl is independently substituted with 0, 1, 2, 3, 4, or 5 $R^{gg}$ groups;

each instance of $R^{ff}$ is, independently, selected from hydrogen, $C_{1-6}$ alkyl, $C_{1-6}$ perhaloalkyl, $C_{2-6}$ alkenyl, $C_{2-6}$ alkynyl, $C_{3-10}$ cycloalkyl, 3-10 membered heterocyclyl, $C_{6-10}$ aryl and 5-10 membered heteroaryl, or two $R^{ff}$ groups are joined to form a 3-14 membered heterocyclyl or 5-14 membered heteroaryl ring, wherein each alkyl, alkenyl, alkynyl, cycloalkyl, heterocyclyl, aryl, and heteroaryl is independently substituted with 0, 1, 2, 3, 4, or 5 $R^{gg}$ groups; and each instance of $R^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3$$^+$X$^-$, —NH(C$_{1-6}$ alkyl)$_2$$^+$X$^-$, —NH$_2$(C$_{1-6}$ alkyl)$^+$X$^-$, —NH$_3$$^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$—C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)$_2$(C$_{1-6}$ alkyl), —P(=O)(C$_{1-6}$ alkyl)$_2$, —OP(=O)(C$_{1-6}$ alkyl)$_2$, —OP(=O)(OC$_{1-6}$ alkyl)$_2$, C$_{1-6}$ alkyl, C$_{1-6}$ perhaloalkyl, C$_{2-6}$ alkenyl, C$_{2-6}$ alkynyl, C$_{3-10}$ cycloalkyl, C$_{1-6}$ aryl, 3-10 membered heterocyclyl, 5-10 membered heteroaryl; or two terminal $R^{gg}$ substituents can be joined to form =O or =S; wherein X$^-$ is a counterion.

These and other exemplary substituents are described in more detail in the Detailed Description, Examples, and claims. The invention is not intended to be limited in any manner by the above exemplary listing of substituents.

Compounds

Described herein are compounds that inhibit Factor XIa or kallikrein.

In one aspect, described herein is a compound of formula (II):

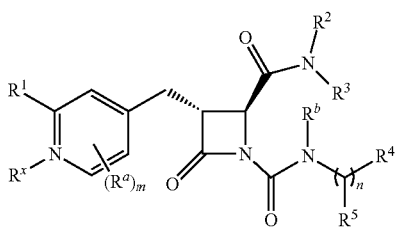

(II)

or a pharmaceutically acceptable salt thereof, wherein $R^1$ is hydrogen or —$NR^8R^9$; $R^a$ is $C_{1-6}$ alkyl, $C_{1-6}$ haloalkyl, halo, cyano, or —$OR^6$; $R^b$ is hydrogen or $C_{1-6}$ alkyl; $R^2$ is optionally substituted 5-membered heteroaryl or optionally substituted 5-membered heterocylyl; $R^3$ is hydrogen, $C_{1-6}$ alkyl, or $C_{1-6}$ haloalkyl; $R^4$ is $C_{1-6}$ alkyl, $C_{1-6}$ haloalkyl, cycloalkyl, heterocyclyl, aryl, or heteroaryl, wherein the cycloalkyl, heterocyclyl, aryl, or heteroaryl is optionally substituted with one, two, or three independent occurrences of halo, $C_{1-6}$ alkyl, $C_{1-6}$ haloalkyl, cyano, or —$OR^6$; $R^5$ is hydrogen, $C_{1-6}$ alkyl, $C_{1-6}$ haloalkyl, cycloalkyl, or aryl, wherein the cycloalkyl or aryl is optionally substituted with one, two, or three independent occurrences of halo, $C_{1-6}$ alkyl, $C_{1-6}$ haloalkyl, cyano, or —$OR^6$ or $R^4$ and $R^5$, taken together with the carbon atom to which they are attached form a ring; $R^6$ is hydrogen, $C_{1-6}$ alkyl, or $C_{1-6}$ haloalkyl; each $R^8$ and $R^9$ is independently hydrogen, $C_{1-6}$ alkyl, —$C(O)R^{10}$, or —$C(O)OR^{10}$; $R^{10}$ is $C_{1-6}$ alkyl or $C_{1-6}$ haloalkyl; $R^x$ is —O or absent, wherein when $R^x$ is —O, the nitrogen atom of the pyridyl ring is positively charged and $R^x$ is negatively charged, thereby forming a pyridyl N-oxide; m is 0, 1, 2, or 3; and n is 0 or 1, wherein if n is 0, then $R^5$ is hydrogen and $R^4$ is absent.

In one aspect, the present invention is directed to a compound of formula (II):

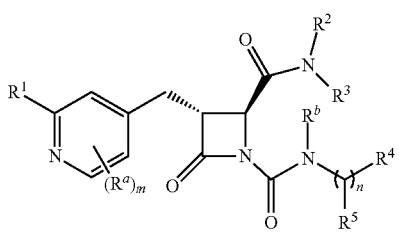

(II)

or a pharmaceutically acceptable salt thereof, wherein $R^1$ is hydrogen or —$NR^8R^9$; $R^a$ is $C_{1-6}$ alkyl, $C_{1-6}$ haloalkyl, halo, cyano, or —$OR^6$; $R^b$ is hydrogen or $C_{1-6}$ alkyl; $R^2$ is optionally substituted 5-membered heteroaryl; $R^3$ is hydrogen, $C_{1-6}$ alkyl, or $C_{1-6}$ haloalkyl; $R^4$ is $C_{1-6}$ alkyl, $C_{1-6}$ haloalkyl, cycloalkyl, heterocyclyl, aryl, or heteroaryl, wherein the cycloalkyl, heterocyclyl, aryl, or heteroaryl is optionally substituted with one, two, or three independent occurrences of halo, $C_{1-6}$ alkyl, $C_{1-6}$ haloalkyl, cyano, or —$OR^6$; $R^5$ is hydrogen, $C_{1-6}$ alkyl, $C_{1-6}$ haloalkyl, cycloalkyl, or aryl, wherein the cycloalkyl or aryl is optionally substituted with one, two, or three independent occurrences of halo, $C_{1-6}$ alkyl, $C_{1-6}$ haloalkyl, cyano, or —$OR^6$ or $R^4$ and $R^5$, taken together with the carbon atom to which they are attached form a ring; $R^6$ is hydrogen, $C_{1-6}$ alkyl, or $C_{1-6}$ haloalkyl; each $R^8$ and $R^9$ is independently hydrogen, $C_{1-6}$ alkyl, —$C(O)R^{10}$, or —$C(O)OR^{10}$; $R^{10}$ is $C_{1-6}$ alkyl or $C_{1-6}$ haloalkyl; m is 0, 1, 2, or 3; and n is 0 or 1, wherein if n is 0, then $R^5$ is hydrogen and $R^4$ is absent.

In some embodiments, $R^x$ is absent.

In some embodiments, the compound is a compound of Formula (I):

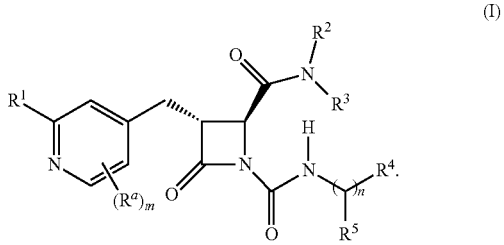

(I)

In some embodiments, $R^6$ is $C_{1-6}$ alkyl or $C_{1-6}$ haloalkyl. In some embodiments, $R^6$ is —$CH_3$ or —$CF_3$.

In some embodiments, $R^1$ is hydrogen, —$NH_2$, or —$NHCH_3$. In some embodiments, $R^1$ is hydrogen. In some embodiments, $R^1$ is —$NH_2$. In some embodiments, $R^1$ is —$NHCH_3$.

In some embodiments, 5-membered heterocyclyl is nitrogen-containing 5-membered heterocyclyl. In some embodiments, nitrogen-containing 5-membered heterocyclyl is saturated or unsaturated.

In some embodiments, $R^2$ is a 5-membered heterocyclyl optionally substituted with one, two, three, or four independent occurrences of $C_{1-6}$ alkyl, $C_{2-6}$ alkenyl, $C_2$-$C_6$ alkynyl, $C_{1-6}$ alkoxyl, $C_{1-6}$ haloalkyl, $C_{1-6}$ haloalkoxyl, halo, cyano, $C_{3-8}$ carbocyclyl, $C_{3-8}$ heterocyclyl, aryl, or heteroaryl. In some embodiments, the nitrogen-containing 5-membered heterocyclyl is optionally substituted with oxo (═O). In some embodiments, $R^2$ is 5-membered heterocyclyl optionally substituted with one or two independent occurrences of $C_{1-6}$ alkyl.

In some embodiments, $R^2$ is a 5-membered heteroaryl optionally substituted with one, two, three, or four independent occurrences of $C_{1-6}$ alkyl, $C_{2-6}$ alkenyl, $C_2$-$C_6$ alkynyl, $C_{1-6}$ alkoxyl, $C_{1-6}$ haloalkyl, $C_{1-6}$ haloalkoxyl, halo, cyano, $C_{3-8}$ carbocyclyl, $C_{3-8}$ heterocyclyl, aryl, or heteroaryl.

In some embodiments, $R^2$ is 5-membered heteroaryl optionally substituted with one or two independent occurrences of $C_{1-6}$ alkyl. In some embodiments, $R^2$ is pyrazolyl, imidazolyl, thienyl, isothiazolyl, or thiazolyl, wherein the imidazolyl, thienyl, isothiazolyl, or thiazolyl is optionally substituted with one or two independent occurrences of $C_{1-6}$ alkyl. In some embodiments, $R^2$ is pyrazolyl, imidazolyl, thienyl, isothiazolyl, thiazolyl, oxadiazolyl, or thiadiazolyl, wherein the imidazolyl, thienyl, isothiazolyl, thiazolyl, oxadiazolyl, or thiadiazolyl is optionally substituted with one or two independent occurrences of $C_{1-6}$ alkyl. In some embodiments, $R^2$ is pyrazolyl, imidazolyl, thienyl, isothiazolyl, or thiazolyl, wherein the imidazolyl, thienyl, isothiazolyl, or thiazolyl is optionally substituted with one or two occurrences of —$CH_3$. In some embodiments, $R^2$ is pyrazolyl, imidazolyl, thienyl, isothiazolyl, thiazolyl, oxadiazolyl, or thiadiazolyl, wherein the imidazolyl, thienyl, isothiazolyl, thiazolyl, oxadiazolyl, or thiadiazolyl is optionally substituted with one or two occurrences of —$CH_3$.

In some embodiments, R² is

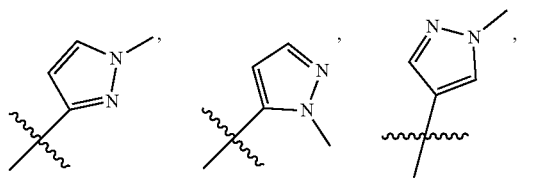
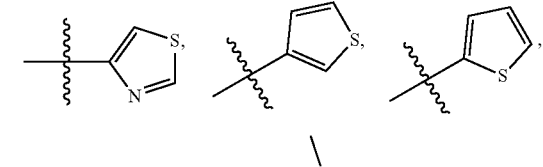
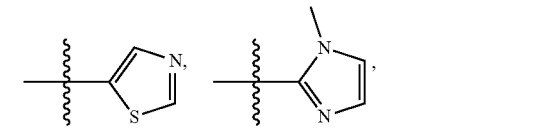
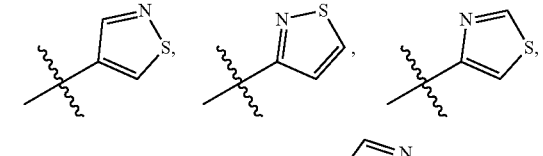
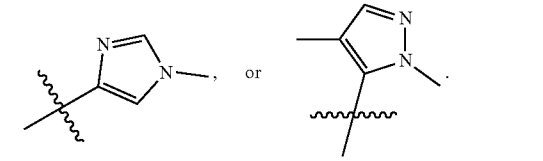

In some embodiments, R² is

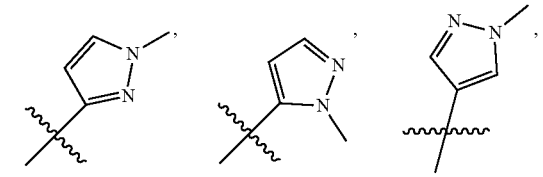
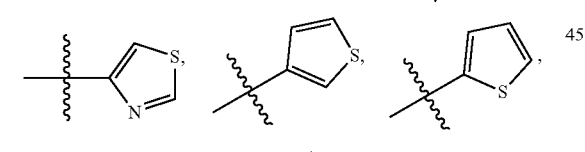
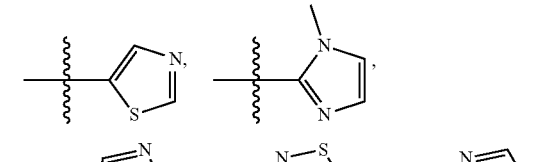
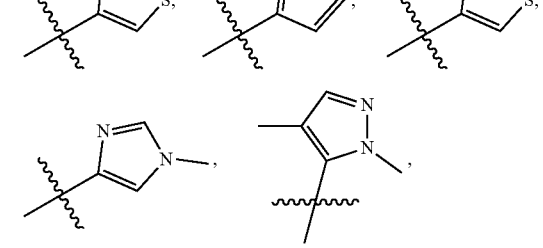

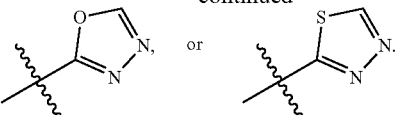

In some embodiments, R² is

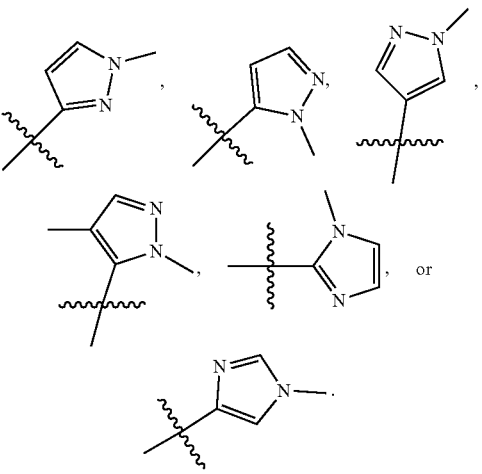

In some embodiments, R² is

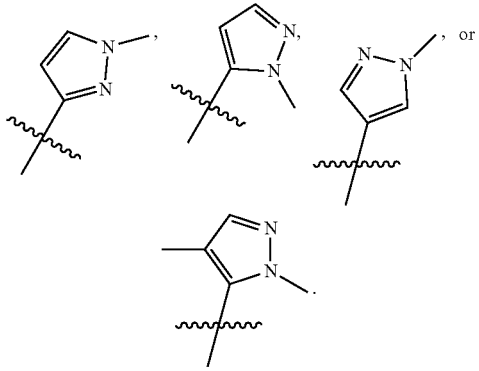

In some embodiments, R² is

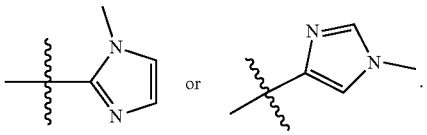

In some embodiments, R³ is $C_{1-6}$ alkyl. In some embodiments, R³ is —$CH_3$.

In some embodiments, R⁴ is $C_{1-6}$ alkyl, cycloalkyl, aryl, or heteroaryl, wherein the cycloalkyl, aryl, or heteroaryl is optionally substituted with one, two, or three independent occurrences of halo or $C_{1-6}$ alkyl. In some embodiments, R⁴ is cyclohexyl, cylcopropyl, phenyl, pyridyl, pyrazolyl, thienyl, or $C_{1-6}$ alkyl, wherein the cyclohexyl, cylcopropyl, phenyl, pyridyl, pyrazolyl, or thienyl is optionally substituted with one, two, or three independent occurrences of halo or $C_{1-6}$ alkyl. In some embodiments, $R^4$ is cyclohexyl, phenyl, pyridyl, pyrazolyl, or thienyl, wherein the cyclohexyl, phenyl, pyridyl, pyrazolyl, or thienyl is optionally substituted with one, two, or three independent occurrences of halo or $C_{1-6}$ alkyl. In some embodiments, $R^4$ is phenyl optionally substituted with one, two, or three occurrences of —F, —Cl, or $C_{1-6}$ alkyl.

In some embodiments, $R^4$ is $C_{1-6}$ alkyl, $C_{1-6}$ haloalkyl, cycloalkyl, heterocyclyl, aryl, or heteroaryl, wherein the cycloalkyl, heterocyclyl, aryl, or heteroaryl is optionally substituted with one, two, or three independent occurrences of halo, $C_{1-6}$ alkyl, $C_{1-6}$ haloalkyl, cyano, or —$OR^6$ and $R^5$ is hydrogen, $C_{1-6}$ alkyl, $C_{1-6}$ haloalkyl, cycloalkyl, or aryl, wherein the cycloalkyl or aryl is optionally substituted with one, two, or three independent occurrences of halo, $C_{1-6}$ alkyl, $C_{1-6}$ haloalkyl, or —$OR^6$ or $R^4$ and $R^5$, taken together with the carbon atom to which they are attached form a ring.

In some embodiments, $R^4$ is $C_{1-6}$ alkyl, cycloalkyl, heterocyclyl, aryl, or heteroaryl, wherein the cycloalkyl, aryl, or heteroaryl is optionally substituted with one, two, or three independent occurrences of halo or $C_{1-6}$ alkyl. In some embodiments, $R^4$ is cyclohexyl, cylcopropyl, phenyl, tetrahydropyranyl, pyridyl, pyrazolyl, thienyl, or $C_{1-6}$ alkyl, wherein the cyclohexyl, cylcopropyl, phenyl, tetrahydropyranyl, pyridyl, pyrazolyl, or thienyl is optionally substituted with one, two, or three independent occurrences of halo or $C_{1-6}$ alkyl. In some embodiments, $R^4$ is cyclohexyl, phenyl, pyridyl, pyrazolyl, or thienyl, wherein the cyclohexyl, phenyl, pyridyl, pyrazolyl, or thienyl is optionally substituted with one, two, or three independent occurrences of halo or $C_{1-6}$ alkyl. In some embodiments, $R^4$ is phenyl optionally substituted with one, two, or three occurrences of —F, —Cl, or $C_{1-6}$ alkyl.

In some embodiments, $R^5$ is hydrogen, —$CH_3$, —$CH_2CH_3$, —$CH_2CH_2CH_3$, —$CH(CH_3)_2$, —$CH_2CH_2CH_2CH_3$, —$CF_3$, or unsubstituted cyclopropyl. In some embodiments, $R^5$ is —$CH_2CH_3$, —$CF_3$, or unsubstituted cyclopropyl.

In some embodiments, the compound is a compound of formula (I-a):

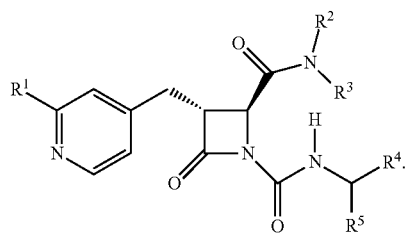
(I-a)

In some embodiments, the compound is a compound of formula (I-b):

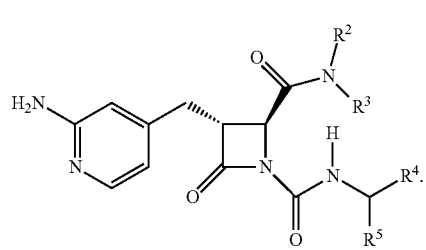
(I-b)

In some embodiments, the compound is a compound of formula (I-c), formula (I-d), formula (I-e), formula (I-f), formula (I-g), formula (I-i), or formula (I-j):

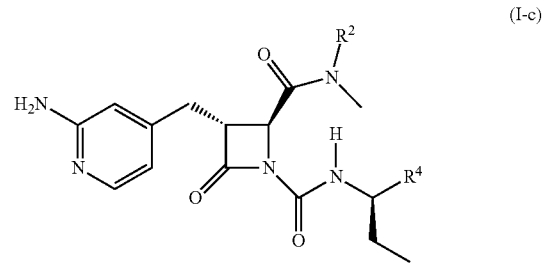
(I-c)

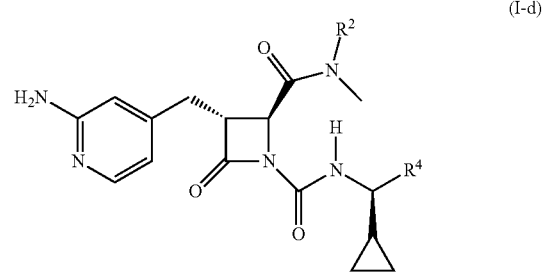
(I-d)

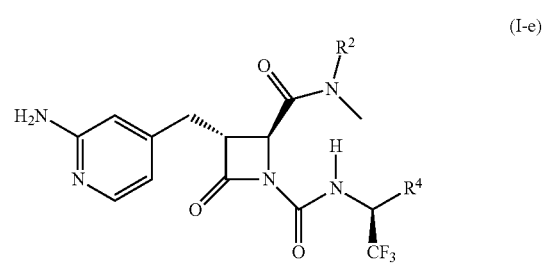
(I-e)

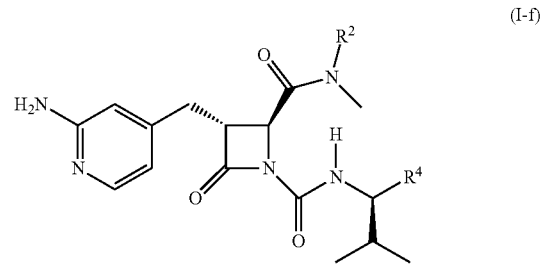
(I-f)

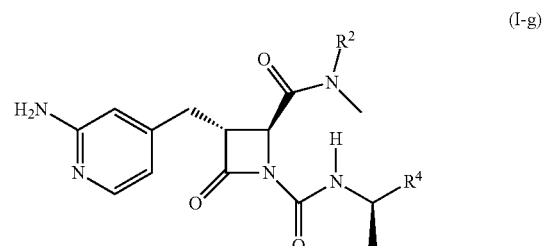
(I-g)

(I-h)
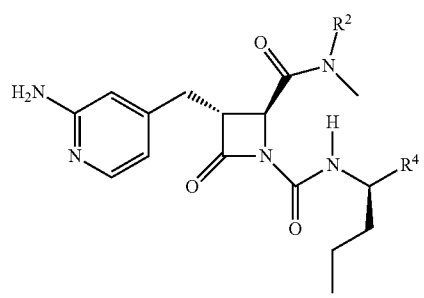
(I-i)
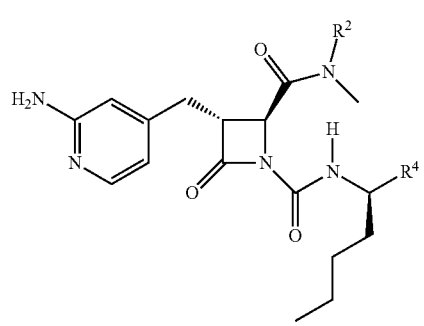
(I-j)
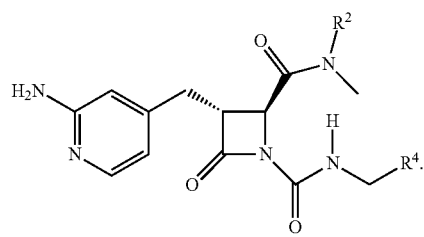
In some embodiments, the compound is a compound of formula (I-c):
(I-c)
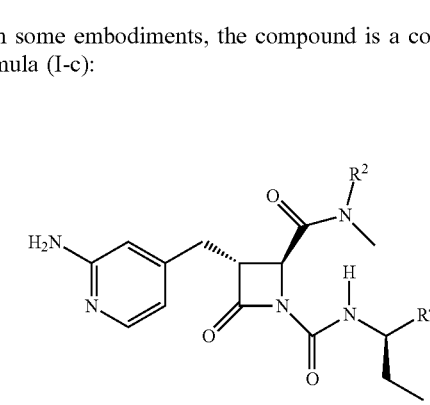
In some embodiments, the compound is a compound of formula (I-e), formula (I-k), formula (I-l), formula (I-m), formula (I-o), formula (I-p), formula (I-t), formula (I-u), or formula (I-v):
(I-k)
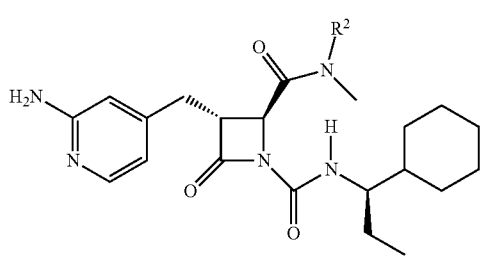
(I-l)
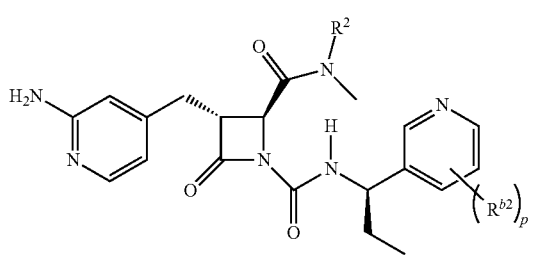
(I-m)
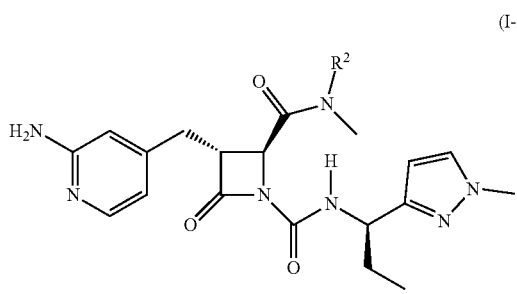
(I-n)
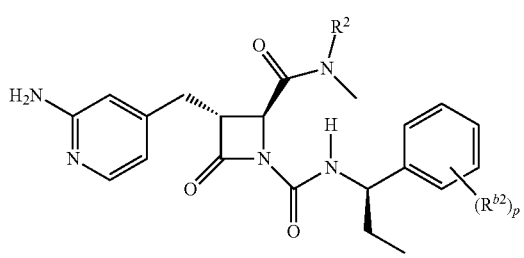
(I-o)
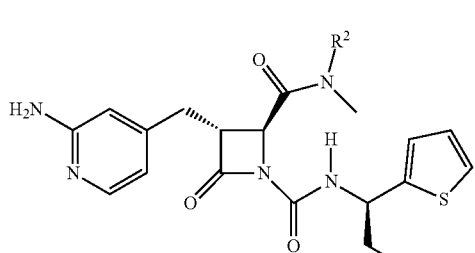
(I-p)
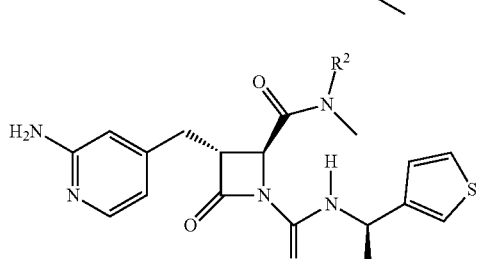

-continued (I-t)

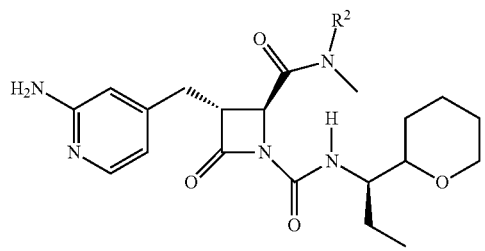

(I-u)

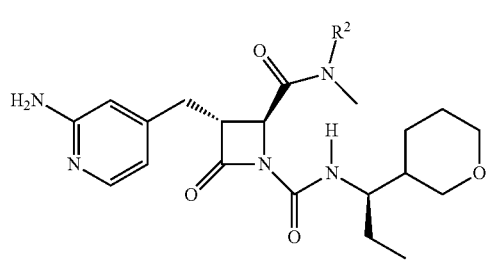

(I-v)

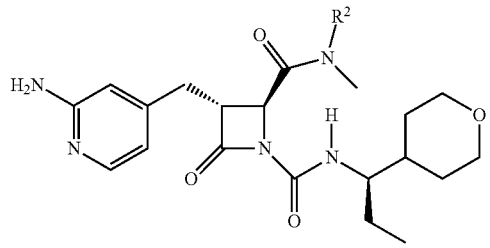

wherein each of $R^{b2}$ is independently halo, $C_{1-6}$ alkyl, $C_{1-6}$ haloalkyl, cyano, or —$OR^6$; and p is 0, 1, 2, or 3.

In some embodiments, $R^a$ is —$C_{1-6}$ alkyl. In some embodiments, $R^a$ is —$CH_3$. In some embodiments, $R^a$ is —$CH_3$ and m is 1. In some embodiments, m is 1. In some embodiments, $R^a$ is halo or —$C_{1-6}$ alkyl. In some embodiments, $R^a$ is F or —$CH_3$. In some embodiments, $R^b$ is $C_{1-6}$ alkyl. In some embodiments, $R^b$ is —$CH_3$.

In some embodiments, the compound is a compound of formula (I-q):

(I-q)

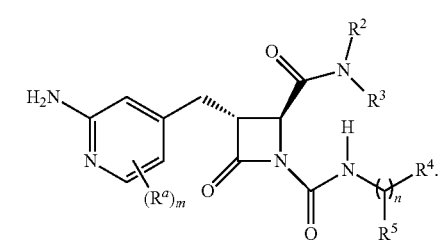

In some embodiments, the compound is a compound of formula (I-r):

(I-r)

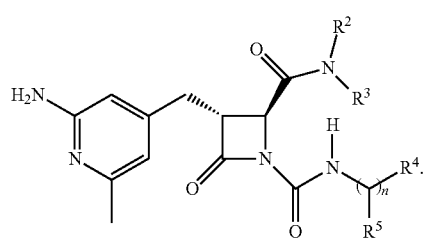

In some embodiments, the compound is a compound of formula (I-s):

(I-s)

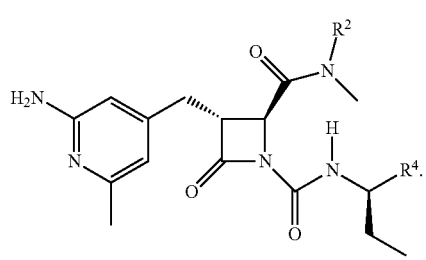

In some embodiments, the compound is a compound of formula (I-s1) or formula (I-s2):

(I-s1)

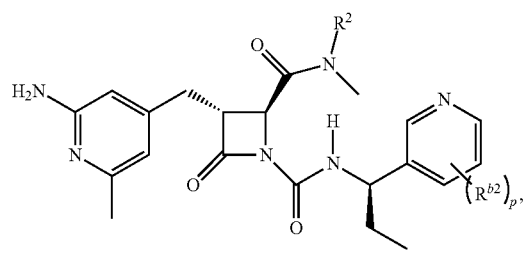

(I-s2)

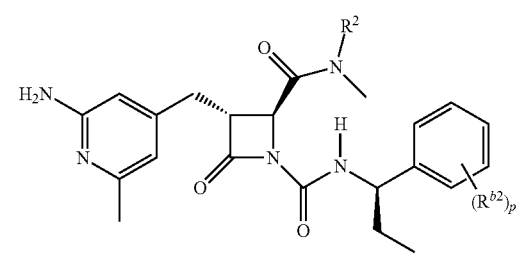

wherein each of $R^{b2}$ is independently halo, $C_{1-6}$ alkyl, $C_{1-6}$ haloalkyl, cyano, or —$OR^6$; and p is 0, 1, 2, or 3.

In some embodiments, $R^b$ is $C_{1-6}$ alkyl. In some embodiments, $R^b$ is —$CH_3$.

Exemplary compounds include, but are not limited to, the compounds described in Table 1 below:

TABLE 1
Exemplary compounds.
| Compound Number | Structure |
|---|---|
| 1-3 | 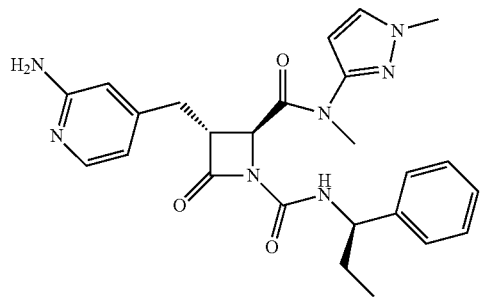 [SMILES: CC[C@@H](NC(=O)N1C(=O)[C@H](Cc2ccnc(N)c2)[C@H]1C(=O)N(C)c1ccn(C)n1)c1ccccc1] |
| 1-4 | 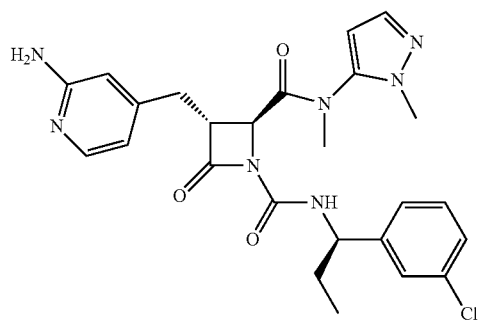 [SMILES: CC[C@@H](NC(=O)N1C(=O)[C@H](Cc2ccnc(N)c2)[C@H]1C(=O)N(C)c1ccnn1C)c1cccc(Cl)c1] |
| 1-5 | 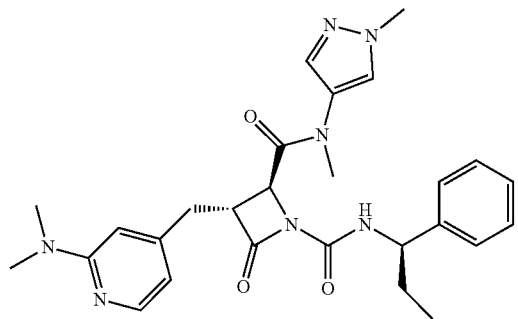 [SMILES: CC[C@@H](NC(=O)N1C(=O)[C@H](Cc2ccnc(N(C)C)c2)[C@H]1C(=O)N(C)c1cnn(C)c1)c1ccccc1] |
| 1-6 | 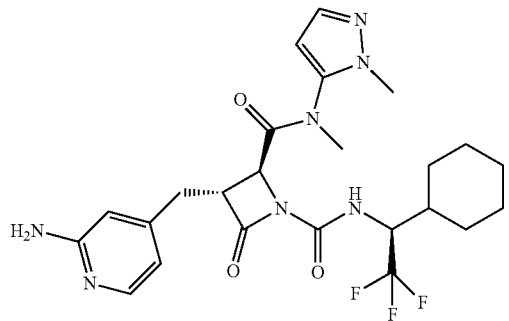 [SMILES: CN(C(=O)[C@@H]1[C@@H](Cc2ccnc(N)c2)C(=O)N1C(=O)N[C@@H](C1CCCCC1)C(F)(F)F)c1ccnn1C] |

TABLE 1-continued

Exemplary compounds.

| Compound Number | Structure |
|---|---|
| 1-7 | 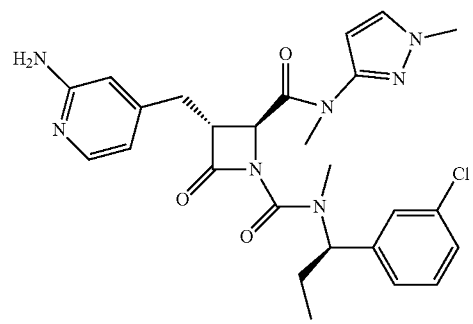 [SMILES: CC[C@H](c1cccc(Cl)c1)N(C)C(=O)N1C(=O)[C@H](Cc2ccnc(N)c2)[C@H]1C(=O)N(C)c1ccn(C)n1] |
| 1-8 | 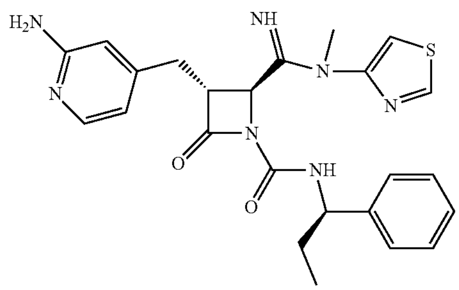 [SMILES: CC[C@@H](NC(=O)N1C(=O)[C@H](Cc2ccnc(N)c2)[C@H]1C(=N)N(C)c1cscn1)c1ccccc1] |
| 1-9 | 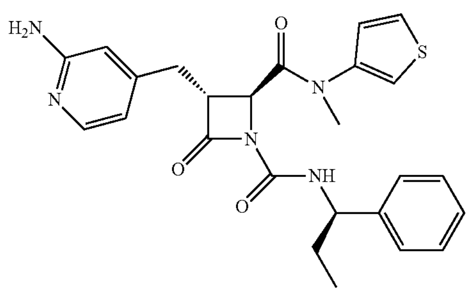 [SMILES: CC[C@@H](NC(=O)N1C(=O)[C@H](Cc2ccnc(N)c2)[C@H]1C(=O)N(C)c1ccsc1)c1ccccc1] |
| 1-10 | 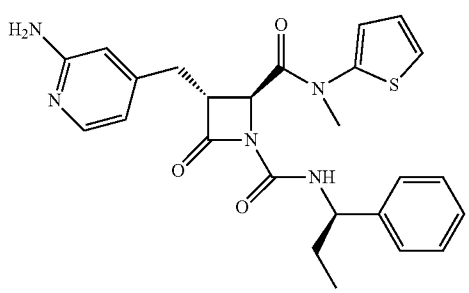 [SMILES: CC[C@@H](NC(=O)N1C(=O)[C@H](Cc2ccnc(N)c2)[C@H]1C(=O)N(C)c1cccs1)c1ccccc1] |
| 1-11 | 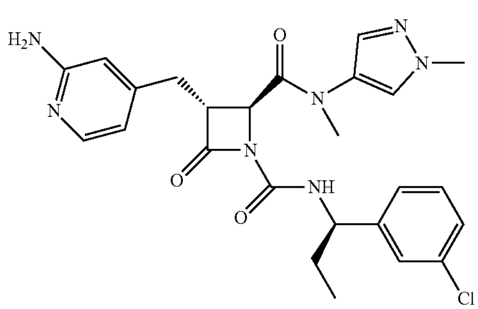 [SMILES: CC[C@@H](NC(=O)N1C(=O)[C@H](Cc2ccnc(N)c2)[C@H]1C(=O)N(C)c1cnn(C)c1)c1cccc(Cl)c1] |

TABLE 1-continued
Exemplary compounds.
| Compound Number | Structure |
|---|---|
| 1-12 | 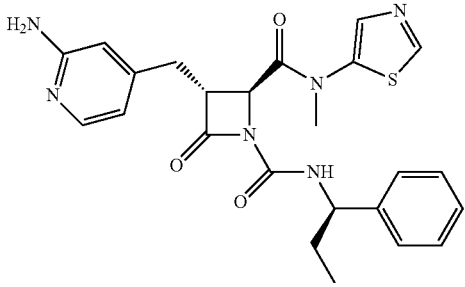 [SMILES: CC[C@@H](NC(=O)N1C(=O)[C@H](Cc2ccnc(N)c2)[C@H]1C(=O)N(C)c1cncs1)c1ccccc1] |
| 1-13 | 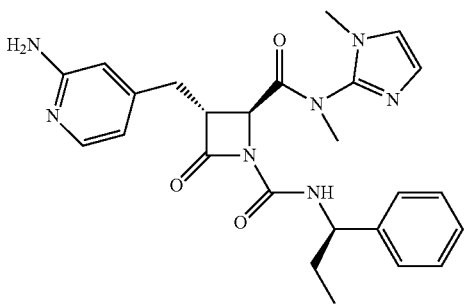 [SMILES: CC[C@@H](NC(=O)N1C(=O)[C@H](Cc2ccnc(N)c2)[C@H]1C(=O)N(C)c1nccn1C)c1ccccc1] |
| 1-14 | 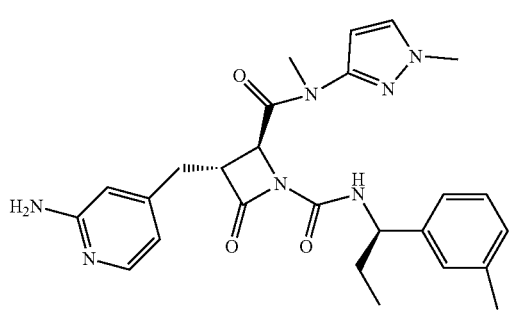 [SMILES: CC[C@@H](NC(=O)N1C(=O)[C@H](Cc2ccnc(N)c2)[C@H]1C(=O)N(C)c1ccn(C)n1)c1cccc(C)c1] |
| 1-15 | 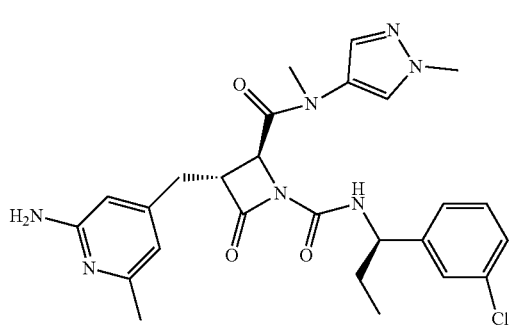 [SMILES: CC[C@@H](NC(=O)N1C(=O)[C@H](Cc2cc(C)nc(N)c2)[C@H]1C(=O)N(C)c1cnn(C)c1)c1cccc(Cl)c1] |
| 1-16 | 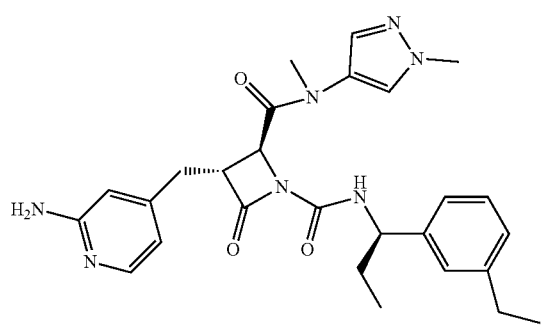 [SMILES: CCc1cccc([C@@H](CC)NC(=O)N2C(=O)[C@H](Cc3ccnc(N)c3)[C@H]2C(=O)N(C)c2cnn(C)c2)c1] |

TABLE 1-continued
Exemplary compounds.
| Compound Number | Structure |
|---|---|
| 1-17 | 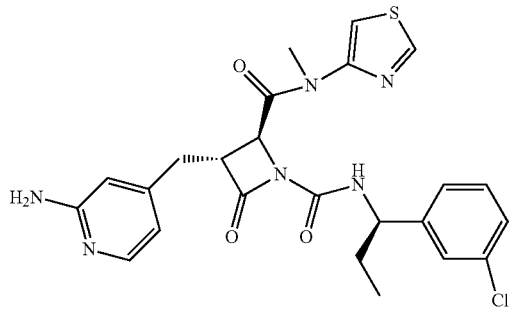 [SMILES: CC[C@@H](NC(=O)N1C(=O)[C@H](Cc2ccnc(N)c2)[C@H]1C(=O)N(C)c1cscn1)c1cccc(Cl)c1] |
| 1-18 | 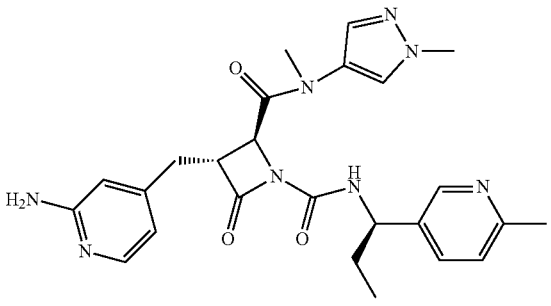 [SMILES: CC[C@@H](NC(=O)N1C(=O)[C@H](Cc2ccnc(N)c2)[C@H]1C(=O)N(C)c1cnn(C)c1)c1ccc(C)nc1] |
| 1-19 | 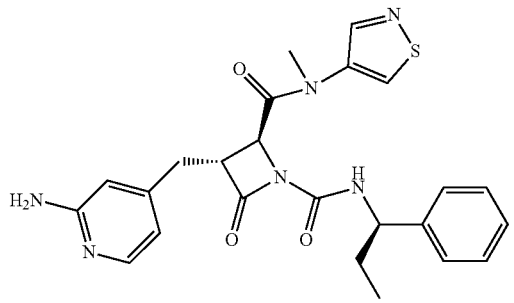 [SMILES: CC[C@@H](NC(=O)N1C(=O)[C@H](Cc2ccnc(N)c2)[C@H]1C(=O)N(C)c1cnsc1)c1ccccc1] |
| 1-20 | 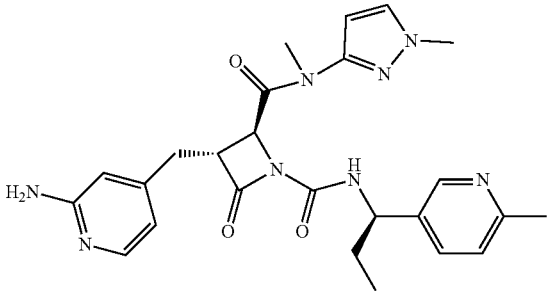 [SMILES: CC[C@@H](NC(=O)N1C(=O)[C@H](Cc2ccnc(N)c2)[C@H]1C(=O)N(C)c1ccn(C)n1)c1ccc(C)nc1] |

TABLE 1-continued

Exemplary compounds.

| Compound Number | Structure |
|---|---|
| 1-21 | 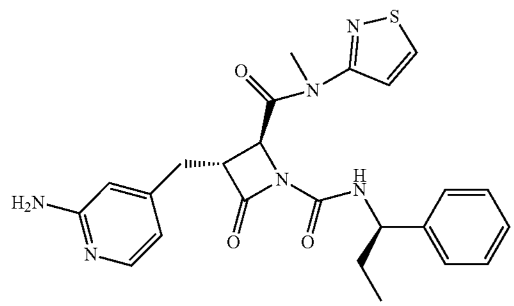 [SMILES: CC[C@@H](NC(=O)N1C(=O)[C@H](Cc2ccnc(N)c2)[C@H]1C(=O)N(C)c1ccsn1)c1ccccc1] |
| 1-22 | 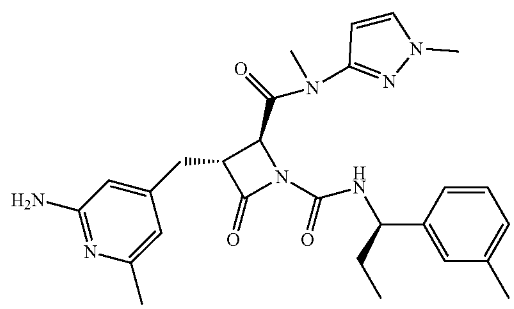 [SMILES: CC[C@@H](NC(=O)N1C(=O)[C@H](Cc2cc(C)nc(N)c2)[C@H]1C(=O)N(C)c1ccn(C)n1)c1cccc(C)c1] |
| 1-23 | 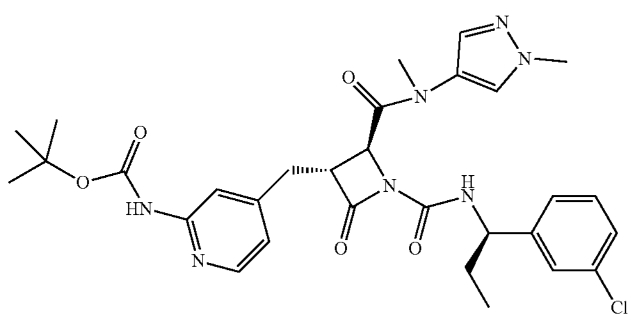 [SMILES: CC[C@@H](NC(=O)N1C(=O)[C@H](Cc2ccnc(NC(=O)OC(C)(C)C)c2)[C@H]1C(=O)N(C)c1cnn(C)c1)c1cccc(Cl)c1] |
| 1-24 | 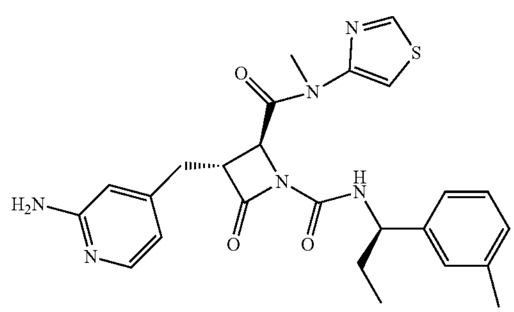 [SMILES: CC[C@@H](NC(=O)N1C(=O)[C@H](Cc2ccnc(N)c2)[C@H]1C(=O)N(C)c1cscn1)c1cccc(C)c1] |
| 1-25 | 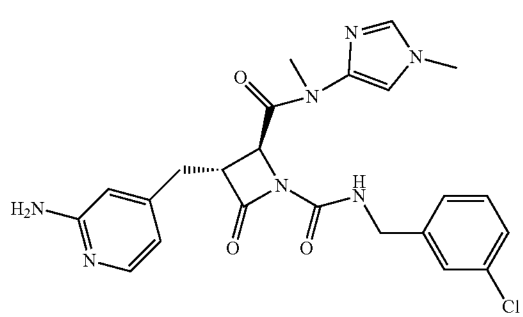 [SMILES: CN(C(=O)[C@@H]1[C@@H](Cc2ccnc(N)c2)C(=O)N1C(=O)NCc1cccc(Cl)c1)c1cn(C)cn1] |

TABLE 1-continued
Exemplary compounds.
| Compound Number | Structure |
|---|---|
| 1-26 | 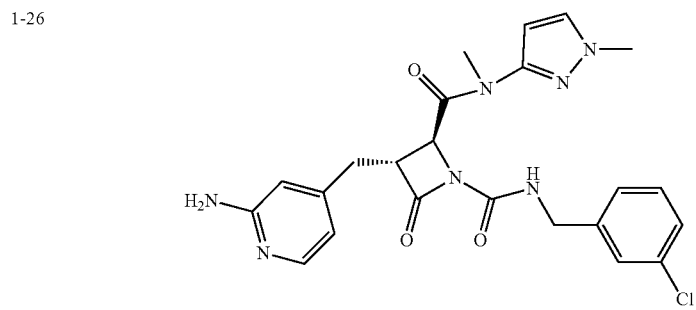 |
| 1-27 | 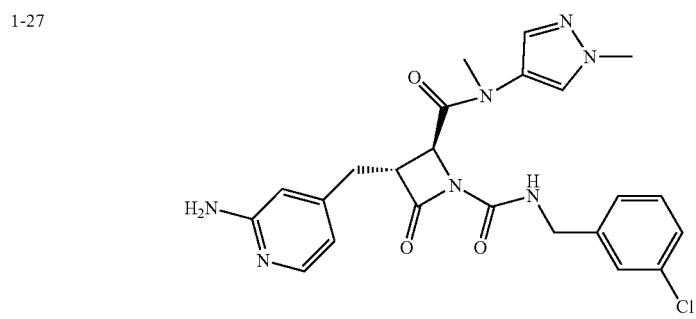 |
| 1-28 | 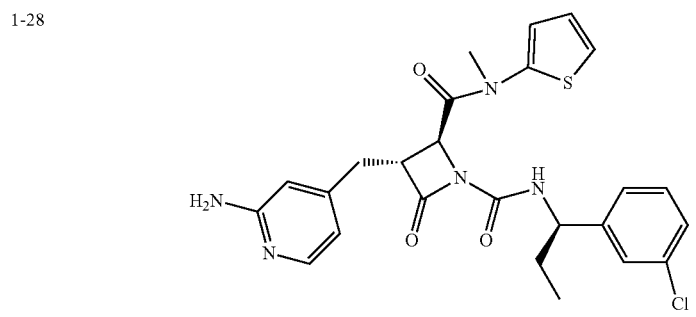 |
| 1-29 | 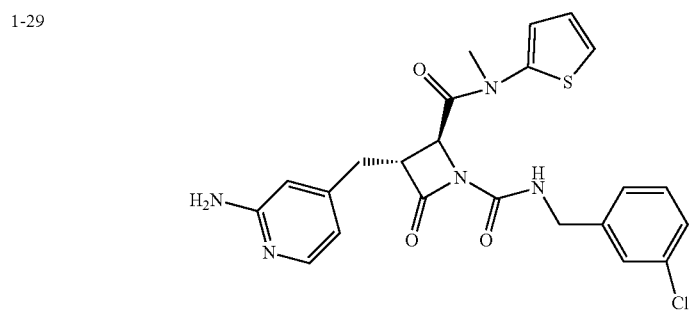 |

TABLE 1-continued

Exemplary compounds.

| Compound Number | Structure |
| --- | --- |
| 1-30 | 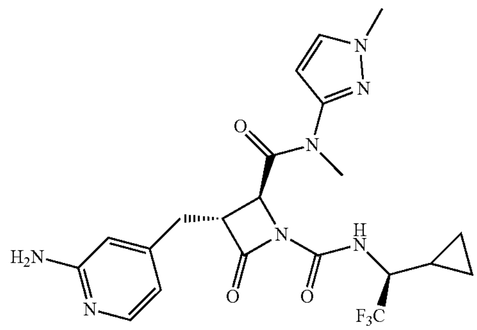 [SMILES: CN(C(=O)[C@@H]1[C@@H](Cc2ccnc(N)c2)C(=O)N1C(=O)N[C@@H](C1CC1)C(F)(F)F)c1ccn(C)n1] |
| 1-31 | 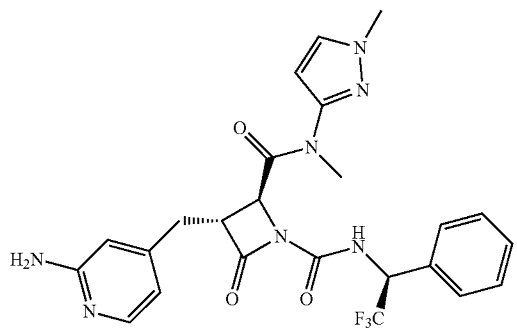 [SMILES: CN(C(=O)[C@@H]1[C@@H](Cc2ccnc(N)c2)C(=O)N1C(=O)N[C@@H](c1ccccc1)C(F)(F)F)c1ccn(C)n1] |
| 1-32 | 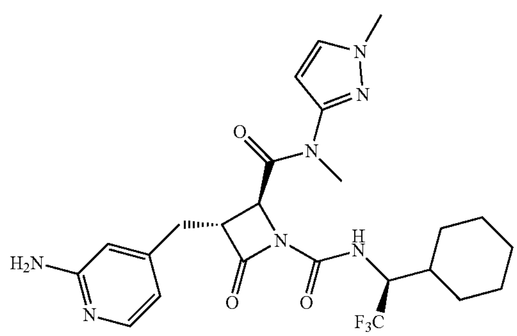 [SMILES: CN(C(=O)[C@@H]1[C@@H](Cc2ccnc(N)c2)C(=O)N1C(=O)N[C@@H](C1CCCCC1)C(F)(F)F)c1ccn(C)n1] |
| 1-33 | 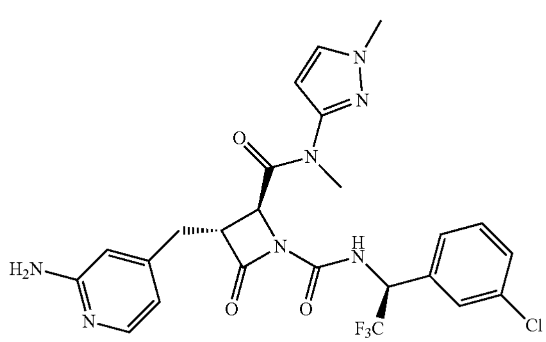 [SMILES: CN(C(=O)[C@@H]1[C@@H](Cc2ccnc(N)c2)C(=O)N1C(=O)N[C@@H](c1cccc(Cl)c1)C(F)(F)F)c1ccn(C)n1] |

TABLE 1-continued

Exemplary compounds.

| Compound Number | Structure |
| --- | --- |
| 1-34 | 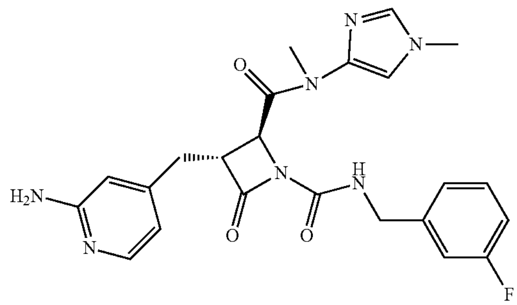 [SMILES: CN(C(=O)[C@@H]1[C@@H](Cc2ccnc(N)c2)C(=O)N1C(=O)NCc1cccc(F)c1)c1cn(C)cn1] |
| 1-35 | 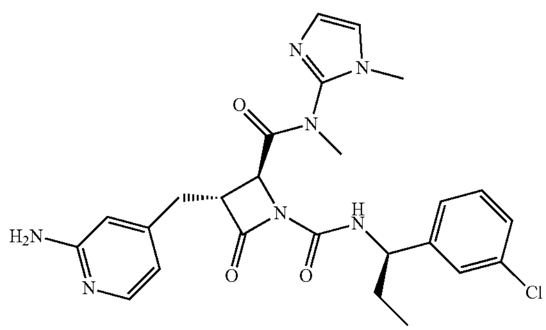 [SMILES: CC[C@@H](NC(=O)N1C(=O)[C@H](Cc2ccnc(N)c2)[C@H]1C(=O)N(C)c1nccn1C)c1cccc(Cl)c1] |
| 1-36 | 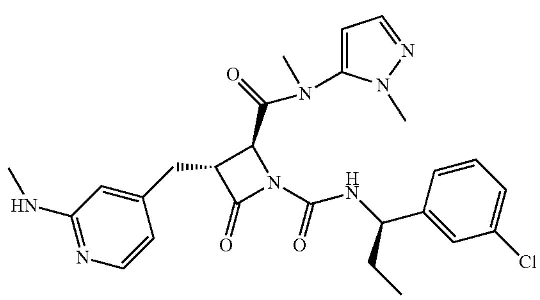 [SMILES: CC[C@@H](NC(=O)N1C(=O)[C@H](Cc2ccnc(NC)c2)[C@H]1C(=O)N(C)c1ccnn1C)c1cccc(Cl)c1] |
| 1-37 | 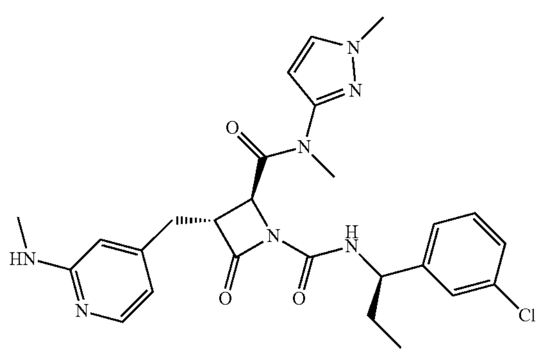 [SMILES: CC[C@@H](NC(=O)N1C(=O)[C@H](Cc2ccnc(NC)c2)[C@H]1C(=O)N(C)c1ccn(C)n1)c1cccc(Cl)c1] |

TABLE 1-continued
Exemplary compounds.
| Compound Number | Structure |
| --- | --- |
| 1-38 | 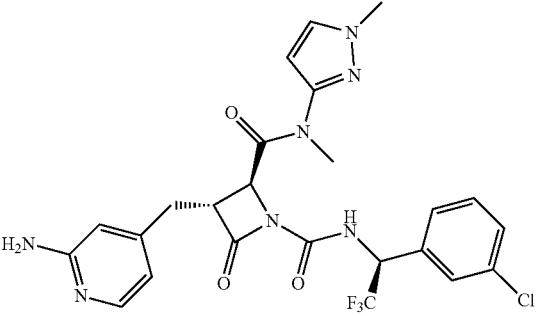 [SMILES: CN(C(=O)[C@@H]1[C@@H](Cc2ccnc(N)c2)C(=O)N1C(=O)N[C@@H](c1cccc(Cl)c1)C(F)(F)F)c1ccn(C)n1] |
| 1-39 | 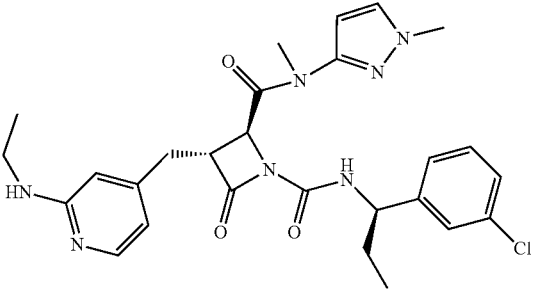 [SMILES: CCNc1cc(C[C@H]2C(=O)N(C(=O)N[C@H](CC)c3cccc(Cl)c3)[C@@H]2C(=O)N(C)c2ccn(C)n2)ccn1] |
| 1-40 | 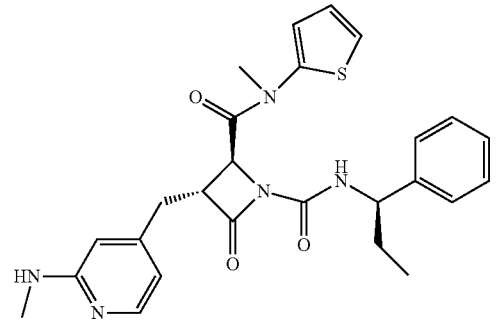 [SMILES: CC[C@@H](NC(=O)N1C(=O)[C@H](Cc2ccnc(NC)c2)[C@H]1C(=O)N(C)c1cccs1)c1ccccc1] |
| 1-41 | 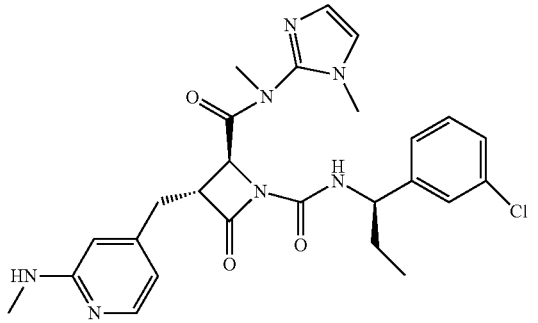 [SMILES: CC[C@@H](NC(=O)N1C(=O)[C@H](Cc2ccnc(NC)c2)[C@H]1C(=O)N(C)c1nccn1C)c1cccc(Cl)c1] |

TABLE 1-continued

Exemplary compounds.

| Compound Number | Structure |
| --- | --- |
| 1-42 | 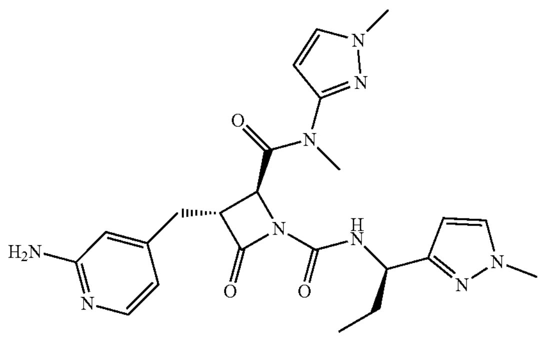 [SMILES: CC[C@@H](NC(=O)N1C(=O)[C@H](Cc2ccnc(N)c2)[C@H]1C(=O)N(C)c1ccn(C)n1)c1ccn(C)n1] |
| 1-43 | 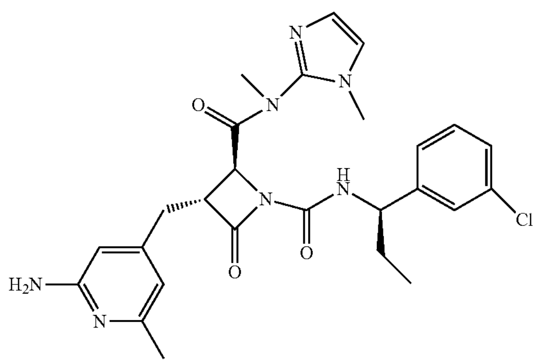 [SMILES: CC[C@@H](NC(=O)N1C(=O)[C@H](Cc2cc(C)nc(N)c2)[C@H]1C(=O)N(C)c1nccn1C)c1cccc(Cl)c1] |
| 1-44 | 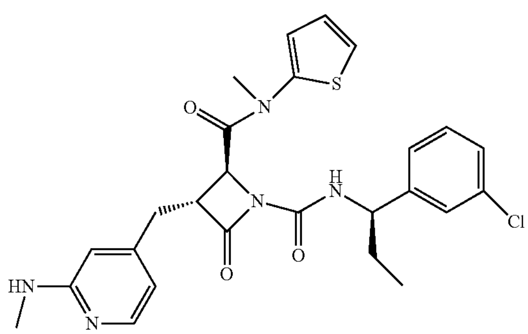 [SMILES: CC[C@@H](NC(=O)N1C(=O)[C@H](Cc2ccnc(NC)c2)[C@H]1C(=O)N(C)c1cccs1)c1cccc(Cl)c1] |
| 1-45 | 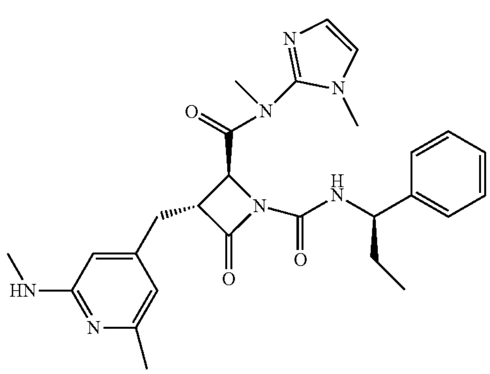 [SMILES: CC[C@@H](NC(=O)N1C(=O)[C@H](Cc2cc(C)nc(NC)c2)[C@H]1C(=O)N(C)c1nccn1C)c1ccccc1] |

TABLE 1-continued

Exemplary compounds.

| Compound Number | Structure |
|---|---|
| 1-46 | 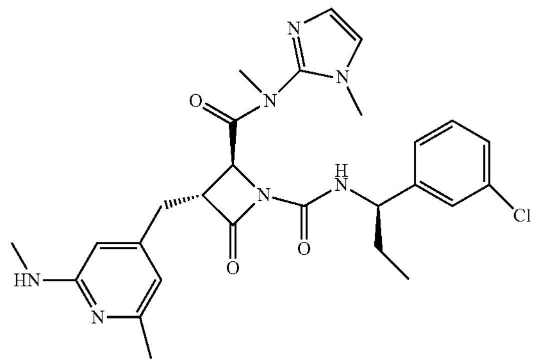 [SMILES: CC[C@@H](NC(=O)N1C(=O)[C@H](Cc2cc(C)nc(NC)c2)[C@H]1C(=O)N(C)c1nccn1C)c1cccc(Cl)c1] |
| 1-47 | 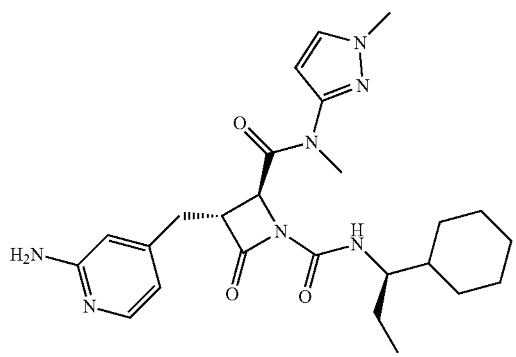 [SMILES: CC[C@@H](NC(=O)N1C(=O)[C@H](Cc2ccnc(N)c2)[C@H]1C(=O)N(C)c1ccn(C)n1)C1CCCCC1] |
| 1-48 | 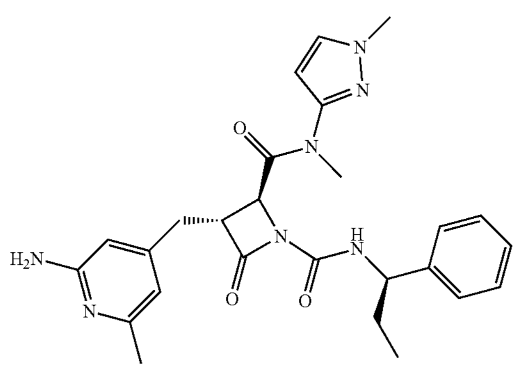 [SMILES: CC[C@@H](NC(=O)N1C(=O)[C@H](Cc2cc(C)nc(N)c2)[C@H]1C(=O)N(C)c1ccn(C)n1)c1ccccc1] |
| 1-49 | 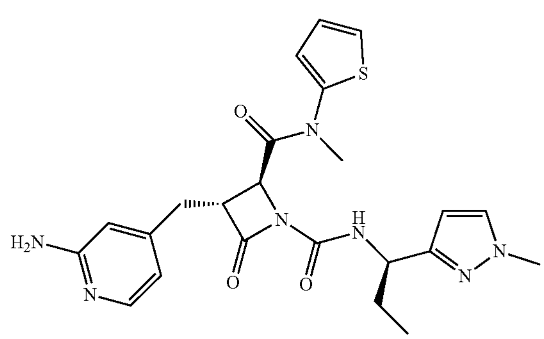 [SMILES: CC[C@@H](NC(=O)N1C(=O)[C@H](Cc2ccnc(N)c2)[C@H]1C(=O)N(C)c1cccs1)c1ccn(C)n1] |

TABLE 1-continued
Exemplary compounds.
| Compound Number | Structure |
|---|---|
| 1-50 | 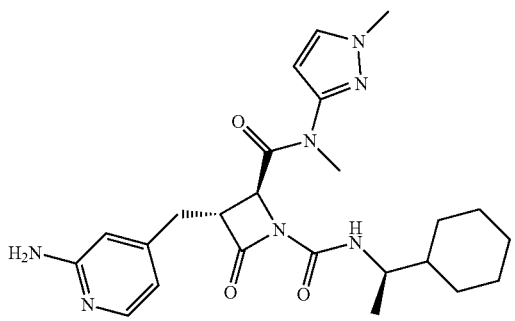 [SMILES: C[C@@H](NC(=O)N1C(=O)[C@H](Cc2ccnc(N)c2)[C@H]1C(=O)N(C)c1ccn(C)n1)C1CCCCC1] |
| 1-51 | 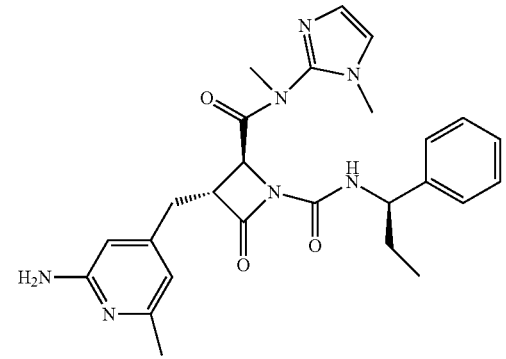 [SMILES: CC[C@@H](NC(=O)N1C(=O)[C@H](Cc2cc(C)nc(N)c2)[C@H]1C(=O)N(C)c1nccn1C)c1ccccc1] |
| 1-52 | 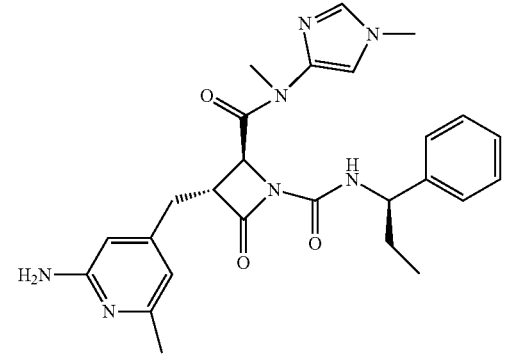 [SMILES: CC[C@@H](NC(=O)N1C(=O)[C@H](Cc2cc(C)nc(N)c2)[C@H]1C(=O)N(C)c1cn(C)cn1)c1ccccc1] |
| 1-53 | 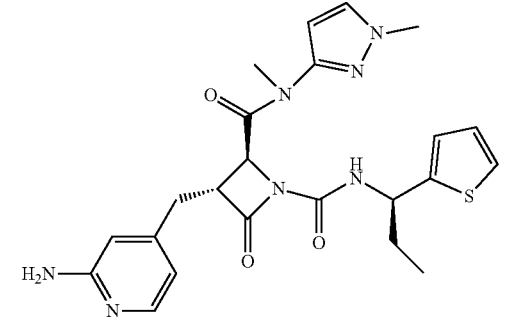 [SMILES: CC[C@@H](NC(=O)N1C(=O)[C@H](Cc2ccnc(N)c2)[C@H]1C(=O)N(C)c1ccn(C)n1)c1cccs1] |

TABLE 1-continued
Exemplary compounds.
| Compound Number | Structure |
|---|---|
| 1-54 | 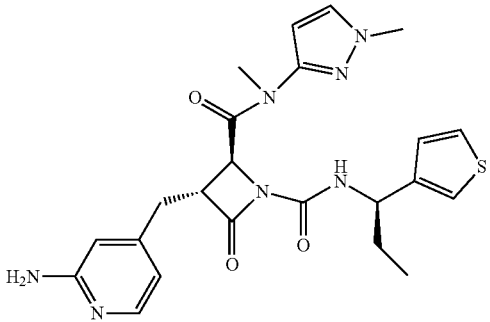 [SMILES: CC[C@@H](NC(=O)N1C(=O)[C@H](Cc2ccnc(N)c2)[C@H]1C(=O)N(C)c1ccn(C)n1)c1ccsc1] |
| 1-55 | 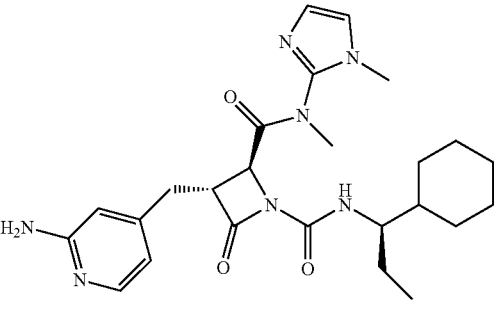 [SMILES: CC[C@@H](NC(=O)N1C(=O)[C@H](Cc2ccnc(N)c2)[C@H]1C(=O)N(C)c1nccn1C)C1CCCCC1] |
| 1-56 | 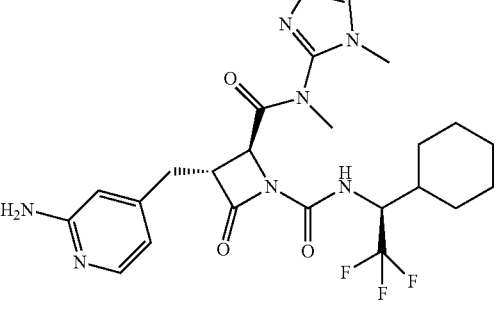 |
| 1-57 | 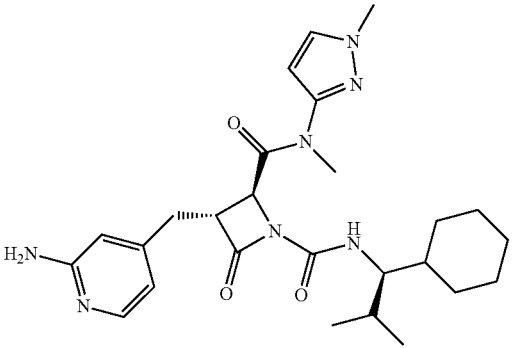 [SMILES: CC(C)[C@@H](NC(=O)N1C(=O)[C@H](Cc2ccnc(N)c2)[C@H]1C(=O)N(C)c1ccn(C)n1)C1CCCCC1] |

TABLE 1-continued

Exemplary compounds.

| Compound Number | Structure |
|---|---|
| 1-58 | 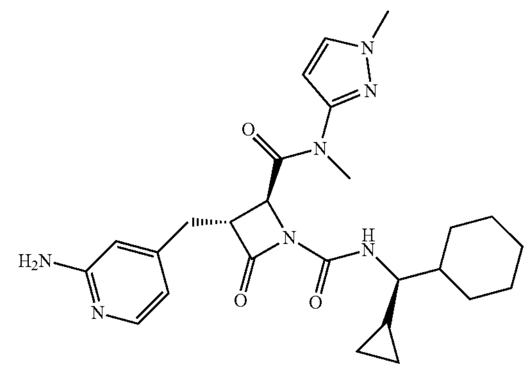 [SMILES: CN(C(=O)[C@@H]1[C@@H](Cc2ccnc(N)c2)C(=O)N1C(=O)N[C@@H](C1CCCCC1)C1CC1)c1ccn(C)n1] |
| 1-60 | 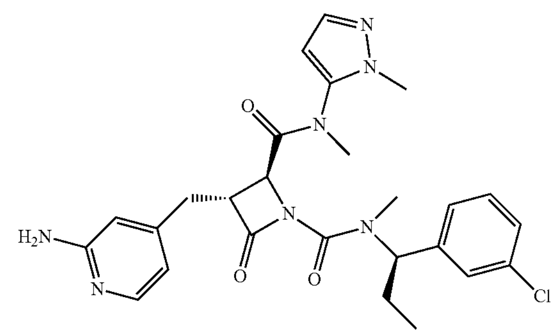 [SMILES: CC[C@H](c1cccc(Cl)c1)N(C)C(=O)N1C(=O)[C@H](Cc2ccnc(N)c2)[C@H]1C(=O)N(C)c1ccnn1C] |
| 1-61 | 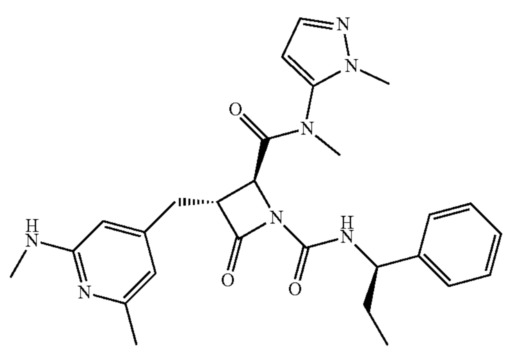 [SMILES: CC[C@@H](NC(=O)N1C(=O)[C@H](Cc2cc(C)nc(NC)c2)[C@H]1C(=O)N(C)c1ccnn1C)c1ccccc1] |
| 1-62 | 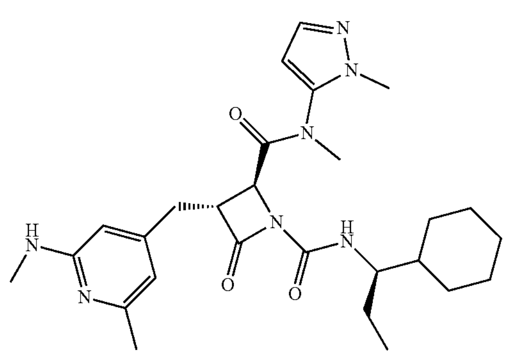 [SMILES: CC[C@@H](NC(=O)N1C(=O)[C@H](Cc2cc(C)nc(NC)c2)[C@H]1C(=O)N(C)c1ccnn1C)C1CCCCC1] |

TABLE 1-continued

Exemplary compounds.

| Compound Number | Structure |
| --- | --- |
| 1-63 | 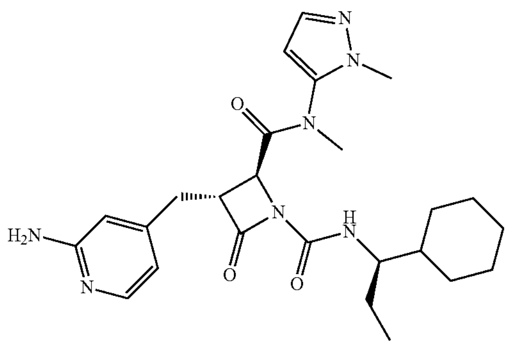 [SMILES: CC[C@@H](NC(=O)N1C(=O)[C@H](Cc2ccnc(N)c2)[C@H]1C(=O)N(C)c1ccnn1C)C1CCCCC1] |
| 1-64 | 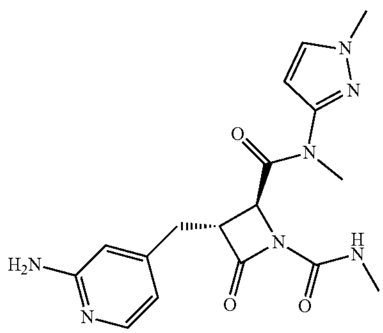 [SMILES: CNC(=O)N1C(=O)[C@H](Cc2ccnc(N)c2)[C@H]1C(=O)N(C)c1ccn(C)n1] |
| 1-65 | 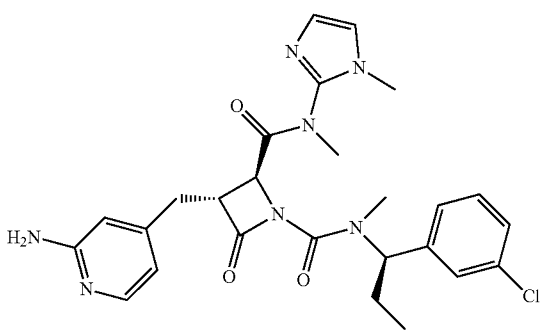 [SMILES: CC[C@H](c1cccc(Cl)c1)N(C)C(=O)N1C(=O)[C@H](Cc2ccnc(N)c2)[C@H]1C(=O)N(C)c1nccn1C] |
| 1-66 | 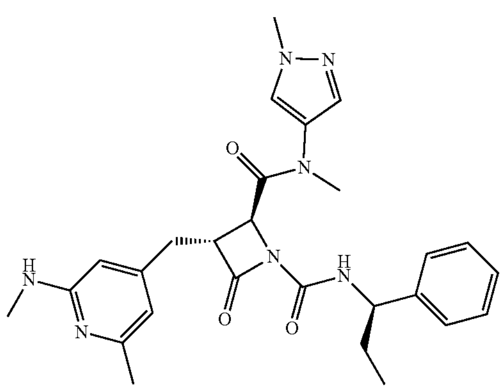 [SMILES: CC[C@@H](NC(=O)N1C(=O)[C@H](Cc2cc(C)nc(NC)c2)[C@H]1C(=O)N(C)c1cnn(C)c1)c1ccccc1] |

TABLE 1-continued

Exemplary compounds.

| Compound Number | Structure |
| --- | --- |
| 1-67 | 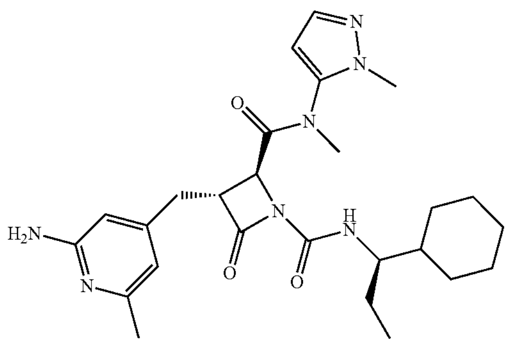 [SMILES: CC[C@@H](NC(=O)N1C(=O)[C@H](Cc2cc(C)nc(N)c2)[C@H]1C(=O)N(C)c1ccnn1C)C1CCCCC1] |
| 1-68 | 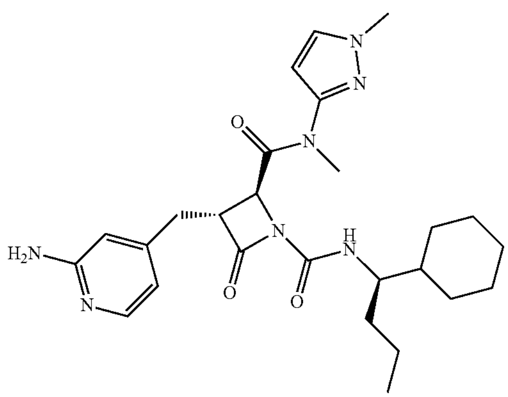 [SMILES: CCC[C@@H](NC(=O)N1C(=O)[C@H](Cc2ccnc(N)c2)[C@H]1C(=O)N(C)c1ccn(C)n1)C1CCCCC1] |
| 1-69 | 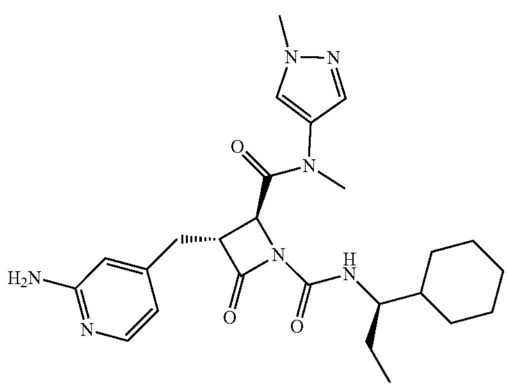 [SMILES: CC[C@@H](NC(=O)N1C(=O)[C@H](Cc2ccnc(N)c2)[C@H]1C(=O)N(C)c1cnn(C)c1)C1CCCCC1] |
| 1-70 | 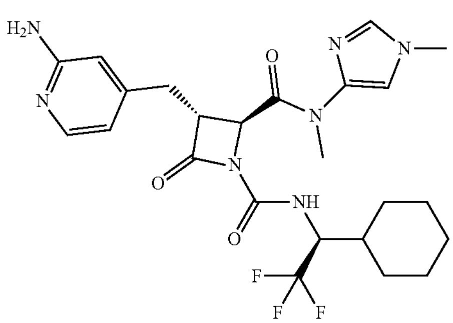 [SMILES: CN(C(=O)[C@@H]1[C@@H](Cc2ccnc(N)c2)C(=O)N1C(=O)N[C@@H](C1CCCCC1)C(F)(F)F)c1cn(C)cn1] |

TABLE 1-continued

Exemplary compounds.

| Compound Number | Structure |
|---|---|
| 1-71 | 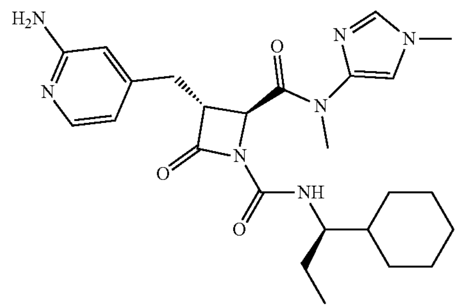 [SMILES: CC[C@@H](NC(=O)N1C(=O)[C@H](Cc2ccnc(N)c2)[C@H]1C(=O)N(C)c1cn(C)cn1)C1CCCCC1] |
| 1-72 | 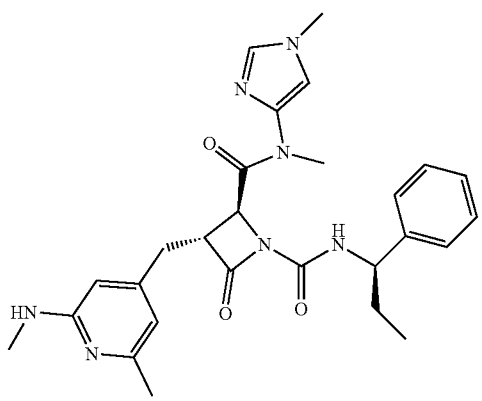 [SMILES: CC[C@@H](NC(=O)N1C(=O)[C@H](Cc2cc(C)nc(NC)c2)[C@H]1C(=O)N(C)c1cn(C)cn1)c1ccccc1] |
| 1-73 | 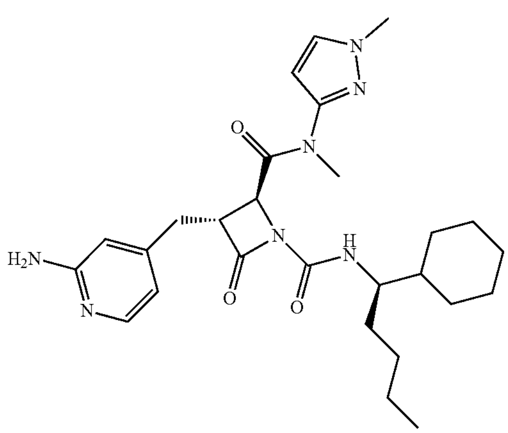 [SMILES: CCCC[C@@H](NC(=O)N1C(=O)[C@H](Cc2ccnc(N)c2)[C@H]1C(=O)N(C)c1ccn(C)n1)C1CCCCC1] |
| 1-74 | 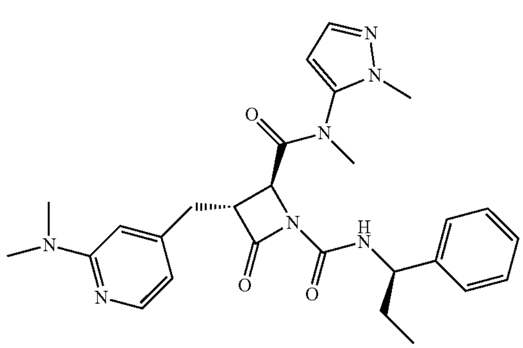 [SMILES: CC[C@@H](NC(=O)N1C(=O)[C@H](Cc2ccnc(N(C)C)c2)[C@H]1C(=O)N(C)c1ccnn1C)c1ccccc1] |

TABLE 1-continued

Exemplary compounds.

| Compound Number | Structure |
|---|---|
| 1-75 | 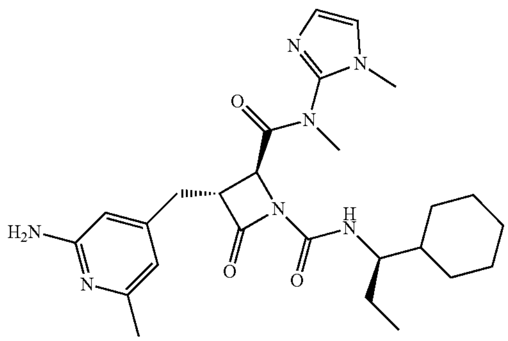 [SMILES: CC[C@@H](NC(=O)N1C(=O)[C@H](Cc2cc(C)nc(N)c2)[C@H]1C(=O)N(C)c1nccn1C)C1CCCCC1] |
| 1-76 | 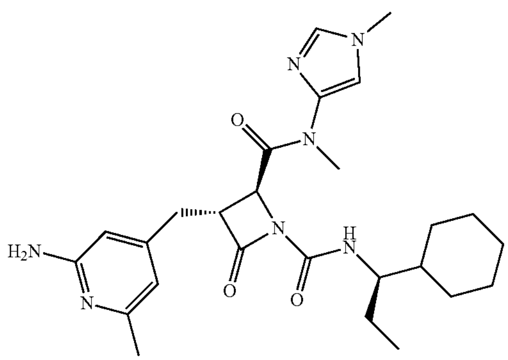 [SMILES: CC[C@@H](NC(=O)N1C(=O)[C@H](Cc2cc(C)nc(N)c2)[C@H]1C(=O)N(C)c1cn(C)cn1)C1CCCCC1] |
| 1-77 | 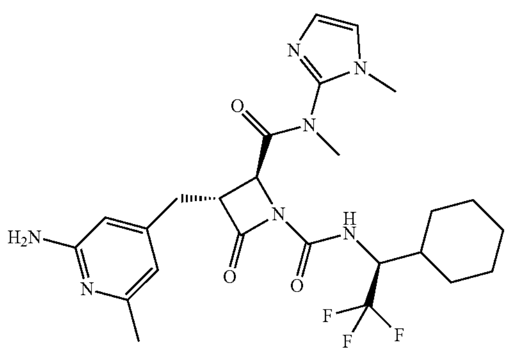 [SMILES: Cc1cc(C[C@H]2C(=O)N(C(=O)N[C@@H](C3CCCCC3)C(F)(F)F)[C@@H]2C(=O)N(C)c2nccn2C)cc(N)n1] |
| 1-78 | 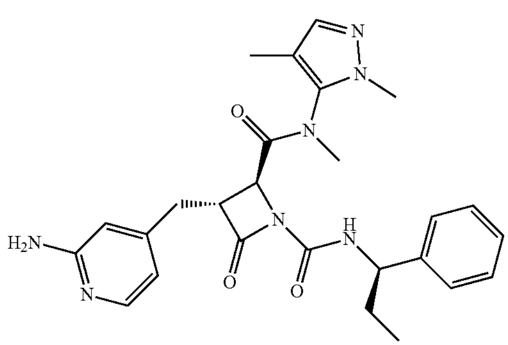 [SMILES: CC[C@@H](NC(=O)N1C(=O)[C@H](Cc2ccnc(N)c2)[C@H]1C(=O)N(C)c1c(C)cnn1C)c1ccccc1] |

TABLE 1-continued

Exemplary compounds.

| Compound Number | Structure |
|---|---|
| 1-79 | 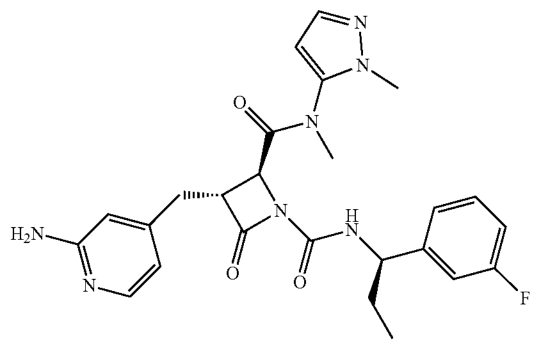 [SMILES: CC[C@@H](NC(=O)N1C(=O)[C@H](Cc2ccnc(N)c2)[C@H]1C(=O)N(C)c1ccnn1C)c1cccc(F)c1] |
| 1-80 | 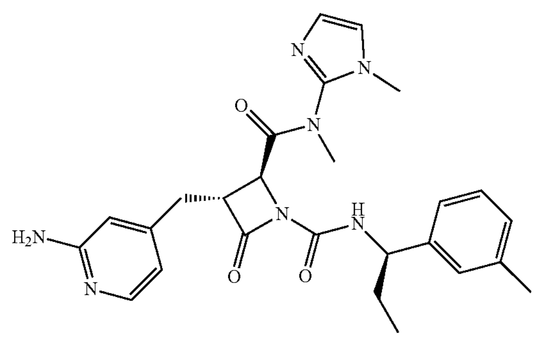 [SMILES: CC[C@@H](NC(=O)N1C(=O)[C@H](Cc2ccnc(N)c2)[C@H]1C(=O)N(C)c1nccn1C)c1cccc(C)c1] |
| 1-81 | 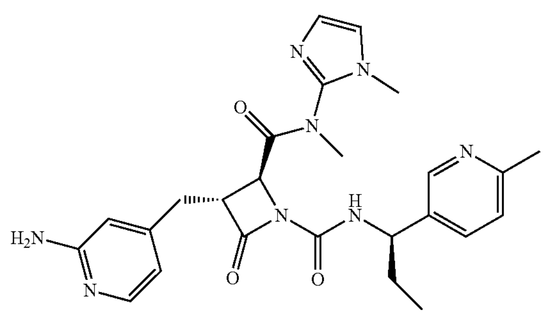 [SMILES: CC[C@@H](NC(=O)N1C(=O)[C@H](Cc2ccnc(N)c2)[C@H]1C(=O)N(C)c1nccn1C)c1ccc(C)nc1] |
| 1-82 | 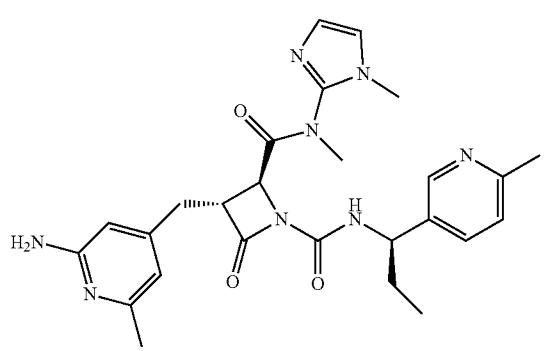 [SMILES: CC[C@@H](NC(=O)N1C(=O)[C@H](Cc2cc(C)nc(N)c2)[C@H]1C(=O)N(C)c1nccn1C)c1ccc(C)nc1] |

TABLE 1-continued

Exemplary compounds.

| Compound Number | Structure |
|---|---|
| 1-83 | 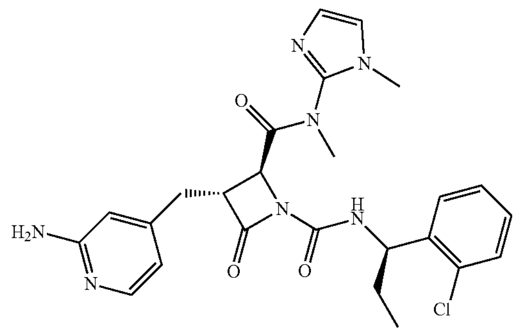 [SMILES: CC[C@@H](NC(=O)N1C(=O)[C@H](Cc2ccnc(N)c2)[C@H]1C(=O)N(C)c1nccn1C)c1ccccc1Cl] |
| 1-84 | 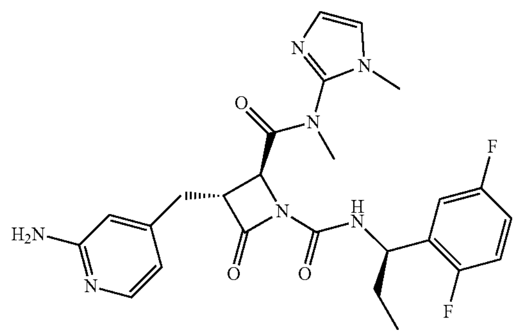 [SMILES: CC[C@@H](NC(=O)N1C(=O)[C@H](Cc2ccnc(N)c2)[C@H]1C(=O)N(C)c1nccn1C)c1cc(F)ccc1F] |
| 1-85 | 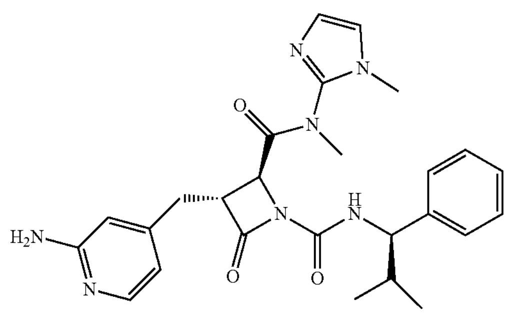 [SMILES: CC(C)[C@@H](NC(=O)N1C(=O)[C@H](Cc2ccnc(N)c2)[C@H]1C(=O)N(C)c1nccn1C)c1ccccc1] |
| 1-86 | 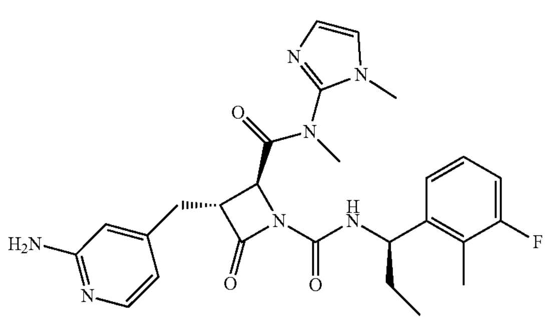 [SMILES: CC[C@@H](NC(=O)N1C(=O)[C@H](Cc2ccnc(N)c2)[C@H]1C(=O)N(C)c1nccn1C)c1cccc(F)c1C] |

TABLE 1-continued

Exemplary compounds.

| Compound Number | Structure |
|---|---|
| 1-87 | 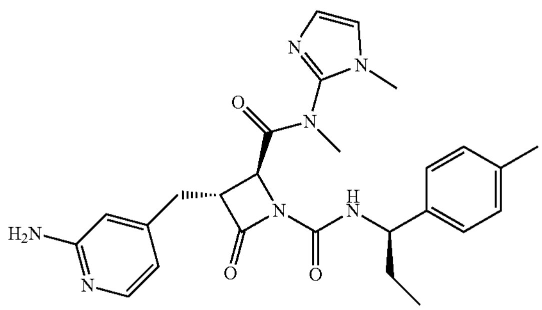 [SMILES: CC[C@@H](NC(=O)N1C(=O)[C@H](Cc2ccnc(N)c2)[C@H]1C(=O)N(C)c1nccn1C)c1ccc(C)cc1] |
| 1-88 | 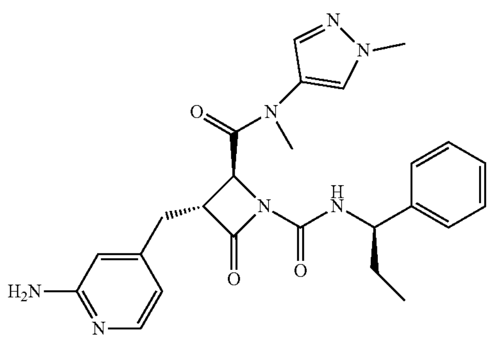 [SMILES: CC[C@@H](NC(=O)N1C(=O)[C@H](Cc2ccnc(N)c2)[C@H]1C(=O)N(C)c1cnn(C)c1)c1ccccc1] |
| 1-89 | 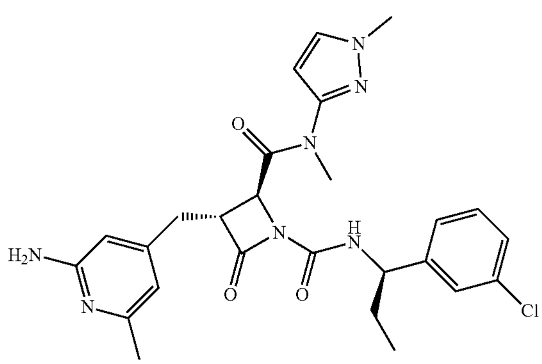 [SMILES: CC[C@@H](NC(=O)N1C(=O)[C@H](Cc2cc(C)nc(N)c2)[C@H]1C(=O)N(C)c1ccn(C)n1)c1cccc(Cl)c1] |
| 1-90 | 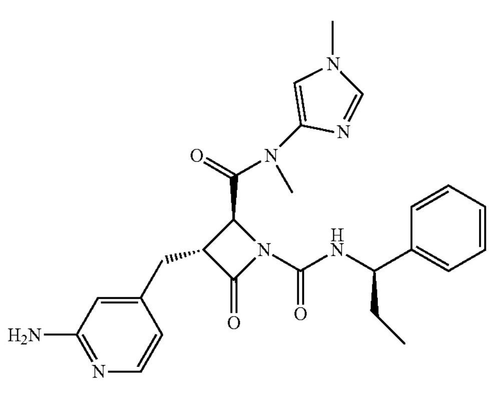 [SMILES: CC[C@@H](NC(=O)N1C(=O)[C@H](Cc2ccnc(N)c2)[C@H]1C(=O)N(C)c1cn(C)cn1)c1ccccc1] |

TABLE 1-continued

Exemplary compounds.

| Compound Number | Structure |
|---|---|
| 1-91 | 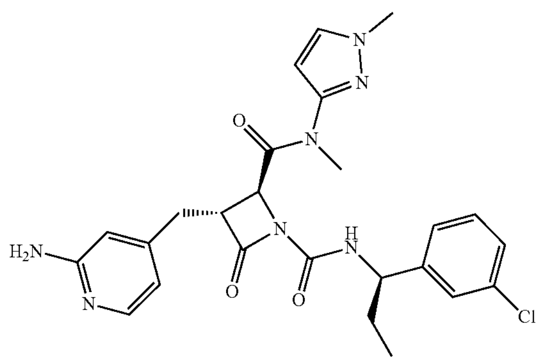 [SMILES: CC[C@@H](NC(=O)N1C(=O)[C@H](Cc2ccnc(N)c2)[C@H]1C(=O)N(C)c1ccn(C)n1)c1cccc(Cl)c1] |
| 1-92 | 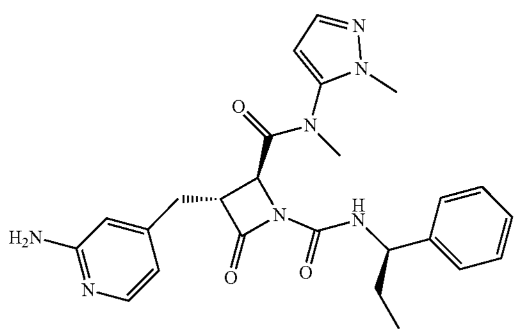 [SMILES: CC[C@@H](NC(=O)N1C(=O)[C@H](Cc2ccnc(N)c2)[C@H]1C(=O)N(C)c1ccnn1C)c1ccccc1] |
| 1-93 | 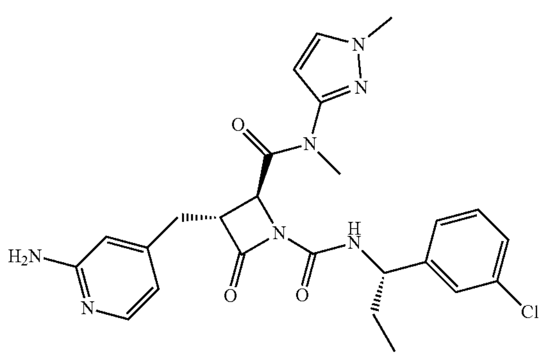 [SMILES: CC[C@H](NC(=O)N1C(=O)[C@H](Cc2ccnc(N)c2)[C@H]1C(=O)N(C)c1ccn(C)n1)c1cccc(Cl)c1] |

TABLE 1-continued
Exemplary compounds.
| Compound Number | Structure |
|---|---|
| | 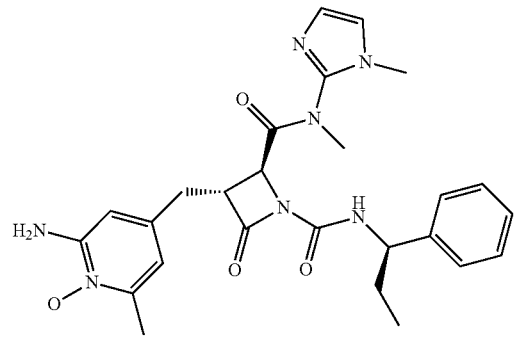 |
| | 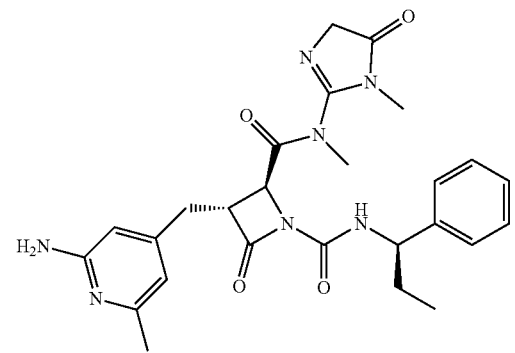 [SMILES: CC[C@@H](NC(=O)N1C(=O)[C@H](Cc2cc(C)nc(N)c2)[C@H]1C(=O)N(C)C1=NCC(=O)N1C)c1ccccc1] |
| 1-94 | 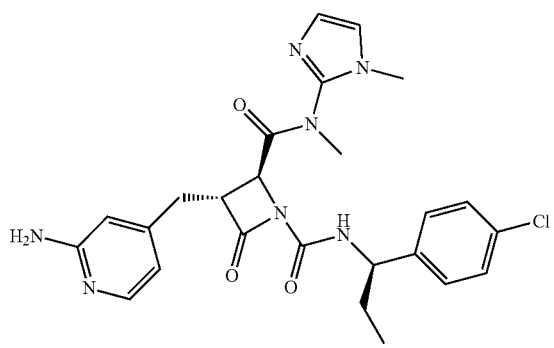 [SMILES: CC[C@@H](NC(=O)N1C(=O)[C@H](Cc2ccnc(N)c2)[C@H]1C(=O)N(C)c1nccn1C)c1ccc(Cl)cc1] |
| 1-95 | 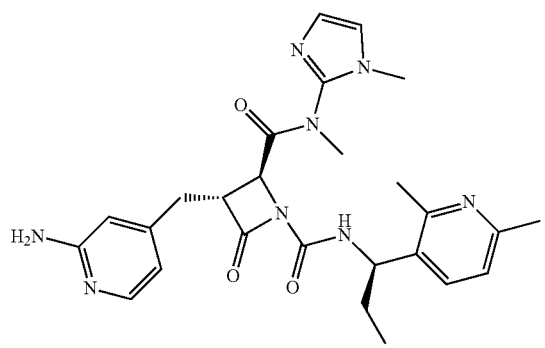 [SMILES: CC[C@@H](NC(=O)N1C(=O)[C@H](Cc2ccnc(N)c2)[C@H]1C(=O)N(C)c1nccn1C)c1ccc(C)nc1C] |

TABLE 1-continued

Exemplary compounds.

| Compound Number | Structure |
|---|---|
| 1-96 | 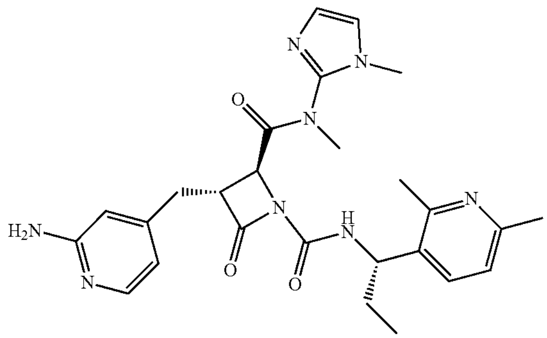 [SMILES: CC[C@H](NC(=O)N1C(=O)[C@H](Cc2ccnc(N)c2)[C@H]1C(=O)N(C)c1nccn1C)c1ccc(C)nc1C] |
| 1-97 | 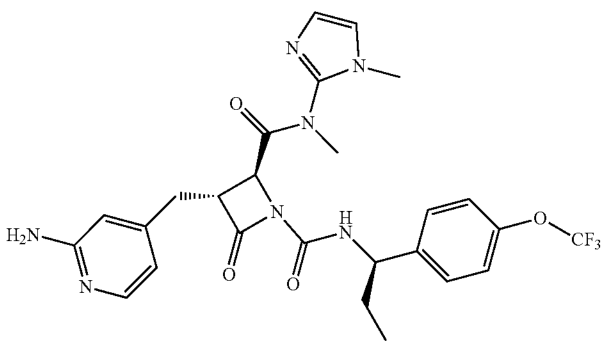 [SMILES: CC[C@@H](NC(=O)N1C(=O)[C@H](Cc2ccnc(N)c2)[C@H]1C(=O)N(C)c1nccn1C)c1ccc(OC(F)(F)F)cc1] |
| 1-98 | 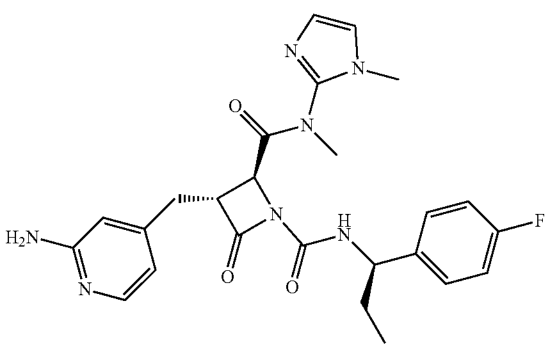 [SMILES: CC[C@@H](NC(=O)N1C(=O)[C@H](Cc2ccnc(N)c2)[C@H]1C(=O)N(C)c1nccn1C)c1ccc(F)cc1] |
| 1-99 | 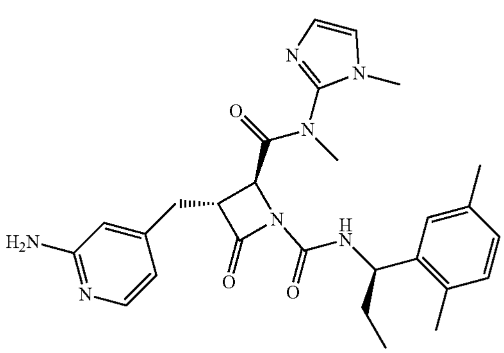 [SMILES: CC[C@@H](NC(=O)N1C(=O)[C@H](Cc2ccnc(N)c2)[C@H]1C(=O)N(C)c1nccn1C)c1cc(C)ccc1C] |

TABLE 1-continued

Exemplary compounds.

| Compound Number | Structure |
|---|---|
| 1-100 | 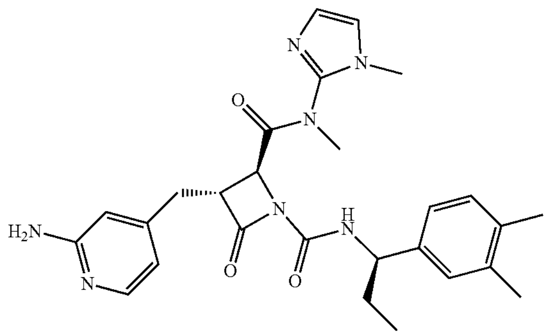 [SMILES: CC[C@@H](NC(=O)N1C(=O)[C@H](Cc2ccnc(N)c2)[C@H]1C(=O)N(C)c1nccn1C)c1ccc(C)c(C)c1] |
| 1-101 | 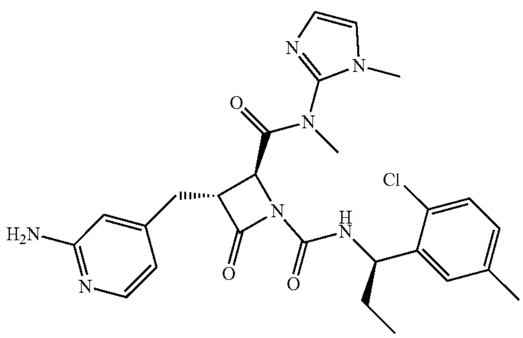 [SMILES: CC[C@@H](NC(=O)N1C(=O)[C@H](Cc2ccnc(N)c2)[C@H]1C(=O)N(C)c1nccn1C)c1cc(C)ccc1F] |
| 1-102 | 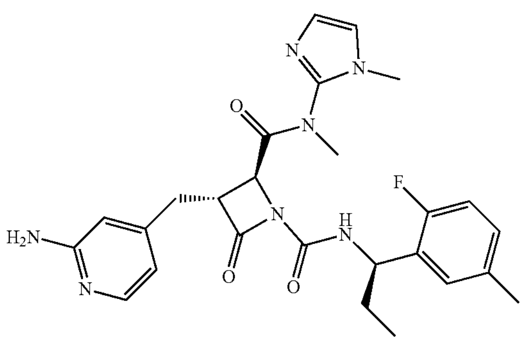 |
| 1-103 | 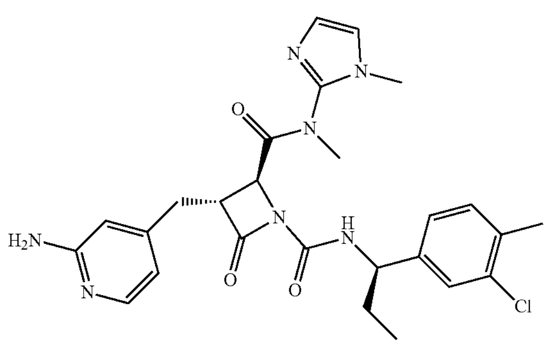 [SMILES: CC[C@@H](NC(=O)N1C(=O)[C@H](Cc2ccnc(N)c2)[C@H]1C(=O)N(C)c1nccn1C)c1ccc(C)c(Cl)c1] |

TABLE 1-continued

Exemplary compounds.

| Compound Number | Structure |
|---|---|
| 1-104 | 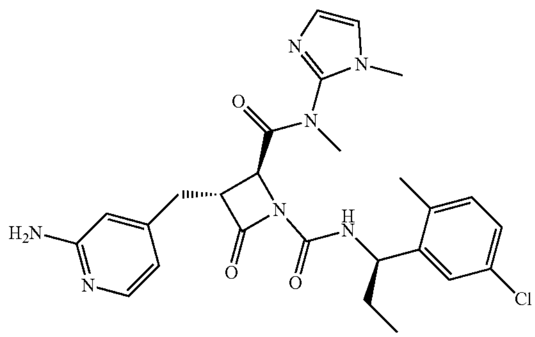 [SMILES: CC[C@@H](NC(=O)N1C(=O)[C@H](Cc2ccnc(N)c2)[C@H]1C(=O)N(C)c1nccn1C)c1cc(Cl)ccc1C] |
| 1-105 | 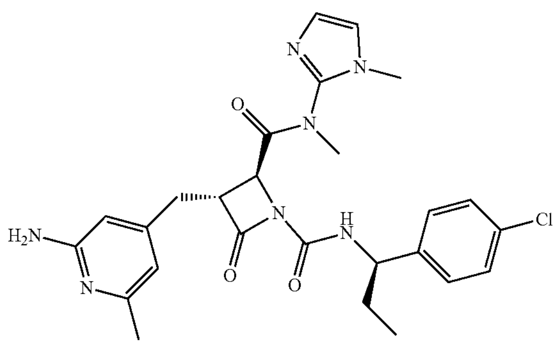 [SMILES: CC[C@@H](NC(=O)N1C(=O)[C@H](Cc2cc(C)nc(N)c2)[C@H]1C(=O)N(C)c1nccn1C)c1ccc(Cl)cc1] |
| 1-106 | 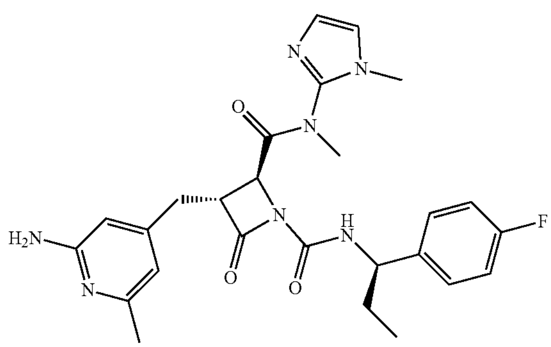 [SMILES: CC[C@@H](NC(=O)N1C(=O)[C@H](Cc2cc(C)nc(N)c2)[C@H]1C(=O)N(C)c1nccn1C)c1ccc(F)cc1] |
| 1-107 | 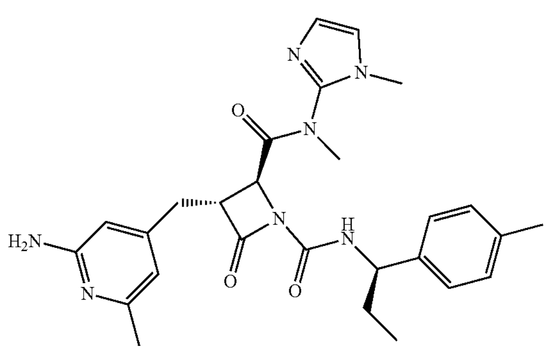 [SMILES: CC[C@@H](NC(=O)N1C(=O)[C@H](Cc2cc(C)nc(N)c2)[C@H]1C(=O)N(C)c1nccn1C)c1ccc(C)cc1] |

TABLE 1-continued

Exemplary compounds.

| Compound Number | Structure |
|---|---|
| 1-108 | 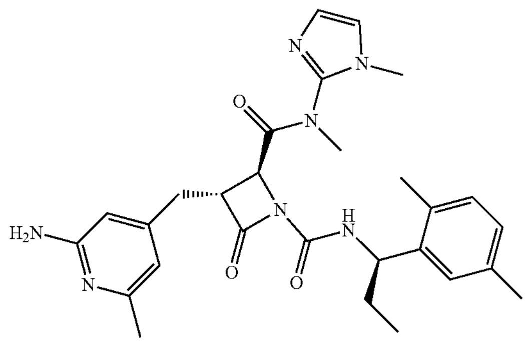 [SMILES: CC[C@@H](NC(=O)N1C(=O)[C@H](Cc2cc(C)nc(N)c2)[C@H]1C(=O)N(C)c1nccn1C)c1cc(C)ccc1C] |
| 1-109 | 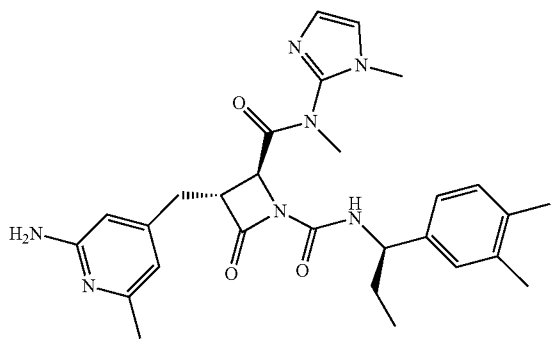 [SMILES: CC[C@@H](NC(=O)N1C(=O)[C@H](Cc2cc(C)nc(N)c2)[C@H]1C(=O)N(C)c1nccn1C)c1ccc(C)c(C)c1] |
| 1-110 | 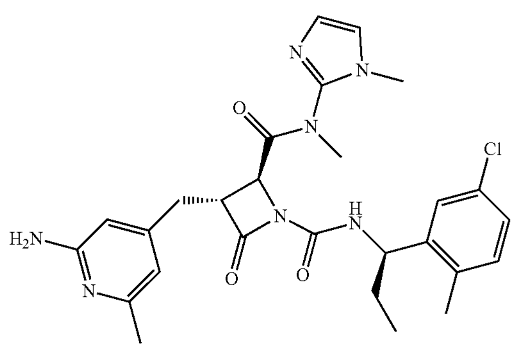 [SMILES: CC[C@@H](NC(=O)N1C(=O)[C@H](Cc2cc(C)nc(N)c2)[C@H]1C(=O)N(C)c1nccn1C)c1cc(Cl)ccc1C] |
| 1-111 | 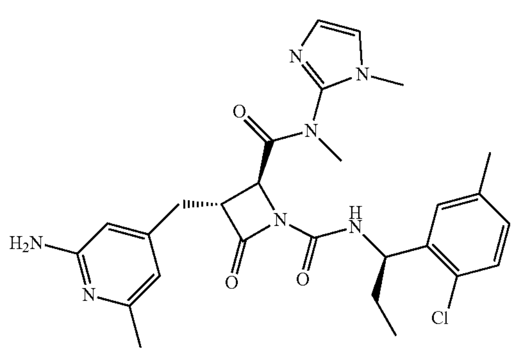 |

TABLE 1-continued

Exemplary compounds.

| Compound Number | Structure |
|---|---|
| 1-112 | 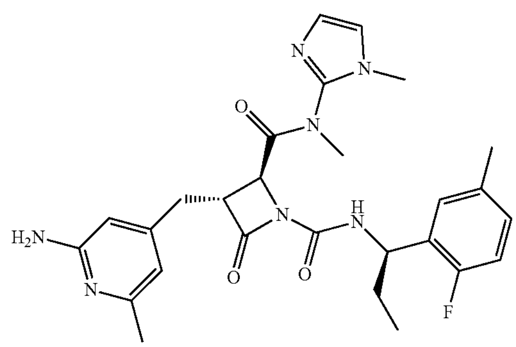 [SMILES: CC[C@@H](NC(=O)N1C(=O)[C@H](Cc2cc(C)nc(N)c2)[C@H]1C(=O)N(C)c1nccn1C)c1cc(C)ccc1F] |
| 1-113 | 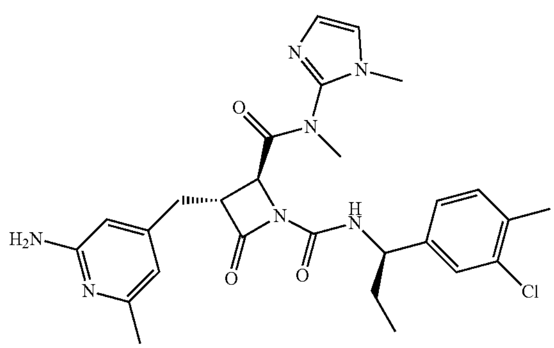 |
| 1-114 | 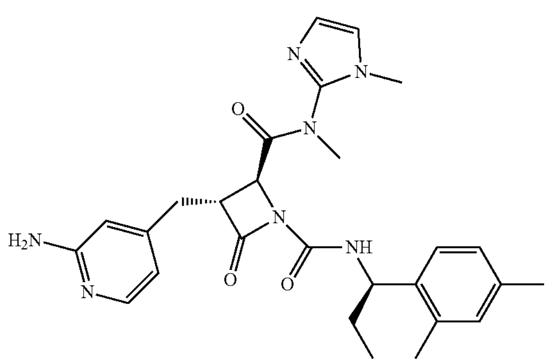 [SMILES: CC[C@@H](NC(=O)N1C(=O)[C@H](Cc2ccnc(N)c2)[C@H]1C(=O)N(C)c1nccn1C)c1ccc(C)cc1C] |
| 1-115 | 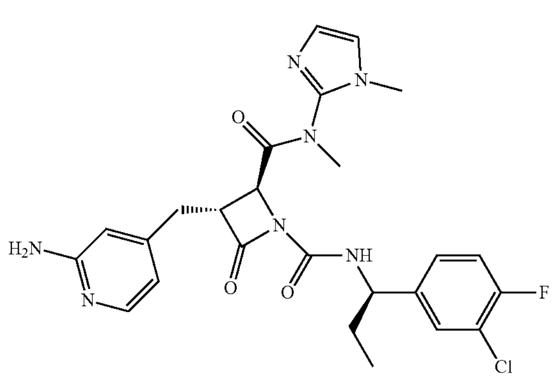 [SMILES: CC[C@@H](NC(=O)N1C(=O)[C@H](Cc2ccnc(N)c2)[C@H]1C(=O)N(C)c1nccn1C)c1ccc(F)c(Cl)c1] |

TABLE 1-continued

Exemplary compounds.

| Compound Number | Structure |
|---|---|
| 1-116 | 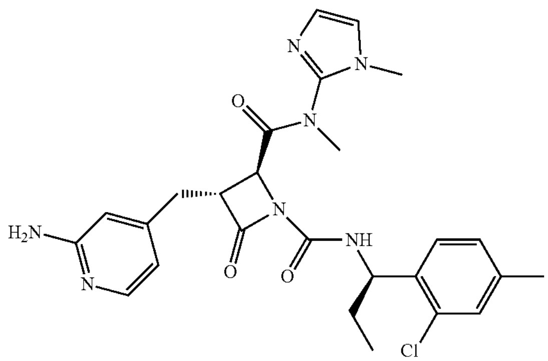 |
| 1-117 | 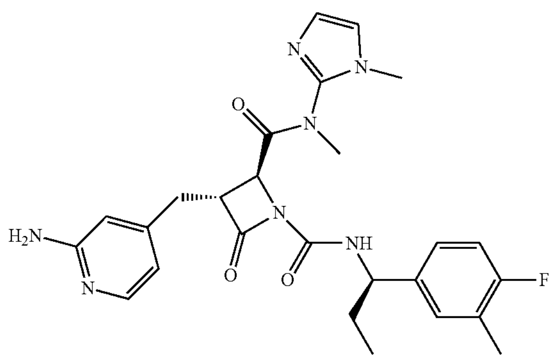 [SMILES: CC[C@@H](NC(=O)N1C(=O)[C@H](Cc2ccnc(N)c2)[C@H]1C(=O)N(C)c1nccn1C)c1ccc(F)c(C)c1] |
| 1-118 | 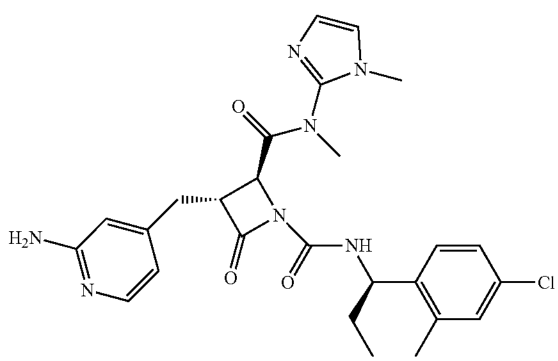 [SMILES: CC[C@@H](NC(=O)N1C(=O)[C@H](Cc2ccnc(N)c2)[C@H]1C(=O)N(C)c1nccn1C)c1ccc(Cl)cc1C] |
| 1-119 | 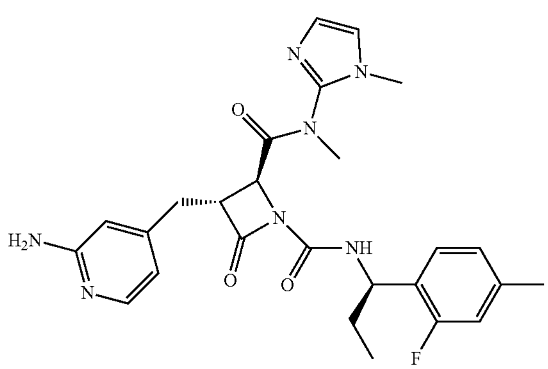 [SMILES: CC[C@@H](NC(=O)N1C(=O)[C@H](Cc2ccnc(N)c2)[C@H]1C(=O)N(C)c1nccn1C)c1ccc(C)cc1F] |

TABLE 1-continued

Exemplary compounds.

| Compound Number | Structure |
|---|---|
| 1-120 | 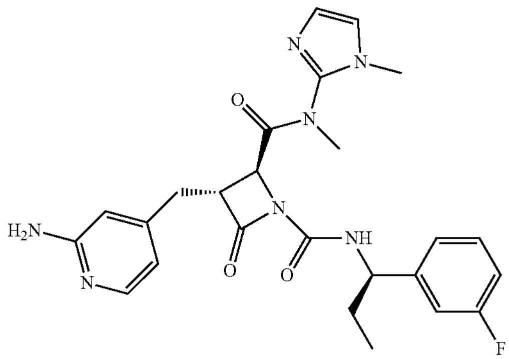 [SMILES: CC[C@@H](NC(=O)N1C(=O)[C@H](Cc2ccnc(N)c2)[C@H]1C(=O)N(C)c1nccn1C)c1cccc(F)c1] |
| 1-121 | 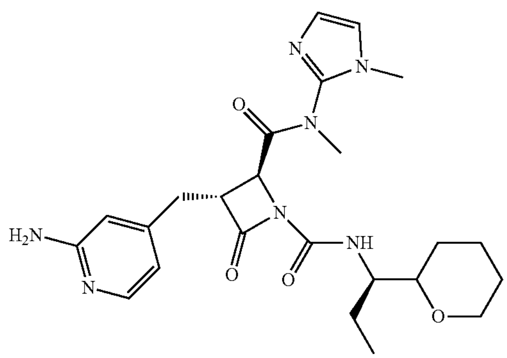 [SMILES: CC[C@@H](NC(=O)N1C(=O)[C@H](Cc2ccnc(N)c2)[C@H]1C(=O)N(C)c1nccn1C)C1CCCCO1] |
| 1-122 | 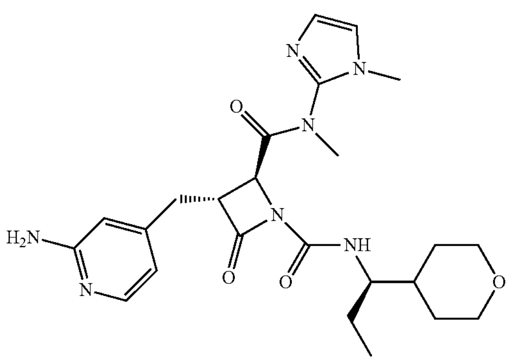 [SMILES: CC[C@@H](NC(=O)N1C(=O)[C@H](Cc2ccnc(N)c2)[C@H]1C(=O)N(C)c1nccn1C)C1CCOCC1] |
| 1-123 | 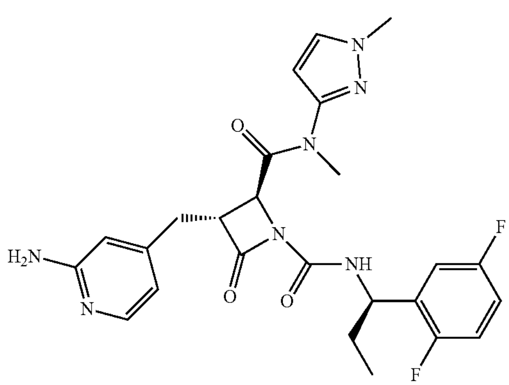 [SMILES: CC[C@@H](NC(=O)N1C(=O)[C@H](Cc2ccnc(N)c2)[C@H]1C(=O)N(C)c1ccn(C)n1)c1cc(F)ccc1F] |

TABLE 1-continued

Exemplary compounds.

| Compound Number | Structure |
|---|---|
| 1-124 | 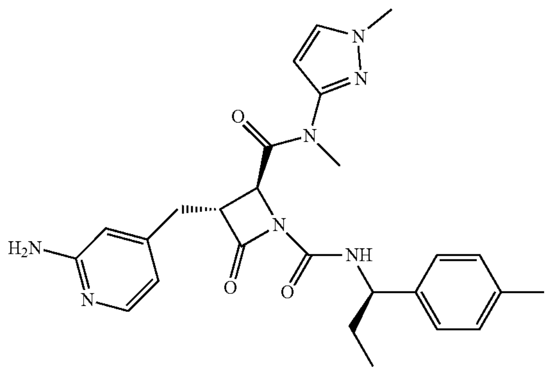 [SMILES: CC[C@@H](NC(=O)N1C(=O)[C@H](Cc2ccnc(N)c2)[C@H]1C(=O)N(C)c1ccn(C)n1)c1ccc(C)cc1] |
| 1-125 | 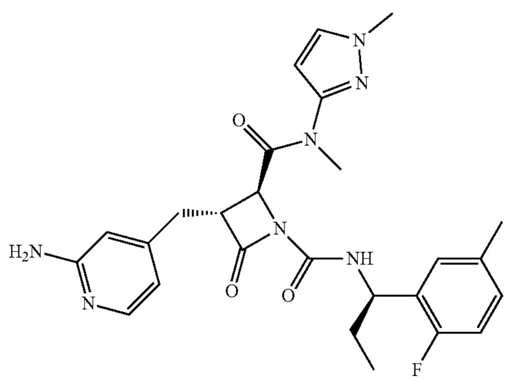 [SMILES: CC[C@@H](NC(=O)N1C(=O)[C@H](Cc2ccnc(N)c2)[C@H]1C(=O)N(C)c1ccn(C)n1)c1cc(C)ccc1F] |
| 1-126 | 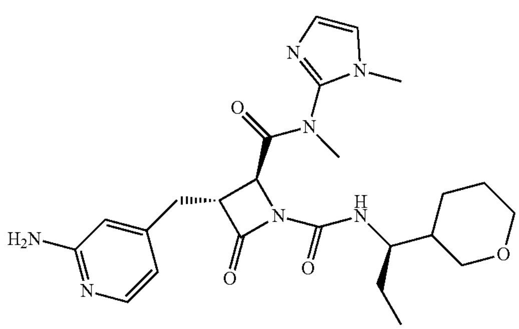 [SMILES: CC[C@@H](NC(=O)N1C(=O)[C@H](Cc2ccnc(N)c2)[C@H]1C(=O)N(C)c1nccn1C)C1CCCOC1] |
| 1-127 | 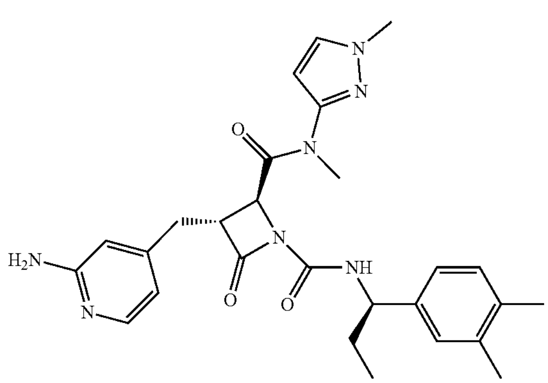 [SMILES: CC[C@@H](NC(=O)N1C(=O)[C@H](Cc2ccnc(N)c2)[C@H]1C(=O)N(C)c1ccn(C)n1)c1ccc(C)c(C)c1] |

TABLE 1-continued

Exemplary compounds.

| Compound Number | Structure |
|---|---|
| 1-128 | 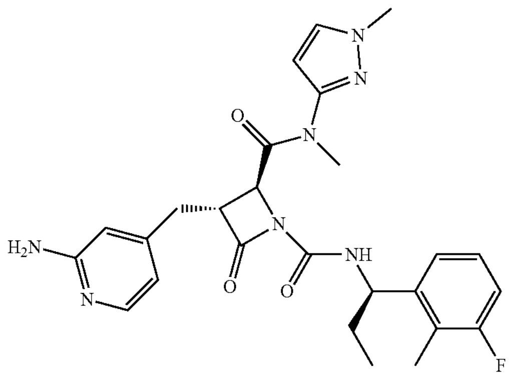 |
| 1-129 | 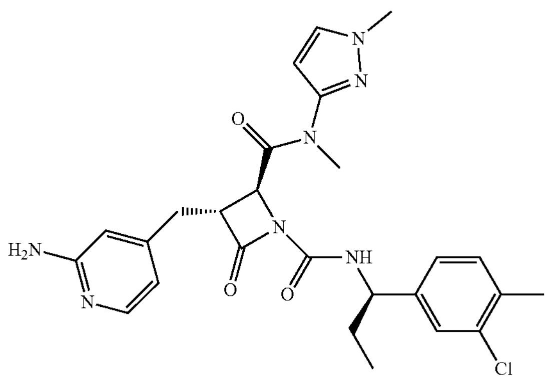 [SMILES: CC[C@@H](NC(=O)N1C(=O)[C@H](Cc2ccnc(N)c2)[C@H]1C(=O)N(C)c1ccn(C)n1)c1ccc(C)c(Cl)c1] |
| 1-130 | 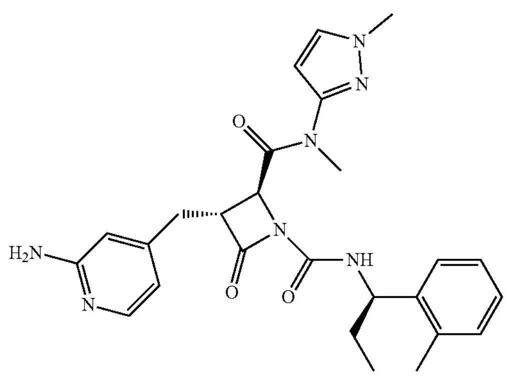 [SMILES: CC[C@@H](NC(=O)N1C(=O)[C@H](Cc2ccnc(N)c2)[C@H]1C(=O)N(C)c1ccn(C)n1)c1ccccc1C] |
| 1-131 | 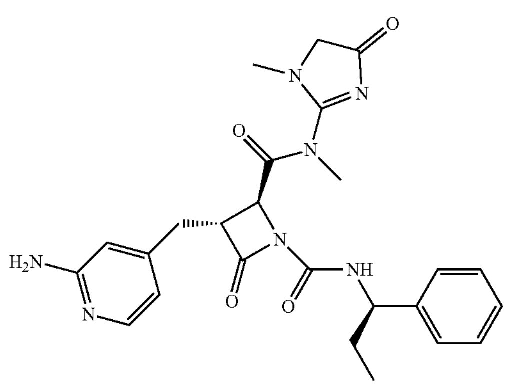 [SMILES: CC[C@@H](NC(=O)N1C(=O)[C@H](Cc2ccnc(N)c2)[C@H]1C(=O)N(C)C1=NC(=O)CN1C)c1ccccc1] |

TABLE 1-continued

Exemplary compounds.

| Compound Number | Structure |
|---|---|
| 1-132 | 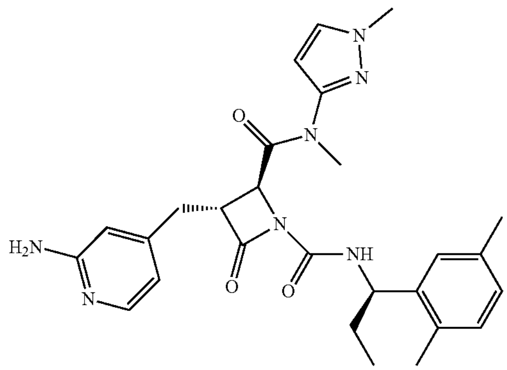 [SMILES: CC[C@@H](NC(=O)N1C(=O)[C@H](Cc2ccnc(N)c2)[C@H]1C(=O)N(C)c1ccn(C)n1)c1cc(C)ccc1C] |
| 1-133 | 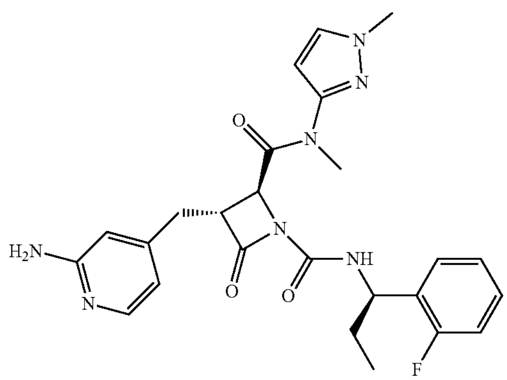 |
| 1-134 | 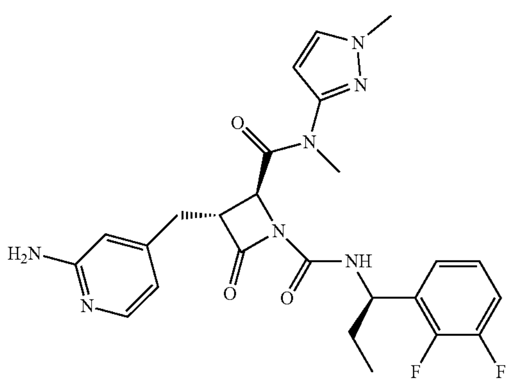 [SMILES: CC[C@@H](NC(=O)N1C(=O)[C@H](Cc2ccnc(N)c2)[C@H]1C(=O)N(C)c1ccn(C)n1)c1cccc(F)c1F] |
| 1-135 | 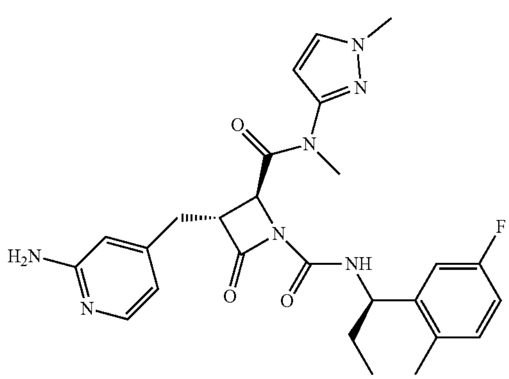 [SMILES: CC[C@@H](NC(=O)N1C(=O)[C@H](Cc2ccnc(N)c2)[C@H]1C(=O)N(C)c1ccn(C)n1)c1cc(F)ccc1C] |

TABLE 1-continued
Exemplary compounds.
| Compound Number | Structure |
|---|---|
| 1-136 | 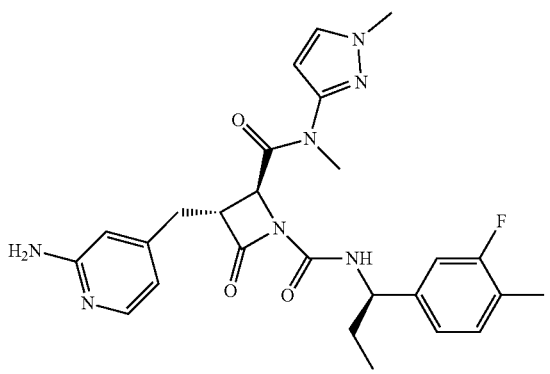 [SMILES: CC[C@@H](NC(=O)N1C(=O)[C@H](Cc2ccnc(N)c2)[C@H]1C(=O)N(C)c1ccn(C)n1)c1ccc(C)c(F)c1] |
| 1-137 | 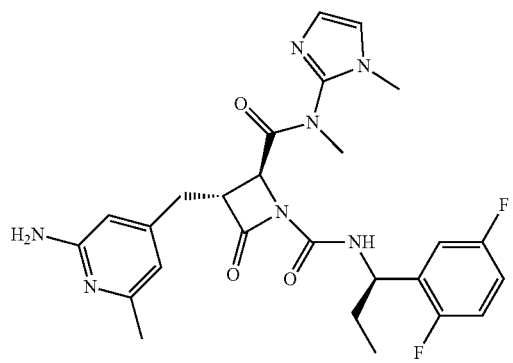 [SMILES: CC[C@@H](NC(=O)N1C(=O)[C@H](Cc2cc(C)nc(N)c2)[C@H]1C(=O)N(C)c1nccn1C)c1cc(F)ccc1F] |
| 1-138 | 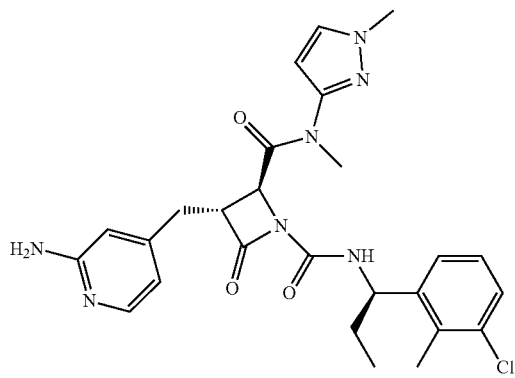 [SMILES: CC[C@@H](NC(=O)N1C(=O)[C@H](Cc2ccnc(N)c2)[C@H]1C(=O)N(C)c1ccn(C)n1)c1cccc(Cl)c1C] |
| 1-139 | 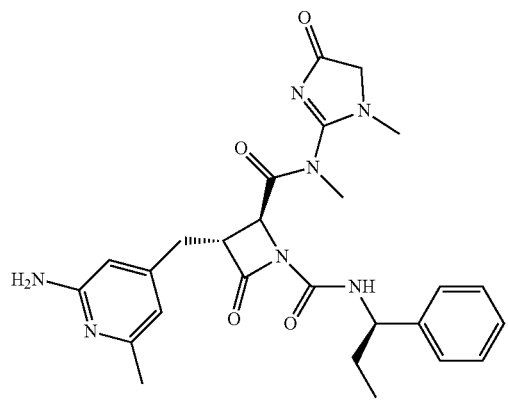 [SMILES: CC[C@@H](NC(=O)N1C(=O)[C@H](Cc2cc(C)nc(N)c2)[C@H]1C(=O)N(C)C1=NC(=O)CN1C)c1ccccc1] |

TABLE 1-continued

Exemplary compounds.

| Compound Number | Structure |
|---|---|
| 1-140 | 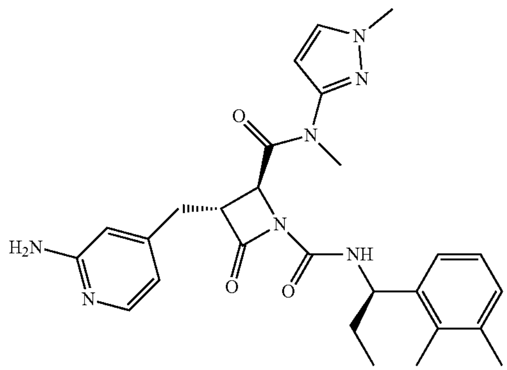 [SMILES: CC[C@@H](NC(=O)N1C(=O)[C@H](Cc2ccnc(N)c2)[C@H]1C(=O)N(C)c1ccn(C)n1)c1cccc(C)c1C] |
| 1-141 | 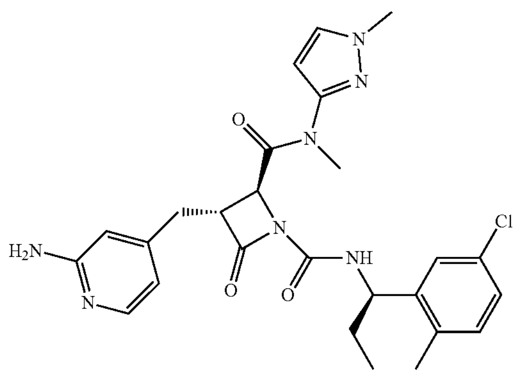 [SMILES: CC[C@@H](NC(=O)N1C(=O)[C@H](Cc2ccnc(N)c2)[C@H]1C(=O)N(C)c1ccn(C)n1)c1cc(Cl)ccc1C] |
| 1-142 | 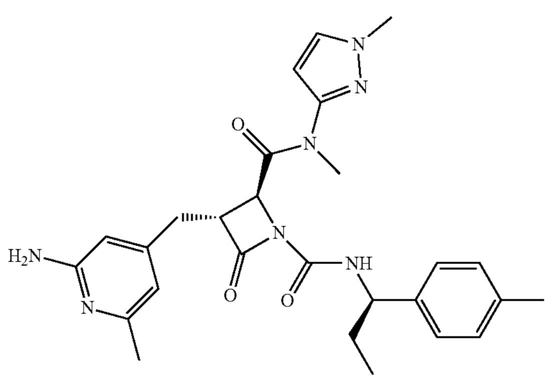 [SMILES: CC[C@@H](NC(=O)N1C(=O)[C@H](Cc2cc(C)nc(N)c2)[C@H]1C(=O)N(C)c1ccn(C)n1)c1ccc(C)cc1] |
| 1-143 | 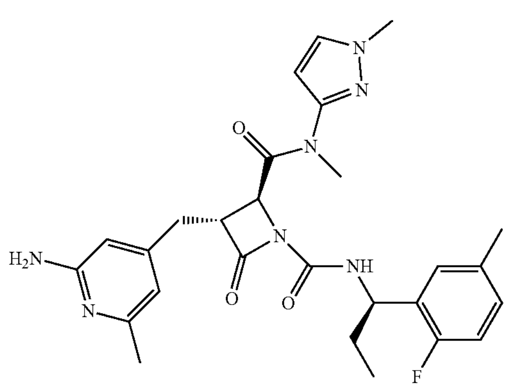 [SMILES: CC[C@@H](NC(=O)N1C(=O)[C@H](Cc2cc(C)nc(N)c2)[C@H]1C(=O)N(C)c1ccn(C)n1)c1cc(C)ccc1F] |

TABLE 1-continued
Exemplary compounds.
| Compound Number | Structure |
|---|---|
| 1-144 | 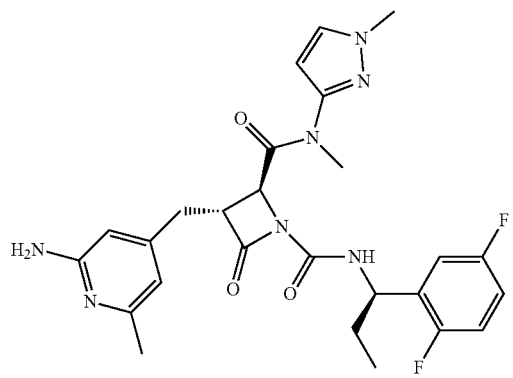 [SMILES: CC[C@@H](NC(=O)N1C(=O)[C@H](Cc2cc(C)nc(N)c2)[C@H]1C(=O)N(C)c1ccn(C)n1)c1cc(F)ccc1F] |
| 1-145 | 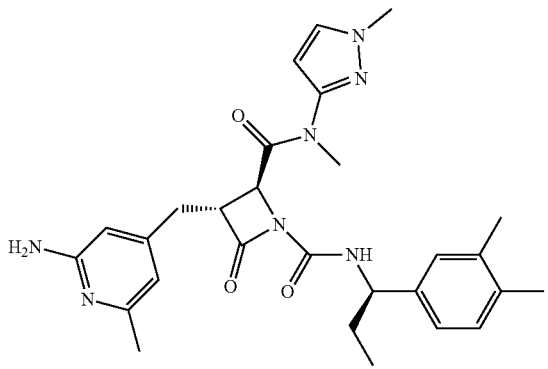 [SMILES: CC[C@@H](NC(=O)N1C(=O)[C@H](Cc2cc(C)nc(N)c2)[C@H]1C(=O)N(C)c1ccn(C)n1)c1ccc(C)c(C)c1] |
| 1-146 | 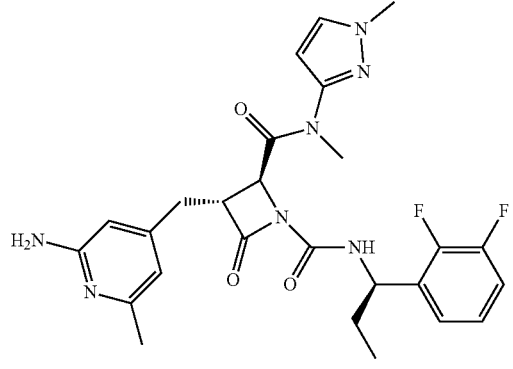 [SMILES: CC[C@@H](NC(=O)N1C(=O)[C@H](Cc2cc(C)nc(N)c2)[C@H]1C(=O)N(C)c1ccn(C)n1)c1cccc(F)c1F] |
| 1-147 | 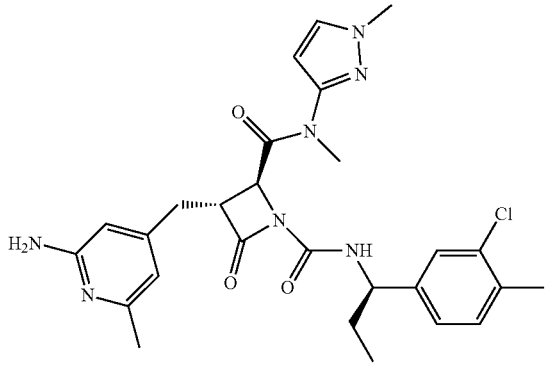 [SMILES: CC[C@@H](NC(=O)N1C(=O)[C@H](Cc2cc(C)nc(N)c2)[C@H]1C(=O)N(C)c1ccn(C)n1)c1ccc(C)c(Cl)c1] |

TABLE 1-continued

Exemplary compounds.

| Compound Number | Structure |
|---|---|
| 1-148 | 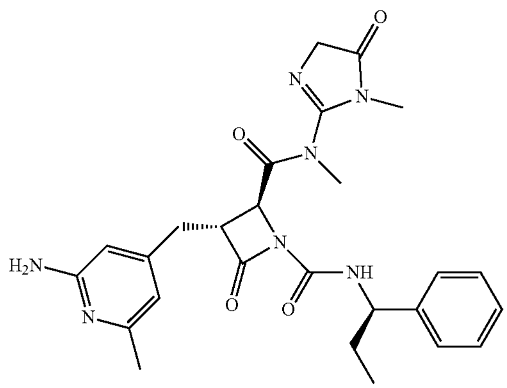 [SMILES: CC[C@@H](NC(=O)N1C(=O)[C@H](Cc2cc(C)nc(N)c2)[C@H]1C(=O)N(C)C1=NCC(=O)N1C)c1ccccc1] |
| 1-149 | 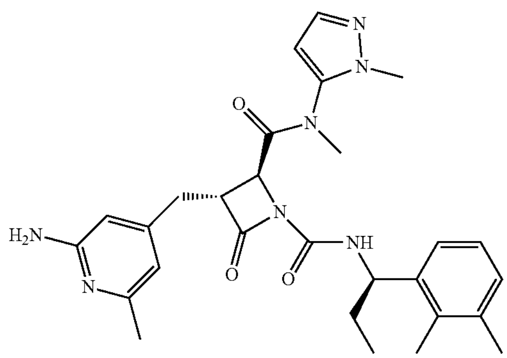 [SMILES: CC[C@@H](NC(=O)N1C(=O)[C@H](Cc2cc(C)nc(N)c2)[C@H]1C(=O)N(C)c1ccnn1C)c1cccc(C)c1C] |
| 1-150 | 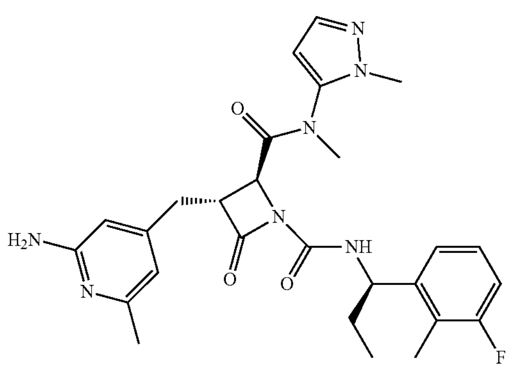 |
| 1-151 | 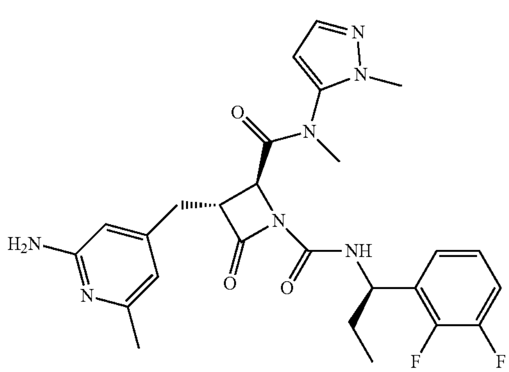 [SMILES: CC[C@@H](NC(=O)N1C(=O)[C@H](Cc2cc(C)nc(N)c2)[C@H]1C(=O)N(C)c1ccnn1C)c1cccc(F)c1F] |

TABLE 1-continued
Exemplary compounds.
| Compound Number | Structure |
|---|---|
| 1-152 | 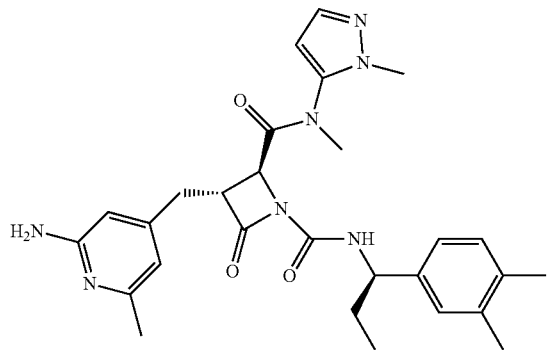 [SMILES: CC[C@@H](NC(=O)N1C(=O)[C@H](Cc2cc(C)nc(N)c2)[C@H]1C(=O)N(C)c1ccnn1C)c1ccc(C)c(C)c1] |
| 1-153 | 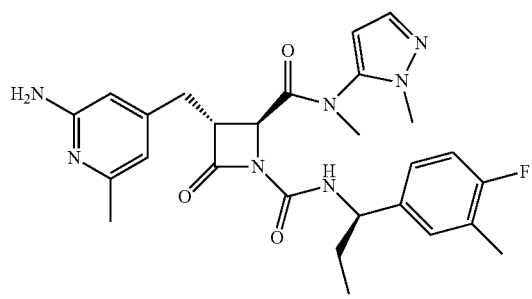 [SMILES: CC[C@@H](NC(=O)N1C(=O)[C@H](Cc2cc(C)nc(N)c2)[C@H]1C(=O)N(C)c1ccnn1C)c1ccc(F)c(C)c1] |
| 1-154 | 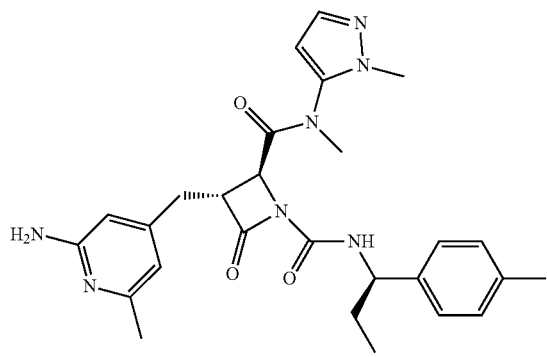 |
| 1-155 | 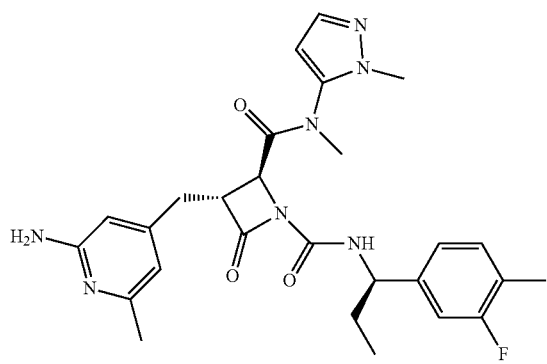 [SMILES: CC[C@@H](NC(=O)N1C(=O)[C@H](Cc2cc(C)nc(N)c2)[C@H]1C(=O)N(C)c1ccnn1C)c1ccc(C)c(F)c1] |

TABLE 1-continued
Exemplary compounds.
| Compound Number | Structure |
|---|---|
| 1-156 | 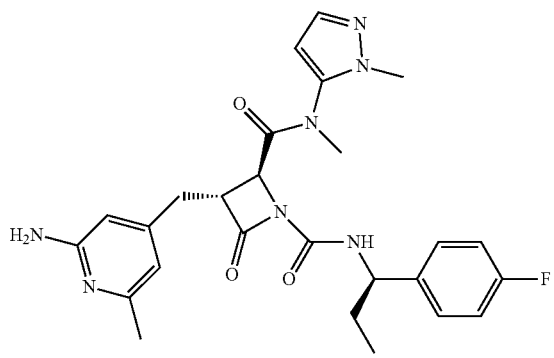 [SMILES: CC[C@@H](NC(=O)N1C(=O)[C@H](Cc2cc(C)nc(N)c2)[C@H]1C(=O)N(C)c1ccnn1C)c1ccc(F)cc1] |
| 1-157 | 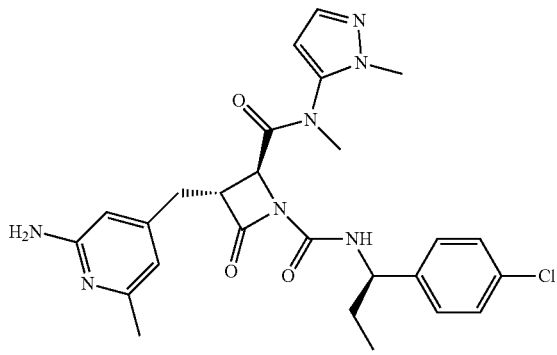 [SMILES: CC[C@@H](NC(=O)N1C(=O)[C@H](Cc2cc(C)nc(N)c2)[C@H]1C(=O)N(C)c1ccnn1C)c1ccc(Cl)cc1] |
| 1-158 | 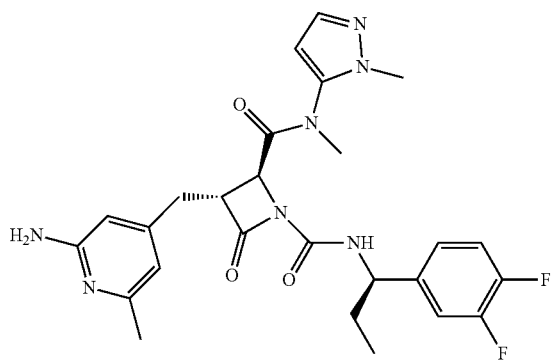 [SMILES: CC[C@@H](NC(=O)N1C(=O)[C@H](Cc2cc(C)nc(N)c2)[C@H]1C(=O)N(C)c1ccnn1C)c1ccc(F)c(F)c1] |
| 1-159 | 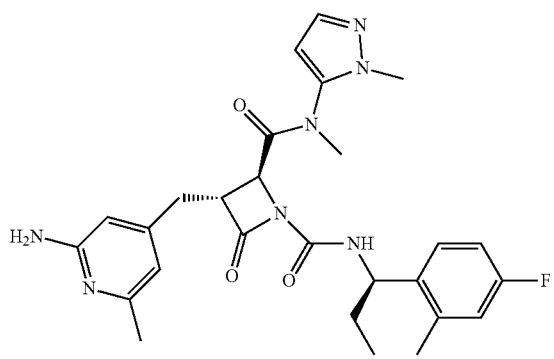 [SMILES: CC[C@@H](NC(=O)N1C(=O)[C@H](Cc2cc(C)nc(N)c2)[C@H]1C(=O)N(C)c1ccnn1C)c1ccc(F)cc1C] |

TABLE 1-continued

Exemplary compounds.

| Compound Number | Structure |
|---|---|
| 1-160 | 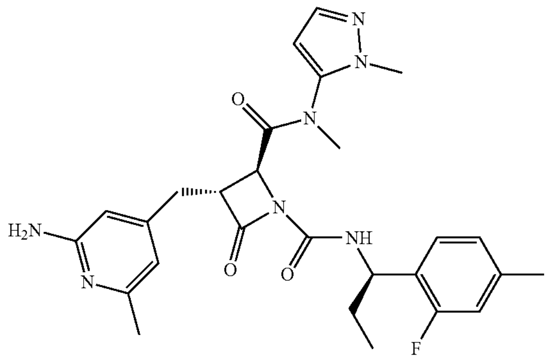 [SMILES: CC[C@@H](NC(=O)N1C(=O)[C@H](Cc2cc(C)nc(N)c2)[C@H]1C(=O)N(C)c1ccnn1C)c1ccc(C)cc1F] |
| 1-161 | 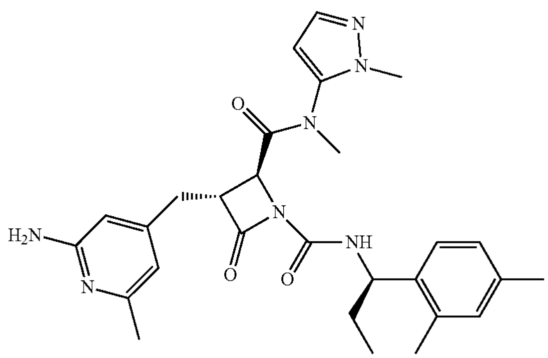 [SMILES: CC[C@@H](NC(=O)N1C(=O)[C@H](Cc2cc(C)nc(N)c2)[C@H]1C(=O)N(C)c1ccnn1C)c1ccc(C)cc1C] |
| 1-162 | 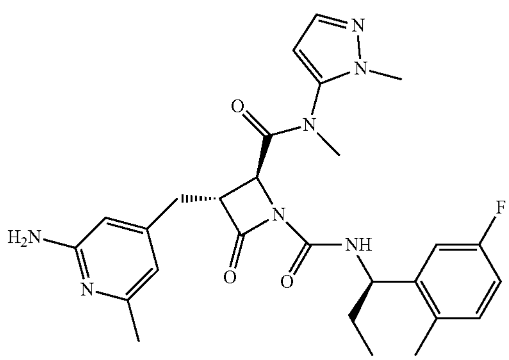 [SMILES: CC[C@@H](NC(=O)N1C(=O)[C@H](Cc2cc(C)nc(N)c2)[C@H]1C(=O)N(C)c1ccnn1C)c1cc(F)ccc1C] |
| 1-163 | 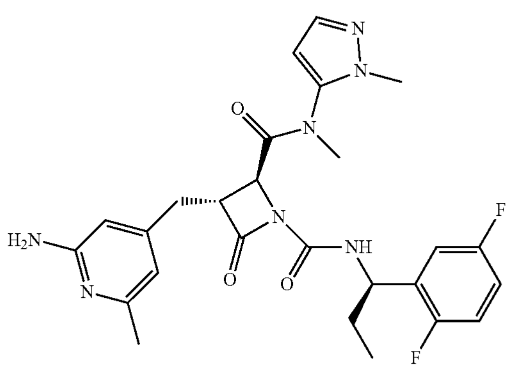 [SMILES: CC[C@@H](NC(=O)N1C(=O)[C@H](Cc2cc(C)nc(N)c2)[C@H]1C(=O)N(C)c1ccnn1C)c1cc(F)ccc1F] |

TABLE 1-continued
Exemplary compounds.
| Compound Number | Structure |
|---|---|
| 1-164 | 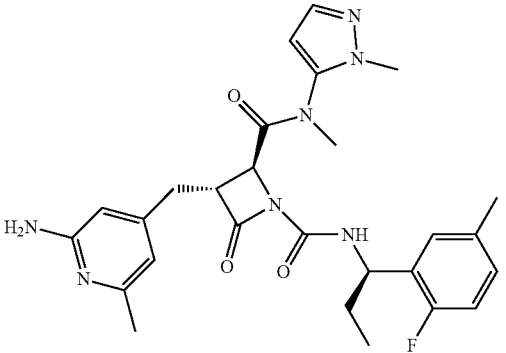 [SMILES: CC[C@@H](NC(=O)N1C(=O)[C@H](Cc2cc(C)nc(N)c2)[C@H]1C(=O)N(C)c1ccnn1C)c1cc(C)ccc1F] |
| 1-165 | 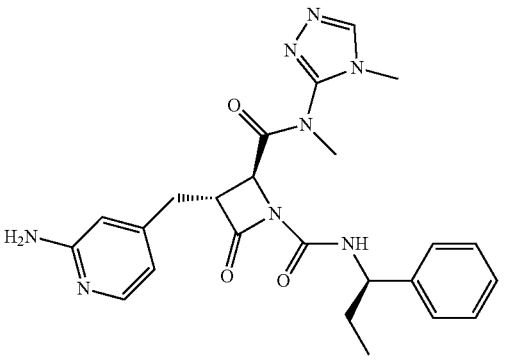 [SMILES: CC[C@@H](NC(=O)N1C(=O)[C@H](Cc2ccnc(N)c2)[C@H]1C(=O)N(C)c1nncn1C)c1ccccc1] |
| 1-166 | 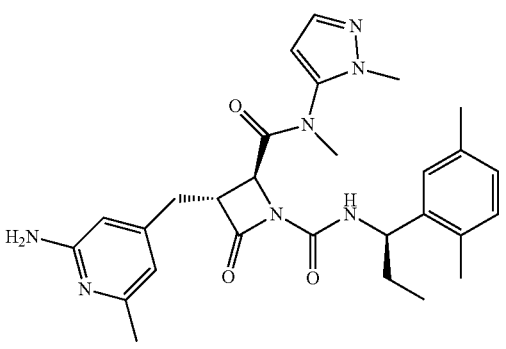 [SMILES: CC[C@@H](NC(=O)N1C(=O)[C@H](Cc2cc(C)nc(N)c2)[C@H]1C(=O)N(C)c1ccnn1C)c1cc(C)ccc1C] |
| 1-167 | 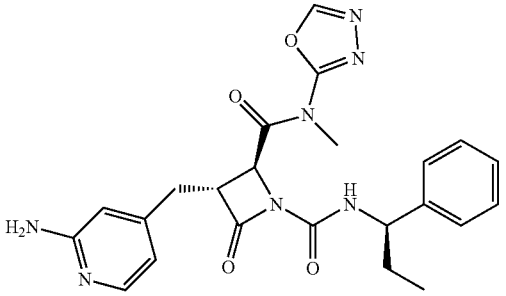 |

TABLE 1-continued
Exemplary compounds.
| Compound Number | Structure |
|---|---|
| 1-168 | 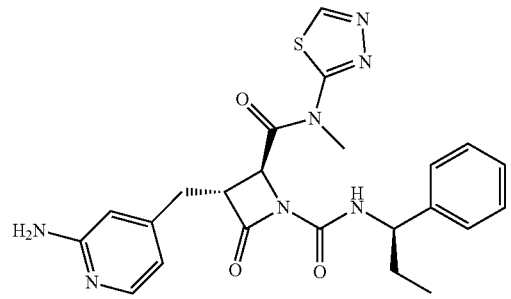 [SMILES: CC[C@@H](NC(=O)N1C(=O)[C@H](Cc2ccnc(N)c2)[C@H]1C(=O)N(C)c1nnco1)c1ccccc1] |
| 1-169 | 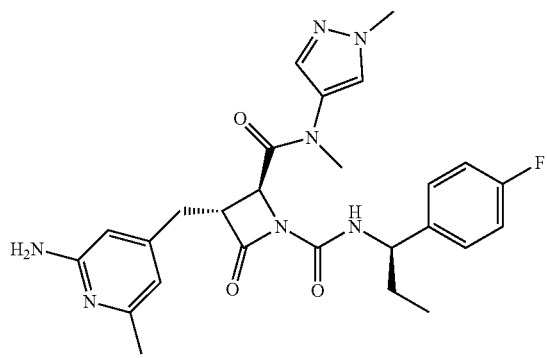 [SMILES: CC[C@@H](NC(=O)N1C(=O)[C@H](Cc2cc(C)nc(N)c2)[C@H]1C(=O)N(C)c1cnn(C)c1)c1ccc(F)cc1] |
| 1-170 | 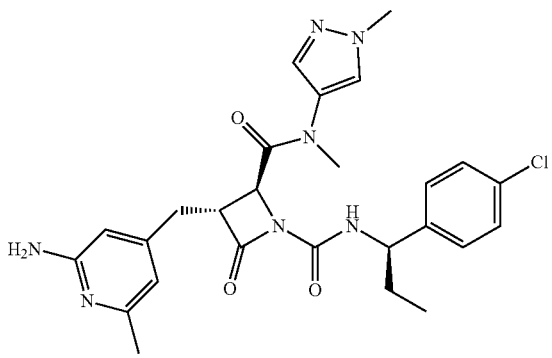 [SMILES: CC[C@@H](NC(=O)N1C(=O)[C@H](Cc2cc(C)nc(N)c2)[C@H]1C(=O)N(C)c1cnn(C)c1)c1ccc(Cl)cc1] |
| 1-171 | 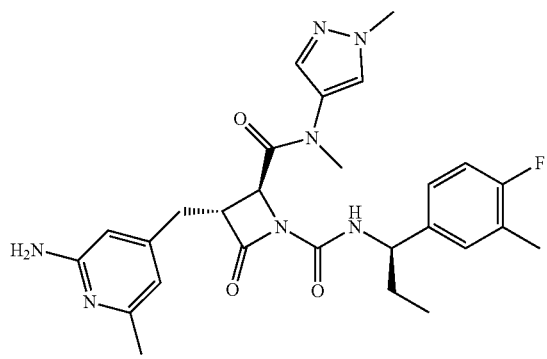 [SMILES: CC[C@@H](NC(=O)N1C(=O)[C@H](Cc2cc(C)nc(N)c2)[C@H]1C(=O)N(C)c1cnn(C)c1)c1ccc(F)c(C)c1] |

TABLE 1-continued
Exemplary compounds.
| Compound Number | Structure |
|---|---|
| 1-172 | 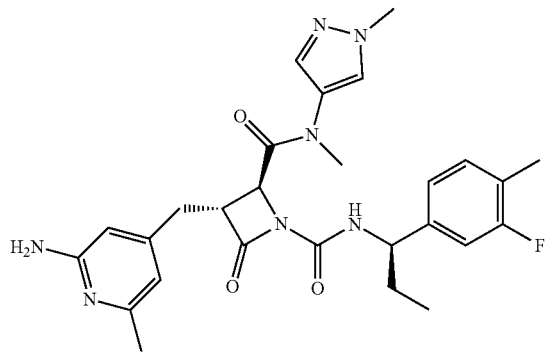 [SMILES: CC[C@@H](NC(=O)N1C(=O)[C@H](Cc2cc(C)nc(N)c2)[C@H]1C(=O)N(C)c1cnn(C)c1)c1ccc(C)c(F)c1] |
| 1-173 | 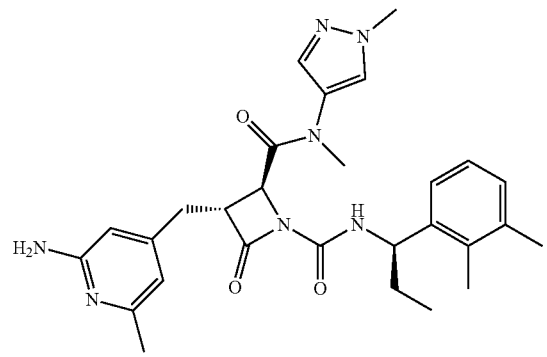 [SMILES: CC[C@@H](NC(=O)N1C(=O)[C@H](Cc2cc(C)nc(N)c2)[C@H]1C(=O)N(C)c1cnn(C)c1)c1cccc(C)c1C] |
| 1-174 | 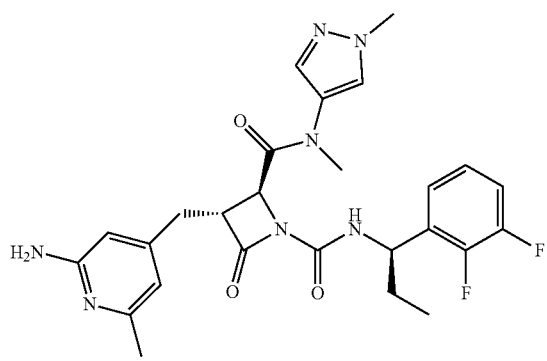 |
| 1-175 | 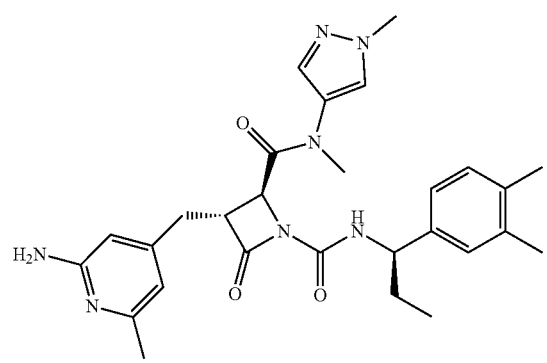 [SMILES: CC[C@@H](NC(=O)N1C(=O)[C@H](Cc2cc(C)nc(N)c2)[C@H]1C(=O)N(C)c1cnn(C)c1)c1ccc(C)c(C)c1] |

TABLE 1-continued

Exemplary compounds.

| Compound Number | Structure |
|---|---|
| 1-176 | 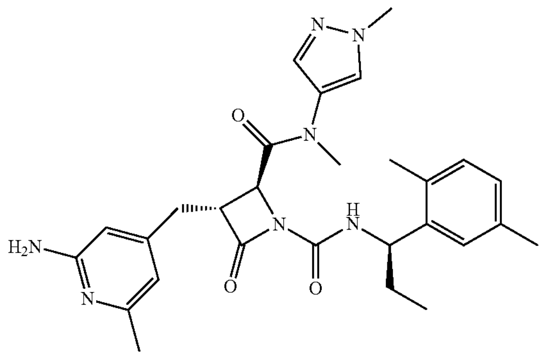 [SMILES: CC[C@@H](NC(=O)N1C(=O)[C@H](Cc2cc(C)nc(N)c2)[C@H]1C(=O)N(C)c1cnn(C)c1)c1cc(C)ccc1C] |
| 1-177 | 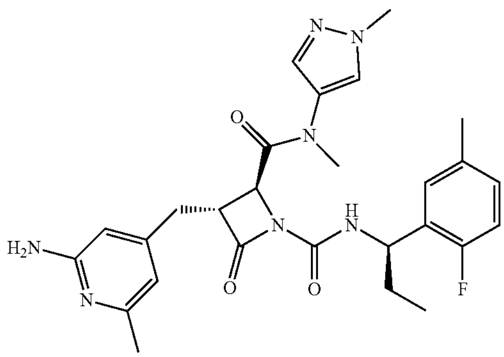 [SMILES: CC[C@@H](NC(=O)N1C(=O)[C@H](Cc2cc(C)nc(N)c2)[C@H]1C(=O)N(C)c1cnn(C)c1)c1cc(C)ccc1F] |
| 1-178 | 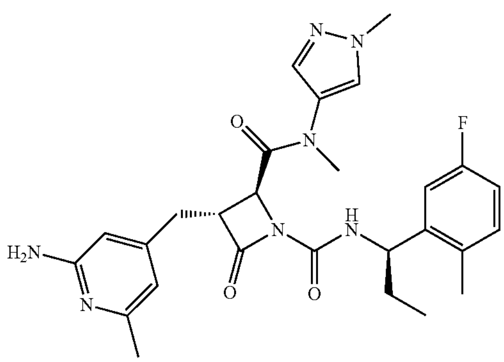 [SMILES: CC[C@@H](NC(=O)N1C(=O)[C@H](Cc2cc(C)nc(N)c2)[C@H]1C(=O)N(C)c1cnn(C)c1)c1cc(F)ccc1C] |
| 1-179 | 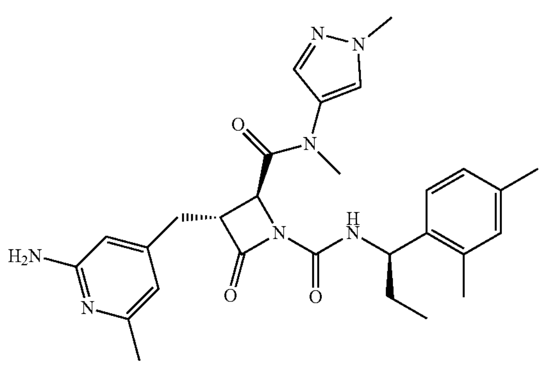 [SMILES: CC[C@@H](NC(=O)N1C(=O)[C@H](Cc2cc(C)nc(N)c2)[C@H]1C(=O)N(C)c1cnn(C)c1)c1ccc(C)cc1C] |

TABLE 1-continued

Exemplary compounds.

| Compound Number | Structure |
|---|---|
| 1-180 | 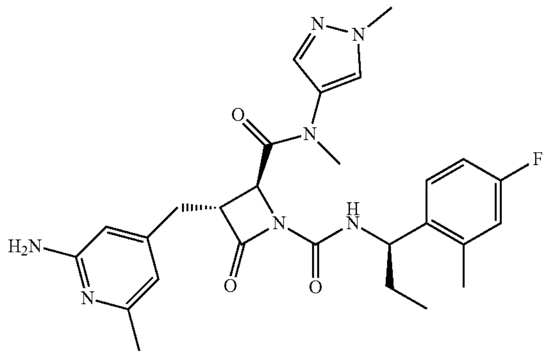 [SMILES: CC[C@@H](NC(=O)N1C(=O)[C@H](Cc2cc(C)nc(N)c2)[C@H]1C(=O)N(C)c1cnn(C)c1)c1ccc(F)cc1C] |
| 1-181 | 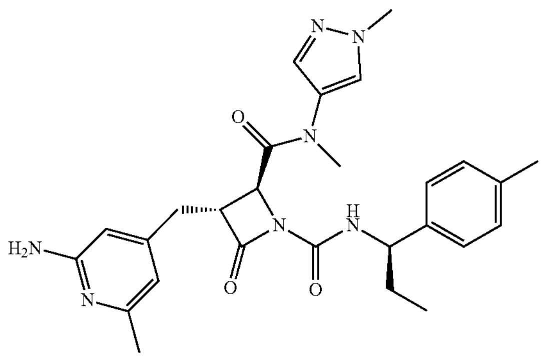 [SMILES: CC[C@@H](NC(=O)N1C(=O)[C@H](Cc2cc(C)nc(N)c2)[C@H]1C(=O)N(C)c1cnn(C)c1)c1ccc(C)cc1] |
| 1-182 | 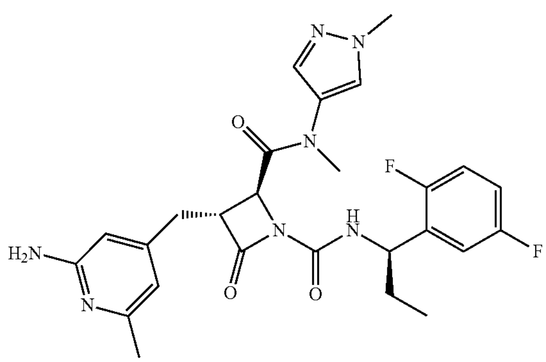 [SMILES: CC[C@@H](NC(=O)N1C(=O)[C@H](Cc2cc(C)nc(N)c2)[C@H]1C(=O)N(C)c1cnn(C)c1)c1cc(F)ccc1F] |
| 1-183 | 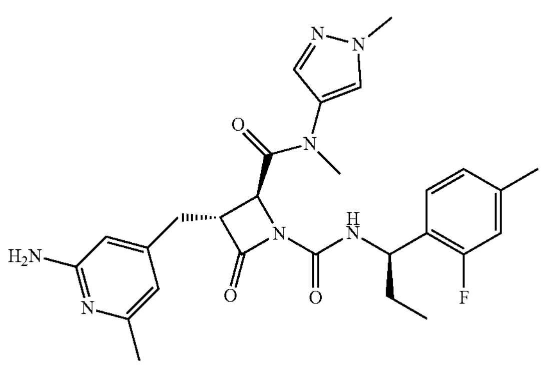 [SMILES: CC[C@@H](NC(=O)N1C(=O)[C@H](Cc2cc(C)nc(N)c2)[C@H]1C(=O)N(C)c1cnn(C)c1)c1ccc(C)cc1F] |

TABLE 1-continued

Exemplary compounds.

| Compound Number | Structure |
|---|---|
| 1-184 | 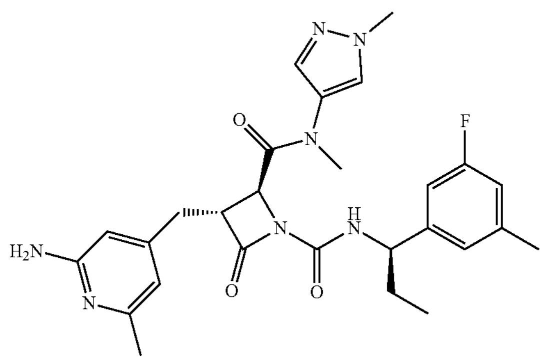 [SMILES: CC[C@@H](NC(=O)N1C(=O)[C@H](Cc2cc(C)nc(N)c2)[C@H]1C(=O)N(C)c1cnn(C)c1)c1cc(C)cc(F)c1] |
| 1-185 | 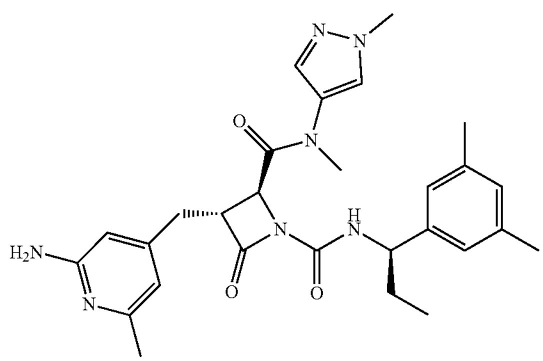 [SMILES: CC[C@@H](NC(=O)N1C(=O)[C@H](Cc2cc(C)nc(N)c2)[C@H]1C(=O)N(C)c1cnn(C)c1)c1cc(C)cc(C)c1] |
| 1-186 | 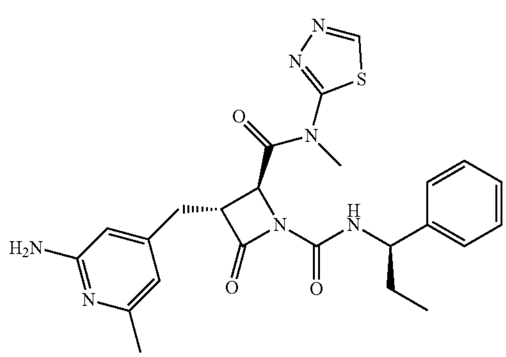 [SMILES: CC[C@@H](NC(=O)N1C(=O)[C@H](Cc2cc(C)nc(N)c2)[C@H]1C(=O)N(C)c1nnco1)c1ccccc1] |
| 1-187 | 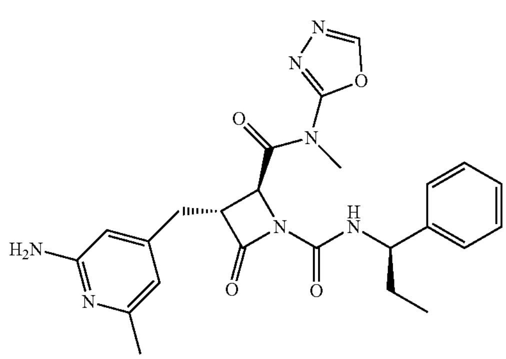 |

TABLE 1-continued

Exemplary compounds.

| Compound Number | Structure |
|---|---|
| 1-188 | 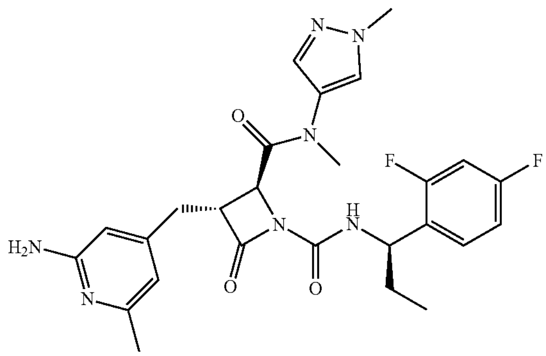 [SMILES: CC[C@@H](NC(=O)N1C(=O)[C@H](Cc2cc(C)nc(N)c2)[C@H]1C(=O)N(C)c1cnn(C)c1)c1ccc(F)cc1F] |
| 1-189 | 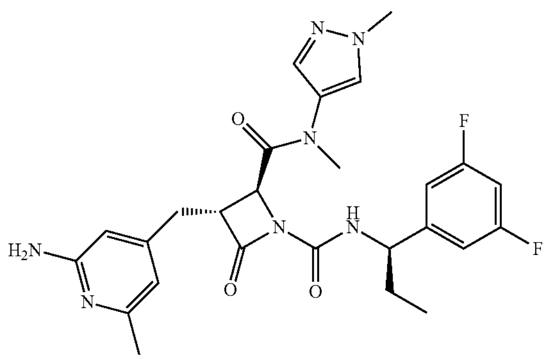 [SMILES: CC[C@@H](NC(=O)N1C(=O)[C@H](Cc2cc(C)nc(N)c2)[C@H]1C(=O)N(C)c1cnn(C)c1)c1cc(F)cc(F)c1] |
| 1-190 | 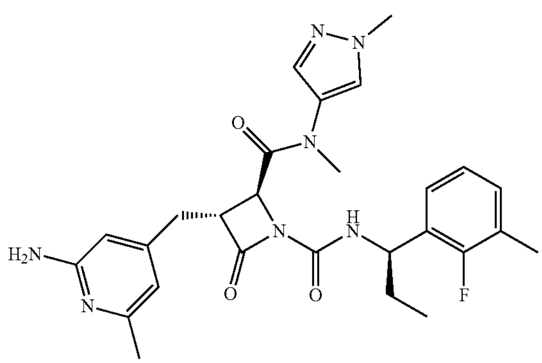 [SMILES: CC[C@@H](NC(=O)N1C(=O)[C@H](Cc2cc(C)nc(N)c2)[C@H]1C(=O)N(C)c1cnn(C)c1)c1cccc(C)c1F] |
| 1-191 | 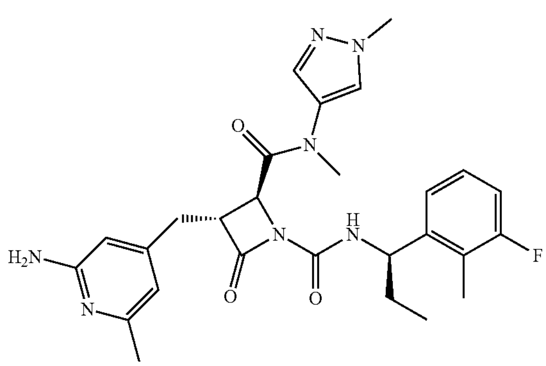 [SMILES: CC[C@@H](NC(=O)N1C(=O)[C@H](Cc2cc(C)nc(N)c2)[C@H]1C(=O)N(C)c1cnn(C)c1)c1cccc(F)c1C] |

TABLE 1-continued

Exemplary compounds.

| Compound Number | Structure |
|---|---|
| 1-192 | 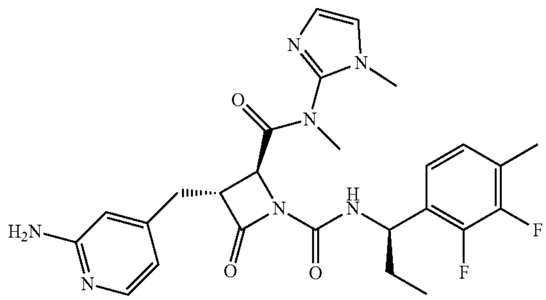 |
| 1-193 | 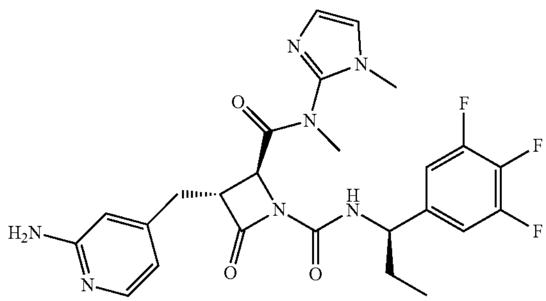 [SMILES: CC[C@@H](NC(=O)N1C(=O)[C@H](Cc2ccnc(N)c2)[C@H]1C(=O)N(C)c1nccn1C)c1cc(F)c(F)c(F)c1] |
| 1-194 | 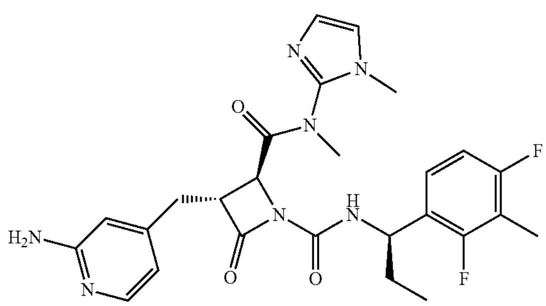 [SMILES: CC[C@@H](NC(=O)N1C(=O)[C@H](Cc2ccnc(N)c2)[C@H]1C(=O)N(C)c1nccn1C)c1ccc(F)c(C)c1F] |
| 1-195 | 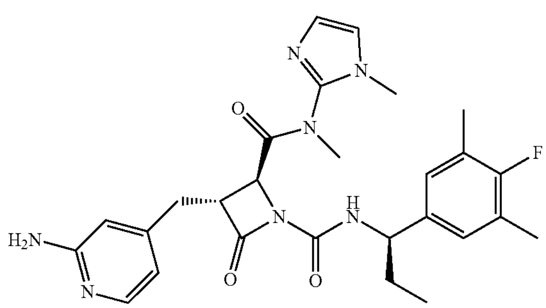 [SMILES: CC[C@@H](NC(=O)N1C(=O)[C@H](Cc2ccnc(N)c2)[C@H]1C(=O)N(C)c1nccn1C)c1cc(C)c(F)c(C)c1] |
| 1-196 | 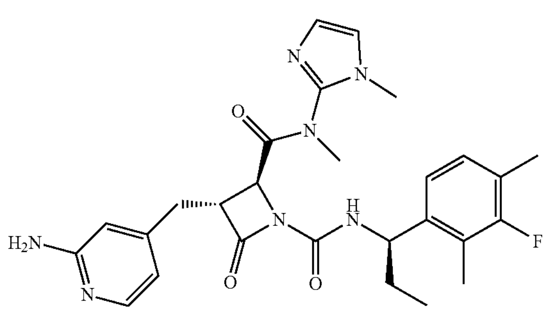 |

TABLE 1-continued
Exemplary compounds.
| Compound Number | Structure |
|---|---|
| 1-197 | 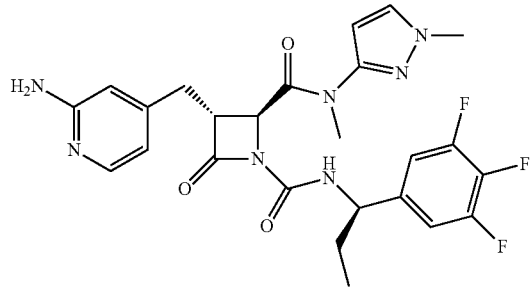 |
| 1-198 | 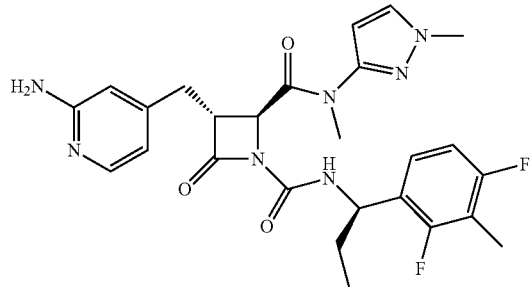 [SMILES: CC[C@@H](NC(=O)N1C(=O)[C@H](Cc2ccnc(N)c2)[C@H]1C(=O)N(C)c1ccn(C)n1)c1ccc(F)c(C)c1F] |
| 1-199 | 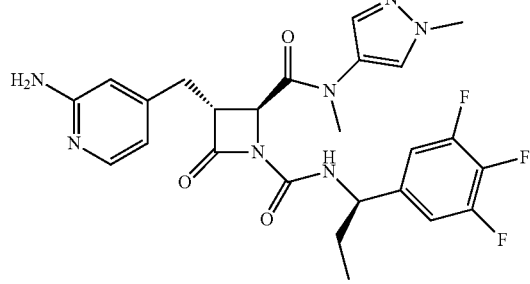 |
| 1-200 | 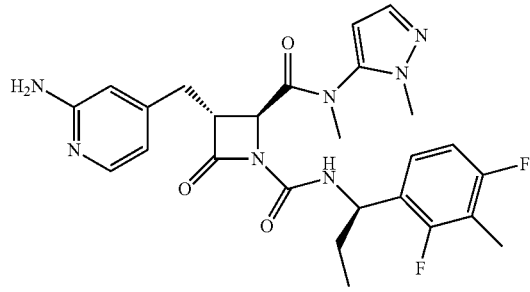 |
| 1-201 | 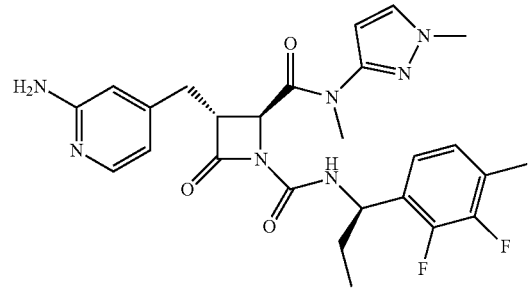 [SMILES: CC[C@@H](NC(=O)N1C(=O)[C@H](Cc2ccnc(N)c2)[C@H]1C(=O)N(C)c1ccn(C)n1)c1ccc(C)c(F)c1F] |

TABLE 1-continued
Exemplary compounds.
| Compound Number | Structure |
|---|---|
| 1-202 | 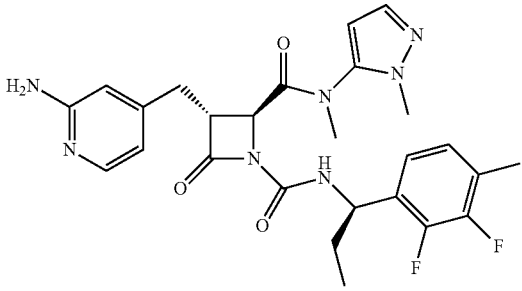 [SMILES: CC[C@@H](NC(=O)N1C(=O)[C@H](Cc2ccnc(N)c2)[C@H]1C(=O)N(C)c1ccnn1C)c1ccc(C)c(F)c1F] |
| 1-203 | 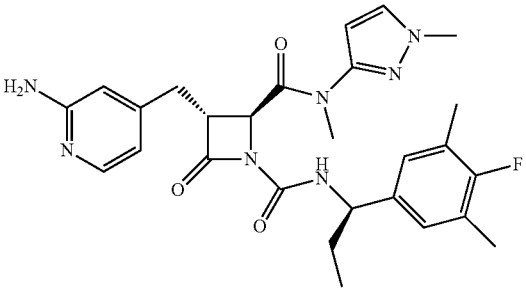 [SMILES: CC[C@@H](NC(=O)N1C(=O)[C@H](Cc2ccnc(N)c2)[C@H]1C(=O)N(C)c1ccn(C)n1)c1cc(C)c(F)c(C)c1] |
| 1-204 | 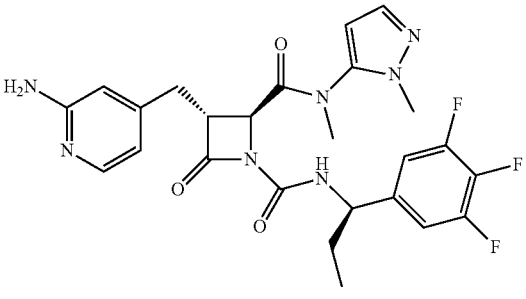 [SMILES: CC[C@@H](NC(=O)N1C(=O)[C@H](Cc2ccnc(N)c2)[C@H]1C(=O)N(C)c1ccnn1C)c1cc(F)c(F)c(F)c1] |
| 1-205 | 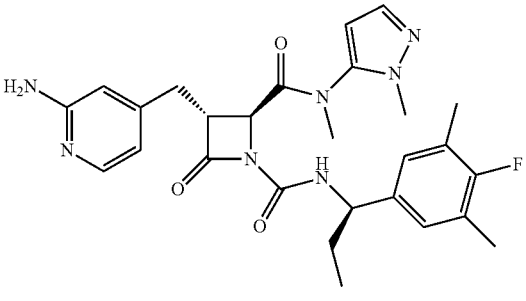 [SMILES: CC[C@@H](NC(=O)N1C(=O)[C@H](Cc2ccnc(N)c2)[C@H]1C(=O)N(C)c1ccnn1C)c1cc(C)c(F)c(C)c1] |
| 1-206 | 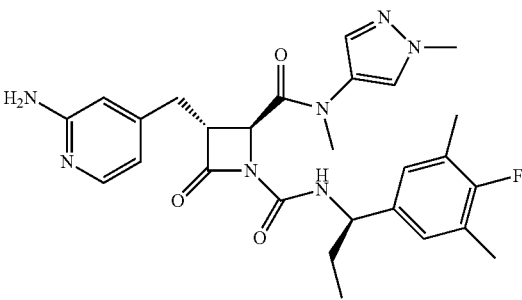 [SMILES: CC[C@@H](NC(=O)N1C(=O)[C@H](Cc2ccnc(N)c2)[C@H]1C(=O)N(C)c1cnn(C)c1)c1cc(C)c(F)c(C)c1] |

US 11,691,962 B2
139                                                                                                     140
TABLE 1-continued
Exemplary compounds.
| Compound Number | Structure |
|---|---|
| 1-207 | 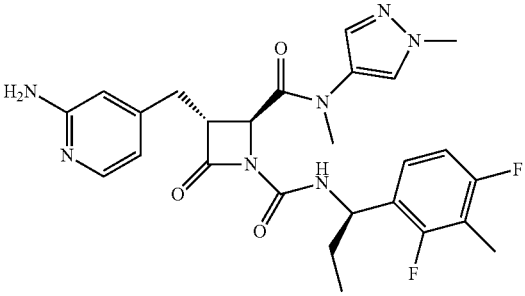 [SMILES: CC[C@@H](NC(=O)N1C(=O)[C@H](Cc2ccnc(N)c2)[C@H]1C(=O)N(C)c1cnn(C)c1)c1ccc(F)c(C)c1F] |
| 1-208 | 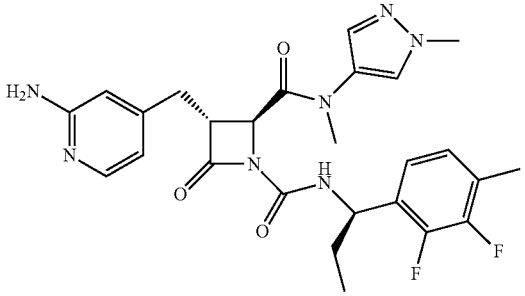 [SMILES: CC[C@@H](NC(=O)N1C(=O)[C@H](Cc2ccnc(N)c2)[C@H]1C(=O)N(C)c1cnn(C)c1)c1ccc(C)c(F)c1F] |
| 1-209 | 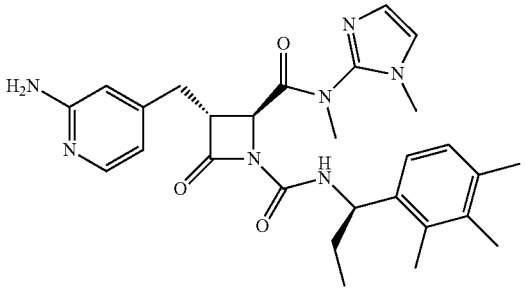 |
| 1-210 | 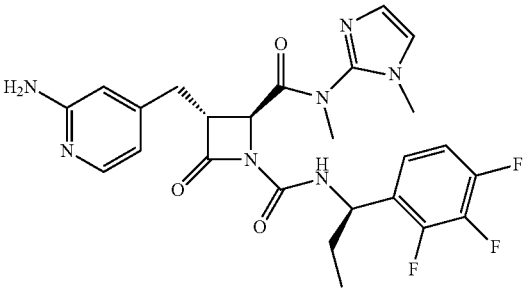 [SMILES: CC[C@@H](NC(=O)N1C(=O)[C@H](Cc2ccnc(N)c2)[C@H]1C(=O)N(C)c1nccn1C)c1ccc(F)c(F)c1F] |
| 1-211 | 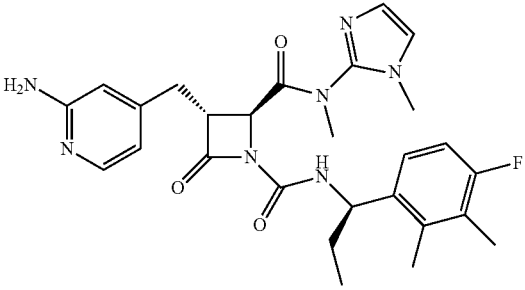 |

TABLE 1-continued

Exemplary compounds.

| Compound Number | Structure |
|---|---|
| 1-212 | 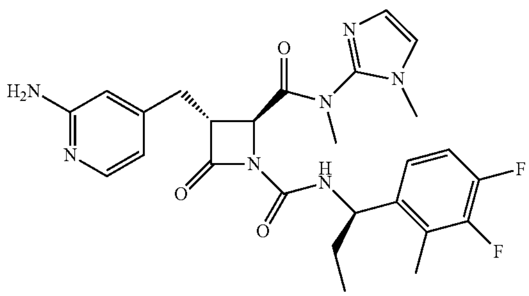 |
| 1-213 | 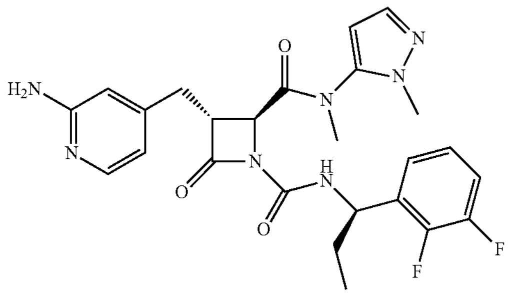 [SMILES: CC[C@@H](NC(=O)N1C(=O)[C@H](Cc2ccnc(N)c2)[C@H]1C(=O)N(C)c1ccnn1C)c1cccc(F)c1F] |
| 1-214 | 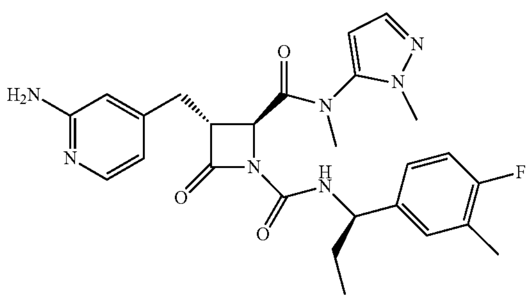 |
| 1-215 | 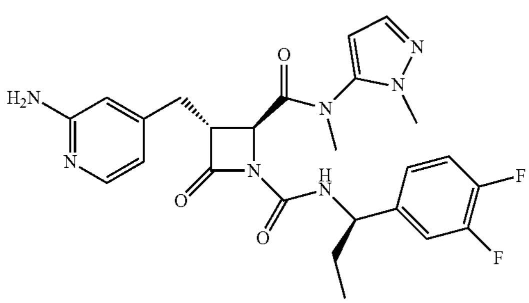 [SMILES: CC[C@@H](NC(=O)N1C(=O)[C@H](Cc2ccnc(N)c2)[C@H]1C(=O)N(C)c1ccnn1C)c1ccc(F)c(F)c1] |
| 1-216 | 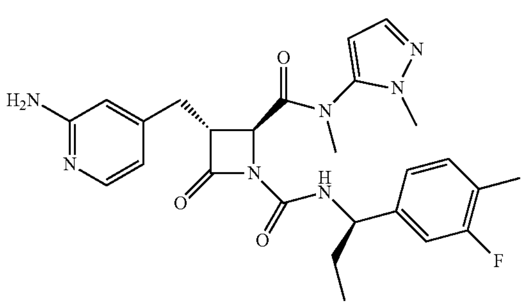 [SMILES: CC[C@@H](NC(=O)N1C(=O)[C@H](Cc2ccnc(N)c2)[C@H]1C(=O)N(C)c1ccnn1C)c1ccc(C)c(F)c1] |

TABLE 1-continued
Exemplary compounds.
| Compound Number | Structure |
|---|---|
| 1-217 | 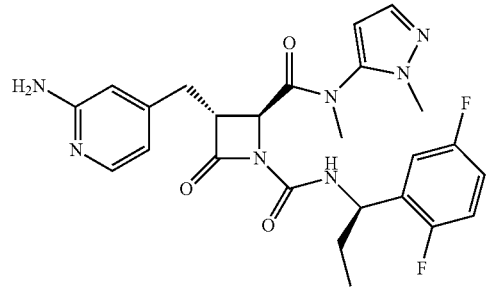 [SMILES: CC[C@@H](NC(=O)N1C(=O)[C@H](Cc2ccnc(N)c2)[C@H]1C(=O)N(C)c1ccnn1C)c1cc(F)ccc1F] |
| 1-218 | 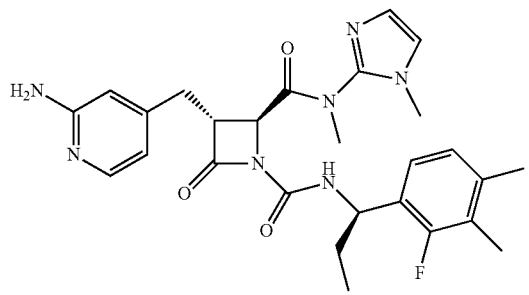 |
| 1-219 | 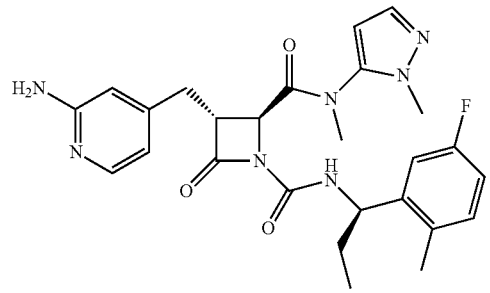 |
| 1-220 | 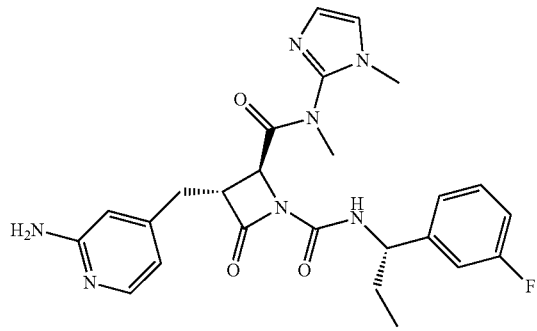 [SMILES: CC[C@H](NC(=O)N1C(=O)[C@H](Cc2ccnc(N)c2)[C@H]1C(=O)N(C)c1nccn1C)c1cccc(F)c1] |

TABLE 1-continued

Exemplary compounds.

Compound
Number  Structure 1-221

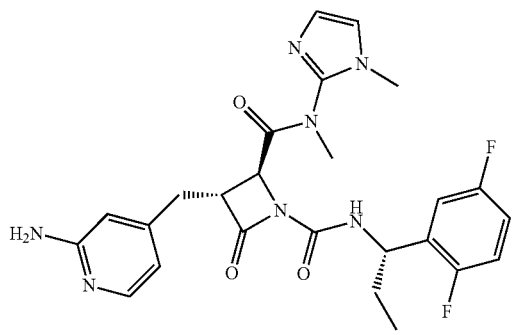 [SMILES: CC[C@H](NC(=O)N1C(=O)[C@H](Cc2ccnc(N)c2)[C@H]1C(=O)N(C)c1nccn1C)c1cc(F)ccc1F]

In some embodiments, a compound described herein is formed into a salt. A compound described herein can be administered as a free acid, a zwitterion or as a salt. A salt can also be formed between a cation and a negatively charged substituent on a compound described herein. Suitable cationic counterions include sodium ions, potassium ions, magnesium ions, calcium ion, and ammonium ions (e.g., a tetraalkyl ammonium cation such as tetramethylammonium ion). In compounds including a positively charged substituent or a basic substituent, a salt can be formed between an anion and a positively charged substituent (e.g., amino group) or basic substituent (e.g., pyridyl) on a compound described herein. Suitable anions include chloride, bromide, iodide, sulfate, nitrate, phosphate, citrate, methanesulfonate, trifluoroacetate, and acetate.

Pharmaceutically acceptable salts of the compounds described herein (e.g., a compound of formula (II), formula (I), formula (I-a), formula (I-b), formula (I-c), formula (I-d), formula (I-e), formula (I-f), formula (I-g), formula (I-h), formula (I-i), formula (I-j), formula (I-k), formula (I-l), formula (I-m), formula (I-n), formula (I-o), formula (I-p), formula (I-r), formula (I-s), formula (I-s1), formula (I-s2), formula (I-t), formula (I-u), formula (I-v), or a compound of Table 1) also include those derived from pharmaceutically acceptable inorganic and organic acids and bases. Examples of suitable acid salts include acetate, 4-acetamidobenzoate, adipate, alginate, 4-aminosalicylate, aspartate, ascorbate, benzoate, benzenesulfonate, bisulfate, butyrate, citrate, camphorate, camphorsulfonate, carbonate, cinnamate, cyclamate, decanoate, decanedioate, 2,2-dichloroacetate, digluconate, dodecylsulfate, ethanesulfonate, ethane-1,2-disulfonate, formate, fumarate, galactarate, glucoheptanoate, gluconate, glucoheptonate, glucoronate, glutamate, glutarate, glycerophosphate, glycolate, hemisulfate, heptanoate, hexanoate, hippurate, hydrochloride, hydrobromide, hydroiodide, 1-hydroxy-2-naphthoate, 2-hydroxyethanesulfonate, isobutyrate, lactate, lactobionate, laurate, malate, maleate, malonate, mandelate, methanesulfonate, naphthalene-1,5-disulfonate, 2-naphthalenesulfonate, nicotinate, nitrate, octanoate, oleate, oxalate, 2-oxoglutarate, palmitate, palmoate, pectinate, persulfate, 3-phenylpropionate, phosphate, phosphonate, picrate, pivalate, propionate, pyroglutamate, salicylate, sebacate, succinate, stearate, sulfate, tartrate, thiocyanate, toluenesulfonate, tosylate, trifluoroacetate, and undecanoate.

Salts derived from appropriate bases include alkali metal (e.g., sodium), alkaline earth metal (e.g., magnesium), ammonium and N-(alkyl)$_4^+$ salts. This invention also envisions the quaternization of any basic nitrogen-containing groups of the compounds disclosed herein. Water or oil-soluble or dispersible products may be obtained by such quaternization.

As used herein, the compounds of this invention, including the compounds of formula (II), are defined to include pharmaceutically acceptable derivatives or prodrugs thereof. A "pharmaceutically acceptable derivative or prodrug" means any pharmaceutically acceptable salt, ester, salt of an ester, or other derivative of a compound of this invention which, upon administration to a recipient, is capable of providing (directly or indirectly) a compound of this invention. Particularly favored derivatives and prodrugs are those that increase the bioavailability of the compounds of this invention when such compounds are administered to a mammal (e.g., by allowing an orally administered compound to be more readily absorbed into the blood), or which enhance delivery of the parent compound to a biological compartment (e.g., the brain or lymphatic system) relative to the parent species. Preferred prodrugs include derivatives where a group which enhances aqueous solubility or active transport through the gut membrane is appended to the structure of formulae described herein.

Any formula or a compound described herein herein is also intended to represent unlabeled forms as well as isotopically labeled forms of the compounds, isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as $^2H$, $^3H$, $^{11}C$, $^{13}C$, $^{14}C$, $^{15}N$, $^{18}F$ $^{51}P$, $^{32}P$, $^{35}S$, $^{36}Cl$, $^{125}I$ respectively. The invention includes various isotopically labeled compounds as defined herein, for example, those into which radioactive isotopes, such as $^3H$, $^{13}C$, and $^{14}C$ are present. Such isotopically labelled compounds are useful in metabolic studies (with $^{14}C$), reaction kinetic studies (with, for example $^1H$ or $^3H$), detection or imaging techniques, such as positron emission tomography (PET) or single-photon emission computed tomography (SPECT) including drug or substrate tissue distribution assays, or in radioactive treatment of patients. In particular, an $^{18}F$ or labeled compound may be particularly desirable for PET or SPECT studies, isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

Further, substitution with heavier isotopes, particularly deuterium (i.e., $^2$H or D) may afford certain therapeutic advantages resulting from greater metabolic stability, for example increased in vivo half-life or reduced dosage requirements or an improvement in therapeutic index. It is understood that deuterium in this context is regarded as a substituent of a compound of a formula described herein. The concentration of such a heavier isotope, specifically deuterium, may be defined by the isotopic enrichment factor. The term "isotopic enrichment factor" as used herein means the ratio between the isotopic abundance and the natural abundance of a specified isotope If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 8633.3 (99.5% deuterium incorporation).

Isotopically-labelled compounds described herein can generally be prepared by conventional techniques known to those skilled in the art or by processes analogous to those described in the accompanying Examples and Preparations using an appropriate isotopically-labeled reagents in place of the non-labeled reagent previously employed. Pharmaceutically acceptable solvates in accordance with the invention include those wherein the solvent of crystallization may be isotopically substituted, e.g, D$_2$O, D$_2$-acetone, D$_2$-DMSO.

Any asymmetric atom (e.g., carbon or the like) of the compound(s) of the present invention can be present in racemic or enantiomerically enriched, for example the (R)-(S)- or (RS)-configuration, in certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. Substituents at atoms with unsaturated bonds may, if possible, be present in cis-(Z)- or trans-(E)-form Accordingly, as used herein a compound of the present invention can be in the form of one of the possible isomers, rotamers, atropisomers, tautoroers or mixtures thereof, for example, as substantially pure geometric (cis or trans) isomers, diastereorners, optical isomers (antipodes), racemates or mixtures thereof. Any resulting mixtures of isomers can be separated on the basis of the physicochemical differences of the constituents, into the pure or substantially pure geometric or optical isomers, diastereomers, racemates, for example, by chromatography or fractional crystallization.

Methods of synthesizing a compound described herein (e.g., a compound of Formula (II) may independently result in the formation of compositions comprising a mixture of two or more diastereomers of that compound. The "diastereomeric excess" ("d.e.") or "% diastereomeric excess" ("% d.e.") of a composition as used herein refers to an excess of one diastereomer relative to one or more different diasteromers present in the composition.

In some embodiments, the d.e. of a composition with respect to a diastereomer described herein with respect to other is greater than 90%. In some embodiments, the d.e. of a composition with respect to a diastereomer described herein is greater than 95%. In some embodiments, the d.e. of a composition with respect to a diastereomer described herein is greater than 97%. In some embodiments, the d.e. of a composition with respect to a diastereomer described herein is greater than 99%. In some embodiments, the d.e. of a composition with respect to a diastereomer described herein is greater than 99.9%.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, (+)—O,O'-Di-p-toluoyl-D-tartaric acid, mandelic acid, malic acid or camphor-10-sulfonic acid. Racemic products can also be resolved by chiral chromatography, e.g., high pressure liquid chromatography (HPLC) using a chiral adsorbent.

The compounds described herein (e.g., a compound of formula (II)) may also be represented in multiple tautomeric forms, for example, a compound of formulas (II), (I), (I-a), (I-b), (I-c), (I-d), (I-e), (I-f), (I-g), (I-h), (I-i), (I-j), (I-k), (I-l), (I-m), (I-n), (I-o), (I-p), (I-q), (I-r), (I-s), (I-s1), (I-s2), (I-t), (I-u), or (I-v). In such instances, the invention expressly includes all tautomeric forms of the compounds described herein. All crystal forms of the compounds described herein are expressly included in this invention.

A compound described herein (e.g., a compound of formula (II)) can be evaluated for its ability to modulate (e.g., inhibit) Factor XIa or kallikrein.

Methods of Synthesizing Compounds

The compounds described herein can be synthesized by conventional methods using commercially available starting materials and reagents. For example, compounds can be synthesized utilizing the methods set forth in U.S. Pat. No. 7,501,404, or as described in the methods described herein.

Methods of Treatment, Prophylaxis, or Reduction of Risk

The compounds described herein (e.g., compounds of formula (II)) can inhibit Factor XIa or kallikrein. In some embodiments, a compound described herein can inhibit both Factor XIa and kallikrein. As a result, these compounds can be useful in the treatment, prophylaxis, or reduction in the risk of a disorder described herein. Exemplary disorders include thrombotic events associated with coronary artery and cerebrovascular disease, venous or arterial thrombosis, coagulation syndromes, ischemia (e.g., coronary ischemia) and angina (stable and unstable), deep vein thrombosis (DVT), hepatic vein thrombosis, disseminated intravascular coagulopathy, Kasabach-Merritt syndrome, pulmonary embolism, myocardial infarction (e.g., ST-elevation myocardial infarction or non-ST-elevation myocardial infarction (e.g., non-ST-elevation myocardial infarction before catheterization), cerebral infarction, cerebral thrombosis, transient ischemic attacks, atrial fibrillation (e.g., non-valvular atrial fibrillation), cerebral embolism, thromboembolic complications of surgery (e.g., hip or knee replacement, orthopedic surgery, cardiac surgery, lung surgery, abdominal surgery, or endarterectomy) and peripheral arterial occlusion and may also be useful in treating or preventing myocardial infarction, stroke, angina and other consequences of atherosclerotic plaque rupture. The compounds of the invention possessing Factor XIa or kallikrein inhibition activity may also be useful in preventing thromboembolic disorders, e.g., venous thromboembolisms, in cancer patients, including those receiving chemotherapy and/or those with elevated lactase dehydrogenase (LDH) levels, and to prevent thromboembolic events at or following tissue plasminogen activator-based or mechanical restoration of blood vessel patency. The compounds of the invention possessing Factor XIa or kallikrein inhibition activity may also be useful as inhibitors of blood coagulation such as during the preparation, storage and fractionation of whole blood. Additionally, the compounds described herein may be used in acute hospital settings or periprocedurally, where a patient is at risk of a thromboembolic disorder or complication, and also in patients who are in a heightened coagulation state, e.g., cancer patients.

Factor XIa inhibition, according to the present invention, can be a more effective and safer method of inhibiting thrombosis compared to inhibiting other coagulation serine proteases such as thrombin or Factor Xa. Administration of a small molecule Factor XIa inhibitor should have the effect of inhibiting thrombin generation and clot formation with no or substantially no effect on bleeding times and little or no impairment of haemostasis. These results differ substantially from that of other "direct acting" coagulation protease inhibitors (e.g., active-site inhibitors of thrombin and Factor Xa), which demonstrate prolongation of bleeding time and less separation between antithrombotic efficacy and bleeding time prolongation. A preferred method according to the invention comprises administering to a mammal a pharmaceutical composition containing at least one compound of the invention.

The compounds described herein (e.g., a compound of formula (II)) can inhibit kallikrein, for example, a compound of formulas (II), (I), (I-a), (I-b), (I-c), (I-d), (I-e), (I-f), (I-g), (I-h), (I-i), (I-j), (I-k), (I-l), (I-m), (I-n), (I-o), (I-p), (I-q), (I-r), (I-s), (I-s1), (I-s2), (I-t), (I-u), or (I-v). As a result, these compounds can be useful in the treatment, prophylaxis, or reduction in the risk of of diseases involved in inflammation, such as edema (e.g., cerebral edema, macular edema, and angioedema (e.g., hereditary angioedema)). In some embodiments, the compounds of the invention can be useful in the treatment or prevention of hereditary angioedema. The compounds described herein (e.g., compounds of formula (II)) can also be useful in the treatment, prophylaxis, or reduction in the risk of, e.g., stroke, ischemia (e.g., coronary ischemia), and perioperative blood loss for example, a compound of formula (II), e.g., a compound of formulas (I), (I-a), (I-b), (I-c), (I-d), (I-e), (I-f), (I-g), (I-h), (I-i), (I-j), (I-k), (I-l), (I-m), (I-n), (I-o), (I-p), (I-q), (I-r), (I-s), (I-s1), (I-s2), (I-t), (I-u), or (I-v). The methods of the present invention are useful for treating or preventing those conditions which involve the action of Factor XIa or kallikrein. Accordingly, the methods of the present invention are useful in treating consequences of atherosclerotic plaque rupture including cardiovascular diseases associated with the activation of the coagulation cascade in thrombotic or thrombophilic states.

More particularly, the methods of the present invention can be used in the treatment, prophylaxis, or reduction in the risk of acute coronary syndromes such as coronary artery disease, myocardial infarction, unstable angina (including crescendo angina), ischemia (e.g., ischemia resulting from vascular occlusion), and cerebral infarction. The methods of the present invention further may be useful in the treatment, prophylaxis, or reduction in the risk of stroke and related cerebral vascular diseases (including cerebrovascular accident, vascular dementia, and transient ischemic attack); venous thrombosis and thrombo-embolism, such as deep vein thrombosis (DVT) and pulmonary embolism; thrombosis associated with atrial fibrillation, ventricular enlargement, dilated cardiac myopathy, or heart failure; peripheral arterial disease and intermittent claudication; the formation of atherosclerotic plaques and transplant atherosclerosis; restenosis following arterial injury induced endogenously (by rupture of an atherosclerotic plaque), or exogenously (by invasive cardiological procedures such as vessel wall injury resulting from angioplasty or post-cranial artery stenting); disseminated intravascular coagulopathy, Kasabach-Merritt syndrome, cerebral thrombosis, and cerebral embolism.

Additionally, the methods of the present invention can be used in the treatment, prophylaxis (e.g., preventing), or reduction in the risk of thromboembolic consequences or complications associated with cancer, surgery (e.g., hip replacement, orthopedic surgery), endarterectomy, introduction of artificial heart valves, peripheral vascular interventions (e.g., of the limbs), cerebrovascular interventions, large bore interventions used in the treatment of aneurysms, vascular grafts, mechanical organs, and implantation (e.g., trans-catheter aeortic valve implantation) or transplantation of organs, (e.g., transplantation of the liver), tissue, or cells); percutaneous coronary interventions; catheter ablation; hemophilia therapy; hemodialysis; medications (such as tissue plasminogen activator or similar agents and surgical restoration of blood vessel patency) in patients suffering myocardial infarction, stroke, pulmonary embolism and like conditions; medications (such as oral contraceptives, hormone replacement, and heparin, e.g., for treating heparin-induced thrombocytopenia); sepsis (such as sepsis related to disseminated intravascular coagulation); pregnancy or childbirth; and another chronic medical condition. The methods of the present invention may be used to treat thrombosis due to confinement (e.g., immobilization, hospitalization, bed rest, or limb immobilization, e.g., with immobilizing casts, etc.).

Additionally, the compounds described herein (e.g., a compound of formula (II)) or pharmaceutically acceptable salts thereof or compositions thereof can be useful in the treatment, prophylaxis and reduction in the risk of a thromboembolic disorder, e.g., a venous thromboembolism, deep vein thrombosis or pulmonary embolism, or associated complication in a subject, wherein the subject is exposed to an artificial surface. The artificial surface can contact the subject's blood, for example, as an extracorporeal surface or that of an implantable device. Such articifical surfaces include, but are not limited to, those of dialysis catheters, cardiopulmonary bypass circuits, artificial heart valves, e.g., mechanical heart valves (MHVs), ventricular assist devices, small caliber grafts, central venous catheters, extracorporeal membrane oxygenation (ECMO) apparatuses. Further, the thromboembolic disorder or associated complication may be caused by the artificial surface or associated with the artificial surface. For example, foreign surfaces and various components of mechanical heart valves (MHVs) are pro-thrombotic and promote thrombin generation via the intrinsic pathway of coagulation. Further, thrombin and FXa inhibitors are contraindicated with thromboembolic disorders or associated complications caused by artificial surfaces such as those MHVs, as these inhibitors are ineffective at blocking the intrinsic pathway at plasma levels that will not cause heavy bleeding. The compounds of the present invention, which can be used as, for example, Factor XIa inhibitors, are thus contemplated as alternative therapeutics for these purposes.

The compounds described herein (e.g., a compound of formula (II)) or pharmaceutically acceptable salts thereof or compositions thereof can also be useful for the treatment, prophylaxis, or reduction in the risk of atrial fibrillation in a subject in need thereof. For example, the subject can have a high risk of developing atrial fibrillation. The subject can also in need of dialysis, such as renal dialysis. The compounds described herein (e.g., a compound of formula (II)) or pharmaceutically acceptable salts thereof or compositions thereof can be administered before, during, or after dialysis. Direct oral anticoagulants (DOACs) currently available on the market, such as certain FXa or thrombin inhibitors, are contraindicated for atrial fibrillation under such a condition. The compounds of the present invention, which can be used as, for example, Factor XIa inhibitors, are thus contemplated as alternative therapeutics for these purposes. Additionally, the subject can be at a high risk of bleeding. In some embodiments, the subject can have end-stage renal disease. In other cases, the subject is not in need of dialysis, such as renal dialysis. Further, the atrial fibrillation can be associated with another thromboembolic disorder such as a blood clot.

Furthermore, the compounds described herein (e.g., a compound of formula (II)) or pharmaceutically acceptable salts thereof or compositions thereof can be used in the treatment, prophylaxis, or reduction in the risk of hypertension, e.g., arterial hypertension, in a subject. In some embodiments, the hypertension, e.g., arterial hypertension, can result in atherosclerosis. In some embodiments, the hypertension can be pulmonary arterial hypertension.

Furthermore, the compounds described herein (e.g., a compound of formula (II)) or pharmaceutically acceptable salts thereof or compositions thereof can be used in the treatment, prophylaxis, or reduction in the risk of disorders such as heparin-induced thrombocytopenia, heparin-induced thrombocytopenia thrombosis, or thrombotic microangiopathy, e.g., hemolytic uremic syndrome (HUS) or thrombotic thrombocytopenic purpura (TTP).

The the compounds described herein (e.g., a compound of formula (II)) or pharmaceutically acceptable salts thereof or compositions thereof can be used to reduce inflammation in a subject. In some embodiments, the inflammation can be vascular inflammation. In some embodiments, the vascular inflammation can be accompanied by atherosclerosis. In some embodiments, the vascular inflammation can be accompanied by a thromboembolic disease in the subject. In some embodiments, the vascular inflammation can be angiotensin II-induced vascular inflammation.

The the compounds described herein (e.g., a compound of formula (II)) or pharmaceutically acceptable salts thereof or compositions thereof can be used in the treatment, prophylaxis, or reduction in the risk of renal disorders or dysfunctions, including end-stage renal disease, hypertension-associated renal dysfunction in a subject, kidney fibrosis, and kidney injury.

The methods of the present invention may also be used to maintain blood vessel patency, for example, in patients undergoing transluminal coronary angioplasty, or in connection with vascular surgery such as bypass grafting, arterial reconstruction, atherectomy, vascular grafts, stent patency, and organ, tissue or cell implantation and transplantation. The inventive methods may be used to inhibit blood coagulation in connection with the preparation, storage, fractionation, or use of whole blood. For example, the inventive methods may be used in maintaining whole and fractionated blood in the fluid phase such as required for analytical and biological testing, e.g., for ex vivo platelet and other cell function studies, bioanalytical procedures, and quantitation of blood-containing components, or for maintaining extracorpeal blood circuits, as in a renal replacement solution (e.g., hemodialysis) or surgery (e.g., open-heart surgery, e.g., coronary artery bypass surgery). In some embodiments, the renal replacement solution can be used to treat patients with acute kidney injury. In some embodiments, the renal replacement solution can be continuous renal replacement therapy.

In addition, the methods of the present invention may be useful in treating and preventing the prothrombotic complications of cancer. The methods may be useful in treating tumor growth, as an adjunct to chemotherapy, for preventing angiogenesis, and for treating cancer, more particularly, cancer of the lung, prostate, colon, breast, ovaries, and bone.

In one aspect, provided herein is a method of reducing the risk of stroke in a subject that has suffered an ischemic event, comprising administering to the subject an effective amount of a compound described herein, e.g., a compound of formula (II), or a pharmaceutically acceptable salt thereof, or a composition described herein, e.g., a composition comprising a compound of formula (II). In some embodiments, the administering reduces the risk of stroke in a subject as compared to a subject who is not administered with the compound.

In one aspect, provided herein is a method of reducing the risk of stroke or systemic embolism in a subject suffering from atrial fibrillation, comprising administering to the subject an effective amount of a compound described herein, e.g., a compound of formula (II), or a pharmaceutically acceptable salt thereof, or a composition described herein, e.g., a composition comprising a compound of formula (II).

In another aspect, provided herein is a method of reducing non-central nervous system systemic embolism in a subject that has suffered an ischemic event, comprising administering to the subject an effective amount of a compound described herein, e.g., a compound of formula (II), or a pharmaceutically acceptable salt thereof, or a composition described herein, e.g., a composition comprising a compound of formula (II). In some embodiments, the administering reduces non-central nervous system systemic embolism in a subject as compared to a subject who is not administered with the compound.

In one aspect, provided herein is a method of treating deep vein thrombosis, comprising administering to a subject that has suffered an ischemic event an effective amount of a compound described herein, e.g., a compound of formula (II), or a pharmaceutically acceptable salt thereof, or a composition described herein, e.g., a composition comprising a compound of formula (II).

In one aspect, provided herein is a method of reducing the risk of recurrence of deep vein thrombosis, comprising administering to a subject that has suffered deep vein thrombosis an effective amount of a compound described herein, e.g., a compound of formula (II) or a pharmaceutically acceptable salt thereof, or a composition described herein, e.g., a composition comprising a compound of formula (II). In some embodiments, the administering reduces the risk of recurrence of deep vein thrombosis in a subject as compared to a subject who is not administered with the compound.

In an aspect, provided herein is a method of prophylaxis of deep vein thrombosis in a subject, comprising administering to a subject an effective amount of a compound described herein, e.g., a compound of formula (II) or a pharmaceutically acceptable salt thereof, or a composition described herein, e.g., a composition comprising a compound of formula (II). In some embodiments, the subject is undergoing orthopedic surgery or knee or hip replacement surgery.

In an aspect, provided herein is a method of reducing the risk of recurrence of pulmonary embolism comprising administering to a subject that has suffered a pulmonary embolism an effective amount of a compound described herein, e.g., a compound of formula (II) or a pharmaceutically acceptable salt thereof, or a composition described herein, e.g., a composition comprising a compound of formula (II).

In an aspect, provided herein is a method of reducing the risk of recurrence of pulmonary embolism, comprising administering to a subject that has suffered deep vein thrombosis an effective amount of a compound described herein, e.g., a compound of formula (II) or a pharmaceutically acceptable salt thereof, or a composition described herein, e.g., a composition comprising a compound of formula (II). In some embodiments, the administering reduces the risk of recurrence of pulmonary embolism in a subject as compared to a subject who is not administered with the compound.

In an aspect, provided herein is a method of treating pulmonary embolism in a subject that has suffered deep vein thrombosis, comprising administering to a subject an effective amount of a compound described herein, e.g., a compound of formula (II) or a pharmaceutically acceptable salt thereof, or a composition described herein, e.g., a composition comprising a compound of formula (II).

In an aspect, provided herein is a method of prophylaxis of pulmonary embolism in a subject that has suffered a pulmonary embolism, comprising administering to a subject an effective amount of a compound described herein, e.g., a compound of formula (II) or a pharmaceutically acceptable salt thereof, or a composition described herein, e.g., a composition comprising a compound of formula (II).

In an aspect, provided herein is a method of prophylaxis of pulmonary embolism in a subject that has suffered a pulmonary embolism comprising administering to a subject an effective amount of a compound described herein, e.g., a compound of formula (II) or a pharmaceutically acceptable salt thereof, or a composition described herein, e.g., a composition comprising a compound of formula (II).

In an aspect, provided herein is a method of prophylaxis of pulmonary embolism in a subject that has suffered deep vein thrombosis, comprising administering to a subject an effective amount of a compound described herein, e.g., a compound of formula (II) or a pharmaceutically acceptable salt thereof, or a composition described herein, e.g., a composition comprising a compound of formula (II).

In an aspect, provided herein is a method of treating a subject that has had an ischemic event comprising: administering a compound described herein, e.g., a compound of formula (II) or a pharmaceutically acceptable salt thereof, or a composition described herein, e.g., a composition comprising a compound of formula (II), to the subject within 12 hours or less, 10 hours or less, 9 hours or less, 8 hours or less, 7 hours or less, 6 hours or less, or 1 hour or less after the onset of the ischemic event in the subject.

In an aspect, provided herein is a method of treating deep vein thrombosis to a subject that has been previously administered an anticoagulant, comprising administering to the subject an effective amount of a compound described herein, e.g., a compound of formula (II) or a pharmaceutically acceptable salt thereof, or a composition described herein, e.g., a composition comprising a compound of formula (II).

In an aspect, provided herein is a method of treating pulmonary embolism to a subject that has been previously administered an anticoagulant, comprising administering to the subject an effective amount of a compound described herein, e.g., a compound of formula (II) or a pharmaceutically acceptable salt thereof, or a composition described herein, e.g., a composition comprising a compound of formula (II). In some embodiments, the anticoagulant was administered parenterally for 5-10 days.

In an aspect, provided herein is a method of treating a subject that has had an ischemic event comprising: administering a compound described herein, e.g., a compound of formula (II) or a pharmaceutically acceptable salt thereof, or a composition described herein, e.g., a composition comprising a compound of formula (II), to the subject within more than 2 hours to 12 hours, e.g., more than 2 hours to 10 hours or less, more than 2 hours to 8 hours or less, after the onset of the ischemic event in the subject.

In an aspect, provided herein is a method of treating acute coronary syndrome in a subject, comprising administering to a subject in need thereof a compound described herein, e.g., a compound of formula (II) or a pharmaceutically acceptable salt thereof, or a composition described herein, e.g., a composition comprising a compound of formula (II).

In an aspect, provided herein is a method of inhibiting Factor XIa in a subject, comprising administering to a subject that has suffered ischemia an effective amount of a compound described herein, e.g., a compound of formula (II) or a pharmaceutically acceptable salt thereof, or a composition described herein, e.g., a composition comprising a compound of formula (II). In some embodiments, the ischemia is coronary ischemia.

In an aspect, provided herein is a method of treating a subject that has edema, comprising administering a compound described herein, e.g., a compound of formula (II) or a pharmaceutically acceptable salt thereof, or a composition described herein, e.g., a composition comprising a compound of formula (II).

In an aspect, provided herein is a method of inhibiting kallikrein in a subject, comprising administering to a subject with edema, an effective amount of a compound described herein, e.g., a compound of formula (II) or a pharmaceutically acceptable salt thereof, or a composition described herein, e.g., a composition comprising a compound of formula (II).

In an aspect, provided herein is a method of treating a thromboembolic consequence or complication in a subject, comprising administering to a subject an effective amount of a compound described herein, e.g., a compound of formula (II) or a pharmaceutically acceptable salt thereof, or a composition described herein, e.g., a composition comprising a compound of formula (II). In some embodiments, the thromboembolic consequence or complication is associated with a peripheral vascular intervention, hemodialysis, catheter ablation, a cerebrovascular intervention, transplantation of an organ, surgery, a trans-catheter aeortic valve implantation, a large bore intervention used to treat an aneurysm, a percutaneous coronary intervention, or hemophilia therapy. In some embodiments, the surgery is orthopedic surgery, lung surgery, abdominal surgery, or cardiac surgery.

In an aspect, provided herein is a method of treating restenosis following arterial injury in a subject, comprising administering to a subject an effective amount of a compound described herein, e.g., a compound of formula (II) or a pharmaceutically acceptable salt thereof, or a composition described herein, e.g., a composition comprising a compound of formula (II). In some embodiments, the arterial injury occurs after a cranial artery stenting.

In an aspect, provided herein is a method of treating hepatic vessel thrombosis in a subject, comprising administering to a subject an effective amount of a compound described herein, e.g., a compound of formula (II) or a pharmaceutically acceptable salt thereof, or a composition described herein, e.g., a composition comprising a compound of formula (II).

In an aspect, provided herein is a method of treating a non-ST-elevation myocardial infarction or ST-elevetion myocardial infarction), comprising administering to a subject an effective amount of a compound described herein, e.g., a compound of formula (II) or a pharmaceutically acceptable salt thereof, or a composition described herein, e.g., a composition comprising a compound of formula (II).

In an aspect, provided herein is a method of maintaining blood vessel patency, comprising administering to a subject an effective amount of a compound described herein, e.g., a compound of formula (II) or a pharmaceutically acceptable salt thereof, or a composition described herein, e.g., a composition comprising a compound of formula (II). In some embodiments, the subject is has acute kidney injury. In some embodiments, the subject additionally undergoes continuous renal replacement therapy.

In an aspect, provided herein is a method of treating hypertension in a subject, comprising administering to the subject an effective amount of a compound described herein, e.g., a compound of formula (II) or a pharmaceutically acceptable salt thereof, or a composition described herein, e.g., a composition comprising a compound of formula (II). In some embodiments, the hypertension is arterial hypertension.

In an aspect, provided herein is a method of reducing the risk of hypertension in a subject, comprising administering to the subject an effective amount of a compound described herein, e.g., a compound of formula (II) or a pharmaceutically acceptable salt thereof, or a composition described herein, e.g., a composition comprising a compound of formula (II). In some embodiments, the hypertension is arterial hypertension.

In an aspect, provided herein is a method of prophylaxis of hypertension in a subject, comprising administering to the subject an effective amount of a compound described herein, e.g., a compound of formula (II) or a pharmaceutically acceptable salt thereof, or a composition described herein, e.g., a composition comprising a compound of formula (II). In some embodiments, the hypertension is arterial hypertension.

In an aspect, provided herein is a method of reducing inflammation in a subject, comprising administering to the subject an effective amount of a compound described herein, e.g., a compound of formula (II) or a pharmaceutically acceptable salt thereof, or a composition described herein, e.g., a composition comprising a compound of formula (II). In some embodiments, the inflammation is vascular inflammation. In some embodiments, the vascular inflammation is angiotensin II-induced vascular inflammation.

In an aspect, provided herein is a method of preventing vascular leukocyte infiltration in a subject, comprising administering to the subject an effective amount of a compound described herein, e.g., a compound of formula (II) or a pharmaceutically acceptable salt thereof, or a composition described herein, e.g., a composition comprising a compound of formula (II).

In an aspect, provided herein is a method of preventing angiotensin II-induced endothelial dysfunction in a subject, comprising administering to the subject an effective amount of a compound described herein, e.g., a compound of formula (II) or a pharmaceutically acceptable salt thereof, or a composition described herein, e.g., a composition comprising a compound of formula (II).

In an aspect, provided herein is a method of preventing thrombin propagation in a subject, comprising administering to the subject an effective amount of a compound described herein, e.g., a compound of formula (II) or a pharmaceutically acceptable salt thereof, or a composition described herein, e.g., a composition comprising a compound of formula (II).

In an aspect, provided herein is a method of treating hypertension-associated renal dysfunction in a subject, comprising administering to the subject an effective amount of a compound described herein, e.g., a compound of formula (II) or a pharmaceutically acceptable salt thereof, or a composition described herein, e.g., a composition comprising a compound of formula (II).

In an aspect, provided herein is a method of prophylaxis of hypertension-associated renal dysfunction in a subject, comprising administering to the subject an effective amount of a compound described herein, e.g., a compound of formula (II) or a pharmaceutically acceptable salt thereof, or a composition described herein, e.g., a composition comprising a compound of formula (II).

In an aspect, provided herein is a method of reducing the risk of hypertension- associated renal dysfunction in a subject, comprising administering to the subject an effective amount of a compound described herein, e.g., a compound of formula (II) or a pharmaceutically acceptable salt thereof, or a composition described herein, e.g., a composition comprising a compound of formula (II).

In an aspect, provided herein is a method of treating hypertension-associated renal dysfunction in a subject, comprising administering to the subject an effective amount of a compound described herein, e.g., a compound of formula (II) or a pharmaceutically acceptable salt thereof, or a composition described herein, e.g., a composition comprising a compound of formula (II).

In an aspect, provided herein is a method of prophylaxis of hypertension-associated renal dysfunction in a subject, comprising administering to the subject an effective amount of a compound described herein, e.g., a compound of formula (II) or a pharmaceutically acceptable salt thereof, or a composition described herein, e.g., a composition comprising a compound of formula (II).

In an aspect, provided herein is a method of reducing the risk of hypertension- associated renal dysfunction in a subject, comprising administering to the subject an effective amount of a compound described herein, e.g., a compound of formula (II) or a pharmaceutically acceptable salt thereof, or a composition described herein, e.g., a composition comprising a compound of formula (II).

In an aspect, provided herein is a method of treating kidney fibrosis in a subject, comprising administering to the subject an effective amount of a compound described herein, e.g., a compound of formula (II) or a pharmaceutically acceptable salt thereof, or a composition described herein, e.g., a composition comprising a compound of formula (II).

In an aspect, provided herein is a method of prophylaxis of kidney fibrosis in a subject, comprising administering to the subject an effective amount of a compound described herein, e.g., a compound of formula (II) or a pharmaceutically acceptable salt thereof, or a composition described herein, e.g., a composition comprising a compound of formula (II).

In an aspect, provided herein is a method of reducing the risk of kidney fibrosis in a subject, comprising administering to the subject an effective amount of a compound described herein, e.g., a compound of formula (II) or a pharmaceutically acceptable salt thereof, or a composition described herein, e.g., a composition comprising a compound of formula (II).

In an aspect, provided herein is a method of treating kidney injury in a subject, comprising administering to the subject an effective amount of a compound described herein, e.g., a compound of formula (II) or a pharmaceutically acceptable salt thereof, or a composition described herein, e.g., a composition comprising a compound of formula (II).

In an aspect, provided herein is a method of prophylaxis of kidney injury in a subject, comprising administering to the subject an effective amount of a compound described herein, e.g., a compound of formula (II) or a pharmaceutically acceptable salt thereof, or a composition described herein, e.g., a composition comprising a compound of formula (II).

In an aspect, provided herein is a method of reducing the risk of kidney injury in a subject, comprising administering to the subject an effective amount of a compound described herein, e.g., a compound of formula (II) or a pharmaceutically acceptable salt thereof, or a composition described herein, e.g., a composition comprising a compound of formula (II).

In an aspect, provided herein is a method of treating a thromboembolic disorder in a subject need thereof, comprising administering to the subject an effective amount of a compound described herein, e.g., a compound of formula (II) or a pharmaceutically acceptable salt thereof, or a composition described herein, e.g., a composition comprising a compound of formula (II), wherein the subject is exposed to an artificial surface.

In an aspect, provided herein is a method of reducing the risk of a thromboembolic disorder in a subject need thereof, comprising administering to the subject an effective amount of a compound described herein, e.g., a compound of formula (II) or a pharmaceutically acceptable salt thereof, or a composition described herein, e.g., a composition comprising a compound of formula (II), wherein the subject is exposed to an artificial surface.

In an aspect, provided herein is a method of prophylaxis of a thromboembolic disorder in a subject need thereof, comprising administering to the subject an effective amount of a compound described herein, e.g., a compound of formula (II) or a pharmaceutically acceptable salt thereof, or a composition described herein, e.g., a composition comprising a compound of formula (II), wherein the subject is exposed to an artificial surface.

In an aspect, provided herein is a method of treating heparin-induced thrombocytopenia in a subject in need thereof, comprising administering to the subject an effective amount of a compound described herein, e.g., a compound of formula (II) or a pharmaceutically acceptable salt thereof, or a composition described herein, e.g., a composition comprising a compound of formula (II).

In an aspect, provided herein is a method of reducing the risk of heparin-induced thrombocytopenia in a subject in need thereof, comprising administering to the subject an effective amount of a compound described herein, e.g., a compound of formula (II) or a pharmaceutically acceptable salt thereof, or a composition described herein, e.g., a composition comprising a compound of formula (II).

In an aspect, provided herein is a method of prophylaxis of heparin-induced thrombocytopenia in a subject in need thereof, comprising administering to the subject an effective amount of a compound described herein, e.g., a compound of formula (II) or a pharmaceutically acceptable salt thereof, or a composition described herein, e.g., a composition comprising a compound of formula (II).

In an aspect, provided herein is a method of treating heparin-induced thrombocytopenia thrombosis in a subject in need thereof, comprising administering to the subject an effective amount of a compound described herein, e.g., a compound of formula (II) or a pharmaceutically acceptable salt thereof, or a composition described herein, e.g., a composition comprising a compound of formula (II).

In an aspect, provided herein is a method of reducing the risk of heparin-induced thrombocytopenia thrombosis in a subject in need thereof, comprising administering to the subject an effective amount of a compound described herein, e.g., a compound of formula (II) or a pharmaceutically acceptable salt thereof, or a composition described herein, e.g., a composition comprising a compound of formula (II).

In an aspect, provided herein is a method of prophylaxis of heparin-induced thrombocytopenia thrombosis in a subject in need thereof, comprising administering to the subject an effective amount of a compound described herein, e.g., a compound of formula (II) or a pharmaceutically acceptable salt thereof, or a composition described herein, e.g., a composition comprising a compound of formula (II).

In an aspect, provided herein is a method of prophylaxis of thromboembolic disorder in a subject in need thereof, comprising administering to the subject an effective amount of a compound described herein, e.g., a compound of formula (II) or a pharmaceutically acceptable salt thereof, or a composition described herein, e.g., a composition comprising a compound of formula (II), wherein the subject has cancer.

In an aspect, provided herein is a method of treating thrombotic microangiopathy in a subject in need thereof, the method comprising administering to the subject an effective amount of a compound of formula (II) described herein, e.g., a compound of formula (II) or a pharmaceutically acceptable salt thereof, or a composition described herein, e.g., a composition comprising a compound of formula (II).

In an aspect, provided herein is a method of reducing the risk of thrombotic microangiopathy in a subject in need thereof, the method comprising administering to the subject an effective amount of a compound described herein, e.g., a compound of formula (II) or a pharmaceutically acceptable salt thereof, or a composition described herein, e.g., a composition comprising a compound of formula (II).

In another aspect, the present invention features a method of prophylaxis of thrombotic microangiopathy in a subject in need thereof, the method comprising administering to the subject an effective amount of a compound described herein, e.g., a compound of formula (II) or a pharmaceutically acceptable salt thereof, or a composition described herein, e.g., a composition comprising a compound of formula (II).

In some embodiments, the subject is a subject with non-valvular atrial fibrillation. In some embodiments, the subject has one or more of the following risk factors for stroke: a prior stroke, transient ischemic attack, or non-CNS systemic embolism. In some embodiments, the subject has one or more of the following risk factors for stroke: 75 years or older of age, hypertension, heart failure or left ventricular ejection fraction, or diabetes mellitus.

Extracorporeal Membrane Oxygenation (ECMO)

The compounds of the present invention can be used in the treatment, prophylaxis, or reduction in the risk of a thromboembolic disorder in a subject in need thereof, wherein the subject is exposed to an artificial surface such as that of an extracorporeal membrane oxygenation (ECMO) apparatus (vide supra), which can be used as a rescue therapy in response to cardiac or pulmonary failure. The surface of an ECMO apparatus that directly contacts the subject can be a pro-thrombotic surface that can result in a thromboembolic disorder such as a venous thromboembolism, e.g., deep vein thrombosis or pulmonary embolism, leading to difficulties in treating a patient in need of ECMO. Clots in the circuit are the most common mechanical complication (19%). Major clots can cause oxygenator failure, and pulmonary or systemic emboli.

ECMO is often administered with a continuous infusion of heparin as an anticoagulant to counter clot formation. However, cannula placement can cause damage to the internal jugular vein, which causes massive internal bleeding. Bleeding occurs in 30-40% of patients receiving ECMO and can be life-threatening. This severe bleeding is due to both the necessary continuous heparin infusion and platelet dysfunction. Approximately 50% of reported deaths are due to severe bleeding complications. Aubron et al. *Critical Care,* 2013, 17:R73 looked at the factors associated with ECMO outcomes.

The compounds of the present invention, which can be used as, for example, Factor XIa inhibitors, are thus contemplated as an alternative replacement for heparin in ECMO therapy. The compounds of the present invention are contemplated as effective agents for blocking the intrinsic pathway at plasma levels that will not cause heavy bleeding.

Ischemia

"Ischemia" or an "ischemic event" is a vascular disease generally involving vascular occlusion or a restriction in blood supply to tissues. Ischemia can cause a shortage of oxygen and glucose needed for cellular metabolism. Ischemia is generally caused by problematic blood vessels that result in damage or dysfunction of tissue. Ischemia can also refer to a local loss in blood or oxygen in a given part of the body resulting from congestion (e.g., vasoconstriction, thrombosis, or embolism). Causes include embolism, thrombosis of an atherosclerosis artery, trauma, venous problems, aneurysm, heart conditions (e.g., myocardial infarction, mitral valve disease, chronic arterial fibrillation, cardiomyopathies, and prosthesis), trauma or traumatic injury (e.g., to an extremity producing partial or total vessel occlusion), thoracic outlet syndrome, atherosclerosis, hypoglycemia, tachycardia, hypotension, outside compression of a blood vessel (e.g., by a tumor), sickle cell disease, localized extreme cold (e.g., by frostbite), tourniquet application, glutamate receptor stimulation, arteriovenous malformations, rupture of significant blood vessels supplying a tissue or organ, and anemia.

A transient ischemic event generally refers to a transient (e.g., short-lived) episode of neurologic dysfunction caused by loss of blood flow (e.g., in the focal brain, spinal cord, or retinal) without acute infarction (e.g., tissue death). In some embodiments, the transient ischemic event lasts for less than 72 hours, 48 hours, 24 hours, 12 hours, 10 hours, 8 hours, 4 hours, 2 hours, 1 hour, 45 minutes, 30 minutes, 20 minutes, 15 minutes, 10 minutes, 5 minutes, 4 minutes, 3 minutes, 2 minutes, or 1 minute.

Angioedema

Angioedema is the rapid swelling of the dermis, subcutaneous tissue, mucosa, and submucosal tissues. Angioedema is typically classified as either hereditary or acquired.

"Acquired angioedema" can be immunologic, non-immunologic, or idiopathic; caused by e.g., allergy, as a side effect of medications, e.g., ACE inhibitor medications.

"Hereditary angioedema" or "HAE" refers to a genetic disorder that results in acute periods of edema (e.g., swelling) that may occur in nearly all parts of the body, including the face, limbs, neck, throat, larynx, extremities, gastrointestinal tract, and genitalia. Attacks of HAE can often be life-threatening, with severity depending on the area affected, e.g., abdominal attacks may result in intenstinal obstruction, while swelling of the larynx and upper airway can lead to asphyxiation. Pathogenesis of hereditary angioedema may be related to unopposed activation of the contact pathway by the initial generation of kallikrein or clotting factors (e.g., Factor XII).

Signs and symptoms include swelling, e.g., of the skill of the face, mucosa of the mouth or throat, and tongue. Itchiness, pain, decreased sensation in the affected areas, urticaria (i.e., hives), or stridor of the airway may also be a sign of angioedema. However, there can be no associated itch, or urticaria, e.g., in hereditary angioedema. HAE subjects can experience abdominal pain (e.g., abdominal pain lasting one to five days, abdominal attacks increasing a subject's white blood cell count), vomiting, weakness, watery diarrhea, or rash.

Bradykinin plays an important role in angioedema, particularly hereditary angioedema. Bradykinin is released by various cell types in response to numerous different stimuli and is a pain mediator. Interfering with bradykinin production or degradation can lead to angioedema. In hereditary angioedema, continuous production of enzyme kallikrein can facilitate bradykinin formation. Inhibition of kallikrein can interfere with bradykinin production; and treat or prevent angioedema.

Pharmaceutical Compositions

The compositions described herein include the compound described herein (e.g., a compound of formula (II), e.g., a compound of formulas (I), (I-a), (I-b), (I-c), (I-d), (I-e), (I-f), (I-g), (I-h), (I-i), (I-j), (I-k), (I-l), (I-m), (I-n), (I-o), (I-p), (I-q), (I-r), (I-s), (I-s1), (I-s2), (I-t), (I-u), or (I-v). as well as additional therapeutic agents, if present, in amounts effective for achieving the treatment of a disease or disease symptoms (e.g., such as a disease associated with Factor XIa or kallikrein).

Pharmaceutically acceptable carriers, adjuvants and vehicles that may be used in the pharmaceutical compositions provided herewith include, but are not limited to, ion exchangers, alumina, aluminum stearate, lecithin, self-emulsifying drug delivery systems (SEDDS) such as d-α-tocopherol polyethyleneglycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β-, and γ-cyclodextrin, or chemically modified derivatives such as hydroxyalkylcyclodextrins, including 2- and 3-hydroxypropyl-β-cyclodextrins, or other solubilized derivatives may also be advantageously used to enhance delivery of compounds of the formulae described herein.

Routes of Administration

The pharmaceutical compositions provided herewith may be administered orally, rectally, or parenterally (e.g., intravenous infusion, intravenous bolus injection, inhalation, implantation). The term parenteral as used herein includes subcutaneous, intracutaneous, intravenous (e.g., intravenous infusion, intravenous bolus injection), intranasal, inhalation, pulmonary, transdermal, intramuscular, intraarticular, intraarterial, intrasynovial, intrasternal, intrathecal, intralesional and intracranial injection or other infusion techniques. The pharmaceutical compositions provided herewith may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form.

The pharmaceutical compositions may be in the form of a sterile injectable preparation, for example, as a sterile injectable aqueous or oleaginous solution or suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, or carboxymethyl cellulose or similar dispersing agents which are commonly used in the formulation of pharmaceutically acceptable dosage forms such as emulsions and or suspensions. Other commonly used surfactants such as Tweens or Spans or other similar emulsifying agents or bioavailability enhancers which are commonly used in the manufacture of pharmaceutically acceptable solid, liquid, or other dosage forms may also be used for the purposes of formulation.

The pharmaceutical compositions provided herewith may be orally administered in any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions or emulsions are administered orally, the active ingredient may be suspended or dissolved in an oily phase is combined with emulsifying or suspending agents. If desired, certain sweetening or flavoring or coloring or taste masking agents may be added.

The compounds described herein can, for example, be administered by injection, intravenously (e.g., intravenous infusion, intravenous bolus injection), intraarterially, subdermally, intraperitoneally, intramuscularly, or subcutaneously; or orally, buccally, nasally, transmucosally, topically with a dosage ranging from about 0.5 to about 100 mg/kg of body weight, alternatively dosages between 1 mg and 1000 mg/dose, every 4 to 120 hours, or according to the requirements of the particular drug. The methods herein contemplate administration of an effective amount of compound or compound composition to achieve the desired or stated effect. Typically, the pharmaceutical compositions provided herewith will be administered from about 1 to about 6 times per day (e.g., by intravenous bolus injection) or alternatively, as a continuous infusion. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Alternatively, such preparations contain from about 20% to about 80% active compound.

In some embodiments, a pharmaceutical composition formulated for oral administration or intravenous administration is administered to a subject from 1 time per day to 6 times per day (e.g., 2 times per day or 4 times per day). In some embodiments, a pharmaceutical composition formulated for oral administration is administered to a subject from 1 time per day to 6 times per day (e.g., 2 times per day or 4 times per day) for about 3 to 9 months. In some embodiments, a pharmaceutical composition formulated for oral administration is administered to a subject from 1 time per day to 6 times per day (e.g., 2 times per day or 4 times per day) for the rest of his or her life.

In some embodiments, the compound is administered orally or parenterally. In some embodiments, the compound is administered orally. In some embodiments, the compound is administered parenterally. In some embodiments, the compound or pharmaceutically acceptable salt thereof or pharmaceutical composition thereof is administered after the subject has discontinued use of a direct oral anticoagulant. In some embodiments, the subject used the direct oral anticoagulant. In some embodiments, the subject is a mammal. In some embodiments, the mammal is a human.

Combinations

In carrying out the methods of the present invention, it may be desired to administer the compounds of the invention (e.g., Factor XIa or kallikrein inhibitors) in combination with each other and one or more other agents for achieving a therapeutic benefit such as antithrombotic or anticoagulant agents, anti-hypertensive agents, anti-ischemic agents, anti-arrhythmic agents, platelet function inhibitors, and so forth. For example, the methods of the present invention may be carried out by administering the small molecule Factor XIa or kallikrein inhibitors in combination with a small molecule Factor XIa or kallikrein inhibitor. More particularly, the inventive methods may be carried out by administering the small molecule Factor XIa or kallikrein inhibitors in combination with aspirin, clopidogrel, ticlopidine or CS-747, warfarin, low molecular weight heparins (such as LOVENOX), GPIIb/GPIIIa blockers, PAI-1 inhibitors such as XR-330 and T-686, P2Y1 and P2Y12 receptor antagonists; thromboxane receptor antagonists (such as ifetroban), prostacyclin mimetics, thromboxane A synthetase inhibitors (such as picotamide), serotonin-2-receptor antagonists (such as ketanserin); compounds that inhibit other coagulation factors such as FVII, FVIII, FIX, FX, prothrombin, TAFI, and fibrinogen, or other compounds that inhibit FXI or kallikrein; fibrinolytics such as TPA, streptokinase, PAI-1 inhibitors, and inhibitors of α-2-antiplasmin such as anti-α-2-antiplasmin antibody fibrinogen receptor antagonists, inhibitors of α-1-antitrypsin, hypolipidemic agents, such as HMG-CoA reductase inhibitors (e.g., pravastatin, simvastatin, atorvastatin, fluvastatin, cerivastatin, AZ4522, and itavastatin), and microsomal triglyceride transport protein inhibitors (such as disclosed in U.S. Pat. Nos. 5,739,135, 5,712,279 and 5,760,246); antihypertensive agents such as angiotensin-converting enzyme inhibitors (e.g., captopril, lisinopril or fosinopril); angiotensin-II receptor antagonists (e.g., irbesartan, losartan or valsartan); ACE/NEP inhibitors (e.g., omapatrilat and gemopatrilat); or β-blockers (such as propranolol, nadolol and carvedilol). The inventive methods may be carried out by administering the small molecule Factor XIa or kallikrein inhibitors in combination with anti-arrhythmic agents such as for atrial fibrillation, for example, amiodarone or dofetilide. The inventive methods may also be carried out in combination continuous renal replacement therapy for treating, e.g., acute kidney injury.

In carrying out the methods of the present invention, it may be desired to administer the compounds of the invention (Factor XIa or kallikrein inhibitors) in combination with agents that increase the levels of cAMP or cGMP in cells for a therapeutic benefit. For example, the compounds of the invention may have advantageous effects when used in combination with phosphodiesterase inhibitors, including PDE1 inhibitors (such as those described in Journal of Medicinal Chemistry, Vol. 40, pp. 2196-2210 [1997]), PDE2 inhibitors, PDE3 inhibitors (such as revizinone, pimobendan, or olprinone), PDE4 inhibitors (such as rolipram, cilomilast, or piclamilast), PDE7 inhibitors, or other PDE inhibitors such as dipyridamole, cilostazol, sildenafil, denbutyline, theophylline (1,2-dimethylxanthine), ARIFLOT™ (i.e., cis-4-cyano-[3-(cyclopentylox-y)-4-methoxyphenyl] cyclohexane-1-carboxylic acid), arofyline, roflumilast, C-11294A, CDC-801, BAY-19-8004, cipamfylline, SCH351591, YM-976, PD-189659, mesiopram, pumafentrine, CDC-998, IC-485, and KW-4490.

The inventive methods may be carried out by administering the compounds of the invention in combination with prothrombolytic agents, such as tissue plasminogen activator (natural or recombinant), streptokinase, reteplase, activase, lanoteplase, urokinase, prourokinase, anisolated streptokinase plasminogen activator complex (ASPAC), animal salivary gland plasminogen activators, and the like.

The inventive methods may be carried out by administering the compounds of the invention in combination with β-adrenergic agonists such as albuterol, terbutaline, formoterol, salmeterol, bitolterol, pilbuterol, or fenoterol; anticholinergics such as ipratropium bromide; anti-inflammatory cortiocosteroids such as beclomethasone, triamcinolone, budesonide, fluticasone, flunisolide or dexamethasone; and anti-inflammatory agents such as cromolyn, nedocromil, theophylline, zileuton, zafirlukast, monteleukast and pranleukast.

Small molecule Factor XIa or kallikrein inhibitors may act synergistically with one or more of the above agents. Thus, reduced doses of thrombolytic agent(s) may be used, therefore obtaining the benefits of administering these compounds while minimizing potential hemorrhagic and other side effects.

Course of Treatment

The compositions described herein include an effective amount of a compound of the invention (e.g., a Factor XIa or kallikrein inhibitor) in combination and one or more other agents (e.g., an additional therapeutic agent) such as antithrombotic or anticoagulant agents, anti-hypertensive agents, anti-ischemic agents, anti-arrhythmic agents, platelet function inhibitors, and so forth for achieving a therapeutic benefit.

In some embodiments, the additional therapeutic agent is administered following administration of the compound of the invention (e.g., a Factor XIa or kallikrein inhibitor). In some embodiments, the additional therapeutic agent is administered 15 minutes, 30 minutes, 1 hour, 2 hours, 4 hours, 6 hours, 8 hours, 10 hours, 12 hours, 14 hours, 18 hours, 24 hours, 48 hours, 72 hours or longer after administration of the compound of the invention (e.g., a Factor XIa or kallikrein inhibitor). In some embodiments, the additional therapeutic agent is administered (e.g., orally) after discharge from a medical facility (e.g., a hospital).

In some embodiments, the compound of the invention (e.g., a Factor XIa or kallikrein inhibitor) and the additional therapeutic agent are co-formulated into a single composition or dosage. In some embodiments, the compound of the invention (e.g., a Factor XIa or kallikrein inhibitor) and the additional therapeutic agent are administered separately. In some embodiments, the compound of the invention (e.g., a Factor XIa or kallikrein inhibitor) and the additional therapeutic agent are administered sequentially. In some embodiments, the compound of the invention (e.g., a Factor XIa or kallikrein inhibitor) and the additional therapeutic agent are administered separately and sequentially. In general, at least one of the compound of the invention (e.g., a Factor XIa or kallikrein inhibitor) and the additional therapeutic agent is administered parenterally (e.g., intranasally, intramuscularly buccally, inhalation, implantation, transdermal, intravenously (e.g., intravenous infusion, intravenous bolus injection), subcutaneous, intracutaneous, intranasal, pulmonary, transdermal, intraarticular, intraarterial, intrasynovial, intrasternal, intrathecal, intralesional and intracranial injection or other infusion techniques); orally; or rectally, for example, intramuscular injection or intravenously (e.g., intravenous infusion, intravenous bolus injection)). In some embodiments, compound of the invention is administered parenterally (e.g., intranasally, buccally, intravenously (e.g., intravenous infusion, intravenous bolus injection) or intramuscularly). In some embodiments, the additional therapeutic agent is administered orally. In some embodiments, the compound of the invention (e.g., a Factor XIa or kallikrein inhibitor) is administered parenterally (e.g., intranasally, buccally, intravenously (e.g., intravenous infusion, intravenous bolus injection) or intramuscularly) and the additional therapeutic agent is administered orally.

In some embodiments, the compound of the invention (e.g., a Factor XIa or kallikrein inhibitor) may be administered once or several times a day. A duration of treatment may follow, for example, once per day for a period of about 1, 2, 3, 4, 5, 6, 7 days or more. In some embodiments, the treatment is chronic (e.g., for a lifetime). In some embodiments, either a single dose in the form of an individual dosage unit or several smaller dosage units or by multiple administrations of subdivided dosages at certain intervals is administered. For instance, a dosage unit can be administered from about 0 hours to about 1 hr, about 1 hr to about 24 hr, about 1 to about 72 hours, about 1 to about 120 hours, or about 24 hours to at least about 120 hours post injury. Alternatively, the dosage unit can be administered from about 0.5, 1, 1.5, 2, 3, 4, 5, 6, 7, 8, 9, 10, 11, 12, 13, 14, 15, 16, 17, 18, 19, 20, 21, 22, 23, 24, 30, 40, 48, 72, 96, 120 hours or longer post injury. Subsequent dosage units can be administered any time following the initial administration such that a therapeutic effect is achieved. In some embodiments, the initial dose is administered orally. In some embodiments, doses subsequent to the initial dose are administered parenterally (e.g., intranasally, intramuscularly buccally, inhalation, implantation, transdermal, intravenously (e.g., intravenous infusion, intravenous bolus injection), subcutaneous, intracutaneous, intranasal, pulmonary, transdermal, intraarticular, intraarterial, intrasynovial, intrasternal, intrathecal, intralesional and intracranial injection or other infusion techniques); orally; or rectally.

In some embodiments, compounds of the invention (e.g., a Factor XIa or kallikrein inhibitor) is administered orally, e.g., as an liquid or solid dosage form for ingestion, for about 5 minutes to about 1 week; about 30 minutes to about 24 hours, about 1 hour to about 12 hours, about 2 hours to about 12 hours, about 4 hours to about 12 hours, about 6 hours to about 12 hours, about 6 hours to about 10 hours; about 5 minutes to about 1 hour, about 5 minutes to about 30 minutes; about 12 hours to about 1 week, about 24 hours to about 1 week, about 2 days to about 5 days, or about 3 days to about 5 days. In one embodiment, the compound of the invention (e.g., a Factor XIa or kallikrein inhibitor) is administered orally as a liquid dosage form. In another embodiment, the compound of the invention (e.g., a Factor XIa or kallikrein inhibitor) is administered orally as a solid dosage form.

Where a subject undergoing therapy exhibits a partial response, or a relapse following completion of the first cycle of the therapy, subsequent courses of therapy may be needed to achieve a partial or complete therapeutic response (e.g., chronic treatment, e.g., for a lifetime).

In some embodiments, the compound of the invention (e.g., a Factor XIa or kallikrein inhibitor) is administered intravenously, e.g., as an intravenous infusion or intravenous bolus injection, for about 5 minutes to about 1 week; about 30 minutes to about 24 hours, about 1 hour to about 12 hours, about 2 hours to about 12 hours, about 4 hours to about 12 hours, about 6 hours to about 12 hours, about 6 hours to about 10 hours; about 5 minutes to about 1 hour, about 5 minutes to about 30 minutes; about 12 hours to about 1 week, about 24 hours to about 1 week, about 2 days to about 5 days, or about 3 days to about 5 days. In one embodiment, the compound of the invention (e.g., a Factor XIa or kallikrein inhibitor) is administered as an intravenous infusion for about 5, 10, 15, 30, 45, or 60 minutes or longer; about 1, 2, 4, 6, 8, 10, 12, 16, or 24 hours or longer; about 1, 2, 3, 4, 5, 6, 7, 8, 9, or 10 days or longer.

In some embodiments, the compound is administered after an ischemic event. In some embodiments, the compound is administered about 1, 2, 3, 4, 5, 6, 7, 8, 9, 10, 11, 12, 13, or 14 days or more after an ischemic event. In some embodiments, the compound is administered about 1, 2, 3, 4, 5, 6, 7, or 8 weeks or more after an ischemic event. In some embodiments, the compound is administered about 1, 2, 3, 4, 5, or 6 months or more after an ischemic event.

In some embodiments, the compound is administered in combination with an additional therapeutic agent. In some embodiments, the additional therapeutic agent is administered after administration of the compound. In some embodiments, the additional therapeutic agent is administered orally. In some embodiments, the additional therapeutic agent is administered at least 1, 2, 3, 4, 5, 6, 7, 8, 10, 12, 14, 16, 18, 20, or 24 hours or more after administration of the compound. In some embodiments, the additional therapeutic agent is administered at least 1, 2, 3, 4, 5, 6, 7, 14, 21, or 28 days or more after administration of the compound. In some embodiments, the additional therapeutic agent is administered about 1 day, about 2 days, about 3 days, about 4 days, about 5 days, about 6 days, about 7 days or more after administration of the compound. In some embodiments, the additional therapeutic agent is administered chronically after administration of the compound. In some embodiments, the additional therapeutic agent is a NSAID, platelet aggregation inhibitor, or anticoagulant. In some embodiments, the additional therapeutic agent results in an additive therapeutic effect. In some embodiments, the additional therapeutic agent results in a synergistic therapeutic effect.

Dosages and Dosing Regimens

The effective amount of a small molecule Factor XIa or kallikrein inhibitor administered according to the present invention may be determined by one of ordinary skill in the art. The specific dose level and frequency of dosage for any particular subject may vary and will depend upon a variety of factors, including the activity of the specific compound employed, the metabolic stability and length of action of that compound, the species, age, body weight, general health, sex and diet of the subject, the mode and time of administration, rate of excretion, drug combination, and severity of the particular condition.

Upon improvement of a patient's condition, a maintenance dose of a compound, composition or combination provided herewith may be administered, if necessary. Subsequently, the dosage or frequency of administration, or both, may be reduced, as a function of the symptoms, to a level at which the improved condition is retained when the symptoms have been alleviated to the desired level. Patients may, however, require intermittent treatment on a long-term basis upon any recurrence of disease symptoms.

EXAMPLES

Starting materials and various intermediates described in the following examples may be obtained from commercial sources, prepared from commercially available organic compounds, or prepared using known synthetic methods. Representative examples of methods suitable for preparing intermediates of the invention are also set forth below.

General Procedures

All non-aqueous reactions were run under an atmosphere of nitrogen to maintain an anhydrous atmosphere and to maximize yields. All reactions were stirred using an overhead stirring assembly or magnetically, with the aid of a Teflon-coated stir bar. The description 'drying over' refers to drying of a reaction product solution over a specified drying agent, for example magnesium sulfate or sodium sulfate, and then filtration of the solution though a suitable filter paper or through a sintered glass funnel. The descriptions 'was concentrated', 'was concentrated at reduced pressure', or 'evaporated' refers to removal of solvents under reduced pressure using a rotary evaporator. Chromatography or chromatographed refers to the use of flash column chromatography on silica gel unless otherwise specified. Flash chromatography may use gas pressure (nitrogen for example) or may use a mechanical pump to apply solvent pressure such as with a commercial system as supplied by Biotage or other vendors. Preparative TLC refers to thin layer chromatorgraphy on silica gel plates. Flash chromatography refers to column chromatography under pressure and may be run using a commercial unit such as that produced by Biotage, for example. Retention time refers to the elution time of the product by HPLC under the specified conditions. Unless otherwise specified, all NMR spectra are proton spectra ($^{1}$H) in the specified solvent.

In the following Examples, high performance liquid chromatography/mass spectrometry (HPLC/MS) conditions used for the characterization of the compounds herein are:

1. Analytical HPLC/MS instrumentation: Analysis are performed using a Waters 2545 Binary Gradient Module (Waters Corporation, Milford, Mass.), a Waters SFO System Fluidics Organizer, a Waters 2996 Diode Array Detector and a Waters 2767 auto-sampler, 3100 mass detector. Data are acquired using MassLynx™ 4.0 software, with OpenLynx™ and AutoLynx™ processing.

2. Analytical HPLC conditions: 4.6×50 mm column; UV 10 spectra/sec, 220-340 nm summed; flow rate 2.0 mL/min; injection volume 5 µL;

Gradient condition A: mobile phase A is Water with 0.1% formic acid; mobile phase B is acetonitrile with 0.1% formic acid, and the gradient is 1.50 minutes 99.0% A to 95.0% B; 0.5 minutes hold; then recycle to 99.0% A over 0.5 minutes.

Gradient condition B: mobile phase A is Water with 0.1% formic acid; mobile phase B is acetonitrile with 0.1% formic acid, and the gradient is 3.00 minutes 95.0% A to 95.0% B; 2.0 minutes hold; then recycle to 95.0% A over 0.5 minutes.

Abbreviations used in the experimental examples are listed in the Abbreviations Table below.

| Abbreviation Table | |
|---|---|
| ACN | Acetonitrile |
| Ammonium chloride solution | Saturated aqueous ammonium chloride solution |
| Aqueous ammonium chloride | Saturated aqueous ammonium chloride solution |
| Aqueous NaHCO$_3$ | Saturated aqueous sodium bicarbonate solution |
| Brine | Saturated aqueous sodium chloride solution |
| BOC or Boc | Tert-butyloxycarbonyl |
| Celite ® | Diatomaceous earth |
| DBU | 1,8-Diazabicyclo[5.4.0]undec-7-ene |
| DCM | Dichloromethane |
| DMSO | Dimethylsulfoxide |
| EA | Ethyl acetate |
| Ether | Diethyl ether |
| H | Hours |
| HATU | 1-[Bis(dimethylamino)methylene]-1H-1,2,3-triazolo[4,5-b] pyridinium 3-oxide hexafluorophosphate |
| LC-MS | HPLC/MS |
| LDA | Lithium diisopropylamide |
| Min | Minutes |
| NMR | Nuclear magnetic resonance instrument |
| Pd/C | Palladium on carbon |
| PMB | 4-methoxybenzyl |
| Ret. Time | HPLC retention time |
| RT | Room temperature |
| TBME | Tert-butyl methyl ether |
| TEA | Triethylamine |
| Tert | Tertiary |
| THF | Tetrahydrofuran |
| TMAF | Tetramethylammonium fluoride |
| ACN | Acetonitrile |
| DMF | N-N-Dimethylformamide |
| TLC | Thin layer chromatography |
| X-phos | 2-Dicyclohexylphosphino-2',4',6'-triisopropylbiphenyl |
| Chromatography or Chromatographed | Purification of products using flash column chromatography on silica gel |
| Concentrated or concentrated in vacuo | Concentration of organic solutions under reduced pressure with the use of a rotary evaporator |

Scheme 1

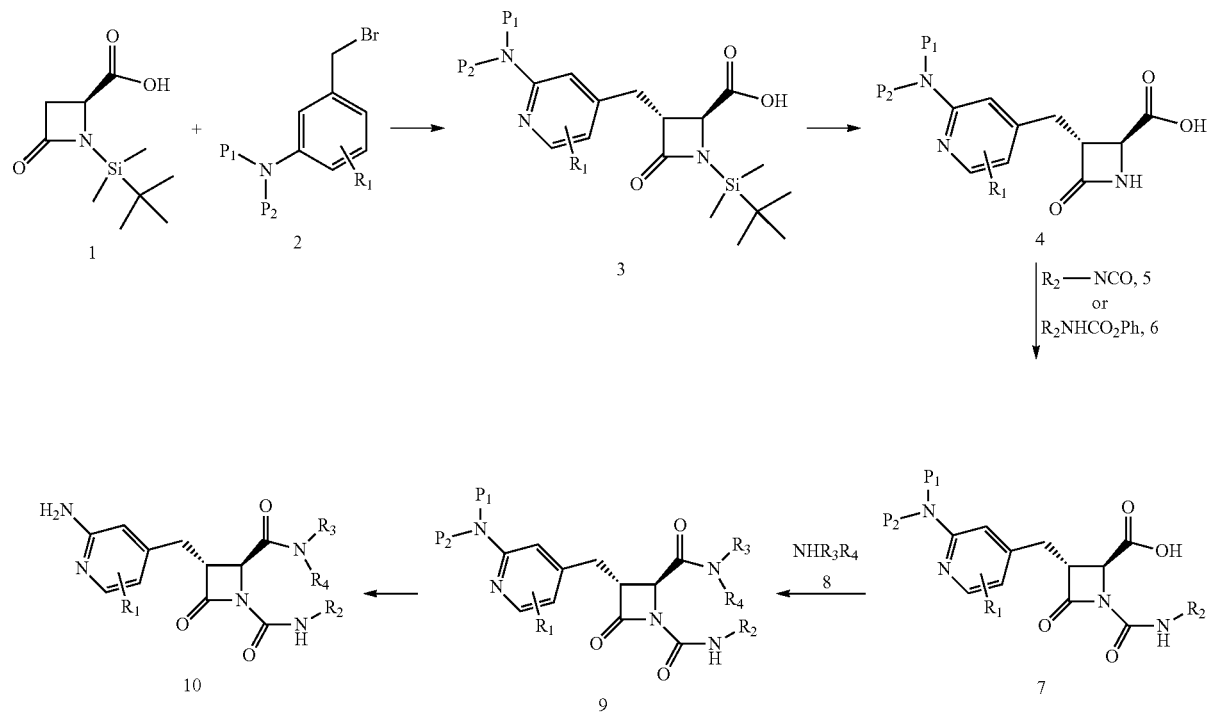

Scheme 1 illustrates a general method for the preparation of (2S, 3R)-trans-disubstituted-4-oxoazetidines of general structure 10 containing an amide group at the 2-position. Alkylation of the dianion of compound 1 with a commercially available or readily prepared compound 2 (as described in the intermediates 7 and 8) affords the desired compound 3 as predominately the trans product and with retention of the stereochemistry at the 2-position (Baldwin, J. E., et al., Tetrahedron, 1990, 46, 4733). Removal of the TBS protecting group at N-1 provides compound 4, which is then reacted with the isocyanate 5 or phenyl carbamate 6 to give compound 7. Coupling of the carboxylic acid 7 with a commercially available or readily prepared amine 8 (as described in the intermediate 6) in the presence of a base and coupling reagent affords compound 9. Subsequent removal of protection groups P1 and P2 provides compound 10.

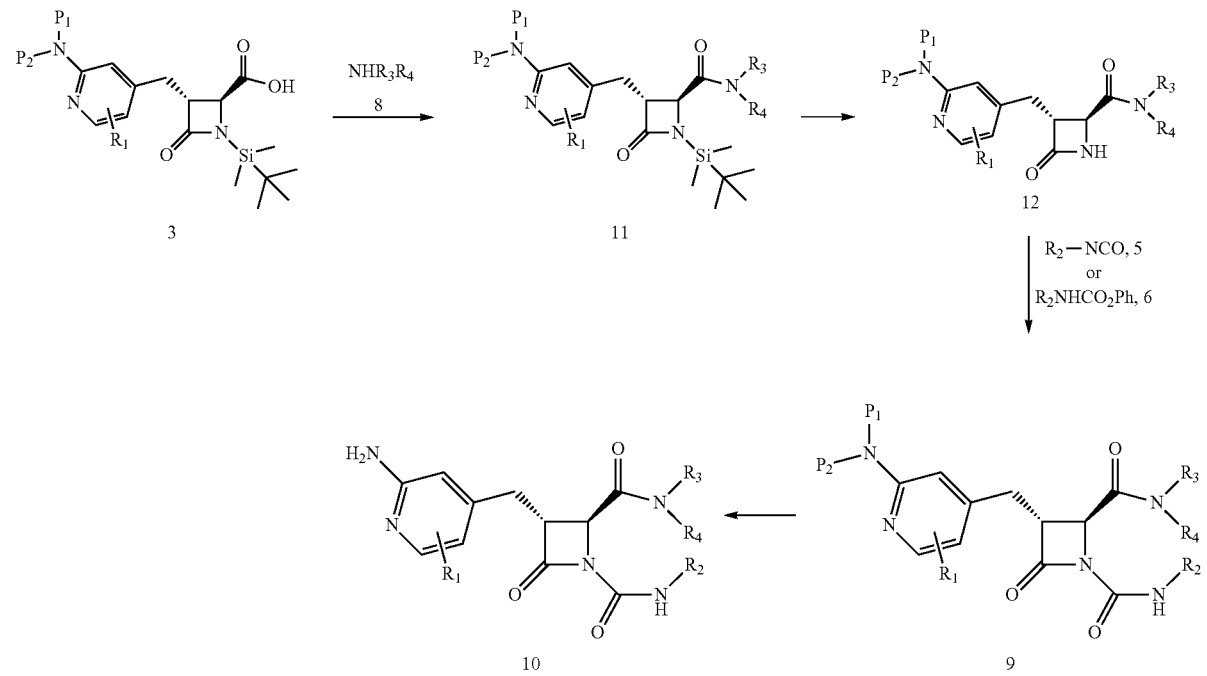

Scheme 2

Scheme 2 illustrates an alternative method for the preparation of compound 10. Coupling of the carboxylic acid 3 with a commercially available or readily prepared amine 8 (as described in the intermediate 6) in the presence of a base and coupling reagent affords compound 11. Removal of the TBS protecting group at N-1 provides compound 12, which is then reacted with the isocyanate 5 or phenyl carbamate 6 to give compound 9. Subsequent removal of protection groups P1 and P2 provides examples of the general compound 10.

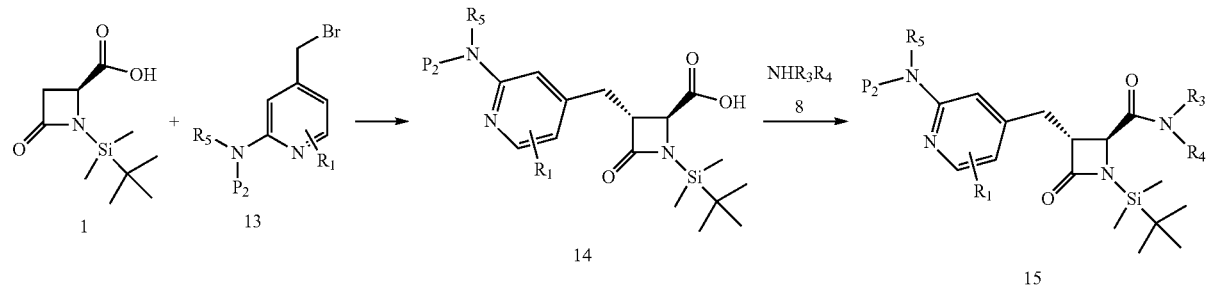

Scheme 3

-continued

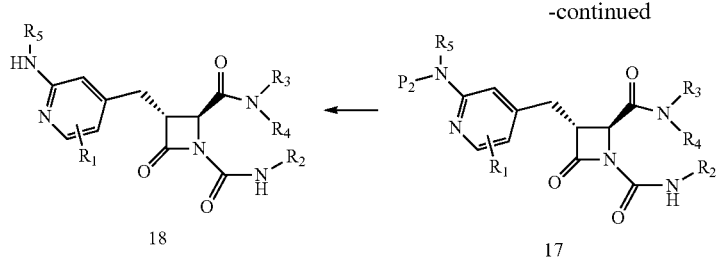 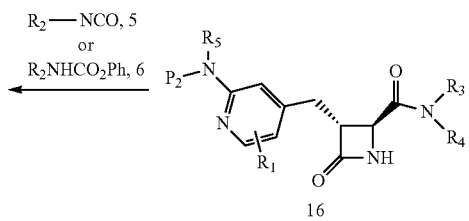

Scheme 3 illustrates a general method for the preparation of compound 18. Alkylation of the dianion of compound 1 with a commercially available or readily prepared compound 13 (prepared as described for intermediate 9) affords the desired compound 14. Coupling of the carboxylic acid 14 with a commercially available or readily prepared amine 8 (as described in the intermediate 6) in the presence of a base and coupling reagent affords compound 15. Removal of the TBS protecting group at N-1 provides compound 16, which is then reacted with the isocyanate 5 or phenyl carbamate 6 to give compound 17. Subsequent removal of protection group P2 provides compound 18.

Scheme 4

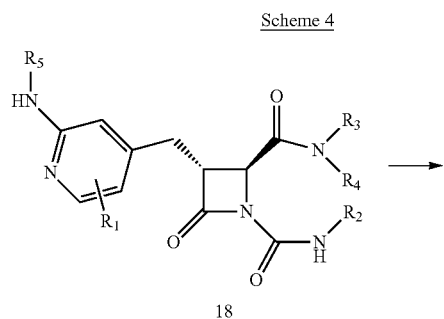

Scheme 4 illustrates a general method for the preparation of compound 19. Alkylation of compound 18 ($R_5$=hydrogen or alkyl) with alkyl halide in the presence of a base or the reaction of compound 18 with alkyl aldehyde in the presence of a reducing agent (such as $NaBH_3CN$ etc.) affords the compound 19.

Scheme 5

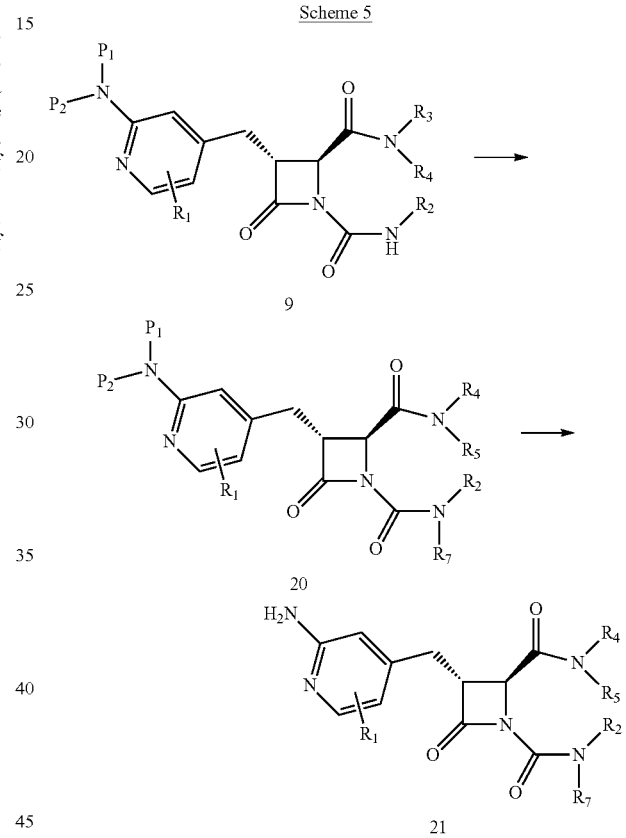

Scheme 5 illustrates a general method for the preparation of compound 21. Alkylation of compound 9 with alkyl halide in the presence of a base affords the compound 20. Subsequent removal of protection groups P1 and P2 provides the compound 21.

Example 1. Preparation of Intermediates.

Intermediate 1: Phenyl N-[(1S)-1-cyclohexyl-2,2,2-trifluoroethyl]carbamate

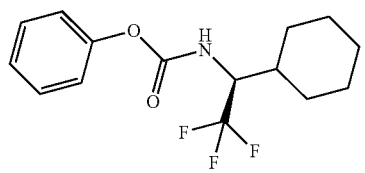 [SMILES: O=C(N[C@@H](C1CCCCC1)C(F)(F)F)Oc1ccccc1]

To a stirred solution of phenylchloroformate (714 µL, 5.69 mmol) in dry THF (30 mL) at 0° C. was added a solution of (1S)-1-cyclohexyl-2,2,2-trifluoroethanamine (1.00 g, 5.52 mmol) and pyridine (536 µL, 6.63 mmol) in THF (18 mL) dropwise over 45 min. After an additional 45 min at 0° C., the mixture was diluted with EA (50 mL), washed with aqueous NaHCO$_3$ (50 mL), water (40 mL) and brine (30 mL), dried over MgSO$_4$ and concentrated. The resulting solid was triturated with hexanes (35 mL), isolated by filtration, washed with small amounts of hexanes and dried to give 1.51 g (91%) of the title compound as a white solid which was used without further purification. $^1$H NMR (400 MHz, CDCl$_3$) δ 7.40 (m, 2H), 7.24 (m, 1H), 7.17 (m, 2H), 5.20 (br d, 1H), 4.25 (m, 1H), 1.92-1.68 (m, 6H), 1.40-1.05 (m, 5H); MS (ESI+) m/z 302.1 (M+H)$^+$, retention time: 2.03 min. (Method A).

Intermediate 2: Phenyl N-[(1R)-1-cyclohexylpropyl]carbamate 7.97 (1H, d, J=4.6 Hz), 2.47 (1H, m), 1.92-1.68 (7H, m), 1.67-1.35 (3H, m), 1.20 (9H, s).

Step 2. Preparation of [S(S)]-N-((1R)-1-cyclohexyl-propyl)-2-methyl-2-propanesulfinamide

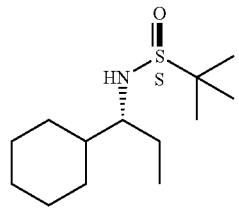

[N(E),S(S)]-N-(cyclohexylmethylene)-2-methyl-2-propanesulfinamide (32.3 g, 0.15 mol) was dissolved in TBME (500 mL). The reaction was cooled to −40° C. and ethyl Scheme 6

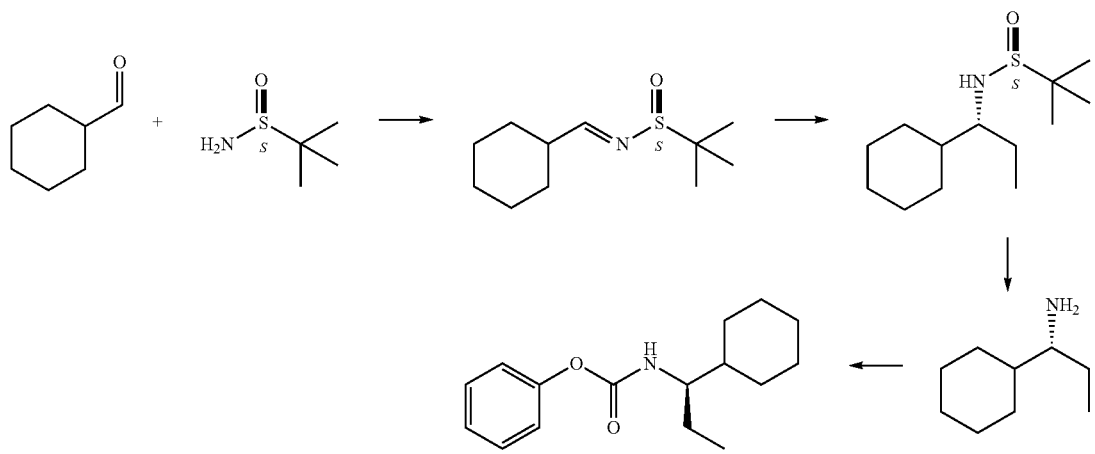

Step 1. Preparation of [N(E),S(S)]-N-(cyclohexylmethylene)-2-methyl-2-propanesulfinamide

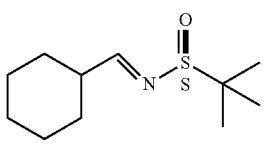

To a solution of cyclohexanecarbaldehyde (25 g, 0.223 mol), (S)-(-)-2-methyl-2-propanesulfinamide (28.4 g, 0.234 mol) in THF (300 mL) was added titanium (IV) ethoxide (101.7 g, 0.446 mol). The resulting reaction mixture was heated at 75° C. for 2 h. The mixture was cooled to RT. Brine (250 mL) was added and the mixture was vigously stirred, then filtered through Celite®, and washed with EA (300 mL). The aqueous layer was extracted with EA (2×200 mL). The combined organic phase was dried over MgSO$_4$, filtered and concentrated. The crude product was chromatographed (eluted with 4:1 hexane:EA) to give the product as a colorless oil (45.6 g, 95%). $^1$H NMR (400 MHz, CDCl$_3$) δ magnesium bromide (3M in ether, 100 mL, 0.3 mol) was added dropwise and the reaction was stirred at −25° C. for 4 h. Aqueous mmonium chloride and then EA were added. The layers separated and the aqueous layer was extracted with EA twice. The combined organic phase was washed with brine, dried over sodium sulfate, concentrated, and chromatographed (eluted with 2:1 of hexane:EA) to afford [S(S)]-N4(1R)-1-cyclohexylpropyl)-2-methyl-2-propanesulfinamide as a colorless oil (22 g, 60%). $^1$H NMR (400 MHz, CDCl$_3$) δ 0.90-1.00 (m, 4H), 1.12 (m, 1H), 1.20 (s, 9H), 1.44 (m, 1H), 1.52-1.80 (m, 9H), 2.88-3.00 (m, 2H).

Step 3. Preparation of (R)-1-cyclohexylpropan-1-amine hydrochloride

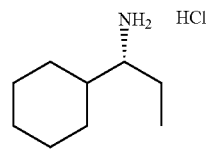

[S(S)]-N-((1R)-1-cyclohexylpropyl)-2-methyl-2-propanesulfinamide (31.86 g, 0.129 mol) was dissolved in methanol (200 mL) and 4M HCl in 1,4-dioxane (100 mL) was added slowly. The reaction solution was stirred for 60 min. The reaction was concentrated to leave a solid resudue. Hexane (200 mL) was added to the solid and the resulting suspension was stirred at RT for 60 min. The solid was filtered, rinsed with hexanes and dried to give (R)-1-cyclohexylpropan-1-amine hydrochloride as a white solid (12.8 g, 56%).

Step 4. Preparation of phenyl N-[(1R)-1-cyclohexylpropyl]carbamate

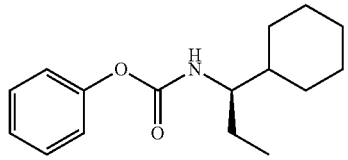 [SMILES: CC[C@@H](NC(=O)Oc1ccccc1)C1CCCCC1]

To a stirred suspension of (R)-1-cyclohexylpropan-1-amine hydrochloride (5 g, 28.1 mmol) in DCM (100 mL) at 0° C. was added TEA (6.82 g, 67.4 mmol); then phenylchloroformate (4.84 g, 31 mmol) was added slowly. After stirring an additional 45 min at RT, the mixture was diluted with DCM (50 mL), washed with aqueous NaHCO$_3$ (50 mL), water (40 mL) and brine (30 mL), dried over MgSO$_4$ and concentrated. The resulting solid was triturated with hexane (35 mL). The solid was collected by filtration, washed with small amounts of hexane and dried to give 6.3 g (85%) of the title compound as a white solid which was used without further purification. $^1$H NMR (400 MHz, CDCl$_3$) δ 7.40 (m, 2H), 7.24 (m, 1H), 7.17 (m, 2H), 4.75 (br d, 1H), 3.50 (m, 1H), 1.92-1.68 (m, 6H), 1.50-1.05 (m, 10H). MS (ESI+) 262.2 (M+H)$^+$, Retention time: 2.09 min (method A).

Intemediate 3. (R)-1-(3-Pyridinyl)-1-propanamine dihydrochloride

Scheme 7

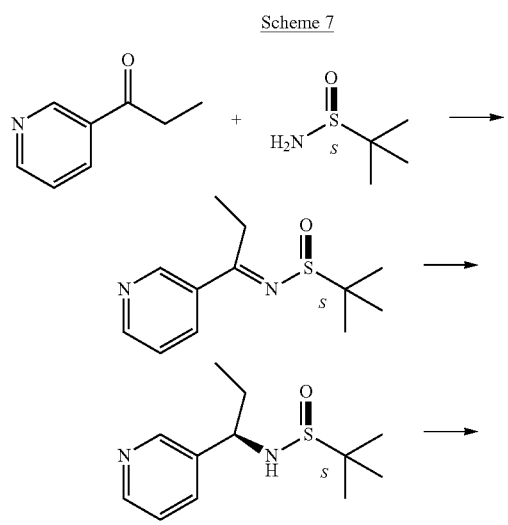

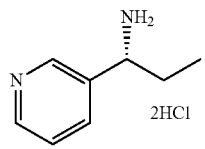

Step 1. Preparation of [S(S)]-N-[1-(pyridin-2-yl)propylidene]-2-methylpropane-2-sulfinamide

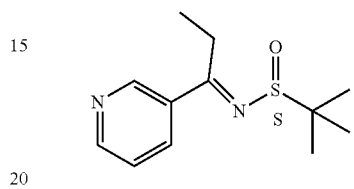

A solution of the 3-propionylpyridine (5 g, 37 mmol), (S)-(-)-2-methylpropane-2-sulfinamide (4.7 g, 38.8 mmol) and titanium (IV) ethoxide (17.8 g, 78 mmol) in THF (100 mL) was heated at 80° C. for 3 days. After cooling, brine (100 mL) and EA (100 mL) were added. The mixture was stirred at RT for 1 h. The mxture was filtered through Celite®, and the pad was washed with EA. The organic phase was seperated, concentrated, and the residue was chromatographed (eluted with 2:1 hexane:EA) to give the product as a colorless oil (8.15 g, 92%).

Step 2. Preparation of [S(S),R]-N-[1-(pyridin-2-yl)propyl]-2-methylpropane-2-sulfinamide

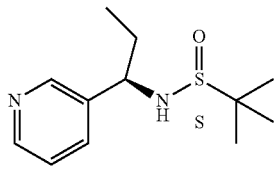

To a solution of [(S(S)]-N-[1-(pyridin-2-yl)propylidene]-2-methylpropane-2-sulfinamide (8.15 g, 34.2 mmol) in THF (150 mL) at −78° C., was added a solution of tri-sec-butylborohydride (L-selectride, 1M solution in THF, 68 mL, 68 mmol). The reaction mixture was stirred for 3 h at −78° C. The reaction was quenched with aqueous ammonium chloride (150 mL). The mixture was filtered through Celite® and the pad was rinsed with EA. The organic phase was separated, dried over Na$_2$SO$_4$, and concentrated. The residue was chromatographed (eluted with 1:1 of hexane:EA) to give product as a colorless oil (4.3 g, 53%).

Step 3. (R)-1-(3-Pyridinyl)-1-propanamine dihydrochloride

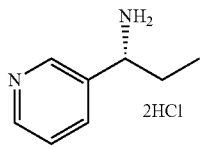

To a solution of [S(S),R]-N-[1-(pyridin-2-yl)propyl]-2-methylpropane-2-sulfinamide (4.3 g, 17.9 mmol) in methanol (50 mL), was slowly added 4M HCl in 1,4-dioxane (22 mL). The reaction was stirred for 1 h. The reaction was concentrated to a solid residue. Hexane (50 mL) was added to the solid and the resulting suspension was stirred at RT for 1 h. The solid was filtered, rinsed with hexanes and dried to give (R)-1-(3-pyridinyl)-1-propanamine dihydrochloride as a white solid (3.3 g, 90%). $^1$H NMR (400 Hz, DMSO-$d_6$) δ 0.80 (t, 2H), 1.90 (m, 1H), 2.10 (m,1H), 4.20 (m, 1H), 8.04 (d, 1H), 8.80 (d, 1H), 8.90 (m, 2H), 9.20 (br, 4 H). MS (ESI+) m/z 137.1 (M+H)$^+$. Retention time: 0.35 min. (Method A).

Intermediate 4.
(S)-1-cyclopropyl-2,2,2-trifluoroethylamine hydrochloride

Scheme 8

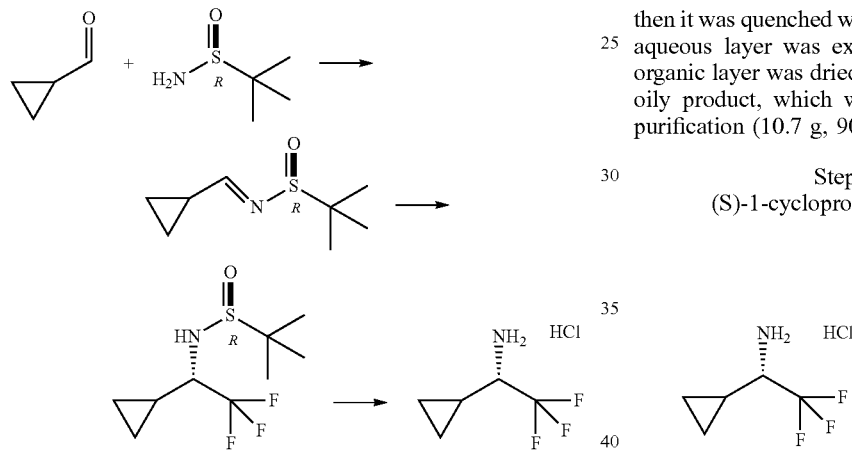

Step 1. Preparation of [N(E),R(S)]-N-(cyclopropylmethylene)-2-methyl-2-propanesulfinamide

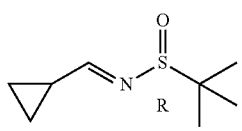

To a solution of cyclopropanecarboxaldehyde (10 g, 0.14 mol) in THF (100 mL) was added (R)-2-methyl-2-propanesulfinamide (18.2 g, 0.15 mol), and titanium (IV) ethoxide (65.1 g, 0.285 mol). The resulting mixture was heated at 75° C. for 2 h. The mixture was cooled to RT. Brine (150 mL) was added and the mixture was vigously stirred; then it was filtered through Celite® and the pad was washed with EA (300 mL). The aqueous layer was extracted with EA (2×200 mL). The combined organic extracts were dried over MgSO$_4$ and concentrated. The residue was chromatographed (eluted with 4:1 of hexane:EA) to give the product as colorless oil (22.2 g, 90%).

Step 2. Preparation of [R(S)]-N-((1S)-1-cyclopropyl-2,2,2-trifluoroethyl)-2-methyl-2-propanesulfinamide

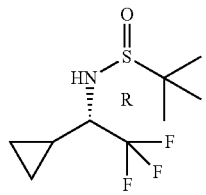

To a solution of [N(E),R(S)]-N-(cyclopropylmethylene)-2-methyl-2-propanesulfinamide (7.8 g, 45 mmol) in THF (150 mL) was added TMAF (5 g, 53.7 mmol). The solution was degassed with nitrogen and was then cooled to −55° C. A solution of trifluoromethyltrimethylsilane (9.6 g, 67.5 mmol) in THF (150 mL) was added dropwise and the reaction mixture was allowed to stir at −55° C. for 2 h. The reaction mixture was slowly allowed to warm to −10° C.; then it was quenched with aqueous ammonium chloride. The aqueous layer was extracted with EA and the combined organic layer was dried and concentracted to yield a yellow oily product, which was carried forward without further purification (10.7 g, 90%).

Step 3. Preparation of (S)-1-cyclopropyl-2,2,2-trifluoroethylamine hydrochloride

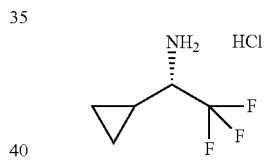

[R(S)]-N-((1S)-1-cyclopropyl-2,2,2-trifluoroethyl)-2-methyl-2-propanesulfinamide (10.7 g, 44 mmol) was dissolved in methanol (100 mL) and 4M HCl in 1,4-dioxane (44 mL) was added slowly. The solution was stirred for 1 h. The solvent was evaporated leaving a solid residue. Hexane (100 mL) was added to the solid to give a suspension which was stirred at RT for 1 h. The solid was filtered, rinsed with hexanes and dried to give (S)-1-cyclopropyl-2,2,2-trifluoroethylamine hydrochloride as a white solid (5.4 g, 70%). $^1$H NMR (400 Hz, DMSO-$d_6$) δ 0.50-0.70 (m, 4H), 1.04 (m, 1H), 3.60 (m, 1H) 9.20 (br, 3H).

Intermediate 5. Synthesis of (R)-(+)-1-Phenylpropyl isocyanate

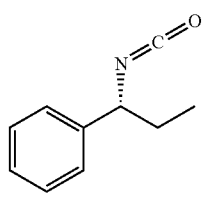

To a solution of R-(+)-1-phenylpropylamine (5 g, 37 mmol) in DCM (80 mL) was added 1N aqueous NaHCO₃ solution (86 mL). The mixture was cooled to 0° C., and triphosgene (3.73 g, 12.6 mmol) was added. The reaction was stirred for 15 min at 0° C. under. The reaction was extracted with DCM twice. The combined organic phase was dried over Na₂SO₄, and concentrated to afford (R)-(+)-1-phenylpropyl isocyanate as a colorless oil (5.4 g, 91%), which was used for the next step without purification. ¹H NMR (400 Hz, CDCl₃) δ 0.97 (t, 3H), 1.85 (m, 2H), 4.52 (t, 1H), 7.29 (m, 3H), 7.34 (m, 2H).

Intermediate 6. N,1-Dimethyl-1H-pyrazl-5-amine hydrochloride

Scheme 9

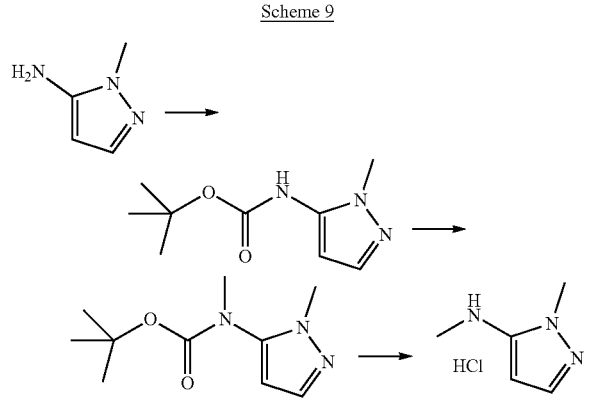

Step 1. Prepararion of tert-butyl N-(1-methyl-1H-pyrazol-5-yl)carbamate

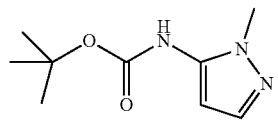

To a solution of 1-methyl-1H-pyrazol-5-ylamine (5 g, 51 mmol) in DCM (30 mL) at RT was added di-tert-butyldicarbonate (12.4 g, 56.8 mml) and then TEA (10.4 g, 103 mml). The resulting mixture was stirred at RT overnight. The mixture was washed with water. The organic layer was dried, evaporated to give product as a white solid (10 g, 98%), which was used for the next step without purification. ¹H NMR (400 Hz, CDCl₃) δ 1.40 (s, 9H), 1.74 (s, 1H), 3.16 (s, 3H), 6.02 (d, 1H), 7.40 (d, 1H).

Step 2. Preparation of tert-butyl N-methyl-N-(1-methyl-1H-pyrazol-5-yl)carbamate

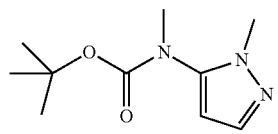

To a solution of tert-butyl N-(1-methyl-1H-pyrazol-5-yl) carbamate (10 g, 51 mmol) in THF (100 mL) at 0° C. was added sodium hydride in portion (2.5 g, 60% in mineral oil). The mixture was allowed to warm to RT and stirred for 30 min. To the reaction, iodomethane (10.8 g, 76 mmol) was added slowly. The resulting mixture was stirred at RT overnight. The reaction was quenched with aqueous ammonium chloride (30 mL). The mixture was extracted with EA (50 mL×3). The combined organics were washed with brine, dried over MgSO₄ and concentrated. The residue was chromatographed (eluted with 4:1 of hexane:EA) to give the product as colorless oil (9.5 g, 89%). ¹H NMR (400 Hz, CDCl₃) δ 1.40 (s, 9H), 3.16 (s, 3H), 3.64 (s, 3H), 6.10 (d, 1H), 7.42 (d, 1H).

Step 2. Preparation of N,1-Dimethyl-1H-pyrazl-5-amine hydrochloride

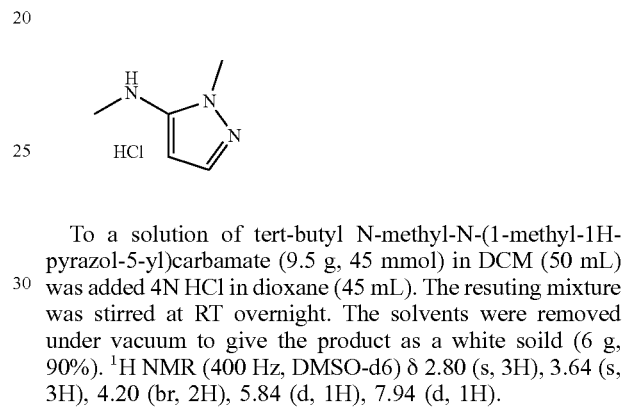

To a solution of tert-butyl N-methyl-N-(1-methyl-1H-pyrazol-5-yl)carbamate (9.5 g, 45 mmol) in DCM (50 mL) was added 4N HCl in dioxane (45 mL). The resuting mixture was stirred at RT overnight. The solvents were removed under vacuum to give the product as a white soild (6 g, 90%). ¹H NMR (400 Hz, DMSO-d6) δ 2.80 (s, 3H), 3.64 (s, 3H), 4.20 (br, 2H), 5.84 (d, 1H), 7.94 (d, 1H).

Intermediate 7: tert-Butyl [4-(bromomethyl)-6-methylpyridin-2-yl] (4-methoxybenzyl)carbamate Scheme 10

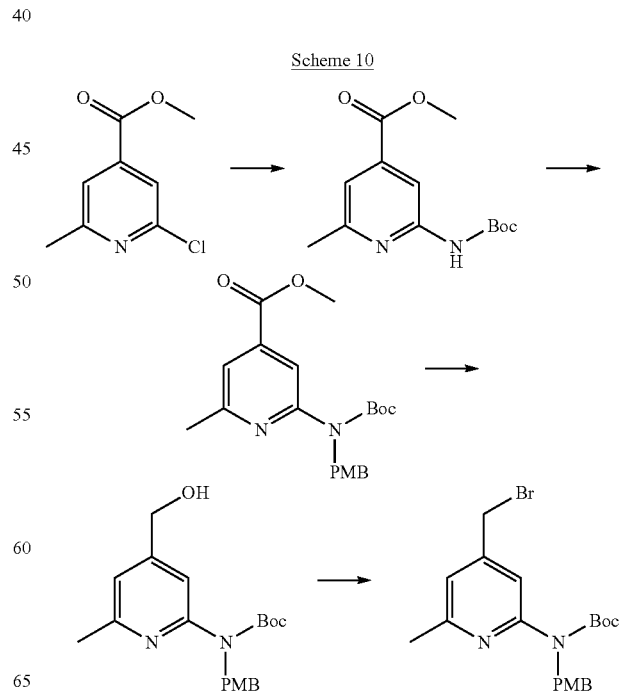

Step 1. Preparation of methyl 2-((tert-butoxycarbonyl)amino)-6-methylpyridine-4-carboxylate

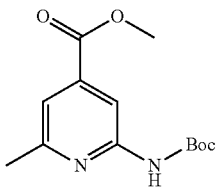 [SMILES: COC(=O)c1cc(C)nc(NC(=O)OC(C)(C)C)c1]

A mixture of methyl 2-chloro-6-methylpyridine-4-carboxylate (20 g, 107.8 mmol), tert-Butyl carbamate (15.2 g, 129.7 mmol), cesium carbonate (70.2 g, 215.5 mmol), X-phos (5.14 g, 10.8 mmol) and palladium acetate (1.2 g, 5.3 mmol) in 1,4-dioxane (300 mL) was purged with nitrogen and then stirred at 90° C. under nitrogen for two hours. The mixture was cooled to RT, and diluted with water (300 mL), and then extracted with EA (150 mL×2). The organic extracts were combined and washed with brine, dried (MgSO$_4$), and concentrated. The residue was chromatographed (eluted with 0-30% EA in hexane) to give methyl 2-((tert-butoxycarbonyl)amino)-6-methylpyridine-4-carboxylate as a white solid (25.8 g, 90%). $^1$H NMR (400 Hz, CDCl$_3$) δ 1.52 (s, 9H), 2.48 (s, 3H), 3.92 (s, 3H), 7.36 (s, 1H), 7.40 (s, 1H), 8.24 (s, 1H).

Step 2. Preparation of methyl 2-((tert-butoxycarbonyl)(4-methoxybenzyl)amino)-6-methylpyridine-4-carboxylate

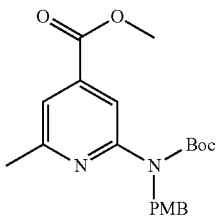

To a solution of methyl 2-((tert-butoxycarbonyl)amino)-6-methylpyridine-4-carboxylate (12.3 g, 46.2 mmol) in DMF (100 mL) was added potassium tert-butoxide (7.3 g, 60.2 mmol) in portion. The mixture was stirred at RT for 5 min, and then p-methoxy benzyl chloride (9.38 g, 59.9 mmol) was added. The resulting mixture was stirred at RT for 12 h. The water (150 mL) was added and the mixture was extracted with EA (100 mL×2). The combined organic phase was washed with brine, dried (MgSO$_4$), and concentrated. The residue was chromatographed (eluted with 0-20% EA in hexane) to give methyl 2-((tert-butoxycarbonyl)(4-methoxybenzyl)amino)-6-methylpyridine-4-carboxylate as a white solid (12.8 g, 72%). MS (ESI$^+$) m/z 387.2 (M+H)$^+$, retention time: 2.15 min (method A) . $^1$H NMR (400 Hz, CDCl$_3$) δ 1.45 (s, 9H), 2.52 (s, 3H), 3.76 (s, 3H), 3.91 (s, 3H), 5.14 (s, 2H), 6.78 (d, 2H), 7.22 (d, 2H), 7.38 (s, 1H), 7.97 (s, 1H).

Step 3. Preparation of tert-butyl (4-(hydroxymethyl)-6-methylpyridin-2-yl)(4-methoxybenzyl)carbamate

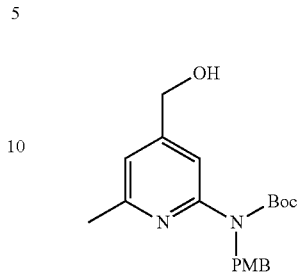

To a solution of methyl 2-((tert-butoxycarbonyl)(4-methoxybenzyl)amino)-6-methylpyridine-4-carboxylate (12.8 g, 33.1 mmol) in THF (100 mL) at RT was added lithium borohydride (1.5 g, 68.9 mmol). The mixture was heated at 40° C. for 4 h. The reaction was cooled to 0° C., and was carefully quenched by the slow, dropwise addition of aqueous NaHCO$_3$ (30 mL). The mixture was diluted with water (100 mL) and extracted with EA (50 mL×2). The combined organic phase was washed with brine (50 mL), dried (MgSO4), and concentrated. The residue was chromatographed (eluted with 40% EA in hexane) to give tert-butyl (4-(hydroxymethyl)-6-methylpyridin-2-yl)(4-methoxybenzyl)carbamate as a colorless oil (11.3 g, 95%). MS (ESI$^+$) m/z 359.1 (M+H)$^+$, retention time: 1.76 min (method A). $^1$H NMR (400 Hz, CDCl$_3$) δ 1.40 (s, 9H), 2.48 (s, 3H), 3.76 (s, 3H), 4.62 (m, 2H), 5.14 (s, 2H), 6.80 (d, 2H), 6.84 (s, 1H), 7.20 (d, 2H), 7.40 (s, 1H).

Step 4. Preparation of tert-butyl (4-(bromomethyl)-6-methylpyridin-2-yl)(4-methoxybenzyl)carbamate

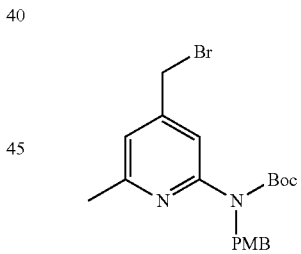

To a solution of tert-butyl (4-(hydroxymethyl)-6-methylpyridin-2-yl)(4-methoxybenzyl)carbamate (11.3 g, 31.5 mmol) and carbon tetrabromide (12.3 g, 37.1 mmol) in DCM (150 mL) at 0° C., was added triphenylphosphine (9.7 g, 37.1 mmol) in one portion. The reaction was stirred for 20 min, and allowed to warm to RT and then stirred for one h. The mixture was diluted with DCM (100 mL), and extracted with aqueous NaHCO$_3$ (50 mL×1). The organic layer was dried (MgSO$_4$), and concentrated. The residue was chromatographed (eluted with 0-20% EA in hexane) to give tert-butyl (4-(bromomethyl)-6-methylpyridin-2-yl)(4-methoxybenzyl)carbamate as a white solid (10.6 g, 80%). MS (ESI+) m/z 422.1 (M+H)$^+$. Retention time: 2.18 min. (Method A). $^1$H NMR (400 Hz, CDCl$_3$) δ 1.40 (s, 9H), 2.46 (s, 3H), 3.78 (s, 3H), 4.38 (s, 2H), 5.14 (s, 2H), 6.80 (d, 2H), 6.84 (s, 1H), 7.22 (d, 2H), 7.46 (s, 1H).

Intermediate 8: 4-(bromomethyl)-N,N-bis(4-methoxybenzyl)pyridin-2-amine

Scheme 11

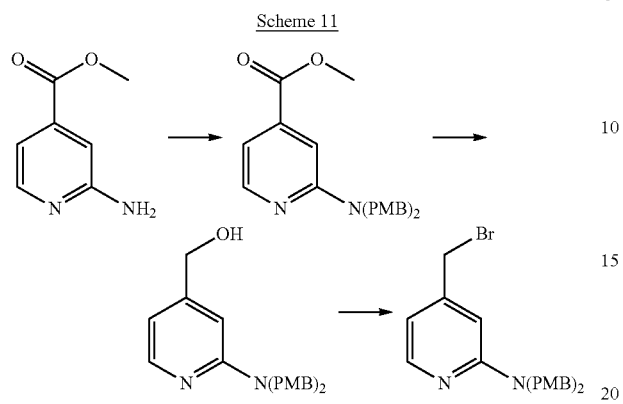

Step 1. Preparation of 2-[Bis-(4-methoxy-benzyl)-amino]-isonicotinic acid methyl ester

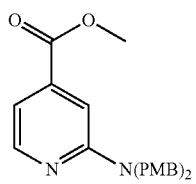

A mixture of 2-amino pyridine4-carboxylic acid methyl ester (5.5 g) and 4-methoxybenzyl chloride (14.64 g) in 33 mL of acetonitrile is heated to reflux for 3 h; then TEA (7.3 g) is added slowly into the refluxing mixture. The reaction is allowed to cool to room temperature and stir overnight. The reaction is concentrated to remove solvents and water is added to the residue causing a solid precipitate to form. The solids are collected by filtration and are recrystallized from isopropanol to afford 2-[bis-(4-methoxy-benzyl)-amino]-isonicotinic acid methyl ester (3 g, 21%) as a white solid.

Step 2. Preparation of {2-[Bis-(4-methoxy-benzyl)-amino]-pyridin-4-yl}-methanol

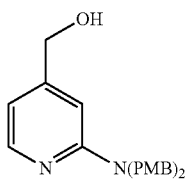

Lithium aluminum hydride (388 mg) is added portionwise to THF (16 mL) precooled to 0° C. Then 2-[bis-(4-methoxy-benzyl)-amino]-isonicotinic acid methyl ester (4 g) in THF (16 mL) is added into the mixture in dropwise while the reaction is kept at 0 to −5° C. EA (900 mg), water (388 mg) and 15% NaOH aqueous solution (388 mg) are then slowly added to the reaction, successively. The mixture is stirred 10 min; then anhydrous Na$_2$SO$_4$ (1.3 g) is added. The mixture is stirred 30 min. The solids are removed by filtration and rinsed with THF (12 mL). The filtrate was concentrated to afford {2-[bis-(4-methoxy-benzyl)-amino]-pyridin-4-yl}-methanol that is used directly in the next step without purification.

Step 3. Preparation of 4-Bromomethyl-pyridin-2-yl)-bis-(4-methoxy-benzyl)-amine

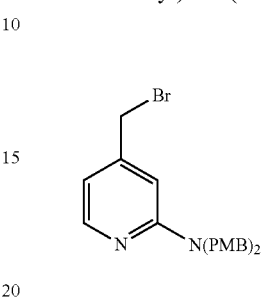

A solution of {2-[bis-(4-methoxy-benzyl)-amino]-pyridin-4-yl}-methanol (5 g) and CBr$_4$ (5 g) in DCM (25 mL) is chilled to 0-10° C. A solution of PPh$_3$ (4.32 g) in DCM (10 mL) is added dropwise. The reaction is monitored by TLC. If the starting alcohol is still present, additional PPh$_3$ is added to the reaction until the reaction is complete. The reaction is concentrated and the oily residue is treated with 50% aqueous ethanol (16 mL) and is stirred for 1 h at RT. The solids are filtered and are washed with a small quantity of 50% aqueous ethanol. The residual filter cake is is suspended and stirred again in 50% aqueous ethanol (8 mL) for another 1 h at RT. The solids are again filtered and dried to afford the title product as an off-white crystalline solid 5.2 g that has $^1$H NMR (CDCl$_3$): 8.17 (d, 1H), 7.14 (d, 4H), 6.84 (d, 4H), 6.60 (d, 1H), 6.45 (s, 1H), 4.69 (s, 4H), 4.23 (s, 2H), 3.79 (s, 6H). MS (ESI+) m/z 427.2 (M+H)$^+$; retention time: 1.82 min. (Method A).

Intermediate 9. tert-Butyl (4-(bromomethyl)pyridine-2-yl)methylcarbamate

Scheme 12

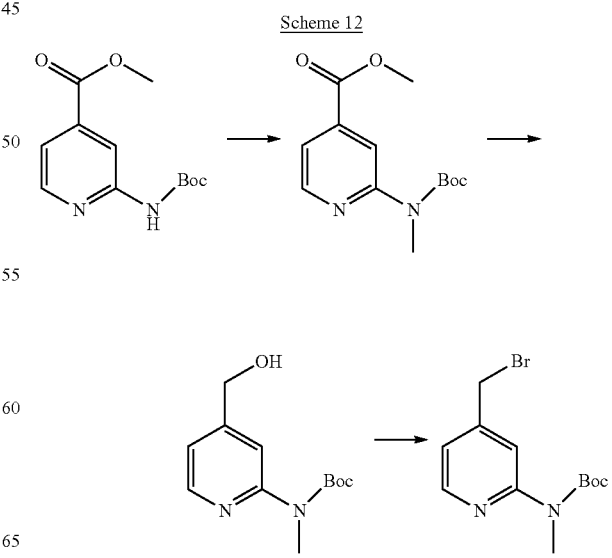

Step 1. Preparation of methyl 2-(tert-butoxycarbonyl)(methyl)amino)isonicotinate

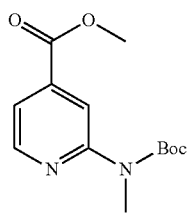 [SMILES: COC(=O)c1ccnc(N(C)C(=O)OC(C)(C)C)c1]

A slurry of methyl 2-((tert-butoxycarbonyl)amino)isonicotinate (50.4 g, 200 mmol) in DMF (500 mL) was cooled to 0° C. and sodium hydride (10.4 g, 60% in mineral oil, 260 mmol) was added portion wise. The mixture was allowed to warm to RT and stirred for 30 min. To the mixture, iodomethane (37.2 g, 262 mmol) was added slowly. The reaction was stirred at RT overnight. The reaction was quenched by addition of aqueous ammonium chloride (100 mL) and diluted with water (400 mL). The mixture was extracted with EA (250 mL×2). The combined organics were washed with water (100 mL) and brine (100 mL), dried over MgSO$_4$ and concentrated. The residue was chromatographed (eluted with 5:1 of hexane:EA) to give the product as colorless oil (48.9 g, 92%). $^1$H NMR (400 Hz, CDCl$_3$) δ 1.54 (s, 9H), 3.42 (s, 3H), 3.94 (s, 3H), 7.52 (d, 1H), 8.27 (s, 1H), 8.48 (d, 1H).

Step 2. Preparation of tert-butyl (4-(hydroxymethyl)pyridin-2-yl)methylcarbamate

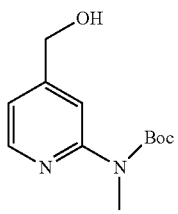 [SMILES: CN(C(=O)OC(C)(C)C)c1cc(CO)ccn1]

To a solution of methyl 2-(tert-butoxycarbonyl)(methyl)amino)isonicotinate (48.48 g, 182.1 mmol) in THF (500 mL) at RT was added lithium borohydride (5.15 g, 236.5 mmol). The mixture was heated at 40° C. for 4 h. The reaction was cooled to 0° C., and was carefully quenched by slow, drop wise addition of aqueous NaHCO$_3$ (50 mL). The mixture was diluted with water (500 mL) and extracted with EA (250 mL×2). The combined organic phase was washed with brine (150 mL), dried (MgSO$_4$), and concentrated. The residue was chromatographed (eluted with 40% EA in hexane) to give tert-butyl (4-(hydroxymethyl)pyridin-2-yl)methylcarbamate as a colorless oil (41.2 g, 95%). MS (ESI+) m/z 239.1 (M+H)$^+$, retention time: 1.36 min. (Method A). $^1$H NMR (400 Hz, CDCl$_3$) δ 1.54 (s, 9H), 3.40 (s, 3H), 4.68 (s, 2H), 7.02 (d, 1H), 7.64 (s, 1H), 8.34 (d, 1H).

Step 3. Preparation of tert-butyl (4-(bromomethyl)pyridine-2-yl)methylcarbamate

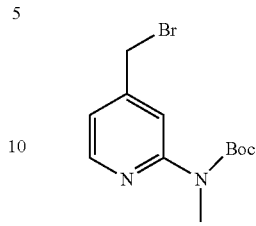

To a solution of tert-butyl (4-(hydroxymethyl)pyridin-2-yl)methylcarbamate (20.52 g, 86.1 mmol) and carbon tetrabromide (33.41 g, 100.7 mmol) in DCM (400 mL) at 0° C., was added triphenylphosphine (26.43 g, 100.7 mmol) in one portion. The reaction was stirred for 20 min, and allowed to warm to RT and then stirred for one h. The mixture was diluted with DCM (100 mL), and washed with aqueous NaHCO$_3$ (150 mL) and brine (150 mL). The organic layer was dried (MgSO4), and concentrated. The residue was chromatographed (eluted by 0-20% EA in hexane) to give tert-butyl (4-(bromomethyl)pyridine-2-yl)methylcarbamate as a colorless oil (20.7 g, 80%). 1H NMR (400 MHz, CDCl3) δ 1.54 (s, 9H), 3.41 (s, 3H), 4.39 (s, 2H), 6.92-7.12 (m, 1H), 7.66-7.84 (m, 1H), 8.24-8.43 9 (m, 1H).

Intermediate 10. tert-Butyl (4-(bromomethyl)-6-methylpyridine-2-yl)methylcarbamate Scheme 13

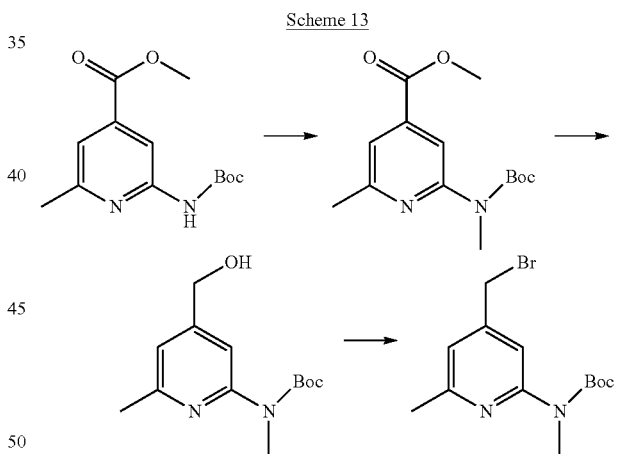

Step 1. Preparation of methyl 2-(tert-butoxycarbonyl)(methyl)amino)-6-methylpyridine-4-carboxylate

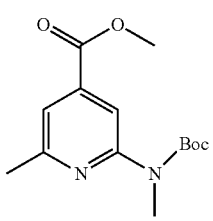 [SMILES: COC(=O)c1cc(C)nc(N(C)C(=O)OC(C)(C)C)c1]

A slurry of methyl 2-((tert-butoxycarbonyl)amino)-6-methylpyridine-4-carboxylate (20 g, 75.2 mmol) in DMF (200 mL) was cooled to 0° C. and sodium hydride (3.9 g, 60% in mineral oil, 97.5 mmol) was added portion wise. The mixture was allowed to warm to RT and stirred for 30 min. To the reaction, iodomethane (12.8 g, 90.1 mmol) was added slowly. The reaction was stirred at RT overnight. The reaction was quenched by addition of aqueous ammonium chloride (50 mL) and diluted with water (200 mL). The mixture was extracted with EA (250 mL×2). The combined organics were washed with water (100 mL) and brine (100 mL), dried over MgSO₄ and concentrated. The residue was chromatographed (eluted with 5:1 of hexane:EA) to give the product as colorless oil (18.9 g, 90%). MS (ESI+) m/z 281.1 (M+H)⁺. Retention time: 2.03 min. (Method A).

Step 2. Preparation of tert-butyl (4-(hydroxymethyl)-6-methylpyridin-2-yl)methylcarbamate

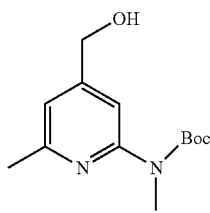 [SMILES: Cc1cc(CO)cc(N(C)C(=O)OC(C)(C)C)n1]

To a solution of methyl 2-(tert-butoxycarbonyl)(methyl)amino)-6-methylpyridine-4-carboxylate (27 g, 96.4 mmol) in THF (300 mL) at RT was added lithium borohydride (2.1 g, 96.4 mmol). The mixture was heated at 40° C. for 4 h. The reaction was cooled to 0° C., and was carefully quenched by the slow, drop wise addition of aqueous NaHCO₃ (50 mL). The mixture was diluted with water (200 mL) and extracted with EA (250 mL×2). The combined organic phase was washed with brine (150 mL), dried (MgSO4), and concentrated. The residue was chromatographed (eluted with 40% EA in hexane) to give tert-butyl (4-(hydroxymethyl)-6-methylpyridin-2-yl)methylcarbamate as a colorless oil (20 g, 82%). MS (ESI+) m/z 253.1 (M+H)⁺, retention time: 1.31 min. (Method A).

Step 3. Preparation of tert-butyl (4-(bromomethyl)-6-methylpyridin-2-yl)methylcarbamate

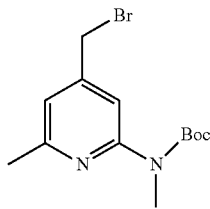 [SMILES: Cc1cc(CBr)cc(N(C)C(=O)OC(C)(C)C)n1]

To a solution of tert-butyl (4-(hydroxymethyl)-6-methylpyridin-2-yl)methylcarbamate (20 g, 79.4 mmol) and carbon tetrabromide (30.8 g, 92.8 mmol) in DCM (400 mL) at 0° C., was added triphenylphosphine (224.4 g, 93.0 mmol) in one portion. The reaction was stirred for 20 min, and allowed to warm to RT and then stirred for one h. The mixture was diluted with DCM (100 mL), and extracted with aqueous NaHCO₃ (150 mL) and brine (150 mL). The organic layer was dried (MgSO₄), and concentrated. The residue was chromatographed (eluted with 0-20% EA in hexane) to give tert-butyl (4-(bromomethyl)-6-methylpyridin-2-yl)methylcarbamate as a colorless oil (20.7 g, 80%). MS (ESI+) m/z 315.2 (M+H)⁺, retention time: 2.02 min. (Method A).

Intermediate 11: tert-Butyl [4-(bromomethyl)-5-fluoropyridin-2-yl] (4-methoxybenzyl)carbamate Scheme 14

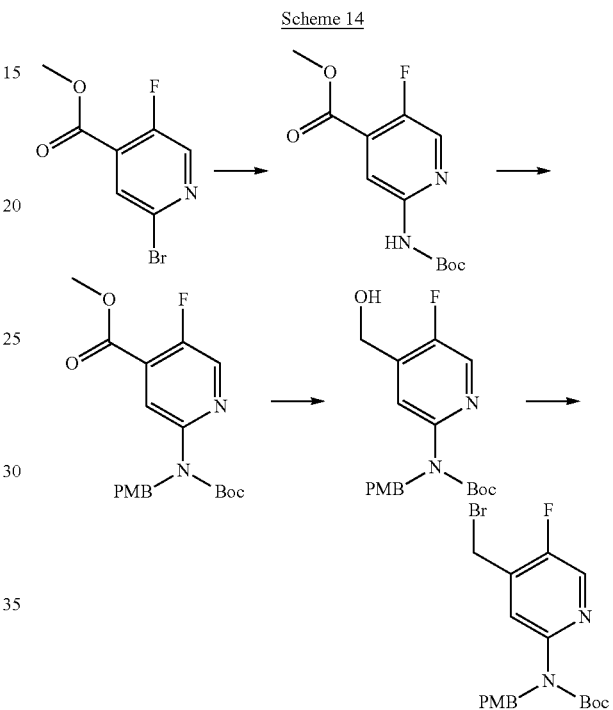

Step 1. Preparation of methyl 2-((tert-butoxycarbonyl)amino)-5-fluoropyridine-4-carboxylate

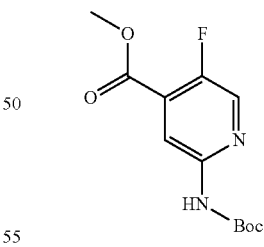

A mixture of methyl 2-bromo-5-fluoropyridine-4-carboxylate (6.64 g, 28.4 mmol), tert-Butyl carbamate (4.0 g, 34.1 mmol), cesium carbonate (13.0 g, 39.8 mmol), X-phos (657 mg, 1.1 mmol) and Pd(dba)₂ (520 mg, 0.9 mmol) in 1,4-dioxane (100 mL) was purged with nitrogen and then stirred at 100° C. under nitrogen for 6 h. The mixture was cooled to RT, diluted with water (100 mL), and extracted with EA (150 mL×2). The combined organic phase was washed with brine, dried over MgSO₄, and concentrated. The residue was chromatographed, eluting with 0-30% EA in hexane to give methyl 2-(((tert-butoxycarbonyl) amino)-

5-fluoropyridine-4-carboxylate as a white solid (4.5 g, 56%). MS (ESI+) m/z 271.1 (M+H)⁺, retention time: 1.81 min. (Method A). ¹H NMR (400 MHz, CDCl₃) δ 1.52 (s, 9H), 3.96 (s, 3H), 8.24 (s, 1H), 8.40 (d, 1H), 9.00 (s, 1H).

Step 2. Preparation of methyl 2-((tert-butoxycarbonyl)(4-methoxybenzyl)amino)-5-fluoropyridine-4-carboxylate

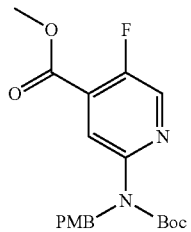

To a solution of methyl 2-((tert-butoxycarbonyl)amino)-5-fluoropyridine-4-carboxylate (4.5 g, 16.6 mmol) in DMF (50 mL) was added potassium tert-butoxide (2.33 g, 19.2 mmol) in portion. The mixture was stirred at RT for 5 min; then p-methoxy benzyl chloride (3.2 g, 20.4 mmol) was added. The resulting mixture was stirred at RT for 12 h. The water (50 mL) was added and the mixture was extracted with EA (50 mL×2). The combined organic phase was washed with brine, dried over MgSO₄, and concentrated. The residue was chromatographed, eluting with 0-20% EA in hexane to give methyl 2-((tert-butoxycarbonyl)(4-methoxybenzyl)amino)-5-fluoropyridine-4-carboxylate as a white solid (4.8 g, 75%). MS (ESI⁺) m/z 391.0 (M+H)⁺, retention time: 2.09 min (method A).

Step 3. Preparation of tert-butyl (4-(hydroxymethyl)-5-fluoropyridin-2-yl)(4-methoxybenzyl)carbamate

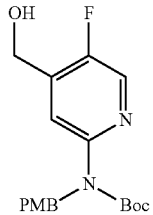

To a solution of methyl 2-((tert-butoxycarbonyl)(4-methoxybenzyl)amino)-5-fluoropyridine-4-carboxylate (7.7 g, 19.7 mmol) in THF (100 mL) at RT was added lithium borohydride (0.5 g, 23.0 mmol). The mixture was heated at 40° C. for 4 h. The reaction was cooled to 0° C., and was carefully quenched by the slow, dropwise addition of aqueous NaHCO₃ (30 mL). The mixture was diluted with water (100 mL) and extracted with EA (50 mL×2). The combined organic phase was washed with brine (50 mL), dried over MgSO₄, and concentrated. The residue was chromatographed, eluting with 40% EA in hexane to give tert-butyl (4-(hydroxymethyl)-5-fluoropyridin-2-yl)(4-methoxybenzyl)carbamate as a colorless oil (5.5 g, 77%). MS (ESI⁺) m/z 363.2 (M+H)⁺, retention time: 1.86 min (method A). ¹H NMR (400 MHz, CDCl₃) δ 1.40 (s, 9H), 2.48 (s, 3H), 3.76 (s, 3H), 4.62 (m, 2H), 5.14 (s, 2H), 6.80 (d, 2H), 6.84 (s, 1H), 7.20 (d, 2H), 7.40 (s, 1H).

Step 4. Preparation of tert-Butyl [4-(bromomethyl)-5-fluoropyridin-2-yl] (4-methoxybenzyl)carbamate

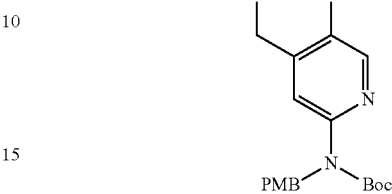

To a solution of tert-butyl (4-(hydroxymethyl)-5-fluoropyridin-2-yl)(4-methoxybenzyl)carbamate (5.5 g, 15.2 mmol) and carbon tetrabromide (5.9 g, 17.8 mmol) in DCM (60 mL) at 0° C., was added triphenylphosphine (4.7 g, 17.9 mmol) in one portion. The reaction was stirred for 20 min, and allowed to warm to RT and stirred another 1 h. The mixture was diluted with DCM (100 mL), extracted with aqueous NaHCO₃ (50 mL×1), dried over MgSO₄, and concentrated. The residue was chromatographed, eluting with 0-20% EA in hexane to give tert-Butyl [4-(bromomethyl)-5-fluoropyridin-2-yl] (4-methoxybenzyl)carbamate as a white solid (10.6 g, 80%). MS (ESI+) m/z 421.1 (M+H)⁺. Retention time: 2.18 min. (Method A). ¹H NMR (400 MHz, CDCl₃) δ 1.40 (s, 9H), 2.46 (s, 3H), 3.78 (s, 3H), 4.38 (s, 2H), 5.14 (s, 2H), 6.80 (d, 2H), 6.84 (s, 1H), 7.22 (d, 2H), 7.46 (s, 1H).

Intermediate 12: tert-Butyl [4-(bromomethyl)-5-methylpyridin-2-yl] (4-methoxybenzyl)carbamate Scheme 15

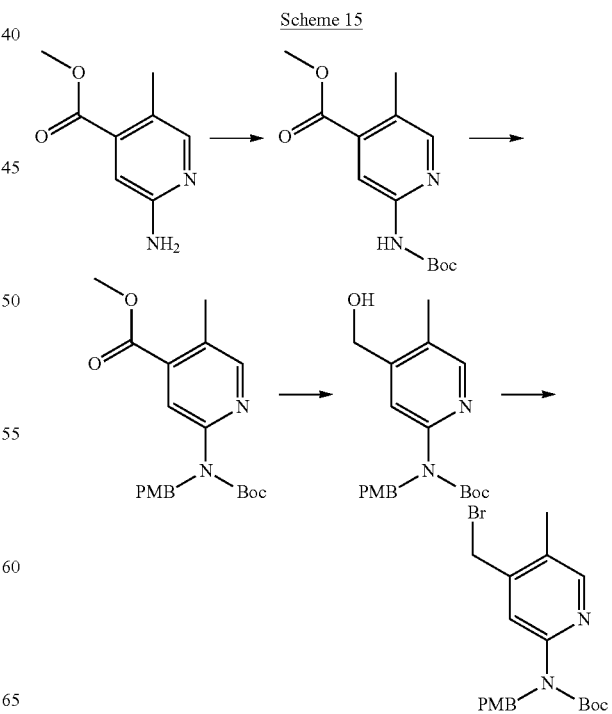

Step 1. Preparation of methyl 2-((tert-butoxycarbonyl)amino)-5-methylpyridine-4-carboxylate

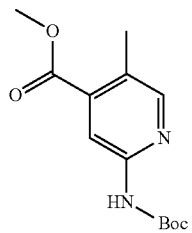 [SMILES: COC(=O)c1cc(NC(=O)OC(C)(C)C)ncc1C]

To a solution of methyl 2-amino-5-methylpyridine-4-carboxylate (6 g, 36.1 mmol) in acetone (20 mL) and tert-butyl alcohol (60 mL), 4-dimethylaminopyridine (220 mg, 1.8 mmL) and di-tert-butyl dicarbonate (9.5 g, 43.5 mmol) were added. The mixture was stirred at RT overnight. The reaction was concentrated and the residue was chromatographed, eluting with 0-30% EA in hexane to give methyl 2-((tert-butoxycarbonyl)amino)-5-methylpyridine-4-carboxylate as a white solid (7.7 g, 85%). ¹H NMR (400 MHz, CDCl₃) δ 1.52 (s, 9H), 2.44 (s, 3H), 3.92 (s, 3H), 8.04 (s, 1H), 8.20 (s, 1H), 8.32 (s, 1H).

Step 2. Preparation of methyl 2-((tert-butoxycarbonyl)(4-methoxybenzyl)amino)-5-methylpyridine-4-carboxylate

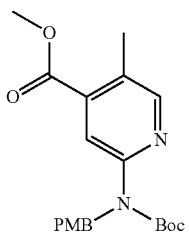

To a solution of methyl 2-((tert-butoxycarbonyl)amino)-5-methylpyridine-4-carboxylate (5 g, 18.8 mmol) in DMF (50 mL) was added potassium tert-butoxide (3 g, 24.8 mmol) in portion. The mixture was stirred at RT for 5 min, and then p-methoxy benzyl chloride (3.82 g, 24.4 mmol) was added. The resulting mixture was stirred at RT for 12 h. The water (50 mL) was added and the mixture was extracted with EA (50 mL×2). The combined organic phase was washed with brine, dried over MgSO₄, and concentrated. The residue was chromatographed, eluting with 0-20% EA in hexane to give methyl 2-((tert-butoxycarbonyl)(4-methoxybenzyl)amino)-5-methylpyridine-4-carboxylate as a white solid (6.1 g, 84%). MS (ESI⁺) m/z 387.2 (M+H)⁺, retention time: 2.14 min (method A).

Step 3. Preparation of tert-butyl (4-(hydroxymethyl)-5-methylpyridin-2-yl)(4-methoxybenzyl)carbamate

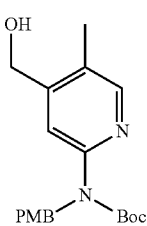

To a solution of methyl 2-((tert-butoxycarbonyl)(4-methoxybenzyl)amino)-5-methylpyridine-4-carboxylate (6 g, 15.5 mmol) in THF (50 mL) at RT was added lithium borohydride (0.75 g, 34.4 mmol). The mixture was heated at 40° C. for 4 h. The reaction was cooled to 0° C. and was carefully quenched by the slow, dropwise addition of aqueous NaHCO₃ (20 mL). The mixture was diluted with water (50 mL) and extracted with EA (50 mL×2). The combined organic phase was washed with brine (50 mL), dried over MgSO₄, and concentrated. The residue was chromatographed, eluting with 40% EA in hexane to give tert-butyl (4-(hydroxymethyl)-5-methylpyridin-2-yl)(4-methoxybenzyl)carbamate as a colorless oil (4.78 g, 89%). MS (ESI⁺) m/z 359.2 (M+H)⁺, retention time: 1.74 min (method A).

Step 4. Preparation of tert-butyl (4-(bromomethyl)-5-methylpyridin-2-yl)(4-methoxybenzyl)carbamate

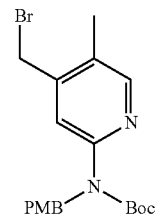

To a solution of tert-butyl (4-(hydroxymethyl)-5-methylpyridin-2-yl)(4-methoxybenzyl)carbamate (4.78 g, 13.3 mmol) and carbon tetrabromide (5.17 g, 15.6 mmol) in DCM (50 mL) at 0° C., was added triphenylphosphine (4.1 g, 15.6 mmol) in one portion. The reaction was stirred for 20 min, allowed to warm to RT, and stirred another 1 h. The mixture was diluted with DCM (100 mL), washed with aqueous NaHCO₃ (50 mL×1), dried over MgSO₄, and concentrated. The residue was chromatographed, eluting with 0-20% EA in hexane to give tert-butyl (4-(bromomethyl)-5-methylpyridin-2-yl)(4-methoxybenzyl)carbamate as a white solid (4.2 g, 75%). MS (ESI+) m/z 422.1 (M+H)⁺. Retention time: 2.18 min. (Method A). ¹H NMR (400 MHz, CDCl₃) δ 1.40 (s, 9H), 2.34 (s, 3H), 3.76 (s, 3H), 4.38 (s, 2H), 5.14 (s, 2H), 6.80 (d, 2H), 7.20 (d, 2H), 7.60 (s, 1H), 8.20 (s, 1H).

Intermediate 13. Preparation of (2S,3R)-3-((2-((tert-butoxycarbonyl)(4-methoxybenzyl)amino)pyridin-4-yl)methyl)-1-(tert-butyldimethylsilyl)-4-oxoazetidine-2-carboxylic acid

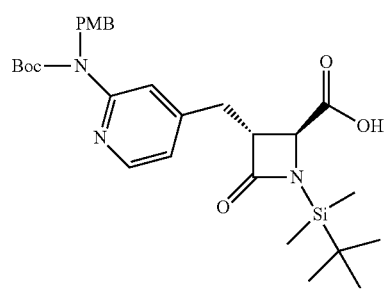

To a solution of 4-methoxybenzyl (2S,3R)-3-((2-((tert-butoxycarbonyl)(4-methoxybenzyl)amino)pyridin-4-yl)

methyl)-1-(tert-butyldimethylsilyl)-4-oxoazetidine-2-carboxylate (1.4 g, 2.1 mmol, prepared as described in WO 2015/120062) in methanol (20 mL) was added 10% Pd/C (0.2 g). The mixture was hydrogenated at 30 psi for 2 h. The mixture was filtered through Celite® and the pad was washed with methanol. The solvent was removed to give the product as a white solid (0.97 g, 95%). MS (ESI+) 556.2 (M+H)$^+$. Retention time: 3.64 min (Method B).

Intermediate 14. Preparation of (2S,3R)-1-[(1,1-dimethylethyl)dimethylsilyl]-4-oxo-3-(pyridine-4-ylmethyl)-2-azetidinecarboxylic acid

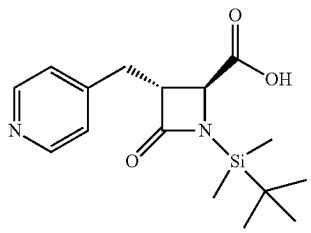 [SMILES: CC(C)(C)[Si](C)(C)N1C(=O)[C@H](Cc2ccncc2)[C@H]1C(=O)O]

To a solution of 4-picolyl chloride hydrochloride (10.0 g, 61 mmol) in 100 mL of water was added NaHCO$_3$ (7.7 g, 91.4 mmol) with stirring. The mixture was extracted with TBME (3×100 mL). The extracts were combined, washed with brine, dried over MgSO$_4$ and concentrated to give 4-picolyl chloride as a colorless oil (7.5 g, 97%) which was used without purification.

To a solution of (2S)-1-(tert-butyldimethylsilyl)-4-oxoazetidine-2-carboxylic acid (prepared as described by Baldwin et al, Tetrahedron, 1990, 46, 4733-4788) (5 g, 21.8 mmol) in THF (80 mL) at −25° C., was added LDA (2M in THF, 24 mL) dropwise. The resulting mixture was stirred at −15° C. for 30 min. A solution of 4-picolyl chloride (4 g, 31.3 mmol) in THF (25 mL) was added dropwise. The mixture was stirred at −15° C. for 2 h and then quenched with aqueous ammonium chloride (20 mL) and then EA was added. The organic layer was separated and the aqueous layer was extracted with EA. The combined organic phase was washed with brine, dried over MgSO$_4$, and concentrated. The residue was chromatographed (eluted with EA) to give the product as a white solid (1.5 g, 15%). MS (ESI+) m/z 321.1 (M+H)$^+$, retention time: 1.24 min. (method A).

Intermediate 15. Preparation of (2S,3R)-3-((2-(bis(4-methoxybenzyl)amino)pyridin-4-yl)methyl)-4-oxoazetidine-2-carboxylic acid

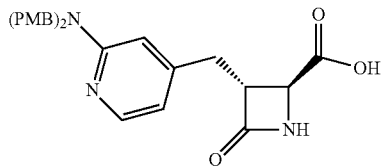

(S)-1-(tert-butyldimethylsilyl)-4-oxoazetidine-2-carboxylic acid (10.0 g, 43 mmol) was dissolved in THF (160 mL) and chilled to −20° C. The reaction was treated with LDA (2M in THF, 47 mL, 94 mmol) at about −10 to −20° C. Then 4-(bromomethyl)-N,N-bis(4-methoxybenzyl)pyridin-2-amine (21.2 g, 49 mmol) in THF (80 mL) was added while maintaining the temperature below −10° C. The reaction was stirred for several hours at −15° C. and then allowed to warm to RT and stir several hours more. The reaction was quenched with water (200 mL) and then refluxed 3 h. The reaction was cooled to TR and treated with 5% aqueous tri-potassium phosphate (250 mL). The phases were separated and the aqueous layer was extracted with EA (150 mL×3) to remove impurities. The aqueous phase was acidified to pH 3.1 with 6 N HCl and then was extracted with EA (300 mL×3). This organic phase was dried and concentrated. Residual EA was chased with heptane (250 mL) to produce a slurry which was cooled and filtered. The filter cake was taken up in 40 volumes of isopropyl alcohol (400 mL) and refluxed about 1 h. The mixture was cooled to RT and undissolved solid impurities were removed by filtration. The isopropyl alcohol filtrate was solvent exchanged with heptane (250 mL), causing the product to precipitate. The heptane slurry was chilled to 5-10° C. and filtered. The filter cake was dried to afford (2S,3R)-3-((2-(bis(4-methoxybenzyl)amino)pyridin-4-yl)methyl)-4-oxoazetidine-2-carboxylic acid (12 g, 59%). MS (ESI+) m/z 462.2 (M+H)$^+$, retention time: 1.23 min. (Method A).

Intermediate 16. Preparation of (2S,3R)-3-((2-(bis(4-methoxybenzyl)amino)pyridin-4-yl)methyl)-1-(tert-butyl(dimethyl)silyl)-4-oxoazetidine-2-carboxylic acid

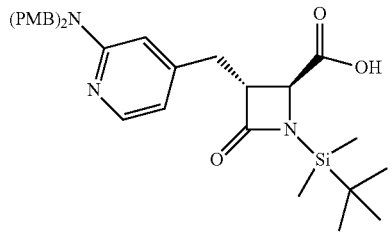

(S)-1-(tert-butyldimethylsilyl)-4-oxoazetidine-2-carboxylic acid (10 g, 43 mmol) was dissolved in THF (160 mL) and chilled to −20° C. To the reaction was treated with LDA (2M in THF, 47 mL, 94 mmol) at about −10 to −20° C. followed by 4-(bromomethyl)-N,N-bis(4-methoxybenzyl)pyridin-2-amine (21.2 g, 49 mmol) in THF (80 mL) while maintaining the temperature below −10° C. The reaction was stirred for several hours at −15° C. and then allowed to warm to RT and stir several hours more. The reaction was quenched with water (200 mL) and then acidified with 10% aqueous citric acid to pH 4. The mixture was extracted with EA (100 mL×3) The combined extracts were dried over MgSO$_4$, and concentrated. The residue was chromatographed (eluted with 20%-100% EA in hexane) to give the product as a white solid (14.5 g, 59%). MS (ESI+) m/z 576.3 (M+H)$^+$, retention time: 1.56 min. (Method A).

Intermediate 17. Preparation of (2S,3R)-3-((2-((tert-butoxycarbonyl)(methyl)amino)pyridin-4-yl)methyl)-1-(tert-butyldimethylsilyl)-4-oxoazetidine-2-carboxylic acid

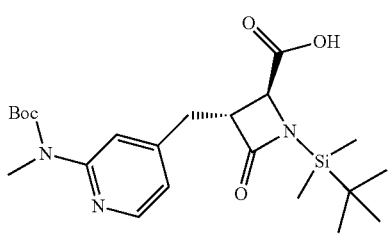 [SMILES: CN(C(=O)OC(C)(C)C)c1cc(C[C@H]2C(=O)N([Si](C)(C)C(C)(C)C)[C@@H]2C(=O)O)ccn1]

(S)-1-(tert-butyldimethylsilyl)-4-oxoazetidine-2-carboxylic acid (12.2 g, 53.2 mmol) was dissolved in THF (195 mL) and chilled to −20° C. The reaction was treated with LDA (2M in THF, 60 mL, 120 mmol) at about −10 to −20° C. followed by tert-butyl (4-(bromomethyl)pyridine-2-yl)methylcarbamate (16 g, 53.1 mmol) in THF (80 mL) while maintaining the temperature below −10° C. The reaction was stirred for several hours at −15° C. and then allowed to warm to RT and stir several hours more. The reaction was quenched with water (200 mL) and then acidified with 10% aqueous citric acid to pH 4. The mixture was extracted with EA (100 mL×3). The combined organic phase was dried over MgSO$_4$, and concentrated. The residue was chromatographed (eluted with 20%-100% EA in hexane) to give the product as a white solid (14.4 g, 60%). MS (ESI+) m/z 450.2 (M+H)$^+$, retention time: 1.85 min. (Method A).

Intermediate 18. Preparation of (2S,3R)-3-((2-((tert-butoxycarbonyl)(4-methoxybenzyl)amino)-5-methylpyridin-4-yl)methyl)-1-(tert-butyldimethylsilyl)-4-oxoazetidine-2-carboxylic acid

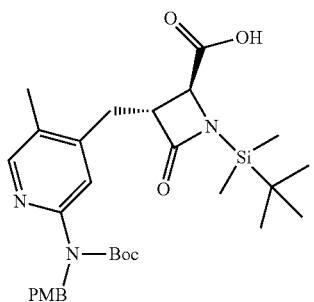

(S)-1-(tert-butyldimethylsilyl)-4-oxoazetidine-2-carboxylic acid (2.42 g, 10.6 mmol) was dissolved in THF (36 mL) and chilled to −20° C. The reaction was treated with LDA (2M in THF, 12 mL, 24 mmol) at about −10 to −20° C. followed by tert-Butyl [4-(bromomethyl)-5-methylpyridin-2-yl] (4-methoxybenzyl)carbamate (4.44 g, 10.5 mmol) in THF (10 mL) while maintaining the temperature below −10° C. The reaction was stirred for several hours at −15° C. and then allowed to warm to RT and stir several hours more. The reaction was quenched with water (20 mL) and then acidified with 10% aqueous citric acid to pH 4. The mixture was extracted with EA (30 mL×3). The combined organic phase was dried over MgSO$_4$, and concentrated. The residue was chromatographed (eluted by 20%-100% EA in hexane) to give the product as a white solid (3.12 g, 53%). MS (ESI+) m/z 570.3 (M+H)$^+$, retention time: 2.09 min. (Method A).

Intermediate 19. Preparation of (2S,3R)-3-((2-((tert-butoxycarbonyl)(4-methoxybenzyl)amino)-6-methylpyridin-4-yl)methyl)-1-(tert-butyldimethylsilyl)-4-oxoazetidine-2-carboxylic acid

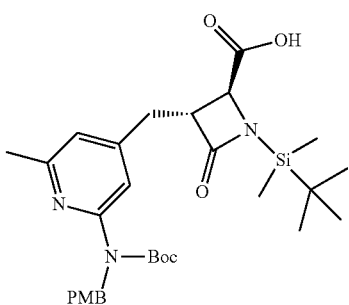

(S)-1-(tert-butyldimethylsilyl)-4-oxoazetidine-2-carboxylic acid (7.1 g, 30.9 mmol) was dissolved in THF (120 mL) and chilled to −20° C. The reaction was treated with LDA (2M in THF, 34 mL, 68 mmol) at about −10 to −20° C. followed by tert-Butyl [4-(bromomethyl)-6-methylpyridin-2-yl] (4-methoxybenzyl)carbamate (13 g, 30.8 mmol) in THF (20 mL) while maintaining the temperature below −10° C. The reaction was stirred for several hours at −15° C. and then allowed to warm to RT and stir several hours more. The reaction was quenched with water (100 mL) and then acidified with 10% aqueous citric acid to pH 4. The mixture was extracted with EA (100 mL×3). The combined organic layer was dried over MgSO$_4$, and concentrated. The residue was chromatographed (eluted with 20%-100% EA in hexane) to give the product as a white solid (10.5 g, 60%). MS (ESI+) m/z 570.3 (M+H)$^+$, retention time: 2.10 min. (Method A).

Intermediate 20. Preparation of (2S,3R)-3-((2-((tert-butoxycarbonyl)(methyl)amino)-6-methylpyridin-4-yl)methyl)-1-(tert-butyldimethylsilyl)-4-oxoazetidine-2-carboxylic acid

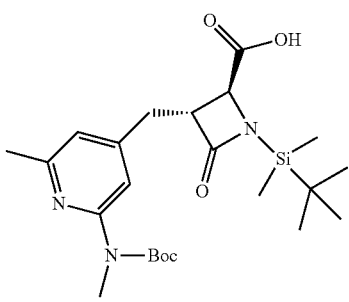 [SMILES: Cc1cc(C[C@H]2C(=O)N([Si](C)(C)C(C)(C)C)[C@@H]2C(=O)O)cc(N(C)C(=O)OC(C)(C)C)n1]

(S)-1-(tert-butyldimethylsilyl)-4-oxoazetidine-2-carboxylic acid (4 g, 17.44 mmol) was dissolved in THF (64 mL) and chilled to −20° C. The reaction was treated with LDA (2M in THF, 20 mL, 40 mmol) at about −10 to −20° C. followed by tert-Butyl (4-(bromomethyl)-6-methylpyridine-2-yl)methylcarbamate (5.5 g, 17.4 mmol) in THF (15 mL)

while maintaining the temperature below −10° C. The reaction was stirred for several hours at −15° C. and then allowed to warm to RT and stir several hours more. The reaction was quenched with water (40 mL) and then acidified with 10% aqueous citric acid to pH 4. The mixture was extracted with EA (60 mL×3). The combined organic phase was dried over MgSO₄, and concentrated. The residue was chromatographed (eluted with 20%-100% EA in hexane) to give the product as a white solid (4.44 g, 55%). MS (ESI+) m/z 464.4 (M+H)⁺, retention time: 3.33 min. (Method B).

Intermediate 21. Preparation of (2S,3R)-3-((2-((tert-butoxycarbonyl)(4-methoxybenzyl)amino)-5-fluoro-pyridin-4-yl)methyl)-1-(tert-butyldimethylsilyl)-4-oxoazetidine-2-carboxylic acid

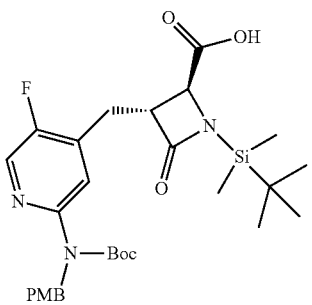

(S)-1-(tert-butyldimethylsilyl)-4-oxoazetidine-2-carboxylic acid (2.2 g, 9.6 mmol) was dissolved in THF (36 mL) and chilled to −20° C. The reaction was treated with LDA (2M in THF, 11 mL, 22 mmol) at about −10 to −20° C. followed by tert-Butyl [4-(bromomethyl)-5-fluoropyridin-2-yl] (4-methoxybenzyl)carbamate (4.1 g, 9.6 mmol) in THF (10 mL) while maintaining the temperature below −10° C. The reaction was stirred for several hours at −15° C. and then allowed to warm to RT and stir several hours more. The reaction was quenched with water (20 mL) and then acidified with 10% aqueous citric acid to pH 4. The mixture was extracted with EA (30 mL×3). The combined organic phase was dried over MgSO₄, and concentrated. The residue was chromatographed (eluted with 20%-100% EA in hexane) to give the product as a white solid (2.49 g, 45%). MS (ESI+) m/z 574.4 (M+H)⁺, retention time: 3.79 min. (Method B).

Intermediate 22. Synthesis of (R)-1-(2,5-dimethylphenyl)propyl isocyanate

Scheme 16

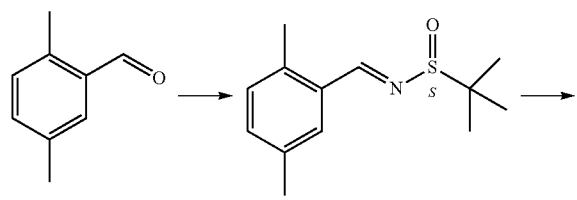

-continued

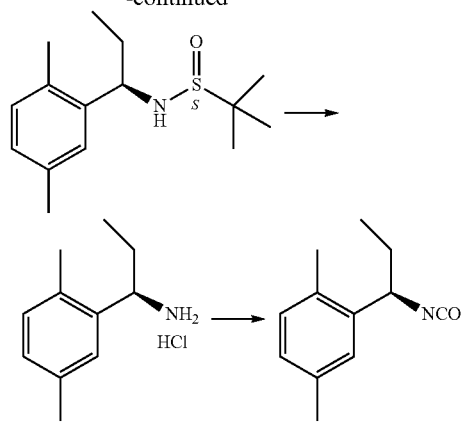

Step 1. Preparation of [N(E),S(S)]-N-[(2,5-dimethylphenyl)methylene]-2-methyl-2-propanesulfinamide

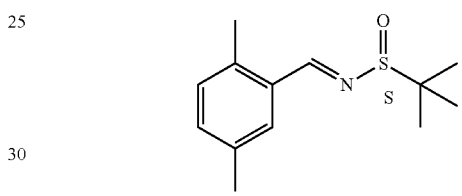

To a solution of 2,5-dimethylbenzaldehyde (5 g, 37.3 mmol), and (S)-(-)-2-methyl-2-propanesulfinamide (5 g, 41.2 mmol) in THF (50 mL) was added titanium (IV) ethoxide (17.8 g, 78.0 mmol). The resulting reaction mixture was heated at 75° C. for 2 h. The mixture was cooled to RT. Brine (50 mL) was added and the mixture was vigously stirred and then filtered through Celite®. The filter pad was washed with EA (200 mL). The phases were separated and the aqueous layer was extracted with EA (2×50 mL). The combined organic phase was dried and concentrated. The residue was chromatographed, eluting with 4:1 hexane:EA, to give [N(E),S(S)]-N-[(2,5-dimethylphenyl)methylene]-2-methyl-2-propanesulfinamide as a colorless oil (8.7 g, 98%). MS (ESI+) 238.1 (M+H)⁺, Retention time: 2.05 min (method A).

Step 2. Preparation of [S(S)]-N-((1R)-1-(2,5-dimethylphenyl)propyl)-2-methyl-2-propanesulfinamide

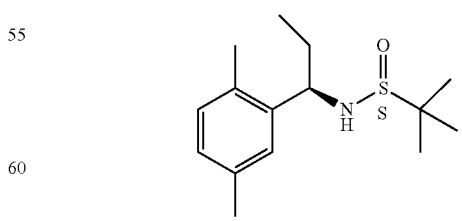

[N(E),S(S)]-N-[(2,5-dimethylphenyl)methylene]-2-methyl-2-propanesulfinamide (8.7 g g, 36.6 mol) was dissolved in TBME (50 mL). The reaction was cooled to −40° C. and ethyl magnesium bromide (3M in ether, 24 mL, 74.3 mmol) was added dropwise and the reaction was stirred at −25° C. for 4 h. Saturated aqueous ammonium chloride and then EA were added. The layers separated and the aqueous layer was extracted with EA (50 mL). The combined organic phase was washed with brine, dried, concentrated. The residue was chromatographed, eluting with 2:1 hexane:EA, to afford [S(S)]-N-((1R)-1-(2,5-dimethylphenyl)propyl)-2-methyl-2-propanesulfinamide as a colorless oil (5.2 g, 53%). MS (ESI+) 268.3 (M+H)$^+$, Retention time: 1.87 min (method A).

Step 3. Preparation of (R)-1-(2,5-dimethylphenyl)propylamine hydrochloride

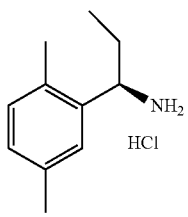

[S(S)]-N-((1R)-1-(2,5-dimethylphenyl)propyl)-2-methyl-2-propanesulfinamide (5.2 g, 19.4 mmol) was dissolved in methanol (20 mL) and 4M HCl in 1,4-dioxane (20 mL) was added slowly. The reaction solution was stirred for 60 min. The reaction was concentrated to leave a solid residue. Hexane (20 mL) was added to the solid and the resulting suspension was stirred at RT for 60 min. The solid was filtered, rinsed with hexanes and dried to give (R)-1-(2,5-dimethylphenyl)propylamine hydrochloride (2 g, 54%). MS (ESI+) 164.1 (M+H)$^+$, Retention time: 1.14 min (method A).

Step 4. Preparation of (R)-1-(2,5-dimethylphenyl)propyl isocyanate

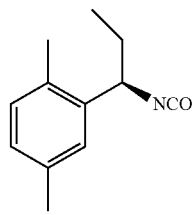

To a suspension of (R)-1-(2,5-dimethylphenyl)propylamine hydrochloride (2 g, 10.0 mmol) in DCM (30 mL) was added 1N aqueous NaHCO$_3$ (34 mL). The mixture was cooled to 0° C., and triphosgene (1 g, 3.4 mmol) was added. The reaction was stirred 15 min at 0° C. and 1 h at RT. The reaction was extracted with DCM twice. The combined organic phase was dried and concentrated to afford (R)-1-(2,5-dimethylphenyl)propyl isocyanate as a colorless oil (1.7 g, 90%), which was used for the next step without purification. $^1$H NMR (400 Hz, CDCl$_3$) δ 7.21 (s, 1H), 7.05 (d, 1H), 7.01 (d, 1H), 4.74 (t, 1H), 2.36 (s, 3H), 2.31 (s, 3H), 1.82 (m, 2H), 1.05 (t, 3H).

Intermediate 23. Synthesis of (R)-1-(4-fluoro-3-methylphenyl)propyl isocyanate

Scheme 17

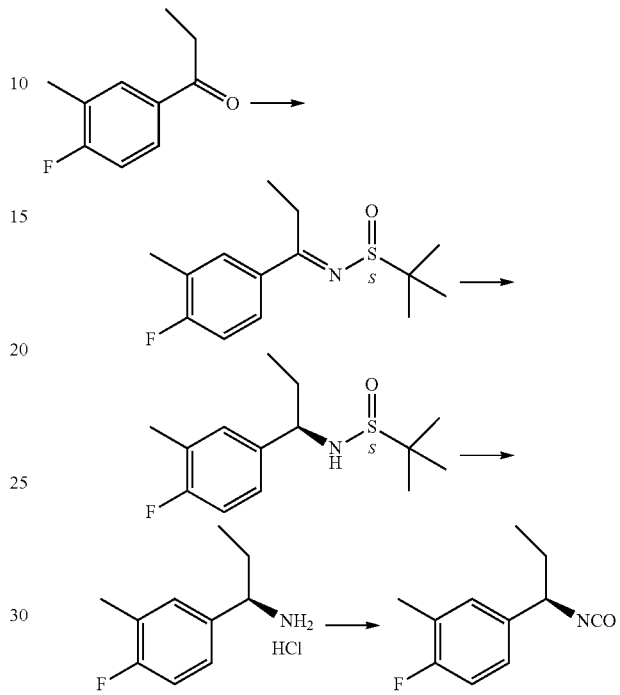

Step 1. Preparation of [S(S)]-N-[1-(4-fluoro-3-methylphenyl)propylidene]-2-methylpropane-2-sulfinamide

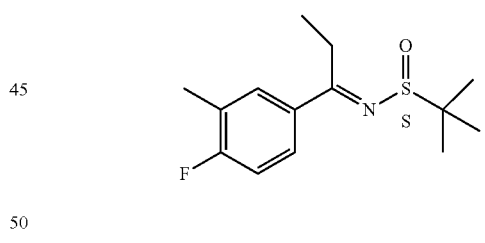

A solution of the 4'-fluoro-3'-methylpropiophenone (5 g, 30 mmol), (S)-(−)-2-methylpropane-2-sulfinamide (4 g, 33 mmol) and titanium (IV) ethoxide (17.4 g, 63 mmol) in THF (100 mL) was heated at 80° C. overnight. After cooling, brine (100 mL) and EA (100 mL) were added. The mixture was stirred at RT for 1 h. The mxture was filtered through Celite®, and the pad was washed with EA. The organic phase was separated, dried, and concentrated. The residue was chromatographed, eluting with 2:1 hexane:EA, to give [S(S)]-N-[1-(4-fluoro-3-methylphenyl)propylidene]-2-methylpropane-2-sulfinamide as a colorless oil (7.27 g, 90%). MS (ESI+) 270.1 (M+H)$^+$, Retention time: 1.97 min (method A).

Step 2. Preparation of [S(S),R]-N-[1-(4-fluoro-3-methylphenyl)propyl]-2-methylpropane-2-sulfinamide

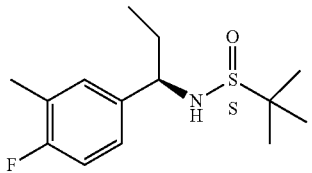

To a solution of [S(S)]-N-[1-(4-fluoro-3-methylphenyl)propylidene]-2-methylpropane-2-sulfinamide (7.27 g, 27 mmol) in THF (80 mL) at 0° C., was added a solution of tri-sec-butylborohydride (L-selectride, 1M solution in THF, 81 mL, 81 mmol). The reaction mixture was stirred for 3 h at 0° C. The reaction was quenched with saturated aqueous ammonium chloride (80 mL). The mixture was filtered through Celite® and the pad was rinsed with EA. The organic phase was separated, dried, and concentrated. The residue was chromatographed, eluting with 1:1 of hexane:EA to give the [S(S),R]-N-[1-(4-fluoro-3-methylphenyl)propyl]-2-methylpropane-2-sulfinamide as a colorless oil (6.1 g, 84%). MS (ESI+) 272.2 (M+H)$^+$, Retention time: 1.83 min (method A).

Step 3. Preparation of (R)-1-(4-fluoro-3-methylphenyl)-1-propanamine hydrochloride

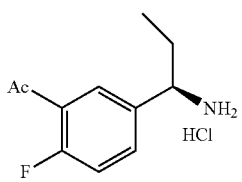

To a solution of [S(S),R]-N-[1-(4-fluoro-3-methylphenyl)propyl]-2-methylpropane-2-sulfinamide (6.1 g, 22.5 mmol) in methanol (50 mL), was slowly added 4M HCl in 1,4-dioxane (23 mL). The reaction was stirred for 1 h. The reaction was concentrated to a solid residue. Hexane (50 mL) was added to the solid and the resulting suspension was stirred at RT for 1 h. The solid was filtered, rinsed with hexanes and dried to (R)-1-(4-fluoro-3-methylphenyl)-1-propanamine hydrochloride (4.1 g, 90%). MS (ESI+) m/z 168.1 (M+H)$^+$. Retention time: 1.13 min. (method A).

Step 4. Preparation of (R)-1-(4-fluoro-3-methylphenyl)propyl isocyanate

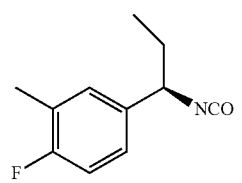

To a suspension of (R)-1-(4-fluoro-3-methylphenyl)-1-propanamine hydrochloride (1 g, 4.9 mmol) in DCM (30 mL) was added 1N aqueous NaHCO$_3$ (17 mL). The mixture was cooled to 0° C., and triphosgene (0.5 g, 1.7 mmol) was added. The reaction was stirred 15 min at 0° C. and 1 h at RT. The reaction was extracted with DCM twice. The combined organic phase was dried and concentrated to afford (R)-1-(4-fluoro-3-methylphenyl)propyl isocyanate as a colorless oil (0.6 g, 63%), which was used for the next step without purification. $^1$H NMR (400 Hz, CDCl$_3$) δ 7.10 (m, 2H), 6.98 (m, 1H), 4.48 (t, 1H), 2.29 (s, 3H), 1.85 (m, 2H), 0.98 (t, 3H).

Intermediate 24. Synthesis of 1,5-dihydro-1-methyl-2-(methylamino)-4H-imidazol-4-one hydrochloride Scheme 18

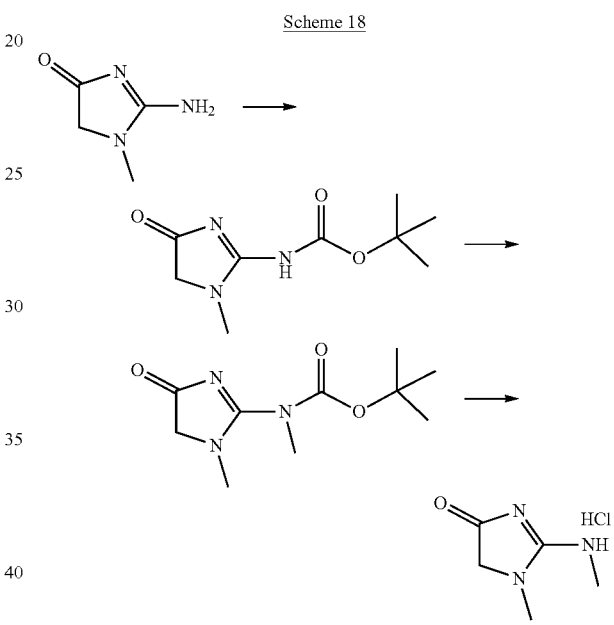

Step 1. Preparation of tert-butyl N-(1-methyl-4-oxo-4,5-dihydro-1H-imidazol-2-yl)carbamate

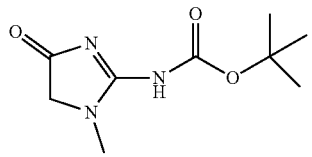

To a solution of 2-imino-1-methyl-4-imidazolidinone (8.2 g, 72.5 mmol) in DMF (30 mL) at RT was added di-tert-butyldicarbonate (17.4 g, 79.7 mmol). The resulting mixture was stirred at 60° C. overnight. The mixture was cooled to RT and quenched with water (30 mL). The mixture was extracted with EA (30 mL×2). The organic layer was dried and concentrated. The residue was chromatographed, eluting with 1:1 of hexane:EA, to give tert-butyl N-(1-methyl-4-oxo-4,5-dihydro-1H-imidazol-2-yl)carbamate as a white solid (14 g, 90%). MS (ESI+) 214.2 (M+H)$^+$, Retention time: 1.25 min (method A).

Step 2. Preparation of tert-butyl N-methyl-N-(1-methyl-4-oxo-4,5-dihydro-1H-imidazol-2-yl)carbamate

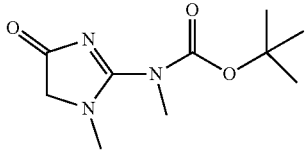 [SMILES: CN1CC(=O)N=C1N(C)C(=O)OC(C)(C)C]

To a solution of tert-butyl N-(1-methyl-4-oxo-4,5-dihydro-1H-imidazol-2-yl)carbamate (14 g, 65.7 mmol) in THF (100 mL) at 0° C. was added sodium hydride (2.9 g, 60% in mineral oil) portionwise. The mixture was allowed to warm to RT and stirred for 30 min. To the reaction, iodomethane (14 g, 95.2 mmol) was added slowly. The resulting mixture was stirred at RT overnight. The reaction was quenched with saturated aqueous ammonium chloride (30 mL). The mixture was extracted with EA (50 mL×3). The combined organics were washed with brine, dried, and concentrated. The residue was chromatographed, eluting with 4:1 of hexane:EA, to give tert-butyl N-methyl-N-(1-methyl-4-oxo-4,5-dihydro-1H-imidazol-2-yl)carbamate as colorless oil (3.5 g, 23%). MS (ESI+) 228.2 (M+H)+, Retention time: 1.35 min (method A).

Step 3. Preparation of 1,5-dihydro-1-methyl-2-(methylamino)-4H-imidazol-4-one hydrochloride

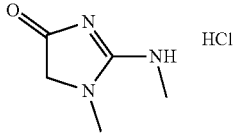

To a solution of tert-butyl N-methyl-N-(1-methyl-4-oxo-4,5-dihydro-1H-imidazol-2-yl)carbamate (3.5 g, 15.4 mmol) in DCM (25 mL) was added 4N HCl in dioxane (15 mL). The resuting mixture was stirred at RT overnight. The solvents were removed under vacuum to give 1,5-dihydro-1-methyl-2-(methylamino)-4H-imidazol-4-one hydrochloride as a white soild (1.7 g, 90%). MS (ESI+) 128.0 (M+H)+, Retention time: 0.33 min (method A).

Intermediate 25. Synthesis of (S)-1-(3-chlorophenyl)propyl isocyanate

Scheme 19

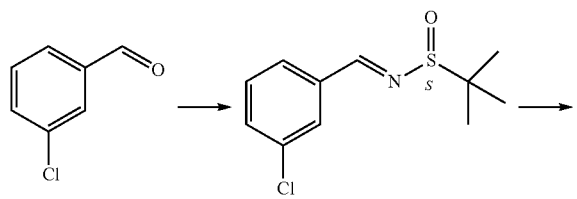

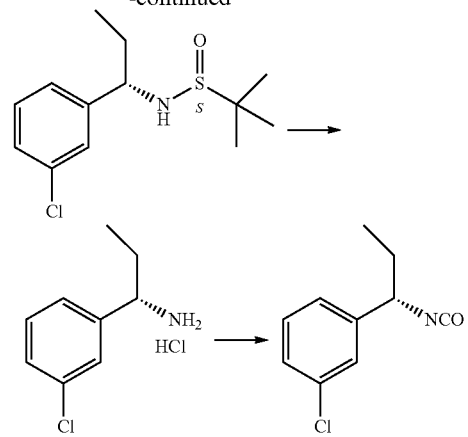

Step 1. Preparation of [N(E),S(S)]-N-[(3-chlorophenyl)methylene]-2-methyl-2-propanesulfinamide

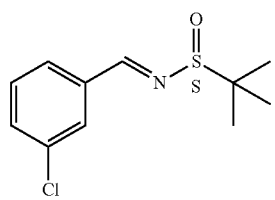

To a solution of 3-chlorobenzaldehyde (58.5 g, 416 mmol), and (S)-(-)-2-methyl-2-propanesulfinamide (53 g, 437 mmol) in THF (500 mL) was added titanium (IV) ethoxide (190 g, 832 mmol). The resulting reaction mixture was heated at 75° C. for 4 h. The mixture was cooled to RT. Brine (500 mL) was added and the mixture was vigously stirred and then filtered through Celite®. The filter pad was washed with EA (600 mL). The phases were separated and the aqueous layer was extracted with EA (2×150 mL). The combined organic phase was dried and concentrated. The residue was chromatographed, eluting with 4:1 hexane:EA, to give [N(E),S(S)]-N-[(3-chlorophenyl)methylene]-2-methyl-2-propanesulfinamide as a colorless oil (100 g, 98%). MS (ESI+) 244.1 (M+H)+, Retention time: 2.01 min (method A).

Step 2. Preparation of [S(S)]-N-((1S)-1-(3-chlorophenyl)propyl)-2-methyl-2-propanesulfinamide

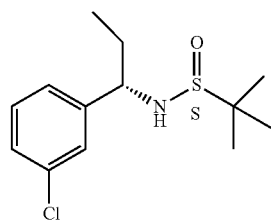

[N(E),S(S)]-N-[(3-chlorophenyl)methylene]-2-methyl-2-propanesulfinamide (100 g, 410 mol) was dissolved in TBME (500 mL). The reaction was cooled to −20° C. and ethyl magnesium bromide (3M in ether, 274 mL, 820 mmol) was added dropwise and the reaction was stirred at −20° C. for 4 h. Saturated aqueous ammonium chloride and then EA were added. The layers separated and the aqueous layer was extracted with EA (200 mL). The combined organic phase was washed with brine, dried, concentrated. The residue was chromatographed, first eluting with 4:1 hexane:EA, to afford [S(S)]-N-((1S)-1-(3-chlorophenyl)propyl)-2-methyl-2-propanesulfinamide as a colorless oil (65 g, 58%). MS (ESI+) 274.1 (M+H)⁺, Retention time: 1.85 min (method A). The column was further eluted with ethyl acetate to afford [S(S)]-N-((1S)-1-(3-chlorophenyl)propyl)-2-methyl-2-propanesulfinamide as a colorless oil (33 g, 29%). MS (ESI+) 274.1 (M+H)⁺, Retention time: 1.82 min (method A).

Step 3. Preparation of (S)-1-(3-chlorophenyl)propylamine hydrochloride

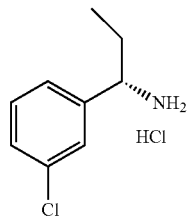

[S(S)]-N-((1S)-1-(3-chlorophenyl)propyl)-2-methyl-2-propanesulfinamide (65 g, 238 mmol) was dissolved in methanol (200 mL) and 4M HCl in 1,4-dioxane (240 mL) was added slowly. The reaction solution was stirred for 60 min. The reaction was concentrated to leave a solid resudue. Hexane (200 mL) was added to the solid and the resulting suspension was stirred at RT for 60 min. The solid was filtered, rinsed with hexanes and dried to give (S)-1-(3-chlorophenyl)propylamine hydrochloride (35 g, 71%). MS (ESI+) 170.1 (M+H)⁺, Retention time: 1.12 min (method A).

Step 4. Preparation of (S)-1-(3-chlorophenyl)propyl isocyanate

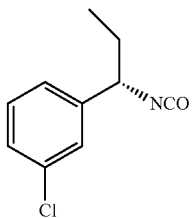

To a suspension of give (S)-1-(3-chlorophenyl)propylamine hydrochloride (9.7 g, 47 mmol) in DCM (150 mL) was added 1N aqueous NaHCO₃ (155 mL). The mixture was cooled to 0° C., and triphosgene (4.8 g, 16 mmol) was added. The reaction was stirred 15 min at 0° C. and 1 h at RT. The reaction was extracted with DCM twice. The combined organic phase was dried and concentrated to afford S)-1-(3-chlorophenyl)propyl isocyanate as a colorless oil (7.3 g, 80%), which was used for the next step without purification. ¹H NMR (400 Hz, CDCl₃) δ 7.31 (m, 3H), 7.16 (s, 1H), 4.54 (t, 1H), 1.86 (m, 2H), 0.99 (t, 3H).

Intermediate 26. Synthesis of (R)-1-(3-chlorophenyl)propyl isocyanate

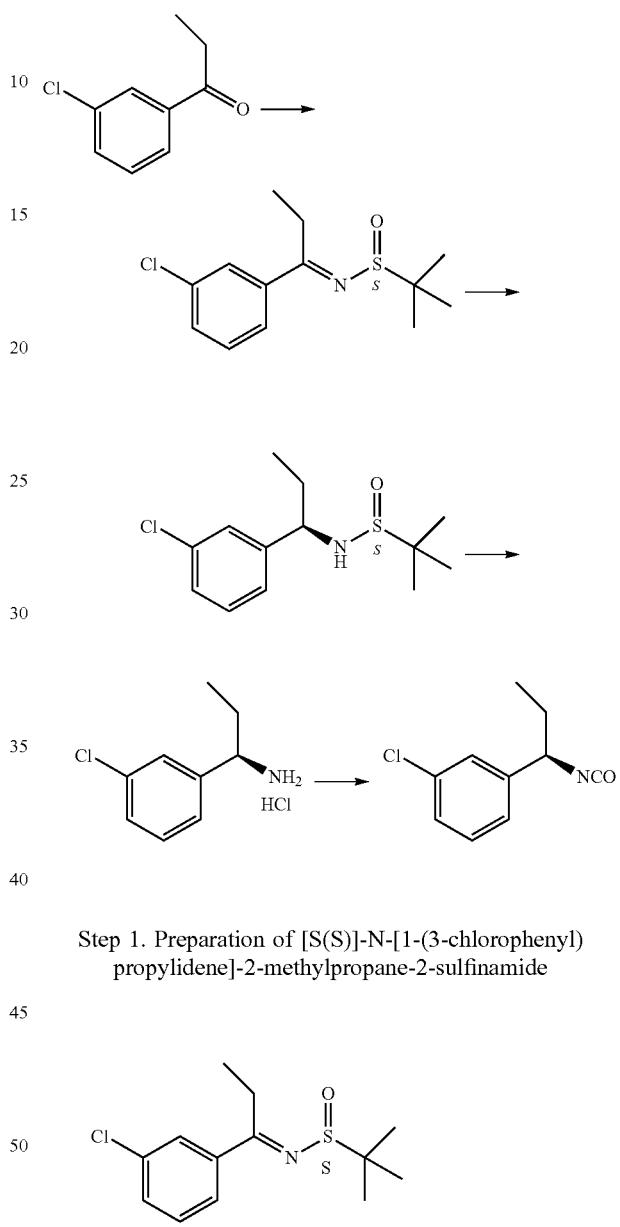

Step 1. Preparation of [S(S)]-N-[1-(3-chlorophenyl)propylidene]-2-methylpropane-2-sulfinamide A solution of the 3'-chloropropiophenone (75 g, 445 mmol), (S)-(-)-2-methylpropane-2-sulfinamide (57 g, 470 mmol) and titanium (IV) ethoxide (213 g, 934 mmol) in THF (700 mL) was heated at 80° C. overnight. After cooling, brine (700 mL) and EA (700 mL) were added. The mixture was stirred at RT for 1 h. The mxture was filtered through Celite®, and the pad was washed with EA. The organic phase was separated, dried, and concentrated. The residue was chromatographed, eluting with 2:1 hexane:EA, to give [S(S)]-N-[1-(3-chlorophenyl)propylidene]-2-methylpropane-2-sulfinamide as a colorless oil (100 g, 83%). MS (ESI+) 272.1 (M+H)⁺, Retention time: 2.00 min (method A).

Step 2. Preparation of [S(S),R]-N-[1-(3-chlorophenyl)propyl]-2-methylpropane-2-sulfinamide

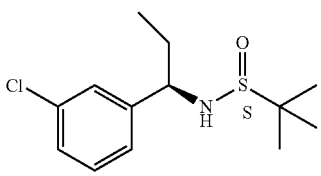

To a solution of [S(S)]-N-[1-(3-chlorophenyl)propylidene]-2-methylpropane-2-sulfinamide (25 g, 92 mmol) in THF (250 mL) at 0° C., was added a solution of tri-sec-butylborohydride (L-selectride, 1M solution in THF, 185 mL, 185 mmol). The reaction mixture was stirred for 3 h at 0° C. The reaction was quenched with saturated aqueous ammonium chloride (250 mL). The mixture was filtered through Celite® and the pad was rinsed with EA. The organic phase was separated, dried, and concentrated. The residue was chromatographed, eluting with 1:1 of hexane: EA to give the [S(S),R]-N-[1-(3-chlorophenyl)propyl]-2-methylpropane-2-sulfinamide as a colorless oil (20.7 g, 82%). MS (ESI+) 274.1 (M+H)$^+$, Retention time: 1.83 min (method A).

Step 3. Preparation of (R)-1-(3-chlorophenyl)-1-propanamine hydrochloride

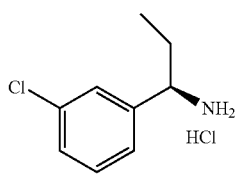

To a solution of [S(S),R]-N-[1-(3-chlorophenyl)propyl]-2-methylpropane-2-sulfinamide (20.7 g, 75.8 mmol) in methanol (150 mL), was slowly added 4M HCl in 1,4-dioxane (76 mL). The reaction was stirred for 1 h. The reaction was concentrated to a solid residue. Hexane (150 mL) was added to the solid and the resulting suspension was stirred at RT for 1 h. The solid was filtered, rinsed with hexanes and dried to (R)-1-(3-chlorophenyl)-1-propanamine hydrochloride (14 g, 90%). MS (ESI+) m/z 170.1 (M+H)$^+$. Retention time: 1.12 min. (method A).

Step 4. Preparation of (R)-1-(3-chlorophenyl)propyl isocyanate

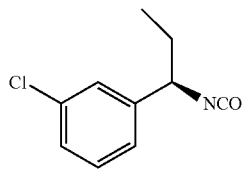

To a suspension of (R)-1-(3-chlorophenyl)-1-propanamine hydrochloride (38.7 g, 188 mmol) in DCM (300 mL) was added 1N aqueous NaHCO$_3$ (646 mL). The mixture was cooled to 0° C., and triphosgene (18.9 g, 63.8 mmol) was added. The reaction was stirred 15 min at 0° C. and 1 h at RT. The reaction was extracted with DCM twice. The combined organic phase was dried and concentrated to afford (R)-1-(3-chlorophenyl)propyl isocyanate as a colorless oil (29.4 g, 80%), which was used for the next step without purification. $^1$H NMR (400 Hz, CDCl$_3$) δ 7.32 (m, 3H), 7.20 (m, 1H), 4.54 (t, 1H), 1.82 (m, 2H), 0.98 (t, 3H).

Example 2. Preparation of Additional Intermediates

The intermediate compounds shown in Tables 2, 3, and 4 below are synthesized as outlined in Schemes 6-20 and experimental methods of Example 1. In some cases, additional functonal group transformations are employed. In general, such transformations will be apparent to those skilled in the art of organic synthesis. In addition, those skilled in the art of organic synthesis will recognize that starting materials and reaction conditions may be varied to produce the desired end products.

TABLE 2

| | | | |
|---|---|---|---|
| Additional intermediate compounds | | | |
| Intermediate Structure | Intermediate Name | LC-MS Retention Time (Min.) | MS (M + H)$^+$ |
| | (R)-1-(thiophen-2-yl)propylamine | 1.04 | 142.1 |
| | (R)-1-(thiophen-3-yl)propylamine | 1.07 | 142.2 |

TABLE 2-continued

Additional intermediate compounds

| Intermediate Structure | Intermediate Name | LC-MS Retention Time (Min.) | MS (M + H)+ |
|---|---|---|---|
| | (R)-1-cyclohexylbutylamine | 1.12 | 156.2 |
| | Phenyl N-[(R)-cyclohexylcyclopropylmethyl]carbamate | 2.09 | 274.2 |
| | Phenyl N-((R)-1-(6-methylpyridin-3-yl)propyl)carbamate | 1.16 | 271.1 |
| | Phenyl N-((R)-1-cyclopropylpropyl)carbamate | 1.83 | 220.1 |
| | Phenyl N-((R)-1-(1-methyl-1H-pyrazol-3-yl)propyl)carbamate | 1.54 | 260.1 |
| | Phenyl N-((S)-1-cyclopropyl-2,2,2-trifluoroethyl)carbamate | 1.80 | 260.0 |

TABLE 3

Additional intermediate compounds

| Intermediate Structure | Intermediate Name | $^1$H NMR (400 Hz, CDCl$_3$ or DMSO-d6) |
|---|---|---|
| | Phenyl N-((R)-1-cyclohexyl-2-mthylpropyl)carbamate | $^1$H NMR (CDCl$_3$) δ 7.38 (m, 2H), 7.20 (m, 1H), 7.17 (m, 2H), 4.70 (brd, 1H), 3.38 (m, 1H), 1.92-1.40 (m, 6 H), 1.38-0.8 (m, 12H). MS: 276.2 (M + H)+, Ret. Time: 2.16 min. |

TABLE 3-continued

Additional intermediate compounds

| Intermediate Structure | Intermediate Name | ¹H NMR (400 Hz, CDCl₃ or DMSO-d6) |
|---|---|---|
| | (R)-1-Cyclohexylbutyl isocyanate | ¹H NMR (CDCl₃) δ 0.95 (t, 3H), 1.00-1.28 (m, 4H), 1.38 (m, 2H), 1.40-1.80 (m, 9H), 3.24 (m, 1H). |
| | (R)-1-(3-chlorophenyl)propyl isocyanate | ¹H NMR (CDCl₃) δ 0.98 (t, 3H), 1.82 (m, 2H), 4.54 (t, 1H), 7.20 (m, 1H), 7.32 (m, 3H). |
| | (R)-1-(3-methylphenyl)propyl isocyanate | ¹H NMR (CDCl₃) δ 0.98 (t, 3H), 1.84 (m, 2H), 2.40 (s, 3H), 4.52 (t, 1H), 7.12 (m, 3H), 7.24 (m, 1H). |
| | (R)-1-(3-ethylphenyl)propyl isocyanate | ¹H NMR (CDCl₃) δ 0.98 (t, 3H), 1.24 (t, 3H), 1.84 (m, 2H), 2.64 (q, 2H), 4.54 (t, 1H), 7.16 (m, 3H), 7.32 (m, 1H). |
| | (R)-1-(3-chlorophenyl)ethyl isocyanate | ¹H NMR (CDCl₃) δ 1.60 (d, 3H), 4.78 (q, 1H), 7.20 (m, 1H), 7.34 (m, 3H). |
| | (R)-1-Cyclohexylpentyl isocyanate | ¹H NMR (CDCl₃) δ 0.90 (t, 3H), 1.00-1.60 (m, 12H), 1.64 (m, 2H), 1.78 (m, 3H), 3.24 (m, 1H). |
| | (R)-1-(thiophen-2-yl)propyl isocyanate | ¹H NMR (CDCl₃) δ 1.02 (t, 3H), 1.96 (, m, 2H), 4.78 (t, 1H), 7.02 (m, 2H), 7.24 (m, 1H). |
| | 1-chloro-3-(isocyanatomethyl)benzene | ¹H NMR (CDCl₃) δ 2.50 (s, 2H), 7.20 (m, 1H), 7.36 (m, 3H). |

TABLE 3-continued

Additional intermediate compounds

| Intermediate Structure | Intermediate Name | $^1$H NMR (400 Hz, CDCl$_3$ or DMSO-d6) |
|---|---|---|
| (structure) | N,1-dimethyl-1H-pyrazol-4-amine hydrochloride | $^1$H NMR (DMSO-d6) δ 2.78 (s, 3H), 3.81 (s, 3H), 4.30 (br, 2H), 7.62 (s, 1H), 8.03 (s, 1H). |
| (structure) | N,1-dimethyl-1H-pyrazol-3-amine hydrochloride | $^1$H NMR (DMSO-d6) δ 2.80 (s, 3H), 3.60 (br, 2H), 3.82 (s, 3H), 6.18 (d, 1H), 7.80 (d, 1H). |
| (structure) | N,1,4-trimethyl-1H-pyrazol-5-amine hydrochloride | $^1$H NMR (DMSO-d6) δ 2.04 (s, 3H), 2.98 (s, 3H), 3.66 (s, 3H), 3.80 (br, 2H), 7.78 (s, 1H). |
| (structure) | N,1-dimethyl-1H-imidazol-4-amine hydrochloride | $^1$H NMR (DMSO-d6) δ 2.62 (s, 3H), 3.69 (s, 3H), 3.80 (br, 2H), 6.60 (s, 1H), 8.50 (s, 1H). |
| (structure) | N-methyl-4-iosthiazolamine hydrochloride | $^1$H NMR (DMSO-d6) δ 2.80 (s, 3H), 4.80 (br, 2H), 8.60 (s, 1H), 8.80 (s, 1H). |
| (structure) | N-methylthiophen-2-amine hydrochloride | $^1$H NMR (DMSO-d6) δ 2.74 (s, 3H), 4.02 (br, 2H), 6.20 (m, 1H), 6.78 (m, 2H). |
| (structure) | N-methylthiophen-3-amine hydrochloride | $^1$H NMR (DMSO-d6) δ 2.80 (s, 3H), 4.06 (br, 2H), 7.56 (m, 1H), 7.64 (m, 2H). |

TABLE 4

Additional intermediate compounds

| Intermediate Structure | Intermediate Name | $^1$H NMR (400 Hz, CDCl$_3$ or DMSO-d6) |
|---|---|---|
| (structure) | (R)-(+)-1-(3,4,5-trifluorophenyl)propyl isocyanate | $^1$H NMR (CDCl$_3$) δ 6.94 (m, 2H), 4.54 (t, 1H), 1.84 (m, 2H), 0.99 (t, 3H) |

TABLE 4-continued

Additional intermediate compounds

| Intermediate Structure | Intermediate Name | $^1$H NMR (400 Hz, CDCl$_3$ or DMSO-d6) |
|---|---|---|
| | (R)-(+)-1-(2,3-difluoro-4-methylphenyl)propyl isocyanate | $^1$H NMR (CDCl$_3$) δ 7.04 (m, 1H), 6.96 (m, 1H), 4.84 (t, 1H), 2.30 (s, 3H). 1.87 (m, 2H), 1.00 (t, 3H) |
| | (R)-(+)-1-(2-fluoro-3-methylphenyl)propyl isocyanate | $^1$H NMR (CDCl$_3$) δ 7.21 (m, 1H), 7.14 (m, 1H), 7.06 (m, 1H), 4.87 (t, 1H), 2.30 (s, 3H). 1.88 (m, 2H), 1.01 (t, 3H) |
| | (R)-(+)-1-(3,5-difluoro phenyl)propyl isocyanate | $^1$H NMR (CDCl$_3$) δ 6.85 (m, 2H), 6.72 (m, 1H), 4.57 (t, 1H), 1.86 (m, 2H), 1.00 (t, 3H) |
| | (R)-(+)-1-(2,4-difluoro phenyl)propyl isocyanate | $^1$H NMR (CDCl$_3$) δ 7.37 (m, 1H), 6.91 (m, 1H), 6.79 (m, 1H), 4.85 (t, 1H), 1.88 (m, 2H), 1.00 (t, 3H) |
| | (R)-(+)-1-(3,5-dimethyl phenyl)propyl isocyanate | $^1$H NMR (CDCl$_3$) δ 6.96 (s, 1H), 6.93 (s, 2H), 4.46 (t, 1H), 2.35 (s, 3H), 2.34 (s, 3H), 1.86 (m, 2H), 1.00 (t, 3H) |
| | (R)-(+)-1-(3-fluoro-5-methylphenyl)propyl isocyanate | $^1$H NMR (CDCl$_3$) δ 6.89 (m, 1H), 6.83 (m, 1H), 6.80 (s, 1H), 4.50 (t, 1H), 2.37 (s, 3H), 1.84 (m, 2H), 0.99 (t, 3H) |
| | (R)-(+)-1-(2,3,4-trimethylphenyl)propyl isocyanate | $^1$H NMR (CDCl$_3$) δ 7.20 (d, 1H), 7.08 (d, 1H), 4.84 (t, 1H), 2.33 (s, 3H), 2.27 (s, 3H), 2.24 (s, 3H), 1.85 (m, 2H), 1.06 (t, 3H) |
| | (R)-(+)-1-(2,3,4-trifluorophenyl)propyl isocyanate | $^1$H NMR (CDCl$_3$) δ 7.15 (m, 1H), 7.01 (m, 1H), 4.87 (t, 1H), 1.88 (m, 2H), 1.01 (t, 3H) |

TABLE 4-continued

| Additional intermediate compounds | | |
|---|---|---|
| Intermediate Structure | Intermediate Name | ¹H NMR (400 Hz, CDCl₃ or DMSO-d6) |
| | (R)-(+)-1-(2,3-dimethyl-4-fluorophenyl)propyl isocyanate | ¹H NMR (CDCl₃) δ 7.23 (m, 1H), 6.92 (m, 1H), 4.80 (t, 1H), 2.25 (s, 3H), 2.21 (s, 3H), 1.82 (m, 2H), 1.04(t, 3H) |
| | (R)-(+)-1-(2-methyl-3,4-difluorophenyl)propyl isocyanate | ¹H NMR (CDCl₃) δ 7.36 (m, 2H), 4.85 (t, 1H), 2.34 (s, 3H), 1.87 (m, 2H), 1.01 (t, 3H) |
| | (R)-(+)-1-(2,3-dimethyl-4-fluorophenyl)propyl isocyanate | ¹H NMR (CDCl₃) δ 7.18 (m, 1H), 6.87 (m, 1H), 4.82 (t, 1H), 2.20 (s, 3H), 2.21 (S, 3H), 1.87 (m, 2H), 1.00 (t, 3H) |
| | (R)-(+)-1-(3,5-dimethyl-4-fluorophenyl)propyl isocyanate | ¹H NMR (CDCl₃) δ 6.92 (s, 1H), 6.94 (s, 1H), 4.42 (t, 1H), 2.28 (s, 3H), 2.27 (S, 3H), 1.83 (m, 2H), 0.97 (t, 3H) |
| | (R)-(+)-1-(3-fluorophenyl)propyl isocyanate | ¹H NMR (CDCl₃) δ 7.32 (m, 1H), 7.09 (m, 1H), 7.01 (m, 1H), 4.56 (t, 1H), 1.86 (m, 2H), 0.99 (t, 3H) |
| | (R)-(+)-1-(2-chloro-5-methylhenyl)propyl isocyanate | ¹H NMR (CDCl₃) δ 7.27 (s, 1H), 7.22 (d, 1H), 7.05 (d, 1H), 5.02 (t, 1H), 2.35 (s, 3H), 1.76 (m, 2H), 1.04 (t, 3H) |
| | (R)-(+)-1-(3,4-difluorophenyl)propyl isocyanate | ¹H NMR (CDCl₃) δ 7.16 (m, 2H), 7.02 (m, 1H), 4.52 (t, 1H), 1.84 (m, 2H), 0.99 (t, 3H) |

TABLE 4-continued

Additional intermediate compounds

| Intermediate Structure | Intermediate Name | ¹H NMR (400 Hz, CDCl₃ or DMSO-d6) |
|---|---|---|
| | (R)-(+)-1-(2-fluoro-4-methylphenyl)propyl isocyanate | ¹H NMR (CDCl₃) δ 7.27 (t, 1H), 6.97 (d, 1H), 6.87 (d, 1H), 4.82 (t, 1H), 2.35 (s, 3H), 1.87 (m, 2H), 0.99 (t, 3H) |
| | (R)-(+)-1-(2-methyl-4-fluorophenyl)propyl isocyanate | ¹H NMR (CDCl₃) δ 7.27 (t, 1H), 6.98 (d, 1H), 6.87 (d, 1H), 4.83 (t, 1H), 2.35 (s, 3H), 1.87 (m, 2H), 0.99 (t, 3H) |
| | (R)-(+)-1-(2,4-dimethylphenyl)propyl isocyanate | ¹H NMR (CDCl₃) δ 7.28 (d, 1H), 7.06 (d, 1H), 6.98 (s, 1H), 4.73 (t, 1H), 2.31 (s, 3H), 2.32 (s, 3H), 1.82 (m, 2H), 1.02 (t, 3H) |
| | (R)-(+)-1-(2,5-difluorophenyl)propyl isocyanate | ¹H NMR (CDCl₃) δ 7.15 (m, 1H), 6.97 (m, 2H), 4.89 (t, 1H), 1.87 (m, 2H), 1.01 (t, 3H) |
| | (R)-(+)-1-(2,3-difluorophenyl)propyl isocyanate | ¹H NMR (CDCl₃) δ 7.17 (m, 1H), 7.12 (m, 2H), 4.91 (t, 1H), 1.90 (m, 2H), 1.02 (t, 3H) |
| | (R)-(+)-1-(2,3-dimethylphenyl)propyl isocyanate | ¹H NMR (CDCl₃) δ 7.28 (d, 1H), 7.14 (m, 2H), 4.85 (t, 1H), 2.32 (s, 3H), 2.23 (s, 3H), 1.83 (m, 2H), 1.05 (t, 3H) |
| | (R)-(+)-1-(3-fluoro-4-methylphenyl)propyl isocyanate | ¹H NMR (CDCl₃) δ 7.17 (m, 1H), 6.95 (m, 2H), 4.50 (t, 1H), 2.28 (s, 3H), 1.84 (m, 2H), 0.99 (t, 3H) |
| | (R)-(+)-1-(4-methylphenyl)propyl isocyanate | ¹H NMR (CDCl₃) δ 7.18 (s, 4H), 4.49 (t, 1H), 2.36 (s, 3H), 1.85 (m, 2H), 0.98 (t, 3H) |

TABLE 4-continued

Additional intermediate compounds

| Intermediate Structure | Intermediate Name | ¹H NMR (400 Hz, CDCl₃ or DMSO-d6) |
| --- | --- | --- |
| | (R)-(+)-1-(4-chlorophenyl)propyl isocyanate | ¹H NMR (CDCl₃) δ 7.34 (d, 2H), 7.24 (d, 2H), 4.54 (t, 1H), 1.84 (m, 2H), 0.98 (t, 3H) |
| | (R)-(+)-1-(4-fluorophenyl)propyl isocyanate | ¹H NMR (CDCl₃) δ 7.28 (m, 2H), 7.06 (m, 2H), 4.53 (t, 1H), 1.86 (m, 2H), 0.98 (t, 3H) |
| | (R)-(+)-1-(2-methyl-4-chlorophenyl)propyl isocyanate | ¹H NMR (CDCl₃) δ 7.32 (d, 1H), 7.27 (d, 1H), 7.16 (s, 1H), 4.73 (t, 1H), 2.31 (s, 3H), 1.82 (m, 2H), 1.04 (t, 3H) |
| | (R)-(+)-1-(3-chloro-4-fluorophenyl)propyl isocyanate | ¹H NMR (CDCl₃) δ 7.36 (m, 1H), 7.16 (m, 2H), 4.54 (t, 1H), 1.84 (m, 2H), 0.99 (t, 3H) |
| | (R)-1-(oxan-2-yl)propyl isocyanate | ¹H NMR (CDCl₃) δ 4.04 (m, 1H), 3.57 (m, 1H), 3.24 (m, 1H), 1.62-1.40 (m, 9H), 0.99 (t, 3H) |
| | (R)-1-(oxan-3-yl)propyl isocyanate | ¹H NMR (CDCl₃) δ 4.02 (m, 1H), 3.42 (m, 1H), 3.22 (m, 1H), 1.68-1.40 (m, 9H), 0.99 (t, 3H) |
| | (R)-1-(oxan-4-yl)propyl isocyanate | ¹H NMR (CDCl₃) δ 4.01 (m, 1H), 3.38 (m, 1H), 3.22 (m, 1H), 1.68-1.40 (m, 9H), 1.01 (t, 3H) |
| | (R)-(+)-1-(4-trifluoromethoxyphenyl)propyl isocyanate | ¹H NMR (CDCl₃) δ 7.33 (d, 2H), 7.22 (d, 2H), 4.58 (t, 1H), 1.86 (m, 2H), 0.99 (t, 3H) |

TABLE 4-continued

Additional intermediate compounds

| Intermediate Structure | Intermediate Name | ¹H NMR (400 Hz, CDCl₃ or DMSO-d6) |
|---|---|---|
| | (S)-(−)-1-(3-fluorophenyl)propyl isocyanate | ¹H NMR (CDCl₃) δ 7.32 (m, 1H), 7.09 (m, 1H), 7.01 (m, 1H), 4.56 (t, 1H), 1.86 (m, 2H), 0.99 (t, 3H) |
| | (S)-(−)-1-(2,5-difluorophenyl)propyl isocyanate | ¹H NMR (CDCl₃) δ 7.15 (m, 1H), 6.97 (m, 2H), 4.89 (t, 1H), 1.87 (m, 2H), 1.01 (t, 3H) |

Example 3. (2S,3R)-3-((2-aminopyridin-4-yl)methyl)-N2-(1-methyl-1H-pyrazol-3-yl)-N1-((R)-1-phenylpropyl)-N2-methyl-4-oxoazetidine-1,2-dicarboxamide (Compound 1-3)

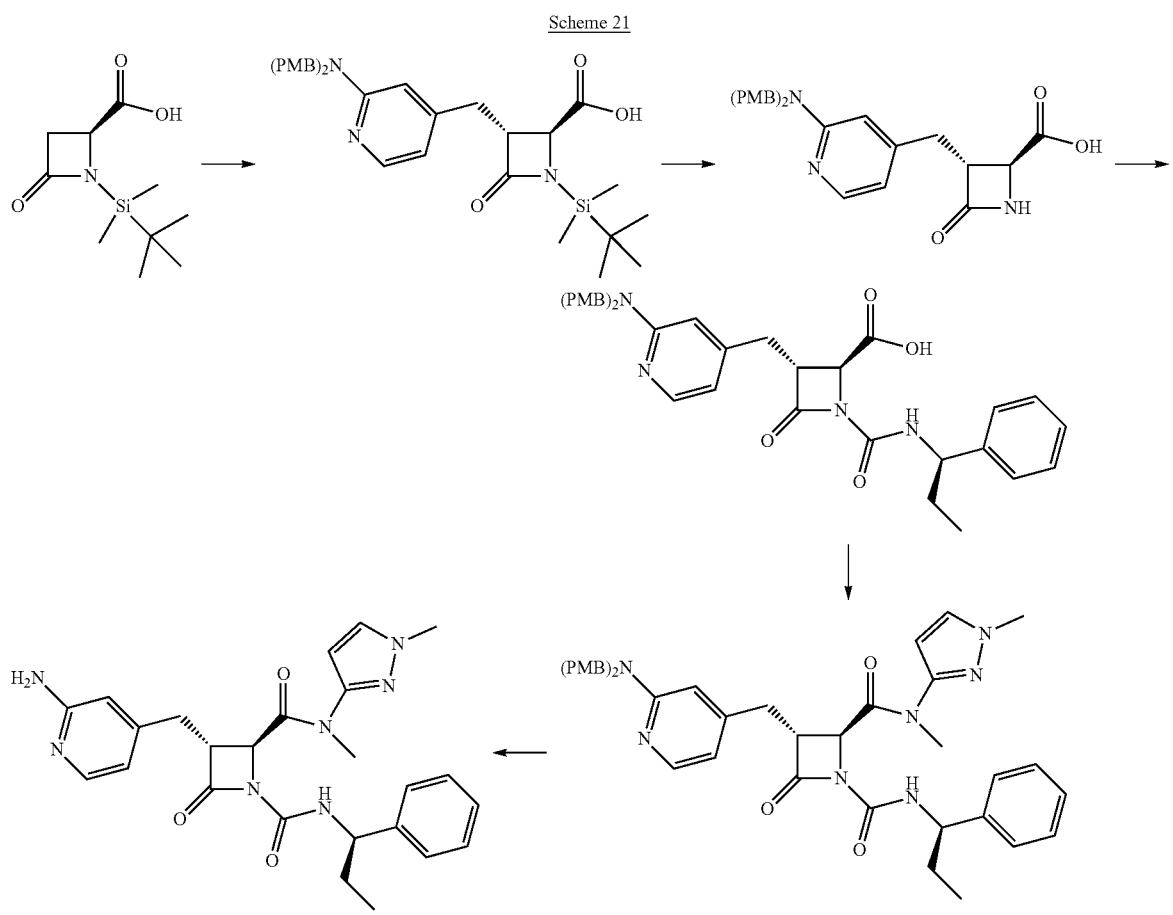

Scheme 21

Step 1. Preparation of (2S,3R)-3-((2-(bis(4-methoxybenzyl)amino)pyridin-4-yl)methyl)-4-oxoazetidine-2-carboxylic acid

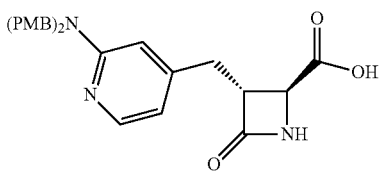

(S)-1-(tert-butyldimethylsilyl)-4-oxoazetidine-2-carboxylic acid (10.0 g, 43 mmol) was dissolved in THF (160 mL) and chilled to −20° C. The reaction was treated with LDA 92M in THF, 47 mL, 94 mmol) at about −10 to −20° C. and 4-(bromomethyl)-N,N-bis(4-methoxybenzyl)pyridin-2-amine (21.2 g, 49 mmol) in THF (80 mL) was added while maintaining the temperature below −10° C. The reaction was stirred for several hours at −15° C. and then allowed to warm to RT and stir several hours more. The reaction was quenched with water (200 mL) and then refluxed 3 h. The reaction was cooled to RT and treated with 5% aqueous tri-potassium phosphate (250 mL). The phases were separated and the aqueous layer was extracted with EA (150 mL×3) to remove impurities. The aqueous phase was acidified to pH 3.1 with 6N HCl and was extracted with EA (300 mL×3). This organic phase was dried over MgSO$_4$ and concentrated. Residual EA was chased with heptane (250 mL) to produce a slurry which was cooled and filtered. The filter cake was taken up in 40 volumes of isopropyl alcohol (400 mL) and refluxed about 1 h. The mixture was cooled to RT and undissolved solid impurities were removed by filtration. The isopropyl alcohol filtrate was solvent exchanged with heptane (250 mL), causing the product to precipitate. The slurry was chilled to 5-10° C. and filtered. The filter cake was dried to afford (2S,3R)-3-((2-(bis(4-methoxybenzyl)amino)pyridin-4-yl)methyl)-4-oxoazetidine-2-carboxylic acid (12 g, 59%). MS (ESI+) m/z 462.2 (M+H)$^+$, retention time: 1.23 min. (Method A).

Step 2. Preparation of (2S,3R)-3-((2-(bis(4-methoxybenzyl)amino)pyridin-4-yl)methyl)-1-(((R)-1-phenylethyl)carbamoyl)-4-oxoazetidine-2-carboxylic acid

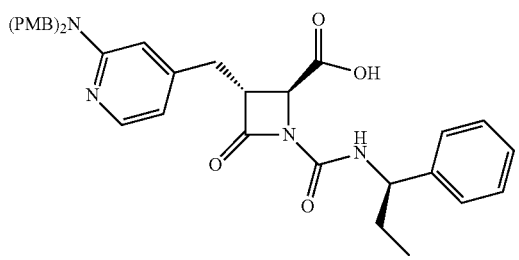

(2S,3R)-3-((2-(Bis(4-methoxybenzyl)amino)pyridin-4-yl)methyl)-4-oxoazetidine-2-carboxylic acid (15 g, 32.5 mmol) was dissolved in DCM (150 mL) and treated with DBU (17.3 g, 113.6 mmol) followed by (R)-(+)-1-phenylpropyl isocyanate (13.1 g, 81.3 mmol) at RT. The reaction was stirred at RT overnight. The mixture was diluted with DCM (150 mL) and the mixture was washed with several portions of 10% aqueous citric acid until no DBU was detected in the organic phase as determined by HPLC. The organic phase was dried over MgSO$_4$ and concentrated. The residue was chromatographed, eluting with 20%-100% EA in hexane to give product as a white solid (19.2 g, 95%). MS (ESI+) m/z 623.3 (M+H)$^+$, retention time: 1.55 min. (Method A).

Step 3. Preparation of (2S,3R)-3-((2-(bis(4-methoxybenzyl)amino)pyridin-4-yl)methyl)-N2-(1-methyl-1H-pyrazol-3-yl)-N1-((R)-1-phenylpropyl)-N2-methyl-4-oxoazetidine-1,2-dicarboxamide

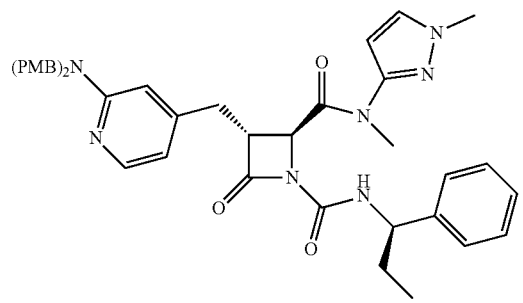

A solution of (2S,3R)-3-((2-(bis(4-methoxybenzyl)amino)pyridin-4-yl)methyl)-1-(((R)-1-phenylethyl)carbamoyl)-4-oxoazetidine-2-carboxylic acid (124 mg, 0.2 mmol) in DCM (3 mL) was treated N,1-dimethyl-1H-pyrazol-3-amine hydrochloride (41 mg, 0.3 mmol) and 2-chloro-1,3-dimethyimidazolinium chloride (50 mg, 0.3 mmol). The mixture was stirred at RT and TEA (61 mg, 0.6 mmol) was added. The reaction was stirred overnight; then it was diluted with DCM (20 mL). The mixture was washed with aqueous NaHCO$_3$, water, dried over MgSO$_4$, and concentrated. The oily residue was purified by preparative TLC with 2:1 hexane/EA to give the product as a white solid (92 mg, 65%). MS (ESI+) m/z 716.4 (M+H)$^+$, retention time: 2.95 min. (Method B).

Step 4. Preparation of (2S,3R)-3-((2-aminopyridin-4-yl)methyl)-N2-(1-methyl-1H-pyrazol-3-yl)-N1-((R)-1-phenylpropyl)-N2-methyl-4-oxoazetidine-1,2-dicarboxamide

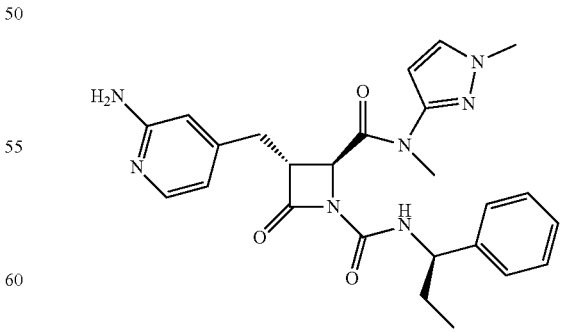

A solution of (2S,3R)-3-((2-(bis(4-methoxybenzyl)amino)pyridin-4-yl)methyl)-N2-(1-methyl-1H-pyrazol-3-yl)-N1-((R)-1-phenylpropyl)-N2-methyl-4-oxoazetidine-1,2-dicarboxamide (63 mg, 0.09 mmol) in DCM (3 mL) was treated with triethylsilane (0.1 mL) and cooled to 0° C. Trifluoroacetic acid (1 mL) was added dropwise and the reaction was slowly warmed to RT. After 21 h, HPLC analysis (Method A) indicated the starting material had been consumed. The reaction was concentrated and the residue was taken up in 5 mL DCM. The mixture was washed with aqueous NaHCO₃, water, dried over MgSO₄, and concentrated. The residue was purified by preparative TLC with EA to afford the title compound as a white solid (21 mg, 50%). MS (ESI+) m/z 476.3 (M+H)⁺, retention time: 1.23 min. (Method A). ¹H NMR (CDCl₃) δ 0.84 (t, 3H), 1.80 (q, 2H), 2.80 (m, 1H), 2.84 (m, 1H), 3.24 (s, 3H), 3.56 (m, 1H), 3.84 (s, 3H), 4.40 (s, 1H), 4.60 (m, 2H), 4.76 (m, 1H), 6.20-6.32 (m, 3H), 6.74 (d, 1H), 7.20-7.40 (m, 6), 7.94 (d, 1H).

Example 4. (2S,3R)-3-((2-aminopyridin-4-yl)methyl)-N2-(1-methyl-1H-pyrazol-5-yl)-N1-((R)-1-(3-chlorophenyl)propyl)-N2-methyl-4-oxoazetidine-1,2-dicarboxamide (Compound 1-4)

Step 1. Preparation of (2S,3R)-3-((2-(bis(4-methoxybenzyl)amino)pyridin-4-yl)methyl)-1-(tert-butyl(dimethyl)silyl)-4-oxoazetidine-2-carboxylic acid

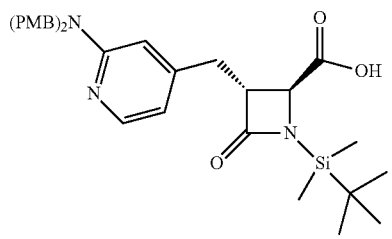

(S)-1-(tert-butyldimethylsilyl)-4-oxoazetidine-2-carboxylic acid (10 g, 43 mmol) was dissolved in THF (160 mL) and chilled to −20° C. The reaction was treated with LDA (2M in THF, 47 mL, 94 mmol) at about −10 to −20° C.

Scheme 22

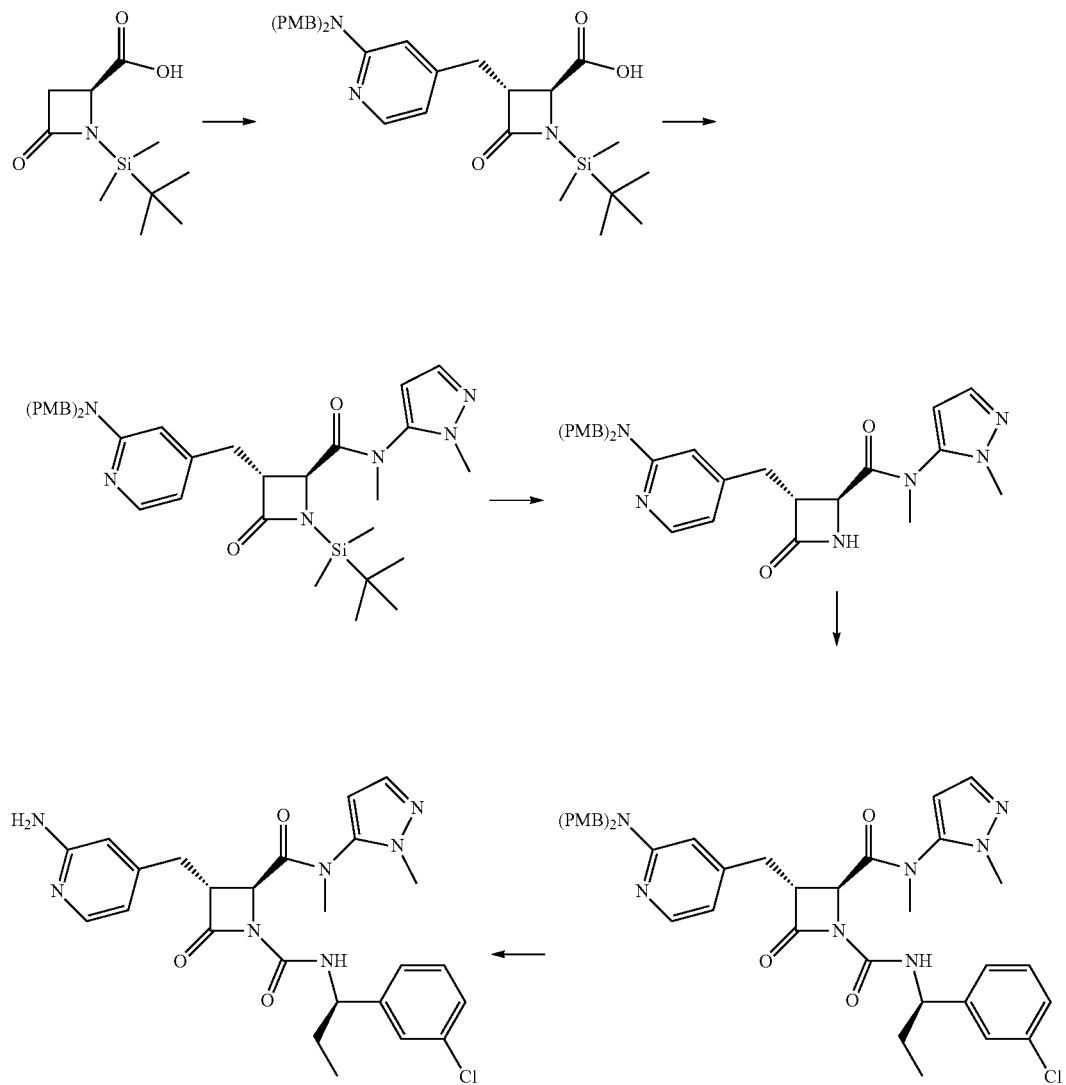

followed by 4-(bromomethyl)-N,N-bis(4-methoxybenzyl)pyridin-2-amine (21.2 g, 49 mmol) in THF (80 mL) while maintaining the temperature below −10° C. The reaction was stirred for several hours at −15° C.; then allowed to warm to RT and stir several hours more. The reaction was quenched with water (200 mL) and acidified with 10% citric acid to pH 4. The mixture was extracted with EA (100 mL×3) and this organic phase was dried over MgSO$_4$, and concentrated. The residue was chromatographed, eluting with 20%-100% EA in hexane to give the product as a white solid (14.5 g, 59%). MS (ESI+) m/z 576.3 (M+H)$^+$, retention time: 1.56 min. (Method A).

Step 2. Preparation of (2 S,3R)-3-((2-(bis(4-methoxybenzyl)amino)pyridin-4-yl)methyl)-1-(tert-butyl(dimethyl)silyl)-N2-(1-methyl-1H-pyrazol-5-yl)-N2-methyl-4-oxoazetidine-2-carboxamide

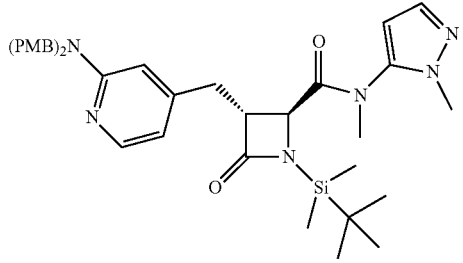

A solution of (2S,3R)-3-((2-(bis(4-methoxybenzy-pamino)pyridin-4-yl)methyl)-1-(tert-butyl(dimethyl)silyl)-4-oxoazetidine-2-carboxylic acid (4 g, 6.9 mmol) in DCM (30 mL) was treated N,1-dimethyl-1H-pyrazol-5-amine hydrochloride (1.6 g, 10.8 mmol) and 2-chloro-1,3-dimethyimidazolinium chloride (1.8 g, 10.6 mmol). The reaction was stirred at RT and TEA (2.5 g, 24.7 mmol) was added. The reaction was stirred overnight; then it was diluted with DCM (20 mL). The mixture was washed with aqueous NaHCO$_3$ and water, dried over MgSO$_4$, and concentrated. The oily residue was chromatographed, eluting with 2:1 hexane/EA to give the product as a white solid (3.2 g, 70%). MS (ESI+) m/z 669.6 (M+H)$^+$, retention time: 1.77 min. (Method A).

Step 3. Preparation of (2S,3R)-3-((2-((bis(4-methoxybenzyl)amino)pyridin-4-yl)methyl)-N2-(1-methyl-1H-pyrazol-5-yl)-N2-methyl-4-oxoazetidine-2-carboxamide

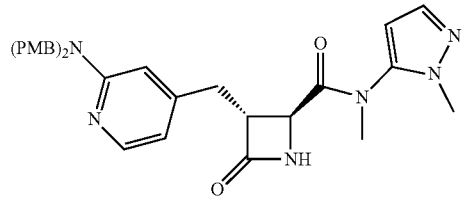

To a solution of (2S,3R)-3-((2-(bis(4-methoxybenzyl)amino)pyridin-4-yl)methyl)-1-(tert-butyl(dimethyl)silyl)-N2-(1-methyl-1H-pyrazol-5-yl)-N2-methyl-4-oxoazetidine-2-carboxamide (3.2 g, 4.8 mmol) in methanol (30 mL) was added 0.5 M NH$_4$F in methanol (15 mL) and acetic acid (1.5 mL). The reaction mixture was stirred at RT for 2 h. The reaction was concentrated and the residue was dissolved in EA (30 mL). The reaction was extracted with aqueous NaHCO$_3$ (10 mL) and brine (10 mL), dried over MgSO$_4$, and concentrated to give the product as a white solid (2.4 g, 90%). MS (ESI+) 555.3 (M+H)$^+$, retention time: 1.28 min. (Method A).

Step 4. Preparation of (2S,3R)-3-((2-(bis(4-methoxybenzyl)amino)pyridin-4-yl)methyl)-N2-(1-methyl-1H-pyrazol-5-yl)-N1-((R)-1-(3-chlorophenyl)propyl)-N2-methyl-4-oxoazetidine-1,2-dicarboxamide

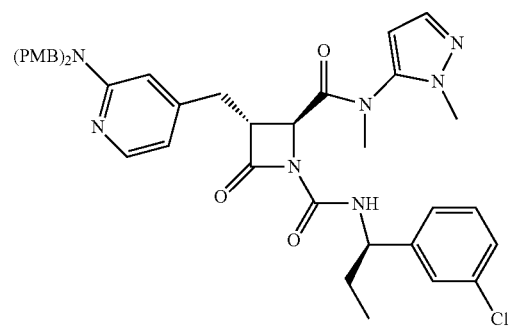

A solution of (2S,3R)-3-((2-((bis(4-methoxybenzyl)amino)pyridin-4-yl)methyl)-N2-(1-methyl-1H-pyrazol-5-yl)-N2-methyl-4-oxoazetidine-2-carboxamide (1.2 g, 2.2 mmol) in DCM (10 mL) was treated with TEA (1.1 g, 10.8 mmol). (R)-1-(3-chlorophenyl)propyl isocyanate (1.1 g, 5.6 mmol) was added and the reaction was stirred at 50° C. until HPLC analysis (Method B) indicated the reaction was complete. The reaction was poured into 40 mL water and the aqueous phase was extracted with DCM (3×15 mL). The combined organic phase was dried over MgSO$_4$ and concentrated. The colorless viscous oily residue was chromatographed (eluted with 2:1 hexane/EA) to give the title compound as a white foam (0.9 g, 60%). MS (ESI+) m/z 750.3 (M+H)$^+$, retention time: 3.17 min. (Method B).

Step 5. Preparation of (2S,3R)-3-((2-aminopyridin-4-yl)methyl)-N2-(1-methyl-1H-pyrazol-5-yl)-N1-((R)-1-(3-chlorophenyl)propyl)-N2-methyl-4-oxoazetidine-1,2-dicarboxamide

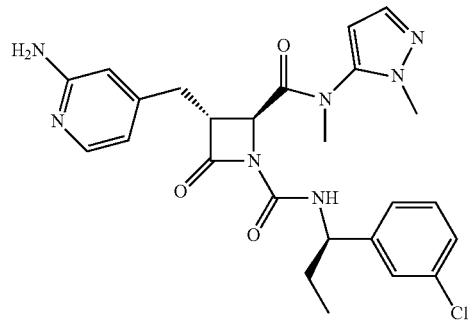 [SMILES: CC[C@@H](NC(=O)N1C(=O)[C@H](Cc2ccnc(N)c2)[C@H]1C(=O)N(C)c1ccnn1C)c1cccc(Cl)c1]

A solution of (2S,3R)-3-((2-(bis(4-methoxybenzyl)amino)pyridin-4-yl)methyl)-N2-(1-methyl-1H-pyrazol-5- yl)-N1-((R)-1-(3-chlorophenyl)propyl)-N2-methyl-4-oxoazetidine-1,2-dicarboxamide (0.9 g, 1.2 mmol) in DCM (10 mL) was treated with triethylsilane (1 mL) and cooled to 0° C. Trifluoroacetic acid (2 mL) was added dropwise and the reaction was slowly warmed to RT. After 21 h, HPLC analysis (Method A) indicated the starting material had been consumed. The reaction was concentrated and the residue was taken up in 5 mL DCM. The mixture was washed with aqueous $NaHCO_3$ and water, dried over $MgSO_4$ and concentrated. The residue was purified by preparative TLC with 10% methanol in DCM to afford the title compound as a white solid (340 mg, 55%). MS (ESI+) m/z 510.2 (M+H)$^+$, retention time: 1.25 min. (Method A).

Example 5. (2S,3R)-3-((2-dimethylaminopyridin-4-yl)methyl)-N2-(1-methyl-1H-pyrazol-4-yl)-N1-((R)-1-phenylpropyl)-N2-methyl-4-oxoazetidine-1,2-dicarboxamide (Compound 1-5)

A solution of (2S,3R)-3-((2-(bis(4-methoxybenzyl)amino)pyridin-4-yl)methyl)-1-(((R)-1-phenylethyl)carbamoyl)-4-oxoazetidine-2-carboxylic acid (product of Example 3, step 2, 100 mg, 0.16 mmol) in DCM (5 mL) was treated N,1-dimethyl-1H-pyrazol-4-amine dihydrochloride (50 mg, 0.27 mmol) and 2-chloro-1,3-dimethyimidazolinium chloride (50 mg, 0.3 mmol). The mixture was stirred at RT and TEA (100 mg, 0.98 mmol) was added. The reaction was stirred overnight; then it was diluted with DCM (20 mL). The mixture was washed with aqueous $NaHCO_3$, water, dried over $MgSO_4$, and concentrated. The oily residue was purified by preparative TLC with 2:1 hexane/EA to give the product as a white solid (69 mg, 60%). MS (ESI+) m/z 716.4 (M+H)$^+$, retention time: 2.95 min. (Method B).

Scheme 23

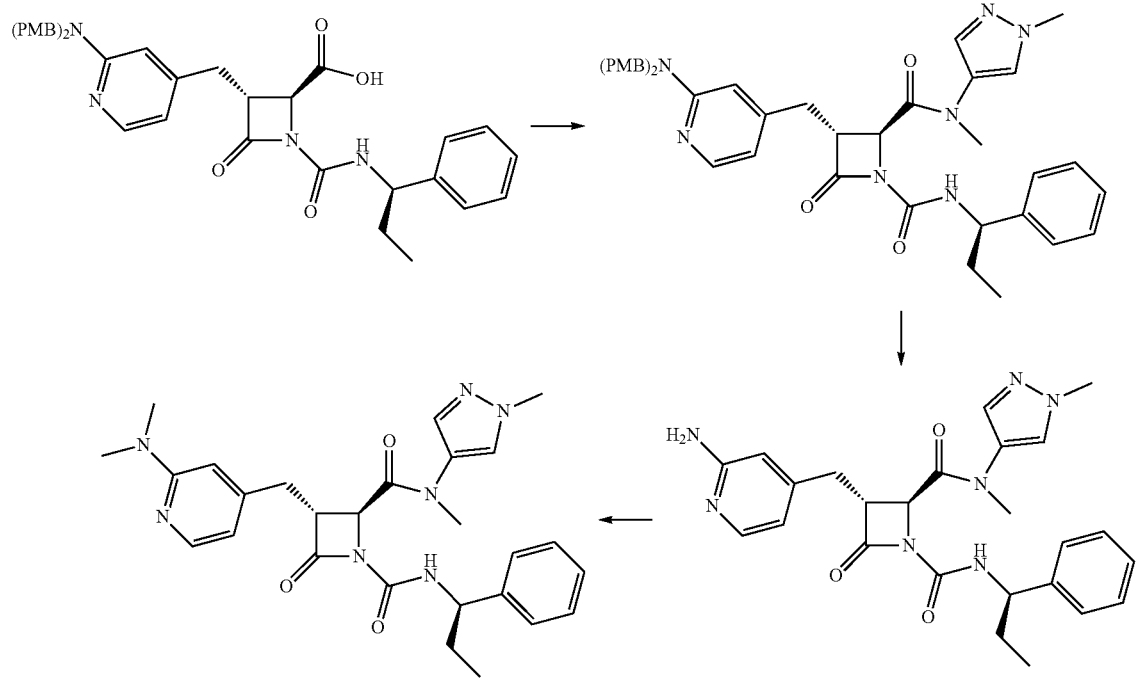

Step 1. Preparation of (2S,3R)-3-((2-(bis(4-methoxybenzyl)amino)pyridin-4-yl)methyl)-N2-(1-methyl-1H-pyrazol-4-yl)-N1-((R)-1-phenylpropyl)-N2-methyl-4-oxoazetidine-1,2-dicarboxamide Step 2. Preparation of (2S,3R)-3-((2-aminopyridin-4-yl)methyl)-N2-(1-methyl-1H-pyrazol-4-yl)-N1-((R)-1-phenylpropyl)-N2-methyl-4-oxoazetidine-1,2-dicarboxamide

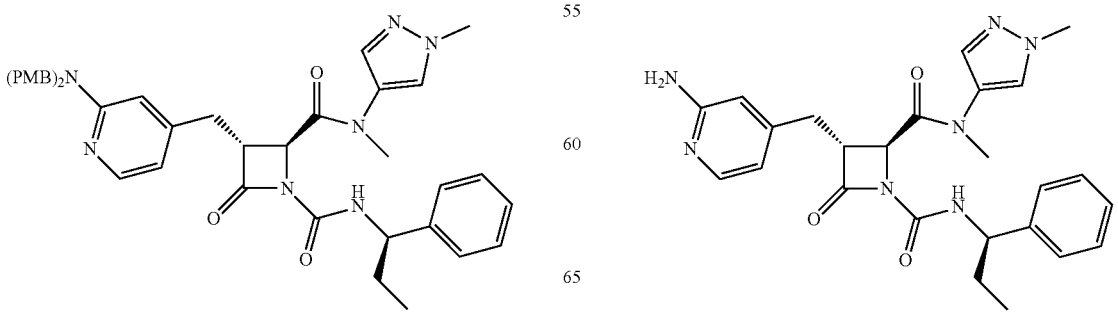

A solution of (2S,3R)-3-((2-(bis(4-methoxybenzyl) amino)pyridin-4-yl)methyl)-N2-(1-methyl-1H-pyrazol-4-yl)-N1-((R)-1-phenylpropyl)-N2-methyl-4-oxoazetidine-1,2-dicarboxamide (69 mg, 0.09 mmol) in DCM (3 mL) was treated with triethylsilane (0.1 mL) and cooled to 0° C. Trifluoroacetic acid (1 mL) was added dropwise and the reaction was slowly warmed to RT. After 21 h, HPLC analysis (Method A) indicated the starting material had been consumed. The reaction was concentrated and the residue was taken up in 5 mL DCM. The mixture was washed with aqueous NaHCO₃, water, dried over MgSO₄, and concentrated. The residue was purified by preparative TLC with EA to afford the title compound as a white solid (38 mg, 83%). MS (ESI+) m/z 476.3 (M+H)⁺, retention time: 1.23 min. (Method A), ¹H NMR (CDCl₃) δ 0.86 (t, 3H),1.80 (q, 2H), 2.10 (m, 2H), 2.62 (m, 1H), 2.84 (m,1H), 3.16 (s, 3H), 3.60 (m, 1H), 3.88 (s, 3H), 4.12 (s, 1H), 4.60 (m, 2H), 4.74 (m, 1H), 6.12 (s, 1H), 6.30 (d, 1H), 6.70 (d, 1H), 7.20-7.40 (m, 5H), 7.96 (d, 1H).

Step 3. Preparation of (2S,3R)-3-((2-dimethylaminopyridin-4-yl)methyl)-N2-(1-methyl-1H-pyrazol-4-yl)-N1-((R)-1-phenylpropyl)-N2-methyl-4-oxoazetidine-1,2-dicarboxamide

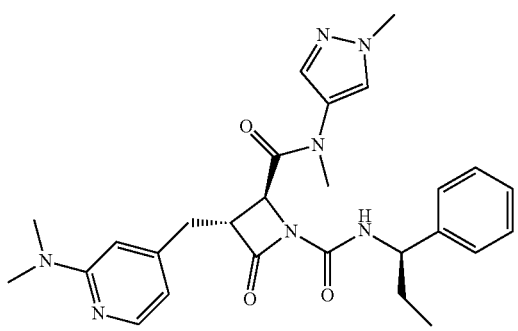 [SMILES: CC[C@@H](NC(=O)N1C(=O)[C@H](Cc2ccnc(N(C)C)c2)[C@H]1C(=O)N(C)c1cnn(C)c1)c1ccccc1]

Acetic acid (40 mg, 0.7 mmol) was added to a solution of (2S,3R)-3-((2-aminopyridin-4-yl)methyl)-N2-(1-methyl-1H-pyrazol-4-yl)-N1-((R)-1-phenylpropyl)-N2-methyl-4-oxoazetidine-1,2-dicarboxamide (36 mg, 0.08 mmol), formaldehyde (160 mg, 37% aqueous solution, 2.0 mmol) and NaBH₃CN (42 mg, 0.7 mmol) in ACN (5 mL) and water (1 mL) at RT. The reaction was stirred for 2 days. The reaction was diluted with water (10 mL) and basified to pH 4 with 1M aqueous NaOH, and then extracted with EA (10 mL×2). The organic layer was washed with brine (5 mL), dried over MgSO₄, and concentrated. The residue was purified by preparative TLC with 10% methanol in DCM to give (2S,3R)-3-((2-dimethylaminopyridin-4-yl)methyl)-N2-(1-methyl-1H-pyrazol-4-yl)-N1-((R)-1-phenylpropyl)-N2-methyl-4-oxoazetidine-1,2-dicarboxamide as a white solid (25 mg, 66%). MS (ESI+) m/z 504.2 (M+H)⁺, retention time: 1.22 min. (Method A).

Example 6. (2S,3R)-3-((2-aminopyridin-4-yl) methyl)-N2-(1-methyl-1H-pyrazol-5-yl)-N1-((R)-1-cyclohexyl-2,2,2-trifluoroethyl)-N2-methyl-4-oxoazetidine-1,2-dicarboxamide (Compound 1-6)

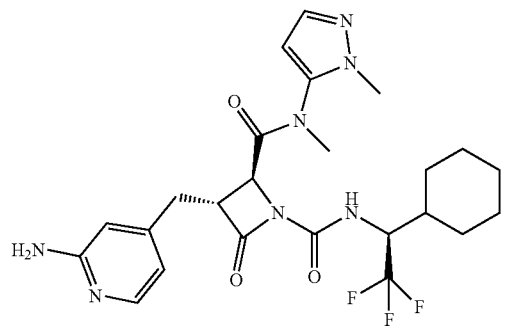 [SMILES: CN(C(=O)[C@@H]1[C@@H](Cc2ccnc(N)c2)C(=O)N1C(=O)N[C@@H](C1CCCCC1)C(F)(F)F)c1ccnn1C]

A solution of (2S,3R)-3-((2-((bis(4-methoxybenzyl) amino)pyridin-4-yl)methyl)-N2-(1-methyl-1H-pyrazol-5-yl)-N2-methyl-4-oxoazetidine-2-carboxamide (product of Example 4, step 3, 100 mg, 0.18 mmol) in DCM (10 mL) was treated with TEA (100 mg, 0.98 mmol). Phenyl [(1S)-1-cyclohexyl-2,2,2-trifluoroethyl]carbamate (100 mg, 0.48 mmol) was added and the reaction was stirred at 50° C. until HPLC analysis (Method B) indicated the reaction was complete. The reaction was poured into 40 mL water and the aqueous phase was extracted with DCM (3×15 mL). The combined organic phase was dried over MgSO₄ and concentrated. The colorless viscous oily residue was chromatographed (eluted with 2:1 hexane/EA) to give compound (2S,3R)-3-((2-(bis(4-methoxybenzyl)amino)pyridin yl)methyl)-N2-(1-methyl-1H-pyrazol-5-yl)-N1-((R)-1-cyclohexyl-2,2,2-trifluoroethyl)-N2-methyl-4-oxoazetidine-1, 2-dicarboxamide as a white foam (105 mg, 70%). MS (ESI+) m/z 762.6 (M+H)⁺, retention time: 1.90 min. (Method A).

A solution of (2S,3R)-3-((2-(bis(4-methoxybenzyl) amino)pyridin-4-yl)methyl)-N2-(1-methyl-1H-pyrazol-5-yl)-N1-((R)-1-cyclohexyl-2,2,2-trifluoroethyl)-N2-methyl-4-oxoazetidine-1,2-dicarboxamide (105 mg, 0.14 mmol) in DCM (3 mL) was treated with triethylsilane (0.1 mL) and cooled to 0° C. Trifluoroacetic acid (1 mL) was added dropwise and the reaction was slowly warmed to RT. After 21 h, HPLC analysis (Method A) indicated the starting material had been consumed. The reaction was concentrated and the residue was taken up in 5 mL DCM. The mixture was washed with aqueous NaHCO₃ and water, dried over MgSO₄ and concentrated. The residue was purified by preparative TLC with EA to afford the title compound as a white solid (36 mg, 50%). MS (ESI+) m/z 522.4 (M+H)⁺, retention time: 1.28 min. (Method A).

Example 7. (2S,3R)-3-((2-aminopyridin-4-yl)methyl)-N2-(1-methyl-1H-pyrazol-3-yl)-N1-((R)-1-(3-chlorophenyl)propyl)-N1-methyl-N2-methyl-4-oxoazetidine-1,2-dicarboxamide (Compound 1-7)

Scheme 24

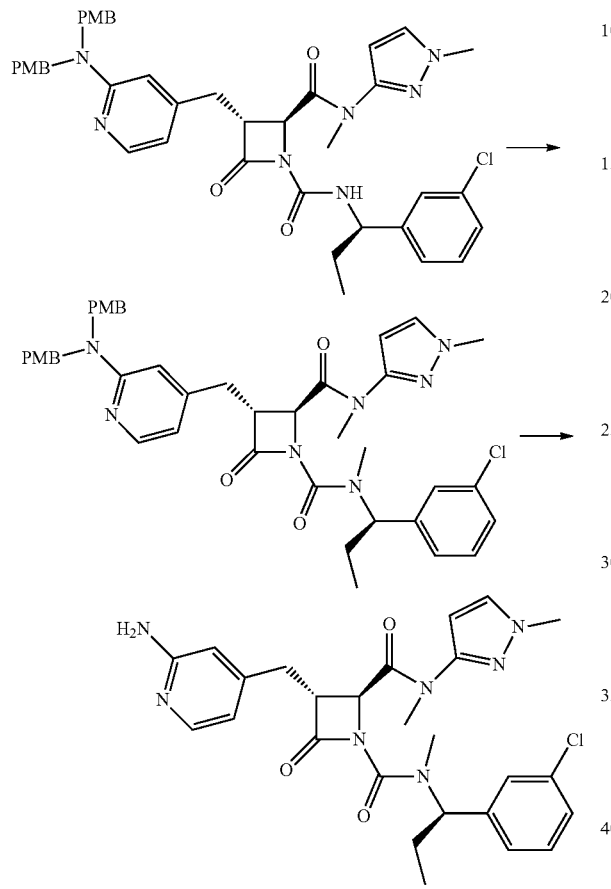

Step 1. Preparation of (2S,3R)-3-((2-(bis(4-methoxybenzyl)amino)pyridin-4-yl)methyl)-N2-(1-methyl-1H-pyrazol-5-yl)-N1-((R)-1-(3-chlorophenyl)propyl)-N1-methyl-N2-methyl-4-oxoazetidine-1,2-dicarboxamide

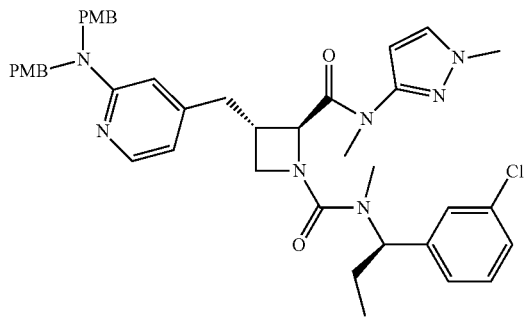

To a solution of (2S,3R)-3-((2-(bis(4-methoxybenzyl)amino)pyridin-4-yl)methyl)-N2-(1-methyl-1H-pyrazol-5-yl)-N1-((R)-1-(3-chlorophenyl)propyl)-N2-methyl-4-oxoazetidine-1,2-dicarboxamide (prepared by the method of Example 4, step 4, 300 mg, 0.4 mmol) in DMF (4 ml) was added sodium hydride (19 mg, 60% in mineral oil, 0.48 mmol). The mixture was stirred for 5 min. Methyl iodide (68 mg, 0.48 mmol) was added. The mixture was stirred at RT for 30 min. The reaction was quenched with a few drop of water. The reaction mixture was diluted with EA (10 ml) and water (10 ml). The organic layer was washed with brine, dried over MgSO$_4$, and concentrated. The crude material was purified by preparative TLC with EA to yield the title compound as a white solid (91 mg, 30%). MS (ESI+) m/z 764.6 (M+H)$^+$, retention time: 1.78 min. (method A).

Step 2. Preparation of (2S,3R)-3-((2-aminopyridin-4-yl)methyl)-N2-(1-methyl-1H-pyrazol-3-yl)-N1-((R)-1-(3-chlorophenyl)propyl)-N1-methyl-N2-methyl-4-oxoazetidine-1,2-dicarboxamide

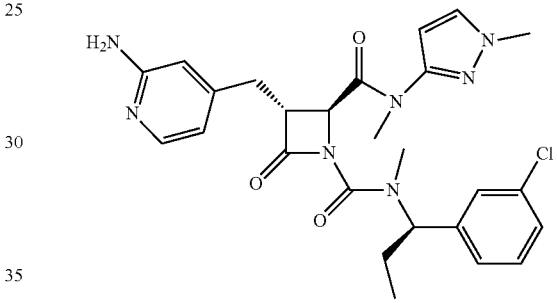

A solution of (2S,3R)-3-((2-(bis(4-methoxybenzyl)amino)pyridin-4-yl)methyl)-N2-(1-methyl-1H-pyrazol-5-yl)-N1-((R)-1-(3-chlorophenyl)propyl)-N1-methyl-N2-methyl-4-oxoazetidine-1,2-dicarboxamide (91 mg, 0.12 mmol) in DCM (2 mL) was treated with triethylsilane (0.1 mL) and cooled to 0° C. The reaction mixture was treated with trifluoroacetic acid (0.5 mL) drop wise with stirring and slowly warmed to RT. After 21 h, HPLC analysis (method A) indicated the starting material had been consumed. The reaction was concentrated and the residue was taken up in DCM (15 mL). The mixture was washed with saturated NaHCO$_3$ and water, and dried over MgSO$_4$, and concentrated. The crude material was purified by preparative TLC with EA to yield the title compound as a white solid (31 mg, 50%). MS (ESI+) m/z 524.4 (M+H)$^+$, retention time: 1.25 min. (method A).

Example 8. Synthesis of (2S,3R)-3-((2-amino-6-methylpyridin-4-yl)methyl)-N2-(1-methyl-1H-imidazol-2-yl)-N1-((R)-1-phenylpropyl)-N2-methyl-4-oxoazetidine-1,2-dicarboxamide Scheme 25

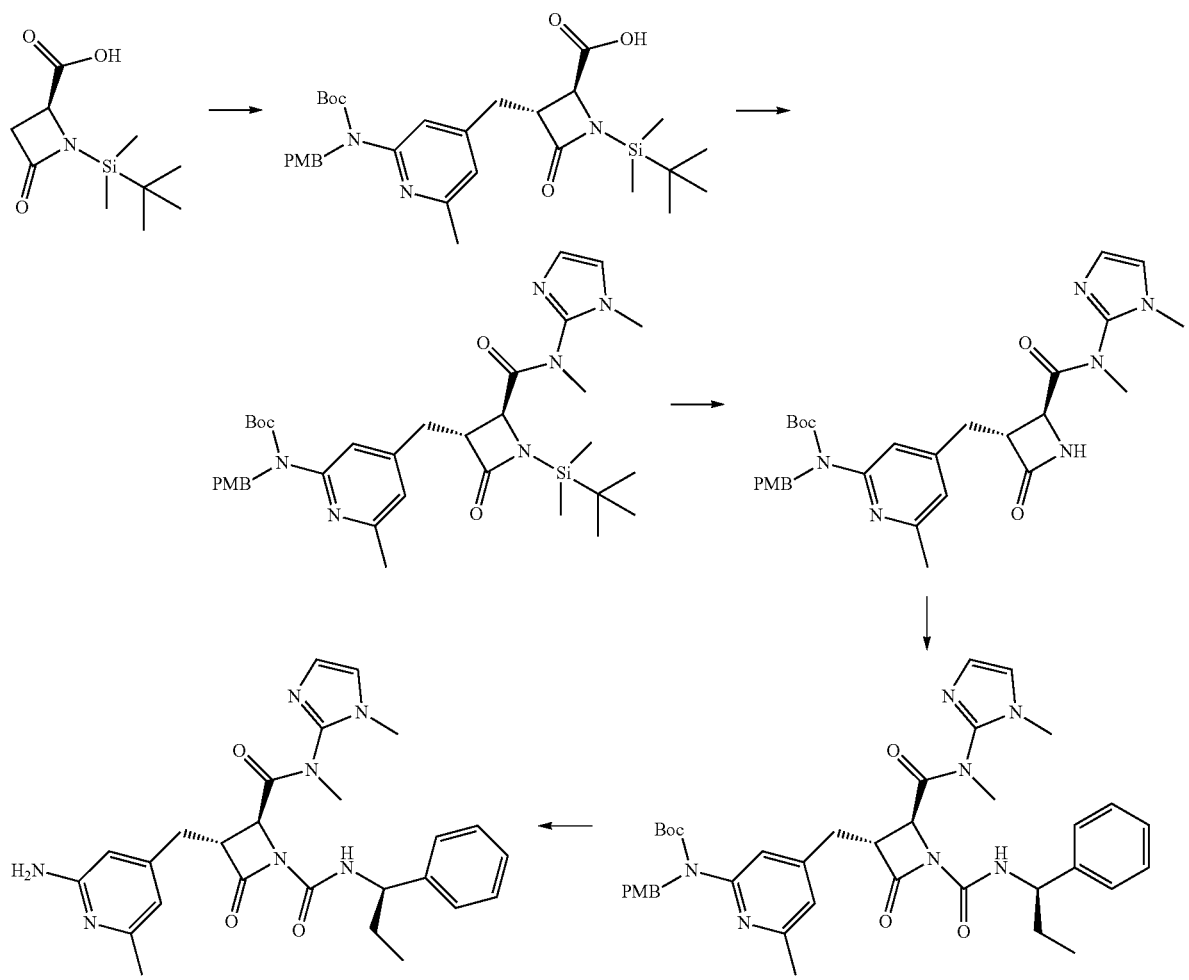

Step 1. Preparation of (2S,3R)-3-((2-((tert-butoxycarbonyl)(4-methoxybenzyl)amino)-6-methylpyridin-4-yl)methyl)-1-(tert-butyldimethylsilyl)-4-oxoazetidine-2-carboxylic acid

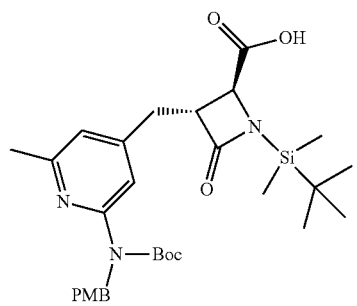

(S)-1-(tert-butyldimethylsilyl)-4-oxoazetidine-2-carboxylic acid (125 g, 545 mmol) was dissolved in THF (2 L) and cooled to −20° C. The reaction was treated with LDA (2M in THF, 600 mL, 1.2 mol) while maintaining the temperature between −10 and −20° C. The resulting gel-like mixture was stirred at −15° C. for 30 min. Then tert-butyl [4-(bromomethyl)-6-methylpyridin-2-yl] (4-methoxybenzyl)carbamate (230 g, 546 mmol) in THF (500 mL) was added while maintaining the temperature below −10° C. After the reaction was stirred at −10° C. for 2 h, the mixture was cooled to −20° C., quenched with water (200 mL), and then acidified to pH 4 with 10% aqueous citric acid while maintaining the temperature below 10° C. The mixture was extracted with EA (500 mL×3). The combined organic layer was dried and concentrated. The residue was chromatographed, eluting with a 20%-50% EA/hexane gradient to give (2S,3R)-3-((2-((tert-butoxycarbonyl)(4-methoxybenzyl)amino)-6-methylpyridin-4-yl)methyl)-1-(tert-butyldimethylsilyl)-4-oxoazetidine-2-carboxylic acid as a white solid (155 g, 50%). MS (ESI+) m/z 570.3 (M+H)+, retention time: 2.10 min. (Method A).

Step 2. Preparation of (2S,3R)-3-((2-((tert-butoxycarbonyl)(4-methoxybenzyl)amino)-6-methylpyridin-4-yl)methyl)-1-(tert-butyldimethylsilyl)-N2-(1-methyl-1H-imidazol-2-yl)-N2-methyl-4-oxoazetidine-2-carboxamide

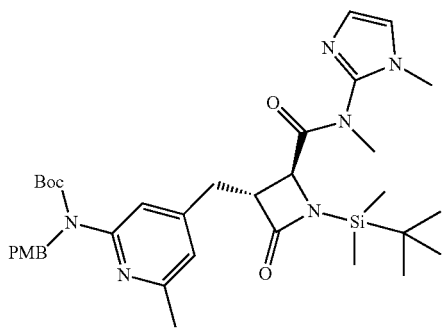

To a solution of (2S,3R)-3-((2-((tert-butoxycarbonyl)(4-methoxybenzyl)amino)-6-methylpyridin-4-yl)methyl)-1-(tert-butyldimethylsilyl)-4-oxoazetidine-2-carboxylic acid (146 g, 256 mmol) in DMF (500 mL), was added HATU (146 g, 384 mmol). The mixture was stirred for 10 min at room temperature. N,1-dimethyl-1H-imidazol-2-amine (37 g, 333 mmol) was added and the resulting solution was stirred for 10 min; then diisopropylethylamine (99.5 g, 770 mmol) was added. The mixture was stirred at RT for 2 h and then brine (600 mL) was added. The mixture was extracted with EA (500 mL×3). The combined organic phase was washed with water (300 mL) and concentrated. The residue was chromatographed, eluting with a 20%-50% EA/hexane gradient to give (2S,3R)-3-((2-((tert-butoxycarbonyl)(4-methoxybenzyl)amino)-6-methylpyridin-4-yl)methyl)-1-(tert-butyldimethylsilyl)-N2-(1-methyl-1H-imidazol-2-yl)-N2-methyl-4-oxoazetidine-2-carboxamide as a semi solid (85 g, 50%). MS (ESI+) m/z 663.7 (M+H)+. Retention time: 2.19 min. (Method A).

Step 3. Preparation of (2S,3R)-3-((2-((tert-butoxycarbonyl)(4-methoxybenzyl)amino)-6-methylpyridin-4-yl)methyl)-N2-(1-methyl-1H-imidazol-2-yl)-N2-methyl-4-oxoazetidine-2-carboxamide

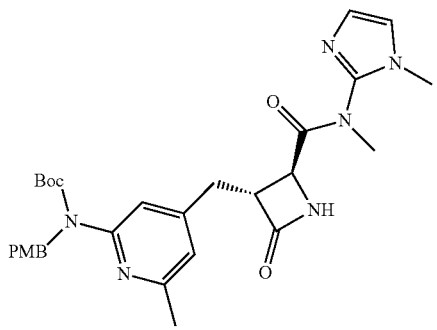

To a solution of (2S,3R)-3-((2-((tert-butoxycarbonyl)(4-methoxybenzyl)amino)-6-methylpyridin-4-yl)methyl)-1-(tert-butyldimethylsilyl)-N2-(1-methyl-1H-imidazol-2-yl)-N2-methyl-4-oxoazetidine-2-carboxamide (118 g, 178 mmol) in methanol (300 mL) was added NH4F (12 g, 324 mmol) and acetic acid (21 g, 333 mmol). The reaction mixture was stirred at RT for 2 h. The reaction was concentrated and the residue was dissolved in EA (500 mL). The mixture was washed with saturated aqueous NaHCO3 (200 mL×2) and brine (200 mL), dried, and concentrated to give (2S,3R)-3-((2-((tert-butoxycarbonyl)(4-methoxybenzyl)amino)-6-methylpyridin-4-yl)methyl)-N2-(1-methyl-1H-imidazol-2-yl)-N2-methyl-4-oxoazetidine-2-carboxamide as a white solid (85 g, 87%). MS (ESI+) 549.4 (M+H)+, retention time: 1.56 min. (Method A).

Step 4. Preparation of (2S,3R)-3-((2-((tert-butoxycarbonyl)(4-methoxybenzyl)amino)-6-methylpyridin-4-yl)methyl)-N2-(1-methyl-1H-imidazol-2-yl)-N1-((R)-1-phenylpropyl)-N2-methyl-4-oxoazetidine-1,2-dicarboxamide

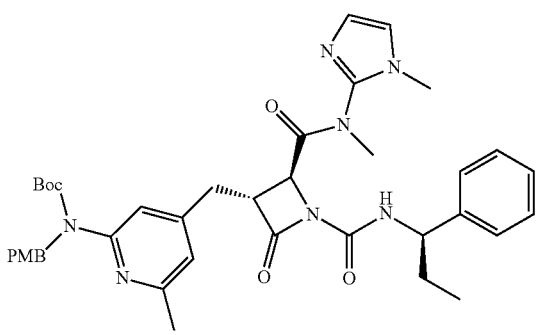

A solution of (2S,3R)-3-((2-((tert-butoxycarbonyl)(4-methoxybenzyl)amino)-6-methylpyridin-4-yl)methyl)-N2-(1-methyl-1H-imidazol-2-yl)-N2-methyl-4-oxoazetidine-2-carboxamide (119 g, 217 mmol) in DCM (500 mL) was treated with TEA (110 g, 1.09 mol). (R)-(+)-1-phenylpropyl isocyanate (87.4 g, 542 mmol) was added and the reaction was stirred at 50° C. for 16 hours. The reaction was poured into water (400 ml) and the phases were separated. The aqueous phase was extracted with DCM (3×150 mL). The combined organic phase was dried and concentrated. The colorless viscous oily residue was chromatographed, eluting with 2:1 hexane/EA to give (2S,3R)-3-((2-((tert-butoxycarbonyl)(4-methoxybenzyl)amino)-6-methylpyridin-4-yl)methyl)-N2-(1-methyl-1H-imidazol-2-yl)-N1-((R)-1-phenylpropyl)-N2-methyl-4-oxoazetidine-1,2-dicarboxamide as a white solid (123 g, 80%). MS (ESI+) 710.6 (M+H)+, retention time: 2.11 min. (Method A).

241

Step 5. Preparation of (2S,3R)-3-((2-amino-6-methylpyridin-4-yl)methyl)-N2-(1-methyl-1H-imidazol-2-yl)-N1-((R)-1-phenylpropyl)-N2-methyl-4-oxoazetidine-1,2-dicarboxamide

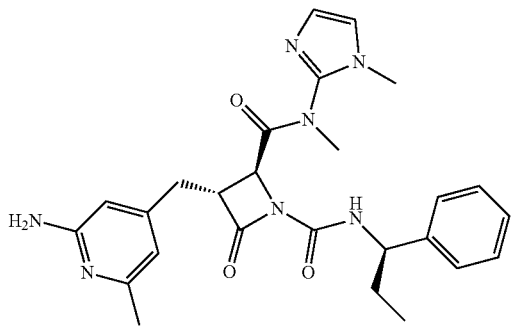 [SMILES: CC[C@@H](NC(=O)N1C(=O)[C@H](Cc2cc(C)nc(N)c2)[C@H]1C(=O)N(C)c1nccn1C)c1ccccc1]

To a solution of (2S,3R)-3-((2-((tert-butoxycarbonyl)(4-methoxybenzyl)amino)-6-methylpyridin-4-yl)methyl)-N2-(1-methyl-1H-imidazol-2-yl)-N1-((R)-1-phenylpropyl)-N2-methyl-4-oxoazetidine-1,2-dicarboxamide (140 g, 197 mmol) in trifluoroacetic acid (800 ml) was added triethylsilane (137.6 g, 1.18 mol) slowly. The resulting mixture was stirred at RT overnight. Solvents were removed under vacuum. The residue was treated with saturated aqueous NaHCO₃ (500 ml). The mixture was extracted with DCM (300 ml×2). The organic phase was dried and concentrated. The residue was chromatographed eluting with 5% methanol/DCM to give an oily material, which was triturated with 8:1 of hexane/EA to give (2S,3R)-3-((2-amino-6-methylpyridin-4-yl)methyl)-N2-(1-methyl-1H-imidazol-2-yl)-N1-((R)-1-phenylpropyl)-N2-methyl-4-oxoazetidine-1,2-dicarboxamide as a white solid (82 g, 85%). MS (ESI+) 490.4 (M+H)⁺, retention time: 2.11 min. (Method B). $^1$H NMR (400 Hz, CDCl₃) δ 0.82 (t, 3H), 1.80 (m, 2H), 2.32 (s, 3H), 2.76 (m, 1H), 2.96 (m, 1H), 3.20 (s, 3H), 3.60 (s, 3H), 3.72 (m, 2H), 4.68 (m, 1H), 5.30 (m, 2H), 6.20 (s, 1H), 6.24 (s, 1H), 6.68 (d, 1H), 6.94 (s, 1H), 7.04 (s, 1H), 7.28 (m, 3H), 7.34 (m, 2H).

242

Example 9. Synthesis of (2S,3R)-3-((1-oxide-2-amino-6-methylpyridin-4-yl)methyl)-N2-(1-methyl-1H-imidazol-2-yl)-N1-((R)-1-phenylpropyl)-N2-methyl-4-oxoazetidine-1,2-dicarboxamide

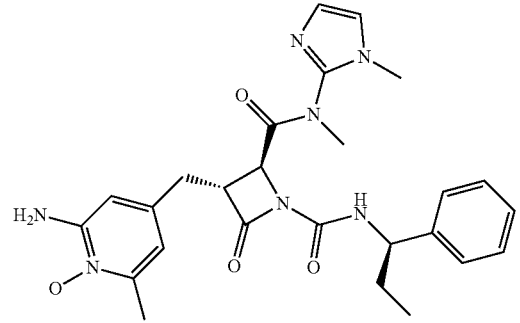

To a solution of (2S,3R)-3-((2-amino-6-methylpyridin-4-yl)methyl)-N2-(1-methyl-1H-imidazol-2-yl)-N1-((R)-1-phenylpropyl)-N2-methyl-4-oxoazetidine-1,2-dicarboxamide (25 mg, 0.05 mmol, product of example 1) in DCM (5 mL) was added meta-chloroperoxybenzoic acid (18 mg, 0.08 mmol). The mixture was stirred 1 h at RT. The mixture was diluted with DCM (10 mL). The mixture was washed with saturated aqueous NaHCO₃ and water, dried, and concentrated. The residue was purified by preparative TLC, developing with 10% methanol/DCM to afford (2S,3R)-3-((1-oxide-2-amino-6-methylpyridin-4-yl)methyl)-N2-(1-methyl-1H-imidazol-2-yl)-N1-((R)-1-phenylpropyl)-N2-methyl-4-oxoazetidine-1,2-dicarboxamide as a white solid (15 mg, 58%). MS (ESI+) m/z 510.2 (M+H)⁺, retention time: 1.25 min. (Method A).

Example 10. Synthesis of (2S,3R)-3-((2-amino-6-methylpyridin-4-yl)methyl)-N2-(5-oxo-1-methyl-4,5-dihydro-1H-imidazol-2-yl)-N1-((R)-1-phenylpropyl)-N2-methyl-4-oxoazetidine-1,2-dicarboxamide Scheme 26

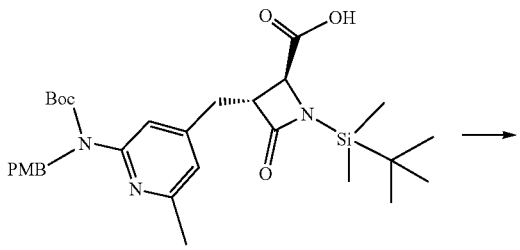

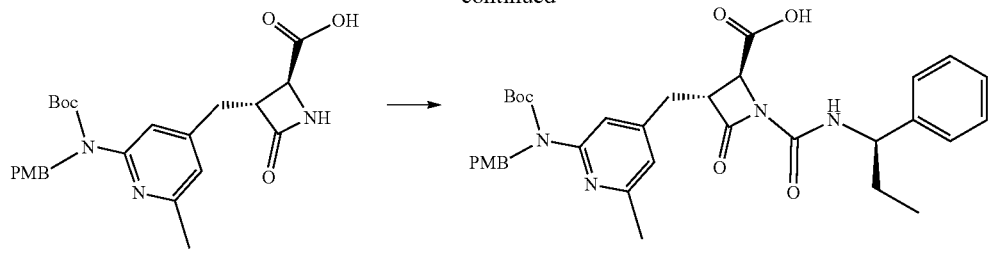

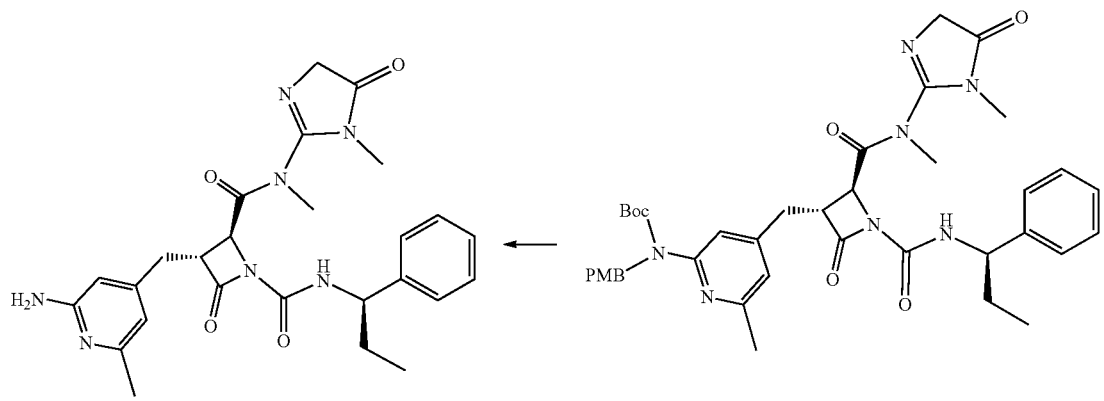

Step 1. Preparation of (2S,3R)-3-((2-((tert-butoxy-carbonyl)(4-methoxybenzyl)amino)-6-methylpyridin-4-yl)methyl)-4-oxoazetidine-2-carboxylic acid Step 2. Preparation of (2S,3R)-3-((2-((tert-butoxy-carbonyl)(4-methoxybenzyl)amino)-6-methylpyridin-4-yl)methyl)-1-(((R)-1-phenylethyl)carbamoyl)-4-oxoazetidine-2-carboxylic acid

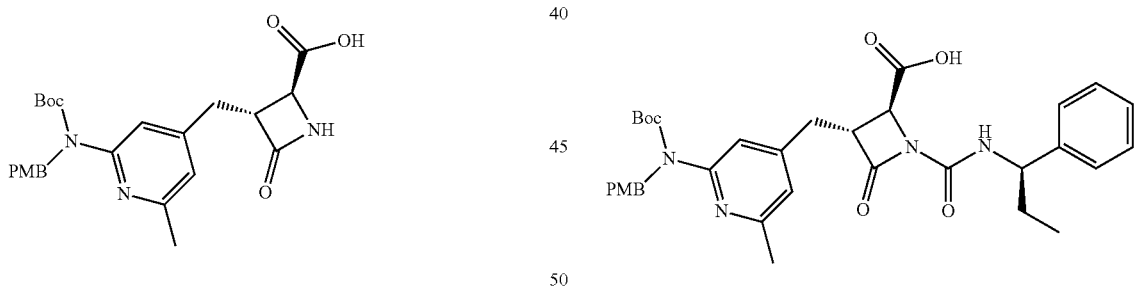

To a solution of (2S,3R)-3-((2-((tert-butoxycarbonyl)(4-methoxybenzyl)amino)-6-methylpyridin-4-yl)methyl)-1-(tert-butyldimethylsilyl)-4-oxoazetidine-2-carboxylic acid (10 g, 17.6 mmol) in methanol (50 mL) was added NH₄F (1.3 g, 35 mmol) and acetic acid (2.1 g, 33.3 mmol). The reaction mixture was stirred at RT for 2 h. The reaction was concentrated and the residue was dissolved in DCM (100 mL). The mixture was washed with water (20 mL) and brine (20 mL), dried, and concentrated to give (2S,3R)-3-((2-((tert-butoxycarbonyl)(4-methoxybenzyl)amino)-6-methylpyridin-4-yl)methyl)-4-oxoazetidine-2-carboxylic acid as a white solid (7 g, 88%). MS (ESI+) m/z 456.2 (M+H)⁺, retention time: 1.55 min. (Method A).

(2S,3R)-3-((2-((tert-butoxycarbonyl)(4-methoxybenzyl)amino)-6-methylpyridin-4-yl)methyl)-4-oxoazetidine-2-carboxylic acid (7.7 g, 16.9 mmol) was dissolved in DCM (100 mL) and treated with DBU (9 g, 59.1 mmol), followed by (R)-(+)-1-phenylpropyl isocyanate (6.9 g, 42.6 mmol) at RT. The reaction was stirred at RT overnight. The mixture was diluted with DCM (50 mL) and the mixture was washed with several portions of 10% aqueous citric acid until no DBU was detected in the organic phase as determined by HPLC (Method A). The organic phase was dried and concentrated. The residue was chromatographed, eluting with a 20% EA/hexane to 100% EA gradient to give (2S,3R)-3-((2-((tert-butoxycarbonyl)(4-methoxybenzyl)amino)-6-methylpyridin-4-yl)methyl)-1-(((R)-1-phenylethyl)carbamoyl)-4-oxoazetidine-2-carboxylic acid as a white solid (9.3 g, 90%). MS (ESI+) m/z 617.3 (M+H)⁺, retention time: 3.66 min. (Method B).

Step 3. Preparation of (2S,3R)-3-((2-((tert-butoxycarbonyl)(4-methoxybenzyl)amino)-6-methylpyridin-4-yl)methyl)-N2-(5-oxo-1-methyl-4,5-dihydro-1H-imidazol-2-yl)-N1-((R)-1-phenylpropyl)-N2-methyl-4-oxoazetidine-1,2-dicarboxamide Step 4. Preparation of (2S,3R)-3-((2-amino-6-methylpyridin-4-yl)methyl)-N2-(5-oxo-1-methyl-4,5-dihydro-1H-imidazol-2-yl)-N1-((R)-1-phenylpropyl)-N2-methyl-4-oxoazetidine-1,2-dicarboxamide

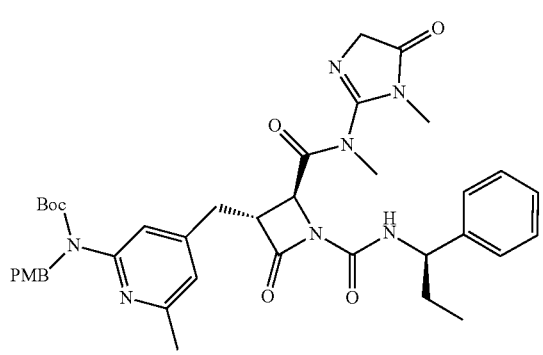

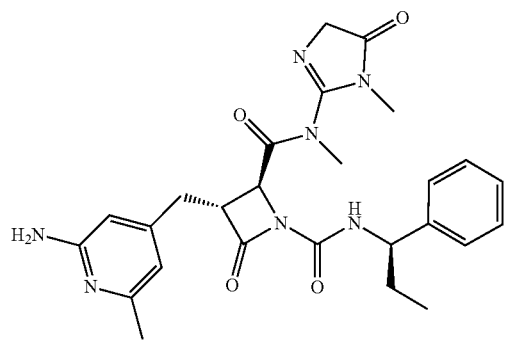 [SMILES: CC[C@@H](NC(=O)N1C(=O)[C@H](Cc2cc(C)nc(N)c2)[C@H]1C(=O)N(C)C1=NCC(=O)N1C)c1ccccc1]

To a solution of (2S,3R)-3-((2-((tert-butoxycarbonyl)(4-methoxybenzyl)amino)-6-methylpyridin-4-yl)methyl)-1-(((R)-1-phenylethyl)carbamoyl)-4-oxoazetidine-2-carboxylic acid (100 mg, 0.16 mmol) in DMF (2 mL), was added HATU (123 mg, 0.32 mmol). The mixture was stirred for 10 min at RT. 1-Methyl-2-methylamino-4,5-dihydro-imidazolo-5-one hydrochloride (83 mg, 0.5 mmol, prepared as described in *J. Org. Chem.*, 1968, 33, 552) was added and the resulting solution was stirred for 10 min. Now diisopropylethylamine (120 mg, 0.9 mmol) was added. The mixture was stirred at RT for 2 hours; then brine (6 mL) was added. The mixture was extracted with EA (5 mL×3). The combined organic phase was washed with water (3 mL) and concentrated. The residue was chromatographed, eluting with a 20%-50% EA/hexane gradient to give (2S,3R)-3-((2-((tert-butoxycarbonyl)(4-methoxybenzyl)amino)-6-methylpyridin-4-yl)methyl)-N2-(5-oxo-1-methyl-4,5-dihydro-1H-imidazol-2-yl)-N1-((R)-1-phenylpropyl)-N2-methyl-4-oxoazetidine-1,2-dicarboxamide as a semi solid (58 mg, 50%). MS (ESI+) m/z 726.7 (M+H)$^+$. Retention time: 2.05 min. (Method A).

A solution of (2S,3R)-3-((2-((tert-butoxycarbonyl)(4-methoxybenzyl)amino)-6-methylpyridin-4-yl)methyl)-N2-(5-oxo-1-methyl-4,5-dihydro-1H-imidazol-2-yl)-N1-((R)-1-phenylpropyl)-N2-methyl-4-oxoazetidine-1,2-dicarboxamide (58 mg, 0.08 mmol) in DCM (3 mL) was treated with triethylsilane (0.1 mL) and cooled to 0° C. Trifluoroacetic acid (1 mL) was added dropwise and the reaction was slowly warmed to RT. After 21 h, HPLC analysis (Method A) indicated the starting material had been consumed. The reaction was concentrated and the residue was taken up in 5 mL DCM. The mixture was washed with saturated aqueous NaHCO$_3$ and water, dried, and concentrated. The residue was purified by preparative TLC developing with EA to afford (2S,3R)-3-((2-amino-6-methylpyridin-4-yl)methyl)-N2-(5-oxo-1-methyl-4,5-dihydro-1H-imidazol-2-yl)-N1-((R)-1-phenylpropyl)-N2-methyl-4-oxoazetidine-1,2-dicarboxamide as a white solid (20 mg, 50%). MS (ESI+) m/z 506.5 (M+H)$^+$, retention time: 1.19 min. (Method A).

Example 11. Additional Product Example Compounds

The compounds shown in Tables 5,6, and 7 below are synthesized via the methods illustrated in Schemes 1-5 and 21-26 and substantially following the experimentals in Examples 3-10.

TABLE 5

Additional product example compounds

| | Product example structure | Product example name | LC-MS Ret. Time (min) | LC-MS (M + H)$^+$ |
|---|---|---|---|---|
| 1-8. | | (2S,3R)-3-((2-aminopyridin-4-yl)methyl)-N2-(4-thiazolyl)-N1-((R)-1-phenylpropyl)-N2-methyl-4-oxoazetidine-1,2-dicarboxamide | 1.25 | 479.4 |

TABLE 5-continued

Additional product example compounds

| | Product example structure | Product example name | LC-MS Ret. Time (min) | LC-MS (M + H)+ |
|---|---|---|---|---|
| 1-9. | | (2S,3R)-3-((2-aminopyridin-4-yl)methyl)-N2-(thiophen-3-yl)-N1-((R)-1-phenylpropyl)-N2-methyl-4-oxoazetidine-1,2-dicarboxamide | 1.25 | 478.4 |
| 1-10. | | (2S,3R)-3-((2-aminopyridin-4-yl)methyl)-N2-(thiophen-2-yl)-N1-((R)-1-phenylpropyl)-N2-methyl-4-oxoazetidine-1,2-dicarboxamide | 1.28 | 478.3 |
| 1-11. | | (2S,3R)-3-((2-aminopyridin-4-yl)methyl)-N2-(1-methyl-1H-pyrazol-4-yl)-N1-((R)-1-(3-chlorophenyl)propyl)-N2-methyl-4-oxoazetidine-1,2-dicarboxamide | 1.25 | 510.3 |
| 1-12. | | (2S,3R)-3-((2-aminopyridin-4-yl)methyl)-N2-(5-thiazolyl)-N1-((R)-1-phenylpropyl)-N2-methyl-4-oxoazetidine-1,2-dicarboxamide | 1.23 | 479.2 |
| 1-13. | | (2S,3R)-3-((2-aminopyridin-4-yl)methyl)-N2-(1-methyl-1H-imidazol-2-yl)-N1-((R)-1-phenylpropyl)-N2-methyl-4-oxoazetidine-1,2-dicarboxamide | 1.22 | 476.5 |

TABLE 5-continued

Additional product example compounds

| Product example structure | Product example name | LC-MS Ret. Time (min) | LC-MS (M + H)+ |
|---|---|---|---|
| 1-14. | (2S,3R)-3-((2-aminopyridin-4-yl)methyl)-N2-(1-methyl-1H-pyrazol-3-yl)-N1-((R)-1-(3-methylphenyl)propyl)-N2-methyl-4-oxoazetidine-1,2-dicarboxamide | 1.24 | 490.4 |
| 1-15. | (2S,3R)-3-((2-amino-6-methylpyridin-4-yl)methyl)-N2-(1-methyl-1H-pyrazol-4-yl)-N1-((R)-1-(3-chlorophenyl)propyl)-N2-methyl-4-oxoazetidine-1,2-dicarboxamide | 1.26 | 524.4 |
| 1-16. | (2S,3R)-3-((2-aminopyridin-4-yl)methyl)-N2-(1-methyl-1H-pyrazol-4-yl)-N1-((R)-1-(3-ethylphenyl)propyl)-N2-methyl-4-oxoazetidine-1,2-dicarboxamide | 1.27 | 504.4 |
| 1-17. | (2S,3R)-3-((2-aminopyridin-4-yl)methyl)-N2-(4-thiazolyl)-N1-((R)-1-(3-chlorophenyl)propyl)-N2-methyl-4-oxoazetidine-1,2-dicarboxamide | 1.28 | 513.3 |

TABLE 5-continued

Additional product example compounds

| | Product example structure | Product example name | LC-MS Ret. Time (min) | LC-MS (M + H)+ |
|---|---|---|---|---|
| 1-18. | | (2S,3R)-3-((2-aminopyridin-4-yl)methyl)-N2-(1-methyl-1H-pyrazol-4-yl)-N1-((R)-1-(6-methylpyridin-3-yl)propyl)-N2-methyl-4-oxoazetidine-1,2-dicarboxamide | 1.06 | 491.3 |
| 1-19. | | (2S,3R)-3-((2-aminopyridin-4-yl)methyl)-N2-(4-isothiazolyl)-N1-((R)-1-phenylpropyl)-N2-methyl-4-oxoazetidine-1,2-dicarboxamide | 1.25 | 479.3 |
| 1-20. | | (2S,3R)-3-((2-aminopyridin-4-yl)methyl)-N2-(1-methyl-1H-pyrazol-3-yl)-N1-((R)-1-(6-methylpyridin-3-yl)propyl)-N2-methyl-4-oxoazetidine-1,2-dicarboxamide | 1.05 | 491.3 |
| 1-21. | | (2S,3R)-3-((2-aminopyridin-4-yl)methyl)-N2-(3-isothiazolyl)-N1-((R)-1-phenylpropyl)-N2-methyl-4-oxoazetidine-1,2-dicarboxamide | 1.25 | 479.3 |
| 1-22. | | (2S,3R)-3-((2-amino-6-methylpyridin-4-yl)methyl)-N2-(1-methyl-1H-pyrazol-3-yl)-N1-((R)-1-(3-methylphenyl)propyl)-N2-methyl-4-oxoazetidine-1,2-dicarboxamide | 1.26 | 504.4 |

TABLE 5-continued

Additional product example compounds

| Product example structure | Product example name | LC-MS Ret. Time (min) | LC-MS (M + H)+ |
|---|---|---|---|
| 1-23. 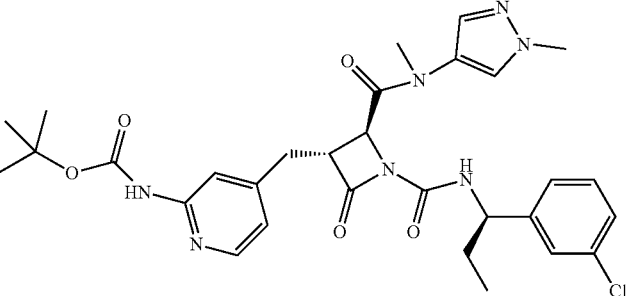 [SMILES: CC[C@@H](NC(=O)N1C(=O)[C@H](Cc2ccnc(NC(=O)OC(C)(C)C)c2)[C@H]1C(=O)N(C)c1cnn(C)c1)c1cccc(Cl)c1] | (2S,3R)-3-((2-(((tert-butoxy)carbonyl)amino)pyridin-4-yl)methyl)-N2-(1-methyl-1H-pyrazol-4-yl)-N1-((R)-1-(3-chlorophenyl)propyl)-N2-methyl-4-oxoazetidine-1,2-dicarboxamide | 1.78 | 610.4 |
| 1-24. 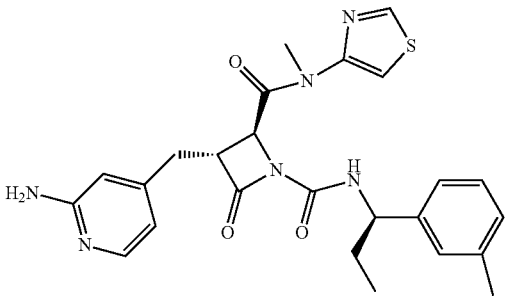 [SMILES: CC[C@@H](NC(=O)N1C(=O)[C@H](Cc2ccnc(N)c2)[C@H]1C(=O)N(C)c1cscn1)c1cccc(C)c1] | (2S,3R)-3-((2-aminopyridin-4-yl)methyl)-N2-(4-thiazolyl)-N1-((R)-1-(3-methylphenyl)propyl)-N2-methyl-4-oxoazetidine-1,2-dicarboxamide | 1.26 | 493.3 |
| 1-25. 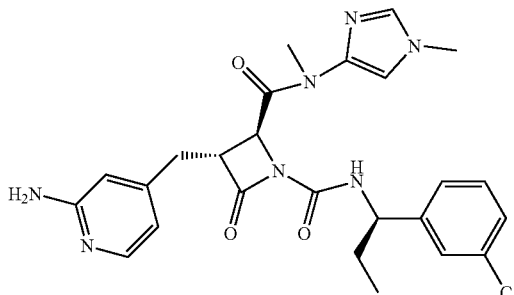 | (2S,3R)-3-((2-aminopyridin-4-yl)methyl)-N2-(1-methyl-1H-imidazol-4-yl)-N1-((R)-1-(3-chlorophenyl)propyl)-N2-methyl-4-oxoazetidine-1,2-dicarboxamide | 1.24 | 510.3 |
| 1-26. 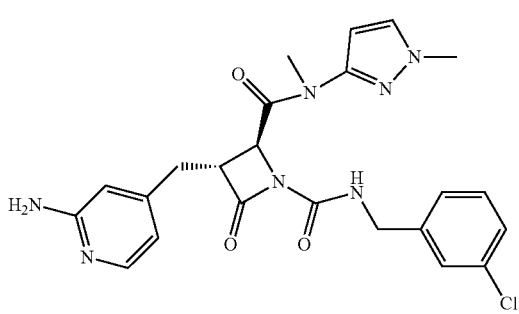 [SMILES: CN(C(=O)[C@@H]1[C@@H](Cc2ccnc(N)c2)C(=O)N1C(=O)NCc1cccc(Cl)c1)c1ccn(C)n1] | (2S,3R)-3-((2-aminopyridin-4-yl)methyl)-N2-(1-methyl-1H-pyrazol-3-yl)-N1-((3-chlorophenyl)methyl)-N2-methyl-4-oxoazetidine-1,2-dicarboxamide | 1.20 | 482.3 |

TABLE 5-continued

Additional product example compounds

| Product example structure | Product example name | LC-MS Ret. Time (min) | LC-MS (M + H)+ |
|---|---|---|---|
| 1-27. | (2S,3R)-3-((2-aminopyridin-4-yl)methyl)-N2-(1-methyl-1H-pyrazol-4-yl)-N1-((3-chlorophenyl)methyl)-N2-methyl-4-oxoazetidine-1,2-dicarboxamide | 1.20 | 482.3 |
| 1-28. | (2S,3R)-3-((2-aminopyridin-4-yl)methyl)-N2-(thiophen-2-yl)-N1-((R)-1-(3-chlorophenyl)propyl)-N2-methyl-4-oxoazetidine-1,2-dicarboxamide | 1.30 | 512.3 |
| 1-29. | (2S,3R)-3-((2-aminopyridin-4-yl)methyl)-N2-(thiophen-2-yl)-N1-((3-chlorophenyl)methyl)-N2-methyl-4-oxoazetidine-1,2-dicarboxamide | 1.26 | 484.3 |
| 1-30. | (2S,3R)-3-((2-aminopyridin-4-yl)methyl)-N2-(1-methyl-1H-pyrazol-3-yl)-N1-((S)-1-cyclopropyl-2,2,2-trifluoroethyl)-N2-methyl-4-oxoazetidine-1,2-dicarboxamide | 1.24 | 480.3 |

TABLE 5-continued

Additional product example compounds

| | Product example structure | Product example name | LC-MS Ret. Time (min) | LC-MS (M + H)+ |
|---|---|---|---|---|
| 1-31. | | (2S,3R)-3-((2-aminopyridin-4-yl)methyl)-N2-(1-methyl-1H-pyrazol-3-yl)-N1-((S)-1-phenyl-2,2,2-trifluoroethyl)-N2-methyl-4-oxoazetidine-1,2-dicarboxamide | 1.24 | 516.4 |
| 1-32. | | (2S,3R)-3-((2-aminopyridin-4-yl)methyl)-N2-(1-methyl-1H-pyrazol-3-yl)-N1-((S)-1-cyclohexyl-2,2,2-trifluoroethyl)-N2-methyl-4-oxoazetidine-1,2-dicarboxamide | 1.29 | 522.4 |
| 1-33. | | (2S,3R)-3-((2-aminopyridin-4-yl)methyl)-N2-(1-methyl-1H-pyrazol-3-yl)-N1-((S)-1-(3-chlorophenyl)ethyl)-N2-methyl-4-oxoazetidine-1,2-dicarboxamide | 1.23 | 496.4 |
| 1-34. | | (2S,3R)-3-((2-aminopyridin-4-yl)methyl)-N2-(1-methyl-1H-imidazol-4-yl)-N1-((3-fluorophenyl)methyl)-N2-methyl-4-oxoazetidine-1,2-dicarboxamide | 1.17 | 466.3 |

TABLE 5-continued

Additional product example compounds

| Product example structure | Product example name | LC-MS Ret. Time (min) | LC-MS (M + H)+ |
|---|---|---|---|
| 1-35. 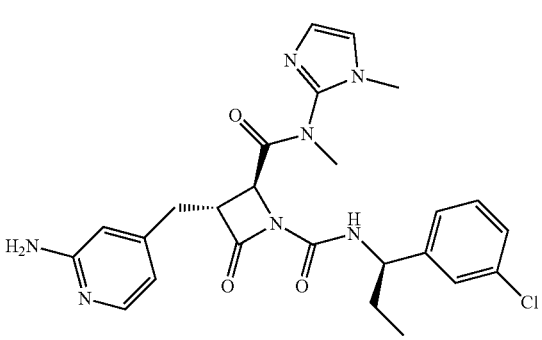 [SMILES: CC[C@@H](NC(=O)N1C(=O)[C@H](Cc2ccnc(N)c2)[C@H]1C(=O)N(C)c1nccn1C)c1cccc(Cl)c1] | (2S,3R)-3-((2-aminopyridin-4-yl)methyl)-N2-(1-methyl-1H-imidazol-2-yl)-N1-((R)-1-(3-chlorophenyl)propyl)-N2-methyl-4-oxoazetidine-1,2-dicarboxamide | 1.25 | 510.3 |
| 1-36. 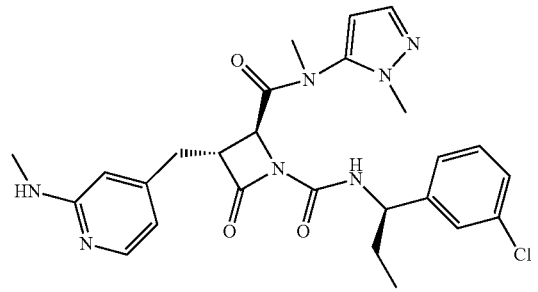 [SMILES: CC[C@@H](NC(=O)N1C(=O)[C@H](Cc2ccnc(NC)c2)[C@H]1C(=O)N(C)c1ccnn1C)c1cccc(Cl)c1] | (2S,3R)-3-((2-methylaminopyridin-4-yl)methyl)-N2-(1-methyl-1H-pyrazol-5-yl)-N1-((R)-1-(3-chlorophenyl)propyl)-N2-methyl-4-oxoazetidine-1,2-dicarboxamide | 1.23 | 524.4 |
| 1-37. 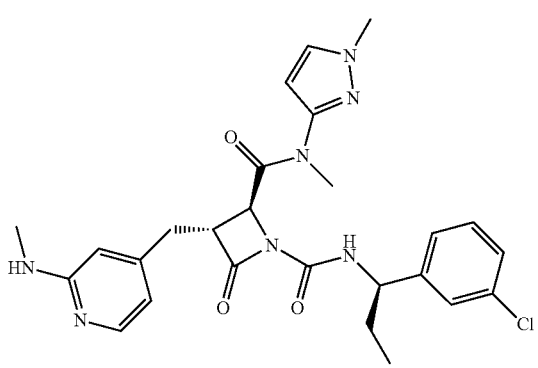 [SMILES: CC[C@@H](NC(=O)N1C(=O)[C@H](Cc2ccnc(NC)c2)[C@H]1C(=O)N(C)c1ccn(C)n1)c1cccc(Cl)c1] | (2S,3R)-3-((2-methylaminopyridin-4-yl)methyl)-N2-(1-methyl-1H-pyrazol-3-yl)-N1-((R)-1-(3-chlorophenyl)propyl)-N2-methyl-4-oxoazetidine-1,2-dicarboxamide | 1.27 | 524.4 |
| 1-38. 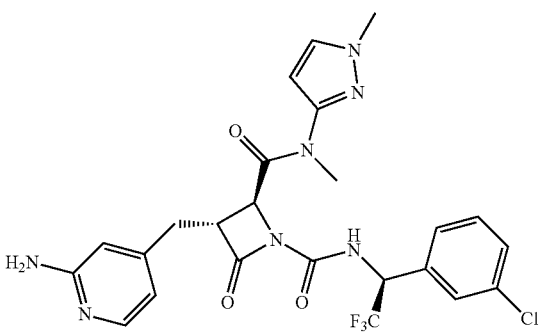 [SMILES: CN(C(=O)[C@@H]1[C@@H](Cc2ccnc(N)c2)C(=O)N1C(=O)N[C@@H](c1cccc(Cl)c1)C(F)(F)F)c1ccn(C)n1] | (2S,3R)-3-((2-aminopyridin-4-yl)methyl)-N2-(1-methyl-1H-pyrazol-3-yl)-N1-((R)-1-(3-chlorophenyl)-2,2,2-trifluoroethyl)-N2-methyl-4-oxoazetidine-1,2-dicarboxamide | 1.26 | 550.4 |

TABLE 5-continued

Additional product example compounds

| | Product example structure | Product example name | LC-MS Ret. Time (min) | LC-MS (M + H)+ |
|---|---|---|---|---|
| 1-39. | | (2S,3R)-3-((2-ethylaminopyridin-4-yl)methyl)-N2-(1-methyl-1H-pyrazol-3-yl)-N1-((R)-1-(3-chlorophenyl)propyl)-N2-methyl-4-oxoazetidine-1,2-dicarboxamide | 1.28 | 538.5 |
| 1-40. | | (2S,3R)-3-((2-methylaminopyridin-4-yl)methyl)-N2-(thiophen-2-yl)-N1-((R)-1-phenylpropyl)-N2-methyl-4-oxoazetidine-1,2-dicarboxamide | 1.27 | 492.4 |
| 1-41. | | (2S,3R)-3-((2-methylaminopyridin-4-yl)methyl)-N2-(1-methyl-1H-imidazol-2-yl)-N1-((R)-1-(3-chlorophenyl)propyl)-N2-methyl-4-oxoazetidine-1,2-dicarboxamide | 1.25 | 524.4 |
| 1-42. | | (2S,3R)-3-((2-aminopyridin-4-yl)methyl)-N2-(1-methyl-1H-pyrazol-3-yl)-N1-((R)-1-(1-methyl-1H-pyrazol-3-yl)propyl)-N2-methyl-4-oxoazetidine-1,2-dicarboxamide | 1.13 | 480.4 |

TABLE 5-continued

Additional product example compounds

| Product example structure | Product example name | LC-MS Ret. Time (min) | LC-MS (M + H)+ |
|---|---|---|---|
| 1-43. | (2S,3R)-3-((2-amino-6-methylpyridin-4-yl)methyl)-N2-(1-methyl-1H-imidazol-2-yl)-N1-((R)-1-(3-chlorophenyl)propyl)-N2-methyl-4-oxoazetidine-1,2-dicarboxamide | 1.25 | 524.4 |
| 1-44. | (2S,3R)-3-((2-methylaminopyridin-4-yl)methyl)-N2-(thiophen-2-yl)-N1-((R)-1-(3-chlorophenyl)propyl)-N2-methyl-4-oxoazetidine-1,2-dicarboxamide | 1.31 | 526.4 |
| 1-45. | (2S,3R)-3-((2-methylamino-6-methylpyridin-4-yl)methyl)-N2-(1-methyl-1H-imidazol-2-yl)-N1-((R)-1-phenylpropyl)-N2-methyl-4-oxoazetidine-1,2-dicarboxamide | 1.23 | 504.4 |
| 1-46. | (2S,3R)-3-((2-methylamino-6-methylpyridin-4-yl)methyl)-N2-(1-methyl-1H-imidazol-2-yl)-N1-((R)-1-(3-chlorophenyl)propyl)-N2-methyl-4-oxoazetidine-1,2-dicarboxamide | 1.27 | 538.4 |

TABLE 5-continued

Additional product example compounds

| Product example structure | Product example name | LC-MS Ret. Time (min) | LC-MS (M + H)+ |
|---|---|---|---|
| 1-47. 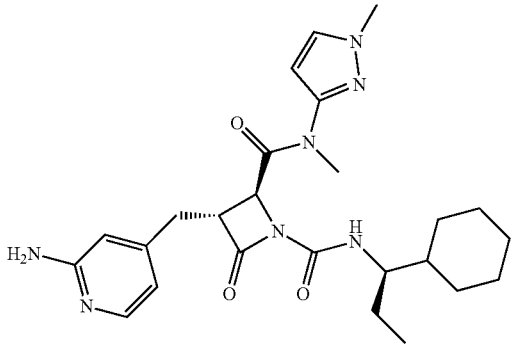 [SMILES: CC[C@@H](NC(=O)N1C(=O)[C@H](Cc2ccnc(N)c2)[C@H]1C(=O)N(C)c1ccn(C)n1)C1CCCCC1] | (2S,3R)-3-((2-aminopyridin-4-yl)methyl)-N2-(1-methyl-1H-pyrazol-3-yl)-N1-((R)-1-cyclohexylpropyl)-N2-methyl-4-oxoazetidine-1,2-dicarboxamide | 1.27 | 482.5 |
| 1-48. 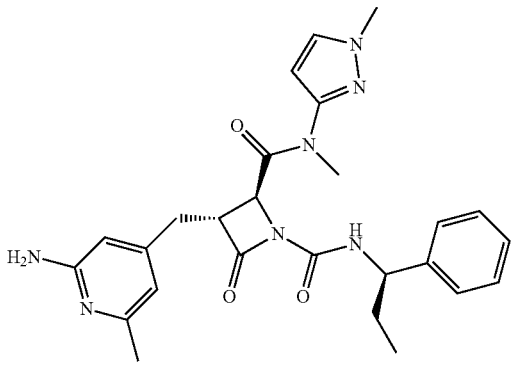 [SMILES: CC[C@@H](NC(=O)N1C(=O)[C@H](Cc2cc(C)nc(N)c2)[C@H]1C(=O)N(C)c1ccn(C)n1)c1ccccc1] | (2S,3R)-3-((2-amino-6-methylpyridin-4-yl)methyl)-N2-(1-methyl-1H-pyrazol-3-yl)-N1-((R)-1-phenylpropyl)-N2-methyl-4-oxoazetidine-1,2-dicarboxamide | 1.23 | 490.4 |
| 1-49. 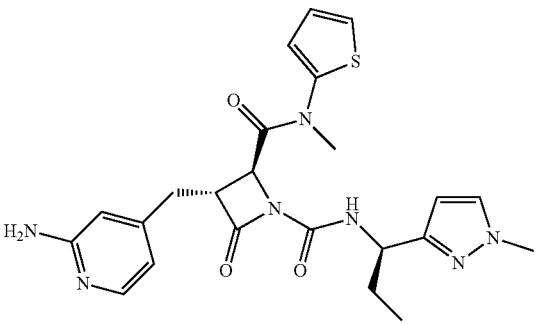 [SMILES: CC[C@@H](NC(=O)N1C(=O)[C@H](Cc2ccnc(N)c2)[C@H]1C(=O)N(C)c1cccs1)c1ccn(C)n1] | (2S,3R)-3-((2-aminopyridin-4-yl)methyl)-N2-(thiophen-2-yl)-N1-((R)-1-(1-methyl-1H-pyrazol-3-yl)propyl)-N2-methyl-4-oxoazetidine-1,2-dicarboxamide | 1.18 | 482.4 |
| 1-50. 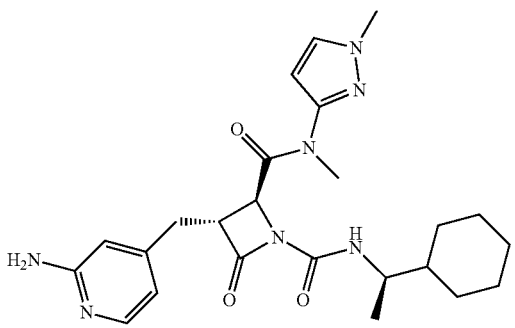 [SMILES: C[C@@H](NC(=O)N1C(=O)[C@H](Cc2ccnc(N)c2)[C@H]1C(=O)N(C)c1ccn(C)n1)C1CCCCC1] | (2S,3R)-3-((2-aminopyridin-4-yl)methyl)-N2-(1-methyl-1H-pyrazol-3-yl)-N1-((R)-1-cyclohexylethyl)-N2-methyl-4-oxoazetidine-1,2-dicarboxamide | 1.24 | 468.4 |

TABLE 5-continued

Additional product example compounds

| | Product example structure | Product example name | LC-MS Ret. Time (min) | LC-MS (M + H)+ |
|---|---|---|---|---|
| 1-51. | | (2S,3R)-3-((2-amino-6-methylpyridin-4-yl)methyl)-N2-(1-methyl-1H-imidazol-2-yl)-N1-((R)-1-phenylpropyl)-N2-methyl-4-oxoazetidine-1,2-dicarboxamide | 1.22 | 490.4 |
| 1-52. | | (2S,3R)-3-((2-amino-6-methylpyridin-4-yl)methyl)-N2-(1-methyl-1H-imidazol-4-yl)-N1-((R)-1-phenylpropyl)-N2-methyl-4-oxoazetidine-1,2-dicarboxamide | 1.18 | 490.4 |
| 1-53. | | (2S,3R)-3-((2-aminopyridin-4-yl)methyl)-N2-(1-methyl-1H-pyrazol-3-yl)-N1-((R)-1-(thiophen-2-yl)propyl)-N2-methyl-4-oxoazetidine-1,2-dicarboxamide | 1.20 | 482.4 |
| 1-54. | | (2S,3R)-3-((2-aminopyridin-4-yl)methyl)-N2-(1-methyl-1H-pyrazol-3-yl)-N1-((R)-1-(thiophen-3-yl)propyl)-N2-methyl-4-oxoazetidine-1,2-dicarboxamide | 1.21 | 482.4 |

TABLE 5-continued

Additional product example compounds

| | Product example structure | Product example name | LC-MS Ret. Time (min) | LC-MS (M + H)+ |
|---|---|---|---|---|
| 1-55. | | (2S,3R)-3-((2-aminopyridin-4-yl)methyl)-N2-(1-methyl-1H-imidazol-2-yl)-N1-((R)-1-cyclohexylpropyl)-N2-methyl-4-oxoazetidine-1,2-dicarboxamide | 1.26 | 482.4 |
| 1-56. | | (2S,3R)-3-((2-aminopyridin-4-yl)methyl)-N2-(1-methyl-1H-imidazol-2-yl)-N1-((R)-1-cyclohexyl-2,2,2-trifluoroethyl)-N2-methyl-4-oxoazetidine-1,2-dicarboxamide | 1.26 | 522.1 |
| 1-57. | | (2S,3R)-3-((2-aminopyridin-4-yl)methyl)-N2-(1-methyl-1H-pyrazol-3-yl)-N1-((R)-1-cyclohexyl-2-methylpropyl)-N2-methyl-4-oxoazetidine-1,2-dicarboxamide | 1.28 | 496.1 |
| 1-58. | | (2S,3R)-3-((2-aminopyridin-4-yl)methyl)-N2-(1-methyl-1H-pyrazol-3-yl)-N1-((R)-cyclohexyl-cyclopropylmethyl)-N2-methyl-4-oxoazetidine-1,2-dicarboxamide | 1.28 | 494.4 |

TABLE 5-continued

Additional product example compounds

| | Product example structure | Product example name | LC-MS Ret. Time (min) | LC-MS (M + H)+ |
|---|---|---|---|---|
| 1-60. | 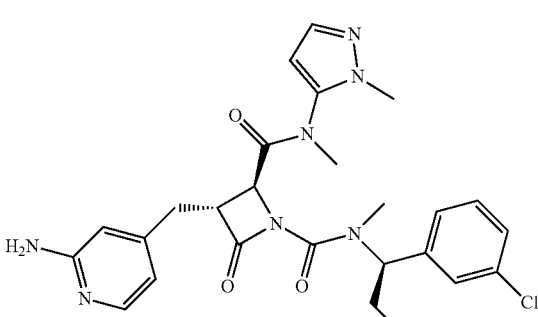 | (2S,3R)-3-((2-aminopyridin-4-yl)methyl)-N2-(1-methyl-1H-pyrazol-5-yl)-N1-((R)-1-(3-chlorophenyl)propyl)-N1-methyl-N2-methyl-4-oxoazetidine-1,2-dicarboxamide | 1.25 | 524.4 |
| 1-61. | 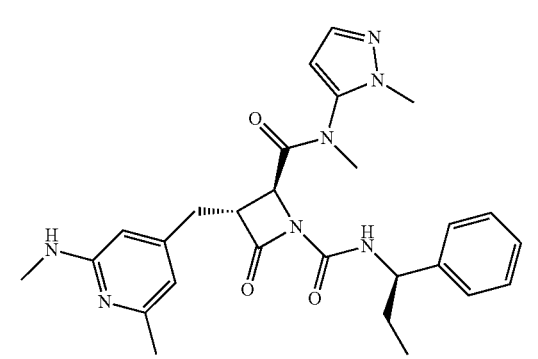 [SMILES: CC[C@@H](NC(=O)N1C(=O)[C@H](Cc2cc(C)nc(NC)c2)[C@H]1C(=O)N(C)c1ccnn1C)c1ccccc1] | (2S,3R)-3-((2-methylamino-6-methylpyridin-4-yl)methyl)-N2-(1-methyl-1H-pyrazol-5-yl)-N1-((R)-1-phenylpropyl)-N2-methyl-4-oxoazetidine-1,2-dicarboxamide | 1.24 | 504.5 |
| 1-62. | 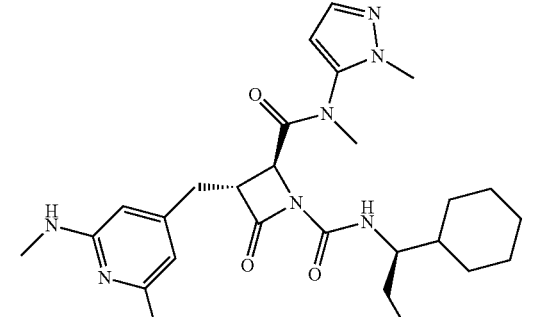 | (2S,3R)-3-((2-methylamino-6-methylpyridin-4-yl)methyl)-N2-(1-methyl-1H-pyrazol-5-yl)-N1-((R)-1-cyclohexylpropyl)-N2-methyl-4-oxoazetidine-1,2-dicarboxamide | 1.29 | 510.5 |
| 1-63. | 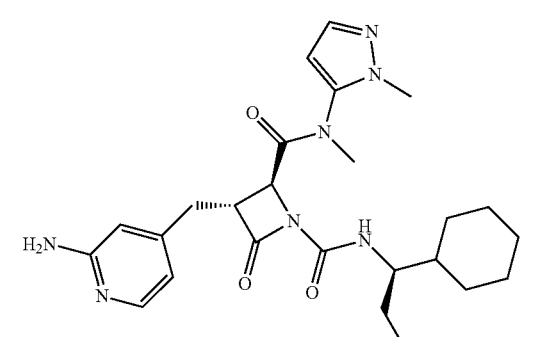 | (2S,3R)-3-((2-aminopyridin-4-yl)methyl)-N2-(1-methyl-1H-pyrazol-5-yl)-N1-((R)-1-cyclohexylpropyl)-N2-methyl-4-oxoazetidine-1,2-dicarboxamide | 1.25 | 482.4 |

TABLE 5-continued

Additional product example compounds

| Product example structure | Product example name | LC-MS Ret. Time (min) | LC-MS (M + H)+ |
|---|---|---|---|
| 1-64. | (2S,3R)-3-((2-aminopyridin-4-yl)methyl)-N2-(1-methyl-1H-pyrazol-3-yl)-N1-methyl-N2-methyl-4-oxoazetidine-1,2-dicarboxamide | 1.04 | 372.3 |
| 1-65. | (2S,3R)-3-((2-aminopyridin-4-yl)methyl)-N2-(1-methyl-1H-imidazol-2-yl)-N1-((R)-1-(3-chlorophenyl)propyl)-N1-methyl-N2-methyl-4-oxoazetidine-1,2-dicarboxamide | 1.24 | 524.4 |
| 1-66. | (2S,3R)-3-((2-methylamino-6-methylpyridin-4-yl)methyl)-N2-(1-methyl-1H-pyrazol-4-yl)-N1-((R)-1-phenylpropyl)-N2-methyl-4-oxoazetidine-1,2-dicarboxamide | 1.23 | 504.5 |
| 1-67. | (2S,3R)-3-((2-amino-6-methylpyridin-4-yl)methyl)-N2-(1-methyl-1H-pyrazol-5-yl)-N1-((R)-1-cyclohexylpropyl)-N2-methyl-4-oxoazetidine-1,2-dicarboxamide | 1.27 | 496.5 |

TABLE 5-continued

Additional product example compounds

| | Product example structure | Product example name | LC-MS Ret. Time (min) | LC-MS (M + H)+ |
|---|---|---|---|---|
| 1-68. | | (2S,3R)-3-((2-aminopyridin-4-yl)methyl)-N2-(1-methyl-1H-pyrazol-3-yl)-N1-((R)-1-cyclohexylbutyl)-N2-methyl-4-oxoazetidine-1,2-dicarboxamide | 1.29 | 496.5 |
| 1-69. | | (2S,3R)-3-((2-aminopyridin-4-yl)methyl)-N2-(1-methyl-1H-pyrazol-4-yl)-N1-((R)-1-cyclohexylpropyl)-N2-methyl-4-oxoazetidine-1,2-dicarboxamide | 1.26 | 482.5 |
| 1-70. | | (2S,3R)-3-((2-aminopyridin-4-yl)methyl)-N2-(1-methyl-1H-imidazol-4-yl)-N1-((R)-1-cyclohexyl-2,2,2-trifluoroethyl)-N2-methyl-4-oxoazetidine-1,2-dicarboxamide | 1.25 | 522.2 |
| 1-71. | | (2S,3R)-3-((2-aminopyridin-4-yl)methyl)-N2-(1-methyl-1H-imidazol-4-yl)-N1-((R)-1-cyclohexylpropyl)-N2-methyl-4-oxoazetidine-1,2-dicarboxamide | 1.23 | 482.3 |

TABLE 5-continued

Additional product example compounds

| | Product example structure | Product example name | LC-MS Ret. Time (min) | LC-MS (M + H)+ |
|---|---|---|---|---|
| 1-72. | | (2S,3R)-3-((2-methylamino-6-methylpyridin-4-yl)methyl)-N2-(1-methyl-1H-imidazol-4-yl)-N1-((R)-1-phenylpropyl)-N2-methyl-4-oxoazetidine-1,2-dicarboxamide | 1.21 | 504.2 |
| 1-73. | | (2S,3R)-3-((2-aminopyridin-4-yl)methyl)-N2-(1-methyl-1H-pyrazol-3-yl)-N1-((R)-1-cyclohexylpentyl)-N2-methyl-4-oxoazetidine-1,2-dicarboxamide | 1.33 | 510.3 |
| 1-74. | | (2S,3R)-3-((2-dimethylaminopyridin-4-yl)methyl)-N2-(1-methyl-1H-pyrazol-3-yl)-N1-((R)-1-phenylpropyl)-N2-methyl-4-oxoazetidine-1,2-dicarboxamide | 1.24 | 504.3 |
| 1-75. | | (2S,3R)-3-((2-amino-6-methylpyridin-4-yl)methyl)-N2-(1-methyl-1H-imidazol-2-yl)-N1-((R)-1-cyclohexylpropyl)-N2-methyl-4-oxoazetidine-1,2-dicarboxamide | 1.24 | 496.3 |

TABLE 5-continued

Additional product example compounds

| | Product example structure | Product example name | LC-MS Ret. Time (min) | LC-MS (M + H)+ |
|---|---|---|---|---|
| 1-76. | 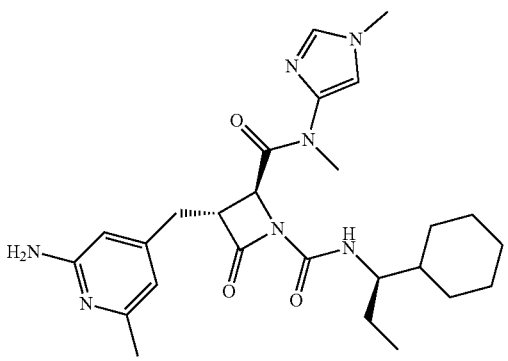 [SMILES: CC[C@@H](NC(=O)N1C(=O)[C@H](Cc2cc(C)nc(N)c2)[C@H]1C(=O)N(C)c1cn(C)cn1)C1CCCCC1] | (2S,3R)-3-((2-amino-6-methylpyridin-4-yl)methyl)-N2-(1-methyl-1H-imidazol-4-yl)-N1-((R)-1-cyclohexylpropyl)-N2-methyl-4-oxoazetidine-1,2-dicarboxamide | 1.23 | 496.3 |
| 1-77. | 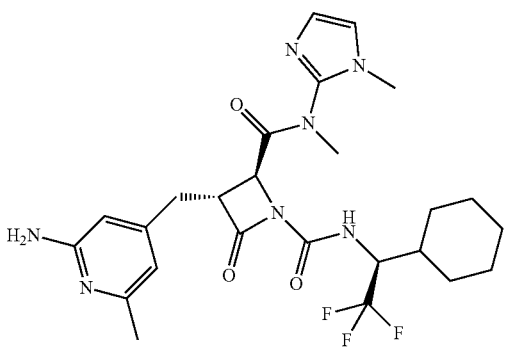 [SMILES: Cc1cc(C[C@H]2C(=O)N(C(=O)N[C@@H](C3CCCCC3)C(F)(F)F)[C@@H]2C(=O)N(C)c2nccn2C)cc(N)n1] | (2S,3R)-3-((2-amino-6-methylpyridin-4-yl)methyl)-N2-(1-methyl-1H-imidazol-2-yl)-N1-((R)-1-cyclohexyl-2,2,2-trifluoroethyl)-N2-methyl-4-oxoazetidine-1,2-dicarboxamide | 1.26 | 536.3 |
| 1-78. | 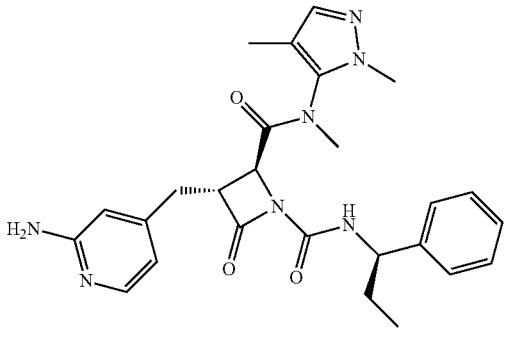 [SMILES: CC[C@@H](NC(=O)N1C(=O)[C@H](Cc2ccnc(N)c2)[C@H]1C(=O)N(C)c1c(C)cnn1C)c1ccccc1] | (2S,3R)-3-((2-aminopyridin-4-yl)methyl)-N2-(1,4-dimethyl-1H-pyrazol-5-yl)-N1-((R)-1-phenylpropyl)-N2-methyl-4-oxoazetidine-1,2-dicarboxamide | 1.22 | 490.2 |
| 1-79. | 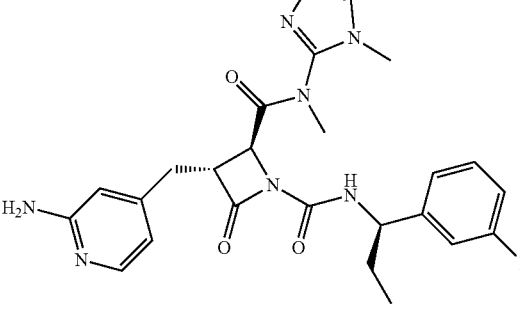 | (2S,3R)-3-((2-aminopyridin-4-yl)methyl)-N2-(1-methyl-1H-imidazol-2-yl)-N1-((R)-1-(3-fluorophenyl)propyl)-N2-methyl-4-oxoazetidine-1,2-dicarboxamide | 1.21 | 494.2 |

TABLE 5-continued

Additional product example compounds

| Product example structure | Product example name | LC-MS Ret. Time (min) | LC-MS (M + H)+ |
|---|---|---|---|
| 1-80. 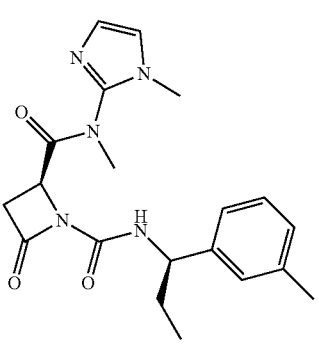 | (2S,3R)-3-((2-aminopyridin-4-yl)methyl)-N2-(1-methyl-1H-imidazol-2-yl)-N1-((R)-1-(3-methylphenyl)propyl)-N2-methyl-4-oxoazetidine-1,2-dicarboxamide | 1.22 | 490.2 |
| 1-81. 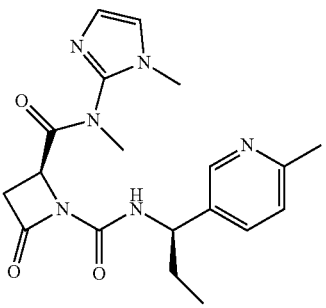 | (2S,3R)-3-((2-aminopyridin-4-yl)methyl)-N2-(1-methyl-1H-imidazol-2-yl)-N1-((R)-1-(6-methylpyridin-3-yl)propyl)-N2-methyl-4-oxoazetidine-1,2-dicarboxamide | 0.59 | 491.2 |
| 1-82. 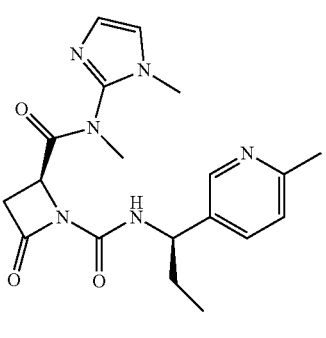 | (2S,3R)-3-((2-amino-6-methylpyridin-4-yl)methyl)-N2-(1-methyl-1H-imidazol-2-yl)-N1-((R)-1-(6-methylpyridin-3-yl)propyl)-N2-methyl-4-oxoazetidine-1,2-dicarboxamide | 1.05 | 505.2 |
| 1-83. 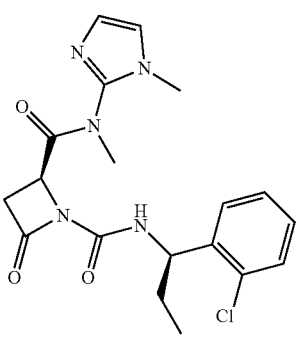 | (2S,3R)-3-((2-aminopyridin-4-yl)methyl)-N2-(1-methyl-1H-imidazol-2-yl)-N1-((R)-1-(4-methylphenyl)propyl)-N2-methyl-4-oxoazetidine-1,2-dicarboxamide | 1.23 | 510.2 |

TABLE 5-continued

Additional product example compounds

| Product example structure | Product example name | LC-MS Ret. Time (min) | LC-MS (M + H)+ |
|---|---|---|---|
| 1-84. 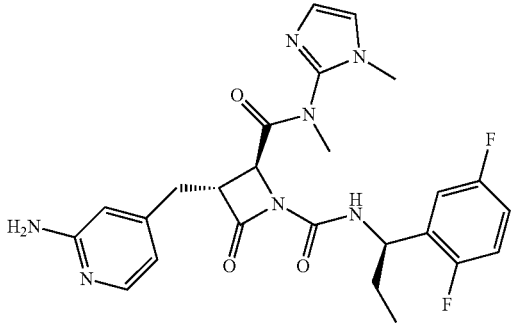 [SMILES: CC[C@@H](NC(=O)N1C(=O)[C@H](Cc2ccnc(N)c2)[C@H]1C(=O)N(C)c1nccn1C)c1cc(F)ccc1F] | (2S,3R)-3-((2-aminopyridin-4-yl)methyl)-N2-(1-methyl-1H-imidazol-2-yl)-N1-((R)-1-(2,5-difluorophenyl)propyl)-N2-methyl-4-oxoazetidine-1,2-dicarboxamide | 1.22 | 512.2 |
| 1-85. 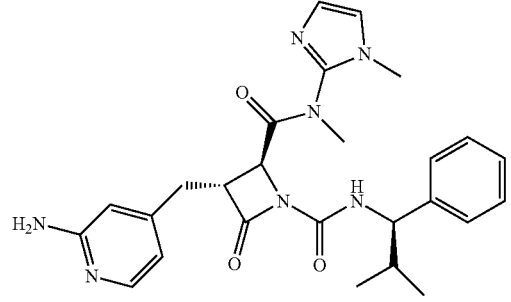 [SMILES: CC(C)[C@@H](NC(=O)N1C(=O)[C@H](Cc2ccnc(N)c2)[C@H]1C(=O)N(C)c1nccn1C)c1ccccc1] | (2S,3R)-3-((2-aminopyridin-4-yl)methyl)-N2-(1-methyl-1H-imidazol-2-yl)-N1-((R)-1-phenyl-2-methylpropyl)-N2-methyl-4-oxoazetidine-1,2-dicarboxamide | 1.22 | 490.3 |
| 1-86. 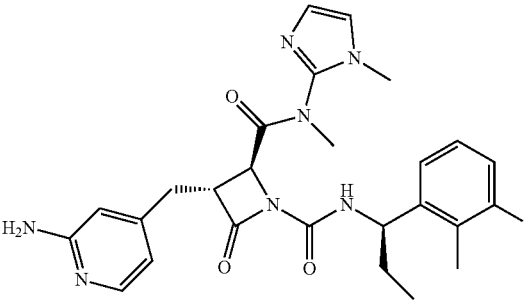 | (2S,3R)-3-((2-aminopyridin-4-yl)methyl)-N2-(1-methyl-1H-imidazol-2-yl)-N1-((R)-1-(3-fluoro-2-methylphenyl)propyl)-N2-methyl-4-oxoazetidine-1,2-dicarboxamide | 1.23 | 508.2 |
| 1-87. 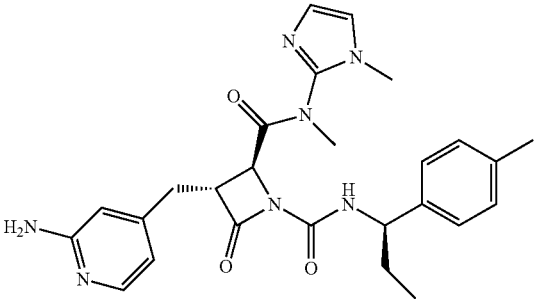 [SMILES: CC[C@@H](NC(=O)N1C(=O)[C@H](Cc2ccnc(N)c2)[C@H]1C(=O)N(C)c1nccn1C)c1ccc(C)cc1] | (2S,3R)-3-((2-aminopyridin-4-yl)methyl)-N2-(1-methyl-1H-imidazol-2-yl)-N1-((R)-1-(4-methylphenyl)propyl)-N2-methyl-4-oxoazetidine-1,2-dicarboxamide | 1.20 | 490.2 |

TABLE 6

Additional product example compounds

| | Product example structure | Product example name | ¹H NMR (CDCl₃)<br>LC-MS (M + H)⁺<br>LC-MS Ret. Time (min) |
|---|---|---|---|
| 1.88 | | (2S,3R)-3-((2-aminopyridin-4-yl)methyl)-N2-(1-methyl-1H-pyrazol-4-yl)-N1-((R)-1-phenylpropyl)-N2-methyl-4-oxoazetidine-1,2-dicarboxamide | ¹H NMR (CDCl₃) δ 0.86 (t, 3H), 1.80 (q, 2H), 2.10 (m, 2H), 2.62 (m, 1H), 2.84 (m, 1H), 3.16 (s, 3H), 3.60 (m, 1H), 3.88 (s, 3H), 4.12 (s, 1H), 4.60 (m, 2H), 4.74 (m, 1H), 6.12 (s, 1H), 6.30 (d, 1H), 6.70 (d, 1H), 7.20-7.40 (m, 5H), 7.96 (d, 1H).<br>(M + H)⁺: 476.3<br>Ret. Time: 1.23 min. |
| 1.89 | | (2S,3R)-3-((2-amino-6-methylpyridin-4-yl)methyl)-N2-(1-methyl-1H-pyrazol-3-yl)-N1-((R)-1-(3-chlorophenyl)propyl)-N2-methyl-4-oxoazetidine-1,2-dicarboxamide | ¹H NMR (CDCl₃) δ 0.88 (t, 3H), 1.80 (q, 2H), 2.30 (s, 3H), 2.72 (m, 1H), 2.84 (m, 1H), 3.16 (s, 3H), 3.54 (m, 1H), 3.70 (m, 1H), 3.84 (s, 3H), 4.20 (s, 1H), 4.60 (m, 3H, 6.02 (s, 1H), 6.20 (s, 1H), 6.24 (d, 1H), 6.78 (d, 1H), 7.10-7.40 (m, 4H).<br>(M + H)⁺: 524.2<br>Ret. Time: 1.26 min. |
| 1.90 | | (2S,3R)-3-((2-aminopyridin-4-yl)methyl)-N2-(1-methyl-1H-imidazol-4-yl)-N1-((R)-1-phenylpropyl)-N2-methyl-4-oxoazetidine-1,2-dicarboxamide | ¹H NMR (CDCl₃) δ 0.88 (t, 3H), 1.82 (q, 2H), 2.84 (m, 2H), 3.16 (s, 3H), 3.60 (m, 1H), 3.72 (s, 3H), 4.50 (s, 1H), 4.78 (m, 3H), 5.04 (m, 2H), 6.22 (s, 1H), 6.38 (d, 1H), 6.80 (d, 1H), 7.04 (s, 1H), 7.20-7.40 (m, 5H), 7.84 (d, 1H).<br>(M + H)⁺: 476.3<br>Ret. Time: 1.19 min. |
| 1.91 | | (2S,3R)-3-((2-aminopyridin-4-yl)methyl)-N2-(1-methyl-1H-pyrazol-3-yl)-N1-((R)-1-(3-chlorophenyl)propyl)-N2-methyl-4-oxoazetidine-1,2-dicarboxamide | ¹H NMR (CDCl₃) δ 0.88 (t, 3H), 1.80 (q, 2H), 2.80 (m, 1H), 2.90 (m, 1H), 3.16 (s, 3H), 3.58 (m, 1H), 3.86 (s, 3H), 4.40 (s, 1H), 4.60-4.78 (m, 3H), 6.20 (d, 1H), 6.22 (d, 1H), 6.38 (d, 1H), 6.76 (d, 1H, 7.10-7.40 (m, 4H), 7.94 (d, 1H).<br>(M + H)⁺: 510.2<br>Ret. Time: 1.26 min. |

TABLE 6-continued

Additional product example compounds

| Product example structure | Product example name | ¹H NMR (CDCl₃)<br>LC-MS (M + H)⁺<br>LC-MS Ret. Time (min) |
|---|---|---|
| 1.92 | (2S,3R)-3-((2-aminopyridin-4-yl)methyl)-N2-(1-methyl 1H-pyrazol-5-yl)-N1-((R)-1-phenylpropyl)-N2-methyl-4-oxoazetidine-1,2-dicarboxamide | ¹H NMR (CDCl₃) δ 0.84 (t, 3H), 1.80 (q, 2H), 2.80 (m, 2H), 3.16 (s, 3H), 3.40 (m, 1H), 3.52 (m, 1H), 3.80 (s, 3H), 4.56 (m, 2H), 4.74 (m, 1H), 5.80 (s, 1H), 5.84 (s, 1H), 6.24 (d, 1H), 6.62 (d, 1H), 7.20-7.40 (m, 5H), 7.54 (d, 1H), 7.86 (d, 1H).<br>(M + H)⁺: 477.2<br>Ret. Time: 1.22 min. |
| 1.93 | (2S,3R)-3-((2-aminopyridin-4-yl)methyl)-N2-(1-methyl-1H-pyrazol-3-yl)-N1-((S)-1-(3-chlorophenyl)propyl)-N2-methyl-4-oxoazetidine-1,2-dicarboxamide | (M + H)⁺: 510.2<br>Ret. Time: 1.23 min. |

TABLE 7

Additional product example compounds

| Product example structure | Product example name | LC-MS Ret. Time (min) (Method A) | LC-MS (M + H)⁺ |
|---|---|---|---|
| 1-94. | (2S,3R)-3-((2-aminopyridin-4-yl)methyl)-N2-(1-methyl-1H-imidazol-2-yl)-N1-((R)-1-(4-chlorophenyl)propyl)-N2-methyl-4-oxoazetidine-1,2-dicarboxamide | 1.23 | 510.1 |

TABLE 7-continued

Additional product example compounds

| Product example structure | Product example name | LC-MS Ret. Time (min) (Method A) | LC-MS (M + H)+ |
|---|---|---|---|
| 1-95. | (2S,3R)-3-((2-aminopyridin-4-yl)methyl)-N2-(1-methyl-1H-imidazol-2-yl)-N1-((R)-1-(2,6-dimethylpyridin-3-yl)propyl)-N2-methyl-4-oxoazetidine-1,2-dicarboxamide | 0.89 | 505.2 |
| 1-96. | (2S,3R)-3-((2-aminopyridin-4-yl)methyl)-N2-(1-methyl-1H-imidazol-2-yl)-N1-((S)-1-(2,6-dimethylpyridin-3-yl)propyl)-N2-methyl-4-oxoazetidine-1,2-dicarboxamide | 1.02 | 505.2 |
| 1-97. | (2S,3R)-3-((2-aminopyridin-4-yl)methyl)-N2-(1-methyl-1H-imidazol-2-yl)-N1-((R)-1-(4-trifluoromethoxyphenyl)propyl)-N2-methyl-4-oxoazetidine-1,2-dicarboxamide | 1.26 | 560.5 |
| 1-98. | (2S,3R)-3-((2-aminopyridin-4-yl)methyl)-N2-(1-methyl-1H-imidazol-2-yl)-N1-((R)-1-(4-fluorophenyl)propyl)-N2-methyl-4-oxoazetidine-1,2-dicarboxamide | 1.23 | 494.1 |

TABLE 7-continued

Additional product example compounds

| Product example structure | Product example name | LC-MS Ret. Time (min) (Method A) | LC-MS (M + H)+ |
|---|---|---|---|
| 1-99. | (2S,3R)-3-((2-aminopyridin-4-yl)methyl)-N2-(1-methyl-1H-imidazol-2-yl)-N1-((R)-1-(2,5-dimethylphenyl)propyl)-N2-methyl-4-oxoazetidine-1,2-dicarboxamide | 1.23 | 504.4 |
| 1-100. | (2S,3R)-3-((2-aminopyridin-4-yl)methyl)-N2-(1-methyl-1H-imidazol-2-yl)-N1-((R)-1-(3,4-dimethylphenyl)propyl)-N2-methyl-4-oxoazetidine-1,2-dicarboxamide | 1.27 | 504.5 |
| 1-101. | (2S,3R)-3-((2-aminopyridin-4-yl)methyl)-N2-(1-methyl-1H-imidazol-2-yl)-N1-((R)-1-(2-chloro-5-methylphenyl)propyl)-N2-methyl-4-oxoazetidine-1,2-dicarboxamide | 1.25 | 524.4 |
| 1-102. | (2S,3R)-3-((2-aminopyridin-4-yl)methyl)-N2-(1-methyl-1H-imidazol-2-yl)-N1-((R)-1-(2-fluoro-5-methylphenyl)propyl)-N2-methyl-4-oxoazetidine-1,2-dicarboxamide | 1.22 | 508.4 |

TABLE 7-continued

Additional product example compounds

| | Product example structure | Product example name | LC-MS Ret. Time (min) (Method A) | LC-MS (M + H)+ |
|---|---|---|---|---|
| 1-103. | | (2S,3R)-3-((2-aminopyridin-4-yl)methyl)-N2-(1-methyl-1H-imidazol-2-yl)-N1-((R)-1-(3-chloro-4-methylphenyl)propyl)-N2-methyl-4-oxoazetidine-1,2-dicarboxamide | 1.25 | 524.4 |
| 1-104. | | (2S,3R)-3-((2-aminopyridin-4-yl)methyl)-N2-(1-methyl-1H-imidazol-2-yl)-N1-((R)-1-(3-chloro-2-methylphenyl)propyl)-N2-methyl-4-oxoazetidine-1,2-dicarboxamide | 1.24 | 524.4 |
| 1-105. | | (2S,3R)-3-((2-amino-6-methylpyridin-4-yl)methyl)-N2-(1-methyl-1H-imidazol-2-yl)-N1-((R)-1-(4-chlorophenyl)propyl)-N2-methyl-4-oxoazetidine-1,2-dicarboxamide | 1.23 | 524.4 |
| 1-106. | | (2S,3R)-3-((2-amino-6-methylpyridin-4-yl)methyl)-N2-(1-methyl-1H-imidazol-2-yl)-N1-((R)-1-(4-fluorophenyl)propyl)-N2-methyl-4-oxoazetidine-1,2-dicarboxamide | 1.21 | 508.4 |

TABLE 7-continued

Additional product example compounds

| | Product example structure | Product example name | LC-MS Ret. Time (min) (Method A) | LC-MS (M + H)+ |
|---|---|---|---|---|
| 1-107. | | (2S,3R)-3-((2-amino-6-methylpyridin-4-yl)methyl)-N2-(1-methyl-1H-imidazol-2-yl)-N1-((R)-1-(4-methylphenyl)propyl)-N2-methyl-4-oxoazetidine-1,2-dicarboxamide | 1.23 | 504.0 |
| 1-108. | | (2S,3R)-3-((2-amino-6-methylpyridin-4-yl)methyl)-N2-(1-methyl-1H-imidazol-2-yl)-N1-((R)-1-(2,5-dimethylphenyl)propyl)-N2-methyl-4-oxoazetidine-1,2-dicarboxamide | 1.25 | 518.1 |
| 1-109. | | (2S,3R)-3-((2-amino-6-methylpyridin-4-yl)methyl)-N2-(1-methyl-1H-imidazol-2-yl)-N1-((R)-1-(3,4-dimethylphenyl)propyl)-N2-methyl-4-oxoazetidine-1,2-dicarboxamide | 1.25 | 518.5 |
| 1-110. | | (2S,3R)-3-((2-amino-6-methylpyridin-4-yl)methyl)-N2-(1-methyl-1H-imidazol-2-yl)-N1-((R)-1-(5-chloro-3-methylphenyl)propyl)-N2-methyl-4-oxoazetidine-1,2-dicarboxamide | 1.24 | 538.4 |

TABLE 7-continued

Additional product example compounds

| | Product example structure | Product example name | LC-MS Ret. Time (min) (Method A) | LC-MS (M + H)+ |
|---|---|---|---|---|
| 1-111. | | (2S,3R)-3-((2-amino-6-methylpyridin-4-yl)methyl)-N2-(1-methyl-1H-imidazol-2-yl)-N1-((R)-1-(2-chloro-5-methylphenyl)propyl)-N2-methyl-4-oxoazetidine-1,2-dicarboxamide | 1.26 | 538.4 |
| 1-112. | | (2S,3R)-3-((2-amino-6-methylpyridin-4-yl)methyl)-N2-(1-methyl-1H-imidazol-2-yl)-N1-((R)-1-(2-fluoro-5-methylphenyl)propyl)-N2-methyl-4-oxoazetidine-1,2-dicarboxamide | 1.24 | 522.4 |
| 1-113. | | (2S,3R)-3-((2-amino-6-methylpyridin-4-yl)methyl)-N2-(1-methyl-1H-imidazol-2-yl)-N1-((R)-1-(3-chloro-4-methylphenyl)propyl)-N2-methyl-4-oxoazetidine-1,2-dicarboxamide | 1.25 | 538.4 |
| 1-114. | | (2S,3R)-3-((2-aminopyridin-4-yl)methyl)-N2-(1-methyl-1H-imidazol-2-yl)-N1-((R)-1-(2,4-dimethylphenyl)propyl)-N2-methyl-4-oxoazetidine-1,2-dicarboxamide | 1.24 | 504.3 |

TABLE 7-continued

Additional product example compounds

| | Product example structure | Product example name | LC-MS Ret. Time (min) (Method A) | LC-MS (M + H)+ |
|---|---|---|---|---|
| 1-115. | | (2S,3R)-3-((2-aminopyridin-4-yl)methyl)-N2-(1-methyl-1H-imidazol-2-yl)-N1-((R)-1-(2-chloro-3-fluorophenyl)propyl)-N2-methyl-4-oxoazetidine-1,2-dicarboxamide | 1.25 | 528.0 |
| 1-116. | | (2S,3R)-3-((2-aminopyridin-4-yl)methyl)-N2-(1-methyl-1H-imidazol-2-yl)-N1-((R)-1-(2-chloro-4-methylphenyl)propyl)-N2-methyl-4-oxoazetidine-1,2-dicarboxamide | 1.26 | 524.3 |
| 1-117. | | (2S,3R)-3-((2-aminopyridin-4-yl)methyl)-N2-(1-methyl-1H-imidazol-2-yl)-N1-((R)-1-(3-methyl-4-fluorophenyl)propyl)-N2-methyl-4-oxoazetidine-1,2-dicarboxamide | 1.24 | 508.4 |
| 1-118. | | (2S,3R)-3-((2-aminopyridin-4-yl)methyl)-N2-(1-methyl-1H-imidazol-2-yl)-N1-((R)-1-(4-chloro-2-methylphenyl)propyl)-N2-methyl-4-oxoazetidine-1,2-dicarboxamide | 1.25 | 524.4 |

TABLE 7-continued

Additional product example compounds

| | Product example structure | Product example name | LC-MS Ret. Time (min) (Method A) | LC-MS (M + H)+ |
|---|---|---|---|---|
| 1-119. | | (2S,3R)-3-((2-aminopyridin-4-yl)methyl)-N2-(1-methyl-1H-imidazol-2-yl)-N1-((R)-1-(2-fluoro-4-methylphenyl)propyl)-N2-methyl-4-oxoazetidine-1,2-dicarboxamide | 1.28 | 508.8 |
| 1-120. | | (2S,3R)-3-((2-amino-6-methylpyridin-4-yl)methyl)-N2-(1-methyl-1H-imidazol-2-yl)-N1-((R)-1-(3-fluorophenyl)propyl)-N2-methyl-4-oxoazetidine-1,2-dicarboxamide | 1.23 | 508.4 |
| 1-121. | | (2S,3R)-3-((2-aminopyridin-4-yl)methyl)-N2-(1-methyl-1H-imidazol-2-yl)-N1-((R)-1-(oxan-2-yl)propyl)-N2-methyl-4-oxoazetidine-1,2-dicarboxamide | 1.17 | 484.0 |
| 1-122. | | (2S,3R)-3-((2-aminopyridin-4-yl)methyl)-N2-(1-methyl-1H-imidazol-2-yl)-N1-((R)-1-(oxan-4-yl)propyl)-N2-methyl-4-oxoazetidine-1,2-dicarboxamide | 1.13 | 484.4 |

TABLE 7-continued

Additional product example compounds

| | Product example structure | Product example name | LC-MS Ret. Time (min) (Method A) | LC-MS (M + H)+ |
|---|---|---|---|---|
| 1-123. | | (2S,3R)-3-((2-aminopyridin-4-yl)methyl)-N2-(1-methyl-1H-pyrazol-3-yl)-N1-((R)-1-(2,5-difluorophenyl)propyl)-N2-methyl-4-oxoazetidine-1,2-dicarboxamide | 1.22 | 512.0 |
| 1-124. | | (2S,3R)-3-((2-aminopyridin-4-yl)methyl)-N2-(1-methyl-1H-pyrazol-3-yl)-N1-((R)-1-(4-methylphenyl)propyl)-N2-methyl-4-oxoazetidine-1,2-dicarboxamide | 1.23 | 490.4 |
| 1-125. | | (2S,3R)-3-((2-aminopyridin-4-yl)methyl)-N2-(1-methyl-1H-pyrazol-3-yl)-N1-((R)-1-(2-fluoro-5-methylphenyl)propyl)-N2-methyl-4-oxoazetidine-1,2-dicarboxamide | 1.24 | 508.4 |
| 1-126. | | (2S,3R)-3-((2-aminopyridin-4-yl)methyl)-N2-(1-methyl-1H-imidazol-2-yl)-N1-((R)-1-(oxan-3-yl)propyl)-N2-methyl-4-oxoazetidine-1,2-dicarboxamide | 1.14 | 484.4 |

TABLE 7-continued

Additional product example compounds

| | Product example structure | Product example name | LC-MS Ret. Time (min) (Method A) | LC-MS (M + H)+ |
|---|---|---|---|---|
| 1-127. | | (2S,3R)-3-((2-aminopyridin-4-yl)methyl)-N2-(1-methyl-1H-pyrazol-3-yl)-N1-((R)-1-(3,4-dimethylphenyl)propyl)-N2-methyl-4-oxoazetidine-1,2-dicarboxamide | 1.26 | 504.4 |
| 1-128. | | (2S,3R)-3-((2-aminopyridin-4-yl)methyl)-N2-(1-methyl-1H-pyrazol-3-yl)-N1-((R)-1-(2-methyl-3-fluorophenyl)propyl)-N2-methyl-4-oxoazetidine-1,2-dicarboxamide | 1.25 | 508.4 |
| 1-129. | | (2S,3R)-3-((2-aminopyridin-4-yl)methyl)-N2-(1-methyl-1H-pyrazol-3-yl)-N1-((R)-1-(3-chloro-4-methylphenyl)propyl)-N2-methyl-4-oxoazetidine-1,2-dicarboxamide | 1.26 | 524.3 |
| 1-130. | | (2S,3R)-3-((2-aminopyridin-4-yl)methyl)-N2-(1-methyl-1H-pyrazol-3-yl)-N1-((R)-1-(2-methylphenyl)propyl)-N2-methyl-4-oxoazetidine-1,2-dicarboxamide | 1.23 | 490.4 |

TABLE 7-continued

Additional product example compounds

| | Product example structure | Product example name | LC-MS Ret. Time (min) (Method A) | LC-MS (M + H)+ |
|---|---|---|---|---|
| 1-131. | | (2S,3R)-3-((2-aminopyridin-4-yl)methyl)-N2-(4-oxo-1-methyl-4,5-dihydro-1H-imidazol-2-yl)-N1-((R)-1-phenylpropyl)-N2-methyl-4-oxoazetidine-1,2-dicarboxamide | 1.22 | 492.4 |
| 1-132. | | (2S,3R)-3-((2-aminopyridin-4-yl)methyl)-N2-(1-methyl-1H-pyrazol-3-yl)-N1-((R)-1-(2,5-dimethylphenyl)propyl)-N2-methyl-4-oxoazetidine-1,2-dicarboxamide | 1.25 | 504.4 |
| 1-133. | | (2S,3R)-3-((2-aminopyridin-4-yl)methyl)-N2-(1-methyl-1H-pyrazol-3-yl)-N1-((R)-1-(2-fluorophenyl)propyl)-N2-methyl-4-oxoazetidine-1,2-dicarboxamide | 1.21 | 494.3 |
| 1-134. | | (2S,3R)-3-((2-aminopyridin-4-yl)methyl)-N2-(1-methyl-1H-pyrazol-3-yl)-N1-((R)-1-(2,3-difluorophenyl)propyl)-N2-methyl-4-oxoazetidine-1,2-dicarboxamide | 1.22 | 512.4 |

TABLE 7-continued

Additional product example compounds

| | Product example structure | Product example name | LC-MS Ret. Time (min) (Method A) | LC-MS (M + H)+ |
|---|---|---|---|---|
| 1-135. | | (2S,3R)-3-((2-aminopyridin-4-yl)methyl)-N2-(1-methyl-1H-pyrazol-3-yl)-N1-((R)-1-(5-fluoro-2-methylphenyl)propyl)-N2-methyl-4-oxoazetidine-1,2-dicarboxamide | 1.25 | 508.4 |
| 1-136. | | (2S,3R)-3-((2-aminopyridin-4-yl)methyl)-N2-(1-methyl-1H-pyrazol-3-yl)-N1-((R)-1-(3-fluoro-4-methylphenyl)propyl)-N2-methyl-4-oxoazetidine-1,2-dicarboxamide | 1.25 | 508.4 |
| 1-137. | | (2S,3R)-3-((2-amino-6-methylpyridin-4-yl)methyl)-N2-(1-methyl-1H-imidazol-2-yl)-N1-((R)-1-(2,5-difluorophenyl)propyl)-N2-methyl-4-oxoazetidine-1,2-dicarboxamide | 1.22 | 526.4 |
| 1-138. | | (2S,3R)-3-((2-aminopyridin-4-yl)methyl)-N2-(1-methyl-1H-pyrazol-3-yl)-N1-((R)-1-(3-chloro-2-methylphenyl)propyl)-N2-methyl-4-oxoazetidine-1,2-dicarboxamide | 1.27 | 524.5 |

TABLE 7-continued

Additional product example compounds

| | Product example structure | Product example name | LC-MS Ret. Time (min) (Method A) | LC-MS (M + H)+ |
|---|---|---|---|---|
| 1-139. | 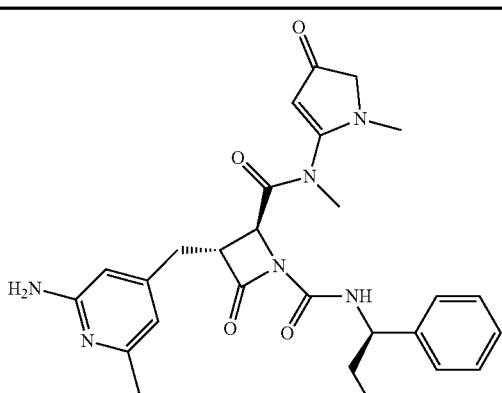 | (2S,3R)-3-((2-amino-6-methylpyridin-4-yl)methyl)-N2-(4-oxo-1-methyl-4,5-dihydro-1H-imidazol-2-yl)-N1-((R)-1-phenylpropyl)-N2-methyl-4-oxoazetidine-1,2-dicarboxamide | 1.23 | 506.5 |
| 1-140. | 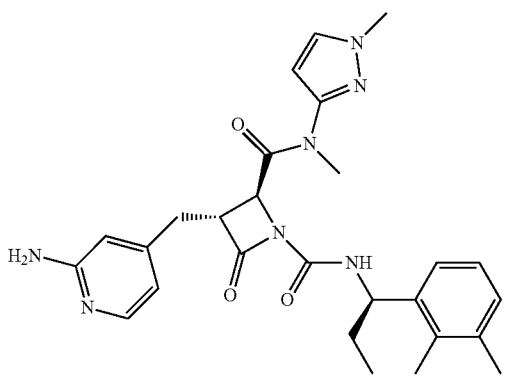 | (2S,3R)-3-((2-aminopyridin-4-yl)methyl)-N2-(1-methyl-1H-pyrazol-3-yl)-N1-((R)-1-(2,3-dimethylphenyl)propyl)-N2-methyl-4-oxoazetidine-1,2-dicarboxamide | 1.25 | 504.5 |
| 1-141. | 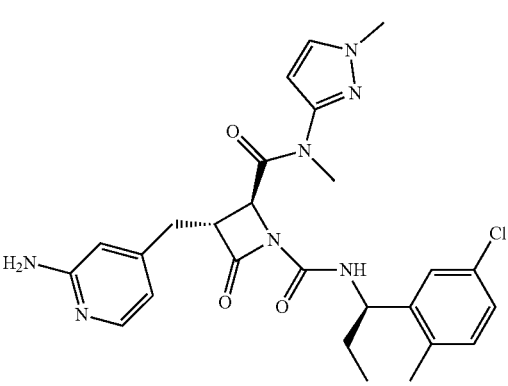 | (2S,3R)-3-((2-aminopyridin-4-yl)methyl)-N2-(1-methyl-1H-pyrazol-3-yl)-N1-((R)-1-(5-chloro-2-methylphenyl)propyl)-N2-methyl-4-oxoazetidine-1,2-dicarboxamide | 1.27 | 524.4 |
| 1-142. | 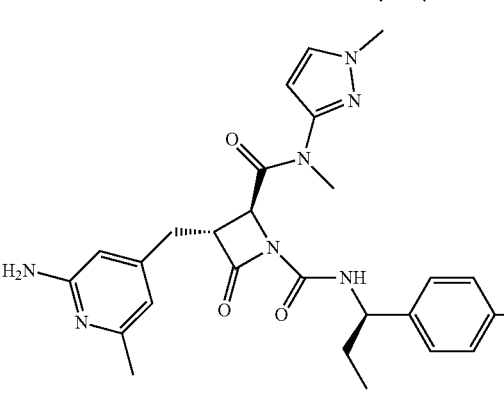 | (2S,3R)-3-((2-amino-6-methylpyridin-4-yl)methyl)-N2-(1-methyl-1H-pyrazol-3-yl)-N1-((R)-1-(4-methylphenyl)propyl)-N2-methyl-4-oxoazetidine-1,2-dicarboxamide | 1.25 | 504.1 |

TABLE 7-continued

Additional product example compounds

| | Product example structure | Product example name | LC-MS Ret. Time (min) (Method A) | LC-MS (M + H)+ |
|---|---|---|---|---|
| 1-143. | | (2S,3R)-3-((2-amino-6-methylpyridin-4-yl)methyl)-N2-(1-methyl-1H-pyrazol-3-yl)-N1-((R)-1-(2-fluoro-5-methylphenyl)propyl)-N2-methyl-4-oxoazetidine-1,2-dicarboxamide | 1.25 | 522.5 |
| 1-144. | | (2S,3R)-3-((2-amino-6-methylpyridin-4-yl)methyl)-N2-(1-methyl-1H-pyrazol-3-yl)-N1-((R)-1-(2,5-difluorophenyl)propyl)-N2-methyl-4-oxoazetidine-1,2-dicarboxamide | 1.24 | 526.5 |
| 1-145. | | (2S,3R)-3-((2-amino-6-methylpyridin-4-yl)methyl)-N2-(1-methyl-1H-pyrazol-3-yl)-N1-((R)-1-(3,4-dimethylphenyl)propyl)-N2-methyl-4-oxoazetidine-1,2-dicarboxamide | 1.27 | 5.18.5 |
| 1-146. | | (2S,3R)-3-((2-amino-6-methylpyridin-4-yl)methyl)-N2-(1-methyl-1H-pyrazol-3-yl)-N1-((R)-1-(2,3-difluorophenyl)propyl)-N2-methyl-4-oxoazetidine-1,2-dicarboxamide | 1.24 | 526.5 |

TABLE 7-continued

Additional product example compounds

| | Product example structure | Product example name | LC-MS Ret. Time (min) (Method A) | LC-MS (M + H)+ |
|---|---|---|---|---|
| 1-147. | | (2S,3R)-3-((2-amino-6-methylpyridin-4-yl)methyl)-N2-(1-methyl-1H-pyrazol-3-yl)-N1-((R)-1-(3-chloro-4-methylphenyl)propyl)-N2-methyl-4-oxoazetidine-1,2-dicarboxamide | 1.28 | 538.5 |
| 1-148. | | (2S,3R)-3-((2-amino-6-methylpyridin-4-yl)methyl)-N2-(5-oxo-1-methyl-4,5-dihydro-1H-imidazol-2-yl)-N1-((R)-1-phenylpropyl)-N2-methyl-4-oxoazetidine-1,2-dicarboxamide | 1.19 | 506.5 |
| 1-149. | | (2S,3R)-3-((2-amino-6-methylpyridin-4-yl)methyl)-N2-(1-methyl-1H-pyrazol-5-yl)-N1-((R)-1-(2,3-dimethylphenyl)propyl)-N2-methyl-4-oxoazetidine-1,2-dicarboxamide | 1.27 | 518.6 |
| 1-150. | | (2S,3R)-3-((2-amino-6-methylpyridin-4-yl)methyl)-N2-(1-methyl-1H-pyrazol-5-yl)-N1-((R)-1-(3-fluoro-2-methylphenyl)propyl)-N2-methyl-4-oxoazetidine-1,2-dicarboxamide | 1.26 | 522.5 |

TABLE 7-continued

Additional product example compounds

| Product example structure | Product example name | LC-MS Ret. Time (min) (Method A) | LC-MS (M + H)+ |
|---|---|---|---|
| 1-151. | (2S,3R)-3-((2-amino-6-methylpyridin-4-yl)methyl)-N2-(1-methyl-1H-pyrazol-5-yl)-N1-((R)-1-(2,3-difluorophenyl)propyl)-N2-methyl-4-oxoazetidine-1,2-dicarboxamide | 1.24 | 526.5 |
| 1-152. | (2S,3R)-3-((2-amino-6-methylpyridin-4-yl)methyl)-N2-(1-methyl-1H-pyrazol-5-yl)-N1-((R)-1-(3,4-dimethylphenyl)propyl)-N2-methyl-4-oxoazetidine-1,2-dicarboxamide | 1.27 | 518.5 |
| 1-153. | (2S,3R)-3-((2-amino-6-methylpyridin-4-yl)methyl)-N2-(1-methyl-1H-pyrazol-5-yl)-N1-((R)-1-(4-fluoro-3-methylphenyl)propyl)-N2-methyl-4-oxoazetidine-1,2-dicarboxamide | 1.25 | 522.5 |
| 1-154. | (2S,3R)-3-((2-amino-6-methylpyridin-4-yl)methyl)-N2-(1-methyl-1H-pyrazol-5-yl)-N1-((R)-1-(4-methylphenyl)propyl)-N2-methyl-4-oxoazetidine-1,2-dicarboxamide | 1.25 | 504.5 |

TABLE 7-continued

Additional product example compounds

| | Product example structure | Product example name | LC-MS Ret. Time (min) (Method A) | LC-MS (M + H)+ |
|---|---|---|---|---|
| 1-155. | | (2S,3R)-3-((2-amino-6-methylpyridin-4-yl)methyl)-N2-(1-methyl-1H-pyrazol-5-yl)-N1-((R)-1-(3-fluoro-4-methylphenyl)propyl)-N2-methyl-4-oxoazetidine-1,2-dicarboxamide | 1.26 | 522.5 |
| 1-156. | | (2S,3R)-3-((2-amino-6-methylpyridin-4-yl)methyl)-N2-(1-methyl-1H-pyrazol-5-yl)-N1-((R)-1-(4-fluorophenyl)propyl)-N2-methyl-4-oxoazetidine-1,2-dicarboxamide | 1.22 | 508.5 |
| 1-157. | | (2S,3R)-3-((2-amino-6-methylpyridin-4-yl)methyl)-N2-(1-methyl-1H-pyrazol-5-yl)-N1-((R)-1-(4-chlorophenyl)propyl)-N2-methyl-4-oxoazetidine-1,2-dicarboxamide | 1.27 | 524.5 |
| 1-158. | | (2S,3R)-3-((2-amino-6-methylpyridin-4-yl)methyl)-N2-(1-methyl-1H-pyrazol-5-yl)-N1-((R)-1-(3,4-difluorophenyl)propyl)-N2-methyl-4-oxoazetidine-1,2-dicarboxamide | 1.24 | 526.5 |

TABLE 7-continued

Additional product example compounds

| | Product example structure | Product example name | LC-MS Ret. Time (min) (Method A) | LC-MS (M + H)+ |
|---|---|---|---|---|
| 1-159. | | (2S,3R)-3-((2-amino-6-methylpyridin-4-yl)methyl)-N2-(1-methyl-1H-pyrazol-5-yl)-N1-((R)-1-(4-fluoro-2-methylhenyl)propyl)-N2-methyl-4-oxoazetidine-1,2-dicarboxamide | 1.27 | 522.5 |
| 1-160. | | (2S,3R)-3-((2-amino-6-methylpyridin-4-yl)methyl)-N2-(1-methyl-1H-pyrazol-5-yl)-N1-((R)-1-(2-fluoro-4-methylphenyl)propyl)-N2-methyl-4-oxoazetidine-1,2-dicarboxamide | 1.27 | 522.6 |
| 1-161. | | (2S,3R)-3-((2-amino-6-methylpyridin-4-yl)methyl)-N2-(1-methyl-1H-pyrazol-5-yl)-N1-((R)-1-(2,4-dimethylphenyl)propyl)-N2-methyl-4-oxoazetidine-1,2-dicarboxamide | 1.28 | 518.6 |
| 1-162. | | (2S,3R)-3-((2-amino-6-methylpyridin-4-yl)methyl)-N2-(1-methyl-1H-pyrazol-5-yl)-N1-((R)-1-(5-fluoro-2-methylphenyl)propyl)-N2-methyl-4-oxoazetidine-1,2-dicarboxamide | 1.24 | 522.5 |

TABLE 7-continued

Additional product example compounds

| | Product example structure | Product example name | LC-MS Ret. Time (min) (Method A) | LC-MS (M + H)+ |
|---|---|---|---|---|
| 1-163. | | (2S,3R)-3-((2-amino-6-methylpyridin-4-yl)methyl)-N2-(1-methyl-1H-pyrazol-5-yl)-N1-((R)-1-(2,5-difluorophenyl)propyl)-N2-methyl-4-oxoazetidine-1,2-dicarboxamide | 1.23 | 526.5 |
| 1-164. | | (2S,3R)-3-((2-amino-6-methylpyridin-4-yl)methyl)-N2-(1-methyl-1H-pyrazol-5-yl)-N1-((R)-1-(2-fluoro-5-methylphenyl)propyl)-N2-methyl-4-oxoazetidine-1,2-dicarboxamide | 1.21 | 522.5 |
| 1-165. | | (2S,3R)-3-((2-aminopyridin-4-yl)methyl)-N2-(4-methyl-4H-1,2,4-triazol-3-yl)-N1-((R)-1-phenylpropyl)-N2-methyl-4-oxoazetidine-1,2-dicarboxamide | 1.20 | 477.5 |
| 1-166. | | (2S,3R)-3-((2-amino-6-methylpyridin-4-yl)methyl)-N2-(1-methyl-1H-pyrazol-5-yl)-N1-((R)-1-(2,5-dimethylphenyl)propyl)-N2-methyl-4-oxoazetidine-1,2-dicarboxamide | 1.27 | 518.6 |

TABLE 7-continued

Additional product example compounds

| Product example structure | Product example name | LC-MS Ret. Time (min) (Method A) | LC-MS (M + H)+ |
|---|---|---|---|
| 1-167. 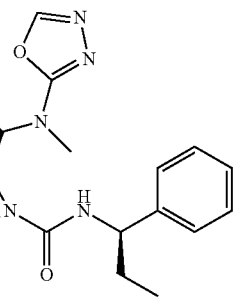 | (2S,3R)-3-((2-aminopyridin-4-yl)methyl)-N2-(1,3,4-oxadiazol-2-yl)-N1-((R)-1-phenylpropyl)-N2-methyl-4-oxoazetidine-1,2-dicarboxamide | 1.22 | 464.4 |
| 1-168. 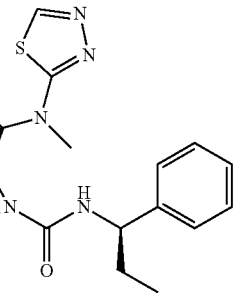 | (2S,3R)-3-((2-aminopyridin-4-yl)methyl)-N2-(1,3,4-thiadiazol-2-yl)-N1-((R)-1-phenylpropyl)-N2-methyl-4-oxoazetidine-1,2-dicarboxamide | 1.23 | 480.4 |
| 1-169. 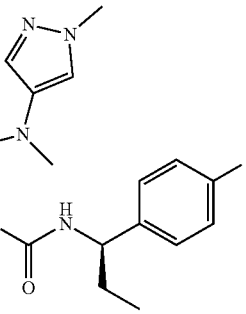 | (2S,3R)-3-((2-amino-6-methylpyridin-4-yl)methyl)-N2-(1-methyl-1H-pyrazol-4-yl)-N1-((R)-1-(4-fluorophenyl)propyl)-N2-methyl-4-oxoazetidine-1,2-dicarboxamide | 1.23 | 508.6 |
| 1-170. 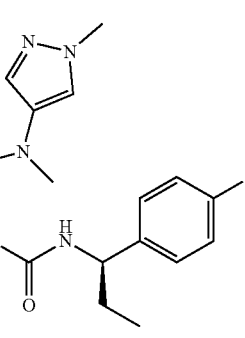 | (2S,3R)-3-((2-amino-6-methylpyridin-4-yl)methyl)-N2-(1-methyl-1H-pyrazol-4-yl)-N1-((R)-1-(4-chlorophenyl)propyl)-N2-methyl-4-oxoazetidine-1,2-dicarboxamide | 1.26 | 524.6 |

TABLE 7-continued

Additional product example compounds

| | Product example structure | Product example name | LC-MS Ret. Time (min) (Method A) | LC-MS (M + H)+ |
|---|---|---|---|---|
| 1-171. | | (2S,3R)-3-((2-amino-6-methylpyridin-4-yl)methyl)-N2-(1-methyl-1H-pyrazol-4-yl)-N1-((R)-1-(4-fluoro-3-methylphenyl)propyl)-N2-methyl-4-oxoazetidine-1,2-dicarboxamide | 1.26 | 522.7 |
| 1-172. | | (2S,3R)-3-((2-amino-6-methylpyridin-4-yl)methyl)-N2-(1-methyl-1H-pyrazol-4-yl)-N1-((R)-1-(3-fluoro-4-methylphenyl)propyl)-N2-methyl-4-oxoazetidine-1,2-dicarboxamide | 1.26 | 522.6 |
| 1-173. | | (2S,3R)-3-((2-amino-6-methylpyridin-4-yl)methyl)-N2-(1-methyl-1H-pyrazol-4-yl)-N1-((R)-1-(2,3-dimethylphenyl)propyl)-N2-methyl-4-oxoazetidine-1,2-dicarboxamide | 1.29 | 518.7 |
| 1-174. | | (2S,3R)-3-((2-amino-6-methylpyridin-4-yl)methyl)-N2-(1-methyl-1H-pyrazol-4-yl)-N1-((R)-1-(2,3-difluorophenyl)propyl)-N2-methyl-4-oxoazetidine-1,2-dicarboxamide | 1.23 | 526.6 |

TABLE 7-continued

Additional product example compounds

| | Product example structure | Product example name | LC-MS Ret. Time (min) (Method A) | LC-MS (M + H)+ |
|---|---|---|---|---|
| 1-175. | | (2S,3R)-3-((2-amino-6-methylpyridin-4-yl)methyl)-N2-(1-methyl-1H-pyrazol-4-yl)-N1-((R)-1-(3,4-dimethylphenyl)propyl)-N2-methyl-4-oxoazetidine-1,2-dicarboxamide | 1.28 | 518.7 |
| 1-176. | | (2S,3R)-3-((2-amino-6-methylpyridin-4-yl)methyl)-N2-(1-methyl-1H-pyrazol-4-yl)-N1-((R)-1-(2,5-dimethylphenyl)propyl)-N2-methyl-4-oxoazetidine-1,2-dicarboxamide | 1.27 | 518.7 |
| 1-177. | | (2S,3R)-3-((2-amino-6-methylpyridin-4-yl)methyl)-N2-(1-methyl-1H-pyrazol-4-yl)-N1-((R)-1-(2-fluoro-5-methylphenyl)propyl)-N2-methyl-4-oxoazetidine-1,2-dicarboxamide | 1.26 | 522.7 |
| 1-178. | | (2S,3R)-3-((2-amino-6-methylpyridin-4-yl)methyl)-N2-(1-methyl-1H-pyrazol-4-yl)-N1-((R)-1-(5-fluoro-2-methylphenyl)propyl)-N2-methyl-4-oxoazetidine-1,2-dicarboxamide | 1.25 | 522.7 |

TABLE 7-continued

Additional product example compounds

| | Product example structure | Product example name | LC-MS Ret. Time (min) (Method A) | LC-MS (M + H)+ |
|---|---|---|---|---|
| 1-179. | | (2S,3R)-3-((2-amino-6-methylpyridin-4-yl)methyl)-N2-(1-methyl-1H-pyrazol-4-yl)-N1-((R)-1-(2,4-dimethylphenyl)propyl)-N2-methyl-4-oxoazetidine-1,2-dicarboxamide | 1.28 | 518.7 |
| 1-180. | | (2S,3R)-3-((2-amino-6-methylpyridin-4-yl)methyl)-N2-(1-methyl-1H-pyrazol-4-yl)-N1-((R)-1-(4-fluoro-2-methylphenyl)propyl)-N2-methyl-4-oxoazetidine-1,2-dicarboxamide | 1.25 | 522.7 |
| 1-181. | | (2S,3R)-3-((2-amino-6-methylpyridin-4-yl)methyl)-N2-(1-methyl-1H-pyrazol-4-yl)-N1-((R)-1-(4-methylphenyl)propyl)-N2-methyl-4-oxoazetidine-1,2-dicarboxamide | 1.25 | 504.6 |
| 1-182. | | (2S,3R)-3-((2-amino-6-methylpyridin-4-yl)methyl)-N2-(1-methyl-1H-pyrazol-4-yl)-N1-((R)-1-(2,5-difluorophenyl)propyl)-N2-methyl-4-oxoazetidine-1,2-dicarboxamide | 1.23 | 526.6 |

TABLE 7-continued

Additional product example compounds

| | Product example structure | Product example name | LC-MS Ret. Time (min) (Method A) | LC-MS (M + H)+ |
|---|---|---|---|---|
| 1-183. | | (2S,3R)-3-((2-amino-6-methylpyridin-4-yl)methyl)-N2-(1-methyl-1H-pyrazol-4-yl)-N1-((R)-1-(2-fluoro-4-methylphenyl)propyl)-N2-methyl-4-oxoazetidine-1,2-dicarboxamide | 1.26 | 522.7 |
| 1-184. | | (2S,3R)-3-((2-amino-6-methylpyridin-4-yl)methyl)-N2-(1-methyl-1H-pyrazol-4-yl)-N1-((R)-1-(3-fluoro-5-methylphenyl)propyl)-N2-methyl-4-oxoazetidine-1,2-dicarboxamide | 1.26 | 522.7 |
| 1-185. | | (2S,3R)-3-((2-amino-6-methylpyridin-4-yl)methyl)-N2-(1-methyl-1H-pyrazol-4-yl)-N1-((R)-1-(3,5-dimethylphenyl)propyl)-N2-methyl-4-oxoazetidine-1,2-dicarboxamide | 1.28 | 518.7 |
| 1-186. | | (2S,3R)-3-((2-amino-6-methylpyridin-4-yl)methyl)-N2-(1,3,4-thiadiazol-2-yl)-N1-((R)-1-phenylpropyl)-N2-methyl-4-oxoazetidine-1,2-dicarboxamide | 1.23 | 494.5 |

TABLE 7-continued

Additional product example compounds

| | Product example structure | Product example name | LC-MS Ret. Time (min) (Method A) | LC-MS (M + H)+ |
|---|---|---|---|---|
| 1-187. | | (2S,3R)-3-((2-amino-6-methylpyridin-4-yl)methyl)-N2-(1,3,4-oxadiazol-2-yl)-N1-((R)-1-phenylpropyl)-N2-methyl-4-oxoazetidine-1,2-dicarboxamide | 1.24 | 478.6 |
| 1-188. | | (2S,3R)-3-((2-amino-6-methylpyridin-4-yl)methyl)-N2-(1-methyl-1H-pyrazol-4-yl)-N1-((R)-1-(2,4-difluorophenyl)propyl)-N2-methyl-4-oxoazetidine-1,2-dicarboxamide | 1.24 | 526.7 |
| 1-189. | | (2S,3R)-3-((2-amino-6-methylpyridin-4-yl)methyl)-N2-(1-methyl-1H-pyrazol-4-yl)-N1-((R)-1-(3,5-difluorophenyl)propyl)-N2-methyl-4-oxoazetidine-1,2-dicarboxamide | 1.24 | 526.7 |
| 1-190. | | (2S,3R)-3-((2-amino-6-methylpyridin-4-yl)methyl)-N2-(1-methyl-1H-pyrazol-4-yl)-N1-((R)-1-(2-fluoro-3-methylphenyl)propyl)-N2-methyl-4-oxoazetidine-1,2-dicarboxamide | 1.26 | 522.7 |

TABLE 7-continued

Additional product example compounds

| | Product example structure | Product example name | LC-MS Ret. Time (min) (Method A) | LC-MS (M + H)+ |
|---|---|---|---|---|
| 1-191. | | (2S,3R)-3-((2-amino-6-methylpyridin-4-yl)methyl)-N2-(1-methyl-1H-pyrazol-4-yl)-N1-((R)-1-(3-fluoro-2-methylphenyl)propyl)-N2-methyl-4-oxoazetidine-1,2-dicarboxamide | 1.24 | 522.7 |
| 1-192. | | (2S,3R)-3-((2-aminopyridin-4-yl)methyl)-N2-(1-methyl-1H-imidazol-2-yl)-N1-((R)-1-(2,3-difluoro-4-methylphenyl)propyl)-N2-methyl-4-oxoazetidine-1,2-dicarboxamide | 1.25 | 526.7 |
| 1-193. | | (2S,3R)-3-((2-aminopyridin-4-yl)methyl)-N2-(1-methyl-1H-imidazol-2-yl)-N1-((R)-1-(3,4,5-trifluorophenyl)propyl)-N2-methyl-4-oxoazetidine-1,2-dicarboxamide | 1.23 | 530.7 |
| 1-194. | | (2S,3R)-3-((2-aminopyridin-4-yl)methyl)-N2-(1-methyl-1H-imidazol-2-yl)-N1-((R)-1-(2,4-difluoro-3-methylphenyl)propyl)-N2-methyl-4-oxoazetidine-1,2-dicarboxamide | 1.25 | 526.7 |

TABLE 7-continued

Additional product example compounds

| | Product example structure | Product example name | LC-MS Ret. Time (min) (Method A) | LC-MS (M + H)+ |
|---|---|---|---|---|
| 1-195. | 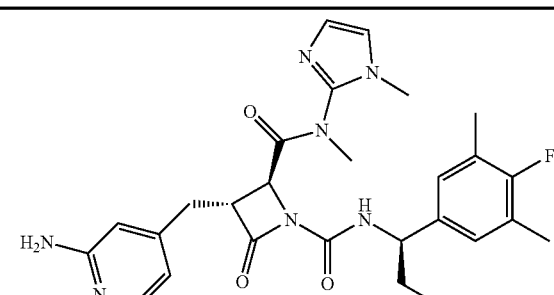 | (2S,3R)-3-((2-aminopyridin-4-yl)methyl)-N2-(1-methyl-1H-imidazol-2-yl)-N1-((R)-1-(3,5-dimethyl-4-fluorophenyl)propyl)-N2-methyl-4-oxoazetidine-1,2-dicarboxamide | 1.26 | 522.7 |
| 1-196. | 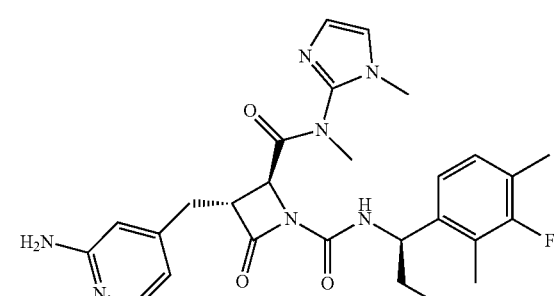 | (2S,3R)-3-((2-aminopyridin-4-yl)methyl)-N2-(1-methyl-1H-imidazol-2-yl)-N1-((R)-1-(2,4-dimethyl-3-fluorophenyl)propyl)-N2-methyl-4-oxoazetidine-1,2-dicarboxamide | 1.25 | 522.5 |
| 1-197. | 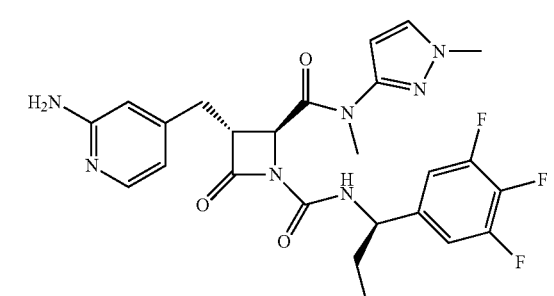 | (2S,3R)-3-((2-aminopyridin-4-yl)methyl)-N2-(1-methyl-1H-pyrazol-3-yl)-N1-((R)-1-(3,4,5-trifluorophenyl)propyl)-N2-methyl-4-oxoazetidine-1,2-dicarboxamide | 1.23 | 530.3 |
| 1-198. | 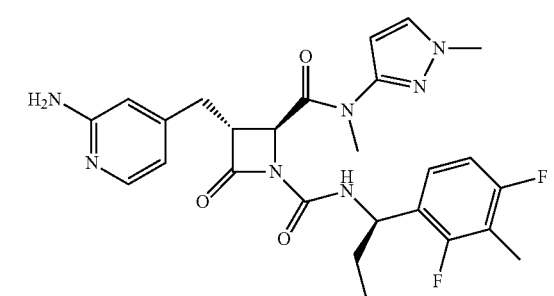 | (2S,3R)-3-((2-aminopyridin-4-yl)methyl)-N2-(1-methyl-1H-pyrazol-3-yl)-N1-((R)-1-(2,4-difluoro-3-methylphenyl)propyl)-N2-methyl-4-oxoazetidine-1,2-dicarboxamide | 1.25 | 526.3 |
| 1-199. | 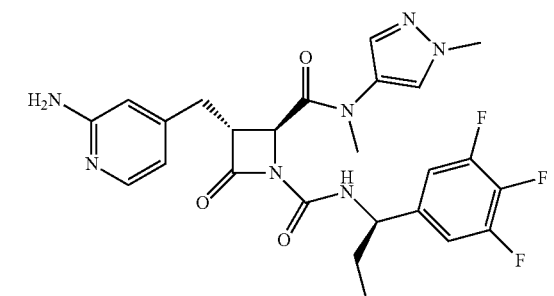 | (2S,3R)-3-((2-aminopyridin-4-yl)methyl)-N2-(1-methyl-1H-pyrazol-4-yl)-N1-((R)-1-(3,4,5-trifluorophenyl)propyl)-N2-methyl-4-oxoazetidine-1,2-dicarboxamide | 1.23 | 530.3 |

TABLE 7-continued

Additional product example compounds

| | Product example structure | Product example name | LC-MS Ret. Time (min) (Method A) | LC-MS (M + H)+ |
|---|---|---|---|---|
| 1-200. | | (2S,3R)-3-((2-aminopyridin-4-yl)methyl)-N2-(1-methyl-1H-pyrazol-5-yl)-N1-((R)-1-(2,4-difluoro-3-methylphenyl)propyl)-N1-methyl-N2-methyl-4-oxoazetidine-1,2-dicarboxamide | 1.26 | 526.4 |
| 1-201. | | (2S,3R)-3-((2-aminopyridin-4-yl)methyl)-N2-(1-methyl-1H-pyrazol-3-yl)-N1-((R)-1-(2,3-difluoro-4-methylphenyl)propyl)-N2-methyl-4-oxoazetidine-1,2-dicarboxamide | 1.24 | 526.3 |
| 1-202. | | (2S,3R)-3-((2-aminopyridin-4-yl)methyl)-N2-(1-methyl-1H-pyrazol-5-yl)-N1-((R)-1-(2,3-difluoro-4-methylphenyl)propyl)-N2-methyl-4-oxoazetidine-1,2-dicarboxamide | 1.25 | 526.3 |
| 1-203. | | (2S,3R)-3-((2-aminopyridin-4-yl)methyl)-N2-(1-methyl-1H-pyrazol-3-yl)-N1-((R)-1-(3,5-dimethyl-4-fluorophenyl)propyl)-N2-methyl-4-oxoazetidine-1,2-dicarboxamide | 1.27 | 522.4 |
| 1-204. | | (2S,3R)-3-((2-aminopyridin-4-yl)methyl)-N2-(1-methyl-1H-pyrazol-5-yl)-N1-((R)-1-(3,4,5-trifluorophenyl)propyl)-N2-methyl-4-oxoazetidine-1,2-dicarboxamide | 1.24 | 530.4 |

TABLE 7-continued

Additional product example compounds

| | Product example structure | Product example name | LC-MS Ret. Time (min) (Method A) | LC-MS (M + H)+ |
|---|---|---|---|---|
| 1-205. | | (2S,3R)-3-((2-aminopyridin-4-yl)methyl)-N2-(1-methyl-1H-pyrazol-5-yl)-N1-((R)-1-(3,5-dimethyl-4-fluorophenyl)propyl)-N2-methyl-4-oxoazetidine-1,2-dicarboxamide | 1.26 | 522.4 |
| 1-206. | | (2S,3R)-3-((2-aminopyridin-4-yl)methyl)-N2-(1-methyl-1H-pyrazol-4-yl)-N1-((R)-1-(3,5-dimethyl-4-fluorophenyl)propyl)-N2-methyl-4-oxoazetidine-1,2-dicarboxamide | 1.25 | 522.4 |
| 1-207. | | (2S,3R)-3-((2-aminopyridin-4-yl)methyl)-N2-(1-methyl-1H-pyrazol-4-yl)-N1-((R)-1-(2,4-difluoro-3-methylphenyl)propyl)-N2-methyl-4-oxoazetidine-1,2-dicarboxamide | 1.24 | 526.4 |
| 1-208. | | (2S,3R)-3-((2-aminopyridin-4-yl)methyl)-N2-(1-methyl-1H-pyrazol-4-yl)-N1-((R)-1-(2,3-difluoro-4-methylphenyl)propyl)-N2-methyl-4-oxoazetidine-1,2-dicarboxamide | 1.24 | 526.4 |
| 1-209. | | (2S,3R)-3-((2-aminopyridin-4-yl)methyl)-N2-(1-methyl-1H-imidazol-2-yl)-N1-((R)-1-(2,3,4-trimethylphenyl)propyl)-N2-methyl-4-oxoazetidine-1,2-dicarboxamide | 1.25 | 518.4 |

TABLE 7-continued

Additional product example compounds

| | Product example structure | Product example name | LC-MS Ret. Time (min) (Method A) | LC-MS (M + H)+ |
|---|---|---|---|---|
| 1-210. | | (2S,3R)-3-((2-aminopyridin-4-yl)methyl)-N2-(1-methyl-1H-imidazol-2-yl)-N1-((R)-1-(2,3,4-trifluorophenyl)propyl)-N2-methyl-4-oxoazetidine-1,2-dicarboxamide | 1.23 | 530.3 |
| 1-211. | | (2S,3R)-3-((2-aminopyridin-4-yl)methyl)-N2-(1-methyl-1H-imidazol-2-yl)-N1-((R)-1-(2,3-dimethyl-4-fluorophenyl)propyl)-N2-methyl-4-oxoazetidine-1,2-dicarboxamide | 1.25 | 522.3 |
| 1-212. | | (2S,3R)-3-((2-aminopyridin-4-yl)methyl)-N2-(1-methyl-1H-imidazol-2-yl)-N1-((R)-1-(3,4-difluoro-2-methylphenyl)propyl)-N2-methyl-4-oxoazetidine-1,2-dicarboxamide | 1.24 | 526.2 |
| 1-213. | | (2S,3R)-3-((2-aminopyridin-4-yl)methyl)-N2-(1-methyl-1H-pyrazol-5-yl)-N1-((R)-1-(2,3-difluorophenyl)propyl)-N2-methyl-4-oxoazetidine-1,2-dicarboxamide | 1.23 | 512.2 |
| 1-214. | | (2S,3R)-3-((2-aminopyridin-4-yl)methyl)-N2-(1-methyl-1H-pyrazol-5-yl)-N1-((R)-1-(4-fluoro-3-methylphenyl)propyl)-N2-methyl-4-oxoazetidine-1,2-dicarboxamide | 1.24 | 508.2 |

TABLE 7-continued

Additional product example compounds

| | Product example structure | Product example name | LC-MS Ret. Time (min) (Method A) | LC-MS (M + H)+ |
|---|---|---|---|---|
| 1-215. | 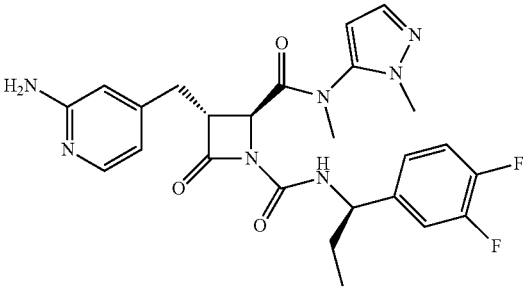 | (2S,3R)-3-((2-aminopyridin-4-yl)methyl)-N2-(1-methyl-1H-pyrazol-5-yl)-N1-((R)-1-(3,4-difluorophenyl)propyl)-N2-methyl-4-oxoazetidine-1,2-dicarboxamide | 1.23 | 512.3 |
| 1-216. | 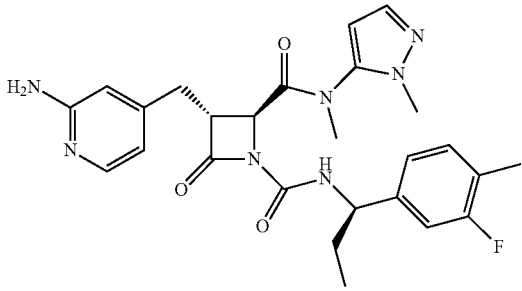 | (2S,3R)-3-((2-aminopyridin-4-yl)methyl)-N2-(1-methyl-1H-pyrazol-5-yl)-N1-((R)-1-(3-fluoro-4-methylphenyl)propyl)-N2-methyl-4-oxoazetidine-1,2-dicarboxamide | 1.24 | 508.3 |
| 1-217. | 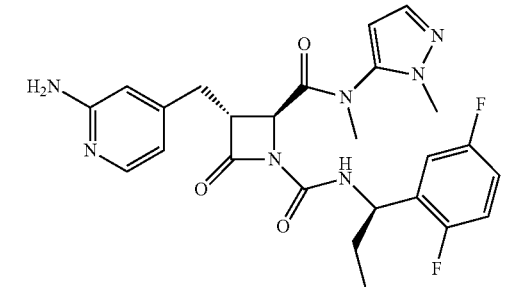 | (2S,3R)-3-((2-aminopyridin-4-yl)methyl)-N2-(1-methyl-1H-pyrazol-5-yl)-N1-((R)-1-(2,5-difluorophenyl)propyl)-N2-methyl-4-oxoazetidine-1,2-dicarboxamide | 1.22 | 512.2 |
| 1-218. | 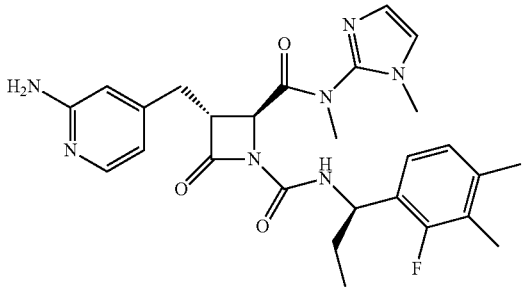 | (2S,3R)-3-((2-aminopyridin-4-yl)methyl)-N2-(1-methyl-1H-imidazol-2-yl)-N1-((R)-1-(2-fluoro-3,4-dimethylphenyl)propyl)-N2-methyl-4-oxoazetidine-1,2-dicarboxamide | 1.26 | 522.3 |
| 1-219. | 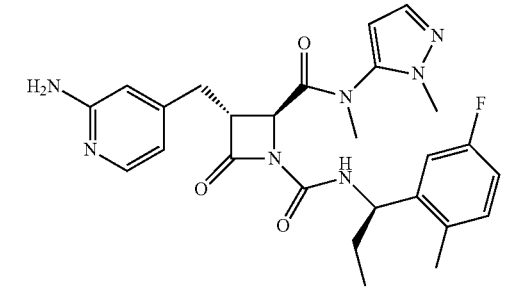 | (2S,3R)-3-((2-aminopyridin-4-yl)methyl)-N2-(1-methyl-1H-pyrazol-5-yl)-N1-((R)-1-(5-fluoro-2-methylphenyl)propyl)-N2-methyl-4-oxoazetidine-1,2-dicarboxamide | 1.23 | 508.3 |

TABLE 7-continued

Additional product example compounds

| | Product example name | LC-MS Ret. Time (min) (Method A) | LC-MS (M + H)+ |
|---|---|---|---|
| 1-220. | (2S,3R)-3-((2-aminopyridin-4-yl)methyl)-N2-(1-methyl-1H-imidazol-2-yl)-N1-((S)-1-(3-fluorophenyl)propyl)-N2-methyl-4-oxoazetidine-1,2-dicarboxamide | 1.21 | 494.2 |
| 1-221. | (2S,3R)-3-((2-aminopyridin-4-yl)methyl)-N2-(1-methyl-1H-imidazol-2-yl)-N1-((S)-1-(2,5-difuorophenyl)propyl)-N2-methyl-4-oxoazetidine-1,2-dicarboxamide | 1.22 | 512.2 |

Example 12. Dose Response Assay for Protease Inhibitors

Materials
Assay buffer: 20 mM Hepes, pH 7.4; 150 mM NaCl; 0.02% Tween 20
Compounds: 10 mM stocks in DMSO
Substrate: 20 mM Glp-Pro-Arg-AMC, 25 mg/2.3 mL $H_2O$ (store at +4° C.) [Factor XIa, thrombin, and trypsin]
20 mM Pro-Phe-Arg-AMC (Bachem I-1295), 25 mg/2.2 mL $H_2O$
or Boc-Leu-Gly-Arg-AMC (Bachem I-1105), 25 mg/2.07 mL $H_2O$
(store at +4° C.) [Factor Xa]
Enzyme: Factor XIa; 0.25 µM in 50% glycerol (20 µg/mL)
Trypsin; 0.2 µM in 50% glycerol (4.8 µg/mL)
Thrombin; 0.2 µM in 50% glycerol (7.34 µg/mL)
Factor Xa; 0.2 µM in 50% glycerol (9.2 µg/mL)
These stocks are aliquoted (~100 µL/aliquot) and stored at −20° C.

Methods:
1. Dilute the substrate to 100 µM in assay buffer (30 µL/6 mL). The enzyme is diluted to 0.5 nM just prior to use (12 µL/6 mL for Factor XIa; 15 µL/6 mL for all of the rest.)
2. Pipette 50 µL of substrate into each well of the 96 well (12×8) microtiter plate. (Column 1 is used as the 100% activity control and receives no compound, and Column 12 is the blank and receives no enzyme.) Add an additional 46 µL to column 2.
3. Pipette 4 µL of each compound into the appropriate well in column 2 of the plate (unknowns assayed in triplicate, standard assayed in duplicate). The final compound concentration will be 1/50$^{th}$ of the stock.
4. Serially two-fold dilute the compound by mixing the sample in column 2, removing 50 µL to the next well (column 3), mix and remove to column 4, etc. until column 11. After mixing column 11, remove 50 µL and discard.
5. Pipette 50 µL of buffer into column 12. Initiate the reaction by adding 50 µL of enzyme solution to each well of columns 1-11 as rapidly as possible.
6. Read the plate in a spectrophotometer (SpectraMax) at 30° C., wherein each well is measured every 60 s for 30 min. For Factor Xa assays, each well is measured every 1 min for a total of 60 min.
7. For Factor XIa assays, the compounds are assayed, in duplicate, at 3 different starting concentrations, 20, 2, and 0.2 µM; 1:10, 1:100, and 1:1000 dilution of 10 mM stock or at 2, 0.2, and 0.02 µM; 1:100, 1:1000, and 1:10,000 dilution of 10 mM stock. Data for each concentration are combined for graphing and data fitting.
8. Data can be used both for estimation of $IC_{50}$ and for estimation of $K_{on}$.

Example 13. Metabolic Stability of Dog Hepatocytes

The following procedure was used to determine the stability of test compounds in beagle dog hepatocytes in a 96-well plate format. The test compounds, including the controls, imipramine and 7-ethoxycoumarin, were dissolved at 10 mM in DMSO, followed by further 5-fold dilution with DMSO to 2 mM. Pooled cryopreserved beagle dog hepatocytes were thawed and transferred into complete medium. Cells were gently centrifuged (700 rpm for 5 min) and the pellet rinsed with KHB (Krebs Henseleit buffer). Cells were resuspended, counted using Trypan blue, and adjusted to 1 million cells/mL in KHB buffer. The 2 mM compound stock solutions were diluted 10-fold with acetonitrile, followed by a further 50-fold dilution with KHB buffer. 200 μL of these compound solutions were transferred to 96-well polypropylene assay plates and an equal volume of the hepatocyte solution was added and mixed to initiate the reaction (final assay concentrations were 2 μM compound and 500,000 cells/mL). Assay plates were incubated at 37° C. in 5% $CO_2$ with gentle agitation. 50 μL aliquots were removed at multiple time points out to 180 minutes and quenched with 6 volumes of cold acetonitrile (containing 250 ng/mL of carbutamide and chrysin as internal standards) to terminate the reaction and precipitate protein. Quenched samples were maintained on ice. The quenched samples were centrifuged at 2000×g (3100 rpm) for 10 minutes at 4° C. 50 μL aliquots of the supernatants were removed and diluted with 100 μL Milli-Q water to reduce the % organic content prior to bioanalysis by LC-MS/MS. Peak areas corresponding to the test compound were recorded. The compound remaining was calculated by comparing the peak area at each time point to time zero. Data were analyzed and results were calculated using Microsoft Excel 2010.

Example 14. Factor XIa Enzyme Inhibition Assays

The ability of compounds of the present invention to inhibit Factor XIa was evaluated by determining the concentration of inhibitor, which resulted in a 50% reduction in enzyme activity ($IC_{50}$) using purified enzyme. Potential inhibitors of Factor XIa were evaluated using the following assay.

PyroGlu-Pro-Arg-7-methylaminocourin (AMC), available from CPC Scientific, Inc., is based on the substrate pyro-Glu-Pro-Arg-pNA (S-2366), available from Diapharma Group, Inc. (Columbus, Ohio), wherein the p-nitroanaline group is replaced with 7-methylaminocoumarin (AMC).

The final concentration of the substrate in the assay was 50 μM, and the final concentration of the enzyme was 0.25 nM. Inhibitors were tested by serial dilution over an appropriate range to yield a dose response curve for determination of the inhibitors' $IC_{50}$ value. The assay mixture was read every minute for 30 minutes in order to generate progress curves. The plates were read in a Spectramax m5 Multimode Plate Reader (Molecular Devices LLC, Sunnyvale, Calif.). Dose response curves were fit to Equation 1 below in which A is the maximum inhibition, B is the minimum inhibition, C is the $IC_{50}$, and D is the Hill coefficient.

$$Y=[(A-B)/(1+(X/C)^D)]+B \qquad \text{(Equation 1)}$$

TABLE 8

Potency, Selectivity, and Stability of Exemplary Compounds Listed In Table 1.

| Compound Number | hFXIa IC50 (nM) | Ratio: FXa/ FXIa | Ratio: Thrombin/ FXIa | Ratio: Trypsin/ FXIa | Dog Hepatocyte Stability ($t_{1/2}$: min) |
|---|---|---|---|---|---|
| 1-3 | A | I | H | G | N |
| 1-4 | A | I | I | G | L |
| 1-5 | D | J | J | J | O |
| 1-6 | B | J | J | J | O |
| 1-7 | B | J | J | J | O |
| 1-8 | A | H | G | G | N |
| 1-9 | A | H | H | G | O |
| 1-10 | A | H | H | G | K |
| 1-11 | A | H | H | G | O |
| 1-12 | A | H | H | G | O |
| 1-13 | A | I | I | G | M |
| 1-14 | B | J | J | J | O |
| 1-15 | B | H | G | G | N |
| 1-16 | A | H | G | G | O |
| 1-17 | A | H | H | G | L |
| 1-18 | B | H | G | G | M |
| 1-19 | A | H | G | G | O |
| 1-20 | A | J | J | J | O |
| 1-21 | B | J | J | J | O |
| 1-22 | A | H | H | G | M |
| 1-23 | D | J | J | J | O |
| 1-24 | A | J | J | J | O |
| 1-25 | A | H | G | G | O |
| 1-26 | B | H | G | G | O |
| 1-27 | B | J | J | J | O |
| 1-28 | A | G | H | G | O |
| 1-29 | B | J | J | J | O |
| 1-30 | B | J | J | J | O |
| 1-31 | B | H | G | G | O |
| 1-32 | A | I | H | G | K |
| 1-33 | A | H | H | G | O |
| 1-34 | C | J | J | J | O |
| 1-35 | A | H | H | G | L |
| 1-36 | B | J | J | J | O |
| 1-37 | B | H | H | G | O |
| 1-38 | A | H | G | G | O |
| 1-39 | B | J | J | J | O |
| 1-40 | B | J | J | J | O |
| 1-41 | B | I | H | G | L |
| 1-42 | C | J | J | J | O |
| 1-43 | A | I | H | G | M |
| 1-44 | A | H | H | G | O |
| 1-45 | B | I | H | G | M |
| 1-46 | A | I | H | G | L |
| 1-47 | A | I | H | G | L |
| 1-48 | A | I | H | G | N |
| 1-49 | B | J | J | J | O |
| 1-50 | B | I | H | G | L |
| 1-51 | A | I | H | G | N |
| 1-52 | B | H | G | G | O |
| 1-53 | B | J | J | J | O |
| 1-54 | B | J | J | J | O |
| 1-55 | A | I | H | G | L |
| 1-56 | A | I | H | G | O |
| 1-57 | B | I | H | G | K |
| 1-58 | A | I | H | G | K |
| 1-60 | B | J | J | J | O |
| 1-61 | B | J | J | J | O |
| 1-62 | B | I | I | G | K |
| 1-63 | A | I | I | G | K |
| 1-64 | C | J | J | J | O |
| 1-65 | B | J | J | J | O |
| 1-66 | B | J | J | J | O |
| 1-67 | B | I | I | G | L |
| 1-68 | B | J | J | J | O |
| 1-69 | B | H | G | G | O |
| 1-70 | A | I | G | G | O |
| 1-71 | A | I | G | G | O |
| 1-72 | B | H | G | G | O |
| 1-73 | B | J | J | J | O |
| 1-74 | D | J | J | J | O |
| 1-75 | B | J | J | J | O |
| 1-76 | B | J | J | J | O |

TABLE 8-continued

Potency, Selectivity, and Stability of Exemplary Compounds Listed In Table 1.

| Compound Number | hFXIa IC50 (nM) | Ratio: FXa/ FXIa | Ratio: Thrombin/ FXIa | Ratio: Trypsin/ FXIa | Dog Hepatocyte Stability ($t_{1/2}$: min) |
|---|---|---|---|---|---|
| 1-77 | B | J | J | J | O |
| 1-78 | B | J | J | J | O |
| 1-79 | A | I | H | G | O |
| 1-80 | A | I | H | G | M |
| 1-81 | B | I | H | G | M |
| 1-82 | B | J | J | J | O |
| 1-83 | B | I | H | G | M |
| 1-84 | A | I | H | G | O |
| 1-85 | B | J | J | J | O |
| 1-86 | C | J | J | J | O |
| 1-87 | A | I | H | G | O |
| 1-88 | A | H | G | G | N |
| 1-89 | A | I | H | G | N |
| 1-90 | A | I | H | G | M |
| 1-91 | A | H | H | G | L |
| 1-92 | A | I | H | G | M |
| 1-93 | B | J | J | J | O |
| 1-94 | A | H | H | G | O |
| 1-95 | B | J | J | J | O |
| 1-96 | C | J | J | J | O |
| 1-97 | B | H | H | G | O |
| 1-98 | A | I | H | G | O |
| 1-99 | A | H | H | G | O |
| 1-100 | A | H | H | G | O |
| 1-101 | A | H | H | G | O |
| 1-102 | A | I | H | G | O |
| 1-103 | A | H | H | G | O |
| 1-104 | A | H | H | G | O |
| 1-105 | B | I | H | G | O |
| 1-106 | A | I | H | G | O |
| 1-107 | B | I | H | G | O |
| 1-108 | B | J | J | J | O |
| 1-109 | A | H | H | G | O |
| 1-110 | A | H | H | G | O |
| 1-111 | A | H | H | G | O |
| 1-112 | B | I | H | G | O |
| 1-113 | A | H | H | G | O |
| 1-114 | A | H | H | G | O |
| 1-115 | A | J | J | J | O |
| 1-116 | A | J | J | J | O |
| 1-117 | A | J | J | J | O |
| 1-118 | A | J | J | J | O |
| 1-119 | A | J | J | J | O |
| 1-120 | A | I | H | G | N |
| 1-121 | B | J | J | J | O |
| 1-122 | B | J | J | J | O |
| 1-123 | A | I | H | G | O |
| 1-124 | A | J | J | J | O |
| 1-125 | A | I | H | G | O |
| 1-126 | B | J | J | J | O |
| 1-127 | A | H | H | G | O |
| 1-128 | A | H | H | G | O |
| 1-129 | A | H | H | G | O |
| 1-130 | A | J | J | J | O |
| 1-131 | B | J | J | J | O |
| 1-132 | A | J | J | J | O |
| 1-133 | B | J | J | J | O |
| 1-134 | A | I | H | G | O |
| 1-135 | A | J | J | J | O |
| 1-136 | A | H | H | G | O |
| 1-137 | A | I | H | G | N |
| 1-138 | A | J | J | J | O |
| 1-139 | B | J | J | J | O |
| 1-140 | A | J | J | J | O |
| 1-141 | A | J | J | J | O |
| 1-142 | A | J | J | J | O |
| 1-143 | A | I | H | G | O |
| 1-144 | A | I | H | G | O |
| 1-145 | A | J | J | J | O |
| 1-146 | A | I | H | G | O |
| 1-147 | A | J | J | J | O |
| 1-148 | C | J | J | J | O |
| 1-149 | B | J | J | J | O |
| 1-150 | A | J | J | J | O |
| 1-151 | A | I | I | G | O |
| 1-152 | A | I | I | G | L |
| 1-153 | A | J | J | J | O |
| 1-154 | A | J | J | J | O |
| 1-155 | A | I | I | G | M |
| 1-156 | A | J | J | J | O |
| 1-157 | B | J | J | J | O |
| 1-158 | A | I | I | G | M |
| 1-159 | A | J | J | J | O |
| 1-160 | A | J | J | J | O |
| 1-161 | A | J | J | J | O |
| 1-162 | A | I | I | G | O |
| 1-163 | A | I | I | G | O |
| 1-164 | A | J | J | J | O |
| 1-165 | B | J | J | J | O |
| 1-166 | A | J | J | J | O |
| 1-167 | A | J | J | J | O |
| 1-168 | A | J | J | J | O |
| 1-169 | B | J | J | J | O |
| 1-170 | B | J | J | J | O |
| 1-171 | B | J | J | J | O |
| 1-172 | A | J | J | J | O |
| 1-173 | B | J | J | J | O |
| 1-174 | B | J | J | J | O |
| 1-175 | A | J | J | J | O |
| 1-176 | B | J | J | J | O |
| 1-177 | B | J | J | J | O |
| 1-178 | A | J | J | J | O |
| 1-179 | A | J | J | J | O |
| 1-180 | B | J | J | J | O |
| 1-181 | B | J | J | J | O |
| 1-182 | A | I | H | G | O |
| 1-183 | A | J | J | J | O |
| 1-184 | A | I | H | G | O |
| 1-185 | A | I | H | G | O |
| 1-186 | A | J | J | J | O |
| 1-187 | A | J | J | J | O |
| 1-188 | B | J | J | J | O |
| 1-189 | B | J | J | J | O |
| 1-190 | A | J | J | J | O |
| 1-191 | B | J | J | J | O |
| 1-192 | A | J | J | J | O |
| 1-193 | A | I | H | G | O |
| 1-194 | A | I | H | H | O |
| 1-195 | A | J | J | J | O |
| 1-196 | A | J | J | J | O |
| 1-197 | A | I | I | H | O |
| 1-198 | A | I | H | H | O |
| 1-199 | A | I | H | H | O |
| 1-200 | A | I | I | H | O |
| 1-201 | A | J | J | J | O |
| 1-202 | A | J | J | J | O |
| 1-203 | A | J | J | J | O |
| 1-204 | A | J | J | J | O |
| 1-205 | A | J | J | J | O |
| 1-206 | A | J | J | J | O |
| 1-207 | A | J | J | J | O |
| 1-208 | A | J | J | J | O |
| 1-209 | A | J | J | J | O |
| 1-210 | A | J | J | J | O |
| 1-211 | A | J | J | J | O |
| 1-212 | A | J | J | J | O |
| 1-213 | A | J | J | J | O |
| 1-214 | A | J | J | J | O |
| 1-215 | A | J | J | J | O |
| 1-216 | A | J | J | J | O |

TABLE 8-continued

Potency, Selectivity, and Stability of Exemplary Compounds Listed In Table 1.

| Compound Number | hFXIa IC50 (nM) | Ratio: FXa/ FXIa | Ratio: Thrombin/ FXIa | Ratio: Trypsin/ FXIa | Dog Hepatocyte Stability ($t_{1/2}$: min) |
|---|---|---|---|---|---|
| 1-217 | A | J | J | J | O |
| 1-218 | A | J | J | J | O |
| 1-219 | A | J | J | J | O |
| 1-220 | B | J | J | J | O |
| 1-221 | C | J | J | J | O |

For Table 8: FXIa and hFXIa refer to Factor XIa and human Factor XIa, respectively.
Potency: "A" indicates < 10 nM, "B" indicates 10-100 nM, "C" indicates 100-1000 nM, and "D" indicates > 1000 nM, and "E" indicates the data is not available or has not been determined.
Selectivity: "F" indicates < 1, "G" indicates 1-100, "H" indicates 101-1000; "I" indicates > 500, and "J" indicates the data is not available or has not been determined.
Dog Hepatocyte Stability: "K" indicates 0-60 min; "L" indicates 61-120 min; "M" indicates 121-240 min; "N" indicates > 240 min; "O" indicates the data is not available or has not been determined.

In Table 8, the activity of Factor XIa enzyme inhibition for Compound 1-79 and Compound 1-84 were incorrectly assigned to Compound 1-220 and Compound 1-221, respectively, in U.S. Ser. No. 62/627,435 to which this application claims priority. The assignment of Factor XIa enzyme inhibition to Compound 1-79, Compound 1-84, Compound 1-220, and Compound 1-221 are correct in the present disclosure.

Example 15. Caco-2 Cell Permeability Assay

The following procedure was used to determine the ability of a test compound to cross Caco-2 cells (human intestinal epithelial cells derived from a colorectal adenocarcinoma). The cells were seeded at $1\times10^5$ cells/cm$^2$ in 96-well Multiscreen™ plates (Millipore). Permeability assays were performed with the cells at days 21-25 post-seeding. Cells are typically used for 15 consecutive passages in culture.

This assay can be performed in either the apical to basolateral (A-B) or basolateral to apical (B-A) direction. The test compound was prepared at 10 µM in HBSS-MES (pH 6.5) or HBSS-HEPES (pH 7.4) with a final DMSO concentration of 1%. The working solution was then centrifuged and the supernatant added to the donor side. The assay plate was incubated at 37° C. with gentle shaking for 60 min or 40 min for the A-B or B-A assay, respectively. Samples were aliquoted from the donor side at time zero and the end point, and from the receiver side at the end point.

Reference compounds, propranolol (highly permeable), labetalol (moderately permeable), ranitidine (poorly permeable), and colchicine (P-glycoprotein substrate) were included in each assay.

Samples are analyzed by HPLC-MS/MS using selected reaction monitoring. The HPLC system consists of a binary LC pump with autosampler, a C-18 column, and a gradient.

The apparent permeability coefficient ($P_{app}$) of the test compound (Equation 2) and its recovery (Equation 3) are calculated as follows:

$$P_{app}(\text{cm/s}) = \frac{V_R \times C_{R,end}}{\Delta t} \times \frac{1}{A \times (C_{D,mid} - C_{R,mid})} \quad \text{(Equation 2)}$$

$$\text{Recovery (\%)} = \frac{V_D \times C_{D,end} + V_R \times C_{R,end}}{V_D \times C_{D0}} \times 100 \quad \text{(Equation 3)}$$

wherein A is the surface area of the cell monolayer (0.11 cm$^2$), C is concentration of the test compound expressed as peak area, D denotes donor, and R is receiver. "0", "mid," and "end" denote time at zero, mid-point, and end of the incubation, respectively. $\Delta t$ is the incubation time. V is the volume of the donor or receiver.

Low recovery indicates that the test compound is lost during the course of the assay. This is most likely due to non-specific binding or degradation.

Example 16. Solubility Assays

The following procedure was used to determine the aqueous solubility of a test compound in phosphate buffered saline (PBS-NaCl 137 mM, KCl 2.7 mM, Na$_2$HPO$_4$ 8.1 mM, KH$_2$PO$_4$ 1.5 mM, pH 7.4) in 96-well plate format by HPLC-UV/VIS analysis. The test compound was prepared at 200 µM in PBS from a 10 mM DMSO stock solution. The final DMSO concentration was 2%. The PBS buffer samples were mixed thoroughly followed by incubation at room temperature for 24 h. At the end of the incubation, the PBS buffer samples were centrifuged and supernatants analyzed by HPLC. The aqueous solubility (µM) of the test compound in PBS was determined by comparing the peak area of the principal peak in the calibration standard (200 µM) with the peak area of the corresponding peak in each of the PBS samples. The range of the assay was approximately 0.5 µM to 200 µM. The reference compounds used in each assay were metoprolol, rifampicin, ketoconazole, phenytoin, haloperidol, simvastatin, diethylstilbestrol, and tamoxifen ranking from fully soluble (200 µM) to poorly soluble (<1 µM).

Example 17. Plasma Protein Binding Assays

The following procedure was used to determine the plasma protein binding of a test compound in pooled plasma from human (mixed gender) via equilibrium dialysis in a 96-well plate format. The dialysate compartment was loaded with phosphate-buffered saline (pH 7.4) and the sample side was loaded with plasma spiked with the test compound at a concentration of 10 µM. After loading, samples were covered and incubated for 4 hours at 37° C. After incubation, each compartment was sampled, diluted with acetonitrile/buffer and centrifuged. The supernatants were analyzed by HPLC-MS/MS. The analyte peak areas obtained from HPLC-MS/MS analysis of each sample were used to calculate protein binding according to the following equation (Equation 4):

$$\text{Plasma Protein Binding (\%)} = \frac{Area_p}{Area_b} \times 100 \quad \text{(Equation 4)}$$

where: AREA$_p$=Peak area of analyte in protein matrix; AREA$_b$=Peak area of analyte in buffer.

The amount measured in the plasma compartment included both free and bound drug, while that on the buffer side represented free drug only; the differences were used to calculate the percentage plasma protein bound. Three reference compounds were tested in each assay: acebutolol, quinidine and warfarin.

Example 18. Determination of Bioavailability in a Dog

The following protocol was used to estimate the bioavailability of test compounds in a dog. Test compounds were formulated in vehicles compatible with intravenous and oral dosing. Test compounds were administered to male beagle dogs via an intravenous bolus at 1 mg/kg (1 mg/mL at a dose volume of 1 mL/kg) or via oral gavage at 5 mg/kg (1 mg/mL at a dose volume of 5 mL/kg). Blood samples were collected via the contralateral (to intravenous bolus) jugular vein or via other accessible vein, at various timepoints following administration out to 24 hours post dose. Plasma samples (EDTA) were obtained by centrifugation (2200×g for 10 minutes at 5° C.) and stored frozen (70° C.) until analyzed for parent compound via LC/MS/MS. Pharmacokinetic parameters were estimated from the plasma concentration time data by standard non-compartmental methods utilizing standard analysis software. By comparing the area under the curve (AUC) for IV and PO administration estimates of oral bioavailability were determined.

TABLE 9

Caco-2 cell permeability (A-B and B-A), aqueous solubility, human plasma protein binding (PPB), and dog bioavailability of exemplary compounds listed in Table 1.

| Compound Number | Caco-2 Permeability (A-B) | Caco-2 Permeability (B-A) | Aqueous Solubility (uM, in PBS) | PPB (%) | Dog Bioavailability (%) |
| --- | --- | --- | --- | --- | --- |
| 1-3 | P | R | W | Z | FF |
| 1-4 | Q | Q | W | Z | FF |
| 1-8 | P | R | W | Z | GG |
| 1-9 | Q | Q | X | CC | GG |
| 1-10 | Q | Q | W | AA | EE |
| 1-11 | P | Q | X | CC | GG |
| 1-13 | P | Q | W | Z | FF |
| 1-15 | P | Q | W | Z | GG |
| 1-17 | Q | Q | W | AA | GG |
| 1-18 | P | P | W | Y | GG |
| 1-22 | P | Q | W | Z | GG |
| 1-32 | Q | Q | W | AA | GG |
| 1-35 | P | R | W | Z | GG |
| 1-41 | P | R | W | Z | GG |
| 1-43 | P | Q | W | Z | GG |
| 1-45 | Q | R | W | Z | EE |
| 1-46 | Q | Q | W | AA | GG |
| 1-47 | P | R | W | AA | GG |
| 1-50 | P | R | W | Z | GG |
| 1-51 | P | R | W | Z | FF |
| 1-55 | P | R | W | Z | GG |
| 1-57 | Q | Q | V | BB | GG |
| 1-58 | Q | Q | W | AA | GG |
| 1-62 | Q | Q | W | Z | GG |
| 1-63 | Q | R | W | Z | GG |
| 1-67 | Q | R | W | Z | GG |
| 1-79 | P | Q | W | Z | GG |
| 1-80 | P | R | W | Z | GG |
| 1-81 | P | P | W | Y | DD |
| 1-83 | P | S | W | AA | GG |
| 1-84 | P | Q | W | Z | GG |
| 1-88 | P | Q | W | Z | GG |
| 1-89 | P | Q | W | Z | FF |
| 1-90 | P | Q | W | Z | GG |
| 1-91 | P | Q | W | Z | FF |
| 1-92 | P | R | W | Z | FF |
| 1-120 | P | Q | W | Z | GG |
| 1-137 | P | Q | W | AA | GG |
| 1-152 | P | Q | W | Z | GG |
| 1-155 | P | Q | W | Z | GG |
| 1-158 | P | Q | W | AA | GG |

For Table 9: Caco-2 Permeability ($P_{app}$): "P" indicates < 10 × 10⁻⁶ cm/s; "Q" indicates 11-30 × 10⁻⁶ cm/s; "R" indicates 31-50 × 10⁻⁶ cm/s; "S" indicates > 50 × 10⁻⁶ cm/s; "T" indicates the data is not available or has not been determined.
Aqueous Solubility: "U" indicates ≤ 10 μM; "V" indicates 10-100 μM; "W" indicates > 100 μM; X indicates the data is not available or has not been determined.
PPB: "Y" indicates > 50%; "Z" indicates 50-90%; "AA" indicates 91-95 %; "BB" indicates > 95%; "CC" indicates the data is not available or has not been determined.
Dog Bioavailability: "DD" indicates < 10%; "EE" indicates 11-30%; "FF" > 30%; "GG" indicates the data is not available or has not been determined.

What is claimed is:

1. A compound of formula (II):

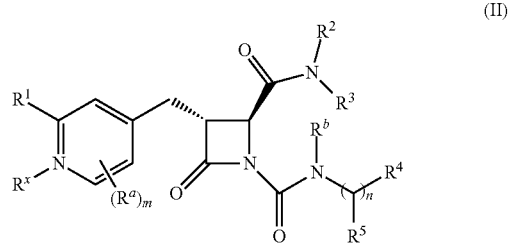

or a pharmaceutically acceptable salt thereof, wherein
$R^1$ is hydrogen or —$NR^8R^9$;
$R^a$ is $C_{1-6}$ alkyl, $C_{1-6}$ haloalkyl, halo, cyano, or —$OR^6$;
$R^b$ is hydrogen or $C_{1-6}$ alkyl;
$R^2$ is optionally substituted 5-membered heteroaryl or optionally substituted 5-membered heterocyclyl;
$R^3$ is hydrogen, $C_{1-6}$ alkyl, or $C_{1-6}$ haloalkyl;
$R^4$ is $C_{1-6}$ alkyl, $C_{1-6}$ haloalkyl, cycloalkyl, heterocyclyl, aryl, or heteroaryl, wherein the cycloalkyl, heterocyclyl, aryl, or heteroaryl is optionally substituted with one, two, or three independent occurrences of halo, $C_{1-6}$ alkyl, $C_{1-6}$ haloalkyl, cyano, or —$OR^6$;
$R^5$ is hydrogen, $C_{1-6}$ alkyl, $C_{1-6}$ haloalkyl, cycloalkyl, or aryl, wherein the cycloalkyl or aryl is optionally substituted with one, two, or three independent occurrences of halo, $C_{1-6}$ alkyl, $C_{1-6}$ haloalkyl, cyano, or —$OR^6$ or
$R^4$ and $R^5$, taken together with the carbon atom to which they are attached form a ring;
$R^6$ is hydrogen, $C_{1-6}$ alkyl, or $C_{1-6}$ haloalkyl;
each $R^8$ and $R^9$ is independently hydrogen, $C_{1-6}$ alkyl, —$C(O)R^{10}$, or —$C(O)OR^{10}$;
$R^{10}$ is $C_{1-6}$ alkyl or $C_{1-6}$ haloalkyl;
$R^x$ is —O or absent, wherein when $R^x$ is —O, the nitrogen atom of the pyridyl ring is positively charged and $R^x$ is negatively charged, thereby forming a pyridyl N-oxide;
m is 0, 1, 2, or 3; and
n is 0 or 1, wherein if n is 0, then $R^5$ is hydrogen and $R^4$ is absent.

2. The compound of claim 1, wherein the compound is a compound of Formula (I):

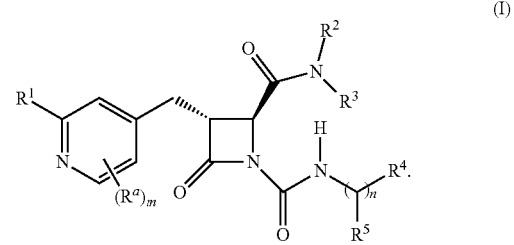

3. The compound of claim 1, wherein $R^1$ is hydrogen, —$NH_2$, or —$NHCH_3$.
4. The compound of claim 1, wherein $R^2$ is 5-membered heteroaryl optionally substituted with one or two independent occurrences of $C_{1-6}$ alkyl.
5. The compound of claim 1, wherein $R^2$ is pyrazolyl, imidazolyl, thienyl, isothiazolyl, thiazolyl, oxadiazolyl, or thiadiazolyl, wherein the imidazolyl, thienyl, isothiazolyl, thiazolyl, oxadiazolyl, or thiadiazolyl is optionally substituted with one or two independent occurrences of $C_{1-6}$ alkyl.

6. The compound of claim 1, wherein $R^3$ is $C_{1-6}$ alkyl.

7. The compound of claim 1, wherein $R^4$ is cyclohexyl, phenyl, pyridyl, pyrazolyl, or thienyl, wherein the cyclohexyl, phenyl, pyridyl, pyrazolyl, or thienyl is optionally substituted with one, two, or three independent occurrences of halo or $C_{1-6}$ alkyl.

8. The compound of claim 1, wherein the compound is a compound of formula (I-a):

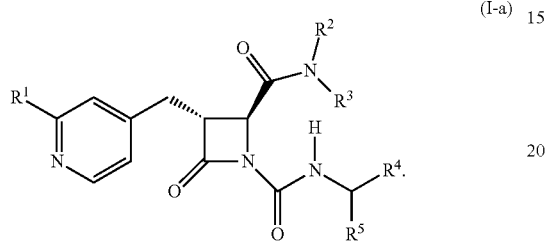
(I-a)

9. The compound of claim 1, wherein the compound is a compound of formula (I-c), formula (I-d), formula (I-e), formula (I-f), formula (I-g), formula (I-i), or formula (I-j):

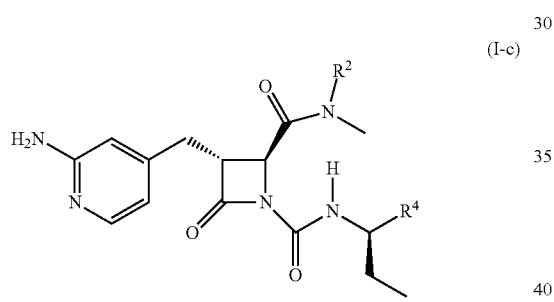
(I-c)

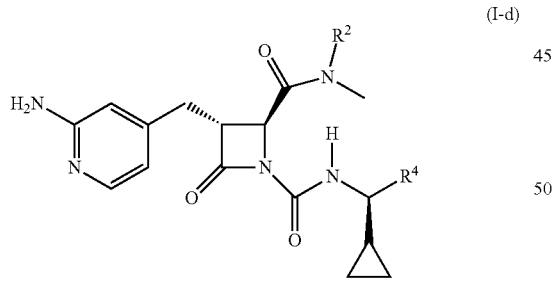
(I-d)

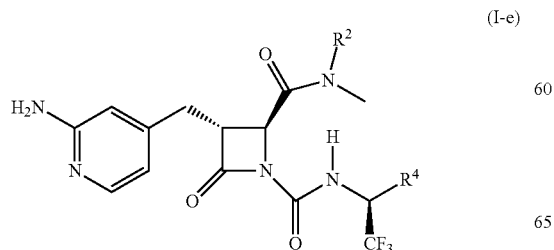
(I-e)

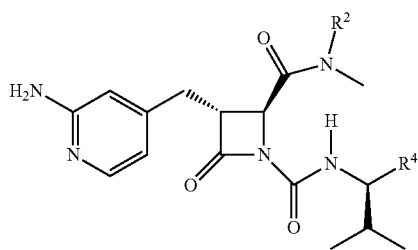
(I-f)

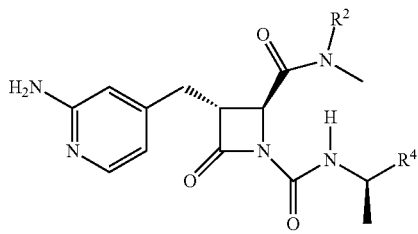
(I-g)

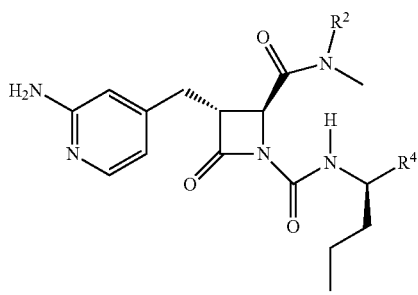
(I-h)

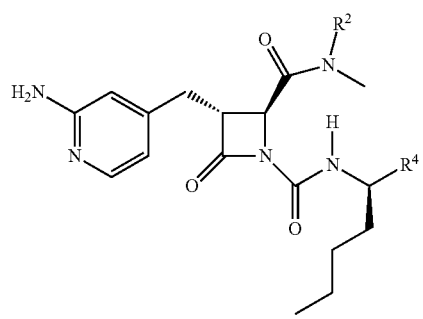
(I-i)

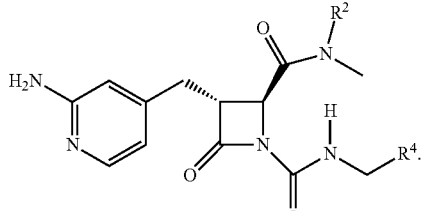
(I-j)

10. The compound of claim 1, wherein the compound is a compound of formula (I-r):

(I-r)
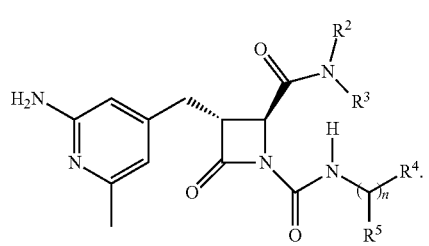
11. The compound of claim 1, wherein the compound is a compound of formula (I-s):
(I-s)
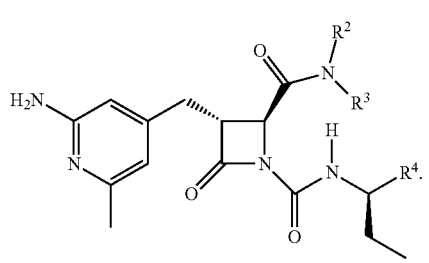
12. The compound of claim 1, wherein the compound is selected from the group consisting of:
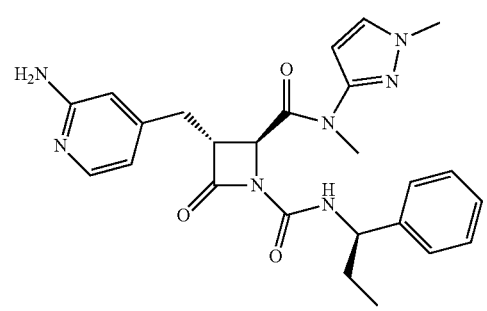
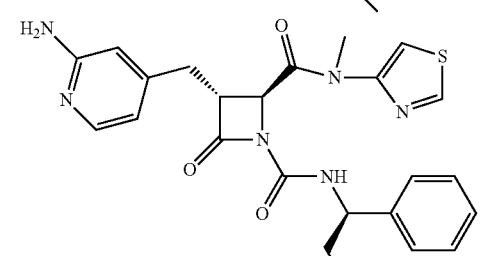
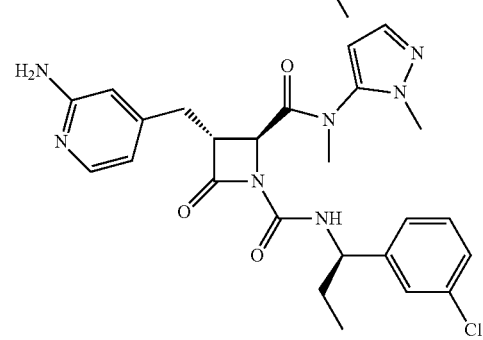
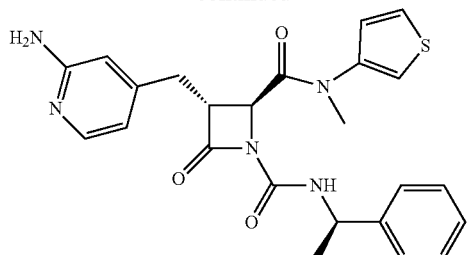
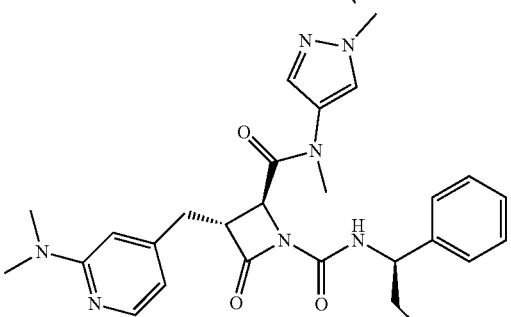
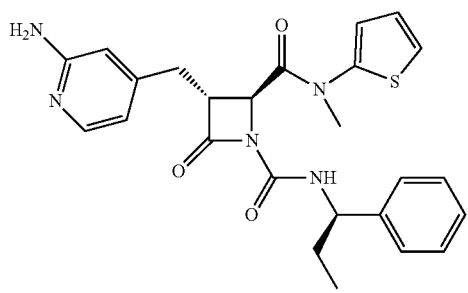
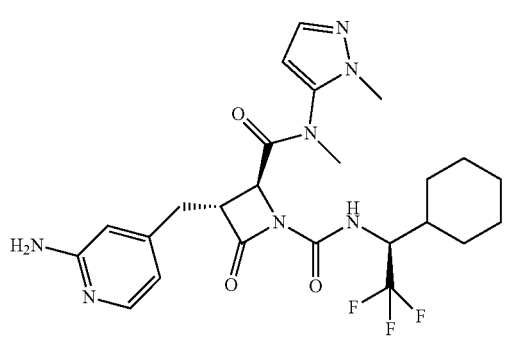
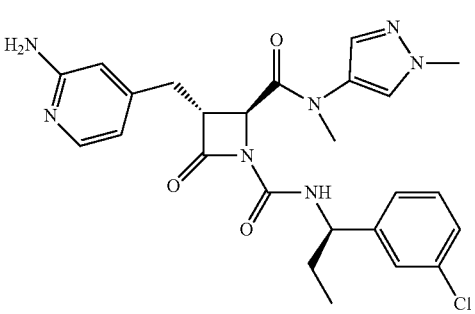

363
-continued
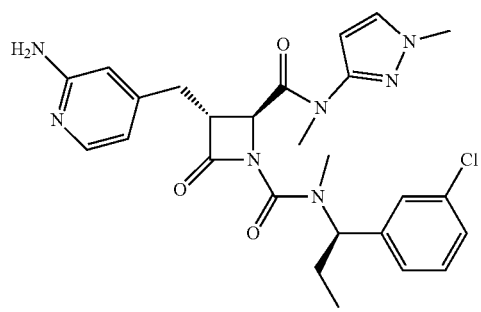
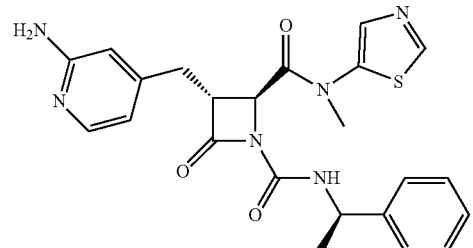
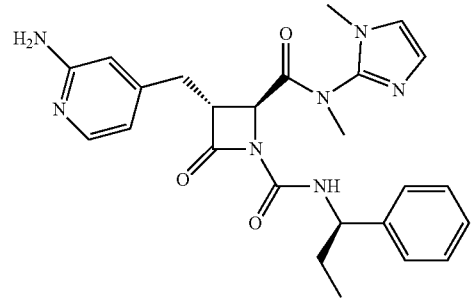
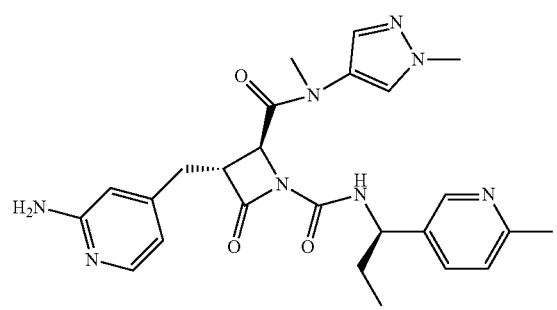
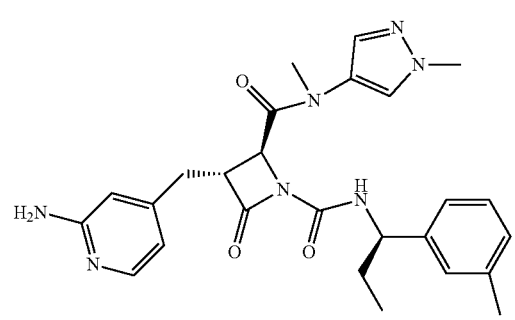
364
-continued
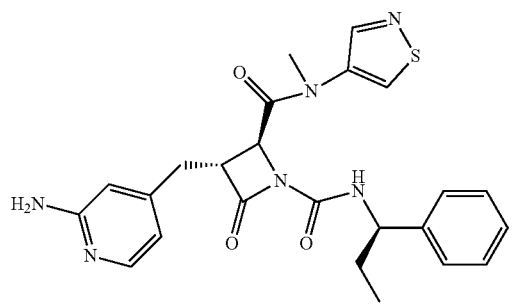
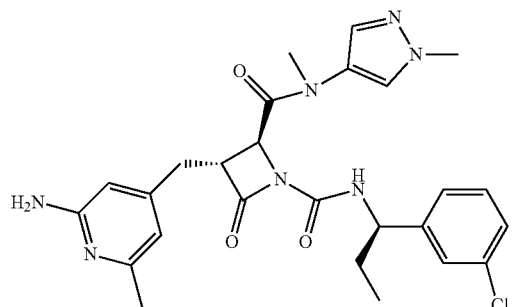
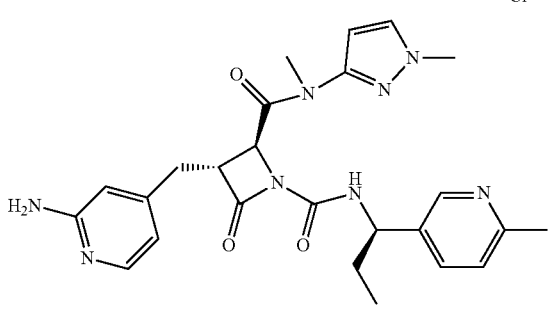
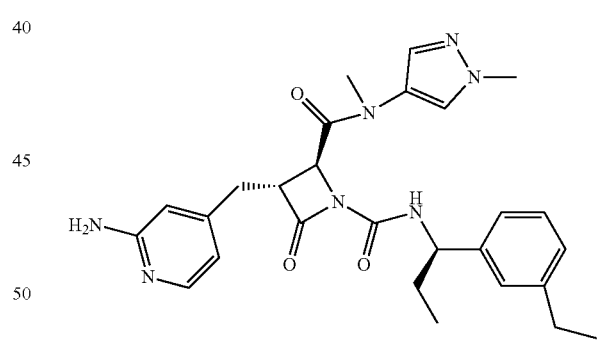
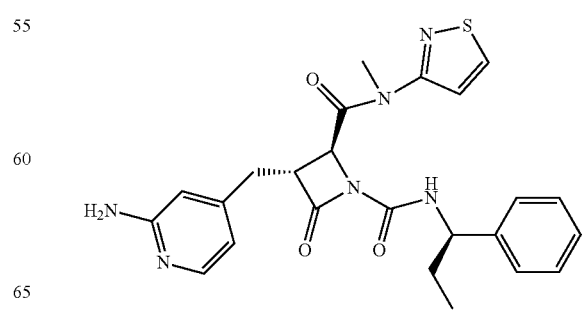

365
-continued
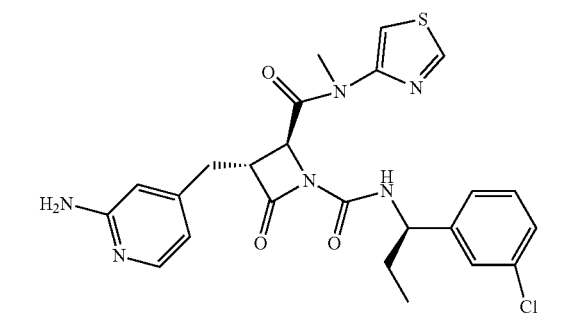
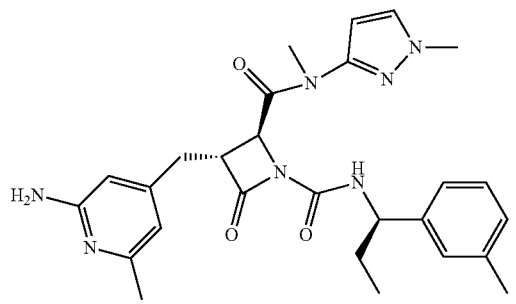
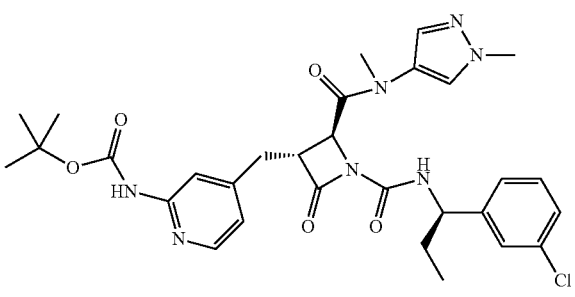
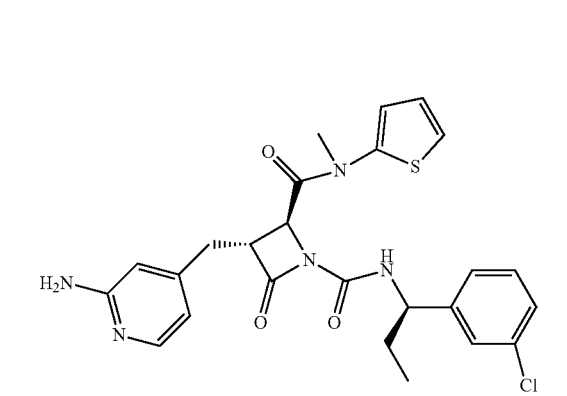
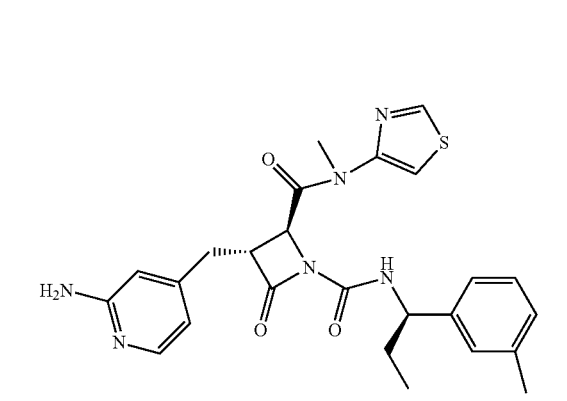
366
-continued
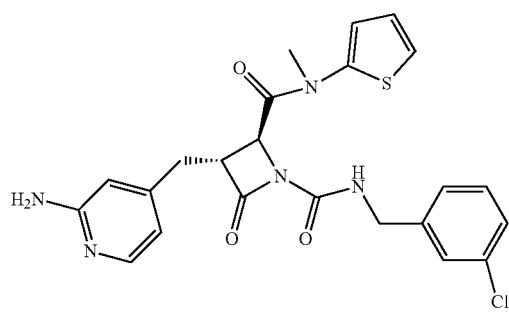
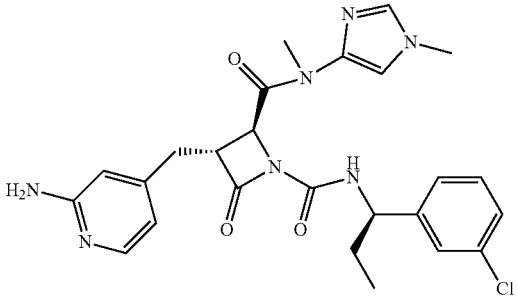
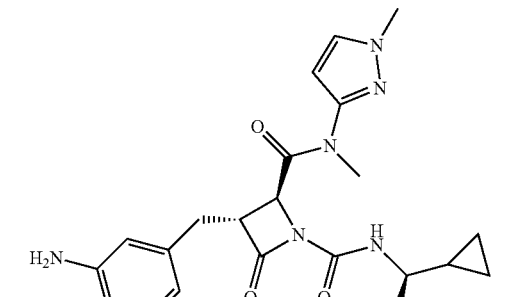
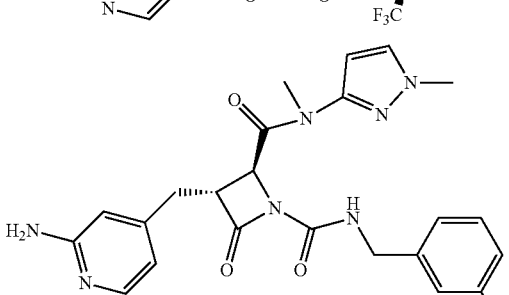
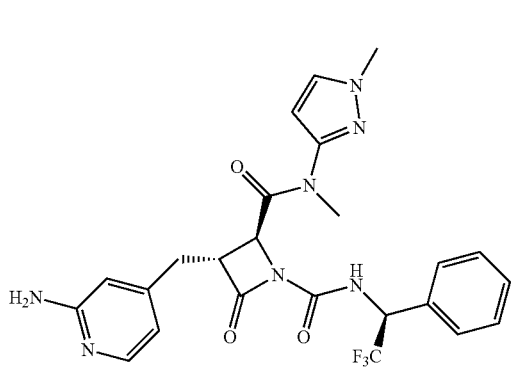

367
-continued
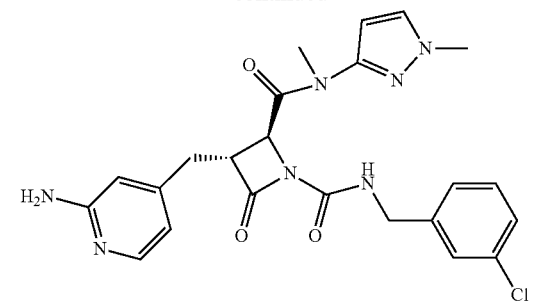
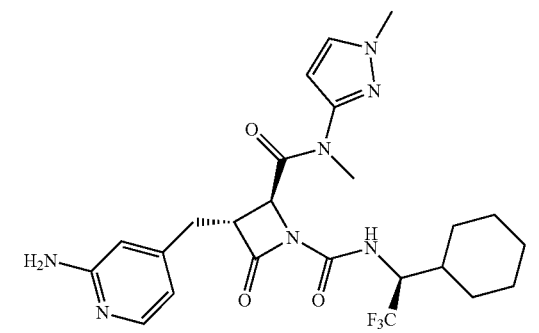
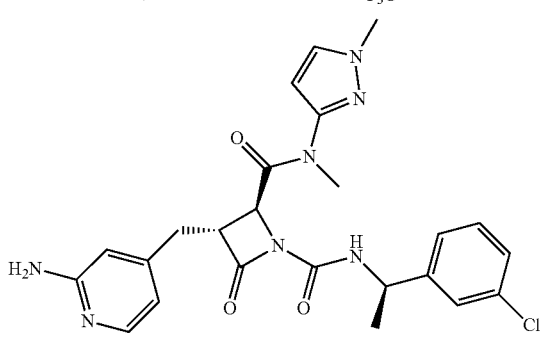
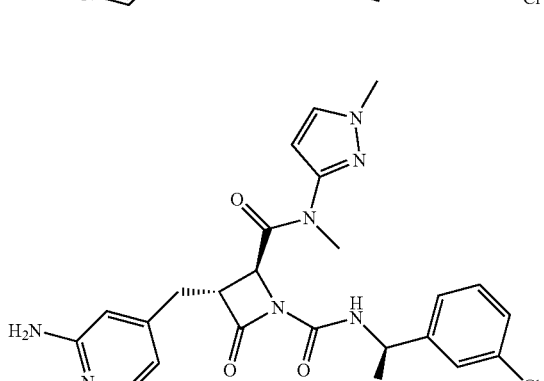
368
-continued
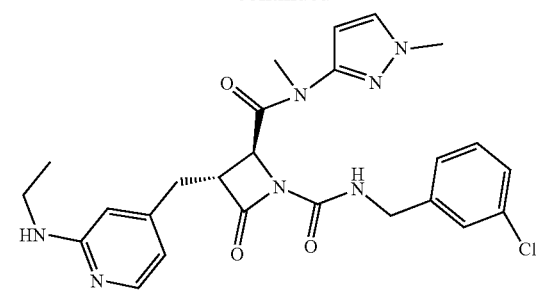
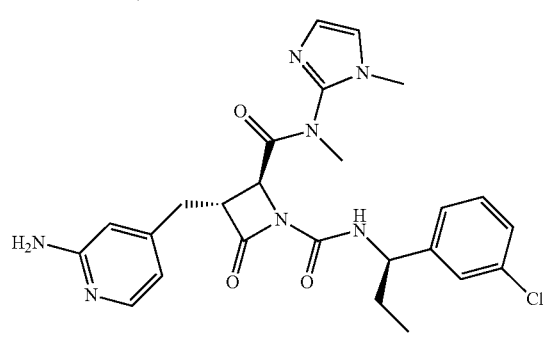
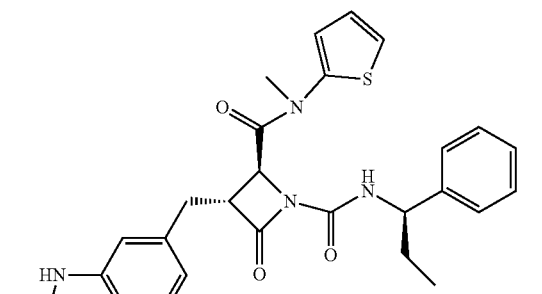
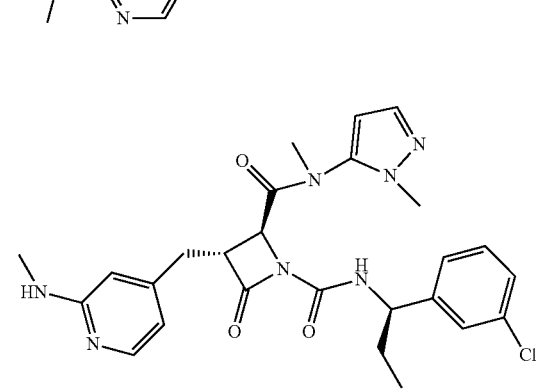

369
-continued
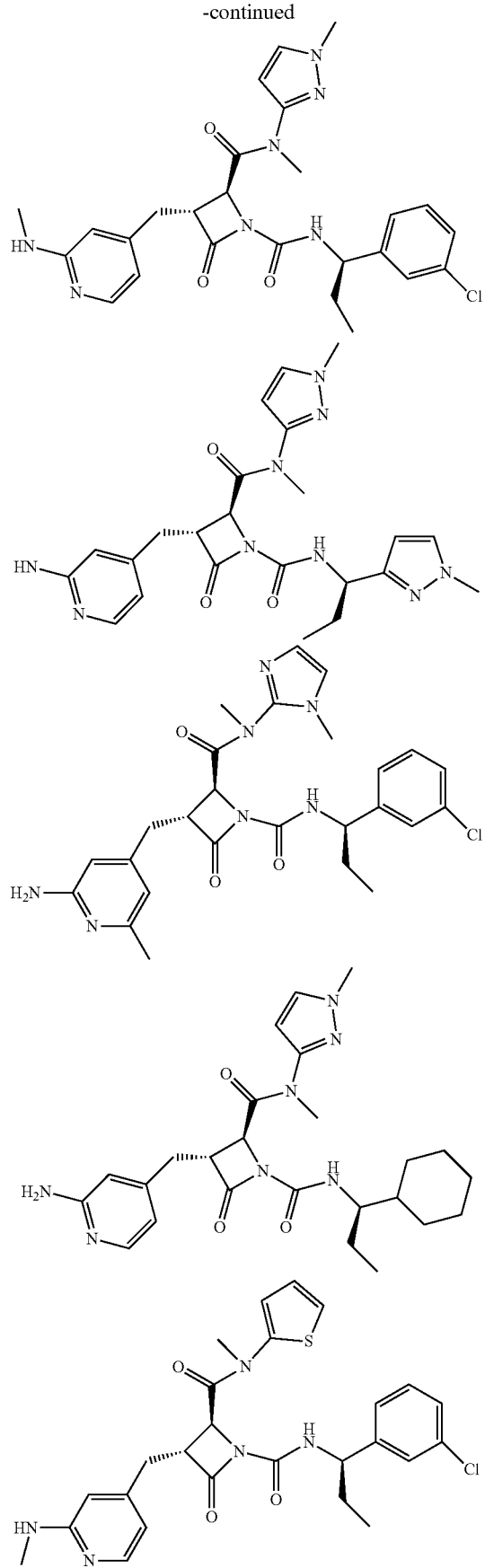
370
-continued
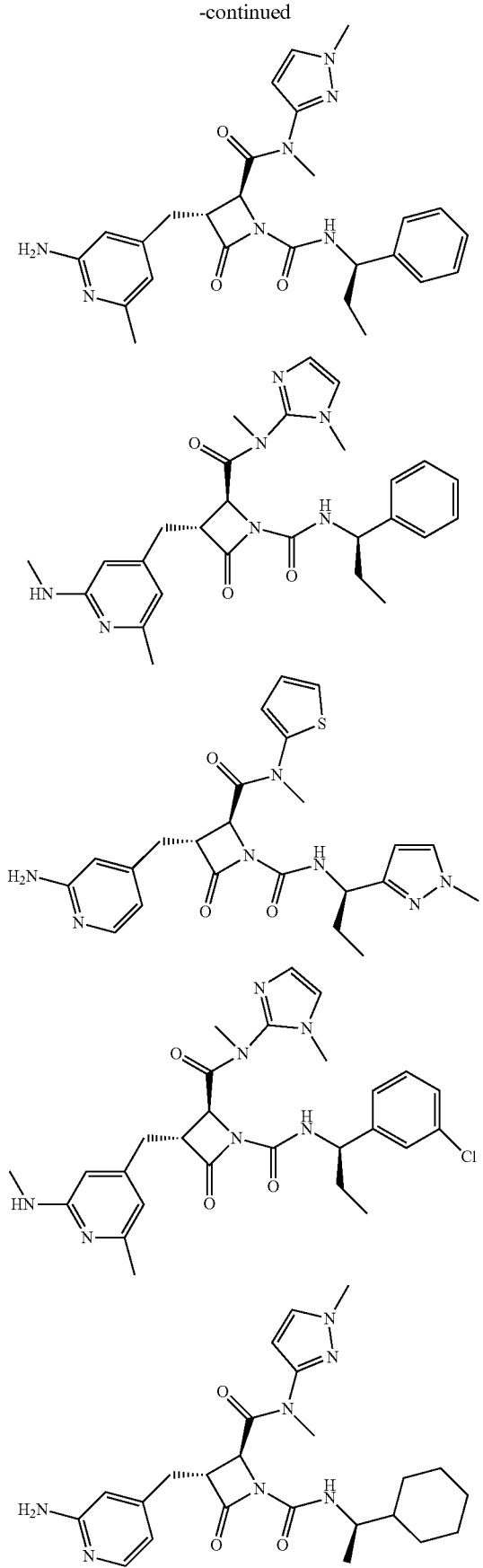

371
-continued
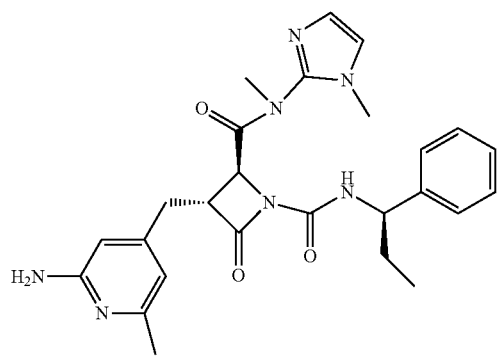
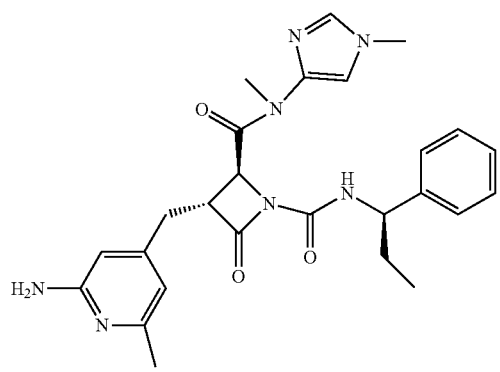
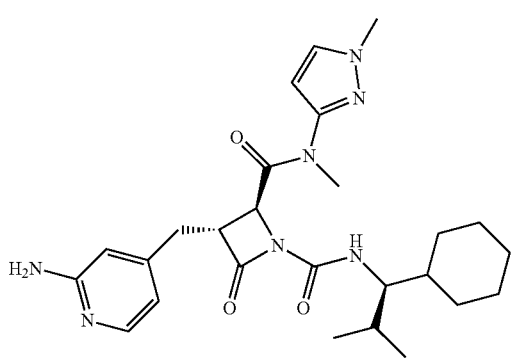
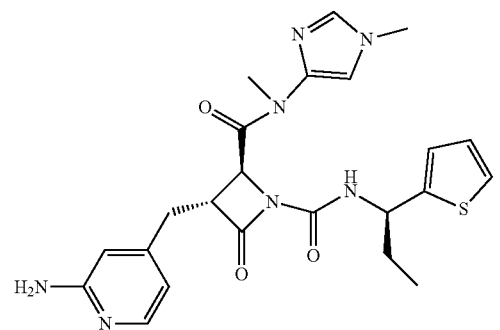
372
-continued
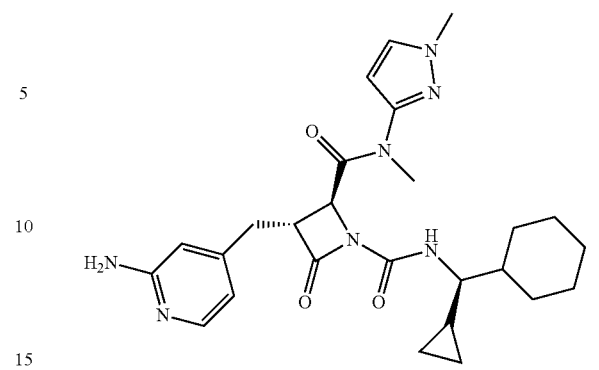
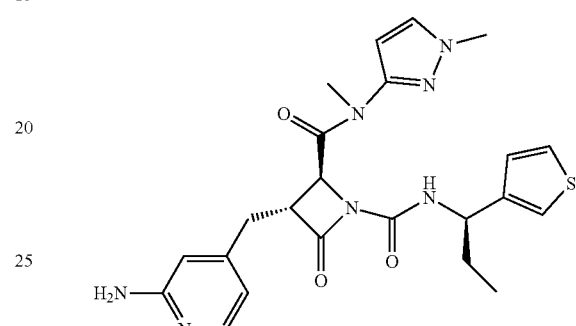
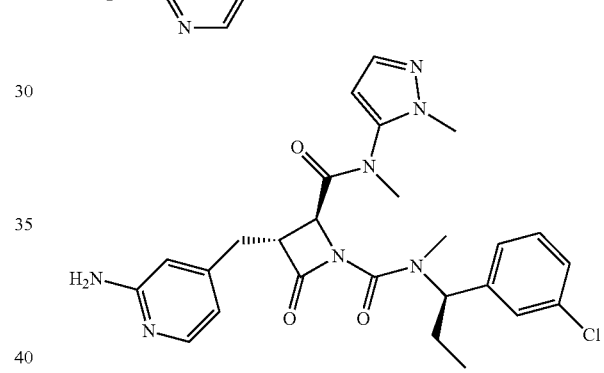
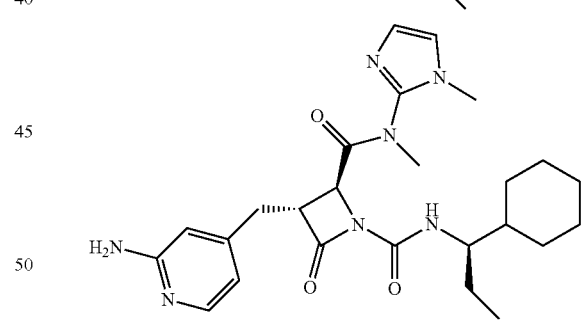
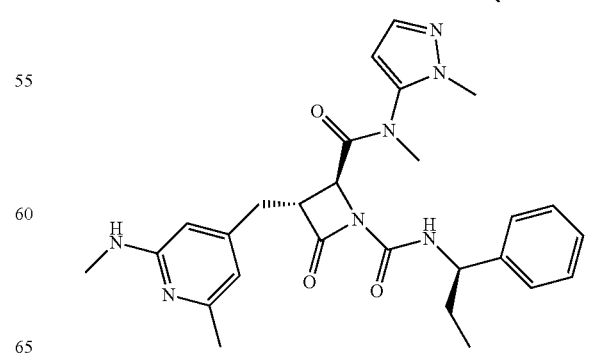

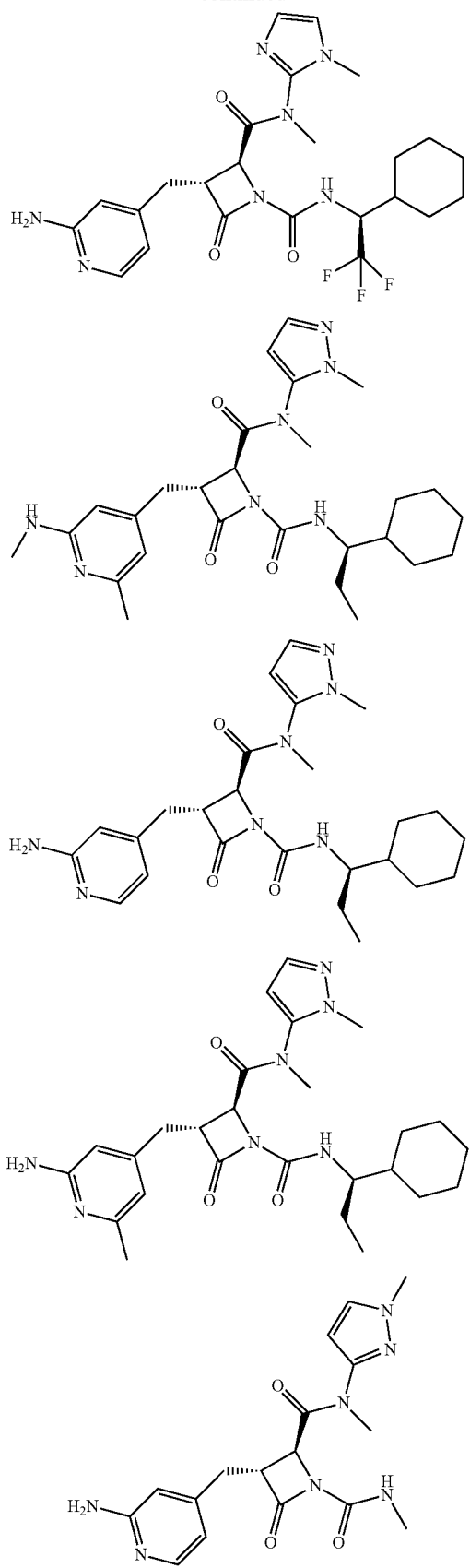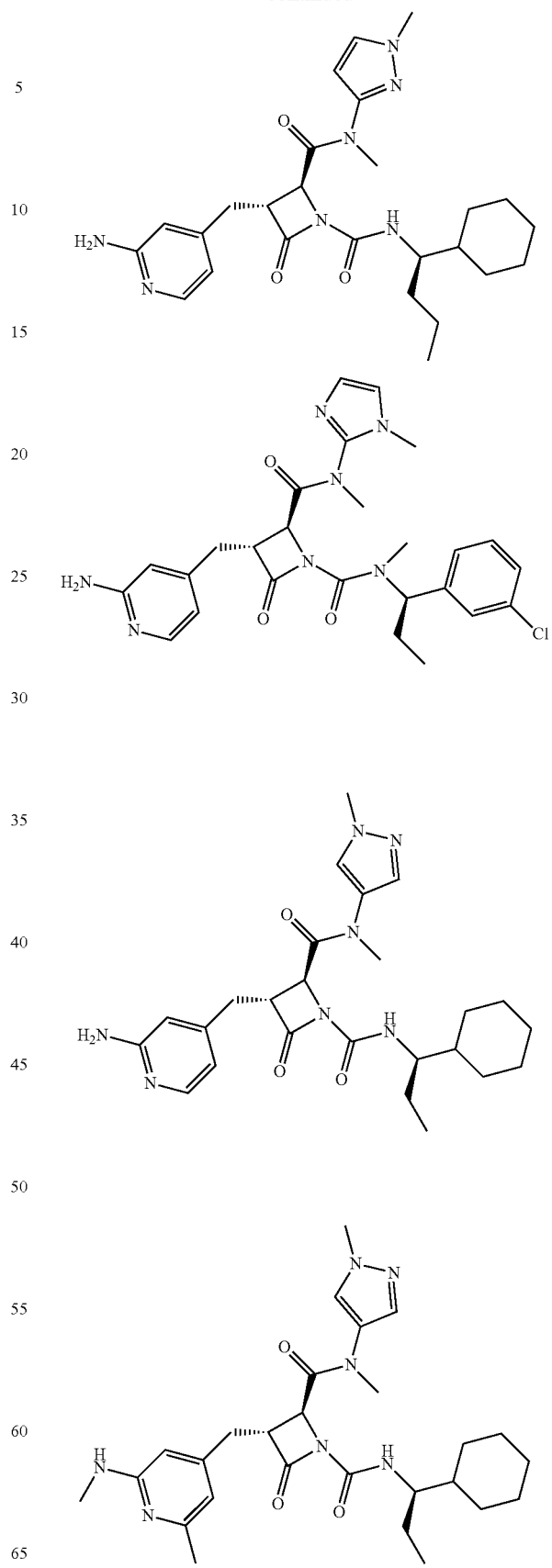

375
-continued
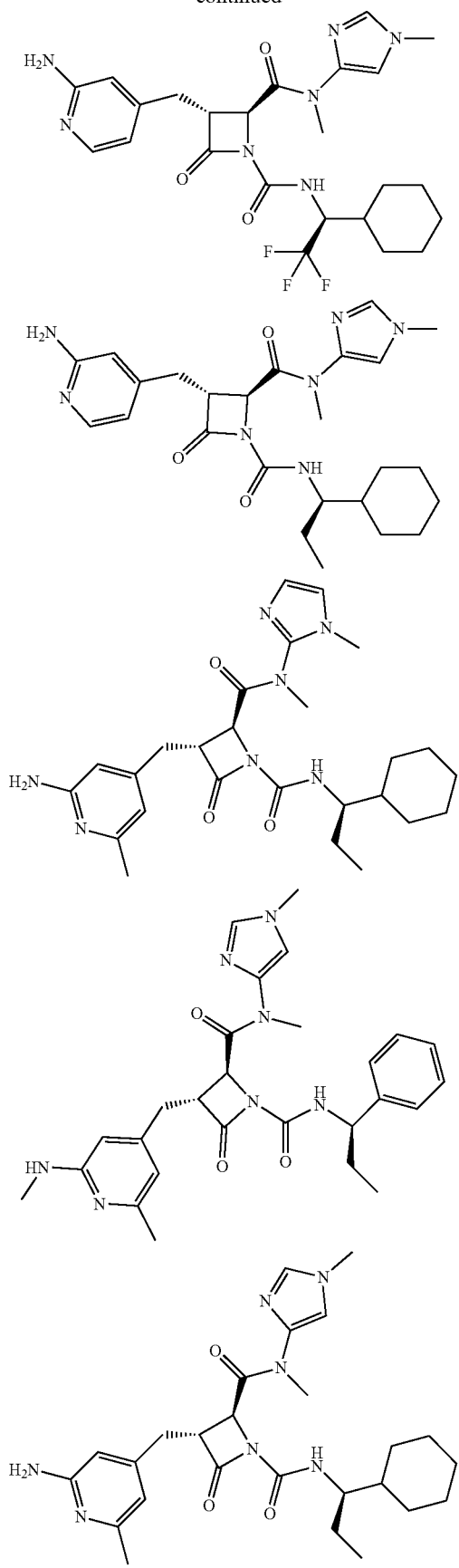
376
-continued
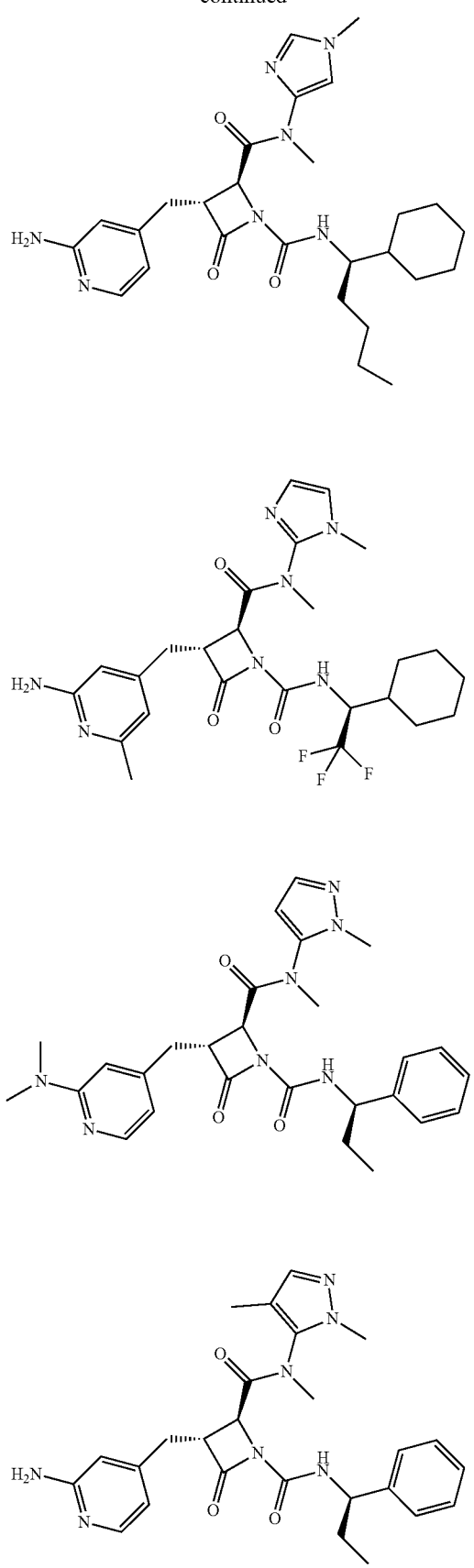

377
-continued
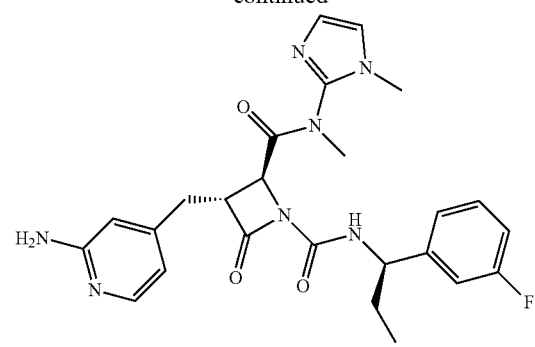
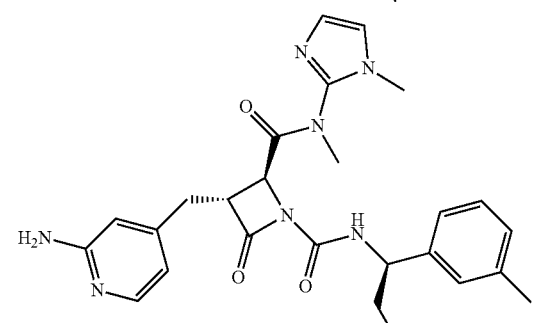
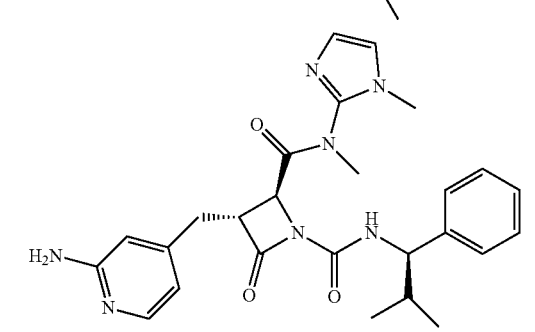
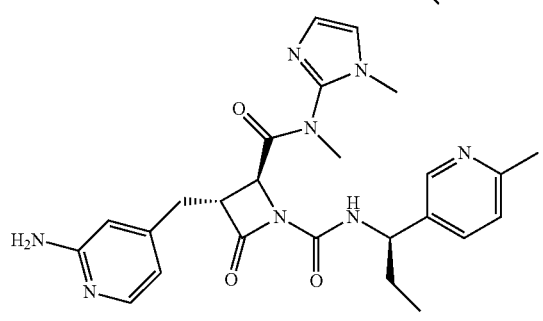
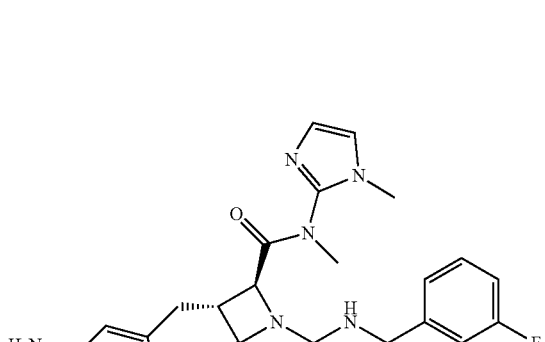
378
-continued
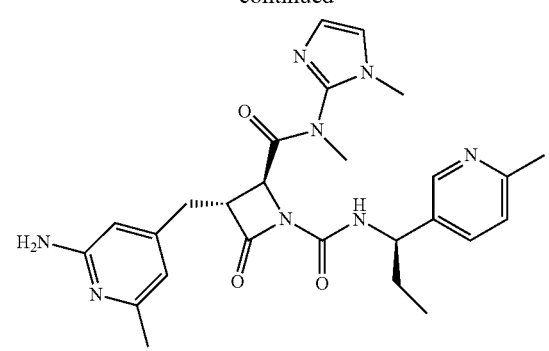
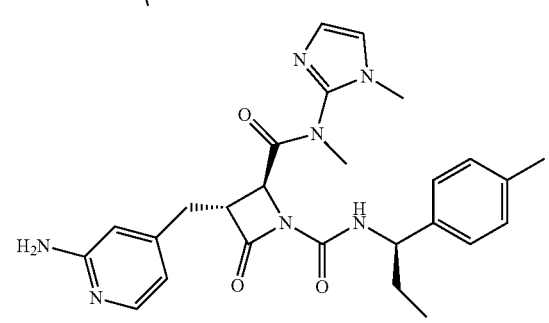
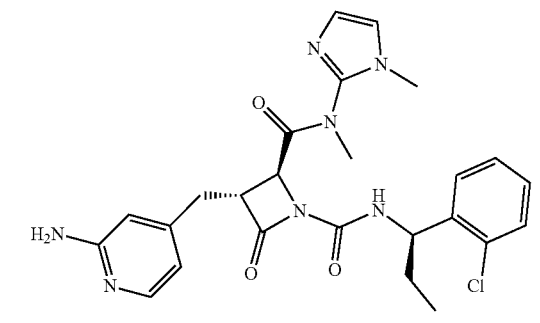
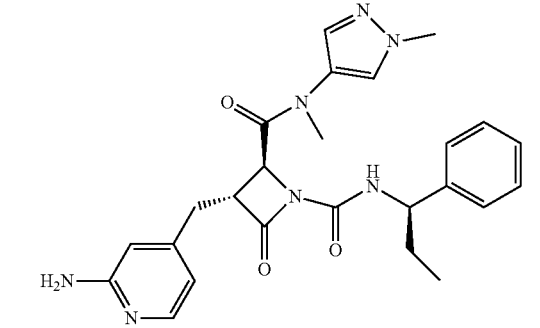
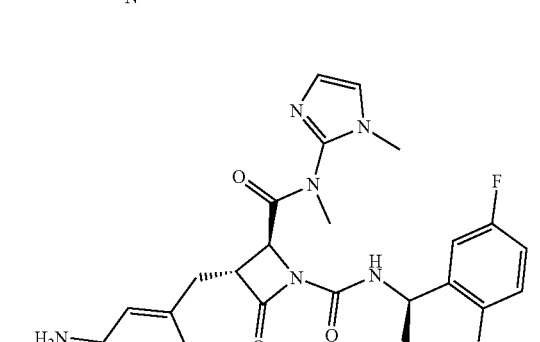

379
-continued
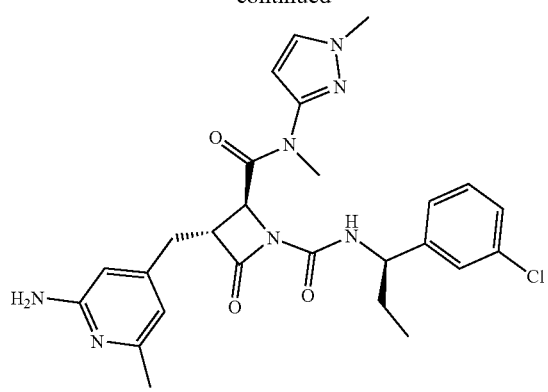
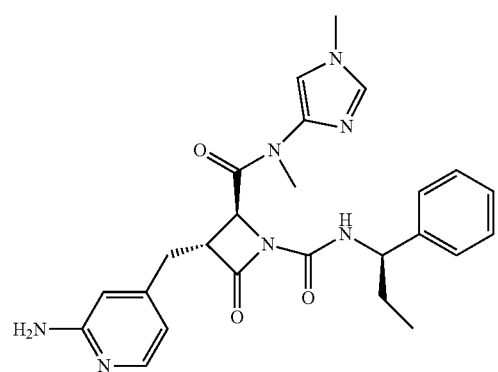
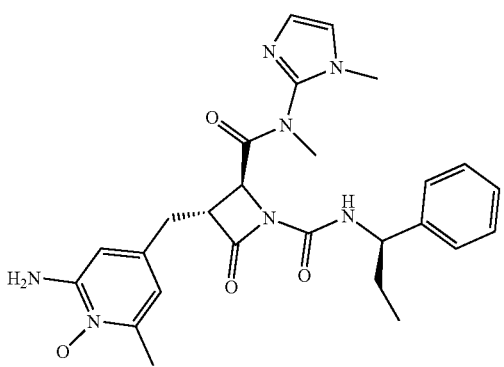
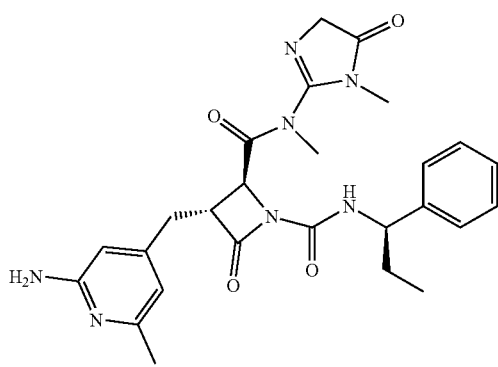
380
-continued
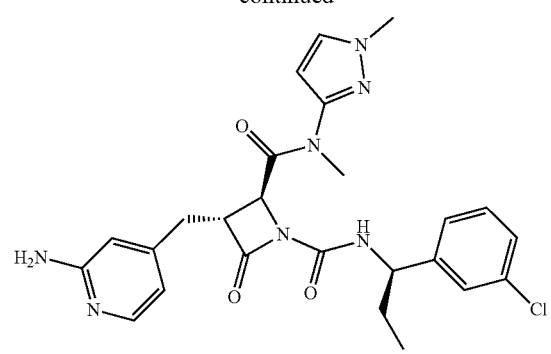
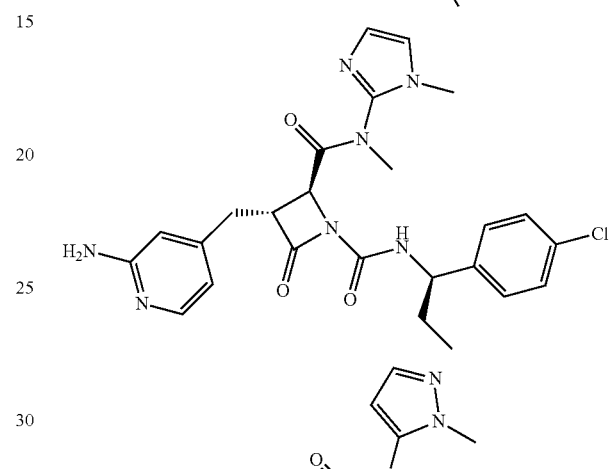
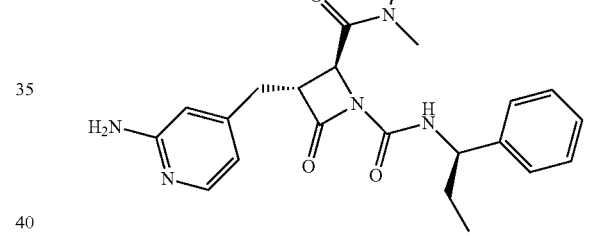
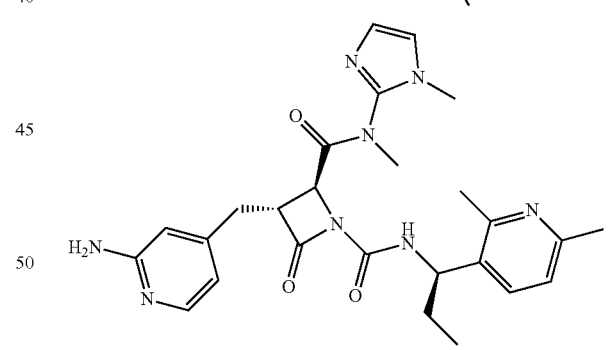
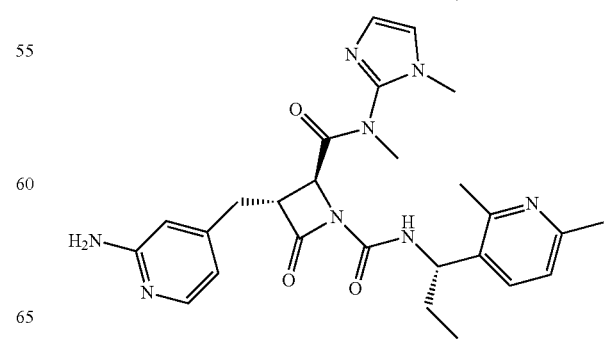

381
-continued
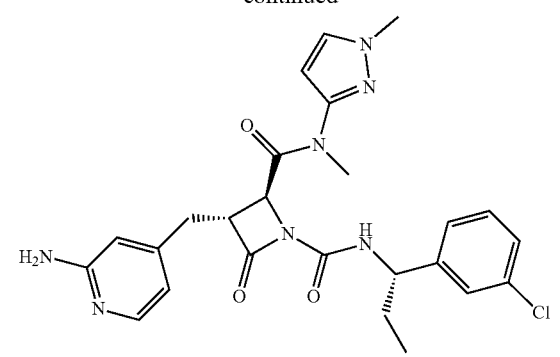
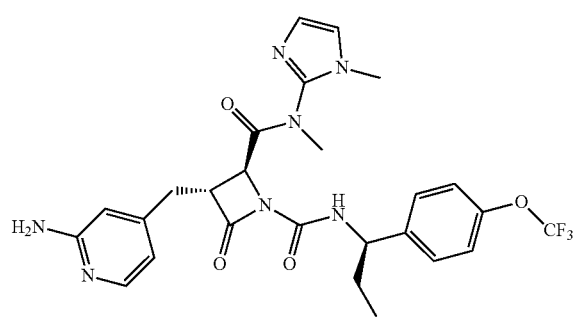
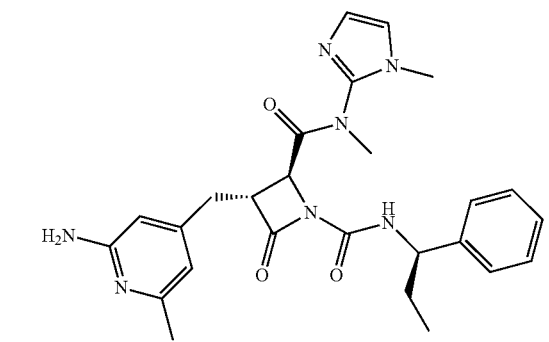
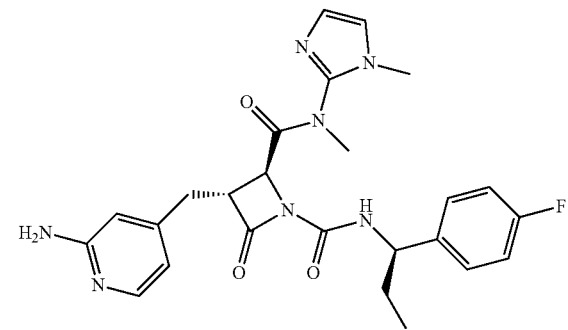
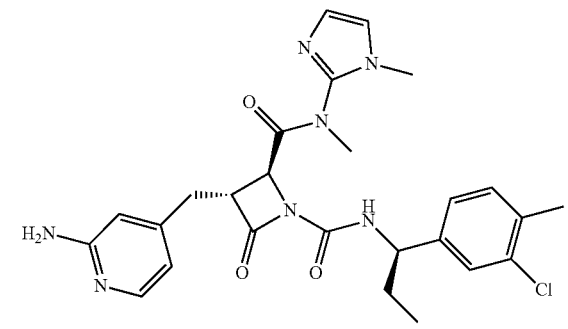
382
-continued
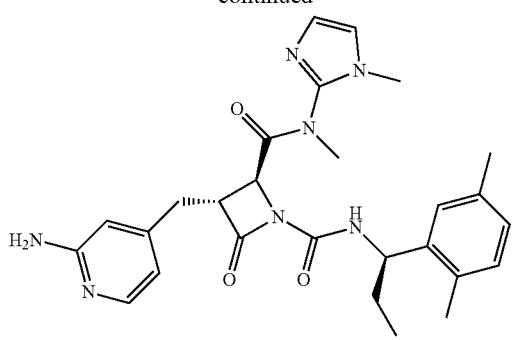
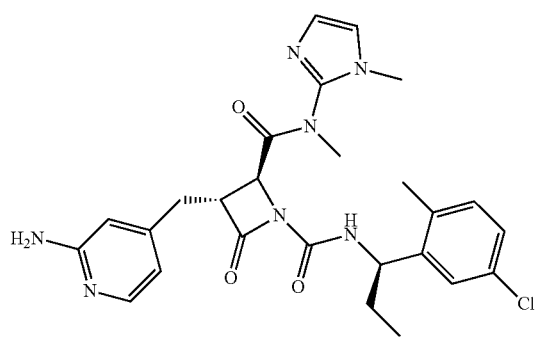
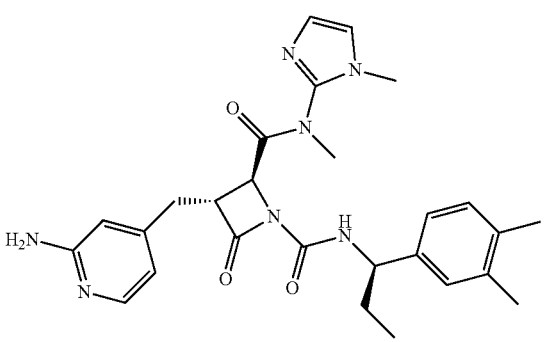 [SMILES: CC[C@@H](NC(=O)N1C(=O)[C@H](Cc2ccnc(N)c2)[C@H]1C(=O)N(C)c1nccn1C)c1ccc(C)c(C)c1]
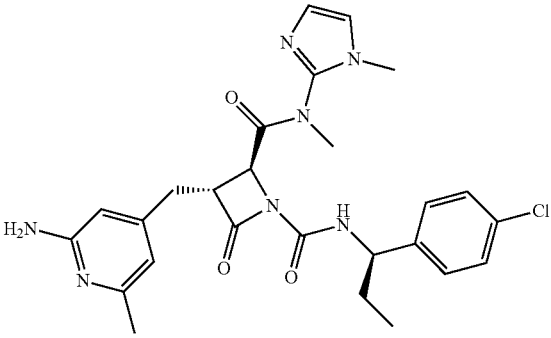 [SMILES: CC[C@@H](NC(=O)N1C(=O)[C@H](Cc2cc(C)nc(N)c2)[C@H]1C(=O)N(C)c1nccn1C)c1ccc(Cl)cc1]

383
-continued
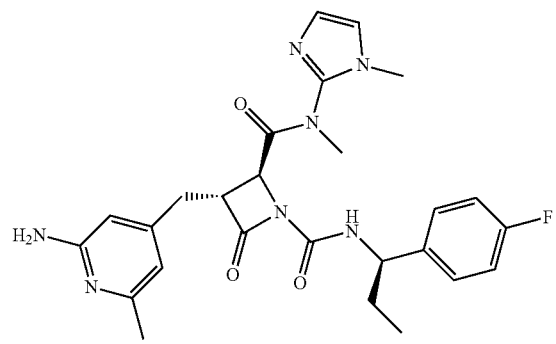 [SMILES: CC[C@@H](NC(=O)N1C(=O)[C@H](Cc2cc(C)nc(N)c2)[C@H]1C(=O)N(C)c1nccn1C)c1ccc(F)cc1]
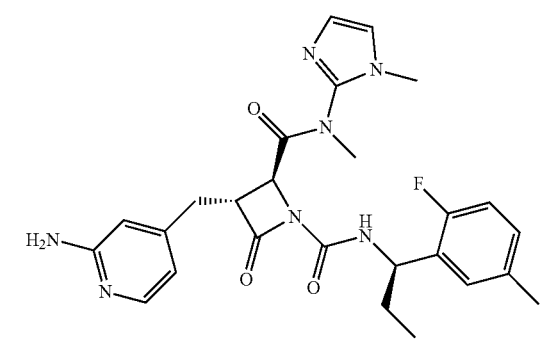
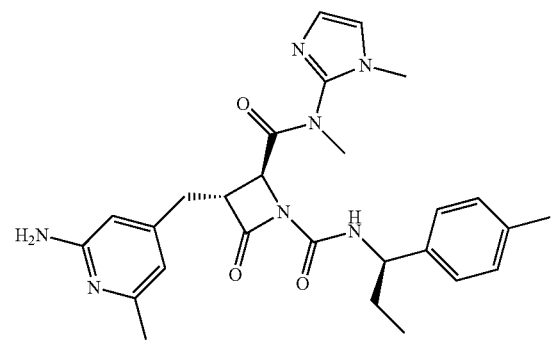 [SMILES: CC[C@@H](NC(=O)N1C(=O)[C@H](Cc2cc(C)nc(N)c2)[C@H]1C(=O)N(C)c1nccn1C)c1ccc(C)cc1]
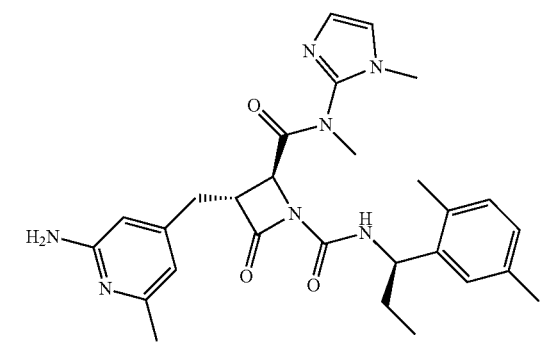 [SMILES: CC[C@@H](NC(=O)N1C(=O)[C@H](Cc2cc(C)nc(N)c2)[C@H]1C(=O)N(C)c1nccn1C)c1cc(C)ccc1C]
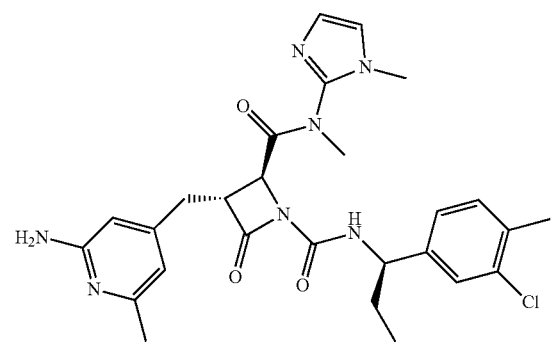
384
-continued
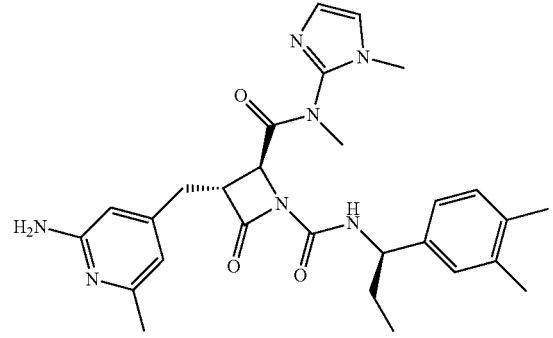 [SMILES: CC[C@@H](NC(=O)N1C(=O)[C@H](Cc2cc(C)nc(N)c2)[C@H]1C(=O)N(C)c1nccn1C)c1ccc(C)c(C)c1]
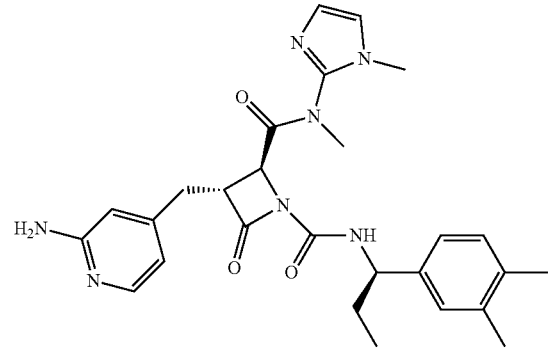
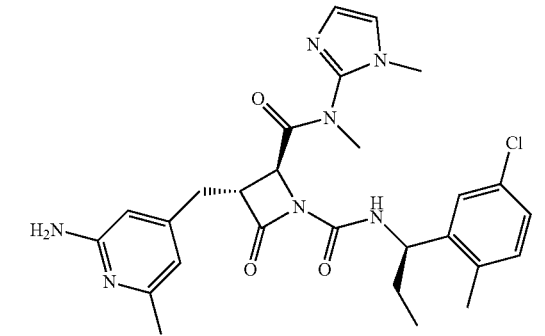
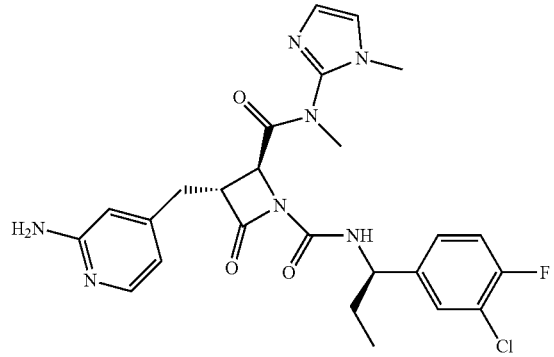 [SMILES: CC[C@@H](NC(=O)N1C(=O)[C@H](Cc2ccnc(N)c2)[C@H]1C(=O)N(C)c1nccn1C)c1ccc(F)c(Cl)c1]
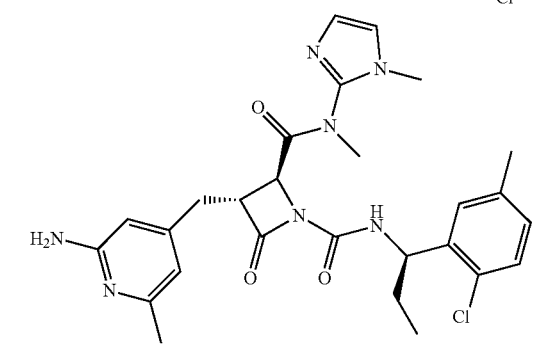

385
-continued
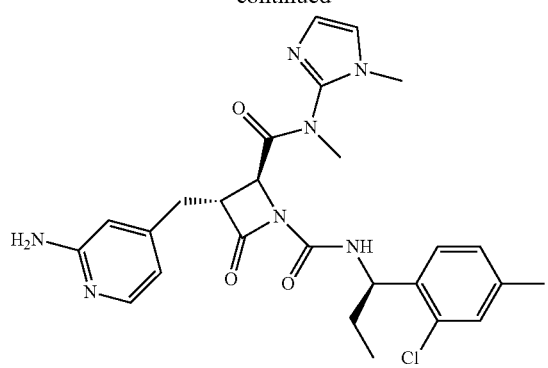
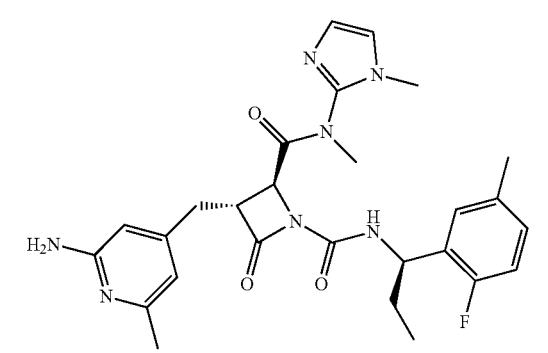
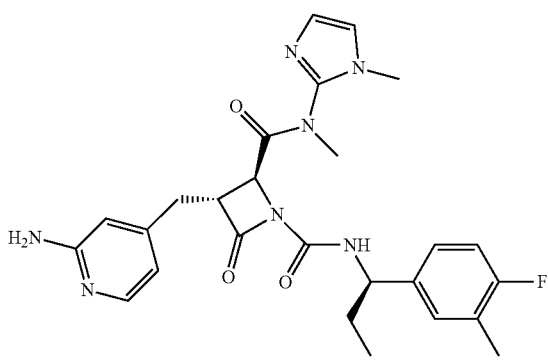 [SMILES: CC[C@@H](NC(=O)N1C(=O)[C@H](Cc2ccnc(N)c2)[C@H]1C(=O)N(C)c1nccn1C)c1ccc(F)c(C)c1]
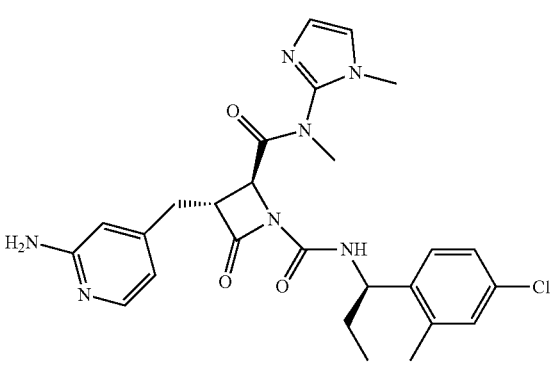 [SMILES: CC[C@@H](NC(=O)N1C(=O)[C@H](Cc2ccnc(N)c2)[C@H]1C(=O)N(C)c1nccn1C)c1ccc(Cl)cc1C]
386
-continued
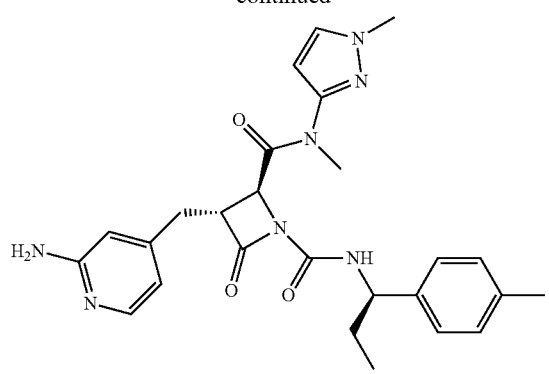
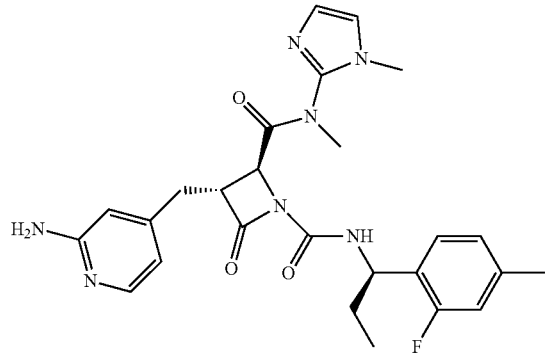 [SMILES: CC[C@@H](NC(=O)N1C(=O)[C@H](Cc2ccnc(N)c2)[C@H]1C(=O)N(C)c1nccn1C)c1ccc(C)cc1F]
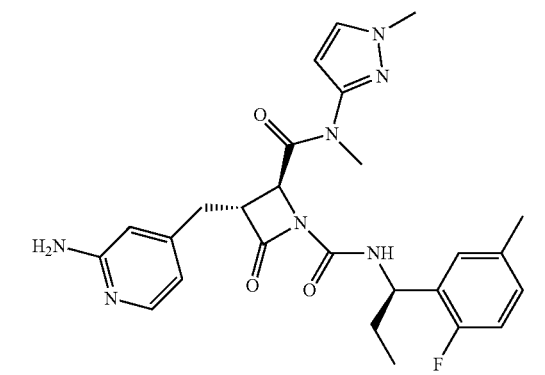
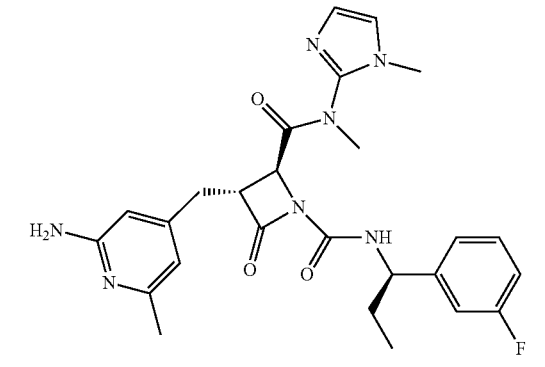 [SMILES: CC[C@@H](NC(=O)N1C(=O)[C@H](Cc2cc(C)nc(N)c2)[C@H]1C(=O)N(C)c1nccn1C)c1cccc(F)c1]

387
-continued
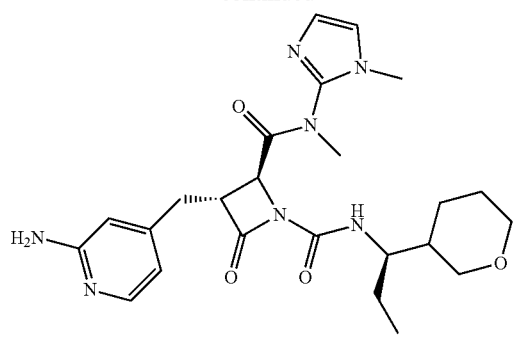
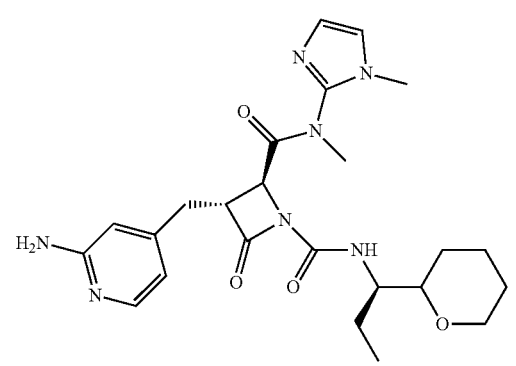 [SMILES: CC[C@@H](NC(=O)N1C(=O)[C@H](Cc2ccnc(N)c2)[C@H]1C(=O)N(C)c1nccn1C)C1CCOCC1]
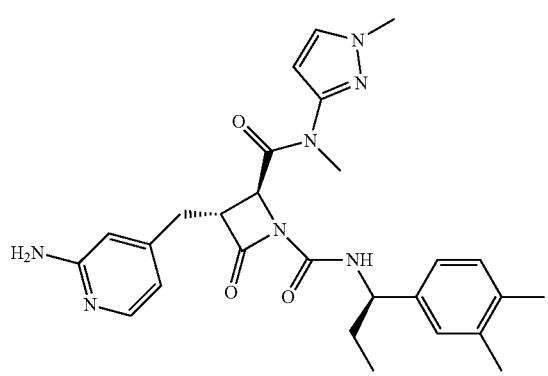 [SMILES: CC[C@@H](NC(=O)N1C(=O)[C@H](Cc2ccnc(N)c2)[C@H]1C(=O)N(C)c1ccn(C)n1)c1ccc(C)c(C)c1]
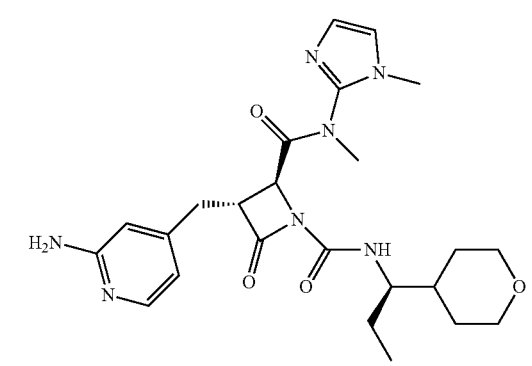
388
-continued
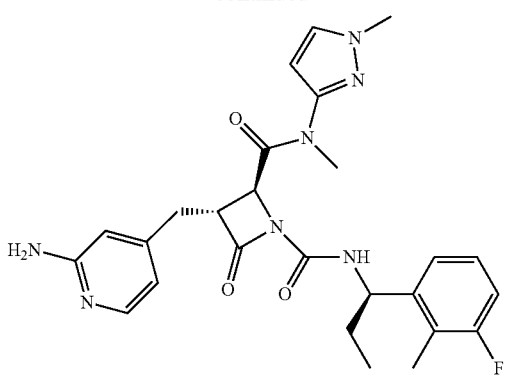 [SMILES: CC[C@@H](NC(=O)N1C(=O)[C@H](Cc2ccnc(N)c2)[C@H]1C(=O)N(C)c1ccn(C)n1)c1cccc(F)c1C]
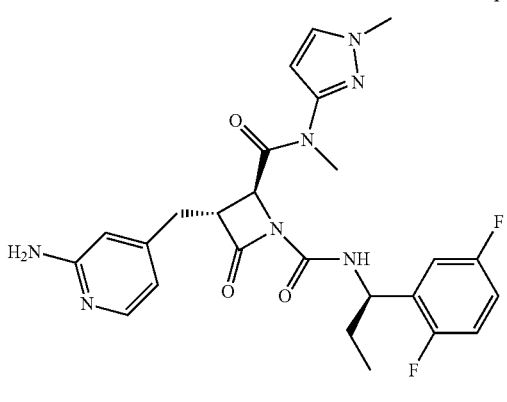
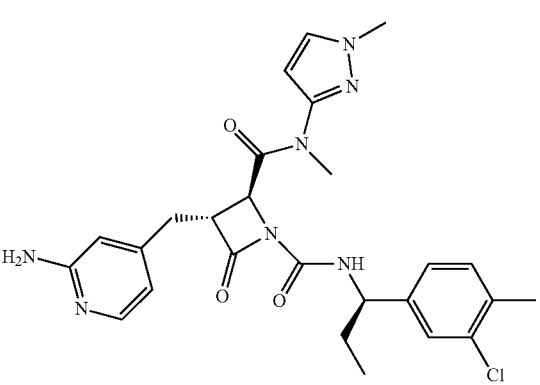 [SMILES: CC[C@@H](NC(=O)N1C(=O)[C@H](Cc2ccnc(N)c2)[C@H]1C(=O)N(C)c1ccn(C)n1)c1ccc(C)c(Cl)c1]
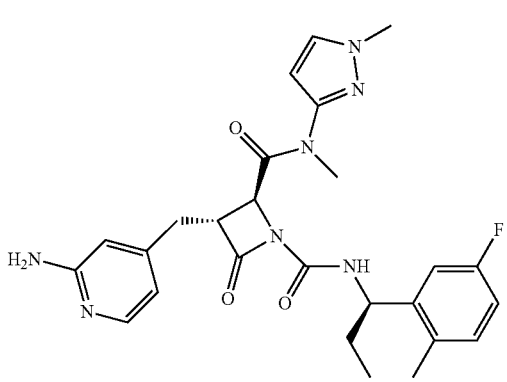

389
-continued
390
-continued
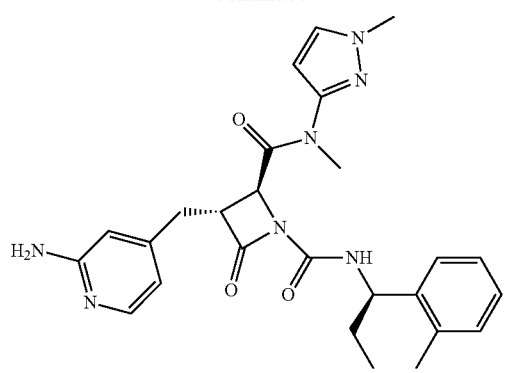 [SMILES: CC[C@@H](NC(=O)N1C(=O)[C@H](Cc2ccnc(N)c2)[C@H]1C(=O)N(C)c1ccn(C)n1)c1ccccc1C]
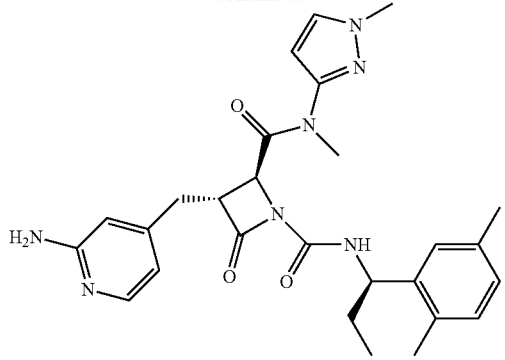 [SMILES: CC[C@@H](NC(=O)N1C(=O)[C@H](Cc2ccnc(N)c2)[C@H]1C(=O)N(C)c1ccn(C)n1)c1cc(F)ccc1C]

391
-continued
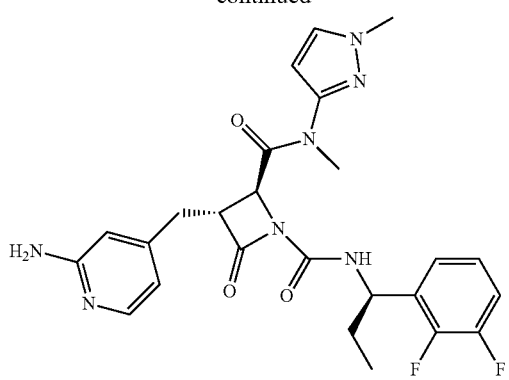
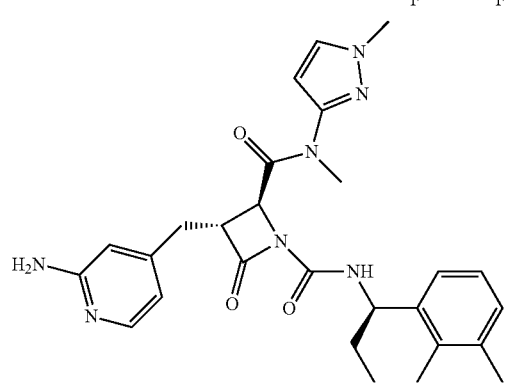
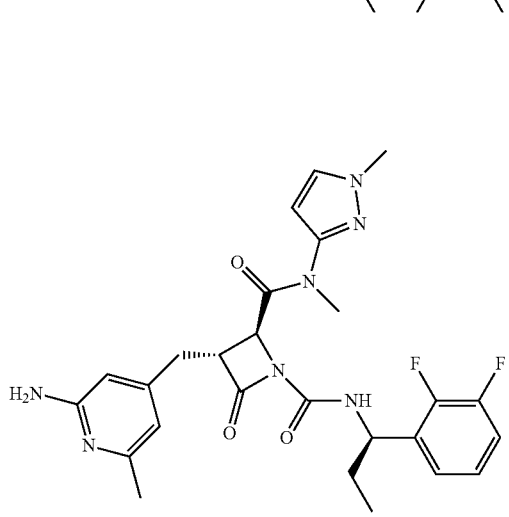
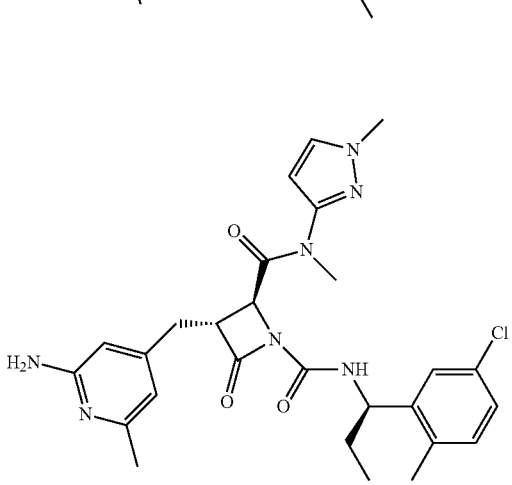
392
-continued
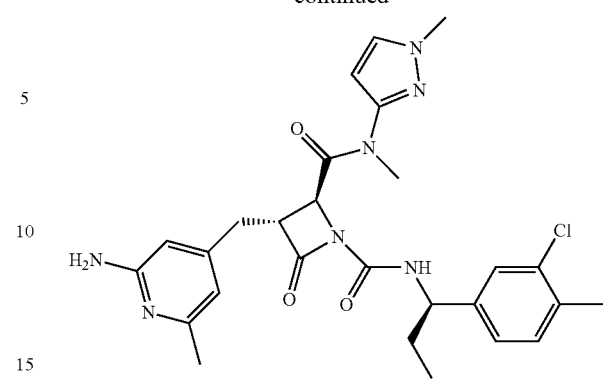
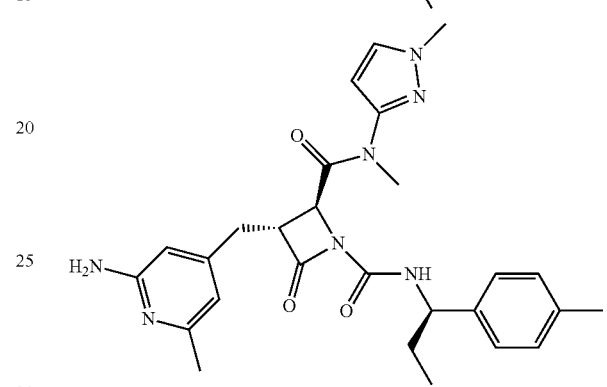
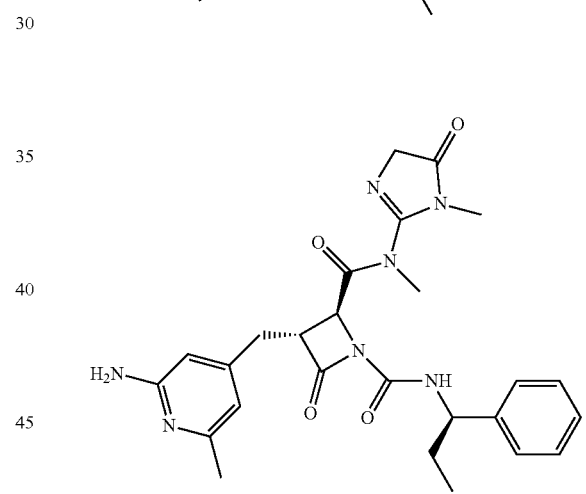
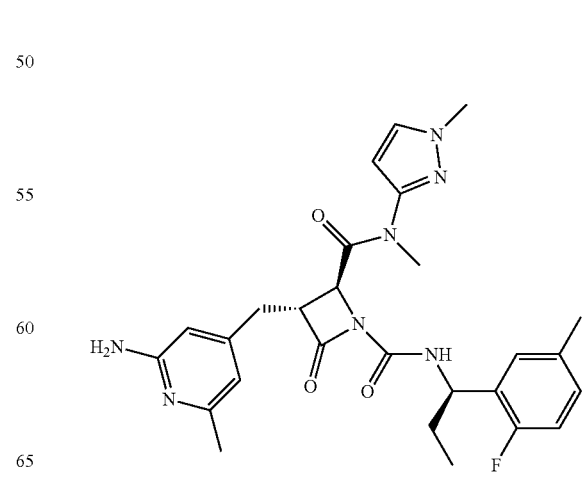

393
-continued
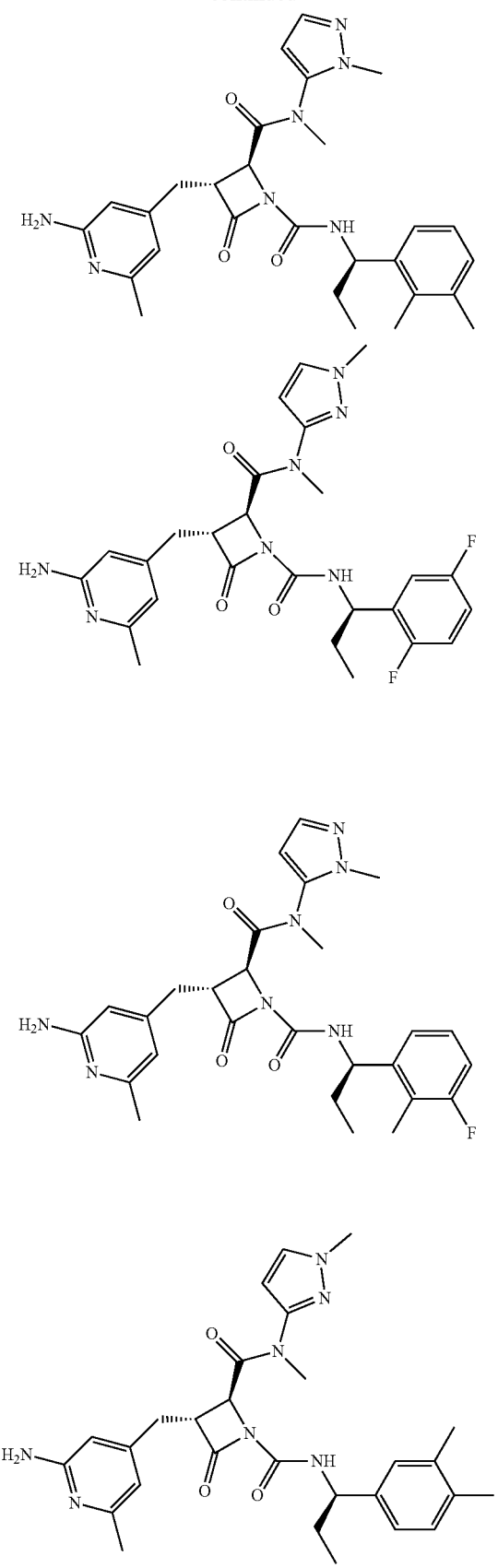
394
-continued
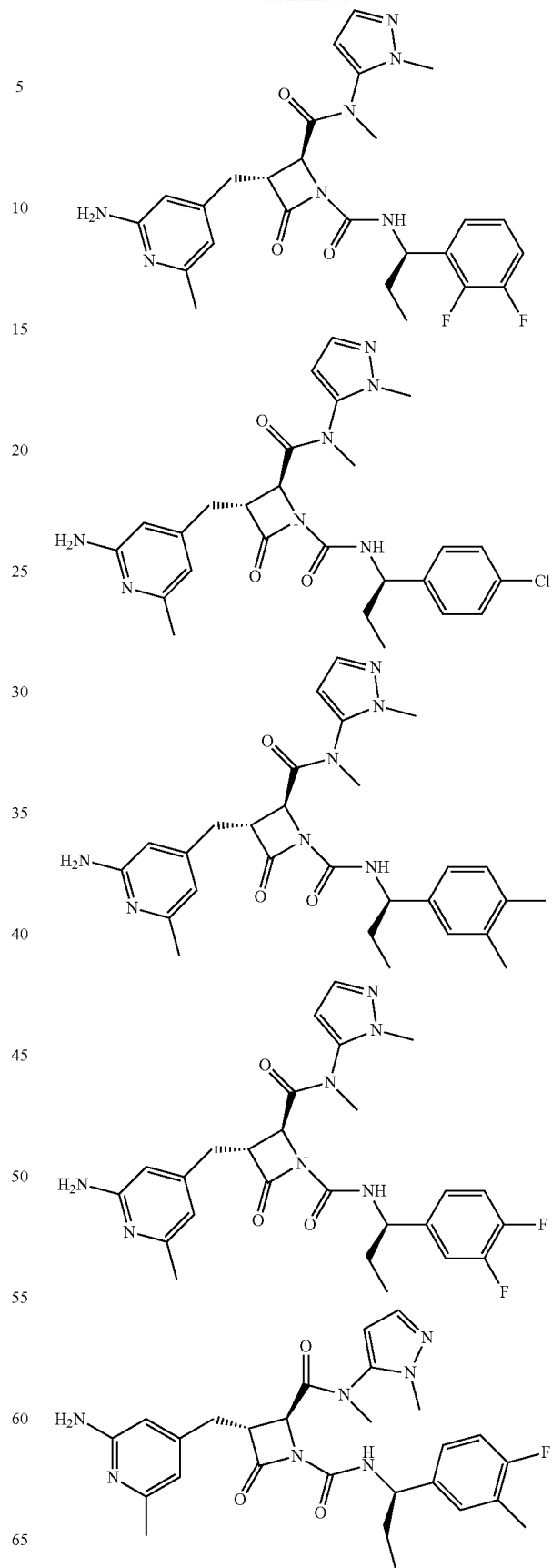

395
-continued
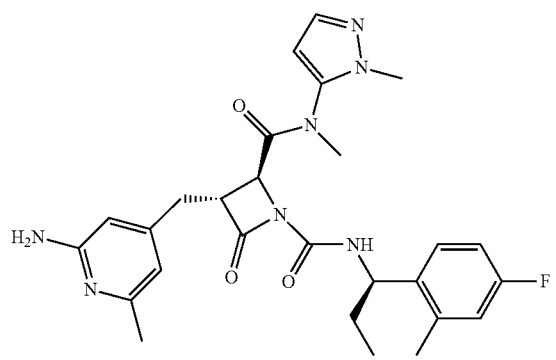
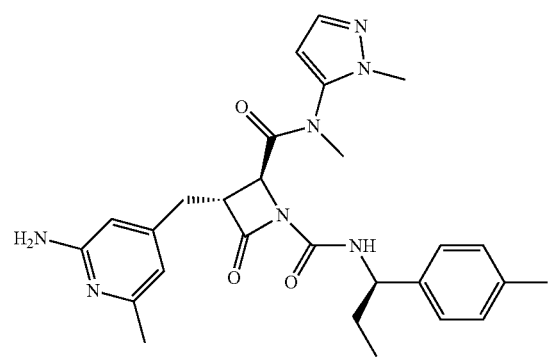
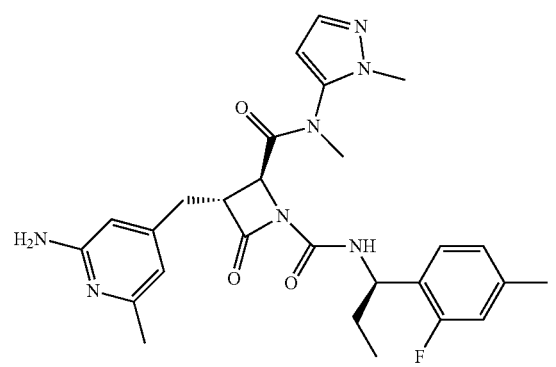
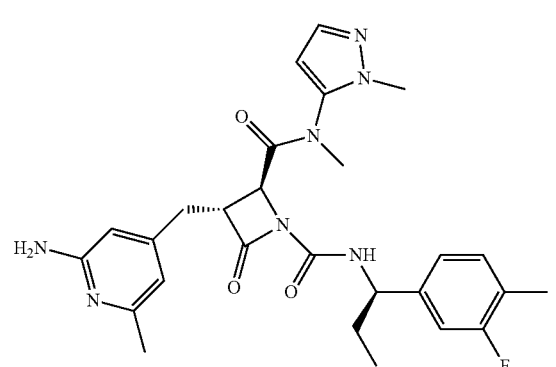 [SMILES: CC[C@@H](NC(=O)N1C(=O)[C@H](Cc2cc(C)nc(N)c2)[C@H]1C(=O)N(C)c1ccnn1C)c1ccc(C)c(C)c1]
396
-continued
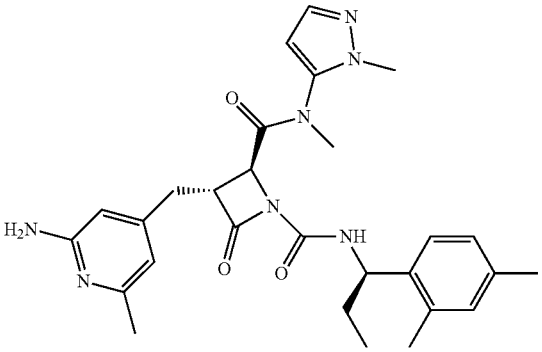
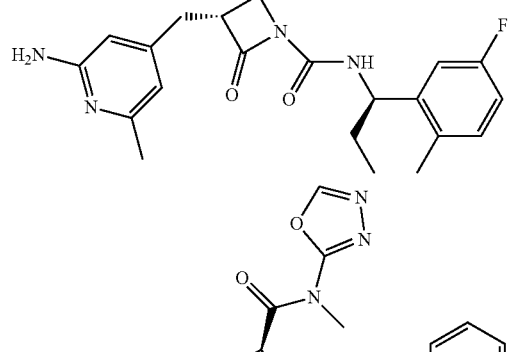
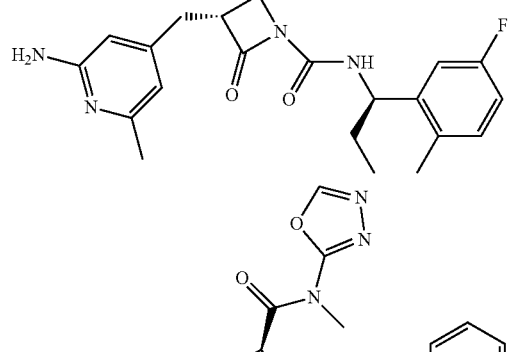
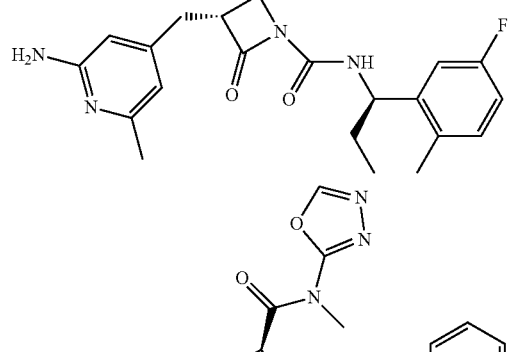
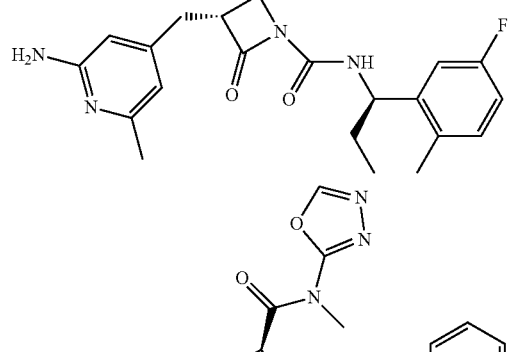

-continued
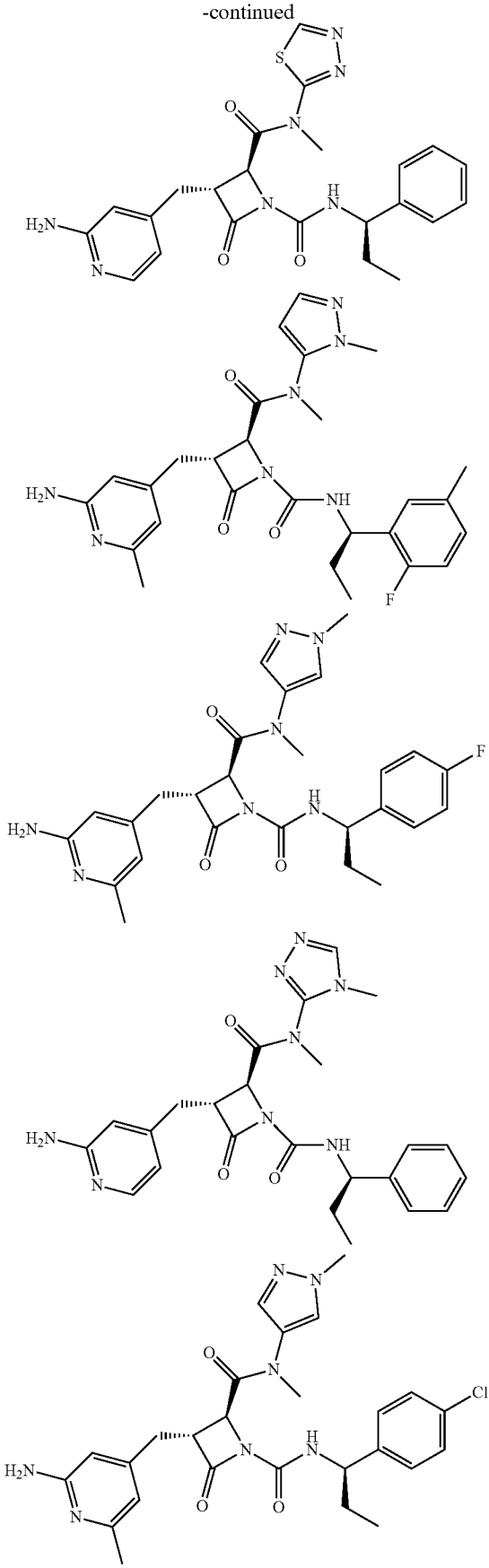
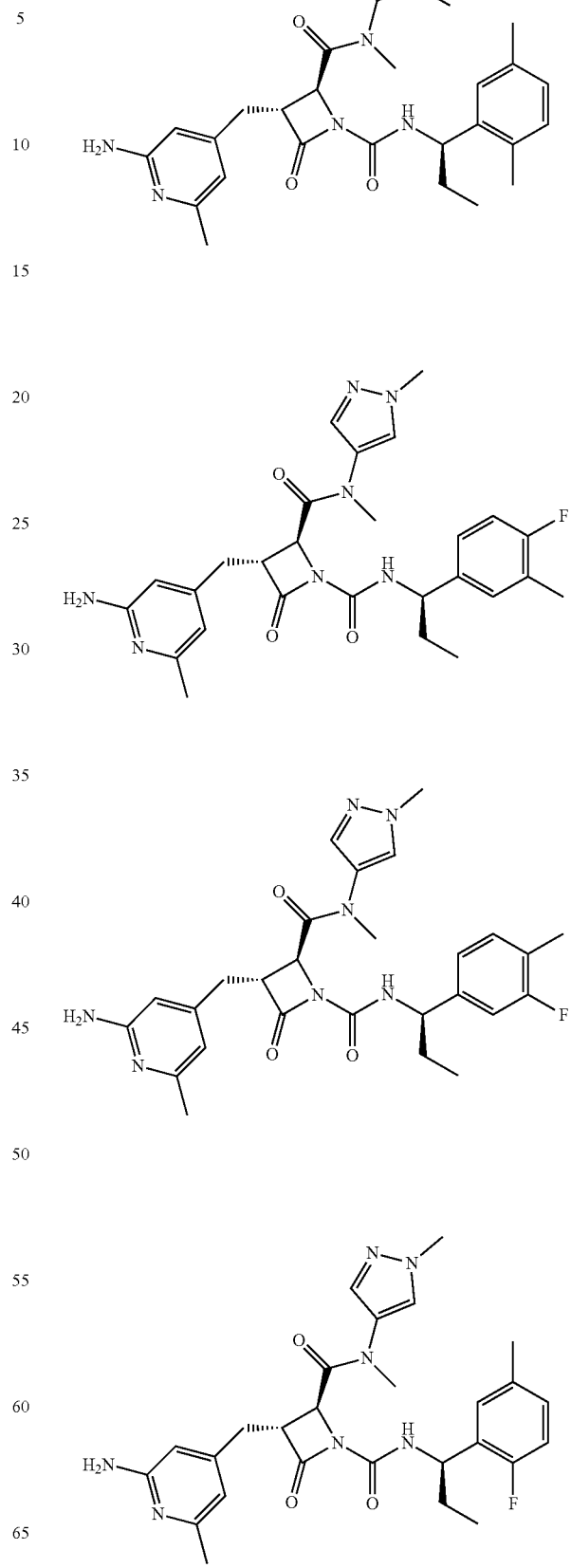

399
-continued
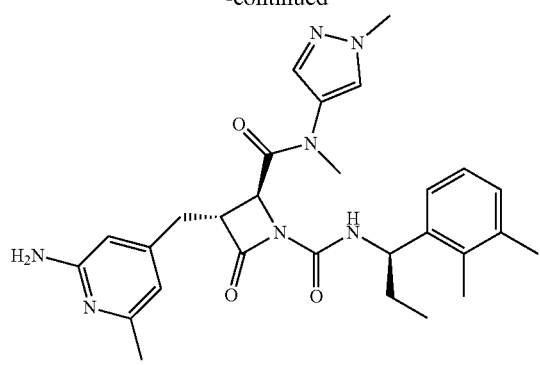
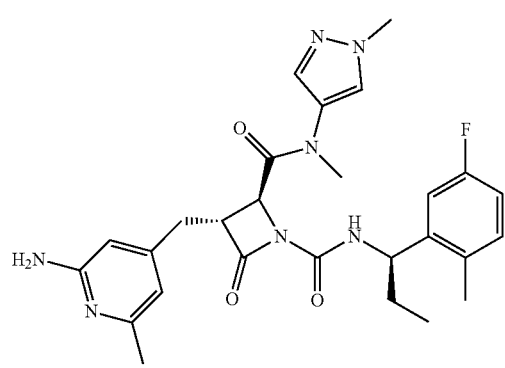
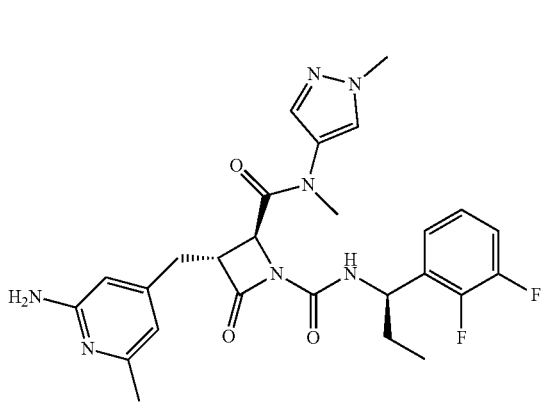 [SMILES: CC[C@@H](NC(=O)N1C(=O)[C@H](Cc2cc(C)nc(N)c2)[C@H]1C(=O)N(C)c1cnn(C)c1)c1cccc(F)c1F]
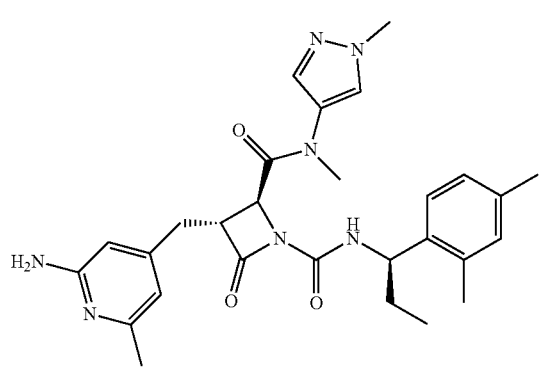 [SMILES: CC[C@@H](NC(=O)N1C(=O)[C@H](Cc2cc(C)nc(N)c2)[C@H]1C(=O)N(C)c1cnn(C)c1)c1ccc(C)cc1C]
400
-continued
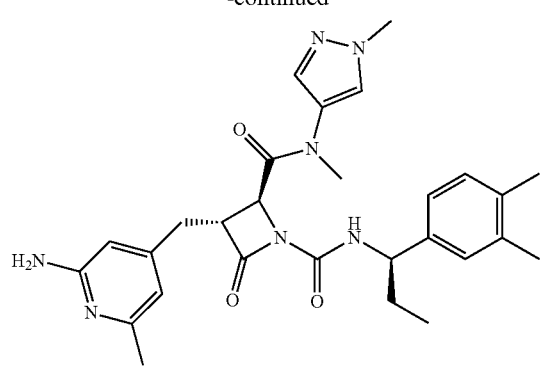
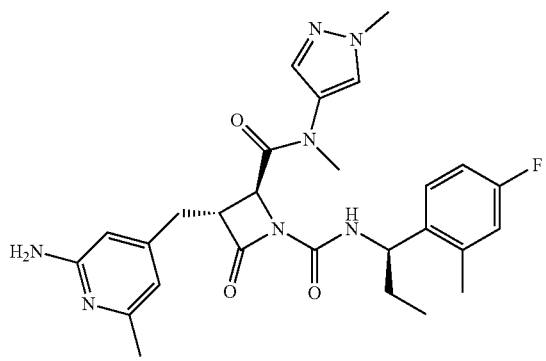 [SMILES: CC[C@@H](NC(=O)N1C(=O)[C@H](Cc2cc(C)nc(N)c2)[C@H]1C(=O)N(C)c1cnn(C)c1)c1ccc(F)cc1C]
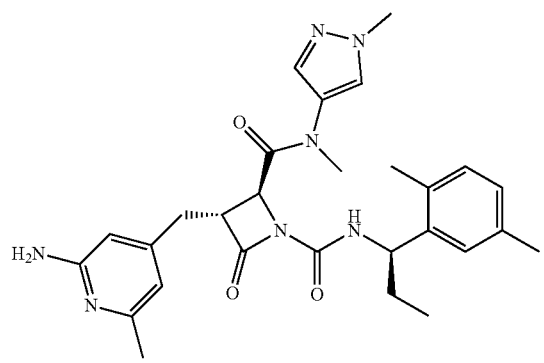
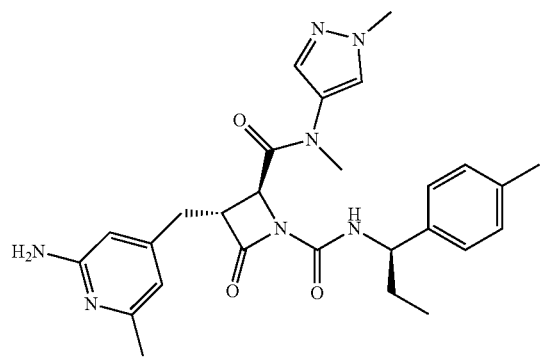 [SMILES: CC[C@@H](NC(=O)N1C(=O)[C@H](Cc2cc(C)nc(N)c2)[C@H]1C(=O)N(C)c1cnn(C)c1)c1ccc(C)cc1]

401
-continued
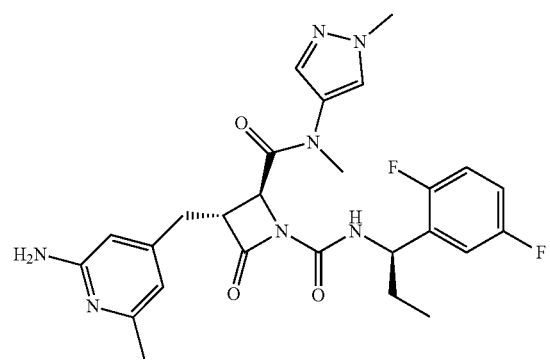 [SMILES: CC[C@@H](NC(=O)N1C(=O)[C@H](Cc2cc(C)nc(N)c2)[C@H]1C(=O)N(C)c1cnn(C)c1)c1cc(F)ccc1F]
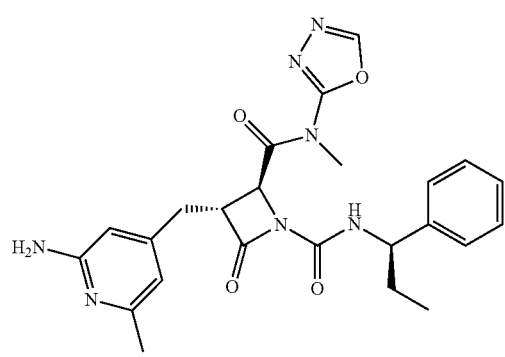
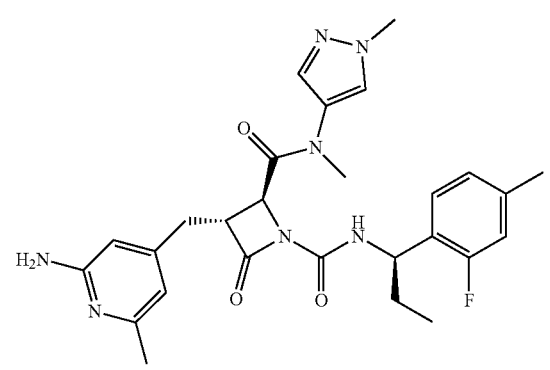
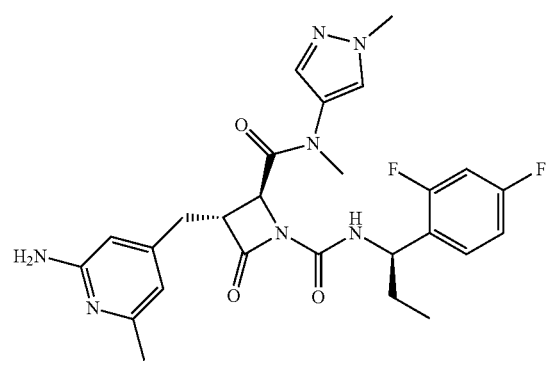
402
-continued
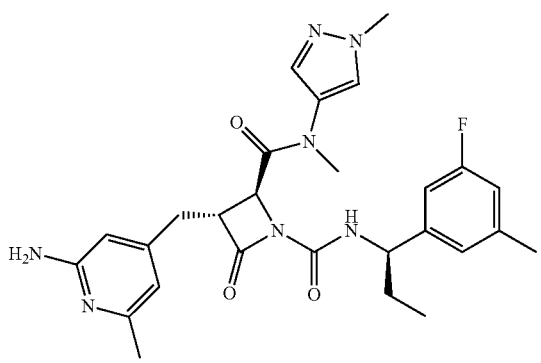 [SMILES: CC[C@@H](NC(=O)N1C(=O)[C@H](Cc2cc(C)nc(N)c2)[C@H]1C(=O)N(C)c1cnn(C)c1)c1cc(C)cc(F)c1]
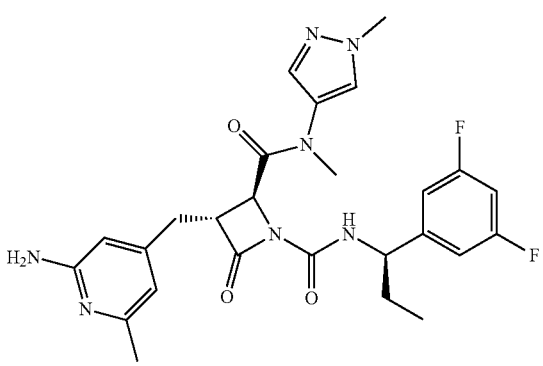
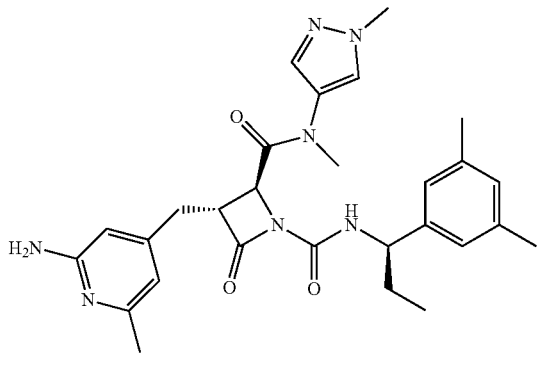 [SMILES: CC[C@@H](NC(=O)N1C(=O)[C@H](Cc2cc(C)nc(N)c2)[C@H]1C(=O)N(C)c1cnn(C)c1)c1cc(C)cc(C)c1]
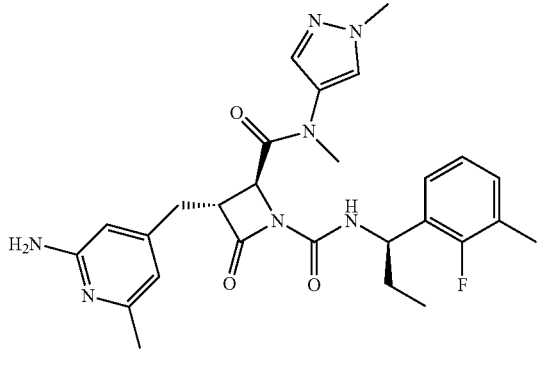

403
-continued
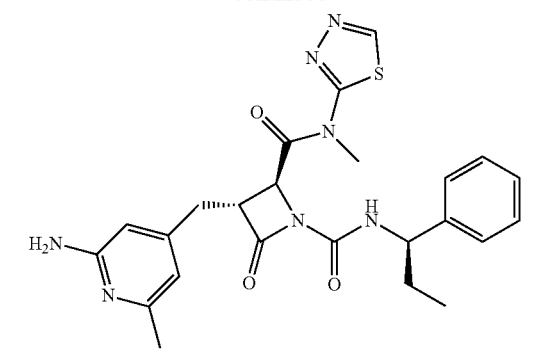
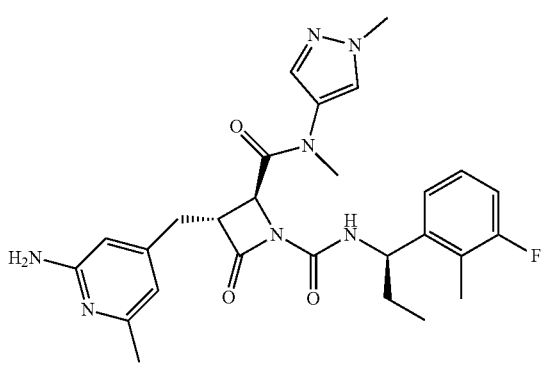 [SMILES: CC[C@@H](NC(=O)N1C(=O)[C@H](Cc2cc(C)nc(N)c2)[C@H]1C(=O)N(C)c1cnn(C)c1)c1cccc(F)c1C]
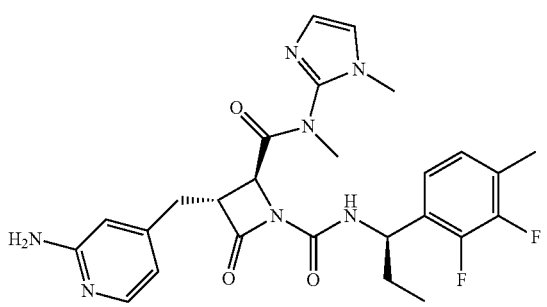 [SMILES: CC[C@@H](NC(=O)N1C(=O)[C@H](Cc2ccnc(N)c2)[C@H]1C(=O)N(C)c1nccn1C)c1ccc(C)c(F)c1C]
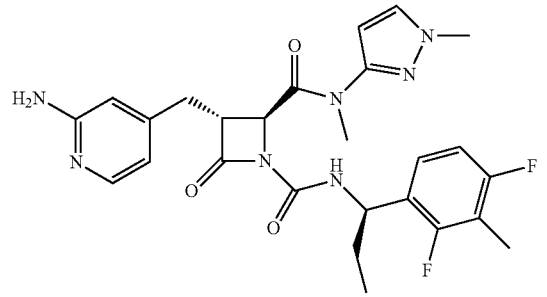
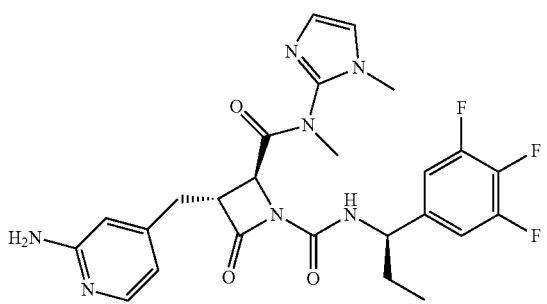
404
-continued
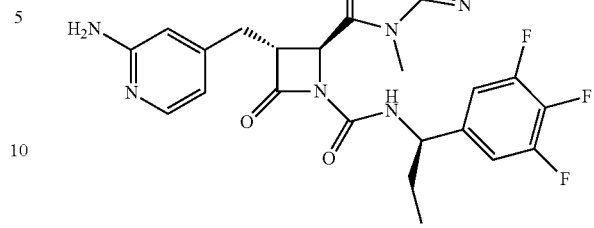
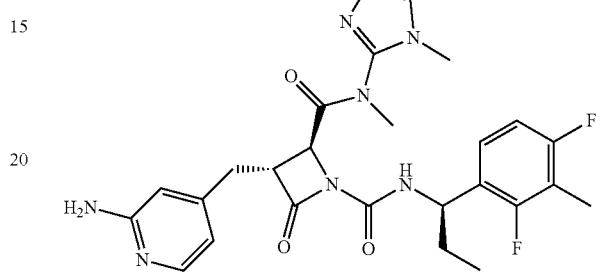
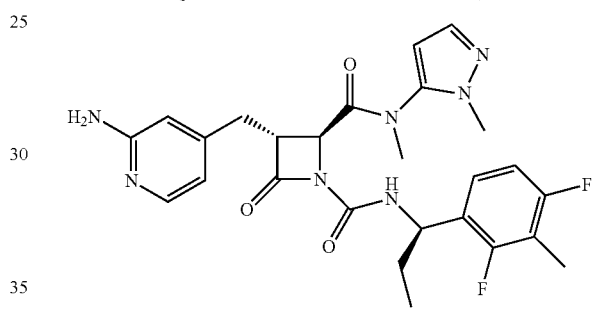
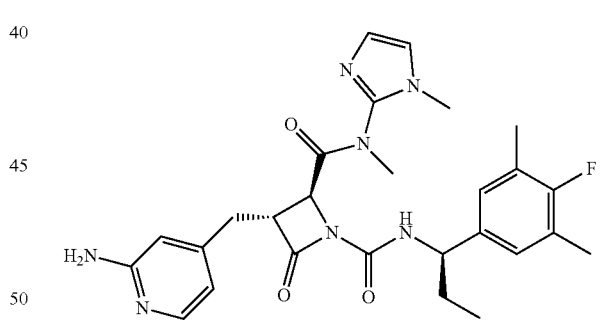
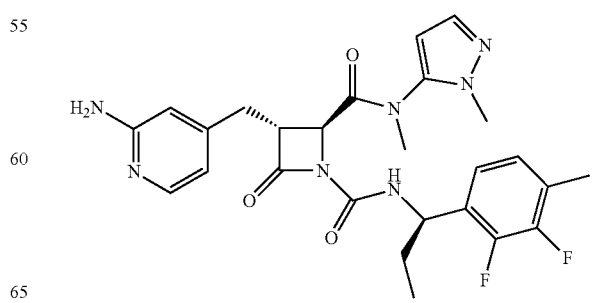

405
-continued
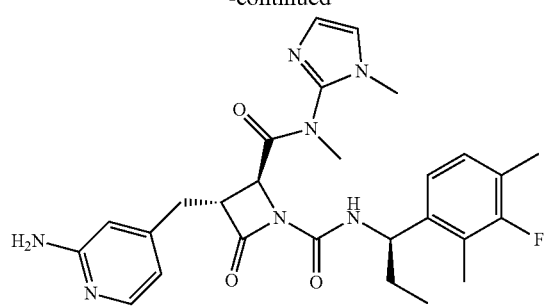
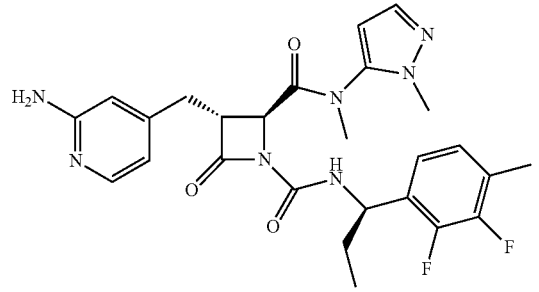
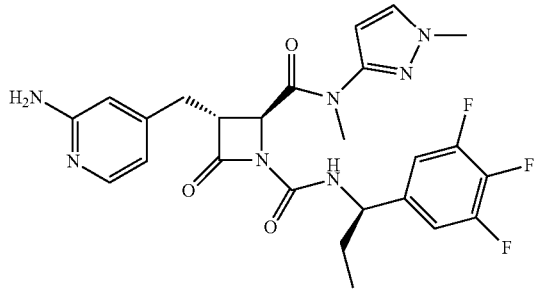
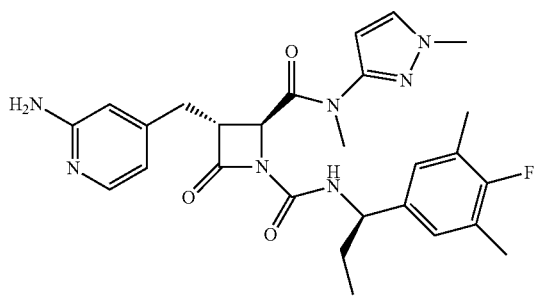
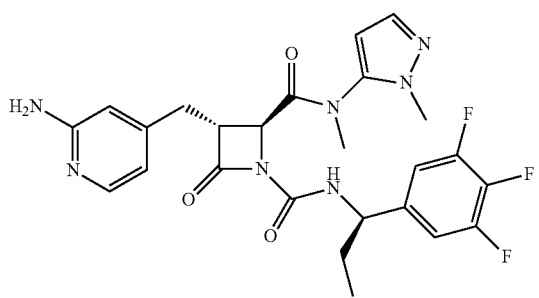
406
-continued
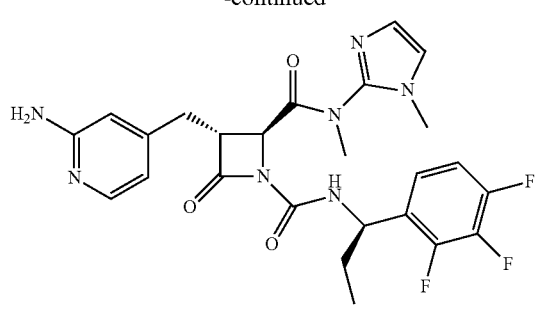
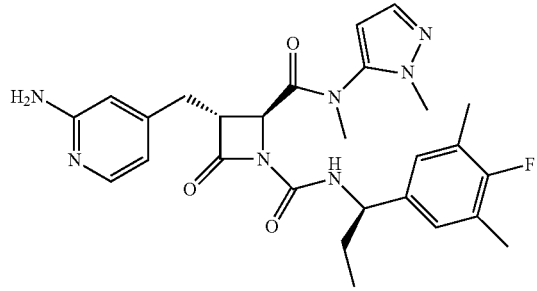
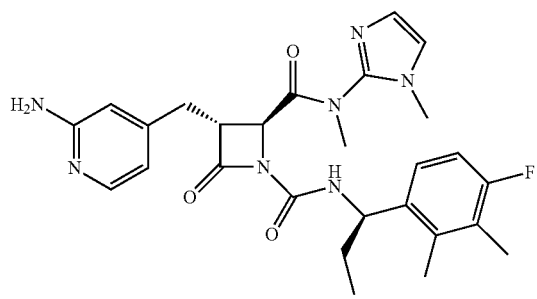
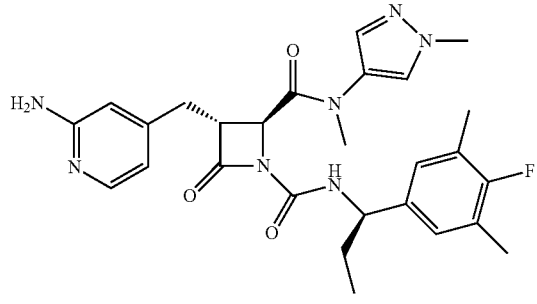
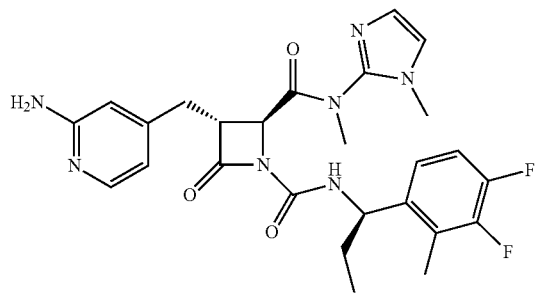

407
-continued
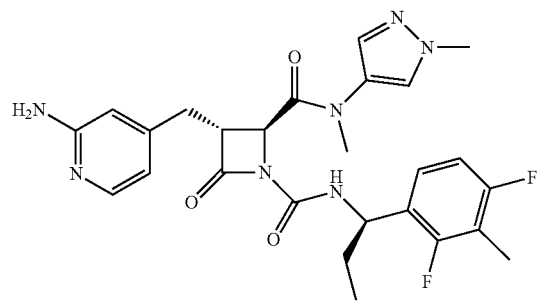
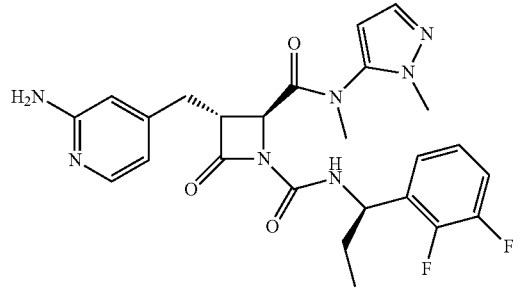
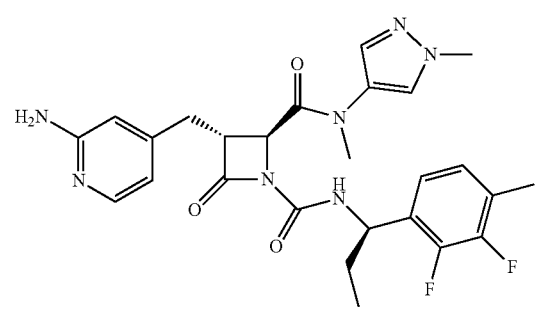
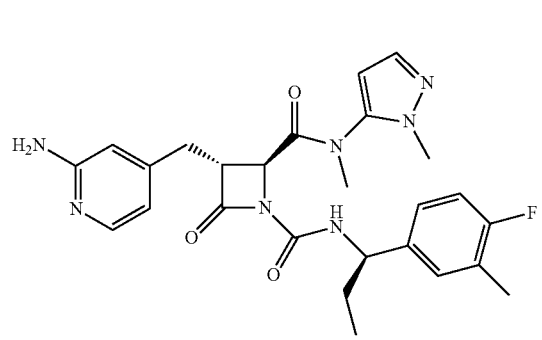
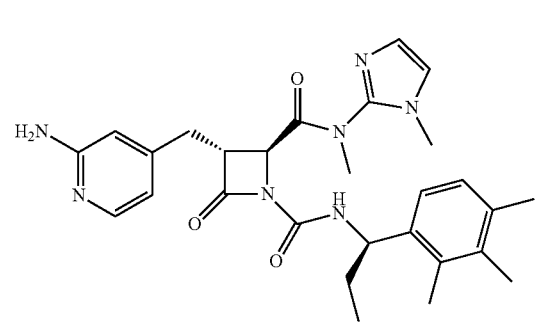
408
-continued
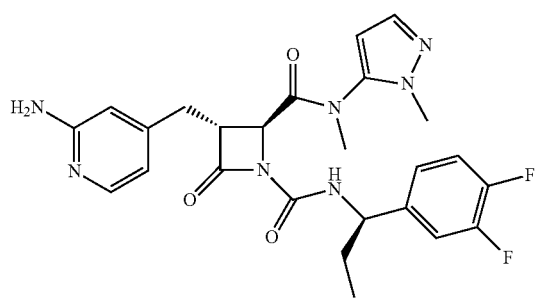
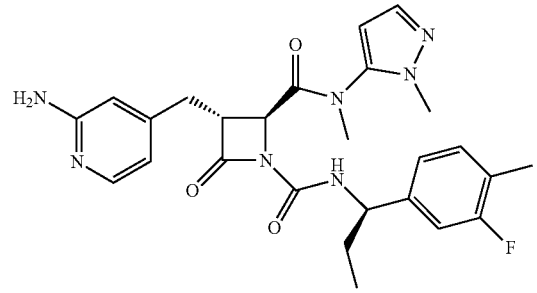
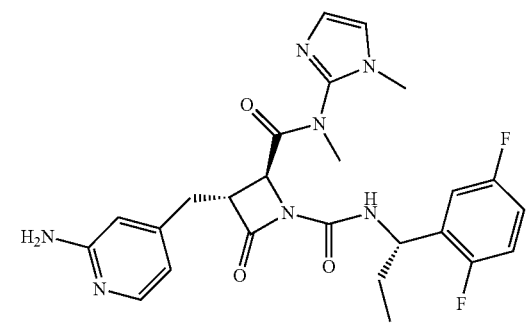
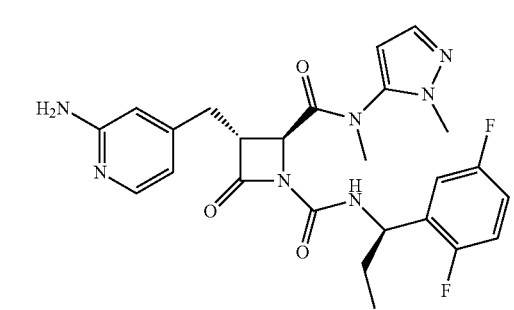
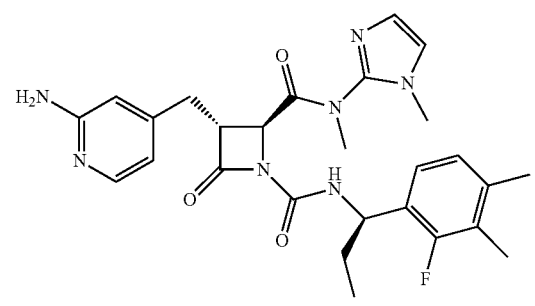

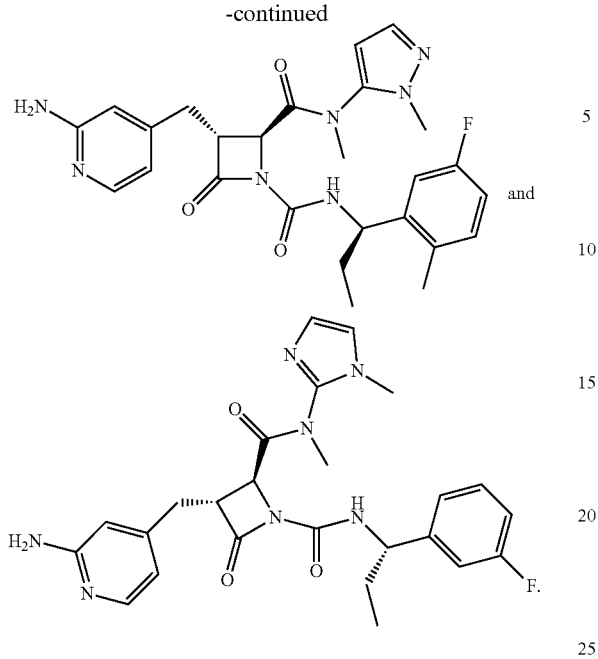
13. A pharmaceutically acceptable salt of the compound of claim 1.
14. A pharmaceutical composition comprising the compound of claim 1 or a pharmaceutically acceptable salt thereof and one or more pharmaceutically acceptable excipients.
* * * * *